US008828657B2

(12) United States Patent
Rafnar et al.

(10) Patent No.: US 8,828,657 B2

(45) Date of Patent: Sep. 9, 2014

(54) SUSCEPTIBILITY VARIANTS FOR LUNG CANCER

(75) Inventors: Thorunn Rafnar, Reykjavik (IS); Thorgeir E. Thorgeirsson, Reykjavik (IS); Patrick Sulem, Reykjavik (IS); Frank Geller, Seltjarnames (IS)

(73) Assignee: deCODE Genetics ehf., Reykjavík (IS)

( * ) Notice: Subject to any disclaimer, the term of this patent is extended or adjusted under 35 U.S.C. 154(b) by 0 days.

(21) Appl. No.: 12/867,680

(22) PCT Filed: Feb. 16, 2009

(86) PCT No.: PCT/IS2009/000001

§ 371 (c)(1), (2), (4) Date: Aug. 13, 2010

(87) PCT Pub. No.: WO2009/101639

PCT Pub. Date: Aug. 20, 2009

(65) Prior Publication Data

US 2011/0091880 A1 Apr. 21, 2011

(30) Foreign Application Priority Data

Feb. 14, 2008 (IS) .............................................. 8716

(51) Int. Cl.
*C12Q 1/68* (2006.01)
*G01N 33/53* (2006.01)

(52) U.S. Cl.
CPC ........ *C12Q 1/6886* (2013.01); *C12Q 2600/172* (2013.01); *C12Q 2600/118* (2013.01)
USPC ........... 435/6.1; 435/6.11; 435/6.12; 435/7.1; 435/6.14

(58) Field of Classification Search
None
See application file for complete search history.

(56) References Cited

U.S. PATENT DOCUMENTS 3,631,865 A * 1/1972 Michelson .................... 131/309
4,376,110 A 3/1983 David et al.
4,851,330 A 7/1989 Kohne
5,223,409 A 6/1993 Ladner et al.
5,288,611 A 2/1994 Kohne
5,288,644 A 2/1994 Beavis et al.
5,445,934 A 8/1995 Fodor et al.
5,700,637 A 12/1997 Southern
5,744,305 A 4/1998 Fodor et al.
5,829,449 A * 11/1998 Hersh et al. .................. 131/202
5,945,334 A 8/1999 Besemer et al.
6,054,270 A 4/2000 Southern
6,300,063 B1 10/2001 Lipshutz et al.
6,429,027 B1 8/2002 Chee et al.
6,733,977 B2 5/2004 Besemer et al.
6,858,394 B1 2/2005 Chee et al.
6,908,631 B1 * 6/2005 Sellers et al. ................. 424/751
7,028,693 B2 * 4/2006 Brue ............................ 131/270
7,364,858 B2 4/2008 Barany et al.
2002/0044941 A1 * 4/2002 Rosen et al. ...................... 435/6
2004/0049355 A1 * 3/2004 Maus et al. ..................... 702/19
2007/0258898 A1 * 11/2007 Ballinger et al. .............. 424/9.1

FOREIGN PATENT DOCUMENTS

EP 373 203 A1 6/1990
EP 619 321 A1 10/1994
WO WO-90/02809 A1 3/1990
WO WO-91/17271 A1 11/1991
WO WO-92/01047 A1 1/1992
WO WO-92/09690 A2 6/1992
WO WO-92/15679 A1 9/1992
WO WO-92/18619 A1 10/1992
WO WO-92/20791 A1 11/1992
WO WO-93/01288 A1 1/1993
WO WO-93/22456 A1 11/1993
WO WO-2007/100919 A2 9/2007

OTHER PUBLICATIONS

Saccone et al. Human Molecular Genetics. 2007. 16(1): 36-49.*
Amos et al. Nature Genetics. 2008. 40: 616-622.*
Hung et al. Nature. 2008. 452: 633-637.*
Hecht. The Lancet Oncology. 2002. 3: 461-469.*
Girard. Clin Cancer Res. 2010. 16: 755-763.*
Guidance for Industry. US Dept of Health and Human services. Sep. 2005.*
CDC guidelines.*
Medical News Today (retrieved on Mar. 4, 2014 from the internet: http://www.medicalnewstoday.com/articles/270799.php).*
The Mayo Clinic (retrieved on Mar. 4, 2014 from the internet: http://www.mayoclinic.org/diseases-conditions/lung-cancer/indepth/lung-ct-scan/art-20044852).*
The CDC (retrieved on Mar. 4, 2014 from the internet: http://www.cdc.gov/cancer/lung/basic_info/screening.htm).*
ss1527503 (retrieved on May 22, 2013 from the internet <http://www.ncbi.nlm.nih.gov/projects/SNP/snp_ss.cgi?subsnp_id=1527503>).*
CDC guidelines. Jun. 12, 2009. vol. 58, No. RR-6.*
Zhang. PLOS ONE. 2012. 7(12): e52938.*
Agami et al., RNAi and related mechanisms and their potential use for therapy, Curr. Opin. Chem. Biol., 6:829-34 (2002).
Altschul et al., Gapped BLAST and PSI-BLAST: a new generation of protein database search Programs, Nucleic Acids Res., 25:3389-402 (1997).
Amarzguioui et al., Approaches for chemically synthesized siRNA and vector-mediated RNAi, FEBS Lett., 579:5974-81 (2005).
Amos et al., Genome-wide association scan of tag SNPs identifies a susceptibility locus for lung cancer at 15q25.1, Nat. Genet., 40:616-22 (2008).

(Continued)

*Primary Examiner* — Stephen Kapushoc
*Assistant Examiner* — Joseph G Dauner
(74) *Attorney, Agent, or Firm* — Marshall, Gerstein & Borun LLP

(57) ABSTRACT

The present invention discloses certain genetic variants as susceptibility variants for lung cancer. The invention relates to methods of risk assessment using such variants. The invention further relates to kits for use in risk assessment of lung cancer.

38 Claims, 2 Drawing Sheets

(56) References Cited

OTHER PUBLICATIONS

Amundadottir et al., A common variant associated with prostate cancer in European and African populations, Nat. Genet., 38:652-8 (2006).
Amundadottir et al., Cancer as a complex phenotype: pattern of cancer distribution within and beyond the nuclear family, PLoS Med., 1:e65 (2004).
Barrett et al., Evaluating coverage of genome-wide association studies, Nat. Genet., 38:659-62 (2006).
Bennett, Efficiency of antisense oligonucleotide drug discovery, Antisense Nucleic Acid Drug Dev., 12:215-24 (2002).
Bier et al., DNA microarrays, Adv. Biochem. Eng. Biotechnol., 109:433-53 (2008).
Bierut et al., Variants in nicotinic receptors and risk for nicotine dependence, Am. J. Psychiatry, 165:1163-71 (2008).
Bosher et al., RNA interference: genetic wand and genetic watchdog, Nat. Cell Biol., 2:E31-6 (2000).
Brennan et al., Effect of cruciferous vegetables on lung cancer in patients stratified by genetic status: a mendelian randomisation approach, Lancet, 366:1558-60 (2005).
Brennan et al., High cumulative risk of lung cancer death among smokers and nonsmokers in Central and Eastern Europe, Am. J. Epidemiol., 164:1233-41 (2006).
Brummelkamp et al., A system for stable expression of short interfering RNAs in mammalian cells, Science, 296:550-3 (2002).
Buckland et al., Strong bias in the location of functional promoter polymorphisms, Hum. Mutat., 26:214-23 (2005).
Campa et al., Association of common polymorphisms in inflammatory genes with risk of developing cancers of the upper aerodigestive tract, Cancer Causes Control, 18:449-55 (2007).
Campa et al., Lack of association between -251 T>A polymorphism of IL8 and lung cancer risk, Cancer Epidemiol. Biomarkers Prev., 14:2457-8 (2005).
Campa et al., Lack of association between polymorphisms in inflammatory genes and lung cancer risk, Cancer Epidemiol. Biomarkers Prey., 14:538-9 (2005).
Carter et al., Methods and strategies for analyzing copy number variation using DNA microarrays, Nat. Genet., 39:S16-21 (2007).
Chen et al., Clinical development of antisense oligonucleotides as anti-cancer therapeutics, Methods Mol. Med., 75:621-36 (2003).
Chen et al., Fluorescence polarization in homogeneous nucleic acid analysis, Genome Res., 9:492-8 (1999).
Chen et al., The evolution of gene regulation by transcription factors and microRNAs, Nat. Rev. Genet., 8:93-103 (2007).
Chi et al., Genomewide view of gene silencing by small interfering RNAs, Proc. Natl. Acad. Sci. USA, 100:6343-6 (2003).
Church et al., Genomic sequencing, Proc. Natl. Acad. Sci. USA, 81:1991-5 (1984).
Conti-Fine et al., Neuronal nicotinic receptors in non-neuronal cells: new mediators of tobacco toxicity?, Eur. J. Pharmacol., 393:279-94 (2000).
Cooke, Angiogenesis and the role of the endothelial nicotinic acetylcholine receptor, Life Sci., 80(24-25):2347-51 (2007).
Cotton et al., Reactivity of cytosine and thymine in single-base-pair mismatches with hydroxylamine and osmium tetroxide and its application to the study of mutations, Proc. Natl. Acad. Sci. USA, 85:4397-401 (1988).
Daly et al., High-resolution haplotype structure in the human genome, Nat. Genet., 29:229-32 (2001).
Dawson et al., A first-generation linkage disequilibrium map of human chromosome 22, Nature, 418:544-8 (2002).
Dempster et al., Manual likelihood from incomplete data via the EM algorithm, J. Royal Stat. Soc. B, 39:1-38 (1977).
Devlin et al., Genomic Control to the extreme, Nat. Genet., 36:1129-30 (2004).
Dias et al., Antisense oligonucleotides: basic concepts and mechanisms, Mol. Cancer Ther., 1:347-55 (2002).
Doll et al., Mortality in relation to smoking: 40 years' observations on male British doctors, BMJ, 309:901-11 (1994).
Emilsson et al., Genetics of gene expression and its effect on disease, Nature, 452:423-8 (2008).
Estivill et al., Copy Number variants and common disorders: filling the gaps and exploring complexity in genome-wide association studies, PLoS Genet., 3:1787-99 (2007).
Falk et al., Haplotype relative risks: an easy reliable way to construct a proper control sample for risk calculations, Ann. Hum. Genet., 51:227-33 (1987).
Fan et al., Illumina universal bead arrays, Methods Enzymol., 410:57-73 (2006).
Fire et al., Potent and specific genetic interference by double-stranded RNA in *Caenorhabditis elegans*, Nature, 391:806-11 (1998).
Flavell et al., Analysis of the beta-delta-globin gene loci in normal and Hb Lepore DNA: direct determination of gene linkage and intergene distance, Cell, 15:25-41 (1978).
Frayling et al., Genome-wide association studies provide new insights into type 2 diabetes aetiology, Nat. Rev. Genet., 8:657-62 (2007).
Fuchs et al., Targeting recombinant antibodies to the surface of *Escherichia coli*: fusion to a peptidoglycan associated lipoprotein, Bio/Technology, 9:1369-72 (1991).
Gabriel et al., The structure of haplotype blocks in the human genome, Science, 296:2225-9 (2002).
Galfre et al., Antibodies to major histocompatibility antigens produced by hybrid cell lines, Nature, 266:550-2 (1977).
Geever et al., Direct identification of sickle cell anemia by blot hybridization, Proc. Natl. Acad. Sci. USA, 78:5081-5 (1981).
Gemignani et al., Development of lung cancer before the age of 50: the role of xenobiotic metabolizing genes, Carcinogenesis, 28:1287-93 (2007).
Gibbs et al., Detection of single DNA base differences by competitive oligonucleotide priming, Nucleic Acids Res., 17:2437-48 (1989).
Goldgar et al., Systematic population-based assessment of cancer risk in first-degree relatives of cancer probands, J. Natl. Cancer Inst., 86:1600-8 (1994).
Goodman et al., Lung cancer. 1: prevention of lung cancer, Thorax, 57:994-9 (2002).
Grant et al., Variant of transcription factor 7-like 2 (TCF7L2) gene confers risk of type 2 diabetes, Nat. Genet., 38:320-3 (2006).
Gretarsdottir et al., The gene encoding phosphodiesterase 4D confers risk of ischemic stroke, Nat. Genet., 35:131-8 (2003).
Griffiths et al., Human anti-self antibodies with high specificity from phage display libraries, EMBO J., 12:725-34 (1993).
Gudmundsson et al., Common sequence variants on 2p15 and Xp11.22 confer susceptibility to prostate cancer, Nat. Genet., 40:281-3 (2008).
Gudmundsson et al., Genome-wide association study identifies a second prostate cancer susceptibility variant at 8q24, Nat. Genet., 39:631-7 (2007).
Gudmundsson et al., Two variants on chromosome 17 confer prostate cancer risk, and the one in TCF2 protects against type 2 diabetes, Nat. Genet., 39:977-83 (2007).
Gulcher et al., Protection of privacy by third-party encryption in genetic research in Iceland, Eur. J. Hum. Genet., 8:739-42 (2000).
Haiman et al., Ethnic and racial differences in the smoking-related risk of lung cancer, N. Engl. J. Med., 354:333-42 (2006).
Haiman et al., Multiple regions within 8q24 independently affect risk for prostate cancer, Nat. Genet., 39:638-44 (2007).
Hall et al., The association of sequence variants in DNA repair and cell cycle genes with cancers of the upper aerodigestive tract, Carcinogenesis, 28:665-71 (2007).
Hashibe et al., Evidence for an important role of alcohol- and aldehyde-metabolizing genes in cancers of the upper aerodigestive tract, Cancer Epidemiol. Biomarkers Prev., 15:696-703 (2006).
Hay at al., Bacteriophage cloning and *Escherichia coli* expression of a human IgM Fab, Hum. Antibodies Hybridomas, 3:81-5 (1992).
Heatherton et al., The Fagerström Test for Nicotine Dependence: a revision of the Fagerström Tolerance Questionnaire, Br. J. Addict., 86:1119-27 (1991).
Heeschen et al., Nicotine stimulates angiogenesis and promotes tumor growth and atherosclerosis, Nat. Med., 7:833-9 (2001).

(56) References Cited

OTHER PUBLICATIONS

Helgadottir et al., A common variant on chromosome 9p21 affects the risk of myocardial infarction, Science, 316:1491-3 (2007).
Ho et al., Tobacco-specific carcinogen 4-(methylnitrosamino)-1-(3-pyridyl)-1-butanone (NNK) induces cell proliferation in normal human bronchial epithelial cells through NFkappaB activation and cyclin D1 up-regulation, Toxicol. Appl. Pharmacol., 205:133-48 (2005).
Hoheisel, Microarray technology: beyond transcript profiling and genotype analysis, Nat. Rev. Genet., 7:200-10 (2006).
Hung et al., A susceptibility locus for lung cancer maps to nicotinic acetylcholine receptor subunit genes on 15q25, Nature, 452:633-7 (2008).
Hung et al., Folate-related genes and the risk of tobacco-related cancers in Central Europe, Carcinogenesis, 28:1334-40 (2007).
Hung et al., Large-scale investigation of base excision repair genetic polymorphisms and lung cancer risk in a multicenter study, J. Natl. Cancer Inst., 97:567-76 (2005).
Hung et al., Sequence variants in cell cycle control pathway, X-ray exposure, and lung cancer risk: a multicenter case-control study in Central Europe, Cancer Res., 66:8280-6 (2006).
Hunter, Genetics: a touch of elegance with RNAi, Curr. Biol., 9:R440-2 (1999).
Huse et al., Generation of a large combinatorial library of the immunoglobulin repertoire in phage lambda, Science, 246:1275-81 (1989).
International Preliminary Report on Patentability for corresponding International Application No. PCT/IS2009/000001, dated Aug. 17, 2010.
International Search Report and Written Opinion from corresponding International Application No. PCT/IS2009/000001, dated Apr. 28, 2009.
Jeffreys et al., Intensely punctate meiotic recombination in the class II region of the major histocompatibility complex, Nat. Genet., 29:217-22 (2001).
Jonsson et al., Familial risk of lung carcinoma in the Icelandic population, JAMA, 292:2977-83 (2004).
Karlin et al., Applications and statistics for multiple high-scoring segments in molecular sequences, Proc. Natl. Acad. Sci. USA, 90:5873-7 (1993).
Kim et al., Strategies for silencing human disease using RNA interference, Nat. Rev. Genet., 8:173-84 (2007).
Kim et al., Synthetic dsRNA Dicer substrates enhance RNAi potency and efficacy, Nat. Biotechnol., 23:222-6 (2005).
Kjaerheim et al., The role of alcohol, tobacco, and dietary factors in upper aerogastric tract cancers: a prospective study of 10,900 Norwegian men, Cancer Causes Control, 9:99-108 (1998).
Kohler et al., Continuous cultures of fused cells secreting antibody of predefined specificity, Nature, 256:495-7 (1975).
Kozbor et al., The production of monoclonal antibodies from human lymphocytes, Immunol. Today, 4:72-9 (1983).
Kraus et al., Detection and isolation of novel protein-tyrosine kinase genes employing reduced stringency hybridization, Methods Enzymol., 200:546-56 (1991).
Kurreck, Antisense technologies. Improvement through novel chemical modifications, Eur. J. Biochem., 270:1628-44 (2003).
Kutyavin et al., A novel endonuclease IV post-PCR genotyping system, Nucleic Acids Res., 34:e128 (2006).
Landi et al., t(14;18) translocations in lymphocytes of healthy dioxin-exposed individuals from Seveso, Italy, Carcinogenesis, 27:2001-7 (2006).
Lavery et al., Antisense and RNAI: powerful tools in drug target discovery and validation, Curr. Opin. Drug Discov. Devel., 6:561-9 (2003).
Lerner, How to make a hybridoma, Yale J. Biol. Med., 54:385-402 (1981).
Lessov-Schlaggar et al., Genetics of nicotine dependence and pharmacotherapy, Biochem. Pharmacol., 75:178-95 (2008).
Li et al., Familial multiple primary lung cancers: a population-based analysis from Sweden, Lung Cancer, 47:301-7 (2005).
Maneckjee et al., Opioid and nicotine receptors affect growth regulation of human lung cancer cell lines, Proc. Natl. Acad. Sci. USA, 87:3294-8 (1990).
Maniatis et al., The first linkage disequilibrium (LD) maps: delineation of hot and cold blocks by diplotype analysis, Proc. Natl Acad. Sci USA, 99:2228-33 (2002).
Mantel et al., Statistical aspects of the analysis of data from retrospective studies of disease, J. Natl. Cancer Inst., 22:719-48 (1959).
Marques et al., A structural basis for discriminating between self and nonself double-stranded RNAs in mammalian cells, Nat. Biotechnol., 24:559-65 (2006).
May et al., Crossover clustering and rapid decay of linkage disequilibrium in the Xp/Yp pseudoautosomal gene SHOX, Nat. Genet., 31:272-5 (2002).
Mcmanus et al., Gene silencing in mammals by small interfering RNAs, Nat. Rev. Genet., 3:737-47 (2002).
Mockler et al., Applications of DNA tiling arrays for whole-genome analysis, Genomics, 85:1-15 (2005).
Myers et al., Detection of single base substitutions by ribonuclease cleavage at mismatches in RNA:DNA duplexes, Science, 230:1242-6 (1985).
Myers et al., The distribution and causes of meiotic recombination in the human genome, Biochem. Soc. Trans., 34:526-30 (2006).
Nicolae et al., Measuring the relative information in allele-sharing linkage studies, Biometrics, 60:368-75 (2004).
Nielsen et al., Peptide nucleic acid (PNA). A DNA mimic with a peptide backbone, Bioconjug. Chem., 5:3-7 (1994).
Nielsen et al., Sequence-selective recognition of DNA by strand displacement with a thymine-substituted polyamide, Science, 254:1497-500 (1991).
Nyren et al., Solid phase DNA minisequencing by an enzymatic luminometric inorganic pyrophosphate detection assay, Anal. Biochem., 208:171-5 (1993).
Orita et al., Detection of polymorphisms of human DNA by gel electrophoresis as single strand conformation polymorphisms, Proc. Natl. Acad. Sci. USA, 86:2766-70 (1989).
Patil et al., Blocks of limited haplotype diversity revealed by high-resolution scanning of human chromosome 21, Science, 294:1719-23 (2001).
Pearson et al., Improved tools for biological sequence comparison, Proc. Natl. Acad. Sci. USA, 85:2444-8 (1988).
Peto et al., Smoking, smoking cessation, and lung cancer in the UK since 1950: combination of national statistics with two case-control studies, BMJ, 321:323 (2000).
Phillips et al., Chromosome-wide distribution of haplotype blocks and the role of recombination hot spots, Nat. Genet., 33:382-7 (2003).
Plasterk et al., The silence of the genes, Curr. Opin. Genet. Dev., 10:562-7 (2000).
Ragoussis et al., Affymetrix GeneChip system: moving from research to the clinic, Expert Rev. Mol. Diagn., 6:145-52 (2006).
Redon et al., Global variation in copy number in the human genome, Nature, 444:444-54 (2006).
Reich et al., Linkage disequilibrium in the human genome, Nature, 411:199-204 (2001).
Reynolds et al., Rational siRNA design for RNA interference, Nat. Biotechnol., 22:326-30 (2004).
Risch et al., The future of genetic studies of complex human diseases, Science, 273:1516-7 (1996).
Risch et al., The relative power of family-based and case-control designs for linkage disequilibrium studies of complex human diseases I. DNA pooling, Genome Res., 8:1273-88 (1998).
Ronaghi et al., Analyses of secondary structures in DNA by pyrosequencing, Anal. Biochem., 267:65-71 (1999).
Ronaghi et al., PCR-introduced loop structure as primer in DNA sequencing, Biotechniques, 25:876-8, 880-2, 884 (1998).
Saccone et al., Cholinergic nicotinic receptor genes implicated in a nicotine dependence association study targeting 348 candidate genes with 3713 SNPs, Hum. Mol. Genet., 16:36-49 (2007).
Sanger et al., DNA sequencing with chain-terminating inhibitors, Proc. Natl. Acad. Sci. USA, 74:5463-7 (1977).

(56) References Cited

OTHER PUBLICATIONS

Sheffield et al., Attachment of a 40-base-pair G + C-rich sequence (GC-clamp) to genomic DNA fragments by the polymerase chain reaction results in improved detection of single-base changes, Proc. Natl. Acad. Sci. USA, 86:232-6 (1989).
Shi, Mammalian RNAi for the masses, Trends Genet., 19:9-12 (2003).
Shuey et al., RNAi: gene-silencing in therapeutic intervention, Drug Discov. Today, 7:1040-6 (2002).
Siolas et al. Synthetic shRNAs as potent RNAi triggers, Nat. Biotechnol., 23:227-31 (2005).
Smith et al., A high-density admixture map for disease gene discovery in african americans, Am. J. Hum. Genet., 74:1001-13 (2004).
Song et al., Acetylcholine is synthesized by and acts as an autocrine growth factor for small cell lung carcinoma, Cancer Res., 63:214-21 (2003).
Spitz et al., Integrative epidemiology: from risk assessment to outcome prediction, J. Clin. Oncol., 23:267-75 (2005).
Stacey et al., Common variants on chromosomes 2q35 and 16q12 confer susceptibility to estrogen receptor-positive breast cancer, Nat. Genet., 39:865-9 (2007).
Steinthorsdottir et al., A variant in CDKAL1 influences insulin response and risk of type 2 diabetes, Nat. Genet., 39:770-5 (2007).
Stellman et al., Lung cancer risk in white and black Americans, Ann. Epidemiol., 13:294-302 (2003).
Stephens et al., Antisense oligonucleotide therapy in cancer, Curr. Opin. Mol. Ther., 5:118-22 (2003).
Strausberg et al., Emerging DNA sequencing technologies for human genomic medicine, Drug Discov. Today, 13:569-77 (2008).
Stumpf et al., Demography, recombination hotspot intensity, and the block structure of linkage disequilibrium, Curr. Biol., 13:1-8 (2003).
Styrkarsdottir et al., Multiple genetic loci for bone mineral density and fractures, N. Engl. J. Med., 358:2355-65 (2008).
Terwilliger et al., A haplotype-based 'haplotype relative risk' approach to detecting allelic associations, Hum. Hered., 42:337-46 (1992).
Thompson, Applications of antisense and siRNAs during preclinical drug development, Drug Discov. Today, 7:912-7 (2002).
Thorgeirsson et al., A variant associated with nicotine dependence, lung cancer and peripheral arterial disease, Nature, 452:638-42 (2008).
Thorgeirsson et al., Anxiety with panic disorder linked to chromosome 9q in Iceland, Am. J. Hum. Genet., 72:1221-30 (2003).
Torelli et al., Advance and Adam: two algorithms for the analysis of global similarity between homologous informational sequnces. CABIOS, 10:3-5 (1984).
Tsurutani et al., Tobacco components stimulate Akt-dependent proliferation and NFkappaB-dependent survival in lung cancer cells, Carcinogenesis, 26:1182-95 (2005).
Vickers et al., Efficient reduction of target RNAs by small interfering Rna and RNase H-dependent antisense agents. A comparative analysis, J. Biol. Chem., 278:7108-18 (2003).
Wall et al., Haplotype blocks and linkage disequilibrium in the human genome, Nat. Rev. Genet., 4:487-97 (2003).
Wang et al., Distribution of recombination crossovers and the origin of haplotype blocks: the interplay of population history, recombination, and mutation, Am. J. Hum. Genet., 71:1227-34 ,(2002).
West et al., Rapid Akt activation by nicotine and a tobacco carcinogen modulates the phenotype of normal human airway epithelial cells, J. Clin. Invest., 111:81-90 (2003).
Xia et al., siRNA-mediated gene silencing in vitro and in vivo, Nat. Biotechnol., 20:1006-10 (2002).
Xu et al., Protein kinase Ciota promotes nicotine-induced migration and invasion of cancer cells via phosphorylation of micro- and m-calpains, J. Biol. Chem., 281:4457-66 (2005).
Yeager et al., Genome-wide association study of prostate cancer identifies a second risk locus at 8q24, Nat. Genet., 39:645-9 (2007).
Zhang et al., A dynamic programming algorithm for haplotype block partitioning, Proc. Natl. Acad. Sci. USA, 99:7335-9 (2002).
Zhang et al., Nicotine induces hypoxia-inducible factor-1alpha expression in human lung cancer cells via nicotinic acetylcholine receptor-mediated signaling pathways, Clin. Cancer Res., 13:4686-94 (2007).
Zhu et al., A single nucleotide polymorphism in the matrix metalloproteinase-1 promoter enhances lung cancer susceptibility, Cancer Res., 61:7825-9 2001.
Altshuler, et al., Guilt beyond a reasonable doubt, Nature Genetics, 39:813-815 (2007).
Barrett, et al., Haploview: analysis and visualization of LD and haplotype maps, Bioinformatics Applications Note, 21(2):263-265 (2005).
Bitton, et al., The Framingham Heart Study's Impact on Global Risk, Prog Cardiovasc Dis. 53(1):68-78 (2010).
Bousman, et al., Alpha-5 and -3 nicotinic receptor gene variants predict nicotine dependence but not cessation: Findings from the COMMIT cohort, Am J Med Genet B Neuropsychiatr Genet., 159B(2):227-235 (2012).
Bowcock, Guilt by Association, Nature 447:645-646 (2007).
Carcereny, et al., Blood-based CHRNA3 single nucleotide polymorphism and outcome in advanced non-small-cell lung cancer patients, Lung Cancer 68:491-497 (2010).
Chen, et al. Good Laboratory Practices for Molecular Genetic Testing for Heritable Diseases and Conditions, Morbidity and Mortality Weekly Report, 58(RR-6):43 pp. (2009).
Declaration of Patrick Sulem executed Nov. 15, 2011 and filed Nov. 22, 2011.
Declaration of Patrick Sulem executed and filed Jul. 12, 2012.
Division of Genomic Medicine, A Catalog of Published Genome-Wide Association Studies, 5 pages. (2013).
Dormandy et al., Management of peripheral arterial disease (PAD). TASC Working Group. TransAtlantic Inter-Society Consensus (TASC), J. Vasc. Surg., 31:S1-296 (2000).
Dormandy et al., the natural history of claudication: risk to life and limb, Semin. Vasc. Surg., 12:123-37 (1999).
Easton, et al., Genome-wide association study identifies novel breast cancer susceptibility loci, Nature 447:1087-1093 (2007).
Eriksson et al., Genotype-phenotype relationships in an investigation of the role of proteases in abdominal aortic aneurysm expansion, Br. J. Surg., 92:1372-6 (2005).
Flex et al., The -174 G/C polymorphism of the interleukin-6 gene promoter is associated with peripheral artery occlusive disease, Eur. J. Vasc. Endovasc. Surg., 24:264-8 (2002).
Frayling, et al., A Common Variant in the FTO Gene is Associated with Body Mass Index and Predisposes to Childhood and Adult Obesity, Science, 316:889-893 (2007).
Greenbaum et al., Why do young women smoke? I. Direct and interactive effects of environment, psychological characteristics and nicotinic cholinergic receptor genes, Mol. Psychiatry, 11:312-22, 223 (2006).
Guidance for Industry, Collection of Race and Ethnicity Data in Clinical Trials, U.S. Department of Health and Huma Services, 21 pages (2005).
Haustein, State of the art--treatment of peripheral occlusive arterial disease (PAOD) with drugs vs. vascular reconstruction or amputation, Int. J. Clin. Pharmacol. Ther., 35:266-74 (1997).
Hunter, et al., A genome-wide association study identifies alleles in FGFR2 associated with risk of sporadic postmenopausal breast cancer, Nature Genetics 39(6):870-874 (2007).
Issue Brief American Academy of Actuaries, Genetic Information and Voluntary Life Insurance, 5 pages. (1998).
Hirsch et al., ACC/AHA 2005 Practice Guidelines for the management of patients with peripheral arterial disease (lower extremity, renal, mesenteric, and abdominal aortic): a collaborative report from the American Association for Vascular Surgery/Society for Vascular Surgery, Society for Cardiovascular Angiography and Interventions, Society for Vascular Medicine and Biology, Society of Interventional Radiology, and the ACC/AHA Task Force on Practice Guidelines (Writing Committee to Develop Guidelines for the Management of Patients With Peripheral Arterial Disease): endorsed by the American Association of Cardiovascular and Pulmonary Rehabilitation;

(56) References Cited

OTHER PUBLICATIONS

National Heart, Lung, and Blood Institute; Society for Vascular Nursing; TransAtlantic Inter-Society Consensus; and Vascular Disease Foundation, Circulation, 113:e463-654 (2006).
Hirschhorn et al., A comprehensive review of genetic association studies, Genet. Med., 4(2):45-61 (2002).
Hooi et al., The prognosis of non-critical limb ischaemia: a systematic review of population-based evidence, Br. J. Gen. Pract., 49:49-55 (1999).
Jones et al., Plasma lipoprotein(a) indicates risk for 4 distinct forms of vascular disease, Clin. Chem., 53:679-85 (2007).
Kaur-Knudsen, et al. Nicotinic Acetylcholine Receptor Polymorphism, Smoking Behavior, and Tobacco-Related Cancer and Lung and Cardiovascular Diseases: a Cohort Study, Journal of Clinical Oncology, 29(21):2875-2882 (2011).
Kingsmore, et al., Genome-Wide Association Studies: Progress in Identifying Genetic Biomarkers in Common, Complex Diseases, Biomarker Insights, 2:283-292 (2007).
Klein, et al., Complement Factor H Polymorphism in Age-Related Macular Degeneration, Science 308:385-388 (2005).
Le Grys, Actuarial Considerations on Genetic Testing, Phil. Trans. R. Soc. Lond. B 352:1057-1061 (1997).
Lips, et al., Association between a 15q25 gene variant, smoking quantity and tobacco-related cancers among 17000 individuals, International Journal of Epidemiology, 29:563-577 (2010).
Lucentini, Gene association studies typically wrong, the Scientist, p. 20 (Dec. 20, 2004).
Myers et al., A fine-scale map of recombination rates and hotspots across the human genome, Science, 310:321-4 (2005).
NCBI, dbSNP Short Genetic Variations, dbSNP Summary Release Build 137, 2 pages (2013).
Ogata et al., Genetic analysis of polymorphisms in biologically relevant candidate genes in patients with abdominal aortic aneurysms, J. Vasc. Surg., 41:1036-42 (2005).
Pearce et al., Abdominal aortic aneurysm as a complex multifactorial disease: interactions of polymorphisms of inflammatory genes, features of autoimmunity, and current status of MMPs, Ann. N Y Acad. Sci., 1085:117-32 (2006).
Powell et al., Risk factors associated with the development of peripheral arterial disease in smokers: a case-control study, Artherosclerosis, 129:41-8 (1997).
Retterstol et al., C-reactive protein predicts death in patients with previous premature myocardial infarction-a 10 year follow-up study, Atherosclerosis, 160:433-40 (2002).
Ridker et al., C-reactive protein levels and outcomes after statin therapy, N. Engl. J. Med., 352:20-8 (2005).
Ridker et al., Comparison of C-reactive protein and low-density lipoprotein cholesterol levels in the prediction of first cardiovascular events, N. Engl. J. Med., 347:1557-65 (2002).
Rutherford et al., Recommended standards for reports dealing with lower extremity ischemia: revised version, J. Vasc. Surg., 26:517-38 (1997).
Saccone, et al., Multiple Independent Loci at Chromosome 15q25.1 Affect Smoking Quantity: a Meta-Analysis and Comparison with Lung Cancer and COPD, PLoS Genetics, 6(8):1-16 (2010).
Saxena, et al., Genome-Wide Association Analysis Identifies Loci for Type 2 Diabetes and Triglyceride Levels, Science, 316:1331-1336 (2007).
Silberberg, Fourth Edition Chemistry, The Molecular Nature of Matter and Change, p. G12 (2006).
Spencer, et al., Designing Genome-Wide Association Studies: Sample Size, Power, Imputation, and the Choice of Genotyping Chip, PLoS Genetics, 5(5):1-13 (2009).
St. Jean et al., Characterization of a dinucleotide repeat in the 92 kDa type IV collagenase gene (CLG4B), localization of CLG4B to chromosome 20 and the role of CLG4B in aortic aneurysmal disease, Ann. Hum. Genet., 59:17-24 (1995).
Stacey, et al., Common variants on chromosomes 2q35 and 16q12 confer susceptibility to estrogen receptor-positive breast cancer, Nature Genetics 39(7):865-869 (2007).
Stein, Laboratory surrogates for anti-atherosclerotic drug development, Am. J. Cardiol., 87:21A-26A (2001).
Suggested standards for reports dealing with lower extremity ischemia. Prepared by the Ad Hoc Committee on Reporting Standards, Society for Vascular Surgery/North American Chapter, International Society for Cardiovascular Surgery, J. Vasc. Surg., 4:80-94 (1986).
The International HapMap Consortum, Nature, 2005, 437:1299-1320.
Vanderweele, et al., Genetic Variants on 15q25.1, Smoking, and Lung Cancer: An Assessment of Mediation and Interaction, Am. J. Epidemiol. 175(10):1013-1020 (2012).
Wacholder et al., Assessing the probability that a positive report is false: An approach for molecular epidemiology studies, J. Natl. Cancer Inst., 96(6):434-42 (2004).
Wang et al., Antisense anticancer oligonucleotide therapeutics, Curr. Cancer Drug Targets, 1:177-96 (2001).
Wassenaar, et al., Relationship Between CYP2A6 and CHRNA5-CHRNA3-CHRNB4 Variation and Smoking Behaviors and Lung Cancer Risk, JNCI 103(17):1342-1346 (2011).
Wilmink et al., The association between cigarette smoking and abdominal aortic aneurysms, J. Vasc. Surg., 30:1099-108 (1999).
Witte, Multiple prostate cancer risk variants on 8q24, Nature Genetics 39(5):579-580 (2007).
Zhang, et al., Association of Single Nucleotide Polymorphisms in TCF2 with Type 2 Diabetes Susceptibility in a Han Chinese Population, PLOS ONE, 7(12):1-6 (2012).
Zick, et al., Genetic Testing for Alzheimer's Disease and Its Impact on Insurance Purchasing Behavior, Health Affairs, 24(2):483-490 (2005).
Zimmerli et al., Urinary proteomic biomarkers in coronary artery disease, Mol. Cell Proteomics, 7:290-8 (2008).

* cited by examiner

SEQUENCE LISTING

```
<160> NUMBER OF SEQ ID NOS: 5

<210> SEQ ID NO 1
<211> LENGTH: 392213
<212> TYPE: DNA
<213> ORGANISM: Homo sapiens
```

<400> SEQUENCE: 1
aaagaagaga ttgtgcttgg tgttaaagga acagcaaaga gcaaggaatg agactaatgc 60
agagtgagca aaggatgtag gagatgaggc caaagaggag gagtcagatc aggaccctgg 120
aggccatcgt gaggactttg aattttacac tgactaagat gggagccagt gtggagttct 180
gagcaaagaa tgacatgagc tggcttccac tttaacagca tcctctggct gttgtgctga 240
gactagttag gaggctgctg tcatcatcca gagcagagat gatagtggcc tgaaccagga 300
tggattgtgt gtgtgtgtgt gtgtgtgtgt gtgtgtgtgt atatatgtgt gtgtgtgtgt 360
gtgtgtgtgt gctttttaga gatagggtct tgctctgtca cccaggctga agtgcagtgg 420
tacagtcata acacattaca gccttcaact cccgggctca agtgatcctc ccacctcagc 480
ctcccaaata gcaaggaaag gactacaggt atgtacaacc acacctggct aatttcttta 540
tttttgtag agacgggatc tcactctgtt gaccaggctg atctccaact cccggcctca 600
agcgatcctc ctgcctcagc ctcctaagtg ctggaattac aagtgtgagc taccatgccc 660
agtccaggat aatatttctt tatcagtggg ggaggagtgg aagtttgtag gagacaggcc 720
cagggcacct gaaaaagtca gattttagtc ttacaggctt tagatgaatg gcctccaaag 780
cagatgctca ccctcaagcc tgacccttct ggtccagtct cagctctgaa ggccactcta 840
aaagaagagt gattgcaatg ttttgagtag ggacagcttc atttggaata gacatctagt 900
ctagtagaat aactgctttg aggctgggta tggtggcttg cccctgaaat cccagcactc 960
tgtgaggctg aggtgggagg tttgcttgag cccaggattt gagacaagcc tgggcaacaa 1020
aattagccag gcatggtggc gtacacctgg cgtgtagtcc ttgctacttg ggaggctgac 1080
gtgggaggat cgcttgagca tgggaagtcg agactgcact aagctatcgc accactgcac 1140
tccagcctgg gcgacagagc aagacccttt ggctttgatt gaaagggcca tttgggtgtt 1200
ttaaatgtta aaaaaaaaat ccgtttttat tgccatgcta caggatacag tgtgaacttc 1260
aatcccttat tgttccctca gtgttttatt aactacggat gtcaaggtca gacgctgctt 1320
attgtctctc tttacatcac tggaagggac aatgcctact gctgcccct ggaggccact 1380
aggcctaaca gcagctcaag ctgtaacttc tgaacttcac ctattttctg ggcacaaacc 1440
atttggttca gcctgcagaa gagcgtggaa gacatatggg actggggccc acaatctggt 1500
ttcccattct tgctctgcca ttatttcact ggataactca ctgtgggaat ttaagcaagt 1560
cccatgctca tatataaagc tattaaacta gatggtttct tatcttccct tcttgtgctg 1620
acatttaatt ttattatttt attcacattt attacaggtg tgaaccacca cgcttggcca 1680
tgtgacattt taaagtgttt atgaaatctg taaattaagt gggacatggc ttccacatca 1740
tcccaaattc cctttatatt cctgtaccct tttttctctc tctccccaaa catccctccc 1800
agcacctaga cactgtcctc tggccatctg ggaaaccaca gtgcaaggcc cctcctgggc 1860
ccatcttccc cttagcaggg gccctaaacg ttagacattt tttcttcttt tgctcttatc 1920
aaaaacgact tttcctagtt ccaccaacta atgagtgagt gctaatgagg gattatattt 1980
ttccacgtct cagttttctt ctctgtacaa cagggctaat aatatttatc ttcaaggtta 2040
ttatgaggat tacaaatagt ttatgcaaac agcctaaact gttgaataca ctgtctgagg 2100
tattcaataa atggcagact gcttttattt tattctatta tttatttatt taagacaggg 2160
tctcattctg tcacccaggc tggaatgcag tggtatgatc atggctcact gcagcccaga 2220
cctccctggg cacaggtgat tcccccatct cagcctccca actagctagg accataggtg 2280
tgcaccacca caccaggcta atatttctat tttttgtaga gtttcagcat ggggtttccc 2340

-continued

```
catgttgacc aggctggtct cgaattcctg tgctcaagcg atctgccctc cttggcttcc   2400
cagagtgttg gaattacagg aatgagccac tgcgcctgcc ttggacactg tttttaaatg   2460
gacacagctc aaaaaaaaat cattttctct taatgtttct tagaaacctt ttttaattcc   2520
ctccaagtgg ggttaaatgt tcttcatctg tgcttaaaag tctatgggaa tgattcactg   2580
agtgctagat acatgtccat acccgaatag accactatgg taggcagaat aattcccccca   2640
cctctccaaa gatgtccatg ccctagtccc tggaacctgt gaataggtga tgttacatgg   2700
caaaggggga aatgaaggct taggatggaa ttatgtttgc taatcagctg actttgagat   2760
tgggagatta tccttcagta tccaatgtcc ccaatgtaat aacgagattc attatcaatg   2820
aaagaaggag gtagagagtc agagatagat gtgaagaccg aggcagaggt ctgagtgaca   2880
ccattgctgg ctttgaagat ggaagagagc cagggccaag ggatgtctga agcctccaga   2940
agccagaaaa ggcgagaaaa tgaattctcc tctagagcct ctggaaagga gtgcagctct   3000
attgacacct tgattttagc ccaataagac ccatttcaga cttctccaga accgtaagat   3060
aattaaattg tgctgtttta agccactaag tttgtggtaa tttgttacag ccaccattgg   3120
aaataaatac aaaccctcac atacatttaa ttggcacaac aatccaagta gtcagtagta   3180
ttgtccccac tttacagctg gggaaactgc agctcagaga tgttaagtaa cttgcccaaa   3240
actgcacagc tagtaaatag ctacatcagt taaattcctt tggtgcaagt tttggaaaac   3300
aaacaaaaac acaaattggg ctgggctcgg tggctcacgc ctctaatttt agcactttgg   3360
gaggctgagg cagaaggatt gcttgaggcc aggagtctga gaccagcctg gataacatag   3420
aaagaccctg tctttacaaa aaataaaaat tagtggggtt tggtagcaca tgcctgtggt   3480
cccagctact cgggaggcac aggtgggagg atcgcttgag cctgggaagt taaaactgca   3540
gtgagccgag atagtgccac tgcattccag ccttggcaac aaagcaagac caaacactag   3600
aacttgtacc ttctctctaa ctatattttt gtacccctta accaacctcc cttcattcac   3660
ccctcaaccc cctaactctc ccccagcctc tggtaactgt cattcttctc tctcactcca   3720
taagatctgc ttttttggct cccacgtgtg catgagaaca tgtgatattt gtatctctgt   3780
gcatggctct gtgaaagaaa aataaaaact cgggaccccc aatataatga cctccagttt   3840
tatccatgtt gctacaaatg ataggattgt attcttttat ggctgaataa tactctattg   3900
tgtatatata ctacattatc tttatccatt catctgttga tggacactta gattgatgcc   3960
ataatttggc tattgtgaac agtgctgcaa taaacataag agtgcagaat ctcattgatt   4020
gatatactga tttcctttct cttggatata tacccagcag tgggattgct gggtcatatg   4080
ttagttctat ttttagtttt gaggaacctc tatattgttc tctattgtgg ttatactaac   4140
ttacattccc accaacggtg tacaagaggc ccccttttctc cacatcctca ccagttattt   4200
tttatctttt tgatgagtca ttttcacttg aatgagatga tatctcatta tggttttgat   4260
ttgcatttcc cagatgatta gtgatattga tcatttttca tatacttgtt cttttgagaa   4320
atgtttatca aaccatttgc ccattttttta attgaattat ttactttttt gttattgagt   4380
tgagcctctt atatatctgg ttattaattc cttgttagtt ggatagtttg caaatatttt   4440
ctcccattct gtaggttgtc ccttcactct gttgatcatt tcctttgctg cacggaagcc   4500
ttgatataat ctcacttgtc tatttttgct ttggtttcct gtgcttttga ggtcttatcc   4560
aaaaaatcgt tccccagact aatgttctga agcatttctc caatgttttc ttctagtagt   4620
ttcatagttc aggtcttaca tttaggtctt tattcaattt tgatttaatt ttcatataag   4680
```

-continued atgagagacg agggtctagt tttgttcttc tgcatataga tatccagttt tcacagcatc 4740
gtttattgaa tatattcccc aatgtatgtt cttttcccaa tgtatgttct tggcaccttt 4800
atgaaaaatc agctggctat aaatgtgtag cctttgtcaa agatgacttg gctataaacc 4860
tgtgggttta catctatctg gcttctctat ttcgttgtat tggtctatgc atctatttta 4920
atgccagtac catgctgttt gggttactat agctttgtag taatattttg ctttgtttgt 4980
ttgtttgttt gtttgtttgt ttgtttttaa gacagagtct cgctctgtcg cccaggctgg 5040
agtgcagtgg tgctatctca gctcacttgc aagctccacc tccaggattc aagtggttct 5100
cccacctcag cctcccgagt agctgggatt acaggcacgc accaccacgc ctggctagtt 5160
tttgtatttt tagtagaaac agggtttcac catgttggcc aggttggtct caaactcctg 5220
acctcaggtg gtccacccac ctcggccttc caaagtgccg ggattacagg cgtgagccac 5280
cgtgcccagc ctgtaataat atcttgaagt ctggtagtgt gatgcctcca gctttgctca 5340
ggataacttt ggctatttgg gatcttttgt gattccatat gaattttaag atttttttc 5400 tatttctgtg aagaatgtca ttgatatttt gatatggaga gatatttaaa caaaactaca 5460
tttgtttttt atttattttt ttacttaaaa aaaatttttt atatttcttt atactttttt 5520
aaaacaaata aacatggggt ctcatgatgt tgcccaagct gctctcaaac tcctggctca 5580
agcctcggct cagcctaatt tgttttgtct tttgacacta taaaataaaa tgagtgttcc 5640
aatgagctga gcagaggagg ttggctttat gggcagaaaa gggctgaaga aaggtagaaa 5700
cggagaacga aaagcagact ggttgtttca aagttacctt ccttgtaagg tagaagcaga 5760
agggacttcc ttatcacacc agctaaagct ggcctgtttg gggatttgac tacttctctt 5820
tcttgatttc ttctaaggtc aggtaaacaa tttaatttag gcttggtggc atggaacttc 5880
agtgtgagtg actccattat ggtttggtct gttgggccta gtgcaggagc tcaattgaaa 5940
ccaatgacct cctatacatt ttaacaccat aaaggaagtt cattggctca cataactgaa 6000
gagaattcca aaggaagttc ttgtagagaa caggtaaggc ttgattcaga atccgaaaga 6060
atgacacccg ggatccagaa tttctctctc ttatctgtgc cttccaccga gaatggcttt 6120
attctcaggt accacacagt ggaggccaca cctccaaact cacccctgtg gtgataaaat 6180
ggctgccgca gttccagatg tcagaacctc actctcacaa cttgttgagg aaaaaagaaa 6240
gcctcccttt ctcagaagcc ccaacaagtc ttgttgtgag ttgttgcttc taattaggtt 6300
acatccccaa tttctgatct gaatactgga tccatggtgg acctatggat gggaattggg 6360
gaagagctga attgcccagg ggaagttcag agtcatctga acaggagaca caggaaatga 6420
ctatcaaatg tccacaaaga tcttgaccac caagtatctg agttcaatta ctactgcctc 6480
tcagtaacat cttttctgac tcctcagaca cattactact gtctgtttct cactgtccca 6540
attcttcaaa ctaagggaca acccttatat cctggagcta gccttatatc ctgtgccccc 6600
agcccttacc acagggcctg gctaagatca gctatcagat acatgtgtgt tgttcaatgg 6660
gactgctctt tactggcagg tgagacattc acaaagctgc tcaagttcca cctttctcta 6720
attctgtaag ggagctgctc tgttacccat gcagctggct aacgtttctg agaaaataca 6780
agaacttcat ttggtacaag gtgtggcttg tattatattg aagccagttt gagttgaatg 6840
tttcttttag ttatagctga aaacaacccg ataccatgcc ttctaggggt gttttgagga 6900
attttttttt ttttttggga ccgggtctca ctctgtcacc caggctggag tacagtggtg 6960
cggagatctc agctcactgc aacctctgcc tcccacattc aagatattgt cccacctcag 7020
cctctccagt agctgggact acaggtgtgt gccaccatac ctagttaatt tttgtatttt 7080

-continued

```
tttgtagaga gggtttcacc atgttgacca ggctggtctt gaactcctga cctcagatga   7140
tctccctgcc ttggcctccc aaagtgctgg gattacaggt gagccactgt gctcatgaga   7200
taatgtatgt aaagtattta acaagttcaa gttttttttt ttttcctttt ttgagatgga   7260
gtccacgctg tcacccaggt tggagtgcag tggtgcaatc ttggctcact acaacctcca   7320
cttcctgggc tcaagcaatc ctcccaactc agcctcctga gtagctggga ccacaggcat   7380
gcaccaccag acccagctaa tttttttgta tatttggtag agacagggtt tcaccatgtt   7440
gcctgggctg atctccaact cctgggctca ggagatccgc cggcctcgac ctcccaaagg   7500
tgtgaaccac tgccctctgc cttaacaagg tttaataggt gttaactatt attactttta   7560
ttatcacttg tactaatgtt atctatttgt aagcttctca agggccggtc tcatcctcct   7620
cactgttctg atattagtac ataatactca aatggtggtt gaaccaaacc aaagtgtcca   7680
ggccaccact ttacaagagt caggtttcca tcgatgggat tttaaaatat aagtcatatt   7740
ttcaaaatca gtaggatagc ttgctattta cagaattcct gtagaaaatt atttttgaaa   7800
gattaatcat ttcataattc aaatcactta tgtctcattt gtctgttgca caggtttgga   7860
acttcttaca tgcagaatca ggtttctttc attcatttat tcattcactt atcaattcat   7920
ttatacaaca agactttctg gagcaatggc catatgccag ggcctgtgct aggagacagg   7980
gagagagagt aaacacttgg tgcttgtgtt cagggagttc agtttagtga atgaacagac   8040
aaacaaagaa ttacggcatg gtgagctaag tgctgtgaga gggaggcatg ggtggctttg   8100
agggcaataa agagggaacc cagggtagcg gtggagggga gtgcatagga gcagaaaaag   8160
cttcaaaaag aggagcttct gcttctgatt gacaactaga agttggctga tgaatgtgca   8220
aaggcttgaa ggagcatgag gcttattttc agggaaatcc aggtggtatt agttctgttt   8280
gtgttccatg ttagttaaga atgggacaag aggtaagact ggagagtagg cgaggatcag   8340
gccgcaaaag gtctcaaagg ctgggctgga aagttatgat ttcatcttga aggtggtcag   8400
ggagattttg aagattttca gcaaacatga tcaaatttgc ctttcagaaa gaatatcctg   8460
atgggactgg gtgcggtggc tcatgcctgt aatcccagca ctttgggagg ctggggtggg   8520
ggaatccctt gaggccagga gttggagacc agcctagcca acatggcaaa actccgtctc   8580
tactaaaaat acgaaaacat tagccaggcg tggtggcatg tgtctgtagt cccggctact   8640
taggaggctg aggcaggaga atcgcttgaa cccagaaggc ggagtttgca gtgaggtgag   8700
attgtgccac tgcactccag cctgggcaac agagtgagac tccatctcaa aaaaacaaaa   8760
acaaaaacaa aaaaaggaag aatatcctgg tgggattgta aagcgtgatt agagcaatga   8820
tgagagggtt ggggaggcaa gcctgaaaca gggacaccac ttaggaaatg actcttaggc   8880
tgacccatat aaaatcacct ttttaaaaat gatcaaatgc cctcaatctc cctcccaaag   8940
caatggtcca gatgagagtg atcggaaccc aaaccaagcc accagtaaaa gagataaacc   9000
aagagacatc aggagctcta atttgatagg acatcatagt gttctttgat gagagaggca   9060
aaggaaagga cttacatctg aaagtggaaa cataaaatca cagtctataa aaatcattct   9120
tgtacctaaa aagtttactt caaccagtga attctgcagc tgaagcctga tagattcatt   9180
caggtcggca tagccacaca gcagaattgg ggcaaggctg ggattgaaac ccaggactcc   9240
tgactgctct gctgcactgt cttcattgta ccttgggtct tccaaaaagg tatttgtatt   9300
cacttcctag gcctgccgtc acaaactact caaactggga gacttaaaca acagaaattt   9360
attgcctaac agttctggag gctggaagtc agaaatgaag gtggtggcag ggttgaatcc   9420
```

ttctaggagt tgtgggaaaa atttgcttca ggcctctctt cctggcttgt agacctgtca 9480
gccctatctc catcttcatg atcccacagc gtttctctct gcgtgctgac tttcttcaca 9540
tgggctttcc cctgtgtgtc tatgtgcctg ttttctcttc ttaggagaac accagtcatt 9600
ggattaggac caaccttact ccagtatgat ttcgtcttaa ctaattacat cggcaatgac 9660
tttatttcca aataaggtca catacacagg tattaggaat taagacttca acatatgaat 9720
tttgtggggg cacaattcaa accataacaa cagtacattt gaaatttatg tttccatgtc 9780
attttactga tggcagttct gcattttccc ttagaaaacg gaattagggt ccaaggaata 9840
agggtctttt ccatttccat atcttgacac agttccaagg acagtgttct gctctataag 9900
cctgcatcaa cattcttaat cacctgctgg caacagacag ggatttcggt gagcttctaa 9960
aaacttttaa tatgtgggct gggtgcggtg gctcacacct gtaatcccag cacattggga 10020
gtctgaggcg ggaggatcac ttgtggtcag gagttcaaga ccaacccagc aaatatggtg 10080
aaaccctgtc tctacaacaa taaaacaatt agccaggcat ggtggcacac acctgcaaat 10140
ccagctactt gggaggctga ggcaggagaa ttgcttgaac ccgggaggtg gatggtggaa 10200
gtgagctgag ttcacaccac tgtactccag cctgggcaac agagcaagac tccatctcaa 10260
aaacaaacaa acaaacaaaa caacaacaac aacaaaacct tttaatgtgt ggtctactct 10320
cattggtgaa gagaaaaaac tcttatctgc attcctcttg acttgatagg cagaacatac 10380
agttacctgc tttggatgag caatggttcc ctttaatttc atatgccaag ggctggcagc 10440
caactgctct cctcttaccc acgatcaggc tcagcagtgg ctacaaaggt cagccacaga 10500
atggcaggag atcttgttta tcatgctttt gattcttgaa gataagacat ttattttgga 10560
actatcaata accaaacaga ctttctctgt gtagaactaa aacatagatt gaaagaacag 10620
agcatcactg aggacttagc tactaagaga tcatactgag atttagaaag gccatgggag 10680
cctccaactc accccctgta ataactgaga ccatgtctaa ccacagaggt gtgggtgggt 10740
gaaaatatgg gctctagagt gtcatggagg ccagccacag tggctcatgc ctgtaatccc 10800
agcattttgg gaggctgagg tgggaggatc acttgagccc aggagttcaa gaccagtctt 10860
gacagcatag ggagaccccg tctctacaaa aaatttaaaa gttagtcagg tgtggtggca 10920
catgcctcta gtcccagcta cttgcagggc tgagatgggg ggatcgcttg agcccaggta 10980
gtcaaggctg cagtcagctg tgattgtgtc actgcactct agcctcagta acagcaagac 11040
cctgtctcaa aagaagaaaa aaaaatagag tctcatggac ctgggcttaa aactctgctc 11100
tgattttaag ttaagtgatg gctccattcc caaaaaaaaa aaaaaaaaaa aaaaaaagag 11160
gaactaagta aaggcaggtg cctcctgata tgatgcacca aaaagaacac aacatgactt 11220
atgtagcata cctaccaaaa atgcataatt aaatgtaatc atgaagaaac agtcaggcta 11280
gcctaaatta aaggacattc cacaatacaa tgggccaata ctctttaaaa atgtcaatac 11340
cataagagaa aatgaaacgc taaggaactg ttccaaatta gagaaaacta aacagatacg 11400
acatctaaat ccaatgcttt atcctggata gcattttgga ttggagaaga gtttctagaa 11460
agaacaatat tgggacaatt gacaaaattt aaatatggat tgtaaactgt gtcaatgttt 11520
gaatatggat tattaataac atttgatgat tcaagttcat aaaatttgga tatgaattgt 11580
attgatacaa ttgattgtgt tgtatcaatt acatttcctg aatttgatca tttttagtag 11640
atacatgata aagtactcag gactgaaggg tcataatctc taaaatttac tctgaaatgg 11700
taccaaaaaa atgagaataa gaaatagcca ggtgcagtgg cacacatctg tagccccagc 11760
tacttgggag gctgaggtag gaggattgat tgaatccagg agttggaggc tacagtgcac 11820

-continued

```
tatgatcttg ctgtgaatac ctactgcact ccagaccagg caacacagtg agactgtgtc  11880
tcaaaaaaag aaaaagaata agaaataatg aggatcttat ctctgaaata gcagagaggg  11940
agagagagac aaggcaaatg tggcaaaatg ttaacagtaa ataaataaac ctaattaagg  12000
tatatatgaa gttttattat aattatcttg caattcttct gtattcttga attttgtttt  12060
tcgaaataaa atgtttaatt taaaaagtag agatgggcca ggtgcagtgg ctcatacctg  12120
taatcccagc actttgggag gccaaggtgg gcagacagct tgagtacaga agtcgagacc  12180
agcctaagga acataggaaa accctgtctc tacaaaaaat accaaaatta gctgggcatg  12240
gtggcgtgcg cctgtggtcc caggaactca ggggctgagg tgggagaatt acttgagccc  12300
aggagatgga ggttgcagtg agtcgagatc accccactgc actccaacct gggcaacaca  12360
gtgagactct ctctcaaaaa aaaaaaagga gaggtgaacc agcctggaca ttgcccgaga  12420
cactgatcta aaagggtgct aaaatctcac tggaaatgta acttgaaaaa aaatgtatag  12480
tgaaaacata ccataagctt ccatttgcat agcattcaaa atagggtgta ggggatgagg  12540
aaatggcagc ctaggaggaa aacagctgcg gttataaaac ggcaacagga aggatccttg  12600
gaaatgttcc atatcttgac tgtagtgatg gccacacaaa gccacacacg tgaactaaat  12660
acacacgtgc atgtgcgcgc acacacacac acacacacac acaccctaca aaggagtaca  12720
tgtagaactg cctaaatctg agtaaggtgg aatgattgta tgaatgtcaa tttgctcgtt  12780
tttatattgt actatgctac atggagaaag actaggtgaa gagtatacgg gatctttatt  12840
acttagtaca actacatgta aatctacaat tgtcacaaaa taagaatgtt taacaatagg  12900
taaattttat gatatttaaa ctaaatctca ataaaactgt taaagctgac tgagatggca  12960
tatgcctgta gtcccagcta cttgggaggc tgaggtggga gaatcccttg aactcaggag  13020
tttgagatcg gtccaggcca aataaacaga cctctgtctt aaaataaata aaattttcaa  13080
aaagtaaata aaactgttaa aaaaaaaaaa aaagtaatga gtccagccac acgggagcat  13140
atcatgattg ttctaagtta gtgcttctca gtggaagcgg gacactgaga aaatgggtgt  13200
ttttgtttgt caccatcatg gggcactttt gggattcaat gaatgttaga ttgcctgcat  13260
tccacactat agaattacac aacaaagaat caaacaaggg ccaggcccgg tggctcacgc  13320
ctgtaatccc agcactttgg gaagctgaga tgggcggatc acgaggtcag gagttcaaga  13380
ccagcctggc caacatggta aaaccctgtc tctactaaaa atataaaact tagctgggca  13440
tgatggcacg tgcctgtatt cccagctact caggaggctg aggcaggaga attgcttgaa  13500
ccgggacccg aggggcggag gttgcagtga gccaagatca tgtcactgca ctccagcctg  13560
ggctacagag caagactccg tctcaaaaaa aaaaagaatc aaacaagacc catactgtca  13620
gatattcaag tacattaaac atacacacaa acataaaaac agtaacaaca aatttgttta  13680
taattatctg agcctagagt ttaaccccat atacaagtaa aaacaaaagt aatttgtgta  13740
tggttttaat atatacggaa ttttctagga atacaactat tgcataaaaa aagcaaaggt  13800
ttttttttt tgttttgaac tttatcaaga gttattcacc atttcagaaa atcacaatag  13860
tgacaacact tccaatattt aagtcactaa catattttca ttagtcttta gaggccattc  13920
atgatatata tgtacatttt atacatatgt gcatttacca tatatgcatt cataatatat  13980
atttatgcat gatatgtatg tatatattga atccttattt tgcaatgtca gacataaaaa  14040
gtgttgacca tattcagctg aatattatct ttttttttt gagacgaagt cttgcattgt  14100
tgcccaggct ggagttcagt ggtgaaatct cggctcactg caagctccgc ctcctgggtt  14160
```

-continued cacgccattc tcctgcctca gcctcccgag tagctggggc tacaggcgcc tgccaccacg 14220
cccgggtaat tttttgtact tttagtagag acggggtttc accgtgttag ccaggatgat 14280
ctcccatctc ctgacctcgt gatccgcccg cctcagcctc ccgaagtgct gggattacag 14340
gcgtgagcca ccgccccggc cttatctttt tttgagacag ggtttcattc tgtctcccag 14400
gttggagtgc agtggcacaa tcatagctca ctgtaatctt gaatttctgg gctcaagtga 14460
tcctcctgcc tctgtctcac ggtagctggt actacaggca tgcaccacta tgtctggcta 14520
actctttaag tttttgtaga gacagggtct caccatgttg cccaggctag tctcaaactc 14580
ctagcatcaa gcgatcctgc agctttggct tcccaaagtg ctgggattac aagcttgagc 14640
taccaactgt gcctggccca gtcgaatatt atatgtcctg taaaaccaaa ctcattcgtt 14700
ataaatagat acaagcatct gactactcaa ttttgtcatc taatatagac atgcctgtgc 14760
agctacgtat tataatacat attattttct aataaattac tttcctattt ttctccttta 14820
tattacagtt aggtcattaa gtagattatt tatcgtgtat gtagattata ttacctatga 14880
atttcatgct gggattgtaa aggagatgtt acaaaatata gcaaggtgaa taaaggaaat 14940
atattggagt ttgggttgac agggcttgga tcaatgatta aagggagtgg atgaaggagt 15000
caggtataat gtgttgattt ctggcttggg caaccaggtg gatggtggcg ccattcgcta 15060
atacaggcaa tacaaaagga atagtaggtt taaggaggga aatgacgagt tcagttttgg 15120
agatttttag tttgaggtgc cttgggatgt ggaggcatcc catgggtact aggatataca 15180
cctccgggtt taggagatag gctcaggtca caggcagact gggaagcatc aacatattaa 15240
ctaataactg aagtcaaagg aagtgtgaga tgggccaggg aaaatggaca gagggaggag 15300
gtacaaggcc agagccctgg gacacattta atgtccaata tattttttt tgagacaggg 15360 tcttgctgtg ttgctcaggc tggagtgcag tggtgcaatc atggctcacc acagcctcaa 15420
tctcctgggc ccaagtgatc ctcccacctc agcctcctga gtagctgaga ctacaggtgc 15480
atgccaccac actcagctaa tttttaaatt ttttttgtag agatagggtc tcactacgtt 15540
gctgtgtttg gtcttgaact tttcagctca agccatcctc ccactttggc ctcctaaagt 15600
gctggaatta caggcatgag ctactgtgcc catcaagtgc ccagtacatt taaaagctgg 15660
gcggaggaag aggtctgcag aggagcctga gatcaagcac ccttaggaga agaaacaaaa 15720
gtagagtctg aagtcacaga agctgatgga agagtatttt tcaacaatgg gagagaacca 15780
gtcaagattg agatatgtga gattagaaag tggagttata gctggccttg gctaaaggca 15840
tttctgggag tggaagccag actggaagag gataagaagt gggtggggga gagccgagta 15900
tgagcgactc tttctggtaa gttgctgcga caggagataa tgctgggtag gtggagaaca 15960
cagggaccgg aggagctgag gcggaaggat ggagaggctt aagcatgtgt taactgccac 16020
tgggaagaag tcggcaatca cggaagctac cggagggtaa gaaaaaattc attcattcaa 16080
cagttgagcg cctcccacgc gcccgatcag tatggccgcc cccacttgaa aacacgcgtg 16140
tgggccgccc acgtctgaca agttaatgca aggctttata gttaggggaa agcggttctc 16200
cttgagctct ttctcctagc agttccgatt ccgaccctga ctccaacaga caccttgcgg 16260
gaacgcaaac accgctcgaa ttcatgaccc caatagaaaa cttaaggccg caactaagta 16320
acggatcgct gcgaaggcca aactagccac gccaacgccc ccactggagc ctccccagcg 16380
ctccgccccc gctcgcgaga acagcggcga cggcgcgaga aatcgctttc tggttagctc 16440
cgccccttcc ctttctttgt tttcctgtcc gacgatctcg cgggagttag gcgacaaatc 16500
ccgcgagcgc agacccgggg ctggctctgc tgctctcgcg atatttgcgc gagcctgctt 16560

-continued

```
ccttctttcc tcccttgcca gtccgcctgt cttcctcccc gtcttccctg cccggcctcc  16620
cccttcttcc cccgctggcc ccctccccgg agggataata tggtctccgg cgatggacgc  16680
cccaaaagca ggtcagtttc gggcctccga gctgggtctg gcagttggaa acgcgcgctg  16740
cctaggcgcc gaattccttg cttttctcgc ctggagtcgc tcggcaggcg cccaggccct  16800
cggggctcgg gttgtgctcc cctcggggcc tgcctgctgg gccgcccttt gagcctaggc  16860
cgcggaagct ggggctcccg atccccaccc tcctgcgcga cacccgcagg gcgggccacc  16920
ccaccgctgg ccttgacccg cacccctctc tctccggtgg ccgctgcctg ctgccagcgg  16980
cttcctggcc cccgtcagca acaccagggg cagggagagg cccaccgtct tctcctgccc  17040
gcccccccatt ggcgagcgat gaaggcgggg gcctgcgtct ccgtgttcgg gtctcacgca  17100
gctagatgtt gattccacgg tccagcctaa ggcccctcag tctctctgtg cctctggaag  17160
ccgaatgagg ggcagtcaag gttgaacatt ggtcagtcag ttctccgacc atttattgca  17220
ccgctgtctc ctcccccgtc cacctccctc tacaaaaaaa aaaaaagaga aaaaaatact  17280
attcattctg aaaatgggct gtgcttatgt tttctccttt tggatgaaag ccttaacaat  17340
gttgagggtc ctggccaccc accgctatga gtctgcacaa aagatctgaa ggttcttttc  17400
aacctcaggg ctgcctcccc gccactgccc cctagaatgt tgggagctga ggcacgttta  17460
aatgagacct ctggatcttt gacttagtag ttcagcttca gttcgtgcaa aaccagaaga  17520
cttgtctctt tcgggtagaa tatgctaatt tcctagagat tctgttactt ttattttcag  17580
tactaagccc tggtaaggac ttaactgaga agttttttttg ttttggttta ttgaatgctc  17640
tgtaaaaatc cgtcttttag tttttttttt taatcagtcc ctctaatgtt aattgtggaa  17700
ttcacaaatt cctgtctctg cagttttcaa gacatgtctt tccaaaacgt ccccgtggat  17760
tatttaaatc attcttattg tccctttcca ggtattctta tcacatttca ggagtgaatt  17820
atcttactag tttttacttg acaaattatg gtttagaact atgctttcca gtgtggtgga  17880
tactagccct gtgtgacttt aaattaatca aaattaaata aattaaaaat tcagttcctc  17940
aggcacgata gccacatttc aggtgctcaa tagccacacg ttgctaatgg ctactttact  18000
ggacagctca aacatagaat atttttacca ttgcagaaaa ttctattgga taaagctagt  18060
ttccaggtat tttcagctga ataaaatatt ttgttgctgc atttaatgaa aatacaattt  18120
tttttcagg atacgccttt gagtacctta ttgaaacatt aaatgacagt tcacataaga  18180
agttcttcga tgtatctaaa cttggcacca agtatggtaa tgttgcttta cattttcttg  18240
ggtttgttta gtctctaata atgaaaatgc atttgtcaag ctgagctgaa gaaattttaa  18300
atgtatttcc accgtattgt aacaggtaca cctacacata cctataccat tttaaaaact  18360
cctcctggga caacttctgt tcagggaaga tgtaggccca caccttaact tctcatttaa  18420
aaatctaagt taattaagca ctagtttttc ccctcaaaga aaccaataat gcagttttca  18480
aacttttttt tttcttgttt ttgtgaagac aggggtcttg ctatgttacc caggctagtt  18540
ttgaacccct gggcccaaat aatcctccca cctctgcctc cccaagtttt gggattacac  18600
atgtaagcta ctgcgcctgg cctaatgtga tttttagaag aacctgactg actgatgata  18660
attctacacc aattaaatgt atattttatt ttctcttttc ttttcttttt ttttttgaga  18720
cagagtcttg ctctgttgcc caggctagag cacagtgttg tgatcatagc tcatacagcc  18780
ttgaactcct gggctaaagc agtcctgcct ctgcctccca agtaacaagg cctacaggtg  18840
tatgccaaca catttatata aaaacatatt tttatatttt ttgtagagtt ggggtcttgc  18900
```

-continued tgtgttgccc agactagtct cagactcctg accttaagtg atgcatctgc ctcagcctca 18960
caaagtattg ggattgcagg cctgagccac tatgcctggc ctgttttact ttgtcaaatg 19020
aacagtgccc acatctattc tttttgccat ctgttgaata ggaatcacca acaggaccca 19080
ttgatttgaa tttttctgaa gtattgggca tggtttgccc caacctacac acctgcagtt 19140
ttggcagaca ttctcattga ccttatcagg gtcaaacctt tctctgtggt ctcagaagag 19200
tgaatgtggg cgacctatag ggcattgaat ggaagttttg actttactaa cagttgagta 19260
actttctcaa ttgggccaat agagagacct ctttagaaga ctcattattc tttgtgaact 19320
tttccatgac aatgacatga aaagataaat tgaatgccac atctgttgca gtcagttttg 19380
gaaggagctt taatcttgtt ttttcttgca ttatttaatt aagacgattg ttcttgtgat 19440
ttttctgtag attttgagga atttaaatat tcttgactgc tatgtgcaat attttttgtg 19500
tattgtgaaa tacagctatt ttggagtatc ttaaagaatc cccattttag aattaggctg 19560
tcatttaaaa ataaacagtt tgccaaaatg agagcaatat cctttacctt gcatgtttag 19620
ctgcagtgat ttgtgttgat acgtttgtta aaggaagttg gtcattttct taatgtatgt 19680
ctttcacatt aattttatcc cttcactgat ggtgagtttg cattaatttt gaaaagaaac 19740
agctagattg atcgtttaca agaatagtca ttttatttcc catttacttc tccaaaataa 19800
tctagtgata ctggcttgga agtcttttaa cccaaatttc atagtttaat aaattaaagg 19860
agcacataag atgttttgaa aattgagtat aaatactttc tgtgtataat ctgtagaaat 19920
gtgcttactt gaaggaagat gacctaaatt tctcaaattt aaggaatcag taggaaactg 19980
tcaaaaacaa ctgtaaaatg cattgaaagg gaatgattga taatctgaaa gttaaatttt 20040
ccctgggaaa taagttgtca tgggaatttg tacataactg tacagagtac atgtgtactt 20100
aacataattc cagaattacc agtttttata accatgataa atgtaataat agaatacctg 20160
tgactataaa tactttcaaa acagaaagtt ggtttttatg tggggtcagt accctggttt 20220
ttattttatt ttattttatt ttattttact tatttttttg agacaggatc ttgctctgtc 20280
acccaggctg gagtgcaatg gtgtgatctc agctcactgc tgcctctgcc tcctgagttc 20340
aagcgattct cgtgccttaa cctcccaagt agctggtact ataggcgtgc atcaccacac 20400
ccagctagtt gtagagatgg tggttttacc atgttggtca gggtgatctc aaactcctga 20460
cctcaagtga tccacccacc tcagcctctc aaagtgctgg gattacagga gtgagccact 20520
gcgcccagcc cctcctgctt ttttaataga gtgcttatta tgagaggtta ttaagtaata 20580
attacttaag taatttccta ataaggaata aaatttgaag aattgacttt gaaagaaagg 20640
aacaagttag gtaggaagta tttggttgtt taaccttaga acaaaaaatc cttattgcat 20700
ttttgaaagg atcagattga attgcctcct agacatatgc ttacaagaag acattgcttt 20760
ggtagtcacc aaggtacaga gccagtcttc tccacctcca ttccacattt tgatgcctgc 20820
taggttgaga atgactgttg taatgagtaa cgattaatga agggaatgga ttctatccct 20880
cataaatgtt acagagtaaa gatagttgag aaacactgtt ctaagctcca tgctgactat 20940
gtcagggatg cctgcagctg caaagaactg aaaacttgct gtccaatgac tttaagaaat 21000
acgagtttat ttttctaaca taacgaagtg tggagattgg cagactgggg ctgtgcagca 21060
ccaatctccg caaggatcta ggctcgtcct ttcttcccgt tctgttttta ttcttttggt 21120
tgcacctcca ggcattatgt ccaagttaaa ttttccctgg gaaataagct gtcatgggaa 21180
tttgtacata actgtacaga gtacatgtgt acttaacata attccagaat taccagtttt 21240
tataaccatg ataaaagccc tctccagggg cttttgcctc tttggccaaa gtatcagtgg 21300

```
ccactcttag cttcaagaag gctgaaagat ggaataatca aggtcttctc ttactcatgg  21360
gggatatgtt ccaagaccct cagtagacac cggagactat gggtactacc aaaccgtgta  21420
tgtactgttt ggtatatatt tttttctata catacatagc tatgataaaa cttaatttat  21480
aaatgaggca cagtagagat taataataac taataataaa atagaacagt tataacaatg  21540
tactgtaata aaagttatgt gaatatggtc tttctctttc aaagtatctt attgtgctgt  21600
tctgcaggta actgaaacca cagaaagcca aaccatagat aagatggggt actgtatttt  21660
acctttacat cttttacaat agagaaagga aagggagaag tggttgggag tgggtggtga  21720
gtgaaccagc ctaatctatc tgcgttacca acctgatgcc ttctcttatt ctgactttag  21780
atagagttca acacagatta tttgatttct gctttttttac tgccatttta tccttttgct  21840
tcccaaattt atactcaggg tatctctatg gaagtgggca catcttagac attgattaca  21900
ttttgatctt gtatgatttt gcttgtgggg aatctccttt gtttttttat tttttgtggg  21960
gtttttttttg tttttttgttt tattttgttt tgttttttttg agacagaggc tcgctctgtt  22020
acctaggctg gagtgcagtg gcatgatctt ggttcattgc cacctccatc tccagggttc  22080
aaacgattct cgtgcctcag cctcccaagt agctgggact acaggtgtgt gccaccacat  22140
ccggctgatt ttttattttt agtagagatg gagtttcgcc atattaacaa ggctggtctc  22200
aaactcctga cctcaagcag tcctcctgcc ttggcctccc aaagtgctgg gattataggc  22260
gtgaaccact gcacgcagcc agttgtgggg aatctcttta atattctgga gctggctgtc  22320
tggcactccc aatgtgctga ctagaaacat gtcaaaatct aggtagtctc aaaatgtaga  22380
ttttgagtaa ctctttaaaa aaaaaaatta taaagatgga gttttactgt caacctggct  22440
ggagtgctct gacatgatga tagctcactg gagccttgaa ctcctgagct caggagatcc  22500
tcccacctca ccctctcaag tagctgattt gggtgactct cttaagtaga tctctgaatt  22560
tgaaactatt gctattttta aggagtggag aaatcagtgg tgtctccatg tatgatggag  22620
gacagttaac atcagagaat tagaatgaac agcataatgg aaacatgaat gactatgttg  22680
aatgaagggg aagatggtgg agagactggc ctggctggag tgaaaggtag ttttgagaga  22740
gtacctgtta ctgggcaaca gggcctctgg tggtgtaaag cccccaggca ccctttatct  22800
caggtcatct tattcaccct ttcttttgtc cttcctgtct gcttgccttt ttaaccacag  22860
tactgcttag tcctccagta gagccgggac ttagtgtcca aatcctacct tgcagccttt  22920
ggaagaaaat cctgtattta attttttagg agagttttta tcatttagaa gaatcacaaa  22980
aagacaagaa cattgcagat ggtacagaaa gtctcatttt tatgtgtata caaaaatata  23040
tgtaaatatg ctacttttaa taaaaataaa gtatatgttg ttttgtaacc cttttttttca  23100
cttaatatat catgaacatc tttccatgtc attgaataca ggtatccctt gctatctgaa  23160
tctacttggt ttctgagtca gggagcttga gttcaggtag aaagggatac ctgtacttct  23220
ctgtggcttc taatagctgc acaatattgc ctgtatgaat gcattgtggt ttagttaaca  23280
gacctttgaa tattgaggct gatagtaact tttctctatt tataaataaa ctttgtatgt  23340
gctaatactt acatttttgt gcaaacttat cattatatag aattgttgga ttgaaagtat  23400
gttatttcct ccaccccatc acacgctttt atttttatac tttcactatt tactgttggt  23460
tccagtcttt atttttttttt ttttttttt gagacagagt cttgctgtgt tgcccaggct  23520
ggagtgcagt ggcacagtct cagttcattg cgtcctccaa ctcctgggtt caagtgattc  23580
ttctgcctca gcctctggag tagctgggat tacaggccca tgccttcaca ccctgctgat  23640
```

```
ttttgtattt ttagtagaga cagggtttcg ccatgctggc caggctggtc tcggaactcc  23700
tggcctcagg tgatccacct gccttggcct cccaaagtgt tgagattaca ggcatgaacc  23760
actgcacccg gtctggttcc agtctttacc ttggactaaa aagaacaaaa actcactcaa  23820
gtaaaaaata ggttgcagtt tccagacatc caaagacaaa ggaagaaagc atagtcaagt  23880
ttcagggaac cagaatttct aagccagagg cagtgttctg tttgtcactt aaaggctgcc  23940
tggtttcctt attttctgtt tctttttgaa tatccagtct tccatctcta cagcctactt  24000
cacttactca tttttgtata atgcccaata tggccactgc tgaccattct tgtatgttat  24060
gactggatta ctaaccggtt aagagtgtac ctctaggtga ctcttttact tgttttgttt  24120
tgtttgtttt gtttttttccc tcagggtctt gctctgttgc ccaggctgga gtgtagtggt  24180
tcgatcatgg ctcactgcag cctggacctc ccgggctcaa gtgatcctct ttcctcagtc  24240
tcccaagtag ttgggactac aagcacatgc catcatgcct ggctaaattt taaatgtttt  24300
gtagagacag ggtctcccta cattgcctag gctggtcttg aatcctggct tcaagtgatc  24360
cttctgcctc agcctcccaa agtgctgggg ttacaggtgt gatccattgt atccagctca  24420
cctgttgttt taacctattt tgactgcact tgtcaggagt ctattgccgg tctggtgatc  24480
ttgctggtag agacacaaat ctgttcatct tgtcttttat gtggactctt gaaaagactg  24540
ggttgggtaa gcaatgtaac agtttgcttg taatttgtac acatagtaca taactttcca  24600
aggattacct ttacctaaca tcatcctact agtccatgta tagccatgtg ctcaccaacc  24660
ctccacattt caactttgtt tttattgcca atttctattc tagattaggc ccttttggtt  24720
ccaaggaaca gacactagct cgagtgaaga aggatttatt gtaatgatac agcgctcccc  24780
aggccaatga aatgtggctg tctctcaaga aaatggtggt ggcccagaat taaggaagtt  24840
gtttattatt ttctcttagg agcttcagat ttctgccctg ttccactctt ctgcttcctc  24900
cacttcacta tagacaagcc tcctctgcct gctcactttg tacatggcct caaatggcaa  24960
cctcagtccc tagcttagct cttaacacct ttccagttca gtctctctgt gtcctgatta  25020
cacatttctg agaggtgaat ctaattgccc cagtgtctcc tttctcacaa gacttttggt  25080
catcagccta ccaggggatt ggcttttgcg tcgctgctgt agccaaggag gccacaggcc  25140
accgagaact gtagcagttt ggacaggcac catgaaggac atctgttgta tagtgttagc  25200
aaagaatgcc agtttacatg cttaccagtg aatgagaaga atatgtgttt ctgcaccttc  25260
atcaatagta gatattattt ttcttgttgg ctcaatttct gtcagtgaat gaagagaaga  25320
aaaaaaactt tcttctacat taaattgggg ggtttattgt gaagatttga aggaaataag  25380
gaaattgagg ggatctgagt gcgtggtcag atcagactct ttgttccctt cagtaggcat  25440
gcatagaacc catgattctg gcttagctga ttttccctat ttctgctttc ctttcttttt  25500
cttttctttc tttcttttt tttttttttg agacaggatc tctctttgtt actcaagctg  25560
gggtacagtg atgcagtcat agttcactgc atcttcaacc tcctggactc aggcaatcct  25620
cccatctcag cctcccacta caagaagaca ccactacacc tggctaattt tttttttttt  25680
tttgagacgg actcttgctc tgtcacccag gctggaatgc agtggcaccg tctcggctca  25740
ctgcaacctc cgcctaccag gttcaagcaa ttctcctgcc tcagcctcct gagtagctgg  25800
gattacaggt gcgtgccacc atacctggct gatttttgta tttttagtag agatggcatt  25860
tcaccatgtt ggctaggctg gtctcaaact cctgacctca gatgatccac ctgcctcggc  25920
ctcccaaagt gctgggagta caggcgtgag ccaccactcc cgctctgatt ttttttttat  25980
cttttataga gacgggagtc tcctgaactc ctgacctcaa gcagtcttcc tgccttggcc  26040
```

tcccagtgtg ctaggattac aggcgtgagc caccatgccc ggcccattat tctgcttttc 26100
tttttctctt ggttcttttt tgtttccatc tgttttctgc cttctcccta agtcaagttc 26160
aaggtatcac agaacgaggc tgaggcagcc tattggacat gacatttgtg cttggcgaac 26220
tccctgtgcc actggccaga ctgtaaattg gttgtctgtt ggaaggctgg ctccaggtcc 26280
cagctattca tgccaggatg gcaaggctac acagagccca ccagcaattg gtatagaagg 26340
aactttttag aaagagggct gtggtatagg cattctgagg acgtgccagt acaggtgaaa 26400
aaacaaaatc ttatgcagga atctgttttg ttttctgctt cctcagactc tctcaatggc 26460
aatgtatgta tgtatgtatg tatatattta tttatttgag acagagtctt gctctgtcat 26520
cccagctgga gtgcagtggc atgatctcag ctcactgtga cctctgtctc ctaagttgaa 26580
gtgattctcg tgcctcagcc acccaagtag ctgggattac aggtgcacgc caccacgccc 26640
ggctgatttc tatattttta gtagagatgc ggtttcacca tgttggccag gctggtctcg 26700
agctcctggc ctcatgtgat ctccctgcct cagcttccca aagtgctggg attacagccg 26760
tgagccatca cgccgggccc aatggcaata tattttaaaa gagagaaaaa aaaggtcaga 26820
atttatttat ttatttgaag aaataaggtc ttgttctgtg gaggtcagac tttgtttatt 26880
ggaaatcagc cctatcccgc ctggttctgg ttagagacag aaacacttac ttgactctag 26940
tcagacatag gcatgggtta gtcctgttgc caggcctgat gggattacag ggccttctag 27000
aacagcttcc ttatcttttc tccaggcccc tagccttcag cagggttagc tttaccctgt 27060
agctatgctg gctggtttct gctctggtgt cctagccccc tttcccagtc tggactccaa 27120
agatggaatc tctttgaggg cttttggcag gcctagagaa cctgtggctt cagagtcttt 27180
ccccccttcct tcaggctgat gggtttctct gttacatgta gttatctaaa gcctgcttac 27240
tagagtacta atattcccta tgggtaattt cttcactact gcttgaactt ggaattttcc 27300
atttctgcaa atatcaaaac ccttttactt cagtgtgctg cttcatgata agcacggaag 27360
atagttttaa atctgttgtg tacagataat acagataagg ttaaaaatct gagtaatttg 27420
cctaaggtca caacatatct tctaggtgag gaaacttagt cttaaactca tatcttctga 27480
tttcaagacc aacgcctttt ctttccaata ccattctgtt tcccggttta gtaatgtcag 27540
taataaaaaa aatttttttta agtatttgtt gagtatgtat ttaccgtatc cagttctata 27600
agctctgtta tacacttggc caaggtccca caactaatta ccgttaccta ctaagtggtg 27660
gaacagaagc atgaacaaaa atcttgattc caaaacctat gcttgtaaaa acctgttaca 27720
gcaggggttg caagctcatg tttataggga tcagagaggc aacgtaaaca agtgaaatgt 27780
tctgctggga attgtgtggc aaacaggaag gcacatgtcc tatatagaga ggtaggtgct 27840
tactaagttc cagcagaagt acaaggttgg tattgtaaag ttttctgatt gaaagacctg 27900
tagtttttta aatgttggca gttaaattta aaatgttaaa actctgcaga acaagcaaaa 27960
catgtctgca agccagcaga catgaaacag agtttgtgac ctctgtactg agagatacac 28020
tgtgttttct aatctttgca gcagctattt agccttgaat agtagaatct gcagtcttgg 28080
gagccttggt ttgcctttca tcggatgctt cccgtataca aatagcagac ctcagcattt 28140
ttttttcaga gccgaaccac ctattggatc ttccactaag taactgatca aaaggatatt 28200
tattgttatc agcttatttt agaagtgtga tgacacgaat tactatacta aaccagttta 28260
aattaccatc atcccagttc ctccatggcg tttttaatta cctgtcctta aagggttagc 28320
tttatggatt catagaattc tagaaattcc tgattagaag aggcagacgt aatccagtgc 28380

-continued

```
atttttttta cttgttgcat gagtctctaa acaatatgat ttaatttatt gagctaatat  28440
ttattgagta cttgtatatt tctagcaaat gaaagatggc taagatagca tctgtgctaa  28500
agaaaagaca cggtttagta atggggacat acatggaaag tatatgtgaa gtacagtact  28560
atgttgtagc aatttgggtc cagtcaggag atagaaacca cataataggt taaacagagg  28620
aagcttaata tacataatta ttaactatgg taagagtaat tgtaatacag gataattgta  28680
tataatactg tagggctaag ggagaatacc caaggaagga caaacttgga agaggttcag  28740
aactcactgg aataggtgtg ggttggccca cagataacag agaagtatat tggttttggc  28800
caggttggag ctggtctgga gttgctgggt aggcagtagg ccaccctctg gagtgcaggc  28860
agggatctga tgatcaggaa ctagtggtgt gggcatgcgt tgggaaaaca gatgctggta  28920
gggggcaaga gcccttcaga gctcatgggc catgtcgggg cttgtagaag gagtgacagc  28980
tcaatatatg accctcgagg cagcttacag atgtagtcca cgtgctgtca gagcagcagg  29040
ccttctttac gggggtgcct cagtccaggt actggcacag gcaggatgcc ttcagagtgt  29100
acagctatgt aggaactcca gctcctaagt tgagagggct gtggtgatat taacaaattt  29160
gtgtgtgtgt gtgtgtgtgt gtgtgtgtgt gtgtgtgtgt gtgtgtgtat tttaatatac  29220
aatgtaatgg tgtccacctt tggaagttct gcataacttg atgaactctt atttctcaaa  29280
gaccaataat gtaatgagca gactgtagaa gcttatttca ttcaaatctt gctctgttgc  29340
ccaggctgga gtgcagtggc tcaatctcgg ctcactgcaa cctccatctc ttaggttcaa  29400
gcgattctcc tgcctcaacc tcccgagtag ctgggattac aggcgcccac caccacacct  29460
ggctaatttt ttgtattttt agtagtgatg ggatttcacc atgttggcca ggctggtctc  29520
gaactcctga cctcagatga tccacccacc tcggcctccc aaagtgctgg gattacaggt  29580
gtgagccacc gtgctcagcc ttcattcact tttgagaaac tttttgccaa atgtacacat  29640
ttgaataacc atagtttgtc agttccttca agtgaaaaac tgttctttaa aaaaaaaaaa  29700
agcttaattt tagcttgcag ctcaatcata caagagtttt tctgcaagca actgatgtac  29760
tttgttttcg agtagaaata ttgtataaat atatttcatt tttgtcacac agaatattaa  29820
gacttgacct cagcagttga gatttaataa aattaacagt ttttctgctt cttagggaca  29880
tttttaagtg aaactggtat tttgtgtgac agtaaacaat acgagtacta caggttgagt  29940
atccctaatc tgaaaatctg aaatctgaaa ctttttgagc actgacgctc aaaggaaatg  30000
ctcattggag cactctggat ttttttcttt tttctttttt taagatggag tttcactcta  30060
gtctcccagg ctggagtgca atggcacaat cttggctcac tgcaacctct gcctctagtt  30120
caagcgattc tcctgcctca gccttcctag tagctggaac tacaggtgtg agccactgcg  30180
tccaacaggg tttcaccatg ttggtcaggc tggtctcaaa ctcctgacct taggtgatcc  30240
actcgcctca acctcccaaa gtgctaggat tacaggagtg agccaccaca cctggtggat  30300
tttggatttt tggattaggg atactcaacc tgtagtacaa tttggtgcca ctgctttgag  30360
tcctgctaag gcatcagcag tttaggacca catttcgaaa atcacagtat agggttgggg  30420
gaccacctag ggaacctaag tgagagatga tgtactggtg gttgggacta gatttaatgg  30480
tgatattgat agaagacaaa aagatgtagg agagaggcat tgaggaaaat gcctcgatgt  30540
tttggcataa acatctggaa ggatggtggt gctatttact gtgctaggga atggaagatg  30600
aggtgatgat aaggggaagg ggcagagggg aaatcactga gttcaagttt aggtactagt  30660
gaagttggga acataccagt attaaagtaa acatgttcac ctcctgaatc gggcatgtgg  30720
ttttggagct tagaagacag acttggacta cagaaaatat tttggaatta ttagtgtaga  30780
```

tgtagtgata attgaagcca taggagcagt tgtactccct ggaggaagca gtatagagta 30840
agaaaaaaag tgagtctcaa tatgaactct gaggaactcc tacatttaga tatcagataa 30900
aggagtagag gttaacaagg aagataggcc tacctagaag tgttaagaac tataaaggag 30960
gcttggcatg gtgacccaca cctgtaatct cagcactttg ggaggctgag gcgggaggat 31020
ctcttgagcc caggagttcg agaccagcct gggcaacata gtgagacccc catttcaatt 31080
ttaaaaaaat gaaaaagaac tataaaggat ctaaaatttt accttccttg gaagttaaca 31140
aattagcctg acgtagtttc atgtatgttg gcaggaggca cccaactcct ggatcagaga 31200
caatggacag tttattactc acagcaaagc attatcctta ttaacagtat ttatgttggt 31260
ttcccaagct ctagtttcta tagggtaatg ttgaagaagg ccaggtaaca cctgcacaca 31320
caggtgttgt gttacttaca gaaaaggaac tgtggcttag gaaacccaag tcttttataa 31380
tgggtagtaa gcatgcctgc tctttgctcc agagcaagac gctatcgtgt atttgaaaac 31440
tattcactat atagacatat ctgaaaaaat agtctggaac aaaggtagtc attacctctg 31500
ttcacaagtc ttgaagaaat gtgagatggg agacatggaa aattgtcttc caacaatatg 31560
ttagaaggaa aactggagga tggtgctgtg gaatccagta gaaagagtgt ttcaaaaagg 31620
aggtaattat tagctctttt gaatattgct acaaggctgt tgggattcta gctagacctg 31680
cttcattcgt gtttaaggac agaaataata ttgattaggg ctaaggtgag tggaaggtag 31740
aaaagtgggc acttttagag aatttgaagg aagcagtact tttgttgtca actggggcta 31800
ggagctgttt aaatgttgat gggaagaaac cagttgaatt gcaaaccagt ttgcaaaaaa 31860
aggagagagg aaatgattga tgactcttga gtcctaaaat ggttaatgga aataggatgc 31920
aaaactccta tagagaagtt atcatttagt aggaggaagt ccgcagctcc cttaactggt 31980
gaaagggtga atccagaggc agcaaggctt gtgggtatag taggaggaag ttgagaggta 32040
ggaactgtta gtttctattt atcagtgagg taggaaacgg ggctaggtcc tctagaagat 32100
aaatagagat taaattttaa ggagagtgga tgaagataag aattaattga tgtggagtgt 32160
gggaaaataa gcagatcaga gaaacattag gatttcgaat agtgaggacc tgattgaggt 32220
tataatcatg tgtttacatt agtgccagtt tctctgcgtt gatgttttag gaatttttc 32280
ctcattcttc ctcctcaaca taaaacttaa aaccacaaca aattaccatt catacctgtt 32340
agaatgggta ctgtataaaa gacagacagt gacaaatgtt ggggaggata tggagaaatg 32400
ggaaacctca tacactgcta gtgggaatgt aaaatagtgc agccactttg ggaaacaatt 32460
tggcagtttg ttaaaaagtt aaacataaat ttaccacgta gcccagcaat atcattccta 32520
agtatctatc caagaaaaat gaaaacattt attacacaaa gattttcaaa tgatcttagc 32580
agcattattc atagccgaaa attgaaacca acttaaatgt cctgcagtgg gtgaatgaat 32640
aggcaaaact ttggtataca atggaatact atttggcagt aaaaagaaat tgactacaga 32700
tacttgctac aatgtggatg aactgtaaaa agcaggctta gtgaaaaaaa tacaggcata 32760
agaaacttta ttttatgatt tcattcatat gaaatgccca ggaaaggcat agagtagatt 32820
ggtggtttct tgggttagag aggaggggga gagggattaa cagtaaatag gcatgagaga 32880
tctgttggga tgatgaaaat gttctaaaac tgatttatga tgttgattgt acaacttggt 32940
aaacttacgt tacaaaaatc gctaaatcat acacttggaa aggatgaatt ataagatata 33000
tacaatatgc cttaataaac ttaggacttg ttttattatt tatttagaga cagggtctta 33060
ctctgtcgcc caggctggag tgcagtggca tgatcacggc tcactgcagc cttgacctcc 33120

-continued

```
tgggctcaag ggagcctccc gcttcagcct cgttagtagt taggatcaca ggtgcacacc  33180
actgtgcctg atgaattttt tattttcttg tagagatgat cttgttatgt tgcccaggtt  33240
gtccgaattc ctagggtcaa gtgatcctct taccttggcc tctcaaagtg ctgggattac  33300
aggcatgagc cactgtgccc agccagtaaa gttagtttta aaaaagagag aatagttctt  33360
aagcagggag gtgatgtgga gtggaccagc tgcggggacg gggtgaaaaa agaacaggat  33420
tggtgttttc ttgggcaaat ggggtaaaag aacaaagagg aaataaatgt agggtttggg  33480
gaagtgagag attgaaccac attgacccta actgcctaag taaggaaagc gtggataggc  33540
tggtgccaac gagtaaggag aaagtcccca cagtattgaa gaacagatgt ggtaagagtg  33600
gggatcagag aggttctgaa gtttaggaag cttgcaagat ggtatagttg gagcacaaga  33660
gcgtatgtag aggtgagatg gggagagtag ggaggaagaa aggaaataaa tgggccttcc  33720
tgaactttat acctgtttga aagtggggac gtagaattaa tattgttgaa aaagcaaacc  33780
aaggctggac atagtgtctc ctgcctttaa tcccagcact ttggaaggcc aaggctggag  33840
gattgctcga ggccagaagt tgggagacca tcctgggcaa cataggaaaa tcccatctct  33900
attgaaaaaa aaaagaaaaa aagaaaaaaa ccagagcata tgtccatttt tcacatctgc  33960
taatttactc tctattgttg taactcttct actggaatat ctacctgtag gtttaattta  34020
agggttaaat ggaataattt atataaagca cctctgcatc tgccccttag tcctaaataa  34080
acaactgcag atgatattgt tggaaaagtt gaggaagaaa agatatttgt tatctattac  34140
tgcataacaa accaaaagca acagtaaaga tttatgacag tcacagtttc tgtaggtcag  34200
gaatttgcag tggcttagtc gatagtcctg gcccaaggcc tcactcacat ggctgacagg  34260
ctggcgctcc ctgatgatgg agaggcttca gttcttttcc ataagggcct ctcctcagtg  34320
ctgctcaata gtctcataat aggctgctgg cttttcaccg agtaatctaa gagaggaagg  34380
ttgaagccaa aagactttta tagcctagct ttggaaggct cacactgtca tctctgccat  34440
actctaaata gagtcagaca agcagaactg atttcaatac agattatatg agagcatgac  34500
tatcagaagg caagtattat tggtatcatc ttggagattg gctaccacag ggagaaataa  34560
gaaattttgt ttttgttttg agagacagtg gtatttttat tcatttgcat cttccctggc  34620
agtaggtctc tagtcattac ttttacaaat ttagacaaat ttgagatagt tggtgcttct  34680
tcatgacaaa atgttgagtt aacatttgtg ggaccaggtg tggtggctgg cttatgcctg  34740
taatcccagt actttgggag gccaaggtgg gaggattgct tgagcccagg agttcgagaa  34800
ctccctgggc aacatggcga aaccctattg ctacaaaaaa aaattacgag aatcagctgg  34860
gcatagtggt atacgcctgt agctcagcta ctctggaggc tgaggtggga ggattgcccg  34920
agcccaggag gtcaagggtg tagtgagcca tgatcgtgcc actgcactct agcttgggtg  34980
acagagcaag tccttatctc aaaaaaaaaa aaaaatacat ttgtgattag tgttttctcg  35040
tagcactctt atttgataat tgctttttaa tttttaaata agaatttttt aataccctac  35100
ttgttaaatt ataactaaaa cagtagcctt ttgccctgtc cccaatttct actccccaga  35160
gaatactatt ttcaattctc ttgactgttt cttcaggtaa tttcctccat gttgttaaat  35220
tgcccttctt atactactct ttcttgattt tccgatttta gactttagta gttttatact  35280
gtgaaaatgg taatttggca cttcttctgt atatttatgc aactcataat ttttggtgga  35340
atcaatgttg agcatttatg ttatgactat aaatgttctt agccaatcct tgtagtaatg  35400
atgattgtat ctcatctctc atataacttt gtatttttcc tgggattaat ggattgcctt  35460
tttttgtttg cttagtactc tatgtcctta tgaataaatc atctctgaac tctccaaaag  35520
```

-continued aactaaattc ctcctcctgg tataatcatg taatctattg gttatttttt tttcttctgt 35580
tgatgacatg ctatctggac ttcatcttct ggtccatctg ggactgactg cattgtagct 35640
tgcacagccg ttgttgtaga agagtctgct ctctctttgt tttggagact ctccaagatt 35700
tagtggtttt ctgtttttttg tttactctct gattttatag agcatgtcct ctactagatt 35760
cctaagaaag gatgcctgag aaatacattt ttgagacctt gcttgattaa ttgatagttt 35820
tcctgtgtgt aaatttcttg gttggaaatt attttcattt ggaattttga aggcattttt 35880
ccattgtctg ctagctttta acactcctca taagaaatct caggcaatcc tgatttccta 35940
aactttgttt ctgcttgcct ttcccccatg tagacatttt aagtttcagc tgtctctcct 36000
ctgttctgct cagtccatta ccagtcatcc atctagtaat actttgtttt tcaaaatttt 36060
tttggctttg cctcaccctg tcactttttt tctagtgggt ttataacttt tataaacaaa 36120
aaatattcct gagattgttt ttccataata attatctaaa taaaaggtta atcttgtata 36180
taatttctgt gataaatatt tccttctcat tatctccaaa tgttctatta aaaaattttt 36240
cccctgtaat tccccttggt ttggggaatt tttatgtttc tgattgaagt aaggatggaa 36300
actaatattg gttaagtgcc aactatttat tgtaatttga gagctttaca tgtaccaact 36360
agatagacga ggtaaggaag atattcttca catctctgtt aggtagctga cagtcccatt 36420
ttagtgagaa aatgtatcaa cttagtcact ttccaaaggc catacctgta gtaaatacag 36480
gctttgaatc tagtatttct gataactgta atccttttttc tactttacgt acaactttat 36540
gggtctttgt gtgtgaaaaa tttcaaacat gaaagtaggg aaatacacaa cactaagagt 36600
gaaccctaat gtaaactgtg gggttggggt gattgtgata tgctgataca ggttcatcaa 36660
ttgtaataaa tatacagctc tggtggggaa tgttgatagt gtgggaggct acgtacttgt 36720
gggagtaggg agtatatggg aaatctctat accttcctct cagttttgct gtgaacctac 36780
aacttctcta aaaaaattaa gcctctcatt atgttggcca ggctagtctc aaactcctca 36840
cctcaaatga tcctccagcc tcacctccca aagtgctagg attacaagca tgagccaccg 36900
ttcccagctg gtcatcatgc tttctcagag gtgccttcac cactcacccc atctaagggt 36960
gttattttct gtcctgaacc ctactcacct ccctcatagc acctgccact gtttctaaat 37020
atttatttgt ttacttgttt atggtctgaa tctcctagta ggcgccagct tcataagagc 37080
agataccacg tctcatttgt tcacctagtg ctggaacata ctagaaaagt caataaatat 37140
attcgttttg ttgttgtttt ttgagacagg gtctcactcc catttcccgg gctggagtgc 37200
agtggcaaga tcagccttga cttcccagcc tcaggtggtt ctcccatctc agcctcccaa 37260
ggagctggag ccacactctc acaccaggat acctggctag ttttttgtat ttttagtaga 37320
gatggggttt ccaccatgtt gcccaggcta gtcttgatct cctggactca agcagtcccc 37380
cctcccaaag tgcggggatt acaggtatgt gccaccatac ctggccaata agtatattct 37440
taacgggaaa aaaaagtagc gtgagaatac ttttgtaacc caccatgtaa ttgtcagcca 37500
tttatcagca ttttgccaat cttttgtttc atatatttta ccatatttta acctgtaaat 37560
attcttccat atgcatagct gttatataaa aggactttta aaaaatcaca gtgccattgt 37620
tatacctaac aaaattaagt aatcccttaa tataattggg ttttttgttt gtttgttttg 37680
gtttttttgt tttttgtttt ttgagacaga gtctcgctct gttgcccagg ctggagtgca 37740
gtggcaaggt ctccgctcgg tgtagaatct gcctcctggg ttcaagcaat tcttgagcct 37800
cagcctcctg aatagcttgg attacaggtg catgccacca tgccaggcta atttttgtat 37860

-continued

```
ttttagtaga gacggggttt cgccatgttg gtcaggctgg tctgtaactc ttgacctcga  37920
gtgatccacc cacgtcggcc tcccaaaatt ttgcgattac aggcggtgag ccaccgtgcc  37980
tggccactta ataaaatcta aaactgagtt cgtattcaga tttttctggt tatctcaaaa  38040
atacattttt acatttggtt tgttgaaaca gtatccaaat agggccaaca cagtatttgg  38100
ttgttacgtc ttttaagttt cttgtaatct gtaatagtct tcctctcctc ttttttcgtg  38160
ccatttttat gttgaaaaac ctaggttctt tatcctgtag aatgtcccac attctagatt  38220
tggctgatag cttctttggg gtttcatttt actttcctac taacccccat gttttcagtt  38280
aactggaagt tagagctaga ggtttaatta gattcaggtt tatttttgca agatagtaag  38340
tgttcttatt tttgcgagaa cacttcctag ttggaacatg tagtttttttg tttcatcagg  38400
aggcaaataa tatctctaat atcttacttt tggtgatgct aagtgggtat gagtgttacc  38460
agcttgtaag cgcgccatcc acataaatcc taatgatttt agcacccatt tgtgaccatt  38520
atctagatcc attatttcat taggtgttgc acattggtga tctttcagat tacatcgttt  38580
cttccacatt tactagctgt aattcttcta taacaaagta cttttgtcta tttggttacc  38640
tgaaaggagg aaagataata ttaactattg attttccccc tttatttgtc agttttcaga  38700
gtaatgagtt gatgccctag caactctcat tggtgatcaa tgaaaggttt tttaagagtc  38760
attatgaact aagggctact tatatatttg atgtattttg gtgaattata gttattactc  38820
attttgatgc tcagattgac ccgttagtgt ccccattagt ctttgataac ttctttggtt  38880
tcggacacaa gatatccagg ctcattttgt acaaatcctt ctccagatta gaatcagtca  38940
tttctctgaa aaactgttct gttgtgtgtg tttaggaaat agtttttaga aacaacaaac  39000
agttgttaag ggtttgttac tgttgggttg ttattctagg cattttcagt gacagagcta  39060
gaaaataccct aatttttagg aagagaaaaa taaatcatga gttcgtatcc atgtttataa  39120
ttgaaatgta aggacttaac ttggctactg tgattttttt ttccagattt taaaaataag  39180
cttcatttta aaaaaaatta acgtgcgcta ttggaaactg aaaaacacaa gaaatgagga  39240
acagagtcat ccacaatcat aagcagtttg acatgccctt ctaggtcttg tgtgtgtata  39300
tacataacat ccatttttat gtgattgaga tcatacagta tgtatcatgc tttttcacat  39360
atcatgaaca tttattagtt cagaacccca aagctacctt ctgccgttca gctgccaacc  39420
tattgaatga gtcctgatac accctaccta ggtggtttaa cagttccatg ttcaagatgc  39480
gtcttttcca tcaattatac caagatattt acaaattggc taactcacta tctctgcttt  39540
ttatcataca ttgtcacctc aggacatcta taaagcttag atgttgcaaa ataaagattg  39600
aactttgttc acagtaaaca gatgagttac caaaaatgca catagagacc tatggttaaa  39660
atctaaaacc tgtcctctgg atatggagac actagtaaag agccttaccc ttcacccctt  39720
ttccctcttc tatcatttca gtgactaagt acattactgc atctagctct tagaagtagg  39780
ttaacaaata ccactcccag aagacaggcc ttcctaaaaa aaaggatgtt taaaaacgga  39840
ttattttact gcctctactt ttaacatact ttgagcctta ggagttgttt atcctttaca  39900
cacaacagta ttaactaaat tacatatata gaacaatggt tagacaatct gaactaatgt  39960
aactcacagg cacagaagtc ttctctctgc atacttcctc ctcctcgccc ccctccacct  40020
cacccagtga gcaggaaatg caaacgctcc tgtgaaataa caaaaaaata cttagtgtta  40080
ctttagctct cattagctac tctgatttta tacttctgtg ctcttgaaac catagtaaca  40140
aaaagtactt ttttgcttgc tgcttgttac accagtcaca atctctgaat agcagcacta  40200
atgactgaat atagttttct ttctttgtga taccttttttg taccaaaaag gtactcccaa  40260
```

-continued

```
taaggaagta cagtggaaat accgtgtgag atatatgctt agttttttg tttatccttt  40320
cgttgtttct ttttgttaaa atatgcatgc taatatattt ttaaaattat atttctcata  40380
atacacattt gatgatctta tgtttatttt aaaataatat attatggata tgtttttaaa  40440
ctctctttct tacaggaaag ttagcatact ataaacactg ttctgccctg ctttttctct  40500
taatgatata tattctggag ctcactgttt atcagcatgt aactcttcac tcctttaaac  40560
agctgcatgg taatccattg tgtggattac agtgatttat tcaactaacc ccatattaat  40620
tcagtcttct ctttaaatcc taaggaaaca cttttgtgtg gcacaatctg gtgtgagaat  40680
ttaatatgat tgaaaatttt aaaatattga aatcactttc tcaattgtgt ccttgaagta  40740
attaagagtg aatcaaagtt ttcgtgaaat gaattttact cactcaggca ttccaattta  40800
cttttaaact ttaatcattt ttgatggaaa attttaaatt tattacagac atttatacag  40860
tttaatcatt ttctttttgc cataccaggg gatgtctgca ttattgaatt gaattctgat  40920
attctgtgct ttttttagt ttttctgtga attccttgaa tatgaagtat ttgtcatagt  40980
tgcagtatga tattcctaaa ttaatgcagc tcttgtatga aggtttttat ctctgctttt  41040
ttcaaggctt tgaggttatg tacaggaaag tcagttacaa aacacctgat gttaacacga  41100
atggtgttac actctagttt gtcagactaa aaatgaattg tttaaattga gaaaacagtg  41160
catttttgtc tttgtctaac tttttgctat ggcattttaa aaataatata taggtatgac  41220
tgtttgctta ttaatagtaa tattttcttg aatcagatgt tctgccttac tcaatacggg  41280
tcttgttgga agctgctgta cgaaattgtg atggcttttt aatgaagaag gaagatgtta  41340
tgaacatttt agactggaaa accaaacaaa gcaatgttga agtgcccttt ttccctgccc  41400
gtgttcttct tcaagatttt acgtgagtaa tgggtttatt ttttgtgaat gaactcttag  41460
agtgtgtttc ctttttaaaa tacagactct tgggtaggtg tggttgttca tacctctaat  41520
cccagtactt tgggaggcca aggcaggaag atcacttgag cctgggagtt tgcagtcagt  41580
ctgggcaaca tagtgagacg ctgtctgtac aaaaaaattt ttttaattag ccgaatgtaa  41640
tggtgcatgc ctgtagtccc agctactctg gaggctgagg tgggaggatt acttaagccc  41700
aggaggttga ggctgcagtg agctgtgatc acaccactgc actccagcct gggtgacaat  41760
gcaagaccct gtctctaaaa ataaaaaata aaataaaaaa tcagacttcc taatggatgg  41820
ctctgtgttt ttttgttttg ttttgttttt gtttgttttt ttaaggttag tttataaact  41880
taaaaatttt gccctttcta aactgaagca attcattaaa aattaggcac tgttttgtac  41940
catttattca aaaactgctt ttgtttaact accttcttat gatctctcaa taggtttctc  42000
aaacttaaca tattgaaaac ttgattttat tttgaggtag tctcactctg tcacctaggc  42060
gagagtgcag taatgcagtc atagttcact gcagcctcaa cctcctgggc tcaagcgatc  42120
ctcctgcctc tgcctcccaa agctctggga ttataggcat gagccaccgt acccagccat  42180
caaaacttga gtttttgatt gtctatctca actcacctat ttctttctaa gtcttttctg  42240
ttatagtaaa tggcaccata cactcccatt tgtttaggct tcaaatctag gagttagcct  42300
tgatttttct ctttctttaa taccctctaa cccagtctat cagcaagctc tgtcagtgct  42360
acctttaaa tatatcttgt gtccaattat ttctttccat ctctatcact gtcattgtgg  42420
ttctagtccc attctctctt aacctggact ataactgcaa tagtctctta actggtatcc  42480
ttgctgtcac acttgcaatc aatagtctgt tctttacaca gtagatggag tgacttggtt  42540
acaaatgtta agtcgtatta tccctccata taccagttgg cttccatcac acttaaaatc  42600
```

-continued cagagccttt accatactct gaaagatttt gcctgatcta ggtgtccaag gattatttat 42660
tggaagagtt aaccttgagc tgagttttga aagaggcgta gaggttagct ggaacatcct 42720
cttcacccac ccactcaaat ctggtttgtg tgccacagct ctttgtaccc tatgtatgct 42780
gctattatgg tacttacgat acatagccgc ataagaaata aatgatattt cttacaccat 42840
ttattcagaa actgcttttc ttaactacct gcttatgatt tccacataac caataggttt 42900
ctcaaactta acatgttgaa aacttgatct tattttgaga tacagtcaca ctctgtcacc 42960
taggctggag tgtagtgatg tgatcatagt tcactgcagc atcgacctcc tgggctcaag 43020
ctgttattgt atgcagctat tatagtactt acgatactat tctttaatca ttatcttccc 43080
taaaattttt ttgagagcca gaactatgtc ttatttggcc ttgtaccatt ggtgtctagc 43140
acactgaagg catttgataa atgcttgttg tatagttggc tggatagatg ggtggatgaa 43200
tgtaaaatgg caaaagctac tgtggatagc tttggggcaa cacgaaggca ctagggggaa 43260
ggggctggaa ctagggaaag gggaaggtgc atcaaaaaaa tacatggcaa gagtttcaca 43320
ggcattttcc ctgaagttcg cttatgcctc aaaaattatc tcttattatt tttggcatat 43380
ttgcccaagt acttcagttc tcagataatg tttaatgtta attcttatta aacaggatac 43440
tcctaactta taaagtacat tatgaaaaat gaatgtaaac tagacaggga tactttttaa 43500
aatatgaaaa tgaaaaagtt tatcatttat taagcatgta taaaaaacaa tttggactat 43560
aatttgacca ttctttattt tttagtggaa taccagcaat ggtggatttt gctgctatga 43620
gggaggcagt gaaaactctt ggaggtgatc ctgagaaagt ccatcctgct tgtccgacag 43680
atcttacagt tgaccattct ttacaaattg acttcagtaa atggtacttc aatgcagata 43740
tttatagaca gccatgcaag ttaattggct ggaaatgtgt catgtagagg aaaaggaata 43800
gagataattt atggcagaga aaagtatgct aaatttagta ttggctagta tataaaagct 43860
aaaactggtg aaaagtttat ggagtggtgg ggtttttttc atgttcttgt atttctgctg 43920
ccgtttttga tagaaatgaa taagcctagg acctgctttt tggagtgaac ctctgtattc 43980
agtctttgtt tcctttttg tttttaacc tacttgtctt tcagaaagaa tcgaaagatg 44040
tgagtcatga atgtttttaa ttatttggtg attaaaaaca ttgaactcac taaagctcta 44100
ttttccttcc tctgaaataa gtttcttgta tttataaggc ccctttgacc aagaccaaac 44160
tagagaagac atatttctgt tgccataaag taacttttta aaaacgttcc ctggagtagt 44220
agaataagac tgcaatttat tatagcccat gagagaggtt ttgccctcga gataaactgt 44280
agctctaaat ttcttttaag ttgttagggg gaaaaaatct atttcagtac ttgctaaaag 44340
ttatttaaat tagtagagta tttgaaagtg attttactgg acgcttagaa ttctgttttc 44400
atttctgtaa atttaaatga cctgtttctt tttttatata tatataatct gagatttgcc 44460
tttgaaacct gagttaaatg atacattagc ctttaaacat cattcagtta cttccagata 44520
gcgttgctaa tgtgcgtttt tttttaagag ctaaatttgt gtccctttta aatggcttta 44580
ttttgttttc tttttggaat gacagtgcaa tacagaatgc accaaatcct ggaggtggtg 44640
acctgcagaa agcaggaaag ctctctccag ttaaagtgca gcctaagaag cttccctgca 44700
gaggccagac tacctgccga ggatcttgtg attctggaga actaggccga aactcaggaa 44760
cattttcttc gcagattgag aatacaccca tcctgtgtcc ttttcatttg caaccagtgc 44820
ctgagtatga gattgttttt cttaaagttt attaatacca ggttattttc cagttaagaa 44880
aatcaaattt attctcttcc cacccaatta ctattatgtt accttcacac ttaagtactg 44940
aattgaattt ttatatgtat ttcctgttat actaaaagaa gtaaatttag tgaaaatggt 45000
gatctctaag taccattctc tcttaccatt actaagaaag caaacttttc ttaagattta 45060
tctgtaaata gaattcatct ttttgacgac tgtaagcaga aaaatgggat ctcattttaa 45120
actaaaattt ttattttagt atatttgtac cattcatata ctcgttagtc attcatattt 45180
cttatgttaa ttccctgtat atatttttaa catttttttc ctactagggg gtttcttatc 45240
ttttcctatt gcattaagag ctctatgttg gctgggcgta gtggctcatg actgtaatcc 45300
tagcactttg ggaggccaga gcaggtggat cacttgagct caggagtttg agaccagcct 45360
gggcagcact ggtgaaaccc tgtgtctaca aaaaattacc cgggtgtggt gtcgcgcccc 45420
tgtggtccca gctagtcagg aggctgaggc aggagaatct cttgaaccca ggaggggagg 45480
ttgcagtgag ccaagatcat gccactgcac tccagcctgg gtgtgacgga gtgagactgt 45540
cgcaaaaaaa aaaaaaaaaa gagccgtatg ttaacgataa aatttttgtt ttttatgttt 45600
caaatctagt aagtccttct aaataagtga tttcctatat ggtaacatgg aaagtagtaa 45660
acatgcctag aaaagaattc tattcctagg atttggctag atttcctaat gtgtaatttt 45720
tttaaataag aaaaagagtt ctatggccag gcgcggtggc gcatgcctgg aattccagca 45780
ctttgggagg ccggggcagg cagatcacct gaggtcagga gttcgaggcc agcctggcaa 45840
acatggcgaa accccatctc tactaaaaat acaaaaattag ccaggcatgg tggcaggaac 45900
ctgtaatccc agatacttgg gtggctgagg catgagaatc gcttgtacca ggaggcaggg 45960
atcacagtga gccgagatca cgccactgca ctccagcctg ggtgacagag caagactctg 46020
tctcagaaaa aaaaaaagtc atacagcttt ttaaaatatg tactataaag tttccaaact 46080
tttaaaattt atttatttat ttttagagac aaggtctcac tatgttgccc atgctggtct 46140
caaactctta ggctcaagcg atctgtctgc cttgaccttc aaaagttggt ttttttttgtt 46200
ttgttttgtt ttgagacaga gtctcactct attgcctggg ctgaagtgca gtgtcataag 46260
catggctcac tgcagtctcg atctcttgga ctcaggtgat cctcccacct cagcttccca 46320
agtagctgga acttcaggca tgcaccacca tgcctggctg atttttttctg tatacagggg 46380
gtgtcactgt gttgcccaga ctggtctcga actcctggcc tcaagtgatg cttccacctt 46440
ggctgcccaa agtgctggga ttataagcat gagctactgt gcccagccat atttttattt 46500
ttaagagagt tatgtgaatt gtttttgtct tagtttaaat aattcatgta aaatataaca 46560
atttatccca ttgttagtaa actgtctttt tttttgagat ggagggtctc tctgtcaccc 46620
aggctgaggt gccgtggcac catctgtagc ccactgcagc ctccaactcc taggcttaaa 46680
tgatcctcct gcctcagcct ccagagtagc tgggactaca ggcacacact gtcaggcctg 46740
acttatttta tctacctttt tttggggtag agatgggcac tatgctgtcc aggctggtct 46800
tgaactgggc tcatgcagtc atcccacctt ggcctcgcaa agtgctggga ctgcaggcat 46860
gtggcactcc acctggcttt tttttttttt aatttagtaa aaaattactt gcactttagg 46920
ttttaaaaag tttaacacat ttaagattta gagtagctaa gagtaatgtc cattcattta 46980
tcctaagtac caaataatac gttaattcct ttgtccctga ctggatcttc caaattctgt 47040
ctagttctaa aatattgggc ttaatatttt tatgaagcca caggttatag tgacctcgtg 47100
tgctcttcct ttctaaggat tcagtataat ctctgagtct tttgccatca aattttgaaa 47160
gttttatgaa gtcactttct tgttcctgtt gcctagttgt cctggttgtt aggagcatgt 47220
tgacttttga gattaacacc tcttatacag aaattaattt cctgaaaagg aagatttatt 47280
gattcaaaat cattgatttc tttagttttt gtttcttttt ataactggca catcgtaagt 47340

-continued gcttagtgct atatttttat ttctaaaaat ccaatctgct gtaacatttc cccataattt 47400
tgactccgaa ttacaaagta ttaagataga ttatattgta gttcctggct atgtgataat 47460
agttactcat ttgtatcttt taatgtgtca gtgaagtatt aattattgac ttaagaagtt 47520
gagtagaaag atgagagcat aacctttggc acttcaaatt accccctagt ttgaagtcag 47580
gttatgagcc aataaatgtt tgtatggcac tttgtagcca taagtgctat tgaaaggtaa 47640
aataattgga gtggctcaga aagctgtttt ccctgaggcc ctgagaaaaa tctcactaag 47700
atatgcttgg cttcaaaaga tgactcaact atgaattatt aaagtaatct ttgtttaaaa 47760
aaaaaaaaag ttgtccgagt gtggtggctc acacctgtaa tcccagcact ttgggaggct 47820
gaggcgggtg gatcagtcac ctgagatcgg gagtttgaga ccagcctgac taacatggag 47880
aaaccccatc tctactaaaa atacaaaatt agccgggtgt ggtggtgcat acctgtaatc 47940
ccagctactc agggggctga ggtaggagaa tcgcttgaac ccggtagggc ggaggttgta 48000
gtgagccgag atcatgtcat tgcactccag cctgggcaac aagagcgaaa ctccgtctca 48060
aaaaaaaaag gttgacaatt aaacaactgt aattatctgg actaattatc tggtccctgg 48120
aggacacgta taatttaagt tatattgata ttctagtcaa cacccagtca ccagctggca 48180
ggtaaaagaa gcagcttaaa gctgtttgaa ataattttta aaaataacta ttagataaaa 48240
ataatttttt aaaaatgata ctatgttact ggttagaggt caattatttt tgtctcttag 48300
tttaaataat tcatgtaaac tatatttata atccatgtaa agtgaactgc tacttataca 48360
taaagtagag ccttcttttg gtatgagatg aatgaaagat ttttgccaaa agctcttttt 48420
aaactgtaaa atgatgttga gatgttgttc gtcaatgctg catagaaata atcagcaccc 48480
atctcctagt ttaattggca caagagccag gtggggagga aagtacatgc ttgtcgttga 48540
agctactact ttcctctttt cttgcagcgg ataacccaac aaagtgtgtt tttattatca 48600
cttgagtaca gttttggaca ttggtgtaat gtggctttct tacactcagt aaaatacaac 48660
tcacttttgt agctttccgg tgtgttattt taaagcagaa ctttgttgaa aaagaaaata 48720
attctgagaa acctagtaaa tagttcttcc aaggatttta agaatatatt tgtgtatata 48780
tatgcctaag aacgatgact tagaaagaaa caaggcaagt ctttttttgta atacatacgt 48840 ttaatgccag ctcttcttcc ttttagacct gaaacagtgt taaaaaatca agaagtagaa 48900
ttcggcagaa atcgagagag gcttcagttt tttaaggtat aaatgattca gggaaatttt 48960
tgtattgtaa tatataaact aatgataggt acaattttta tatctttgtt tctttttctt 49020
ttcctttttt tttttttttt tttttttaag acagaatctc gccctgttac ccaggctgga 49080
gtccagtggc gtgatctcag cttactgcag cctccacctc ctgggttcaa gcagttctcc 49140
tgcctcagcc tcccgagtag ctgggattac aggcgcacac cagcacgcct ggctaatttt 49200
tgtattttta gtagagatag gttttcacca tgttggccag gctggtcttg aacccctggc 49260
ctcaggcaat ctgcctgcct cggccccccc caaagtgctg ggactacagg catgagccac 49320
cgtgcctgcc gtatttatta ttttatttat ttatttattt atttttgagg aagagtcttg 49380
ctattgccca gacaggagta cagtggtgtg atcttggctc actgcaacct ctgcctcttg 49440
ggttcaagcg attcttgtgc ctcagcctcc tgagtagctg ggattacaga tgtgcaccac 49500
tgcctggcta tttttgtatt tttagtagag acggggtttt gccatgttgg ccaggctggt 49560
ctcgagctct tggcctcaag ccatctgcct gccttggcct cccaaagtgc tgcgatcaca 49620
gacatgagcc actctgccca gccactttag tagtttctaa aggttttata gtagtagaac 49680
gcttttgttc ctcaaatgaa atcttaattg gaaaccctat tgtgtagaga aagatgaaaa 49740
cagtggctct agtttaggag agagagcttg gagggagggc cttgtacatt gagcctttct 49800
tccttctcat tcctgagaat ctttggaacg cagttgaata ctgccatttg tctggacttt 49860
ttgaacattt ttatttgacc taaattaatt ttgtcttaat aaaaaataca tttaggttca 49920
gtatctgtat atttgttttt aactatgtga tatgaacttt gtatttacca tattgaacat 49980
tagttaaaat atttttaatg ttaatattac accttgattg tgagcacaaa tttatatact 50040
aacatttgta tttcttaaat ttaaacaaaa tatagtggag ttcaagagtt tttaagaatg 50100
tggcagtgat ccctcctgga actggaatgg ctcatcaaat aaacttagaa tatttgtcaa 50160
gagtggtttt tgaagaaaaa gacctcctct tcccagacag tgtagtcggc acagattcac 50220
acataacgat ggtgaatggt ttagggattc tggggtgggg taagtaaatg actaaatata 50280
tttcatttct tttggggtaa ggatgtcaag aacattgtaa aagaacataa attattgagt 50340
ttgtatagcc tctttgaggc tctgtgtttt tcatctgtaa taacagcagc aacaacaaaa 50400
tcctaattga gagtttgtga tcagtgttgt aaaagaggat ttatgagaag aaatttacac 50460
agtgtctagc acagcactac tatttgtgaa gtaattgaat aattgaatga tgatgatgat 50520
acgtctacaa agtttgcttc tttgtgtaag gtacttttgt ggcttctcct ggtcttcttt 50580
ataagtccag atttcttgcc attttataca aggcatgtcc ctttagccac tcacccacac 50640
ccatcttaga gagactagtc atttctttac ttacgtgggc tgtctctttt cttttttttt 50700
tctttttctt ttttttttgg agacagcatc ttgctctgtc acccaggttg gagtgcagtg 50760
gcacaatctt ggctcactgc agcctccacc tcctgggttc aagcaattct tgtgcctcaa 50820
cctcccaagt agctgggact acaggcacgt gccaccacgc ccagctaatt tttgtatttt 50880
tagtagagat acggttttgc tatgctggcc tggctggttt tgaattccta gccttaagtg 50940
atccacccac ctcgacctcc caaagtgctg ggattacagg cgtgagccac tgagcccagc 51000
tagctatgct cttttatatg ccatgacttt gcataggcta tttcttctgg aagaatgctt 51060
tctgccgacc gtgactttgt tgaaatgtgg ctactattaa ctcatccaag actggcctca 51120
gttatcttct gaaagtctta actcccttgc tgagttcagt gtacctcact ttgtaagctt 51180
actctttcac agggtgttat aaatgttgat ttttttgtgc tttttcatta gactgaactt 51240
gttgaggttg gcagggactg gattctgttt atatctgtat cttgaataca gtgcagtgcc 51300
taacataatg aatacttaaa ctaatgtttt aacttgaata tacttaaaac taatatttta 51360
ccttgaatat aaaggtaaaa taatagtttt tcgaccgtgc gagtggaatc atttcttttg 51420
ggaagccttg ggttcagtgt ccacattaat agcaatatag caactctgca aagtactgtg 51480
taagataagc tcatgaaaca cctagagatt cagatgttac agagataaat gatctttaaa 51540
tatactgtgc taatatacct gtctttatta cgttaggggt tggaggcatt gaaacagaag 51600
cagttatgct tggtctgcca gtttctctta ctttaccaga ggtggttgga tgtgagttaa 51660
ctgggtcatc aaaccctttt gttacatcca tagatgttgt tcttggtatt acaaaggtaa 51720
gttaaagttg tggtagctct atgacttact gaacattatt tttataaaaa ttgaagagct 51780
ctatgagagc agggatttgg gttcattact gcatcctcag gtctcttgac gttagccaca 51840
tcatcatagt tatcatagta ataacaacaa acagagcatt tagtttgtac taataaatac 51900
aaagaaattt gttgtgttca cttatgttag ctcatttagt ccttataaca agcctgtgag 51960
atggatacta ttactattct cattgtaact ctgagaaaac taaggtacag tagggtttag 52020
tgacttacca aagggtcgaa ggcctgagta gtaaggggta gagcaaagat tccaggcagt 52080
cagattcttg agtccattgt cttaaccatt atgccttatt agtgccttgt tgccttaata 52140
aacacttgct gactacatta tttttttct ctttttact tgaatttaaa aaaaatgttt 52200
agcaaaagtt gattgtgtcg tctttaatta aattatttgc ccattagaaa ctgttgctct 52260
actaagtaat gctttcaaaa acatggactg tagaaatgtg atatatcatt tttctgttgc 52320
cgttttaaca tttctctgga ttattatgta aaaatcttct ctctgaattt ttaaaatact 52380
ggcttcagaa cttcaataca tacactgagc ttgttaagca tattaataca caggctcacg 52440
gatttcctag tgaacaataa tttgtaactc ttcttcctaa atgtctggcc tttgctaact 52500
ttattttaat gattaaatcc tattttgtta aatgaatgta cctggaaaat gttccacata 52560
taattccaat ttgagtccca atctcagcat ttttggttag attattggta cgaaggcttt 52620
ccggatactc cagtgtaagg aaatgataat gcctccctct cagcatttgg tattgatcct 52680
tcttccctaa ttagaaaaga atttggcatc ttagagaaat tattgattca acgtatgata 52740
ccaaaagatc aagtagtaaa ttgggaattg caggattatt cctagaggaa aaggagtatc 52800
ccattatgtt tttacagaaa tcaattcttt actttagaca tcctgaaaac taacgctgct 52860
ttttagcctt ctctagctgt tttttcctga caatattact gtgtgttttt tgacatttta 52920
gtttaatgtt aaaaaaattaa tctattatat atgtttacat ttattgaata tattattact 52980 tctttttga gatcctgttc catttgtgat ccttatagga ataatcctgt attgtttttt 53040
tgatgagagc agcatttggt ttgtaatatc taatctgtgt ttctttcatc ctaaaaaata 53100
aaaccatagg ccgggcgcgg tggctcacgc ctgtaatccc agcactttgg gaggccgagg 53160
cgggtggatc atgaggtcag gagatcgaga ccatcctggc taacaaggtg aaaccccgtc 53220
tctactaaaa atacaaaaaa ttagccgggc gcggtggcgg gcgcctgtag tcccagcttc 53280
tcgggaggct gaggcaggag aatggcgtga acccgggagg cggagcttgc agtgagccga 53340
gattgcgcca ctgcagtccg cagtccggcc tgggcgacag agcgagactc tgtctcaaaa 53400
aaaaaaaaaa aaaaaaaaaa accataaatg aggaaacatc tttacactta gggtttgagt 53460
ttctgtatct ataaaaaagg gtttggatta agtgatccct ggcacttata aaatgttagg 53520
gcttaatatt attcatagat cgaggatagt ttcattctta gtcgcctcct tagtcactct 53580
tcctatacca atctgagacc attttacaat ttagaaaaga caaataactg gttgggttac 53640
ttgatagtat aataaccaag aaaaataatt ttagaaggaa ttaagtttga aaccacatgt 53700
taacaaattc taccaaagtg ggatttgcct gtgattaaag atgctgtaaa catttgggcc 53760
agtagttata atttgaaaaa tgtttatagc caatatataa ttttttattt aaatatacag 53820
tttcatcagt ctattagtat ttcattaagt ctaagatgcc atcagtggtt agcaaacacc 53880
actgttttat gcactgctaa gaaagaataa agggctgtgt gcagtggctc acacctgtgg 53940
gacgccaagg caggagcatc acttgaggcc agaagttcaa gaccaacctg gtcaacattg 54000
taagaccctg tctctacaaa aaaaaaaaag ttaaaaatta gctgggtgcg gtggcacatg 54060
cctgtagttc cagctactct ggaggctaag gtgggaggat tgctagagcc acggtgttgg 54120
aagctgcagt gagctgtgac cacaccactg cgctccagcc tgggcaacag agtgagaccc 54180
tgtttctaaa agaaagaaag aaaaagggct gccacctaaa cagacacact attgagttga 54240
ggtaccctga tttcaaagac atgaaaatgt taattatagc caccttgagc tttcaggccc 54300
ctttctaccc tgattaacag tgacattgga ccagtcttct ctttacttct tatcttaaaa 54360
tacccccaaa accagaatga gttgattcat aaggacaatg aaggatctca ttccttcacc 54420
atcactagta ttggttaaaa attttatttt atagttttca gacaatcgtt gctaatctta 54480
tctttgcaat tttgtatgtg tttctgtgta ttccttatat agcacctcag gcaagtagga 54540
gtggctggaa agtttgttga gttttttgga agtggagttt cacaattatc tatagttgat 54600
cgaactacaa tagcaaacat gtgtccggaa tatggtgcta tcctcagctt tttccctgtt 54660
gacaatgtga cattaaaaca tttagaacat acaggtaaga agataaaaga tcactagaat 54720
aaacatgtta catttccaat gtgtttgata atattttata aattactacc ttatccatgt 54780
tatttactat tcacaaaatt acattatgtt gaaacaacaa ctttcaagca aacatcagat 54840
gtctttaaag agtgttgtgt cctcaaaccc tagttccctg tgacacattg aaagcaattt 54900
aaaggaatta ttcaaaccat tgatcctgac ttgactgttt ccccataatg atggatacct 54960
ccacctctac ttaggggtca taggttgcaa tttaatggaa gtcagcctta aacatattca 55020
cagcagtccc cttctacaac caagagtaga ggagctatca gacaaagggg tttggggacc 55080
agtcttctat ctagagaaga agaagaagcg caaaattttg caaaaaacaa cataggacca 55140
cagtttctaa atctttttgt aacctgatta actagaaatt ttggccactc ttccattggc 55200
tgtttagatt aaaacagaaa gtatctacaa aacaagatat gttgatattt cataagtctg 55260
ctatttaaaa agtaagatct ctttttttaa tctctttaat gaggtaatca ttgctgagtt 55320
actcatttct aagtatagat atttatttgg aggatatatt ctagtattct tcagtgtgca 55380
ggcagattat tatgttagtt aatcagacag caaaattgat gaatggttat atagaatcct 55440
ggagggaatg atccccccaa gtgcaaaact tctgcatttg agttagtaga acattcaaag 55500
tagaaatggt tagaagtgcc tcgttccttg catattaatc ttgagttaag gttttagtga 55560
tcctgtgtaa caaattatcc taaaatttag tggcttgcac aagcagtaat tactagctca 55620
tggtttcagt ggggtcggta attcagacag ggcacagtgg ggacagctca tctctgtttc 55680
atgtcttgag cctcaactgc aagatttgaa aggaagggcc tgcaatcctg aaggcttgtt 55740
gtgcttgcat gtctaacagc aaattatgag ctgtcagctg aggacttagg taagtctatc 55800
aggcaaaaca ccctcatgtg gtttctccgt gtagtctggg cttgctcacg tggtagattc 55860
tcaagggtta ggagaaagag aaatgtaaat gaatatgtaa atagtatttg tttcttgttc 55920
atcactggaa ttcagtatcc ttacccccaa agatttcaaa attccttact gaggccaggc 55980
tcagtggctt acagctatga tcctagcact tcgggaggct gaggcgggag gatcacatga 56040
gtccaggagt ttaagactag cttgggcaac atagcaagac cccatctgt acaagaaaat 56100
taaaaattag ccaggtgtgg cagtacagac ttatagtcct agcaacttga gaggctaagg 56160
cgggagaatc acttgaaccc aggagttcaa aactgcagtg ggctatgatg gcaccactgt 56220
actccagcct aggtgacaca gtgagaccct gtttctaaaa ataataaatt tattggcggg 56280
gtgtggtggc tcatacccat aattccagcc ctttgggagg ccaaggcagg aggatctctt 56340
gaggctgaga gttcgaaacc aacctattca aaaaaaacaa gaccctcccg ccacccccatc 56400
tgtacaaaac atttgtaaaa aaaaaaaaaa aaaattaacc aggcacggtg gggtgctact 56460
tgggaggctg acatgggagg attgcttgag ctcgggaggt caaggttgca gtgagctgtg 56520
attgcagcac tgcgctccag cctgggcaac aaagtgaaac cctgtctgaa aaaaataata 56580
actaaataaa tttctcactg cattttgttg ttttgttcat cttcgtttta ggttttagca 56640
aagccaaact cgaatcaatg gaaacatacc ttaaagctgt gaaattgttt cgaaatgacc 56700
agaattcttc aggagaacct gaatactccc aggtatatgc agaataaccc acctcgtagc 56760
aaagagtgta aattgtggtg taatcccagc gctttgaaag gttggggtgg gttgattgtt 56820
tgagttcaag agtttgagac cagcctgggc aatatggtaa aaccctgtca ctgcaaaaaa 56880
actacaaaca ttagctgggc atggcttgcg cctgtggtcc caagtacctg ggaggctgag 56940
gtgggaggat cacttgagcc tgtggggcga aagaaagttg cagtgagctg agattgtgcc 57000
actgcactct agactaggta acagagtgag acttgtgtca aaaaggaaaa aaataataat 57060
aataaattct agagtacctg accacctggg tttgaatccc agctctaaga cgtgttagct 57120
gtataacctt gggcaattta tttagccttt ctgcctcagt tttctcatct gttagatatg 57180
acaatatcta cctctaagga ttcttagata ttaaaaacaa attcatagaa tagttccagg 57240
cacatagtaa atgctcaata aggggtagct aatctttttg ttttgctttt tgagacccag 57300
tccggctctt tcaccagact agagtgcagt ggcacaatca tggttcactg tagcctcaac 57360
ctctgtgctc aagctcccac cttgctggga ttacagacat gagccaccac catgcttaac 57420
ccctgttttg ttttaatatt actatttttt taatattatt attttttgga ccctgggcag 57480
ggtctcattt tattttactg cccaggctgg tctcatactt ctggtttcag gggattctct 57540
agtcttggcc tcccagagtg ctgggattac aggcatgagc cactggacct ggctgagggg 57600
gtagctatca ttattattat tatttaagta atgttattgt agcccagtgc ttttgtttta 57660
ttcattaatt ttacatagag ttttattata gtgaattttg taatatctta tgaagtctag 57720
ttgtggtttt tggatttttt tttttttttt ggtagagaga ggattttgcc gtgttgctta 57780
gggtggtctt aaactcctgg cctcaagcaa ttcctcctgc cttggcctct caaattgctg 57840
ggattacagg tgtgaaccac caagcccagc ctatgaagtc taattttta gtgtttaaaa 57900 taatagtagt gactcttaat tcttgctcta atttatttct actttatgat aagagtaata 57960
tctcccttca gaataatcag tttcgatgtt atctgcatct ggtttacttg tgtattttgc 58020
aaaattccgc tattaaaggt atacactatt atgcagtctt acttgttagt tttaaagata 58080
ttttacaatc taagtaaata ctgaaattat ccaggagtag tggcatgctc ccgtggttcc 58140
acatcctcag gaggctgagt agggacgatg gcttgagccc aggaggtcaa ggctgcagtg 58200
agctgtggtc atgccactgc actctagcct gggcaacaga atgagacagt gtctaaaaaa 58260
aaaaaaaaaa atctgttgga aatttatatc aaaataggca gaattcactt ccagggaagc 58320
cttaatttta ataaaattca ttttctagga gtgtgtcaag gatttctaac aacatggttt 58380
tacagttttg gttaactgtt cattaaactc catgaggaca ggaactttgg tttggtattg 58440
tatccccagc tcctagaaca attgctggca catagtagat attcagtaaa cgtgttaggt 58500
gaataaatga atccatatag gacccataga aattgaattt gtgtgctact ttgggcaaat 58560
ctttttactt ctgatcattt tccaatcatt ttcacctcta ttagatctag tgctttgtcc 58620
attttttttc cttgttcaca ttttttaaaa tccataaatg gaaagaataa gaacaatggg 58680
aaaactttgg tggtagaata aaatgaaata aatatgcctg ttaaaaaccc ttggccaggt 58740
gcggtggctc acgcctgtaa tcccagcact ttgggaggct gaggcaggca gatcacctcc 58800
tgaggtcagg agttcacgac cagcctagcc aacatggtga aaccccatct ctactaaaaa 58860
tacaaaaaaa taaattagcc aggtgtggtg gtgggggcct gtaatcccag ctactcagga 58920
ggctgaggca tgagaatcgc ttgaacccag aaggcggagg ttgcagtgag ctgagatgac 58980
accactacat ttcagcctgg gcaacagaat gagactgtct taaaaaaaaa aaaaaaaaaa 59040
atgtctggcc gggcgtggtg gctcacgcct gtaatcctag cactttggga ggcccgcact 59100
ttgggaggcc gaaacaggca aatcatgagg tcaggaggtc cagaccatcc tgggtaacac 59160
ggtgaaaccc catttctact aaaaatacaa aaaattagct gggcatggtg gcatgcgcct 59220

-continued

```
gtagtcccag ctactcagga ggctgaggca ggagaattgc ttgaacctgg gagacagagg  59280
ttgcaatgag ctgagatggc accactgtat tccagcctgg gcaacagagc gagactctgt  59340
ctcaaaaaaa aaaaaaaatt tcccagcaga ccaggtgtgg tggcttatgc ctgtaattac  59400
aaccctttgg gaggccaagg caagaggatt acttaaggcc agaagttcag gactagcatc  59460
ataagcaagg ccctgtccct agagaaaggg gatggatggc ccgagcccct gagtttgaag  59520
ctgcagtgag ctatgatcga gtcaatgcac tccagccttg agcgatagca agacccaccc  59580
atgctggagt gcagtggcgt gatcacggct cactgcaacc tccatttcct gggttgaagt  59640
gattctcctg cctcagcctc ctgagtagct aggattacag acatgcgcca ccatgcccgg  59700
cttttttttt tgagagaatc tcgctctgtc accaggctgg agtgcagtga cacgatcttg  59760
gctcactcca agctctgcct cccaggttca tgccattctc ctgcctcagc ctcccaggta  59820
gctgagacta caggtgcccg ccaccacacc tcgctaattt tttttttttt tttgtatttt  59880
taatagagac ggggtttcac cgtgttagcc aggatggtct cgatctcctg acctcatgat  59940
ccgcctgcct cggcctccca aagtgcaggg attacaggcc tgagccaccg cgcccggcct  60000
attttttgta tttttagtag agatggggtt tcaccgtgtt ggccaggatg gtctcaaact  60060
cttgacctca agtgatccac ccgcctcagc ctctcaaatt gctgggatac agacatgagc  60120
cgccgcgccc ggcccaagac cctgtctctt aagaaaaaaa caaaaaacaa acctgaccat  60180
gtaaagaaat aaaactaaaa tcattaggat gttgatttca agagaaactt cttaaatgga  60240
tatttatggg caaagactag gatcgcctga atccattaaa tgaaagtata agtaagccag  60300
gtgtggttat tcttgcgtgt aatcccagca ctttgggagg ctgaggcggg aggattgctt  60360
gagctcagga ccagcctggg caacatagtg agacctcacc tctgctaaaa ttcacttagc  60420
caggcgtggt ggcgcatgcc tgtagtccca gctacttgtg gggctaaggc gggaggatca  60480
cttgagccca ggaggttgag gctgcattta gtcctgactg tgccactgcg ctccagcctg  60540
ggcaacagag tgagaccctt tcacaataaa aataataata ataataaata aatacagtgt  60600
aagtagttgg atcagtcaga ataaacaggg atataaaata atgttgaaag ccatgatgaa  60660
aagtttcaag atggttatat tcacataaaa tgcatgaagg aaacgataga aatgccagaa  60720
gaaataaata ggaatctagt tggaagtggg atttttaaca aaaaatacgt ttcttaacca  60780
aggaatagaa ccctgagttg cagcaggctg gccagtgaaa ccctctggaa caggaaaaag  60840
aacgctttct ctgctgtgtc ccttcagcac cctctagtga ccagtcttca cattcttcac  60900
atcatgtgtg ctgacaaagg agaaatgttt actaaccgtt tacctctgtg atcacagagc  60960
gggcaggagg gtagatttgg agctcagagg caataagttg atagctggca taggcatcta  61020
ttttatcatt ggacatctgt taagacagtg tttatctttg tgggaaaaaa cacttgggaa  61080
accaggtttt tttttttttt gagacggagt ctcgctgtgt tacccaggct ggagtgcagt  61140
ggcgcgatct tggctcactg caagctccgc ctcctgggtt cacgccattc ccctgcctca  61200
gcctcccgag tagctgggac tacaggcgcc caccaccacg cccggctaat tttttagtag  61260
agacgaggtt tcactgtgtt agccatgatg gtcttgatct cctgacctcg tgacctgccc  61320
acctcggcct cccagagtgc tgggattaca ggtgtgagcc accgcgcccg gccccagatt  61380
ttgtatatgc agtacaattg gtgttgtggt agtttaattg catactgatc tactagtctt  61440
gattttagca aattttcatg tttcgtacat ttaaatgtgc ttgttttaaa atctttattt  61500
cttggggttg agggtgtatt atactattaa aataaattgc attaaaataa atacgaatat  61560
```

-continued acttactctg ctttagaaag taatgcttca attggaatct gtcgtaagga attaattcta 61620
attccttgtt ctttctcttt ctcatttctt aggtgatcca gattaatctg aattcaatag 61680
ttccatctgt tagtggtcca aaaagacctc aggatagagt tgctgtgaca gatatgaaaa 61740
gcgatttcca ggcttgctta aatgaaaagg taggttactt tattcttatc cgtgtttttc 61800
aacccgcttt gtgctaagta gtaaagaacc aacaaggtga cccataaact caattcactg 61860
ctatgtttta tatattatgg cacacaccag cagccccctt attttccttc tgtctaatgt 61920
gcaagtcagt cattaggtaa gcttgttccc agttccattg tgaggatcag agattgattg 61980
tgtctattta aattaaaatt atatacaatt taaaattgag tttcttagtc acagtagtct 62040
catttttaaa tgctgaatac atatgggtct tgtattgatg aacagcatag ataattgaat 62100
agttacatca tcacagaaac tttttttttt ttttttgaga cagagtctca ctttgttgcc 62160
caagctggag tgcagtggca caatctcggc tcactgcaac ctccccccctc ccgggctcaa 62220 gcgattctcc tgcctcagcc cccaaagtag ttggaattac aggagtctac catcattcct 62280
gggtaatttt tgtattttta gtagagacag ggtttcacca tgttggccag actggtcttc 62340
aactcctgac ctcaagtgat ctgcccacct cagcctccca acagtgctgg gattatagcc 62400
atgagccacc gcacctggcc tacagtcata aaatttggta aatgtgaccg agtagcaagt 62460
ggtctctggc ttttgagggt ttgtattttc tgtctgagaa tcacagtttt agtcttgtca 62520
ctttctctat tctgagatct ctagtacttg gctttccttt cagagccttt ctttttatga 62580
tttcttgact ttttgttcag aaagtgttaa acttgtacaa aaacaaaata gtccactgaa 62640
ttgccatgta cctgtcaatt agcttcaata attagcaact catagccaat cttgtttcag 62700
ctatgctaca ctcacacaca taggatccct ttggaggaaa tcttcggggt catttttaaca 62760 gaaaaaaatt tctgccatct cttgagaatt actataaaca gggatgatta agaacaacaa 62820
agccaaatga gatctggatt ctgggtggta ggctggactc gcttagtaga taaaagtttt 62880
gcttgtgaac atcaccagac tcctgtcgtg cccatgcaga tttatgcttc agctgaatta 62940
caactactga atgttatggg cctttagcat cactcacaaa aaggattttt aatgttaaat 63000
catcaaatgt ccggtatctg ctatgttttc tgccagtctt ttattctgta catacccaga 63060
atatttagtt tatattttttg tggaaatttg tataggttgg atttaaaggc ttccaaattg 63120
cagctgaaaa acaaaaggat attgtctcca ttcattatga aggaagtgaa tataagctgt 63180
ctcatggatc agtggtcatt gctgcagtta tcagttgtac caataattgc aatccatctg 63240
tcatgcttgc tgcaggtggg ttgtggttta tggccatact ttttctttttt ccttaattat 63300 tgttggcttt tctgttattg taactttgtt tcttagatga tgcatgagtg tctacatttg 63360
atattgagag actttctagt attttagtta ggtcttaagg agcctgagtt tgatttatgt 63420
tgtttttatt acaccgaagg taaatttact gtttactata acttacctgt caattaattt 63480
taggttgtat ctgcttctct tgttaattta gaactatagt taattagcag gtatttcttg 63540
attatctaga agttaaccat aacagtgtgg tagatttcat taaaagttat aaaagtagta 63600
aaagatcatt gtcttggcaa ggattgtaaa tgaaattaat ttgtatgccc attggaacaa 63660
ttccttagtt gtataaaacc atgtataatg tgttacattg ctcttattgt aattatgact 63720
ttaaaatggt ttgctttaga aaaaagaaga aagagaaaaa atggttttgt taacatgtac 63780
ttatatatgt gcacctttttg tttactctgt gtgaatgatg tcagcctgta tcttaataat 63840
tttcaacata aaggctgtaa ttttaaattt gttgtaaatg aagcaaatca gtagaataaa 63900
gtggacaaaa taatgacagt aagtttatga attcatactt taatctgtta aataaattac 63960

-continued ttctcacttt ttactttaat atgggtgaga gagggaaaga aacattgcca taataaatca 64020
ttgtttgttg gctgtgcagg tcttttggct aaaaaggctg ttgaagctgg tctgcgtgtt 64080
aaaccttata taagaacaag tttatctcca ggcagtggga tggttacaca ttacctcagt 64140
tcaagtggag tattaccata tctaagtaag cttgggtaag taacagctat cgcacttcat 64200
attgatattg gtgttcagta ggtactgaag ctgcttgttt gtgcctttca tatacaaaga 64260
gaagatagaa aaaatatgct ttagttttac ttgctacctt gccattacca tacaattttt 64320
gatgccttat cactcaggaa acacttattg ggcatatcaa atgagcaaag caccaggttg 64380
gatacacaga agtaggagat gtggtcttag cttcaagata cttagttggg aagacaagac 64440
aaacaagtac aaccaaataa cagttacagt gtaagaaacg ataccaagta tgcacaattt 64500
ctgtgagttg tgtaggtcag ttcaaaaaag aaagaaatct tatagtttgc atttattaac 64560
tgaaaattgt cttaatttta gttttatgag gttattgggt ctataataca taagtttaaa 64620
ttgtccctga actttggaga aagtaactta tgttttttgg gctgggcgcg gtggctcacg 64680
cctgtaatcc cagcacttgg ggaggccgag gcaggcaaat catgaggcca ggagtttgag 64740
accagcctgg ccaatatggt gaaaccccgt ctccacaaaa aataccaaaa ttagccaggc 64800
gtggtgacgc acacccatag tcccagctac tcaggaggct gaggcagaag aattgcttta 64860
acctgggaag cggaggttgc agtgaaccca gatcgtgccg ctgcactcca gcctgggcga 64920
cagagcgaga ctccatctca aaaagaaaaa aaaaaaagta acctatgttt tttatgtaat 64980
ccaaaacaat tgatgctagt tgtgtgggga ttttttggtt ttgagacagt gtcttgctct 65040
attgcccaca ctggagtgca gtggtgcaat cacagctcat tgcagcctcg acctcctagg 65100
ctcaatcagt cttcctacct cagcctcctg agtggctggg accgcaggtg tgcaccacca 65160
cacccagcta atttttatgt ttttagcaga gacagagttt cactgtgttg gccaggctcg 65220
tctcaaactt gttcccttaa gtgatcggct cgtcttggcc cccgaaagtg ttgggattac 65280
aggcctgagc caccacaccc agcctagtta tattttcggt gtgtattttg gaacatatga 65340
gtcatcaatt ccattgcaaa actgataaat tttagacttt tttgctttta gaatagcatc 65400
tgaaagtaat ttagaggact gtgcctgtaa tcttttggtt atattatctt ggatttattg 65460
tcagagactc ttcttgggtt taactggttg ataattgaga gattactcct atcagagtgc 65520
ccaattacaa tcaatgcctc ttttgggacc tttggtcagg ttattatagc caggtcctct 65580
ttacatttta aactcttgga tggaagtaca gtatcaatta ttttaaaagg tcatgttata 65640
ttcctagcaa gtagtatttg ggggaattct cttgtacagt gataagtgct attaaggctc 65700
ttcaaaggtt tgcattcacc tttgagacca gcctgagcat ttttattttt tattttacaa 65760
aaaataaaaa aattagctgg gcctggtggc gagcgcctgt ggccccagct acttaggagg 65820
ccaaggagca ggattgcttg agcccaggag gttaaggctg cagtgagctg gttcaaatag 65880
catgcctgag agttagactt gattgctcag aatcttctga ggtgaatata ttgatgaagg 65940
ttaatccatg tgtcatgaat agtcttttaa gtaatcttat tacagtgata gaaatacaag 66000
ataagacttg tcctttctct ataaatgttg tgatgtgcta ttcagtcact ttttttttga 66060
aatgcagatt tgaaatcgtt ggctatggat gttcaatttg tgtgggaaat acagcaccct 66120
tatcagacgc agttttaaat gcagtaaaac aggtaaaatg tgtggattgg caagacatct 66180
aaatgatttt cttaactatg ttttgttact aaattataga aaatatatat tgatgtgttt 66240
atatttctgt aaactctgca cctcttggca atagtaacct gtgaatcttt aaatgattca 66300

-continued

```
atgaatcatt tgtagatcct tgaaataatt ccttcataat acaaggaatt gatttagttt  66360
atttgcaaga tgcatagttc tatatttaaa aattagtaat atgtttttttg gttaatctcg  66420
ccctcagact ttaagattgc ttatatatga ttatccagat ttgtaccatc tctagaattg  66480
aatttatttg tttgtgtgtt tgtgtttttt tcagggtgat ttggttacct gtggaatttt  66540
atctggaaac aaaaatttttg aaggtcgtct ttgtgattgt gttcgtgcca attatcttgc  66600
ctctccaccc ttagtggtag cttatgccat agcaggcaca gtgaatatag atttccagac  66660
agaacccttta ggtatctttt cctttatgta tatgtatacc tacacatact tttcccaatg  66720
gaagtcgtta tattttttgaa atgtttctta gaccatctat tctttgaatt atttcaggaa  66780
gacgtatgat aatgtatagt tattaatttc tgtgtttatg tgaagaaaat aaaatgtaca  66840
ggtaattagt tcttccagcc gcttaagcct gaagcaccct gttgaatcat ttacttgatt  66900
tccatgatat gtctttgaaa aggtatgaac attttcagag ttattttttt actgagtatc  66960
atgttcaaaa attttaacca ggtactgacc ccaccggcaa gaacatttac ctgcatgata  67020
tttggcctag tcgagaagaa gttcatcgag tagaggaaga acatgttata ctatccatgt  67080
ttaaagcatt aaaagataaa atagaagtaa gagtcttatg tgtttcttaa atagtttaat  67140
caatttgcag tgttctttta tttcatatat cttctgaata gaataaaaat taaaattaca  67200
ttattttgaa tacagttttt aatgtgtaat agtaagtttg tatctggaat ctgtagttaa  67260
aaagaaaatg gcggctgggc acagtggctc acgcctgtaa tcccgacact ttgggaggct  67320
gaagcaggtt gatcacgtga ggtccggagc tcaagaccag cctgaccaac atggagaaac  67380
cgcatctcta ctaaaaatac aaaacaatta gccaggcttg gtggcgcatg cctgtaatcc  67440
cagctactca ggaggctgag gcaggagaat cacttgaacc tgggaggcgg aggttgcggt  67500
gatccgagat cgcgccactg cactccagcc tgggcaacaa gagtgcaact ctgtctcaaa  67560
aaaaaaaaaa aaagaaagaa aatgtcttag aggatcagaa ttcattagtg ttgattggat  67620
gatctgtgca gcaaaccacc atggcacaca tttacctatg taacaaacct gcacatcccg  67680
catatgtacc ccagaagtta aaataacagt tgagggggga aaagaaagaa ttgattaggt  67740
gttcagaata catcattgaa caaaacacaa aattctcctg gggagaggca aataagctgt  67800
aaagagaata attagctaaa ttatgcaata tttattattt tttattattt attttttggt  67860
gtttttgggg agatggcacc ccactctgtc acccaggctg gagtgcagtg gcctgaagca  67920
gctcactgca gccttaacct cctggactca agcaatcctg ctcctcagcc tcctgagtag  67980
ctggggccac aggcgctcac catcaggccc agctaatttt ttattttttg taaaataaaa  68040
aataaaaaat gctcaggctg gtctcaaact cctggactca agtgatccgc ccacctcagc  68100
ctcccaaagt gttgggttta caggcgtgag ccactgtgcc tggcctaaga aatggtgaga  68160
tttttggctg tagtttgaag gcgttgatgt ggaacaaata cattgaaaaa gcagaggttt  68220
ttctccatta taacattctt agacattaac agcatacctc atacatgctt aatctctctg  68280
tagcaacata tagaaatctt tctaaattct ttaacttttt tggactctgt gaagtcttta  68340
tgttctgttt atattgaaac ttgccccttg gagtgttcct gaacatctgg tatgctagaa  68400
tttgaggagc aaatttttaa tcattctgtc caaaaacatc atgatttttt agaacacact  68460
gttttggctg ggcatggtgg ctaatgccta taatcccaac cctcagggag gccaaggccc  68520
acgtatcgct tgagctcagg agtttaagac cagcctgggc aaaaataaaa atttaaaatt  68580
ttttaaaaaa aagaaaagaa tacactctta attttctttc caaatggata aggcctattt  68640
ttgttgttgt tgttgtgacc taagtactat tttattccct tgatcatttt catgcgcctc  68700
```

-continued tttttctgag tccttttatc tttgctttgg ttcatcaacg aaaactgtat tcacagatgg 68760
ggaataaacg gtggaattcc ttagaagcac cggattcagt tttgtttcca tgggacttaa 68820
agtctactta tatcagatgc ccttcatttt ttgataaact tgtaagtact gttttactat 68880
ttgatctttt aaagattgtt ataaactaag aagtcttgta aagagttaaa tgccttgaac 68940
ttttaccttc tagaccaaag agccaattgc actccaggct attgaaaatg cccatgtctt 69000
attatatttg ggagactctg tcacaacaga tcatatatca cctgcaggaa gtatcgctag 69060
gaatagtgct gccgctaagt atttgacaaa cagagggtat gtgtacatgg ctttagagtg 69120
tttttgtttt ttcttgtttc ttactgatta agaggcttct attggtcttg ttcctttttt 69180
ccagtaaata catgctatcg taggtaatct gactgccaat gtgtttgtct taagcaagaa 69240
tggagagtgg cggggtgggg aggcgggggg taccttctgt acttgtcttt gcttgtgact 69300
ttagaaaatg aaattgcaat tttaaattga gcccttatag tctaaataaa cagctgattg 69360
gaaataagat ttttcttttt cagtgctact ttattgaaaa gtcagcttgg ttttacctac 69420
caaatgaagc ctgctcattt ggttaaaacc agcttcccat tattggagta aggaatttaa 69480
atgtgtattt tatgggctat aacatgtacg tgtgtgaggc tgggaatgat atgtacaaat 69540
caaaagacaa tgaatttctg cttcatgagc ctaaaatttt ataggaacaa taaacgtaaa 69600
ggccatttat attggagata taaatttaaa actggtaaga tttcatttct acatgattaa 69660
tcatgtagag ttgccctgtt atcaaaggac tgttttgaca atagagacaa agttttgtta 69720
aaagcaggat ttgtagtact gctacctgat tagcttattg gatgcttgtt tgatgcttga 69780
gtaattaaaa tgacaagctt tttcattgaa atttatttat ttatgtatgt atttatttat 69840
gtatttattt ttgagacaga ctcactctgt cacccaggct ggagtgcagt ggtgtgatct 69900
cagctcactg ccacctctgc atcccgggtt caagcaattc tcctacctca gcctcccaac 69960
tagctgggat tacaggcacg cgccaccatg cccagcaagt ttttatattt ttagtagaga 70020
cagggtttca ccatgttggt caggctggta tcaaactcct gaccaagtga tccgcccacc 70080
tcggcccccc aaattgctgg gattacaggc atgagcaacc gtgcccagcc aaaatgtcaa 70140
tgtagcttgt gttgacatgt gataatattg cacagctttt attataaagt ggtgagaaat 70200
aagtttcctt tcctgtaaat atttttttgg ttgtgatttc catcttcatc ataattgtga 70260
catacctcca aaaaagaaaa acagtcaaca cttctctcaa atgtacaatt tttgtaatta 70320
ttatgcctcc tgatatgtat ttcttagcac atttaatcca gtagtgctca tcaattagaa 70380
ttttctaaaa ataaagacac tcaaacctcc taccactccc atcctgaagt aaaaatttaa 70440
atgcacaaat ttagaatatt gttgcctctg cataaaagac caaatcagag gctgataaaa 70500
gtcagttgtt gattgttgag atacttatgt tcagttattt ttccctaaaa agttatatat 70560
ggtcactaat ccagtagcaa tacccccgc acccagatta tgatttctaa atactgtttc 70620
ccactatagt gaaccagtgc ttcatggaga aattattgat tccagatctg ggactggaaa 70680
atgtacacaa ttttaccaaa aattaccaag attaccaaaa ataaaattac aaagattacc 70740
tgatggtcac agaccatcag gcttctgtct aaaggtctca gggtcaggac cagctcatta 70800
gcttgaaaac tggtaaataa tcaattcttt aaccagcctt tcatgtatgg aatgtatttc 70860
agcataacca aatcattgat gaaggaaagt ttgtcatttg tttgtttgtt tgtttttaga 70920
gacagggtct cactcttgcc tgggctgaaa ggcagtggca cttggccctc tgctgcttgg 70980
aactcgtggg ctcaagcact cctcctgtct caccctcctg agtagcttgg gactacaggc 71040

-continued

```
tcgcaccgtc atgcctggat aatttttaat tttttgtaga gatgagatct ccctttgttg  71100
cacaggctgg tctccaacac atgggctcga gcattcctcc cactttggcc tcccagagtg  71160
ctggtattgc aggcaagagc caacatacct gctggaaagt ttttctttat agaacttttg  71220
tacctaaaaa atgaagaagg aatgggtgaa ttatagtatc actattttac ggtctctaat  71280
aagcaatcta gaccacaatg agcaatcact ggtaacattc caggaaaaga cagttggcta  71340
tcttgtgcct cctaatagaa gtacatatga cctatgaagc attgttgcca aaaattaaaa  71400
acccaaatct tatcaaacca ctggatctga catgtgattt acaagaacag aaggcagaag  71460
aacatgttaa atgattcatg gagatgcagt caacacaatg tgggtacaga aaactataca  71520
agtaacttta ttgcatcaga tagagcacaa gcaggaggaa ggagagggaa catatactgt  71580
cattcttcag tatagatgtg ggactggttc caggaccacc catgtatacc caaatccaca  71640
catactgaat tcctacagtc agccttgcag aagccacata tatgaaaagt cgtatttgca  71700
gttttctgca tcctgtgaat aatatatttt ctgtcagtgt ttggttgaaa aaaaatcgat  71760
gtataagtgg acccacacaa ctcaaattca tgtttaaagg tcaactgtag attaaaacac  71820
ttgagatcaa ctgaacacat ttatgaactg catttggatc ctgatttgaa caaaccaact  71880
tagtttggaa ataatcagtg acaatattga ctatctgatg ttaagaaatt attgtgattt  71940
tttttttttg gtgtaaagat tttttttaa gagtctacat cttttagtga aatgtactga  72000
aaagtatgct gttaaaatta tctcagtttt gcttcaaaat aatctaatgg ggttgactgt  72060
agaagaaacg gagcatctgt taagttatag cttggtgata ggcgcatgga cattcatggt  72120
tttgttttct tttgtgtttg aaattttctg tgataaaaaa atttttcaat aggtcttaca  72180
gctcaatagt atgtgattat tttccacatg taatgaaaac tgactttcat tactttcttg  72240
tagccttacc cctcgtgaat tcaactctta cggagctcga agaggtaatg atgctgtaat  72300
gacaagaggc actttttgcaa atatcaagct ttttaataag tttattggaa aaccagctcc  72360
taaaacaatt cattttccat caggacagac ggtgagaatg caaacaaagt atttagacaa  72420
tttataactg gatcaaaatt tgtattaaaa aattttgtgt ttgttttaat ctacagctag  72480
atgtatttga ggctgcagag ctgtaccaga aagaaggtat cccactgatt attttagcag  72540
gaaagaaata tggttcagga aactccagag actgggctgc caaaggaccg tatttactgg  72600
tattgaatct taaaatttat catcttaagc ttcaaagagt tttaactgtt ccctttttgtc  72660
agtaacatcc tgtcaaagtt tatctggatt ttttatagtt atttgaacct tataggtata  72720
gagggttttg tttgtttgtt tatttcagtg atctttggta atattttgta ctcatctagt  72780
tagtatcatt ttaatactct gagtttggta aaacctacat cagtcttatg tgaagaagtc  72840
agtataatag agggaaagga aattctgttt taaactattg ttttataatt atttatacct  72900
attgatcatt ttttttggtt ttttagtttt gagaccatgt ccttgtcacc cagactggag  72960
tgcagtggcg caatcactgc ttgctgcagc catgacctcc caggtgcaat cagttctcct  73020
gcctcagcct cccaagtagc tgggactacg ccatgagtta ccacacctgg ccaatttttg  73080
tattgtttgt agagatcgga tctctctatt ttgctcaggc tgatcttgaa ctcctgggct  73140
caagtgatcc tcccgctgtg gcctcccagg gtgctgggat tacaggcttg agccatgtgc  73200
ccggccccca ctgttaattt tacttgcctc cttttgattt aattttctcc gatttgcccc  73260
atcagtgggt aaaagactca gaagtagtag gccaagttgc acctttttttc cccctaaata  73320
ggagattgtg gtgcctggct gtctgccagg aggacatttc tcctgagact gtttccttgt  73380
tgcagagcaa ataggccatc tgctgggggg gaatagtcat gtgacatgtg ctttttgcca  73440
```

-continued

```
tttcatactc acagatgctt ctctttacaa ttgtagctgt aaaaaggctg gctgaaacac  73500
agataccatg caggcctcat tcttatttta atctttaata tctcctttaa aatgtaaata  73560
ctctgagggg ctgtgggaat aaaacaaaat ctcatccttc taagatacta attataagta  73620
ttattatgag tattaatgat aggtataggt tatttttatc ctggaaattg ttttagtgtt  73680
tgtttttgat gttggaagct ttccttatat ggcaggtgat gcttggccct ccatttgtta  73740
gacattaaaa aactgattac aagccatgga tgggggctgg gttgtgtcag ttactgggcc  73800
ttactatagg tgactgggtg ataagctacc tttttcatta agcgattcta tatgtcatta  73860
tctgtatttt ctctgaggcc attcagtttc ttgaaggaaa gagactcgtt cagtatgtag  73920
acatctactt agtcccctgt tttcaatctg gtattctcaa gcccctgtgc ccagtgtttg  73980
tcagtttaga gaatgtattc tcttccttat ttctgctata acaaaaaatg agtaaaaatt  74040
tgtaaaaaat gagtaaaaaa gaacaaaaat tggtcctcag gtggtaaaaa aaattctact  74100
ttttgcacat aaagtacaga taagagtaca ttaaaagata cacagcatct ttgtggtact  74160
aaaatttgg agagaaggga ggtgaacagg aagacacaat ttgggggaaa aaagtcttaa  74220
aagactcctt aggtagacag tggagaaaaa agttgaaaaa cacaagtcta gagcctttgg  74280
ctcatttttt ccagagaata aacctctact cttgtggagt ggggattgag ctggatctta  74340
ctgctttgta tggccttgta acctgtgtcc acgagtattc tgagaacctc atgcctctga  74400
atctcaatcc ttttcctggg tcttgtgttg cacattaact cagaccttac tggtatcact  74460
ctctaatttc attttatcat tctgcggttt cagcattgtc ttctaaatca cttacctatc  74520
tctgttttct aaatattcat agaattctct catcctattc cctttgttgc tgtgggctta  74580
taccctcttc attattgttg ttacttattt gtatttttttg gagacagggt ctcactctgt  74640
cgtccaggct ggaatgcagt ggcatgatct cagctccctg caacctccac ttacaacctc  74700
aagtgactct cctgcctcag cctccatagt agctgagatt acaggtgtgc accaccatgt  74760
ccagctaatt tttctgtttt tagatagaga tggagtttca ccatgttggc caggctggtc  74820
tcaaactcct ggcttcaagt gatctgccca cctcggcctc ccatagtgct ggcattacag  74880
gtgtgagcca ctgcatccag cctattcttg ttacttttta ttgtattttt tatttttatg  74940
ttttgtagag acagggtctc actatattgc ccaggctggt ctcaaactcc cggcctcaaa  75000
taatccttct gcctcagcct ccaaagtact gggattataa gcatataagc cactgcgcct  75060
ggccctatat accttcttta ttcctttatt ttagtggcat ttcaagagtg ttgaaaacat  75120
atgttagatc tggcatgttt aaatagaaat ccttctgagc cctactttgg ggtcaaggga  75180
gccggcccat ttatagagct cttatgatgt ggtaggcagc ggcagtactt aaccctagag  75240
cagcagaaag ggatccgaat aatttagaga gctccataaa aattcagaaa aataatctgt  75300
aagaaggttc tgtaaatact ttgataaaat attgattcag tatgagatat tagactaaaa  75360
gtatttagag aaaggccaaa gtagattttt gccccctta aatgctcaat aaataacttt  75420
cagaagtgat tagagggaat aaaatgcaca tttattacag ggtgtgaaag ctgttttggc  75480
cgaaagttat gaaaaaatac acaaagatca tttgattgga attggcatag ctccacttca  75540
gttccttcca ggagaaaatg cagattcctt gggcctctcc ggtagagaaa cattttcttt  75600
aacatttcct gaagaactgt ctcctggaat tacattgaat atacaggtat ctctaaattt  75660
ttcaaatata tgattatgca ctcaaatgtt tatgaattat tgaataagaa tcaattgctg  75720
taaattatat actaatgtca cttaatgaat gttaagttgc catttaagat gactctctct  75780
```

-continued

```
tccatactta gatctagcta tgttaatagt tcatgttctc tgaggaaaag tggaaagaac  75840
tgggtgctta taccagaaaa aaagaacaca tgaaggggaa tcttgacttc cacttaacaa  75900
gtgtcagctt tcttttcatg gtggtcattt ttttgctgtc ctgatctaat tttaaccgag  75960
gcatacatac cactccaaag agagcaaagt tgagcgttca aagttagagc aaaacagact  76020
ttacaactaa gaaaaaaggg gaaagagtag gagttactga ttacatgcaa tcaatatttg  76080
gtgtaaaatg aatgtgagta gtgagtataa cttccccaat taataagtca aaatctaaat  76140
gcagctattt ttctacttaa ctatgaagcc catggtcagg tatctcaggt gtttttcaag  76200
cagcagcaaa gtttcaggca atcagaatat aagaaattag aaccaagata aatcagacag  76260
aatctgtggc aagtatagtc attaaatatg aagacaaatg gtcttaacca tcaagtagca  76320
cctggaagat ttacttgctc acatgagatg tttttgctcc tttcaagaca agcactggaa  76380
aagtattcag cgtgattgct tcgtttgaag atgatgtgga aataacatta tacaaacatg  76440
gaggattatt aaactttgtg gcacgaaaat tctcatagta tctacttacc atagatacct  76500
ttcataactg gtaactgcaa agccttttgt gctggaccca ggaatcctta ccatggagca  76560
gcagatagtc ccagtatact cacttatctc atccatggat gtaaatgatg atgaatcaac  76620
atagtaactg aaatgaaatc ttcttgattt taaataatat acgaatggtg ctattaatat  76680
tgctaaaatc aacgtgtgaa gtgtgttgtg gaagagacct gtaagtatgg ggggggggcg  76740
atattttatc agaccatttt gtaaataaag gcagaatttg tgttgaagat tcttatatga  76800
ataaccttcc tggatttgtt tagttttgca ccaataaaac tgtgtactac tgtttgttgg  76860
tttaagagta gcagattgaa atataagaag ccagattaga ctctaaaatt gtggccattg  76920
gaatctcatt tataaatgga ccttttaagt atattaattc ctcttcagaa ttgagctgga  76980
cacatttggc attcttagtt tgtcatataa ccaggtttat ccttagtcta actgcaaggg  77040
atggaacctg ccccaggtca caatcattct gtccaatcca gccaaggttc cctccacata  77100
tgaagatgga ccatggcagg atacaactga ttgtgtggca ccatgtatta gcagtgggaa  77160
tatgtatcac atatgatgca gcctttcata tttcagcagt ttgccactgt gactgtctgg  77220
caagccccca gatggcgtta tattaattgg attagattat tttgctcacc ttatgtaata  77280
ctgtaacttc ctataaccta atattttcgg tatcattaac caaaatttca cactcatagt  77340
tgctaaagag aatgttattc aatcattaaa ctctgaactg atttcttcta tacatttaaa  77400
ttatccaccc tcaataatac gggtgctcaa ccctatgcat tttttaagtg ttgctatttc  77460
ttaattaaat tgatttcctg tcattttgaa tcatttatca cctgcgatgc atgattctat  77520
taattttgtt atgttactgt tttaaccaaa gctgaccgta aggataaaac acttaagttg  77580
ttgctgagta ctatatatcc tcaatatgca tgtctgccca tcacatcaaa tgttctgtca  77640
acaagatgtt tggtaatttt ttttaaaaag gttggaaaat taattataga aggttctata  77700
ctgttttttt aattaagaaa ctaagtctag caggctaaag gttaattgta gtgatttttt  77760
ttcacataga tatctttcta tgacctagtt agttactgca attcagaatt agttcacatt  77820
gcataaagaa ttacttgttg taagcaaaat gctgaaacta ccaaaccagt ggatgaagac  77880
cactaagaac tttgcacata atcatacaat cttttgaaaa tattttgcaa atatgtgttt  77940
agacaataag atggactaga gttcgacaaa atgatttctt tatttaaatt ttgtataagt  78000
attttcttcg acactttcaa attatattgt gttcttgata tatgctgtat atttatttgt  78060
tagtgcatgt gtttttaatt tacatgaaaa catgagttag gagaaattac aggttgaaag  78120
atgaaatgcc tgtatgtgct ctgaagaaat ggtaattcca gattgtgcag gggaaacaa  78180
```

atctattttg ttttgttttg ttttttgaga cggagtcttg ccctgtggct gggctggagt 78240
gcaatggcgc gatcttggct cactgcaacc tccgcctccc gggttcaggg gattctcctg 78300
cctcagcctc ctgagtagct gggactacaa gcatgcacca ccacgcccag ctaatttttg 78360
tagttttagt agagatgggg tttcaccatg ttggccagat gatctgaatc tcttgacctc 78420
gtgatccgcc cgccttggcc tccacaagtg ctgggattac aggtgtgagc caccacaccc 78480
ggcctatatt gttttgaaag catactctat atatagttat gggcagaggc acaggcatcc 78540
tcagcagctg attcaggaga tgatggtaaa gctagctaac tatgaattaa acattcacat 78600
atccagtcta cctggtccag taataataca agcaaatctt gtatttcagg aacaaatcaa 78660
ggttctctta attttttggc ttatatacaa tgaagtaaaa acttgataaa catggtttca 78720
aattgaggag gagagtcttg gatgtatgtt ttaatatgta taccttataa ttctgcctct 78780
agccaaatgc tatgtttgca aaatgtggca tctgttagtt tttattgtct gtgtcttctt 78840
tgtttactat accttgggta attttgtgtt accaaaaaaa aaaaaaaaaa aaggaagtgt 78900
aatgtcagac acacaagaaa agcaaatcag tgttgtaagc ttaaagtaca atttcaaagg 78960
tcactaccaa cagcagggtt ttttttatac tttgaaaaca ttatgctaca tatcattgcc 79020
attttcatat tttggggttt tgctactctt atacaatgga atcaatggaa atgtcatcca 79080
gccactgaat tgccattatt atatctaaaa agtttctaag atgacagtta tcactatttt 79140
gttttatctc catgctgaca tttgaaagaa ggtactagta tccctctagc cagattgctt 79200
agtttttcgt tggtaatcaa acaacagttg tactaaagga aagtaaagct aggacctaaa 79260
tcagaatcat agttgcctgc atatatggta acaaggtcgt gtgcatttgc tttcacagtg 79320
atgagtgaga ggatgagaag aaattatttg acatttttct gtggttgaat agaagacacc 79380
tttcttttgt ctttaggttt aggaggagat actaagatac tggatgttta tcctatctta 79440
gtttggttgg agtaataaga gagaagaaga gggtggactt tggcttttca gtgtttttttc 79500
ccctaaagag tgatattgct gacgtttcta tcaattttac acataaatatg tggctatgaa 79560
accatatatc tcacttaagt aacaaagtaa tcactttgtc tatcactaag taatagacaa 79620
aaatcattgt ctattattta aagccaacaa aacagtgtaa cagttttaag ttcaataatg 79680
ttaagtattg tatagaaata tattggaggc aaagttcagt tgatgacaat tgtgtatatg 79740
ttactgatgc tgtaaattat ttttaataaa gaaaattgta ttatcacatt tgattcttgt 79800
tctgttttgt agtagttgaa aataaaacaa catgatgtaa aaaatatgct gccatccggc 79860
tgggcacggt ggctcacgcc tgtaatccca gcactttggg aggccgaggc aggcggatca 79920
cgaggtcagg agatcgagac catcctggcc aacacagtga aaccctgtct gtactaaaaa 79980
tacaaaaaaa ttagccggac atgatggcgg gcgcctgtag tcccagctac ttgggaggct 80040
gaggcaggag gatagcataa acccgggagg cagagtttgc agtgagcaga gttcacgcca 80100
ctgcactcca gcctgggcga aacagtgaga ctctgtctca aaaaaaaaaa aaaaaagcaa 80160
aaatgaaatg tcccgccatc cagatgccat ccaggagcag ctgaggatgc ctgctccctg 80220
tgctgcccgt tcattagtgt tcatgaaaca agtcatcgga agctgggagc caggatccca 80280
ggtgtatttg tttgttctcg cattggtata aagaaatgcc tgagactggg taatttattt 80340
taaaaagagg tttaattggc tcatggttct gcaggatgta caggaagcat gatgctggca 80400
tctgcttggc ttctggggag gcctcaggaa acttacaatc aaggtggaag attaagtggg 80460
agcaagcact tcacgtggcc agagcaggag gaacagagag acaggggagg tgccacacac 80520
ttttaaacaa ctagatctca ggagaactca ctattgggac aacaccaagg gggatggtgt 80580
taaaccataa gaaaccaccc ccataatcca gtcacctccc accaggcccc acctccaaca 80640
ctggggatta caatccgaca tgagatttgg gcggggacac tcatccaaaa agacgtatcc 80700
tttcttccca ctattattag caacctaaaa gagtaaggtt tatttcttag aattcagtaa 80760
tcataaacca taattggcac tttattagaa ttttctaagg attccaattt agtattctaa 80820
gaagtttgca ttacctaaag gctaatacca acataggcac aagctgatag tttgaatatg 80880
cagtctagga ggaaacttaa gagcttcatc agtgtagcat ttagttggtt tacagttttc 80940
acttgatgct aattttgctt tttaattaca aagtagcttc agatttacca ttttgatttg 81000
atgtatgttg taaacctgtg ttctgtactt gaaaaatgca tttattgcaa aagcagatgc 81060
atatgtaatt ctcacaaaat ttgctggtat aatgacaagt gtggccaggc gaggtggttc 81120
acactttggg aggccaaggc aggaggcagg aggatcactt gaagtcagga atttgacccc 81180
accctgggca acatagcaag accctgtttc ttaaaaaata ataataatta gtttggtgtg 81240
gtgctgtgca cctgtagtcc cagctagttg ggaggctgag gcaggaggat cgcttgagcc 81300
taggttgagg ctgcagtgag ctatgattta tgccactgca ctccagcctg ggtgacagca 81360
agaccctgtc ttttaaataa gtgtgttgtc actgtgaatt ttgtgtttat gtggtgttag 81420
tactgaattt taagcatttt tttcagtatt tccctatcaa tatctatatg atctgtggca 81480
gggtcccttt ttattaccaa tattggtaat ttgtgttttc tttttttttcc ttgattagtc 81540
tttctaaagg gttagaaatt gagttaattt tttaaagagc caatttttta cattattttc 81600
tccattgttt tctggttttt tgtttggttt tggttttgga ttttttttt ttttttttct 81660
ttttgagacg gaatctggct ctgttgccca ggctggagtg caatggtgcg atctcggctc 81720
actgcaacct ccacctcccg ggttcaagtg attctcctgc ctcagcctcc cgagtagctg 81780
tgattacagg catgcgccac catgtctggc taatttgttt tgtattttta gtagagacgg 81840
ggtttcacca tgttggccag ggtggtctca aactcctgac cttgtgatcc gcccaccggg 81900
gcctcccaaa gtgctgggat tacaggcatg agccaccgtg cccggtttgt tttgttttat 81960
tggtttctgc tctgaagtat ttcctttctg ttacttattt aatttcctcc tttcccccag 82020
ctttgtaaca cttttcctcc aatgtaaatg taaatattta aattttcctc taagtgctgc 82080
tttagctgta gcccaccgtg gaaactaaag ccaatttttga gcattttaaa caacttgtaa 82140
tatataaagg aagtatcata aaactgctgg gatattgttt tatgagacat tgttttataa 82200
tgtaaaatca tgtccataat ctcactgcaa attgttcatt ttgtttcact ccagttttgt 82260
ttttttttt tttttatcgc tgagctcttt tttaaaaaaa ttataaaaat agaggtgggg 82320
gtctcactgt gttgcccagg ctggtcttga acgcctggcc tcaatcagtc ctcccacctc 82380
agcctcccag actgctggga ttacaggcat gagccaccat gaccagccac tgagctatgt 82440
ttgagagcaa ctacttaaaa gtgctccagt agccaactga agaaacgtta atacaatgac 82500
atgacatttt tccccccctag aaacgggtct cactatgtgg cccaggctga cctcgaactc 82560
ctgggctcaa gcacttttcc tgcccaagcc tcctggagta gctgggacta tagacatgca 82620
acaccatgcc ccgcttaaaa tgacatatct ggccggacac ggtggctcac acctgtaatc 82680
ccagcacttt gggatgccaa ggcgggcgga tcacgaggtc agttcgagac cagcctggcc 82740
aacatagtga aaccccgtgt ctactaaaaa tacaaaaatt agctgggtat ggtggcatgt 82800
gcctgtagtc ccagctactc gggaggctga ggcgggagaa tcgcttgaac ccaggaggcg 82860
gtggttgcag tgagctgaga ccgcactgtt gtactccagg ctgggcgaca gagcaagact 82920

-continued

```
ctgtctcaag aaaaaaaaaa aaaatgacaa cgcatcttgt cttacattgg tggaactttt  82980
taaaatgttg taaatgttgt aaatgtttaa aatccaatgt tggtattatt gagaggaaaa  83040
catgatttga caacatgtat taagaggctt agaccgggtg cagtggctca cgcccctaat  83100
cccaacattt tgccaggctg aggtgggagg attgcttaac ccaggagttc aagaccagcc  83160
tgggaaacat ggcgaaaccc gtctctacaa aaaattagcc ggacgtggtg atgcgcacct  83220
gtagtcccag ctactcggga ggctgaggtg ggtggatccc ttgaccccag gaggcggagg  83280
ttgcagtggg ctgagatcac gccactgcac tcccgagtga cagagtgaga ccctgtctca  83340
aaaaataaaa aggccttaaa agtgtttatt ctcttatacc tagtaatatg atgctgagca  83400
gttttaaaca cataaagtgc acgaaagatt tatgtatgag gatattatta tttttttttt  83460
tttttgagac ggagtctcgc tccgtcgccc aggatggagt gcaatggcgc gatctcggct  83520
cactgtaagc tccgcctcct gggttcacac cattctgctt cagcctcccg agtagctggg  83580
actctaggtg cccgccacca tgcccggcta attttttttgt attcttagta cagacggggt  83640
ttcaccgtgt tagccaggat ggtctcgatc tcctgacctt gtgatccgcc tgcctcggcc  83700
tcccaaagtg ctgggattac aggcgtgagc caccgcgccc ggccgaggat attctttaaa  83760
acaaggaaat ggtcacttaa agtgaaaaag gcaatttaca aagtacattt tttttttct  83820
tttttgagac agtattgctc tgtcatgcag gctggagtgc agtggtgcga tctcggctca  83880
ctgcaaactc catctcccag gttcaagcga ttctcctacc tcagcctcct aggagctggg  83940
attacaggcg ctagccacca cgcacggcta atttttgtct ttttagtaga gatggggttt  84000
caccatgtta tccaggcggg tctcaaactc ctgaactcaa gtaagccacc tccatcggcc  84060
tccccaaatg ctcggattac aggcgtgagc caccacaccc taccaaatac tatatttcag  84120
aagaattcag ggagtggaaa tgcacatacc aaagagggca gttgtggatc caatagccct  84180
gcctccaatt ctcacaattt ccagattcaa tcttaattcc cattccctca tcccaagaga  84240
agtagagaaa gaccagtaga gctggaataa tgacaggtgg aaataactca gaagccactc  84300
aaggcaaaaa gcatgcagag gggcctaagg gagccaatag gattccaatt ctggttacag  84360
aaaaatccaa gtcaaaatca ctctttgaca atctaaagga atgagatatt aattatgttc  84420
ccctggggtt gtgaaaaaca gccctgcctt ttggagatta gaagtgaagc aggtaagaac  84480
catatctaaa gcaggagaag aagcttccct cagtaggtgg ttgatagggg tctgggaatc  84540
atccaagtta atcagggtga ctatagataa tccgagtgtg ttatatcctg acagaaaaca  84600
aagggtggat gtgcattggc aaaaacaaaa taagaaacca atttgcaggc atgagtggac  84660
cagtacccag gactctcttc cagtagccta cagtagatag agggctctga cttatcggag  84720
aagtcctgct tggctggaga agggcatcaa gctgtttatc agcgcctcat gcccttaaca  84780
gttaagacca tccaactaac ctggctgtta ctccatgaat ctcgtgcagc tttctgaaaa  84840
tcatggggtc tctgcggact ttcctgcaga aagagagccc actgattcca ctacctagat  84900
aaaggcgtgg tggtgggccc ctgtaatccc aactactcgg tgtaagaatt aaagaaagag  84960
gaaagaaaca cgaaaagtgg cttggtggtc ataagaggtt tattttagag aaaacctgag  85020
aggggcgtct ggccaagtta ggtcagaggc acactctctt acagactaag taagttttta  85080
aggattcgga gtgggagagt ttatcagagg cttggactgc ttctgtgtct ctttgttgtg  85140
cttatctcgg agggagagtt gtgtgtctgt tcccatacat ctttctgcag ctgcagacat  85200
accccctgag tctaattttt gtatttttag tagagagggg tttcaccatg ttggccaggc  85260
```

-continued tggtctcgaa ctcctgacct caggtgatcc tcccgcctcg gtctcccaaa tttctgggat 85320
tacaggcgtg agccatctgc gccctgccta aactgttcgg gttctaacat tccagcatcc 85380
tcctgcggaa cgcagccagg ccttactcag gccttccaat caggaccctt acagttcctg 85440
gggctgggat tgcgagtctc tctggggcca cgctttctaa gcgtatcact tccaggatac 85500
gtgcctccaa cagaaggaat gaaggctagg aaacaaaaac gtggatgcgg gtgaggagct 85560
gtcagtgtta ccgccacgac aacgtggacc ctgcgaaact cggaggtgcc actcaagagc 85620
cgaaagcctg cccactcggg gtggggcggc aacccggaga gccaatcagg aataaggagt 85680
ccggttcatg aaaaggtagc cggattctga ctgggatact cactgtgaga aggctgggcg 85740
gagttgcaga aagtcaacag aagccgaatc tctgaatttc tgttcgcagc ctcctaggcg 85800
gggccgggaa aaaaatccag tagtctgcgc tgactgggcg gcgagggacc gggaggagcc 85860
aatcagaagt caggactcgc ggggcttgga ggaggggcgc gggcgctgcg gcccctgctc 85920
tacctcctag cgccggtgcg cggccgaggc cgcactacct gtctgcggga aagcgggatc 85980
caccccagga cgtcgggtcg ctgccggtga gccaaggagg gggaagcaga gacgagccct 86040
gcgtccccgc tgcgggagtc ggggtcgccc ccgagggcag ggaggctcgc tgcaagtgtg 86100
gagccgggag tcctatgcct caggctcctc cagcccgcgc tatcctcagc tcgctgcgtg 86160
cgtgatgggc aagtcaccct tcttcccgga cctcacctgt aacctaggag ggctgagctg 86220
ggcccccaga atgaaagcgt ggcacccgag aagctgtcga ggccagccct cccgggtctg 86280
tgtggggtcg ctggccgagg gctgtgccgg cgcctggccg gtgtctactg ggagcagtct 86340
ctgagctccg ctgaacctca cttactcatg cgccctcctc ctctcttttc ctgcctcttg 86400
gttcagcagc ccctctgcag cccgctcacc caccactttt tccccttcac ccaccaggaa 86460
gacccttaaa agcacctagt aatgcactgt tgtctttgaa aaactgcaga tgctagattc 86520
cccacctttc tgtttcatga tccccttggg gttgaactgc cccgtgagtc tgtggaatga 86580
aggtcaccct tggttcacca tttaatatta aataagggac tagcctaggg gctgagaata 86640
cagagattga ctgggtataa tcccttggaa ggacgcagca aaagggaatg taggagaaga 86700
aaggtagagt tggaagacat gctaaggtag aatttactag actttgttac acgttgggag 86760
tgagggacag gaaagaatca agaatgactc ctgtttcttg tctggtatac tttgcacaaa 86820
gtacagagct taagttccag ccccctcccg gctgcaggac aaaggtggtg agattctgac 86880
gcagatcttg gagttggaaa tcacacttgc ttcctgcggg ctttttcagg agctaaatac 86940
tgttggccgg atatatagac caacagccta tagtacctga attcctcctc tccctttcaa 87000
tgaagtagga aaaaaagtta ataattttta aaaatgtgtg agtgggcaac atagcgagac 87060
actgtctcta aaaaaataaa aataataaaa tcaaaaagac agccatgatg gcttgcacct 87120
gtaatcccag cactttggga gaccaaggta ggaggattgc ttgagcccag aagttcgaga 87180
ccagcctggg caacatagtg ggaccctctc tctccaaaaa aaaaaaaaaa aaaaaggcca 87240
ggcatggtgg cacctgcctg cagtcccagc tatttgggaa gctcaggtgg gaggatccct 87300
tgagcccagg agttggaagc tgcagtaagc agtgattgtg ccactgtact ccagactggg 87360
tgacagagac cttgtctcaa aaacaaaaaa aaaaaaattc ccctccatac aaaggagaca 87420
tttggttaag acagacatgt ctgataaaca tatttttttc tttgttttta tttactctca 87480
agagttgact tgatctgtgc cattagttct atgatatgga gcgcttatat aaagaaaaaa 87540
ggcgaactta aagaacttta gtggcatgga atactagagc tagaggagac ttttagtaat 87600
aatctaatcc aactctgttt tagaggagac atgactagtc cagagtttca gaggttaggt 87660
agcagaactg ggactaaaat atgtcctatt tctcccagca cagcctttta ttacatcagt 87720
ctatttggat ggccagagct aacaaccttg ctttacatgg ctatggaaaa cagcgctctc 87780
ctaagaggag cttaacaagt caaagattgt atgggaacat ctggaataga aaggagattg 87840
gccttcacca gttgcctcta aggttcctta caactttaag aacttatcat tcatttcaaa 87900
ttcagaattg ttctgacatc gttaacgctt tgggagttga aaatgactcc aggatttcat 87960
cttggagtta atgcttcagt ccatattgca ttttgaatac ttaccttata ccagtttaca 88020
tatctccaga aagaatgtta aaattccttg taaagtttta agcctaaata cagtgtgaca 88080
ggatatgttg gttcccagaa gtttcaagtg caaagattgt tttgaaactc catttaggct 88140
ttgtcacagt accttcagtg aacaaaatct gaacggctta acttgcttct gaaagcaaat 88200
gcctggttag aaagtaaaca ggaaacatga ttgtcaagaa ggcattaact tgcagtaaca 88260
ggtgatggaa accgatcagt ggcacaagct atgcaagtta agaggctgga gcaatcactt 88320
tgggtaggag gatcagggaa ggccatggca ggggctaggg ggtggttagc gtttgagggt 88380
tacctctccc ttattttctc ttctcttttt ttttctttct ttcttttctt tctttctctc 88440
tctctctttc ttctttcttt tctttctttc tttctttctt ctttctcttg ctctctcttc 88500
tctcttttct ttcttttctt tacttttctt tctttttgat ggaattttgg tctttcgccc 88560
aggttggagt gaagtgacgc agtctcatct cactgcaacc tccacccctc tgggttccag 88620
tgattctcct gccgcagcct cctgagtagc tggaattata ggcgccggcc accatgcccg 88680
gctaattttt tttttatttt tatttttatt tttagtagag atggggtttc gccatgttgg 88740
ccaggctggt ctcaaactcc tgacctcagg tgatccaccc acctcagcct cccaaagtgg 88800
tgggattaca ggcgtgaacc actgtcttta cctaccctta ttttaacttg agtcatcagg 88860
ccatagtcct aggactgagg cagggagggg gtcatatagg agatttctgg tatatctccc 88920
tgaatgttat cccctttccc tcactggagt taggtgggtt tttgctatga tacagccaaa 88980
taaattaggc attaacaggc atatggtctg atttttagag ttccaagaaa gtcctaagat 89040
ccacctcctc tgtcctagcc aatttctcag aagcgctctt tctttttttag aggtaaattt 89100
tacattcagt gatattcaca gatcttacta gtttacttag gttttaagtt aagttttgac 89160
aaatgtaagc catgtcgcca aagcctaatc aagatgtaga acacttgcct ctcagaaagt 89220
tctctcatgc cccttccctg tcagaagcaa tacatcttcc actttccaca aaagctaact 89280
cttcatgaga ttcttttttt tttttttttt ttttttttta aatagagaag cgggtctcat 89340
tatgttgccc agactagtct cgaactccta gccttgagtg ttctcccacc ttggcttccc 89400
aaagtgctgg ctgggattac aggtatgagc cactgtgccc agcccataag attattttta 89460
tatagtactg tatcccctga acagcaatca aaacataccc taaaatgcag ctcaccctca 89520
cgatgttatc aattatttac aacttagtat gaaagaagga ttagaataaa actattttgg 89580
gaaaacagca tgagattcta acgaccttaa atatttggtt cctgaagcat gttcagaaga 89640
cctacattgt ctttcatatg tagctggatg ctcagaaaat ataccaggtg tgggtagcag 89700
agggtggaat taccaagaga aagaaaacag tctcctcccc cgcccatgta tccaaatcat 89760
acttaaaaat tcaaggccca gcgtggtggc tcatgcctgt aatcccagca ctttgggatt 89820
acaaagcaga ggcaggcaga tcacttaagc ccagaaattc aagaccagcc tggccaacat 89880
ggtgaaagcc tgtctctgca aaaaatacaa aaaattagcc tgatatggtg gcttctgtag 89940
tcccagccac ctaggaggct gaggttcagg atcattgagc ctggtggttg aggctgcagt 90000

-continued

```
gagttgtagt catgctattg cactccagcc tgggcgacag agcaagaccc tgtctgaaaa  90060
aaataaaaaa aaaaaaatca attcaggcca ggtccagtgg ctcacacctg taatcccagc  90120
actttgggag gcgtaagtgg gaggatcgct tgagaccagg agtttgagac caacctgggc  90180
aacaaagtga gacccccatc tctatcttta aagataaaaa ttcaaatcta tcttctcaag  90240
aatgtcttcc cttaggctgt agtaatttct ctccctctca gcttctgtca cagttttggc  90300
agatattaat ttcataggtc acaaactcaa atgtaacttt attttttgta attgacctta  90360
attttaattt taagccccta ttcctctcag cagtggaaaa catattcttt acaatttaag  90420
gtaaactcag tcacttcagt gttgattcag tcatttcagg ttaatacgta tagttaatac  90480
agggttttct ttggttctct ggccttatct cctccagtga ctcacacaat acttagctca  90540
tcagtctaca tttttctatt tgaaatatgt gtaataaatt agatgatctt ataatttaac  90600
caaactgtta ctataaaaga tcactgtatt tgaatttatt gtttaaccta agacggtagg  90660
aatatagtca aaaggacata atcatggatt agaagtctgg agagctgaat tctttttttc  90720
tttttttct ttttcttttt ttttttttt ttttgagatg gagtctcgcc ctgttgccca  90780
ggctagagtg tagtggtgcg atcttggctc actgcagcct cgacctccca tgttcaagtg  90840
attctcctgc ctcagcctcc cgagtagttg ggattacagg cgcccaccac cacgcccagc  90900
caatttttgt attatcagta gagacagggt ttcaccatgt tggccaggct ggtctcaaac  90960
tcctgacctc aggtgatctg cctgcctcag cctcccaaag tgctgggatt acaggctcga  91020
gccaccacgt ccagccccag agctgaattc ttactgtgac ttaatatgta actttgggca  91080
agtcacttaa cctctcagga ccaaaatttc ccctataaaa ttaatggggg aggaggaggg  91140
aatggacgaa gtgataccaa ggtgctttcc tagtctgtgt ttgggaggta agtttaaaaa  91200
taatttgtcc tataagaatt tgtatgcagt tgtcaaatca tctacttctt gatcttattc  91260
actgatttga ttttcttttt aactttatga gtaaaactta acaatcaaaa gaagtacaga  91320
atcaacagaa acattactgg tctgtcttga gaaaaatcat ttaaataaat atattcatcc  91380
tgtgtcccct ttctgtttgt tgctttttgt tcccctagac ataatgtcaa gtggaaacta  91440
tcagcagtca gaggctctta gcaaacccac tttcagtgag gaacaagcct ctgcgttagt  91500
ggagtcagtg tttgggttga aagtttccaa ggtccggcca cttcctagct atgatgacca  91560
aaactttcat gtctacgttt caaaaaccaa agatggccca actgaatatg tcctcaaaat  91620
aagcaacacc aaggctagca aaaatccaga cctgattgaa gtgcagaatc acatcatcat  91680
gtttctgaaa gccgctggat ttccaacagc ctctgtgtgt cacactaaag gagacaacac  91740
agcttctctc gtgtctgtag gtaagagatg accaattcgc cgatccatta cctatccaga  91800
cacatcactg cattttggcc acaagtagaa ctatgaagag caggttcata attccaagtg  91860
tagatgtggt tgttattatt ttttagcacc tcaatagtac acccttagag gtggttgtgt  91920
tttcggtgct gggagaagct acagcgtcat caaagtggtg attggtcctc tgattgagta  91980
gtggttagag cccaatgtgg tataagtttt ctgtttagaa aggccctgac agatagtaac  92040
taaggggact tgtggaaatc aggggaatat tttttgtttg tttcgtattt tttgtttgtt  92100
ttgttggtgg ttttgggatt ttttatttgt ttgtttgttt tttgagacag gggtctcact  92160
ctatcaccca gactggagta cagtggcgca gtcacagctc actgcagcct tgacctcctg  92220
ggctcaggtg atcctcccac ttcagcctgc tgagtagctg ggactacagg catgcatcac  92280
cacgcccagc taattttgta gtgttctgta gaggcagggt ttcgccatgt tgcccaggct  92340
ggtcttgaac tcctggcctc aagtgatctg ccttcattgg cttcccaaag tgctgggatt  92400
```

-continued

```
acaggcatga gtcaccatgc ctggcctgtt tttttgtttt ttttttttaac cagaaaaata  92460
ataaaacatt tttattattt agagaagcta taaattctgg tgttgtggta tagtagaaag  92520
aatataatac tggaaatcag gaaatcagga attttagatt ttagctttgt cattactgta  92580
tatgtgacct tggacacata gaccacttaa atccctaagg ccgccagtcc tcatctgtga  92640
gacagccctt ttcacctcta aatactaaaa tgctgagaat ggacctaatt cagctcttta  92700
agcaacaggc taaaaccaat ttcttgaaat tttttaaag gttcgaaatc ttgattgtct  92760
ttttctctct taattgttca ccattctttc ttaatttgca ttgctccaaa tacgtgaggc  92820
ccattgtggt ccctgagaca cagttattgt cctgtgttgc aaacacaggc tgtcccacaa  92880
gaagcctgat tctggaagtc atttatttgt acctcactcc cctcaattgt gaacttatga  92940
aagagtatgt gtttttgctt tcatttacca cagtaagtaa tttctgtgta gagctaaggc  93000
cagcagagtt agggctataa ttttgttggt atgtaaatgg ccagttccaa tgttgttaag  93060
gtttgtatat tctaccttct tgcttcatcc actcaactct gcttcataga atcctgccga  93120
gctgttttag gttagcacat ttttgttgtt gttctgtaat ttctgttctt ttcagtaata  93180
cttgcagagg cagaatagct tctaattctg ttatatctaa atacctctct ctctctctct  93240
ctctatatat atatatatat ataaataatt tagtcaaagg atattttatt ccatccattt  93300
agatagtggc tctgaaatca aaagctactt ggtgaggctg ctgacttacc tcccaggaag  93360
acccatcgct gagcttcccg tcagccccca gctattgtat gaaattggaa aactagctgc  93420
caaattggat aagacactgc aggtaagatt tggggcttta ttttattcta agggatgttt  93480
gtttgcttgt tattttattt ttaaaataaa gtatggatca gattctcttt ttatgtatgg  93540
tgctacctaa ggtatgttat gaagggaatg gagtcctaga gtgcatacat tttatgacag  93600
taaggctaac ttctacctaa ctcttactgg tgtaggccag gtgttgtggc ccacgcctgt  93660
aatcccagcg ctttgggagg ctgaggcaga ggaatctaac ttgagaccag gaatttgaga  93720
ccagcctggc caacatagtg aaaccccatc tcttctaaaa aacacaaaaa tttagggcat  93780
ggtggcgtgt gcctgtagtc tcagctactt ggaagactga ggcaggagaa tcgcttgagc  93840
caggaggtgg aggttgcagt gagccgagat cacaccacta tactccagtc tgggtgacag  93900
agtgacactg tctccaaaga aatttttttt tttttttttt tgagacagaa tctcgctctg  93960
tcgtccaggc tggagtgcag tggcacgatc ttggctcact gcaagctctg cctcccagat  94020
tcacgccatt cttctgcctc agcctcccaa gtagctggga ctacaggtgc ccaccaccac  94080
gcccggctaa tttttttgtat ttttagtaga gacgaggttt cactgtgtta gccaggatgg  94140
tctcgatctc ctgacctcgt gatccacccg cctcggcctc ccaaagtgct gggattacag  94200
gcgtgagcca ctgtggccag cccaaaaatt ttttttaaat taaaaaataa ataaatctta  94260
ctggtgtgtt ggaaagatta cctaaatttt tagaaattca tgatattctt catgctgctc  94320
actgaaaaca gtcaatattc acaaatagaa acctgaagat ttcatccagt cacagtataa  94380
tcaactggag ccccatataa agcaatagct aggttgcaaa tggattaata atgtatgtta  94440
aggatgtttt tgccctatag aaacaatata atgtatgaca ggtacctttt agacccaccc  94500
ataaaacatc ttcatttatt caatattgac tgagtacctt ttatgttatt taaaaaaaat  94560
cacaggacaa aggaaatata tttactattt attaagtgga aatggatcat cataaaggtc  94620
ttcattgtca tcctcatttt gagtgggctg aggaggagga agaagagaag ggttggtctt  94680
tttttttttt tttttttga gacagggtct cactctgtct cctaggctgg agtgcagtgg  94740
```

-continued

```
tacagtcaca gcttaatgca gcctcgaatt cccaggctca agcaatcctc ccacctcagc  94800
ctcctgggta gctgggacta caggcgtgtg ccaccacacc catctaattt atttttgtat  94860
tttttgtaga gatggggttt caccatgttg cccaggctgg tctcaaactc ctgagctcaa  94920
gcagtcttcc cgcctctgcc tcccaaagtg ctgggatgac aggcatgagc taccccatgc  94980
ctagccaggg gattggtctt tgtattaggc cattcttgca ctgctataaa gaaatacctg  95040
agactaggta atttatacag aaaagaggtt taggccaggt gtggtgactc acgcctataa  95100
ttcctgcatt ttgggaggcc aaagcaggag gatcactcta aggccaggag tttgggacca  95160
gcctaggcaa catggtgaaa ccctgtctct actaaaaata caaaaaatta ccctggcatg  95220
gtggtgcatg cttgtagtcc cagctacttg ggaggctgag gtgggaggat cacctgagcc  95280
caggaggttg aggctgcagt gagttatcgc accactgcac tccagcttgg gtgacagagc  95340
aagaccttgt ctcaaaaaaa aagaaaaaag aaagaaagaa agacattgct ccacttcttg  95400
cttgcatcag gtccttttct tttctttctt tctttctttc tttctttttt ttttttttt  95460
tttcgagaca gagtttctgt ctgttgccca ggctggagtg caacgctgtg acctctgcct  95520
cccgggctca ttgcattatt tctgacagga aatctgccat cagatcgtcc ctctgaatgt  95580
aatgtgtctt ttgtatgtgt gtggctgctt ttaagacttt ctcttgaggc caggcaaggt  95640
ggctcacacc tgtaatccca gcactttggg aggctgaggc aggcggatca cttgaggtca  95700
ggagttcaag accagctagc ctggcccaca tggcaaaacc ctgtctctac tgaaaataca  95760
aaaattagct gggcatggtg gtgcacgcct ataatcccag ctgctttgga gactgaggca  95820
ggagaattac ttgaacccag gaggtggggg ttgcagtgaa ccaagattgc accactgcac  95880
tccaatctgg gtgacagagt gagactccat cttaaaaaaa aaagaaaaaa aattctcttt  95940
atctccagtt ttgagcagtt tgattaaggc gtgacttgta tagttttcct catgtttgtt  96000
atgcttgtca ttcactggga taccttgagt ggatatactg aagttacttg gaagcagttt  96060
gatccttttg ggtcatgctt ttactacttg atagatggga ccaaggacca atttactact  96120
gatcaaaatc cttcagtgtc ctgtgagctg tgaggttttc cagtgtggat ggtaggaaca  96180
ggcactcttc ctggccctgt gcgtgccatg tactcttccc tctaatcttt tcaggtggct  96240
cgttccccag ttttgagtag tttcctcaca tttacacatg ggtcatacac ccatctgcta  96300
atttctcaag ggggacataa tgcagatccc tgaagtgctt tctctctgca gctctcccat  96360
ccctggtaat ctgtcctgca aactcaaact cctttggtct ccccagactc tcaactctac  96420
ctcctcaact cagagagtcc tctgggctcc gcctgggtct tccctctctg cactgcatcc  96480
tctgtcaagg cagtgagctg gggcaaactg cccttgtgtg ttttattttt tattttttt  96540
gagacagggt ctcactctgt cacccagact agagtgcagt ggcacgatct cagctcaccg  96600
caacctccgc ctcccaggct caagggattc tcctgcctca gcctcctgag tagctgccac  96660
caccgcccgg ctaatttttt ggtatttgta gtagagacag ggtttcacta tgttggccag  96720
gctggtcttg aactcctgac ctcaaatgat ccacccacct tggcttccca aagtgctggg  96780
attataggtg tgagccacca cacctgggcc ccttgtttgt tttcattctc tcagggatca  96840
ctgtttttca ttgcctaacg tctaataact tgaaaaccag tgtttaacgt attttgtcca  96900
ctgtttttgc tttttctggc aggagggtaa gccccgcgtt acaccccctat tggccaaaaa  96960
ctgaagacca ggccgggcgc agtagcttac gcctataatc ccagcacttt gggaggccga  97020
ggcaggtgga tcacctgaag tcaggagtta gagaccagct ggccaacatg gtgaaacccc  97080
atctactaaa aatacaaaaa ttagccaggt atggtggcgg gcgcctataa tcccagctac  97140
```

```
tggggaggct gagacaggag aatcacttga acccaggagg cagaggctgc agtgagccga  97200
gattgcacca ctgcactcca gcctggacaa gacagagcaa gactctgtct aaaaaaaaaa  97260
aaaaaaaaaa ctgaaacccc tgttgcagtg taaatagtat tcatttatcc ttagatcctc  97320
aaatagaaat attgtaacct ttttttctga gtaaaaatcc ttccatgatc cattatttaa  97380
agaaaaccag ataaaaatac aaagaaaaat taagttacca ctaattccat catccagaga  97440
tgacattctc tgaaccattt attccatgcg ccacgctatt ccacagcccc aggggcatac  97500
ttggtgctca gcatatgttt ataaacccac agaccttttt ctatacttac aataatcacc  97560
attttatatt gcactctatc cgtttattca acaaatattt attgagcttc tgcaagggtt  97620
tgggtggtaa acatattaaa catttccgtc aaaatagttt tcaagtaagt ttgagcaaat  97680
tcatttgtgg actttttgtta aaatgttcat ttgttcacaa taatataagt tggatttaaa  97740
tagccctttc taattaatat atttttagga aatcttcaca tattaatttt gtttagaaaa  97800
acctttgaac tgggccgggc acagtggctc actcctataa tcccagcgct ttgagaggcc  97860
aaggtaggtg gatcacttgg ggtcaggagt ttcagaccag cctggccaac ataatgaaac  97920
cccatctcta ctaaaaatac aaaaattatc tgggcttggt ggcaggtgcc tgtagtccca  97980
gctacttggg aggctgaggc aaagagaatc acttgaaccc gggaggcgga ggttgcagtg  98040
aggcgagacc gcaccactgc actccagcct gggtgaaaga gtgagacaac gtctcaaaaa  98100
aaacaaaaac aaaaacaaaa acctttgaac tgattgtagt gctcaataaa gtctgtctac  98160
cttcctcaga cttaaaccta ctattgaggt ttaaatgact gtctgttaca taatagtttt  98220
cctttaccag taacctttcc ttccgcccta tctgtgggct tcattcatat gcctatggcc  98280
actgaacttt caacttttcc tgctatattc tgaaaaagca atacagtttt agagggaaat  98340
agcaccacat cattgctgac agtgagtcaa ttctgctatg catttaggca cctgctgctc  98400
tgctgtgcaa ctttaagttg tcttacagag gacgagggag ctctagaggg aaccaagcat  98460
tcttcatttg gcattacatg cattttatca tgcattattc ctgttgctca tcccctcacc  98520
cagtctcacc ccatgccttt gcaggagctg agttctttat ttatttattt atttatttat  98580
ttatttattt ttattgatca ttcttgggtg tttctcgcag agggggattt ggcagggtca  98640
taggacaata gtggagggaa ggtcagcaga taaacaagtg aacaaaggtc tctggttttc  98700
ctaggcagag gaccctgcgg ccttccacag tgtttgtgtc cctgggtact taagattagg  98760
gagtggtgat gactcttaac gagcatgctg ccttcaagca tctgtttaag aaagcacatc  98820
ttgcaccgcc cttaatccat ttaaccctga gtggacacag cgcatgtttc agagagcaca  98880
gggttggggg taaggtcaca gatcaacagg atcccaaggc agaagaattt ttcttagtac  98940
agaacaaaat gaaaagtctc ccaggtctac ttctttctac acagacacgg caaccatccg  99000
atttctcaat gttttcccca cctctccccc ctttctattc cacaaaaccg ccattgtcat  99060
catggcccgt tctcaatgag ctgttgggta cacctcccag atggggtggt ggccgggcag  99120
aggggctcct cacttcccag taggggcggc cgggcagagg cgcccctcac ctcccggacg  99180
gggcagctgg ccgggcgggg ggctgacccc cccacctccc tcccggatgg ggcggctggc  99240
cgggtggggg gctgaccccc ccacctccct cccggacggg gcagctggcc gggcgggggg  99300
ctgacccccc cacctccctc ccggacgggg cggctgagga gctgagttct tagtttttct  99360
ataagtacta agaatgtaga gtctatgaaa gataatacac aagtgtggta ttttagtcat  99420
gtaggcatgg ccgaggctgt ggctgctctg ctggggacat ggttgggcca ttgaagcttc  99480
```

cagcagttgg tcaggtaggc ctgtgggatc caaagtaggc aggagttctg gggattgtag 99540
gggccagaac tgaggagtta acaagtgaag ggaccaacta gtactggaat ttggttgcca 99600
tttggtcctc agatgggctg gaagtcaatc tcaggagatt tcattaatta taagaaagaa 99660
gaaagtatag gacaggctta tgagtatgat tgtggtcaaa gctttgtact agaggacaca 99720
agatgcatgg gaaatgggag ctggggtatg gggtggagaa tgagggagtt attcgattgg 99780
tgcaaaagta attgcgggtt tgccattact tttaattgca acactgcaat tacttttgca 99840
ccaacctaat aacaagagga gggctaagat aggctaatag agagtactga ttaaattatc 99900
aagaattcag gttggtgtag caaggagtca agaggataga aaagccggag aagtcaggca 99960
gatcaaggac aacactgatt ttaacaaaca tgtattgagc acctatatgt atgaagtttt 100020
catttcatgt cttagtgagt ccacaattga ttgtaaagct ggtaattgat agcttgattt 100080
tgctatctaa ggaaactaaa atctgggata ttaagtggta gagccagttg aaacctagat 100140
ctgtctgagt gaaccccagg attcttccca gtaccccata ctagagctga gaagttctat 100200
ggctgcgtgg gtcaatcgtg ccatcatttc agaagctgac tcagagcctt ccccgagtag 100260
actgtcactc cactggaaac ccaactagaa tattatattt cacttccttt cttcttcttt 100320
ttttttttt ttgtaatgag gtgagatctc actatgttgc ccagggtagt ctgagctcaa 100380
gcgatcctct caccacagcc tcccaactag ttggtattat agacatgagc catgacgccc 100440
agctatttta ctttctttaa aaataaaaat aataaatatg cacagttaaa atttcaaaca 100500
gtactgaaag gtatgaaatg aagatttttt ctcaccacca tcatctccat tcctccacaa 100560
tcccacactc caaaagtaat agctcctaac agtgtttttt cagtgcttac tctgcagtgc 100620
ttttgtgatc tgcattggca tttaacacac aggatgttaa ataaacaaaa gagaagactc 100680
cggttcgaga ccagcctggc caacatggtg aaaccctgtc tctactaaaa aaaaattttt 100740
ttaattagct gggtgtggtg gtgtgtgcct gtaatcccag ctattgtgga ggctgaggca 100800
ggagaatcgt ttgagcctgg gagatggagg ttgcagtgaa ctgagatcac gccattgctc 100860
tccagcctgg gtgacagagt gagactccgt ctcaaaaaaa aaaaaaaaaa aaaaaaggga 100920
agactccaaa gctgggtgcg gtggctcacg cctgtaatct cagcactttg ggaggctgag 100980
gtaggtgaat cagttaaggc caggagttcc agaccagcct ggccaacatg ataaaaccct 101040
gtctgtacta aaaatactaa aaaattaacc ggacatggtg acacatgcct gtaatttcag 101100
ctacttggga ggatgaggca ttagaatcag ttgaaccttg gtggcaaagg ttgcagtgag 101160
ctgagattgt gcaactggac tccagcctgg gcaacagagt gagactctgt ctcagaaaaa 101220
aaaaagaaaa aagagagaga gagggaaagg actccgaggg agcaggagta ctatcctcaa 101280
aaatctggag gactaatcct attccagatg ggcccagagg tcatagttgg aaccagtggc 101340
atggatacta ttagagaggc agaggcagat tttaactgca caaaaggaag aacacaaagc 101400
catctcaata agggtaaaaa gtacctacca tgggaagtgt gttagtccat tctcaaattg 101460
ctataaagaa atacctgaga ctgggtaatc tataaagaaa atgggtttaa ttggcgcatg 101520
cttctgcagg ctgtacagaa agcatagtgg cttctgcttc tgaggaggcc tcaggaagct 101580
tctaatcatg gcggaaggca aagtgggagc aggtgtctta aatggcaggg gcaggagcaa 101640
gagagagcaa gccgggggtg ctgcatacct ttaaacaaca gatttcatga gaacacactc 101700
actgtcatga gagcagcctc aagaggatgg tgctaagcca ttcatgagaa accaccccca 101760
tgatccaatc acctcctacc aggccccacc tccaatactg gggattacag tttggcatga 101820
gatttggtga ggacacagag ccaatccata ttatgctgcc cctgtcctcc caaatgtcat 101880
gtccttcttc caatgcaaaa tacaatcatc ctttctcaac agtcccccaa aattttaact 101940
cattccagca ttaactcaaa agtccacagt ccaaagtctc acctgagaca agacaagtac 102000
ccttctgcct atgagcctat aacatcaaaa acaaggtgtt tacttctaag atacaatggg 102060
agtatagaca ttgggtaaac actcctattc caaaagggag aaatcagcca aaagaaggga 102120
ctacaggcct catgcaagtc caaaacccag cagggcagtc attaaatctt aaagctccaa 102180
aataatctcc tttgactcca tgtcccacat ccaaggcaga ctgatgcaag ggatgggctc 102240
ccaagcctgg ggtagcccca cccctgttgc tttgcaaggt tcagcccctg tggctgctct 102300
caagggctgg tgttgagtgc ctgtggcttt tccaggggca gggtgcaaac tgctagtgga 102360
tctaccattc tggggtctag aggatggtgg ccctcttctc acagcttcac taggcagtac 102420
cccagtgggg actctgtgtg gggctccaa gcccacattt ctcctccaca ctgccctagt 102480
agagtttctc catgagggct ccacccctgc agcaggtttc tgcctgaaca tccaggcttt 102540
tccatacatc ctctgaaatc caggcagagg ttcccaagcc tcaactttta cactctgtgc 102600
acccacatgc ttaacaccac ttggaagcca ccaaggcttc tagcttgcgc tttctgaagc 102660
agtggtccaa gctatacccg taccataccc ctttgatcca tggcttgagc tggcacaact 102720
gggacgtggg gagcaatatc ccaaggctgt gtagggcagc agggccctgg gcctggccca 102780
caaaaccatc ttgtcctcct aaccctccag gcctgtgatg gtaggggctg ccacaagtct 102840
ctgaaatgac ttcaagaact tttccccatt gtcttggcta ttagcgcttg gctccttttt 102900
acttatgcaa atttctgcag ccttcttgag gtcaggagtt cgagatcagc ctggccaaca 102960
tggtaaaacc ccgtctctat taaaaacaca aaaattagct gggcctggtg gtgggtgcct 103020
gtaatcccag ctactgagga ggctgaggca ggagtatcgc ttgaacctgg gaggcagaga 103080
ttgcagtgag ccaggatcgc gccactgcac tccagcctgg gcaacagaga gagactctgc 103140
ctcaaaaaca aacaaacaaa caacaacaac aaaaaacagg tctcatgaga actcactcac 103200
tatcacaaga acagcaccaa aggatagtgc taaaccattc ataagaaacc accccctatga 103260 tccaatcacc acccaccagg ccccacctcc gatattgggg attacagttc tacatgagat 103320
ttggtgggga cacagatcca aaacatatca agaagtattc aaacaggcta cgtgactatt 103380
tagcaagaaa atgctactga taagagaatt atcaggggaa ggttctcaaa ctcccggtca 103440
taatagtgag tactgaaatc catttagagg aacttttttt ttttattttt atttgtttat 103500
ttatttttga gatggagtct cgctctgtcg cccaggctgg agtgcagtgg tgcgatctca 103560
gctcactgca agctctgcct cccagattca tgccattctc ctgcctcagc ctcccaagta 103620
gctgggacta caggcacccg ccaccacacc cagctgattt tttgtatttt ttagtagaga 103680
tgtggtttca ccatgttagc caggatggtc tcgatctcct gacctcgtga tctgcccgcc 103740
ttggcctccc aaagtgttgg gattacaggc gtgagccacc atgcccagcc tagaggaact 103800
tttaaaagaa atctaatttt taaattttat tttttatata tatatttttt gagacagagt 103860
ctcactctgt cgcccaggct gaagtgcagt ggcgcgatct cagctcactg caacctccgc 103920
cctccaggtt caagcgattc tcctgcctca gcctcccaag tagttgggac tacaggcacc 103980
caccaccatg cctggctaat tttgtgtatt tttagtagag acagggtttc accatgttgg 104040
ccaggctggt ctcgaactcc tgacctcaaa tgatccaccc acgttggcct cccaaagtgc 104100
tgggattaca ggcatgagcc accacgccca gccagaatat aatttttaaa aacaccagaa 104160
tatgtcacat gtaatggtct aagtgttgtt tactgagact ttttctttat atgtgtgtgc 104220

-continued ctgtatactg gggttatgat gtaaaatata tttcttactg caagtcatgc aaaaaagttt 104280
gaaatcaact tcactggatg accatcaaag catcttccag cgctcactct gtgaaagagg 104340
tctcaactgt gggtcacaag atccaggtcc tccctcagcc ttataataac aagtcgttat 104400
ccctctatga atctgtttcc ccatttgtgc aatgatagtg aaaattattt acaactttag 104460
atagagtggt caaagtctaa aggcccttcc aattccagaa ttttttaatt ctaagaacat 104520
cctttaattc agcaaatatt gctcaagcag tgccttcaat gtgccaggca ctgttctagg 104580
tgtggggata caggagtgaa caaaacagac aaaaaacagc cctatccctc atggagctta 104640
tattctagtg agagtagaca gtaaaataag taagtgaact atgacaaatg ttagcaataa 104700
gtggtaagaa gaaaaaataa gcagagacga caggtacaaa atatcagaga gagggttgaa 104760
attctagatg gagtggtcag gacattctca cagagaaggc gttttttgag taaagacctg 104820
gtagaaatga cggcactaac catgtggata tctggtgaag ggcatcccca aaaagggaaa 104880
cagcaaaagc aaaaggctgt gaggtgggaa cgtgcctagc atgttccttg aacaacaggg 104940
aggccagggt ggttggagta ggtgagcaaa ggcagtagaa gatgaagtca gagaggttac 105000
aaggggcatg ggtgagaaca gagttcttta gagctgcctc caatttcttt tgtaagctgt 105060
gggcaataat gcctatcttt acataattat gaggatcaag tgagctggga atgtgctccc 105120
caaactgaga gatcctgcac agatatgaag gcttactatt ttgtgagtta aagtaaatgg 105180
ggcaagtcaa tgaccatgag agaatgccag ctctctccct cacagactcc ctggccagtc 105240
tagagcaggt agtcttctga agcagcacat ctcttgtgac agtgagtgag ttctcacaag 105300
acctggttga ttaaaaatgt gtagcaccgg ccgggcgagg tggctcacac ctgtaatccc 105360
agcactttgg gaggcccagg tgggtggatc acctgaggtc aggagtttga gaccagcctg 105420
gccaacatgg tgaaaccctg tctctactaa taatacaaaa aaaaaaaaaa attaaccaag 105480
catggtgaca tatgcctgtg atcccagcta ctcgggaggc tgaggcagaa gaatcgcttg 105540
aacccaggag gtggaggttg cagtgagtcg agatcgtgcc actgcactcc tgcctgggcg 105600
gcagagtaag actctgtctc aaaaaaaaaa aaaaaaaaaa tgtgcagcac ctcccacctc 105660
tctcagcagt ggttgctctg tcaagagact aagaatatct cgcttttgat ttagagattc 105720
catcacccaa agttaagtag tcttcatcgg gagaacttca tctggaatct gaaaaatgtt 105780
cctcttctgg agaaatacct gtatgccctg ggccagaatc gaaaccgaga gattgttgag 105840
catgtcattc atctgttcaa ggaggaagta atgaccaaat taagtcattt tcgagaatgt 105900
gagtattctc ccaattaagt atttttcttg atatttaaac tgtccaattt catatcatca 105960
gaaaagtatg gaggtacaat ttagctttat caaatcttaa aattttgcca tatttgctcc 106020
tattgctttt taaataataa tatttttact ttcctcaaaa ttgctacatt tgaagcctcc 106080
tctaaacttt acatgagtct acctctcttc ttcccattaa atttgcacat tacatatgta 106140
tgatttataa attatttata gtagggtttg tgtttttcaa actttatatc aatggtatca 106200
cactgtgtat tattattctg caacctgcct tttctattca gcatgttttg cagattgatc 106260
catatgaata tttgtagttt taatttagtt tattagtttt aactgctaaa tagtattcca 106320
tagtatgaat ataccataat ttatttgcat gtactataat tttttggtcc attctcttgt 106380
taatggaatt ttaggttgct tcccatttct ttgctacata aattatgctg caatgaaccc 106440
tctagtacag gagtccccaa accccaggaa ctgggccaca cagcaggagg tgagcagagg 106500
gaaagcaagc attactgcct gagctctgcc tcctgtcaaa tcagcagcag catttgattc 106560
tcataggagc acaaacccta ctgtgaactg cgcatgcaag ggatctaagt gagaatctaa 106620
tgcctgatga tctgagatga aacagtttta tcccaaaacc atccttccgc tgtctcctgt 106680
ccatggaaaa attgtcttcc atgaaaccag tccctgatgc caaaaaggtt gggaactact 106740
gctctagtat atatctatct ccctgtgtac acagacaggt gtttctctag gctatatttc 106800
tagatataac cagccttttc atccagcatt aagtactggt caaaggcaag gaactggctg 106860
ggtgtggtgg ctcccgcctg taatcccagc actttgggag gccgaggtgg gtggatcact 106920
tgaggtcagg agtttgagac tagcctggcc aacgtggtga aaccctgttt ctaataaaaa 106980
tgcaaaaact agctgggcat ggtgacgcgt gcctgtaatc tcagctactc agaggctgag 107040
gcagaagaat tgcttgaacc ctagaggtgg aggttgcagt gggcctaggt tgtgccactg 107100
cactccagcc tgggcaacag agcgaaatcc gtctccaaaa aaaaaaaagg gcaaggaact 107160
gaagggcatt tctatcaagg cctaagatag gcagtatgtg tttctcagtg tttccttact 107220
ccgtgtaaac acagtgtaag gtgtagcgta aaaacagagt tgatttttc ccttcaaacc 107280
tgtttttccc ccagtcttat tcatctcatt aaagttgtat ccaccattca cctagttaat 107340
ctggacaaaa agttagcagt cataggcttc actttgtgct ttctctcatg tcacaaatcc 107400
agtcaaattc tatccattct ttcttcaaag gagagcctat gatctggatg attgcagtag 107460
ccttataact ggtctccctg ctcctactct gcctctctac catatatatt cacttgtctt 107520
cccttttttt tctcaatact acttttgtaa gattctgcgt gtcattgcat atgctagagt 107580
tggttaactt ttataactct agaatattgt attcactaat ataccacaca ttattctact 107640
cttaaaagat acttgggttg ttccttattt ggggctatta agaacagtgg tgccgtgaac 107700
atgcttgagt ctcagtatac atgttcatta gtctttgagt gtataccttg cgataggatt 107760
gctaggtcat aggacatgtc tatattcagc ttcactggat aataacaatg ttttcaaaag 107820
tggttctatg aatttatact acagctagca gagtgtaaaa gttttcattg ttctacaccc 107880
ttggtgtggt cagacttcta aaatttttct caatctgatt tgtacataat agttgatcat 107940
cacatcatgg ttttaaaatc catctctcta tttattggcc atttgaaata tattcttgag 108000
aagtgccaaa tcaagtcttt ggcctttttt ctattgaaat tattttttc tcattgattt 108060
gtagaaatgc taaatatatt ctggatatga gtcctttact agttatatgt gttacaaata 108120
ttttgtccca ttctgtggct tgtcttttca tggtacagta tgtttggatg cataattcta 108180
aatttttttt ttgaggcagt cttgctctgt cacccaggct ggagtgcagt ggtacgatca 108240
cagctcactg cagcttcgac ctcctgggcc caagcgatcc tcccacctca gactcccaag 108300
tagctgggac taacctatcc accatcatgc ctggtgaata tttttatttt tgtagagata 108360
gggtctctct atgttgttca gactggcctc aaactcctgg gctcaagcga tcctcccacc 108420
ttagcttccc aaagcactaa gattacatga gcaaccgcac caggcccctg ttattttttt 108480
acagctttat tgagatatag ttcacaaacc atgaaattca accattattt atttattttt 108540
tttttttttt tttgagctgg agtcttgttc tgtcacccag gctggagtgc agtggtgcaa 108600
tctcagctca ctgcaacgtc cacctcctgg gtttaagaga ttctcctgct gcagccatcc 108660
aggtagctgt ggccacaggc gtgtgccacc atgcctggct actttttttg tattattatt 108720
catgggtatt tagaagtata aatcctgttc cccaaaatat gatgaacttt tttggttata 108780
tcttattgtt catttctact gtaattacat tgtgatcaga gaacatactt tatattagtg 108840
ctgtccagta ggattttctt caatgaagga aatgttctat atctgtgttg ttcaatacaa 108900
tagctcctat gtggctatgg gcatttgaaa tgtggctagt gctactaagg atattcctta 108960

-continued ggactttcaa ttttatttaa ccttattgag ctaaaaaatt ttttttata gctggggcta 109020 caggcatgca ttaccatgcc cagcagattt ttttttttat agaaatggag tctcactatg 109080
ttgcccaggc tggtcttgaa ctactggctg caagcgatcc tcccacatca gcctctgaaa 109140
gtgctgggat tacaggcata agccaatgca ctcagcttaa atcctgtttt ggttttttttt 109200 gtttgtttgt ttttgttttt ttaagacaga gtctcactct gttgcccagg ctggagttca 109260
gtggcgtgat ctcggctcac tgcaacctct gcctcctggg ttcaagtgat tctcatgcct 109320
cagcctccct agtagctgaa attatgcacc accacaccac gtaatttttg tatttttagt 109380
agagatggag ttttgccatg ttggtcaggt tggtcttgaa ctcctggcct caagtgatcc 109440
gcccacctaa gcctcccaaa ctgctgggat tacaggcgtg aatcaccaca tccggccctc 109500
cagtttgaat cttaatgaat ttaaatagcc acatatgtct agtggctacc atattagaca 109560
gatcaagctc tatatgattt cagtcaattc aaaagtactt tatcatgtgg tatttggtaa 109620
atttttatga atggttcatg tgtgctttaa aagaaagtat attctgcagt gttgggcata 109680
aagttatatg cccattaggt caagtttgtt aatcattttt aaatttctg taactttcac 109740 ttacattttt gtctgctttt tctaacaatt attgagtaaa gcacatgtta aagtatattt 109800
taatcctact atgattacag attgcctatt ttttgcttgt atttctgtca aattttgcca 109860
tatatatgta tataaaattt ttttgagata gagtctcgct ctgttgccca ggctagagtg 109920
cagtgatgta atctcagctc actgcaatct ctgcatccca ggttcaagtg attctcctgc 109980
ctcagcctcc cgaatagctg ggactacagg tgcccaccac cacgctggct aaattttgta 110040
tttttaatag aaacagggtt tcactacgtt ggataggctg gtctcgaact cctagactca 110100
agcaatccac ctgccttggc ctcccaaagt ggccaaaggg attacaggca tgagccactg 110160
ggcccggtca aattttacct tatatatttt tgagtcaatt atataatata tcccaatttc 110220
agaaatacgt agtttaaaat ctatgattta cagtaatatt gtttctatgt gcccactcac 110280
tgttacattg cttaagcatg atttacacaa tcctaaatca tatagaaaaa gtcagcatta 110340
tatttaaaag ttaaaattat atactttata tcatgtatat gactcagggc ttcattgctc 110400
atggacactt acatctctta ctaatcttta gttggtggct taaatccgtg cttcttagac 110460
tatctatggt aaaagacaag tgtgggtttt ttcccccaac ccattacagt ctgacatatg 110520
gtcctactgt gcatgattca cgtacagttc atgccacatg caactaacca tgggagtttg 110580
acaaaacttg aactcgtgta cgctccattc aatgagacaa ggccactgat cacactcttg 110640
gatgtcatat ccctgtaaaa ttttctaaac actctcaact ctgttcttat ctcatggaga 110700
ctagtaacat tttgtagacc agcactggcc atggacccca ctttgaatag tactgactta 110760
aaatatcacc acctatttta gtaatcaaaa aaagggaaat ttagaattac catgttatca 110820
gaaaattttg tttaaaatcc tagctgaggc cagtcacagt ggctcaggcc tgtaatccca 110880
gcactttggg aggctgaggt gggtagatca tttgaggtca ggagtttgag agcagcctgg 110940
ccaacatggt gaaactccgt ctctactaaa aatacaaaaa ttagctgggt gtggtggtgg 111000
cgcacccctg taatccagct actcaggagg ctgaggcagg agaattgctt gaacccagga 111060
gacaggttgc agtgagccaa gactgtgcca cagtactcca gctgggcaac agagtgagac 111120
tcatctcaaa gaataaaaat ttaaaaataa aataaaatcc tagatgaaaa taaaggtaaa 111180
tctggtccat tctaggactc tttgtttctt ctaacaatat gaatgtgttt ctattctttt 111240
aaacatttct gggtttaagc agttcttttc actttactct tctaatggcc aaaatcaggt 111300
atttgtagta actgcagtct ccagcttctg gccttgtact gatgagaagc aaaagcaaaa 111360
ccaccacccc aaattaactg cttttattct tttcagagga aattatttta tttcaagaaa 111420
aatagggcct ggccctttat ctctgactgc tcatcaaatt atggctttgc ctatgaaaga 111480
gaaatggaag gggaatgaat tgggatattc aataactgtt tttacatgat ttttctactt 111540
tcaggtatca atcacggaga tcttaatgac cataatattt taatagagtc cagcaagtca 111600
gcctctggaa atgctgaata tcaagtgtct gggattttag actttggtga catgagctat 111660
ggctactatg tgtttgaagt ggcaattacc atcatgtaca tgatgattga gagcaagagt 111720
cctatacaag taggaggcca tgtccttgca gggtttgaaa gcatcacccc actgacagct 111780
gtagagaagg gtgctttgtt tttacttgta tgcagtcgtt tttgtcagtc acttgtcatg 111840
gctgcatact cttgccagct atacccagag aacaaagact atctcatggt tactgcaaaa 111900
accgggtgga aacacttaca gcaaatgttt gacatgggtc agaaagctgt agaagaaatc 111960
tggtttgaaa ctgccaaatc ctatgaatct gggatctcca tgtgactgag atctccatgt 112020
gactcaaagt tcactttaac ttgggtaatt aaaataggac ccagtcaaat tttaggaagg 112080
attttcctgc atagttaaaa atcaactgat ggaatggatc aattctgaat atgacagagc 112140
acatgaaatc cctaaggtct tcaagcaatc tcgtgacaat tttttaaaat tcacaaaagt 112200
accacaagca agcatatttt tctgtgagtc ttacttgcca tatctataaa acacatataa 112260
tgataccatt ttgaagcaga taatctcaca agatctattc ctgccctgag attaatgact 112320 atttaattt taaaaataat atatacatat agatatattg acatatttta aatatctgga 112380
cataacatac tgacctagat aacatactac cagttctatg aaacctcctc tgatctctcc 112440
tttctctaga atcccagtgc attgtgtctt tttcatggcc catcactttg tataatggat 112500
cgtggttgtg cagtcatctt gcctgagagc tactgagggc ggagaccatg taaaacttat 112560
ttttgtctcc tcagcccttc tttttttttt tttttttttt ttgagacgga gtctcgctct 112620
gtcgcccagg ctggagtgca gtggcacgat ctcggctcat tgcaagctcc gcttctcgag 112680
ttcacgccat tctcctgcct cagcctcctg agtagctggg actacaggcg cccaccacca 112740
cgcccggcta attttttttg tatttttagt agagacaggg tttcaccgtg ttagccagaa 112800
tggtctcgat ctcctgacct tgtgatccac ccgcctcgat ctcccaaagt gctgggatta 112860
caggcatgag tcaccgtgcc cggcctcctc atcccttctt atcacacctg ctattatagt 112920
gcctttccta cagagaggtc tttaaaaata tttgaaaata aatgcgtgct agaagaaggg 112980
atggagaagg cacacactaa gatgctttag gagaaagcat tgacagcatt cttggagaaa 113040
aaattttaac ttgtctgaga gggtggttga aactggaact ccagagatag atgctggaag 113100
accctgggaa ctgcaaggaa gcaaataatg acatccaggc aaggccacta acccctgagc 113160
tacttaaata taatggttcc tttcagactg ataccaggaa cctccttaag catataagca 113220
tatatttttt aattctctat aatctgtttc tttttggatg actatgaagt agattgggta 113280
gactgaagct cactgtattc ttggctgacg gtatcccact gtgtttcctt cactggtttc 113340
tcgtcatgtc tcctttagta tgatttagta aatggctgtt tactattctt atgatttcaa 113400
ctattcattg tctacagatg actcaagtct agaaccctgg ccattcaaat actcaatagt 113460
tatctttcta tatatatgaa caggcattga tcctatctcc atctttctgt ctacctacct 113520
agtcttccca aactagatat ttctctaaat tgtcttatat ggttcatttt tcacttcttt 113580
gtccctcaat ttcatttcat ttctttttct tttcttttct tttctttttt tttttttttg 113640
gtggtggggc ggcagggaca gggtttcact gcagcctcaa cctcctaggc tcaggtgatc 113700
ctcccacctc agcctcccta gtagctggga cttcaggcat gtgccaccat gtctggctaa 113760
ttctttaatt ttttgtagag attggggtaa tacctatctc atagaattaa tagagttcat 113820
tgtgaagatt tcataagaga acagtgccaa gtgcttaaca cagtgtgtgg cacatagtta 113880
ggactcagta actatttact caataaatga accatattcc aggttaccca aactcaaaat 113940
attggagtaa tttttttgctt gcctctctta tattcagtga gccctactgg tttttagaat 114000
tgtagaattt taggaatctc tgtctttact ggatttttttg tttgttttgg gcttttttgt 114060
ttgtttgttt gagatagggt ctcactccgt caccgacgct ggagtgcagt ggtgtgatca 114120
cagctcactg caacctctac ctcctgggct caagcaatcc tcccacctca gcctcctgag 114180
tagctgggac tacaggcatg tgccaccatg cccaactaat ttatttttatt ttgtagagat 114240 agggtctcac tatgttgccc aggctggtct caaacccctg gactcaagca atcctcctgc 114300
cttggcctcc ctaaatgcta ggattatagg cgtgagctat catacccagc ctgtgttgtt 114360
ttttaacaat atataataaa agccaacatt tattcagcac tgaagtattt tatacacatt 114420
agctcactta atttttacaa caaacctgtg tgggaagtac tgttataatt aatcgtcatt 114480
ttcagataag aaaatagcag ctgaaaaagt aaaaataatt tcctcaaaga cagccagggc 114540
ttaaatcagg cctttctgat gtagaccatg ctcttcacta ccacagagtt ccatgctact 114600
ttctctccct ctccctcctc tcctgtccct gctacacaca cacacacaca cacacacaca 114660
cacacatgca cactcactca cacacactag gaggaacaaa tgagatcatt cacatgaaag 114720
cacttatgtt tctgaaattt aagggactgt ggtttttatc taggttgacc tctcaagcta 114780
aaaactggga accagaataa tggactgaaa cttgggtttc acttccagac cagtgttgat 114840
cctctgaatt gatgaaactg tatagatttc cctcttgatt gcccctgcta acatggattt 114900
cctttcactc aattcctaat gcaaatattg ctgaccactg tttagatgtt tacatgctgc 114960
attacattga tattttacta tttggtgttt gttctaactt gtctccaatc aatcaatttc 115020
atgtggttta tataaactct ttggtggctg tgatggttag ttttaggtgc caacttgcct 115080
ggattaaggg atacagagat aggtagtaaa gcgttattcc taagcatgtc tgtgcggaag 115140
tttccagaag agactggcat ttgaatcagt agctgagtaa ggaagatccc cctcaccaat 115200
atgggtgggc accatccaat ctgttgaggg cctggataga acaaaaagac aaaggaaaga 115260
tggattcagt ctctctcctg ggacagccat cttctcttgc cctcagatag caaaactcca 115320
ggttcttggc cttcaaactc caggacttaa ccagcggccc ctcaggttct taggtcctca 115380
gcctcagact gagttacacc atcatctcct ctggttctca agcctttaga ctcaaactga 115440
aacacataat tggcttcact ggttcttcag cttacagaca gcaattgtgg gacttcctag 115500
cctccataat ttatttccat aataaatccc ctcctgttta tctacctatc catccttcca 115560
tcccattgat tcggtttctc tggaagaccc taatataata cataaattaa atatttattt 115620
tactttactt tcaggaccta gcaccgtgcc aggcccctag aagacccagt aaagatctgt 115680
tgaataaact gtaagaatga acacaccact acaagtgcca ggtcctggtc ctttcaaaca 115740
acgtggagaa aacccagttc cagatttagg aatcaatacc atatgtctgg caaagactct 115800
ttgctcttgc aagtgccttc ttctgttcag gcttttagcg cccctggact acaacagaac 115860
tttactttct ggtattctta gtctccctaa cctctgcact tcatattatg taggcagata 115920
aaaactctgg ttacatatat tgctgtgtga tgaccaaaaa aaattgtggc ttaaaacttt 115980
aatcatttta ttagctcatg gtttctggca gtcatgaatt caggcaggcc ctgggacagt 116040
ttgtctctgc tccccccagt gttggggcct cagctaggaa gactttaagg ctgggagaga 116100
tttgatgcct gggagagact caatcactgt gtaaccgaac acttgcttct tacagagtcc 116160
aattgacaag ggtgaggtat aatagaaaga cagaatttat tagccaaaaa tagtaaaggg 116220
aaagcaatcg gattcctatc caaattaacg gcttctattt ttaggaagaa ggcaggggtt 116280
taaaaaggga aaacttgata aggaaggcag acaagaactg ggctgagtac agtgtctgtg 116340
tgtcttattc tggtggctat cttgggtcct ggtccacctg gaccctgggc tgatggcatt 116400
tcaacaacag ccaggttgtt aactagctgt cttgaagtaa tctctggaac tttgcagctg 116460
ggtctccaga cttggtctgt gtgtctcagg attgacccct ggaacttcta agaagacaca 116520
taattagata ctagtagaca gttggataaa tgtgaaggga gtatatacaa tgagaaaggg 116580
agggatgtgg actctagaaa aggtttctgc agtttgcttc aaggttatat ctttaaaccc 116640
aaggaaaagg ggaaaaaatt tttaatgcag tttgaagcta agctgcctgg ttacaactgg 116700
gtactaggat catctggagg aatcttcact cagctgtctg gcaggtgaca ctgggacttc 116760
atctaggctg ttggccaaac acctctccat gtggcctttg cttcctcaca gcacagtgcc 116820
tgggtcccaa gaacgaccat cccaagagga caagacagaa ccatatcacc atttgtgatt 116880
tgctcttgga agtcacatga tatcacttcc attgtagtca caggctcacc cagattcaga 116940
ataaggggac acagaacctc tcagtgggaa ccatctgtgg cacattgtaa gaggaacatg 117000
tgggatgaga gatgttgagg gttcatcatc ctaaaacatc actttaatcc tgtcttccca 117060
ttactgacca aaacaaattc tggcattaaa ggcactctac acttaggcct caaatgcctt 117120
tccttacttc ctgtattatc tcctccattc agatcagacc gaactactca gtcacccaca 117180
cttgtcagac tcattcttct cttgcccttt ttctcaagga atccctctct tgacctgaga 117240
aattctacct ctcacttaaa agtgactgtt cactgaattc cgcagaatga actaaggtgg 117300
caggcagggg ccctcagaga tgccataagt tacaccacct gaggatgctt tcagagcacc 117360
acctgcgtgt ggctctttgc catcttgcct tggctcactt ccctgtgtgc ttggaaagta 117420
gagacgatag gcgagacctc aaaatgtaac ttacttccaa gctatctcct tttcaaagcc 117480
cagatccccc aataattttg caaccaacat gaagaggagt ttctgcccag tgggctgctt 117540
tttgggagag actgtgagca gatgacttca tattaaccca gatctagtca accttctagc 117600
ctgaaaaaac ctaaaatgca tagtagatag tttacatacg gaccgaggct gaatgagcaa 117660
aaaggtggag agatggataa tgaacacaga aacaagtatg acaatttcag taaagaagat 117720
aaaatggtgc gagtatatgc tgacggtagg gtattgcttt aactgtgctg gtcagggaaa 117780
tcctttctga ctggtgaaaa gcagagaaag agaccaaggt gaaaattccc ccaaaagtgt 117840
gaacctgatc ataatttttt ttaatttaat ttttagagcc agtgtctttc tctgtcaccc 117900
aggctggagt gcagtggtgc gatcatagct cactgcagcc tccaaactcc tagcctcaag 117960
ccatcctcct gcctcagcct cccaaagcgg tgtaattaca agcatgagtc accatgctcg 118020
accctcatca taattttttt tttttgaga tggagtctca ggctggagtg aagtggcgca 118080
ctctcggctc actgcaacct ccgcctcccg agttcaagcg attctcgtgc ctcagcctcc 118140
caagtagctg ggattacagg cgtgcaccac acacccggct aatttttgtt aattttagta 118200
gagacggttt caccatgttg gccaagctgg tctcgaactc ccgacctcag gtgatccacc 118260
cgcctcgacc tcccaaggtg ctgggattac aggcatgagc cacccggcct tcctcatcat 118320
aatgtgtatg tccaaaatgt atgcatcagc agtaaaagtg aaagccagaa tgaaaaagga 118380
aggtgatgag aggggtaaag tctcatgtgg ttggaaccat tttgggaaac aggacaggaa 118440
tgatagcaat taagaagccg gtccacacta tttgctatcc taggtctgaa tagtgaagag 118500
aaaatgaaag gagagcgcca agggtaagag aaagaaatta gctattccac ctcctggttg 118560
gctactgtct tcctgccctc ttccccatgg cacagcaact cctccacctg ctgaggaccc 118620
tagcctaagc tgcagcgccc cagagcctca gcacccccgc gacccagctc ccacgagggg 118680
cacgggttct agctccgccc cgcaagaagg acttccgcgt cctcggccgt cccgctcccc 118740
ccgccccaac ccagcggttc tgcgcatgcg cgggggccat attagcagcg gttattcggt 118800
gagcggtggt ggtttattct tccgtggagt taagggctcc gtggacatct caggtcttca 118860
gggtcttcca tctggtgagc ctttggcccc ttggggcccg cggaagcttg gccgctttcc 118920
cattgggcgg gggtcgtgaa cgtcaagaca gtcggtcccg gcctgcagtt gccgccgagg 118980
agccgtgggc acgatgactc tgcaccgcct cctctgtgac ggaccgaccg ccgggaatgg 119040
cccccgccgg ccgccgtcgg gggcttccca gtgccaagcc tggacgccgg ggcccgcgag 119100
ggggcgggct gagggtgggg gtctgtgggc aggaccgaga gttggggtgg cttccgtcct 119160
caggagttcg gtacgtgaaa gttagctctc ccggaggtgc cggtgaactc aaaatagtgc 119220
tgtgcccggc gtcaggcgtg gagacaacag aaagttgtgc ttaaagctcg aatcagaaat 119280
ccccggcgag tgtctctgtg tcctccctgc ttctctgctc tgtgccatcc ttactttgca 119340
ccattcctat tgcaattacc tcaaccagtt cgctgccctc ggtctctcac cagccagagt 119400
gatcatttaa aatgccaatc agttcctgtg ggccttggga atcattcaga ggagccccat 119460
tggctgagag ataaaattct gtttttacct gggcacgcgg gctctccagg atttgattcc 119520
agcttacctt tccagtcttg attccctata ttccagtatt tggaaatgtg ggccttggac 119580
tgaggcttta ccaaataacg ctgaacacct agtattgcct tttgcacgaa tggtactgat 119640
ggtgcccaag ataactgcct ccacccccaa gttcaggacc cagatcactc tctggagaag 119700
gcctcagcct cttgccttgg ctttcaaggc tctgcgtgat ttggatactc gcttagctct 119760
tatttatata tattttaaaa gcatcagcag tttatctcat gcccactaaa ctatcctgcc 119820
tccgtaccct ttgttcatac tttctgctct gtgtggaatg cccttctttc ttcccctgtt 119880
ctttctctta gacccaaggg ttctcagcct tatttctgcc tctcccatct ctgatttact 119940
ttcattttct gtatcgattt ctcaaaaaat actttcttga ttctttcatc atccctttc 120000 ccaccctacc cccggttcct ctttccacat tataatctat gactgcctct ctcacctaac 120060
tgccagtatt agcttttcag gacaggaact ggttttacac attttggtat tccagcatct 120120
agcataatgc ctgacactta gctgaataaa gggagtaaat aaaacagatt tgtaaagtca 120180
gcaaatgctt tttaatttgt gaatcttatt ttaatgatga tctgattttc tttttacagg 120240
aactatataa agttcagaaa acatggtgag ttaatacaca tgccaataaa cggttgcctg 120300
ataaacagta ttgcttgtac tcagtttaca gacttgagtg ggaaaattga aatagaagga 120360
aagcagtgag aaggtgcctt ttttcttgtc agtttcctct cacctattga actttgtata 120420
ccaggatagg ttttgtaaga tcatttgtag gcttgcagga gttggcctac tttcagtggg 120480
taggaatcac tcatgtgttt ttcctttgca gtctcgaaga tatgactcca ggaccactat 120540
attttctcca gaaggtaaaa tagaaattgt ttaatctgcc tcaagtttaa aaataaatgt 120600
gttagacttt tagaaaaaaa aattacaaac tttttttggt agttgcaaag ttcatccttt 120660
ttgtactttg aagcaattat catcaccagg ttgattatac catagaagag tgaaagtgga 120720
aatttgtttc tagcttgctt cattgctgat ttcttttggg ccagtggtgc aggagcacag 120780
aggagagtct tggcttctca ctgcttttgt tttgtaggtc gcttatacca agttgaatat 120840
gccatggaag ctattggaca tgcaggcacc tgtttgggaa ttttagcaaa tgatggtgtt 120900
ttgcttgcag cagagagacg caacatccac aagcttcttg atgaagtctt tttttctgaa 120960
aaaatttata aactcaatga gtaagtgaga ttttaggaaa gagtttaaaa aaaatctcac 121020
tttctcacat aagtgggatc tatgtaattt gggagggctc ttccgtgcga tgtggtagaa 121080
ttgaaattgt gcctttattt tgcttgaaac ctctttgagg cctggtacca tgtgttactc 121140
cttttaagtg cagggcaaac acttagtgga gaaactagca ttgtgtaatg ataagagtac 121200
agacttagta gtcacacaga tttgggttca actccaggct tcacccatgc aggctatgtg 121260
accttgcacc gattatttaa tttctttggg cctcagagcc tcctaaagtg gttgtggcag 121320
tttaatgaaa taaaatgaat gaaataaaat agtatagtat ctggcattta gtaggccctc 121380
aaagtattgt ttagaatagc tacgcaggat tttgttgaat tacactgaat cttactaaag 121440
aacaagcctc ttagaggtct cgaagaattt agccaagcct tgtacactgt gtgaaatgtt 121500
tgttatattt gagtgtgcag aactttgcag ctcatggaga gctgaccgtg ctaagtagag 121560
actttccttt cagtggtggt gggcttggta aatgctgatt atcagggcct tttgataaac 121620
ttgtccaaag tggtgtcacc cctccacaga gcctctgttg ggaccactca acagctggca 121680
ggcttggcta ggcgtagtca cagggcgagt ctcagctata agagagccag ggcagccctc 121740
aggaagtggg cccaaaaaaa tgaaatgcac ctctagtagg agcctagccc tgtacttcct 121800
aagcaggctt gtaaaccctc ctgccattgt cccctgtcac ctctgtcaag ccaggcctta 121860
ggaaatgaat attactcaag agcagtctgt ctagcaaaat cttttttttt ttttttttt 121920 tgagacagat tcttgctctg tcacccaggc tggagtacgg tgacgccatc ttggctcact 121980
gcagcttctg cctcctgggc tcaagtgatc ctcccacctc agccgcccaa gtagctggga 122040
ctataggtgc gcaccaccac acccagttag tttttgtata ttttgttgag atgggatttt 122100
gccgtattgc ccaggctgtt cttgatctcc tgggctcaag ccctccatct acctcggcct 122160
cccaaagtgc tgggattaca ggcgtgagcc attgtggcaa gcctgtcttt ttattctttg 122220
ttgctgaatc ttcttgagat tacattagct tcttggcgtt aattttgtta tcctattcat 122280
aggtggtaat gataaataca tctattaaat aacttaaagg gtgcatttgt ttatctttca 122340
tgttgagtga catcgagtaa acatctccta caaagataaa acttgtaggt tttttctgaa 122400
ggaagtagct gttgtgaagc aaacatagtg aatttctaat agaaattaga attttttaaa 122460
tacttataaa cactccttgc aagcatcttc cctgcttaca gatcaatgtc ttttttttctt 122520 caagggacat ggcttgcagt gtggcaggca taacttctga tgctaatgtt ctgactaatg 122580
aactaaggct cattgctcaa aggtatggtc ataaatagca taactgatga tacagaaatt 122640
agttttgatg tttctttttt ttttttttga gacagagtct cactctgtca cccaggctgg 122700
agtgcagtgg cacgatcttg gctcactgca acctccgcct cccgggttca agcgattctc 122760
ctgcctcagc ctcccaagta gctgaccacc acaccgggtt aatttttgta tttttagtag 122820
agacggggtt tcactgtgtt agccaggatg gtctcgattt cctgacctcg tgatccgcct 122880
gccttggcct cccaaagtgc tgggattaca ggcattagcc actgcacctg gcctagtttt 122940
gatgtttcta aggagagctc acttttgcaa agattaaagt cattaaaaat ctttgaattg 123000
aaaattacag atttttttca accaaactta caaaatatta tttactatga gaatattcag 123060
atgttgactt gttccctccc cttcaaatta caaatgactg ttaggttgtc cccatggcat 123120
agattgcttt tcagagaata ttttccttag agtctgtctg tgttttagag aaaactacta 123180

-continued atgtgcccat ctctttatcc taggtattta ttacagtatc aggagccaat accttgtgag 123240
cagttggtta cagcgctgtg tgatatcaaa caagcttata cacaatttgg aggtatttaa 123300
tttttttgaa aattttattc gaaaaagtta agacatttta tgagttataa ccccttttgag 123360 gtagtaaaaa attgaaaata gaccctttgt tttaaattaa atttaatttt tttaattggc 123420
aaataagaat tgtacatatt catgaggtac ataatgatgt ttcagtgcac ataatgatca 123480
gatcagggta aatggcacat tcatcatctc aaacacttgt gttgggagcc ttccatatcc 123540
ttctagctat ttgaaactaa tatgttatgg ttaactatat taatcctaca gtagtataga 123600
acactagaat ttcatacatt cttgcttcat gaatgaacgt gttcctccac catgtagatt 123660
accctcgttt tattaatagg atattgaaag tccaaaacaa cattttcaaa tctggaaact 123720
aactgctgtt tacataataa tgaaattcag cactggtcct ttgtctgttc cctcttctgg 123780
ctgtgtccaa atcgtagaaa caaaagtcga atttgtaatg gagcttatct atggtagcca 123840
gaatacaaaa cagtttatga atgcttaagt tcacagagta gggtttagct accttcactg 123900
agctcaagta actgtagtga tactaaattt agattattga tatgtttggc tttttttctt 123960
tgttaaagga aaacgtccct ttggtgtttc attgctgtac attggctggg ataagcacta 124020
tggctttcag ctctatcaga gtgaccctag tggaaattac gggggatgga aggccacatg 124080
cattggaaat aatagcgctg tgagtatttt tgttgtgcta taaaatctag cagaatgtct 124140
aataactgcc ataattttgc catggtgatg aatgtaaaca gtattttaag atagctgcaa 124200
caaccttaat gtgatatgga aatatctgtg atttctgttg gtgacagcat tgctgatata 124260
gctaatatac tggggttcgt taactacatt aataaatgct aattttcagt taggagttgt 124320
gaaattagaa gctgtgattt tgtttcacat ctagtttaca gaccccctgt attctatgac 124380 agacccccttg ggagactgag gaccccaggt taaagacact ctttatagag cattagtacc 124440
ccctcttctc accccgtgcc gtgtgtgccc tccctgtcat caaaattatg tatatgggcc 124500
aggcatggtg gctcatgcct gtaatcccaa cactttggga ggccgaggca ggcaaattgc 124560
tcgagctcag gagttcgaga ccagcctggg caacatagca gaaccccatc tctacaaaaa 124620
atacaaaaat ttgctgggcg ccatggcatg tgcctgtaat cctagctacc caggaggcca 124680
aggtgggagg aggagcacct gagcctgggg agacttgaag atacagtgag ctgagatcat 124740
gccactacac tccagcctgg gcaacagagt gagcccctgt gtcaaaaaaa aaaaaaaaat 124800
tgtttatact tgtaatgcca ataataattc aggcattttt cttctagacc aattcatgtt 124860
tctaaaaaat gtaaaaactt aaaattctat gttgattcat gttttatagg cagctgtgtc 124920
aatgttgaaa caagactata aagaaggaga aatgaccttg aagtcagcac ttgctttagc 124980
tatcaaagta ctaaataaga ccatggatgt tagtaaactc tctgctgaaa aaggtaattc 125040
atatcctctc ctttaattct ttcgactgag tgagggaaat tagcagctgt taagattttt 125100
ttcttttttt tttttttttg agatggagtc tcgctctgtt gccaggctgg agtgcagtgg 125160
cgcaatctca gctcactgca acctccgcct ccttggttca agtgattctc ctgcctcagc 125220
ctgccgagta gctgggacta caggctcgcg ccaccatgcc cagctaattt ttgtattttt 125280
agtagagacg gggtttcacc atgttggcca ggctagtcat gacctcctga cctcaggtga 125340
tcctcccgct tcagcctctc aaagtgctgg gattacaggc gtgagccatt gcgcccagcc 125400
agcaactgtt aagattttaa catgtcatcc tagttcattg aaacagcaac cttacgaatt 125460
aggtgatgtt atccctgtct tctaactgag gacactaggg cttaatgagg ttaagtgagt 125520
tgaccaagat caacattggt aaattgtgga gtcacaatct cacactgtat tccaaactta 125580

-continued aaggcttgat actgaacaat ctcattactc acagatagac atcctgcact gtgctacttt 125640
tagttaacag ttatcaagtc ttctcatcaa tgatatcttt gcttgtgtgt atatatgata 125700
aagcatacgt atgtagttat atatttatac ataggtttgg tatactttac cagagataca 125760
acatttgcgt gggttgtgat accctctcct gttcttctta atctactaat ctcttatttt 125820
aagctcatgt tagcaattcc aaataccttg ttcaacttaa gctatatgac tatataaaag 125880
aatatttcag tcgagcttgg tggctcatgc ctgtaatccc agcactttgg gaggctgagg 125940
tgggtggatc acctgaggcc aggagttcca gatcagcctg gccaacatgg tgaagcccca 126000
tctctactta aaatacaaaa attagctagg catggtggtg catgcctata aatcccagct 126060
acttgggagg ctgaggcagg agaatcactt gaacctggga agcggaggct gcagtgagtt 126120
gagatcatgc cactgcactc cagcgtgggt gacagagaga gactctgtct caaaaaaaaa 126180
aagaatattt ctaaatgttt ttcagaaatt gtggtaaatt aacatgttgc tttatgttag 126240
gacagtttag ctcctggtgt tccttagaaa atgccattta cggccgggca tattggctca 126300
cgcctgtaat ccccagcact ttgggaggcc gaggtgggtg gatcacctga ggtcaggagt 126360
tcaagaccag gttggccaac atggtgaaac ccctgcctct actaaaaata caaaaaatta 126420
gccgggcgtg gtggtgcgca cctgtaatcc tgctactcag gaggctgaaa caggagaatc 126480
acctgaaccc aggaggtgga ggttgcagtg agccgagttt gcgccattgc actccagcct 126540
gggcaacaag agcaaaactc catctcaaaa aaaaaaagaa aaagaaaatg tcatttacat 126600
gcagattgcc ctcttttgtc tacttccacc cagtttcaag gaagcactac tcagtttccc 126660
tggtacaaaa aaattccttc ccctttaggt atcagtctgc ttttcttggc catttcatgc 126720
cttttattta tttatttttt taagagactt gaaaagtcca taaaaaataa gctgttatta 126780
ccagttgaag attctggctg agccctcaga ggttccaaca gttccgtcta atcagcacag 126840
ctaatagcag gccggcaata gcaattggtt gattatactt tttctaaggg agtgacaaaa 126900
tggctgagga gacgatattt aagtaaaaat tataattaaa acattacaag atcaaaagta 126960
tattgttctc ataaaaggga ataatgttaa gtataaaaca taggagagtg ctgaactaac 127020
gtttcaatga tgtggcgagc ataaaccatg agtgcctatt aagcttctct gctaagtatg 127080
cctgcctgcc tgcaatacaa ataaatgtat gtgtttgttt ttagtggaaa ttgcaacact 127140
aacaagagag aatggaaaga cagtaatcag agttctcaaa caaaaagaag tggagcagtt 127200
gatcaaaaaa catgaggaag aagaagccaa agctgagcgt gagaagaaag aaaaagaaca 127260
gaaagaaaag gataaataga atcagagatt ttattactca tttggggcac catttcagtg 127320
taaaagcagt cctactcttc cacactagga aggctttact ttttttaact ggtgcagtgg 127380
gaaaatagga cattacatac tgaattgggt ccttgtcatt tctgtccaat tgaatacttt 127440
attgtaacga tgatggttac ccttcatgga cgtcttaatc ttccacacac atccccttttt 127500 tttggaataa aatttggaaa atggaaatga aggaataaat tctctgtagc agtaattgtt 127560
aaatatacaa aaactgacag ggcgattact ttttgcacat tgtggcttac agtcctttca 127620
caaagatggg cacgttcctc aggctggcca gattattcgt ctctgtctgc aggaattggt 127680
ttgagaatga acacgtgagc tgaacaaagc cagaattgat gtgtgggtgt ggatctcgca 127740
gctaggactg aggctgccca caggcagcag ctcaagctgc gcggaagatg aggtgtagaa 127800
gttaaggcca cagaggaaaa gtggaaccaa gagatgagaa cagttacgtg ttggctgaag 127860
ggagctctgt tgctggggtt tgttcaacct gagttccctt ggctatctgt ggcttcatga 127920

-continued cagaagtgat acagggcagt ggtacttaat gcgtagccat ggtgctttag catcacctat 127980
gcagattctg atgtcccatc ccagatctac tgaattaaaa tctctgaggg tgaaacccag 128040
taatctgttc taacaagctc tgcatgtgat tcttaggaat gctaagtaaa actttaagaa 128100
gtttttgttg catattagaa tcacctagga agcttttgca gcttgtaagc atgctgtatc 128160
gattaactca agctctgtgg tggaacccag atattaacat tgcttaaact cttcaggtga 128220
tttccatcag ctagggtgag tgcattgagc catcatttac ccttctctca gctgttgtca 128280
accaaatatg tgctcccagt ctaatttctc attgtagatt ttcttaatgc agctccctgc 128340
agttttctgt ataggctaaa gtatttacaa gccctatttg cagcactttt ttgaacttct 128400
aaattattct cttactctgt acagcaggtt ctcgttattt ttggtagtta tgttctaaag 128460
tcaccacaaa aactaacaaa atactgaact cttgcaccta gagaaagtac tgggttaggg 128520
tcctacaagc cactggtcac atttttatca actgatcagt acataacctg tttttgtgt 128580 atttctactt aaagacacct ttttaaatgt gtattgtgga ttcattaaca tagaactcag 128640
ccaacagctc tttacgtgaa tgtttttgtt ttgttttgtt ttttgagact gggtcttgct 128700
ctgtcaccca ggctggagtg cagtggcgtg atcatatttc actgcaggct caaacggtct 128760
tcctgccttg acctcccaaa gtgttgacat cacagccctc ttatgcttag gaacaacact 128820
aaacagtgtt tttttcatag agacggtgag cagggaaggt ctcaccatgt ttcccatgcc 128880
ggtctcaagc tcctggactc aagcgatcct cctgcctcag cctcccaaag tgctgacatc 128940
acagccctct tgtgcttagg aacattaaac agcacttcag cactatacct gggtgccatt 129000
tgaaatagta aaatcactaa gaaaaatgca aaaataaacg gcacaaggta gactgcagga 129060
acacttacac ggtgtgagag ctgaaacaag aattcagagt gtcgccttgc tcaacctcag 129120
atgggaacat gtgcacctgg gtactcaaaa ttttcaccac tctgcatgtc aacaaatgac 129180
taaaagtacc acaagtattg gtttgggggt tacatgtaca ttttatgaga atgcaaattt 129240
tgcaaattca caagtacaga atcagcaagt agtgaagatg aatggcacgt cttcaccctc 129300
cagtcttgct acacccagag gttgaggtag tcaataaatc ttattaactc tgtctgcaga 129360
atttacccat aatccagcca ctttccactg caggaacgct ggtccaattc accattatct 129420
ctgacttgga ctattgcaac agcctcctaa ctggttcctt gcctccactt cattccccac 129480
agtcaattct ccagcagcag ccacagtgat cctttcaaaa tgtaaacggt actactgcac 129540
agttttggct caaaaccctc caatggcttc ccatcttgct cagtaagagt caaattcttt 129600
gtactggttc atgaggtatc ctgtattctg gccttgtgct accttccatg tgcttccttc 129660
ctcactcatt catccaaatg agccttctca tcattccctg aatgtgccaa gctcccctca 129720
catcacttgc caatccctct gccttgggaa tgctcttcct gggtatctat tgcccactcc 129780
ctcatctcca ggtctctgct tgcatgtcac ctttttttggg gtacttctgt gaaggagcaa 129840
tctctttccc ctgcacactc acattttcta ttccctatac ataccctgtt gagtttttct 129900
ccatagcact catcaccagc tggcatattt gtttcttgtc tctccccact ggaatacaga 129960
cttccagagc agtactttgt tttcattcaa tagtcgtgtc tcggtaccta gaacagaaac 130020
tggcacgtgt taggcaacaa ataagtactg atgaatgaat aaataccctg gatatgctgg 130080
tgtgaaatcc taaaaaatac ctgctttcca tccagatcag tagcactggt ggattttctg 130140
tatcctgact accccttcaa catttgccta aagctaggac aacttcttca aaggcaatag 130200
tgaataagag agcctggtat agtttgccgc cacattagga aagtcttcag aatttgaccc 130260
taacagcagg caaatttcaa cgtattcatc tttttgttga aataaattca tactgtgagg 130320
aaaagcaaaa gataggaggt gaggcaaaag ctactcttta actgtgagtt ttttttcctt 130380
gcgatggggt ttggctgcct agtctagatt ctcacgctag ccccactttc gtctgctctg 130440
tggcatattt ttaacctgag ttgcaggaca ggtggtttcc agagtgttgc ctgatgcatc 130500
ccaaatgctg ccttagcaat acacatctga acaggggccc atcactaata gcaagcattt 130560
cattaatctg agcaaaactc atgggttttc acagggaccc taccagctca gaagcacgtt 130620
gatataaata agtagaaaac caaagacagc taagttttaa atcttgagtc aaaactttaa 130680
aatcaaagtc aaattgattt cattttggtg agctttcaaa tcatgctttt aaaaataaat 130740
tatgtaaaaa aatcatgtac tcctgtgtat aattttactt ctggtgtttt ttcttaatca 130800
gaaaataaag gaagactctg gaatttgtac agtctagcac tttgaaagtt ccatgagaat 130860
atttgtttta gcagtgcaaa aatattccat actctgaaaa acaaaaccag aaagttgatt 130920
cattccttta ttggacactt accatgttcc tgataatttt aggtggtggg gatatatgga 130980
taagacacgt cctcggctct taacttgcag ccttgcagga aaagcagata atcaacaaca 131040
atattgtgga ggagcgctag actccaggta gctgtgtgcc gaagagtagg gagtaaaggc 131100
agaaggaact gcacgtgcaa aggcttggca atgggaaagc ttcacagtag ctaagcagag 131160
ctagagcaca gcttgctggg gaaataagag agaaggttgg aaatgtgcac taggatgaga 131220
agacagcttt gcaagtcttg aagtttgtgc tctatgcaat gcagaggcag ctgagatttt 131280
ttagtgaatg agaaaaacaa ttactctgac ttgtttagaa caatgattct gggagcccag 131340
aagatggact aggtgggaag agacagagtg agttaggagg ctactgaaat aggcaaggaa 131400
ggatgagggt gtaagactgt agtaaagtga acagagagga agggaagctg ccgcggaatg 131460
acggaggaca gagaaagagg aagggatgac aagggcatca aattcaagta gtcacaatct 131520
gatctaaaag agcactcggt gaacatgatg aactactctt aaaatttcct aatgtctttt 131580
ttgttactat tgttataacc tgaaaccaat tagagttaat atccctagta gggaagaatt 131640
ctgtaaacaa cattgtatat cacacgtcgg agtaaaccca tgtcaaatgc tttttttcccc 131700
ttcttcttcc aggtattatt catttgtatt cttgcatgca ctgtctgatc atcttttttg 131760
cccaatttct atcagataat ttaactttct ataaattcat ttatgagctc ttttaaagat 131820
agttctttgt catctgtgtt accttttttt ttcattgtag catttgcatt tttattttga 131880
ttttgatgct gatgtaccga agggttgttt tgtgtttacg tagacaaagc tatcatttaa 131940
agttcttgtt agtacaatgc acataaaaat attccccatg ccaaagtaca tcaacattat 132000
tctagtaaat ttgtggctca atcatcttta taatacacaa tttgcaaaat ataattgtta 132060
atctcttttt aaaagcagta tttaaattaa tcatgaaact ttaattcaat tgttcagact 132120
acttgggaat tttccattct tgagtgaatt cagaattacg tgaaatgata gttatttacc 132180
tttctccatt tatttttgtt attttttggt aacagcctta ctgagataca gttcacatac 132240
catacaattc acccatttaa aacatacttt tcaatggctt tctgtatact cccagggttg 132300
tgcgaccatc accacaattg atttagaaca tcttcatcac cccaaaaata aaactccaca 132360
cgcttcttag acatcacccc caaatcactg cccagtccta ggcaaccact catctactta 132420
ctgtctctat ggatttgcct attatggaca tttcctgtaa atggaatcat acaatatgtg 132480
atcctttgtg tctggcttct ttcacttagc gtaatgttta caaggtttat ctatgtggta 132540
gtgtgcatca gtaatttctt tactagatta gagaaaaaaa gcagagattt attatttttc 132600
ttccattgta tggttatact acattttgtt tactcattgg caaaaatatg agttatttct 132660

-continued actcttaaga ataatgctgc tgtgaacacc caggtacaag ttttttgtgt ggacatacgt 132720
tttcatttat tttgagtata caccttgaag tagaattttt ggcttatttt aaaatccatc 132780
tttatgccat acattaacat tagtgatatg gatttttaaa agaatctact ttgccctatt 132840
ttctcctata agaacccaat agaaatggga aatgggttga ctgtttgagt aaatgtatat 132900
gaatctgtta gttatagaag taggtctcac agttggagag gattttcact tcctttcatc 132960
ttggcaggaa gaatgttttc tctaagtttc tttatactta actttatact ctctagtgag 133020
aggccaagtc tttgattctg tacctaagag ccttatgtaa taaccttctc tgaaatatta 133080
ggaatcacat ggaatgggag aatccagggt aaactgtctt ctgattccta aacaatctaa 133140
taacttactt tttctgatta ggaaagcaat gcatgatcac tttgaaaaat acacagtgaa 133200
taaaataaaa atcacccata atatcttgcc cagagttagc cactattaac ttgtctcagt 133260
ggcccagttt agatgctgaa cgagcatact ggtaaccttc agcaaattat aggcaagcca 133320
ttttaaaata ctgttttatt ttgttttctt ttgagatgga gtcttgctct gtcacccagg 133380
ctggagtgca gtggcacaat ctcgactcat tgcaacctcc gccttccagg ttcaagcagt 133440
tctgctgcct cagcctccca agtatctggg attacaggcg cctgccacca tactcagctg 133500
ttgttttttg gaatttttag cagagagggg gttttaccat gttggccagg ctggtttcaa 133560
actcctggcc tcaagtgatc catccgcctt ggcctcccaa agtgctggga ttacaggcgc 133620
gagccaccgc ccccagccta aaaatactct taaaggagaa atgtaaaaat actttttcct 133680
tctaattgct tttcttttct ttttcctttt ttgagatgac gtctcgctct tttgcccagg 133740
ctggagtgca gtggcaccat cttggctcac tgcaacctcc gcctcccagg ttcaagccat 133800
tctcctgcct cagcctcctg agtaactggg attacagatg cacaccacca cgcctggcta 133860
attatgtatt tttagtagag atggggtttc tccatgttgg tcaggctggt ctcgaactcc 133920
cgacgtcagg tgatccaccc acctcagcct cccaaagtgc tgggattgca ggcgagagac 133980
accacgcccg gcctctaatt gcttttctaa agtattttgc agccttagaa agccccattt 134040
ctctttacag cagagtagaa gctatcattt gttgattaaa cagtaagtgt cagctacatt 134100
ataaatgtta gtgctaattc tcacaacaac cttgtaaacc cttgagggct tactctgtgc 134160
tcagtgattt agaggcaatc tctctattgt gtagttgagg aaaccaaaga tcagaaaagg 134220
tgagtaattt gtgccaagtc acacaactcc agtgccatca ttccatgcaa gccatcacta 134280
tcatcccttg cctggacttc tataatagct gcccatggcc aggcacagtg gctcacacct 134340
gtaatcctag cactttgaga ggccaaggca ggcagattgc ctgagttcag gagttcgaga 134400
ccagcctggg caacatggtg aaaccctgtc tctactaaaa tacaaaaaaa ttagctgggc 134460
atggcggcat gcacctataa tcccagctac tcgggaggct gaggcaggag aattgcttga 134520
acccgggagg cagaggttgc agtgagccaa gattgtgcca ctacactcca gctgggtgac 134580
agagtgagac tccatctcca aaaaaaaaaa aaagatattt tgcatatgag cgtaacaata 134640
cgttattagg gtctttccca gggccttgga aggagccgtg caaatgaaga ggcttgactc 134700
ttaagctgca ttagcttcac agtaaattgg ggaagttctc tgatgggaaa cctatgcaag 134760
gtttaagaca tgtgttcatg tgctccgatt gacatattaa gaagatccct ctagcagtga 134820
aggggagaat aggttggagg ggaacaagca tgggcagctt cttttttga gacagtcttg 134880 ctttgtcacc caggctggag tgcagtggtg tgatctcagc tcacggcaac ctccacctcc 134940
tgggttcaag ccattctcct gcctcagcct cccgagtagc tgggactaca ggcatccgcc 135000
accgcgcctg gctaattttt tgtattttta gtagagacgg ggtttcaccg tgttagccag 135060
gatggtctcg atctcctgac ctcatgatct gcccgccttg gcctcccaaa gtgctgggat 135120
tacaggcgtg agccaccatg cctggcccaa actatcattt tctagttact gtgatgtttg 135180
tcaactttta caaaatttgt tctggctttg agtgttgtgg tccaaaaaat aatgtaattt 135240
gttgaaaatt tttttgttct aagtaaatat ccaatttcac acgcaatttc acatttgtac 135300
tatcatattc tttttctatt tgtagagata gggttttgct atgttgccca ggctgagtct 135360
tgactttaac tcctgggctt aagcgatcct ccctcctcag ccttcccagt agctgggact 135420
acaggcccgt gccaccacac ctggcttgta ttgtcatatt ctttgcttaa agaggactcc 135480
ttcccacctg cccaaataat acaatcttca atataaaccg gaattagccc cagctttcca 135540
ttgtcccccct atcttgttga gaatctgtac ccctgattcc tctctgcccc tccctctcac 135600
aaacttcttt attctttttt tttttttttt ttttttttg agagacatgt tctctgtcac 135660
cacagctgtg gtacaatcat agttcactgc agcctcaacc tcctgggttc aagtgatact 135720
cccatctcag cctcccaagt agctaggact acaggtgtgc accaccacac tcggataatt 135780
tttattttat ttttagtaga gatgaggtct cactatgttg cccaggctgg tgaactcctg 135840
agctcaagtg atcctcctgc cttggcttcc caaagtgctg agattacagg catgagctac 135900
tgtgcccggc cgtagcaagc tcttttctac caaagggtct ttagctagat cacccctgta 135960
tctggaatgc tcttcccctc catcctgcat gactgccact ttctccatct tctgtcctaa 136020
ctcaggttat cttgtcagga aggcatttcc tgaccacctg attaaaagta aaatccccta 136080
ccccccactg catcaatttc tagttattcc tcaagttttg tttgtttgtt tgtttttgtt 136140
tttgagacag agtcacactc tgtcgccagg ctggagtgca gtggcacaat cttggcttac 136200
tgcaatttct gcctcccggt tagctgggat tacaggcatg cgccaccaca cccagctaat 136260
ttttgtattt ttagtagaga cggggtttca ccatgttggc caggatggtc tccatctcct 136320
gaccttgtga tctacctgcg taggtcaccc aaagtgctgg gattacaggc atgagccact 136380
gcacctagcc ctcctcaata gttcttatca aattctgaaa ttatcttgct tacttgtttt 136440
ttattttatt tttaaagaca aggtcttatg ttgttttttt aaaggcaaag tttatttttt 136500
tttttgaga tggagtttg ctcttgtcac ccaggctgga gtgcagtggc gcactgtctg 136560
ctcactgcaa tctccacctc ctggattcaa gcgattctcc tgcctcagcc tcccaagtag 136620
ttgggattac aggcacatgc caccacgccc agctaatttt tgtattttta gtagagatgg 136680
ggtttcacca tgttacccag gctggtcttg aactcctgac ttcaggtgat ccacccacgc 136740
cagcctccca aagtgctgcg attacaggca tgagccaccg cacccggcca aggtttgttt 136800
tttcaagaca aggtctcagt ctgttggcca ggctagggtg cagcagcagg catgatcata 136860
gctcactgta cccttgaact cctgtgctca agcgaccctc ccacttcagc ctcataagta 136920
gctaggacta caggtgcaca ccaccacacc tggctaatta attttatttt attttatttt 136980
tttgtagaga taagggggct cttgatgttg cccaggctgg tctggatctc ttggccttaa 137040
acaatcctct cacgtcagct ttccaaagtg ctgggatgac aggcgtgagc cccctcgccc 137100
ggctttgttt acttgtttat tgtttgcatt ccttcccaag gcagtacttt ccaagaattc 137160
agggacatta actatcatgt tcactgcatc attcctagaa tttggtgtat acgtgagttg 137220
tttcttaaat atttgttgaa cgaatgaatg aatagctggg agtgacagca aagattcaaa 137280
ctcatgttta tctgactcca caaatcaaag gctgtgcgat tcccaatatg ccaagagctc 137340
tctgtatttc ccaatctgtt atcccataaa gcattgaaaa gatcatgtgt gtgttagaaa 137400

-continued cacaagcagt ttcaattctg gttcaccaat gactgagaag atcagataca atcaaggatc 137460
aaaataccct tttccataca ggtgacttga agtattcttc agttttcaaa aaatttaaaa 137520
cacctaaaat taatcagcca tgttctagaa gagcaaggaa agattgtgtc ttgtgtgaga 137580
cagctgtgga actggaaatt accaaacgat ttccaatttt aagagatttg gatcaggtgg 137640
cttagaatta gattaaagac aatcaattcc ctgaaacaat caatgccata cataatcttc 137700
cgaaggagct ttttctattg ctgagaggtt gctcatctgg tcttgtttct tatccctata 137760
gaaaccttga tgtcaattag tattccacgg gaaatgaagc tagatgagaa agtgaaccct 137820
tgctaaataa attagaagag atgataatta aagcagagat tccaaaccat atcagagaag 137880
cagctctatc ttcattttac cattacttcc ctaaaagcaa tatatggcag tttacaaatt 137940
acacatggaa atgaaatata tttaattttg gatttttttg tgcttttgag aatcagaatt 138000
ttataatatc tcttgactga aggggaatta atctgggaac caataatttg gcaatcaata 138060
cattaaattc taagatggca gttctcctgg tctatagcca caaatatctg gaacatttgt 138120
ggtctaaacc tgcagtataa attgtacttt ggattcactt ctggtataca tagcagtgtc 138180
tataaatacc tctcatgtcc agaatagaaa gcctgaggga gagatagagg ctagatattt 138240
gatattagaa aaatattcca attctacctt ttgcacagaa ttgaatattt gtaattgtat 138300
cttgtagata tcaaattaaa agcataagtt tcattttaac atttataata gtatatcatc 138360
tatggagaac agacaataca tatttatatt acacacattt atatgttcct aataaggtgt 138420
ctttatttag tagacaaatg ttgaactttt gcatattaaa aattattact caaggacttt 138480
atggaaattc atatttgtct taaaaagaaa aattatttta taacgtaatt catcactccc 138540
agatttaaaa gctttcaaca tttaggggac atgggatatt gtattgcact ttcttaaaat 138600
aaaaaacagt atcttcattt ttaacaagaa tgttttgtag gccaggtgtg atggctcatg 138660
cctataatcc cagtacttcg ggaggccgag gcgggcggat cacctgaggt caggaatgcg 138720
aaaccagcct ggccaacatg gtgaaacatc tctactaaaa atacaaaatt agccagacgt 138780
ggtgacgcat gcttgtaatg ccaatacttg ggaggctgag gaaggagaat cacttgaacc 138840
tggggtgcgg aggttgcact gagctgagat cgcgccattg cactccatcc tgggcaacaa 138900
gagtgaaatt ccatctcaaa aaaaaaaaaa atgtttggta gctgaattgc catttcctta 138960
ttaacatgcg tttttctatt ggtaattgaa cctgtgacat tgtgtgatat atacgctatt 139020
attaaattct attgagaagg cttagtttta tatatggctt atatttttgt gatatttgat 139080
tttatgcatt actatttagt tattacaatc taataaaaat gtggcaaatt aattttcttc 139140
tttaaaactc tccacattaa aatatgtctg tacttttaca ttttgattgt ggtcactgaa 139200
atagcccttg aaagagacct ttacttctta tatcatttct tatgaaggat tgaattttaa 139260
tatcccatca aaacttgctt ttttctttta atctgtgaaa atgaatttaa tttcagcagt 139320
aaaattgaca gcatccattt ttatctttaa ttaacttttc agtttggctt tcatcttaaa 139380
ggctcacggc agaatttatt accaagccat aatagaagtg ctgaatggaa gattcagaga 139440
agctgcctag ctctgaattt agctcagttg accccattat aaaaaagaaa agtgaacaac 139500
attgatataa aagacaactc attaggccat accactcaca gatgacaatg tttatttttg 139560
atgtctgcta tttacttggc ctcctaattc cctttccatg cactctcttt ttaactccaa 139620
agcaccaact gccctttact taagggtttt gtaaggatga aagtacgtca gagaataatt 139680
gctacataaa taataatagc taccatctat tgaacactca agcactgtgc taaggacttt 139740
atgaacttta cattctgtga ggcaggtttt atggcactgt ttaaaaagtt agtaataggg 139800
cttaaagaga ttaactttag tttagtgaat ggttaagtcc ttgaagtcag gtcacctgga 139860
ttcgaatccc tgcccactat tttctagctc gctagctctc agatctttgg attcatttat 139920
tcagtgaaag taatgagcag agggagtaca gggcccaact tagagagatt gctttcatac 139980
aagaagtgac gatcagccca gtgctgaagg aggagtagga gttaggcaag gcagaggagg 140040
aggaggggtg gagagagatt agtccaggca gagggaacag catgtgtgaa ggccctaggg 140100
tgggactggg cttggtggtt cctggactga aggggcccat gtggctggaa tttagcatgc 140160
aaaggggagg ggtgtgatgt ggagtttgtg agcgtagcgg gggcccctct aagaatcatg 140220
acaaggactt gggattttgt ttctgtttga agacaatcac tcaggctgcc atctggagag 140280
tgtgttggag gatgcaggga aggagaccca gtgagaggct ggggcaggag tctaagatag 140340
agatgcattt gaataaacta ggagtggaaa ggagatacaa gagatggatt caaaataaat 140400
tcaaggctgg ccaggcacgg tggctcacac ctgtaatccc agcaccttgg gatgctgagg 140460
caggtggatc acctggagtt cgagaccagc ctgaccaaca tggtgaaaca ctatctctac 140520
taaaaataca aaattagctg ggcctggtgg cgcatgcttg taatctcagc tacttgggag 140580
gctgaggcag gagaatcact tgaacctggg aggcagaggt tgcagtgagt tgacatcgca 140640
ccattgcact ccagcctggg caacaagagt gaaactcctt cttaaaaata aatacataaa 140700
aataaataaa taaataaata aattccaggt aaatagcact tagagttgaa ttagactcgg 140760
tgggtgaagc agagggagga actcaggatg acttccagtt ttctagcttg agtaattagt 140820
cagatggtgg tatcattgat tgagatggga aggctaagag gataacatgg tttggaacat 140880
cttaagtgac ataactaagt gattatgatg taaagtacat agtcaaatac actggagctc 140940
agaggtgaga tcagcaccta tctgagtatg aatctggtca tcatcaatat atggatggta 141000
tttacagcca gggaagtgaa taagatcact gagggggga gtttacagag acagaatagg 141060
tcccagattt gagcctctgg aatttccaac atgcaaagcc tgggtagaag aggaggaacc 141120
tgccaagaga actgagaagg tgttggccaa aacaaggata ataaaagtac cactcctgta 141180
atattgatac taaatgaact agcatattaa aacgtgttta aattcttaca gtccccatta 141240
cttagcagtg ttaagataat tgttaaattc tactttctat ggcaaggtac tgactggcaa 141300
gtaggtatta taaaggtgaa caagacatag ccccgctggg tatggtggtt cacactccta 141360
atcccagcat tctgggaggc cgaggtggga ggatctcttg agcccaggag tttgagacaa 141420
gcctagacag catagttaga ccttgtctct accaaaaaaa aaaaaaaaag aaagaaacaa 141480
acaaaaaaat caaaactaaa aaaattagct ggttgtaggg gtgcacccct gtaatcccag 141540
ctacttgata ggcaggggag ggaggatcgc ttgagtttga gccctggagg ttgaggccac 141600
agtgagctat catcacactg ctacacactc cagcctgggc aagagtaaag ccctgtctct 141660
actaggaaaa aaaaaaaaaa aaaaaaaaaa aaaagacata gcctctaggc tgagaaatcc 141720
actatctagt agagaacata attatggaga aatagataaa gagaaggcag gtggcatttg 141780
aaatgagcct tgaagaaagc gtgggtttgg atattcagaa gaggggagaa ggaaggataa 141840
atgaagacag gaaagtgtaa taaaaattcc acaatcttca gaggaaaagg tggtgtctgg 141900
gatgcaagaa ctgtgtaata gtccctttgg ctaagtctca gaaagttggt agatagatgc 141960
cactttaggg gaactttgta ggtggtggct gcagcaacag cagcaatttt cattgtcatt 142020
tggtcagcta atgtctccta gcagtgtgaa gatgcctgtt atcagagtca ggtgtagcac 142080
catatccagc aaccatgagt aattggcgta tccccctgga aaaaccatgt aagatgtaga 142140

-continued cattatattc tgattatttg tttggatttt aaaatgccca acaaatgtca cgctttgcct 142200
ttcacttaat agcaacaatt aatagtgttt ttcatagatt atgtaaataa ccatcattct 142260
catgattatt gatataacat ctaggagttc caattatact tgcagtggct gcactgacaa 142320
ccatttcatt ctagttttgc cactgacagg tactgtgacc ttcagcagtt attcaactcc 142380
tctgtttcaa atcagttagc tgtaaaagca gaataacatt ttaaagtcat ccaaacactg 142440
ttaggatgaa ttgcataagt gcctgtaagt cccataaatt cttcagagta aaatgtaaat 142500
ttgcagtgaa aggatgatag gtactgtctt tcatttctgt gcagaagtgc aattaattac 142560
taatctggtt aacatcttgt gcatcccttt tctgtggccc ctttgtttaa gtcctgttta 142620
aacagattgg ctccattgga tgtaatttac atttttccag ctgtatttgg acctaagaag 142680
agcatcttca ctgaattttg ctgtttagat tctttgcaac caggtttagt tttcacaga 142740
tttactagtc tggagggtgg agtgaaattt ttgctcacaa tgagtcttag aggtgtcacc 142800
tccataaagc gttctgtgaa gagtcagcgg ctccctctgc cactgaagtt taaagataat 142860
tcgcctgaat cccttcagcc aaatgaagct ttctaattat ggacagagag gatgaaatat 142920
agggtctgga gggatttgag acgggtttcc agcagtcggc accaatctcc accagaggtg 142980
ctaagtgtct gtagcagata gtcactaata tttacaaatg ttaattgatg acaacacgga 143040
gggcgatgcc cacgtttgag gcgactgcat atcatttccg gggatggctt gagtgagtgt 143100
cagagctgta ccttcccgag tcctctagtt tatctgcctc ggttcctcgc ttccagacga 143160
ggaaacaggc ccagagagga aagtgacttg cccagggttg tctcgctggt ccacaacaca 143220
ggtctcctgg tggggacccc ttggctgaca cgacagcccc aggaggcagt caagctgcga 143280
ctggtacttc ctggtgagaa agacttgagt gggcagcggg gcccatggag agcgctgcag 143340
cctggagcaa gtcccccacc actgtgattc tgccccagcc tccagcttgt ttctttctga 143400
tcacaactcg gaattacttt atttacattt tctatcagct gggagcaatc tgtccctctg 143460
cttcccctttt tggtgctgag cacagagcag acatcaatga atagctgtta tcttaaggtg 143520
tgcagtgact aggccaagga catccggtgg ttagagaagg acgcgcctgc gatgccagcc 143580
tcaagtcttt gccttcctgg aactctgctc cagggtcgca cctgcccaaa ggaaggcctg 143640
gaggcggggg ccagggcgat ggggctgggc caggcgtgga aaaagaggag ctaggagcag 143700
acagggttgg accagaggcg gggcggggtg gggaaagggt tggtggggat cggaggcggg 143760
gctatgaata gaccggactg ggccaaaagg aacaaggcga ggattgggcg gggccagagg 143820
gaaatagggg cggggctagg cgccgggagc ttccacatgc gtcccgagcc cgccagaagc 143880
tgctaggctg aggctgctgt cccggcggga gctgtggcgc ggagcggccc ctctgctgcg 143940
tctgccctcg ttttgtctca cgactcacac tcagtgctcc attccccaag agttcgcgtt 144000
ccccgcgcgg cggtcgagag gcggctgccc gcggtcccgc gcgggcgcgg ggcgatggcg 144060
gcgcgggggt cagggccccg cgcgctccgc ctgctgctct tggtccagct ggtcgcgggg 144120
cgctgcggtc tagcgggcgc ggcgggcggc gcgcagagag gtaagcccgg gctgcagagg 144180
ggcggggcgg gagctggccc ggactccaca tcgcggtgcc caggaagccg ccaggcgacg 144240
gccgccggaa aacctggttg cgaggggagg tgggtttttt tctcctgggg gcttggagtg 144300
aggtttcagt ttaaatgtcc agatttgctc atttaaatgc agagaaaggg ctacttgggt 144360
gggttttctt tgttgttcca cgacctgcat cgctggagac tacgaggctg gcttagcgta 144420
tacttccaca caactttttc agtaaaagat gccactcttg tccagcaggg ctttcctgtc 144480
ctggtggcag ccaagcttcc cattttgttg cccatttacg ggatatagag actctggggt 144540
tcattctagg ggttgggact tatcttccac ctcctgcccg ccgcctcttc ctccatccct 144600
gtcccctacc caccgcagca tttgaaaacc tttcctttcg ccggagatga aaggtgtgtg 144660
ttgtagcagg ctaggcggcc aacttccctg gcttcggggc taatcgtttg catccagagt 144720
tcctcactag ctccttagag cacagctttt ttcagcctgc tgtttttcaa gaggttttgg 144780
acaggaatgg aaacaacaaa agaaatcgcg tagtcctaca tgtttcaagt gcttgggaaa 144840
gttttagagt cagttctctc aataccttga agaaaaacac gtttgtggag cagctatggt 144900
gtgatctaaa cgtagaaaag ctaagcatcc gttaagcaag atatgattac agaagttcac 144960
tacgtctgta tttcaggttt tatgagtgag tttcttaaat agtggaaata ttgcaagaac 145020
cttttcttgc ctttcctttg ttaaggtttt taatctatgg ctcctgattt taggaagtaa 145080
taagactaga ataattcatt gcaggatgta ttgcttagtg tagaccgaag agaaataaga 145140
tggagggtga tttaaacaaa tgaagaaaat cctgggcaga gagagttaaa cagaaagaaa 145200
ggaatgtgat tttggagcca ggcaaacctg tattcaaatt atggctctgg tgcatcctga 145260
ctggacgaac ttctctcagc tgttttcctt ctttaagaaa tggcgggccg ggcgcggtgg 145320
ctcacgcctg taatcccagc actttgggag gccgaggcgg gcagatcacg aggtcaggag 145380
atcgagacca tcctggctaa cacagtgaaa ccccgtctct actaaaaata caaaaaaatt 145440
agccgggcgt ggtggtgcgc gcctgtagtc ccagctactc gggaggctga ggcaggagaa 145500
tgacgtgaac ccgagaggcg gaggttacag tgagccgaga tcgcgccact gcactccagc 145560
ctgggcaaca cagcgagact ccgtctcaaa aaaaaaaaaa aagaaaagaa aagaaatggg 145620
ggtaataatc atgcttacct ctcagagttc ttttgaggat taaataatgc atataaaatg 145680
ccaggcacag tgcctgacac tcgagaaaat ggtagttctc taccccttt gatgaaactg 145740 aactttaaaa atctgtttca tgtcttttaa tatagaacac tgtagccaag cattaaatag 145800
tgtaaatagc tatctccctt catgcatggt gttcagtgtt ataacaaagt gaaatcgatt 145860
agttcctgct ttctgcccca cttagttaat atctctctca taataaccat ctggttctat 145920
tgcacttctg tttcctcctg cttccacgta agctccttaa gaactgtgat tcttgtttat 145980
ctttgtatcg ccaacacctg ccttaatgta ggagcccagt gaaggtttgc ggaaggaagg 146040
agtggaacag tattacctct ctggatatta gtttctccat ctggatggtg aggggccatt 146100
aaaggatccc ccttccacct tgaaaattat aagattctgt gtgctcttag aagtgatcat 146160
cttgaagaac aaagtgatac tgaatggatg atgtaattgc acacttgctc ttaactgtta 146220
atatgcattt gtgtacaact gtcgttccat gtgggtggct gaaagtactg tctggaaata 146280
ggagacctgc cactcgctgt ctgtgtttcc ttggacgtat tacttgacct tgctgattct 146340
ttgtttctct ctctttaaaa tgaaagggcg gtagtagatg tttttaagtc aactttaagt 146400
tttttaagtt caaatataat tacctttatt tttacaattt attgttttca tattcgtctt 146460
aggttcttaa tagtaacttt tccctgtggt tttctgtgag ccagttccca ggtaaagaga 146520
atatctagtc agcccgcagc tattatttgg ctgatgaacg gtcacagagc tgtggaaagt 146580
ggctcaggag acaattaaag tataatatat taaagtataa tgaactagta catcaagata 146640
atacaagcat tttaaactga cctgtgattg ggacagtgat tatggaagtt agatagtcat 146700
taactaccta actagttata tttcttacta tttcttagct atgtgacatt ttaaagccaa 146760
tggttatatt tcttagctgt gtgacatttt atttttttaa tttttttttt aaaatattac 146820
tttaagttct gggatacatg tgcagaacct gcaggtttgt tacataggta tacatgtgcc 146880
atggtggttt gctacaccta tcaacctgtc atctaggttt taagccccac atgcattagg 146940
tatttgtcct aatgctctcc ctccccttgc cccaacctc ccgacagacc ctgatgtgtg 147000
atgttcccct ccctgtgtcc atggattctc attgttcaac tcccacttat gaaagagaac 147060
atgcggtgtt tggtgtctgt tcctgtgtta gtttgctgag catgatggtt tccagcttca 147120
tccatgtccc tgcaaaggac atgaactcat tctttttat ggctgcacgc tatgtgacat 147180
tttaaatggc tgaaccttaa ttttaattac tatatgtagt ggctgaaaat gaaataggaa 147240
aatgaaataa ttcatagaaa atgagagcta tgaaagattt ttttcttctc atctttagtc 147300
attttcatta acattttcag aagctaacag aaatacacac atactgactg tcagttttac 147360
ttttgttata tatatgtcct tacgtaaact ttatacacaa tttaatttgc aatttaaaat 147420
tattttgatt tccaagaaat actaaatatg tgaactagac tgagcagctg gagggtagga 147480
tttcatttgt ctgtgtattt cctgatacac tgcagatata cctgcattta ttaatgtagc 147540
ctatggattg aactctgagc ttttttcaa cctataatct acaaatgaga tctagcaagt 147600 aatttttat aattaggata tgaagtttta gttcagtaat ttcagtacag aacttttct 147660 tctaatagca ttatttttct taaagcattg gaattaaatt atcagatgat agtttaagtt 147720
cactattaaa taagcatgtc gacaattaga gttgttaaat attggaattt tttttttt 147780 tttttgaga cggagtcttg cactgttgcc caggttggag tgcagtggtg caatctcggc 147840
tcactgcaag ctctgcctcc cgggttcacg ccgttctcct gcctcagcct cccaagtagc 147900
tgggactaca ggcacccgcc accacgcctg gctaattttt tgtattttta gtagagacgg 147960
ggtttcacca tgttagccag gatggtctcg atctcctgac ctcatgaccc gcccgcctcg 148020
gcgtcccaaa gtgctgggat tacaggtgtg agccaccgtg cccggcctgg aattgttttt 148080
gaaagaagtt tagaatttgt ttctttaaac atctgttcca cagaacagca tgggtatagt 148140
gttttttttg tttttgtttt tgtttttttt cttgagacag agtctcactc tgtcgcccag 148200
gctggagtgc agtggcatga tcttgtctca ctgcagcctc tgcctctggg ttcaagtgat 148260
tctcctgcct cagcctccca agtagctggg attacaggca tgtgccacca tgcctggcta 148320
atttttgtat ttttagtaga gatggggttt ctccattttg gccaggctgg tcttgaaaac 148380
tcctgacctc aggtgatccg cctgcctcgg cctcccaaag tgttgggatt acaggcgtga 148440
gccaccgcgc ctggcctggg tatagtttta taatgacaat atgatagaaa ggattattta 148500
aaatcatcct tttctgttct atgatgaaaa atgttaattt agatgttttg ttctcctttg 148560
aggaaacatg atattgtttg tcctactgtt tatttattta ttatttttat tgaggcagag 148620
tcttgctctg tcacctaggc tggagtgcag tggcgtgatc ttggctcact gacacctctg 148680
gctcctgggt ccaaatgatt ctcgtgcctc agcctcccaa gtagctgaaa ttacaggcat 148740
gtgccaccaa tcccggctat tttttttttt tttttttttt ttttagtaaa gacagggttt 148800
caccatgttg gccaggctgg tcttgaactc ctggcctcga atgatccgcc cgccttggct 148860
tcgcaaagtg ctgggattac aggtgtgagc caccacgccc ggcccctcct actgtgttta 148920
attcagtgac ttcatgctct tctcttccaa agtgtgatta taaaatatag ccttttacca 148980
gtaaaaatag gagttaaata tgaatatttg aattctgaca aaaaaggtga tatgaacttt 149040
taggttttat ttttatctgg ttttattttc atttttattt tacattcaac tgtatgtatg 149100
gaattaggca aaactctttc ctctaggtca ggatttctca acctctgaaa ttttgtactg 149160
ggttattctt tgttgtcaga ggggggcgtc ctgtgccttg taggatgttt agcagcatac 149220
tggtctctag ccatgagatg ccagtagcac ccactgaaaa atgtctccag acattgtcag 149280
atgtgccctg ggggcaaaat tgttcttcac atttgctacc ccttgagaac cacttctcta 149340
ggtcttgttg accagggctt ctgaaactta gatgtacaca ggaattccct cagaacgcag 149400
atgctgatcc agtaggtcag aagcagggcc tgagactctg catttctaac aagctcccag 149460
gtgatgtgaa tactgttggt cagtgtatca caattaagta gcaaggttgt agaaaagtcc 149520
acattcatac caactgggtg aactctcaag ggaagccgat gaaagtaatt atggaaatag 149580
tgaatttaca atgaattgta gcccaaacaa tgtaaggcta atagaagcta agaaaacaag 149640
cattatcctg ctgtcctaac aaagcagctg tcttcacttt tccatatttt cttccagtcc 149700
ttagtattca ttcataactc gacatctcta agggggaaat ttgcaagagt cttttcaagg 149760
tcatacaggc aacctcatgc accattaggt gttttattcc ataatattgt aaatatacta 149820
gctcataata catatttata gcctgttgag agatttatag ccccaaatta agataatgaa 149880
ctctgcattt acttgatctg atgatgctct gccttttttt tttttttttt ttgaagtgta 149940
caagttgtct cgtctcctcg agaactattg actgcaccta aattaatacc acctaaggtc 150000
attcattttc ttactgcgag tgttctgaga gtcagggtaa gatattaagt ttactaaggc 150060
atagcagtta cagtgtaact ttatcctata attctgtgat aaaaatcaat ataaaatata 150120
atgaaaatcc tggagcgaaa aaaatccctc tatattttat ctgtaatact taaaataatg 150180
attggtaagc attcttgttt gtcacattga aaatgttgga tataatacac attttccctc 150240
gtttacaaaa tggttacgtt cactgcttta tcttgctgtt gcttaaaata gccctcctag 150300
gactgctgca aagaggattt ttttttcaaa agagtacaag tcactttttg ctaacttata 150360
aaaagatgca aggagacttc aggggtagat taactgctcc aggaatgcct tgattatgaa 150420
ttggggaggt ataatataca tcactcttca aatcttttta gatatattat cttatttcct 150480
tcttatggca gcctgtgaag aagaaaagga agatattggc agcacctagc aagatttaaa 150540
atgtgcgccc ccttgactca gcagttttac ttctgagaat cattgctata gaaatctttg 150600
catcagtatg gaaaaagaga tttgttaatt acagcatttt ttcccattgt aacattatta 150660
gaaataacca aaaactgaag actataaatg ccaatcagtg gtgaaaactt aaataaagtc 150720
taatgcactc ataatgatca ctttgcagct tgtgaaggaa gactggagat agttggacat 150780
ctactggtat atagtttata tagttgtgtt ttttattttt tattttattt tttttgagac 150840
ggagttttgc tcttgttgcc caggctggag ttcagtggcg tgatctcggc tcactgcaac 150900
ctctgcctcc cgggttcaag tgattctcct gcctcagcct cccaagtagc tgggattaca 150960
ggcatgcacc accacgcctg gctaattttg tattttttagt agagacggag tttctccatg 151020
ttggtcatac tggtctcgaa ctcccgacct caagtgatcc cccacctcag cctcccaaag 151080
tgctgggatt acaggcgtga accaccacac ctggctggta tatagtattg aatgaaaaaa 151140
agttgcagaa cttagaggaa aacatgtttc tgtgtgtgag tgaacatgca tgtaatttaa 151200
aatatctaca cgtcaaactt aatggttacc cttggaagga aggcgaagga gaggaggagg 151260
gagaattctt actctttatg agcttctgga tttgaatttt gacagtgacc acacattcct 151320
tttgcaatta tagcatcatt ttgagaaaaa acaaaataaa tctgggtcct agttctactt 151380
ctgctgctta ttagctacta gtgtcacaac agtggtttgc aagaagggtc agttttgctc 151440
cccctcacca acatttggca atgtctggag acatgattgg ttgtcatgtg gggcggtggt 151500
atgtctagtg ggtagaagcc agggatgccg ctaaacatac agggcacagg acagccctcc 151560
acaacaggga attgtccagc ccaaaatgtc cgtagtgcca agttgagaaa tcctgtgtta 151620

-continued gactccagag ctgcagtgct gttggaatat gcaggtgatg cactgtgcag tggcaggggc 151680
gccattctca ctgtggggtg tactttgcat agccatagaa ttataagtat gatataataa 151740
ggtaaataaa tatgcaagtt tttaccccag gaagacaggc accaggtctt cgttttctgc 151800
tctccctctg gcacctggca cagaggttgg cacagtaagc agctagttgg catttgttga 151860
attaacgaat tgaacaagat atcacgttag gctctagtgt ggccaagttg tagcagatgc 151920
taaagattta agaataattt gtggcagaaa ctttaaatta tagttaatgt ctgtttttat 151980
ctgcaggttg gcaaaagact gctaatatcc acatttagtt gctgaacatg ttggttgact 152040
tttttccaaa tcattacctt ttgataagaa aatcatgatt cttcatggaa aaatgccaga 152100
gcaaagcact atcaaatgtt cctagaattt tttttttttt tttgagacgg agtttcactc 152160
tgtcacccag tctggagtgc agtggcacaa tctcggctca ctgcaacctc cacctcccag 152220
gttcaagtga ttcttcttct tctgcctcag cctcctgagt agctgggact acaggcgtgc 152280
accaccacgc ctggctaatt tttttttttt tttttttttt tgtattttta gtagagacag 152340
ggtttcacca tgttggccag gatggtctca aactcctaac ctcgtgatcc gcccacctcg 152400
gcctcccaaa gtgctgggat tacaggcgtg agccaccgtg cccggcctag aattggtttt 152460
ttaaatcctc agggggaggc caaggcgggc ggatcacctg aggtcgggag ttcaaaacca 152520
gcctgaccaa catggagaaa ccccgtctct actaaaaata caaaattatc cgggcgtggt 152580
ggcacatgcc tgtagtccca gctactcagg aggctgaggc aggagaattg cttgaacctg 152640
ggaggtggag gttgcagtga gccgagatcg caccaatgca ctccagcctg gccaacagga 152700
gctaaacgct gtctcaaaaa aaaaaaaaaa aaatcctcag gtatcttttt ggctacatac 152760
tatatttagt gaagaaggtt tttttaaaaa aatcttaaac tacctagaca ctacctaaca 152820
tagtaagata atgtacttta tttcatttga ttcagacgag agtgaagcag ctaagcagag 152880
gttctccttt ttattaatgt tttttaatgg aaaaataatg ttcacaagaa tggtccaaag 152940
taatgaatca aaaagtcgtt gccataccca tttaacaatt attgacatat tgctaacaga 153000
tatccttatt ttatataggc tagaaaattg tgggccagac acggtggctg acacctgtaa 153060
tcccagcact ttgggaggcc gagacaggtg gatttcttga gctcaggagt tcaagaccag 153120
cctgagcaac atggcaaaac cctgtctcta caaaaaaatt agctgggcat ggtggcgagt 153180
gcctgttgtc ccagctactc gggaggttga ggcaggagga ttgcttgagc acaggagatc 153240
gaggctgcag tgagccaaga tcgtgccact gtacttcagc ttgggcgacc aagtgagacc 153300
ctgtcttaaa aaaaaaaaaa aaaggaaagg aaaaaaattg tggcttatgg atggaggtta 153360
acagcttatt agtggtgcca agtattcaaa ttaaggtttt cagctttgca gttctgtgtc 153420
ctttcctttt caccatacta aaactaagga gcaaggttac atttctttga aaataaatgt 153480
ggtttcacca aatgatttga ctgtgatttt tttaaatgtc attctcccag ttcctcaaac 153540
tttaggcaat gaatgatagt aagagttaaa attgaatttg taaaaccaaa atgtaaatat 153600
ataaaagtgt tagtgacatt actgtataca catttatacc tttgttaggt attcaactta 153660
gtttttctct tagcagctgt acttttaact actttagaag aattatccca tttaattttt 153720
ttttgttctt atcctatttt tagtgtgctt cactgcttgg tttcctttgt ttttctgaga 153780
tatgtggttt atatgctatt agcaggttgt attataatta ttattatttg gtttcaagaa 153840
gagacttgag gaaagcttta tagtgaccca ttattgcact gtgttaagag tgcccaatgc 153900
cacaagcata ttcttccttt gtatttttgc aaagttccat tgcctgggac tgtctggaga 153960
cagtctttgt tggtctatca gttaccatta ctttagcaat catttatgga agaataagaa 154020
cgaccctgtg ctggcactta tatctacact gttagctaat ccttacaatg acctcataag 154080
ggaggtactt ttttaatacc tgtgtcacag atgaagaaaa atcatatcca aagttgagta 154140
acttatctat ctttttggtt atagccaatc ctattaggtg tgaagtgctg tttcattgtg 154200
gtattgattt gtgttttcct gatggctaaa ggtgttgagc atcttttcat atgcttactg 154260
gcctttcttt ggagaaatgt ctaagttaat ttagatctct tgcccattta aaaattggat 154320
tattgaatct ttttattatt catttataat agttctttat agattttaga tacaagtccc 154380
ctatcagata catgatttgc aaatattttc tctgggttgt atatcctttt gatgtaaggg 154440
atcttttgaa gtcaagtttt ttgttttgtt tgtttgtttt tttttttgtt gttgtttttg 154500
agttagagtc tctctctgtc tccctgactg gagtgcagtg gcacagtctt ggctcactgc 154560
aacctctgcc tcccaggttc aatagatcct cctacctcag cctccctagt agctgggacc 154620
acaggcgcgt gctacacgcc cagctcatta ttgtgttttt agtagagaca gggtttctcc 154680
atgttggcca ggctggtctc gaactcctgg cctcaagtga tccatttgcc tcggcctccc 154740
aaagtgctgg gattacaggc gtgagccacc gcgcctggcc caagtcaact atttttaaga 154800
caaggaaggg aagaaaaatt aaaatgtaat aatgtaataa gtaaggccgg gcgtggtgga 154860
tcttgtagca ctttgggaga ttaaggtggg aggattgctt gagcccaaga gttcaagacc 154920
agcctgagct acaaaaagag accctgtctc tacaaaaaat aaataaatta gctgggtgtg 154980
gtggaacgca cctgtagttc cagctctgtg ggagcttgag ataggaggga ggctgaggtg 155040
ggaggattgc ttgagtccag gagttccagg ctgcagtgag ccgtgatggc gccattgcac 155100
tccagtctgg gtgacagggc gagacccagt ctcaaaaaaa aaaaaaaaca aaaaaagcaa 155160
ttactgtcat cagcctatat gtagtgctat agagatgcca aaaaagtgtt catttgaat 155220
aggatgagca aatattaact atttaaaaca acttctaaaa agaatttttc catttgattc 155280
agtttattta gaatttacct tacatatagt gtcagtcttt cctactggat agtaaatgtc 155340
gatgttgtct gttttgttta ccagtgtgtt cccagtgcct gtctgataaa tgtttgttaa 155400
atgaatgaat aagtaaacat caatgtgggc tagagctatc gggggtgtgg cattcattaa 155460
gttaatctag aaagttgtca caagatggaa gatgttaggg tgatgagagc atgaagccaa 155520
ggtgcccctc agagccctgc ggtttatgaa ctctgtagca gcaacccttc ttttcatacg 155580
tatatcctga tttgtaaaat gaggggatgc attggattgt ctcctttta acatgctgag 155640
gtttgtgaac agtggaaact taaaacattt acagccagct aaaaaagcat gactgctaag 155700
aagaatttaa gtgcactatc aaggttttat gctaagatac ctttgacatt tgcactggac 155760
actgctgtaa agtgtcctaa gaaaatggta tttctagtat gggatgtatt acgaagatat 155820
tcacaaagca gtatcttgaa gattctcatt aggtagaatg ttgggattac tattttattt 155880
ataccctgtc tactttcttt caaagaagat ttgagatagc gactcaagct agtttttccc 155940
ccactcaggc aaaggttcct ttagatgcta ttgacagaca ttttaggctg ggtgcagtga 156000
ctcacacctg taatctcagc actttgggag gcagaggcta gcagatcgct tgagctcagg 156060
agttcaagac cagtctgggc aacatggtga aaccccatct ctaccaaaaa tacaaaacat 156120
tagccaggtg tggtgcacgc ctgtggtccc agttactcag gaggctgagg tgggaggatc 156180
gcttgagtcc aggaggttga ggctgcagtg agccaagatt gcaccattgc actccagact 156240
gagtgacaga gaccctgtct caaaaaaaaa aaaaaagaca ttttatttat taatactttt 156300
atcttttaac ccttaaattt ttggtatttc agggactata ggaggattag aagaggagaa 156360

-continued atggttcaat aatgctattt taacttgaag ctctaaaatt aatggctttt aaacattaag 156420
aatgactcta gtgtataatt ttctaaatta atctaaatat cttcaatgct gtgcatttca 156480
gcataaggtg acttttacag gcgtcaccac acaaactcca tagtatttgt agattaaact 156540
aagtatctta aactagttac tgcctggcgc agtggctcac gcctgtaatc ccagcacttt 156600
gggaggccga ggcgggtgga tcacctaagg tcaggagttc aagaccagcc tgaccagtag 156660
ggtgaaaccc catctctact aaaaatacaa aaattagcca ggcgtggtgg cgtgtgcctg 156720
tggtccctgc tgttcgggag gctgagacag agaatcactt gaacctggga ggtggaggtt 156780
gcagtgagcc gagatcacac cactgcactc cagcctgggt gacagagtga gactccgtct 156840
caagataaat aaataaaaaa taaataattt tttaaaatta aactagttat tcagggaagc 156900
aggacacaaa ctcttgagga gtaggttatt tatgaaaaag agaaccagga aataggtttc 156960
ctccagctag agtacctgga tattctttca tatctctgta tggaaaacat ggtctatcat 157020
cataaagaga agattttgtg aaagtgctaa tttctctcca accatttctt ttaggttgga 157080
gaagaacaat cacttgctac tgtaatcctt atgtgtatat ttgctgatta ataagccagt 157140
gacattttgg tttcaagtaa aagtggtttt ttcgtaatat cattagtctt aagtaaaagt 157200
catgcttgaa tttttataca tttcacattt ccttaagtga tcccaggcca gacaacagtg 157260
aaaactcatt tcttcagaga tgcttatttg agctctgtag tagcataagc ataactgtga 157320
tccccaaatc taaccagtct ttggccatag tatccaaaac attttatatt ttgacttttt 157380
tttttttttt aacaacttag gtccttaaat agattttttt gaagaaacaa gtttcttttt 157440
agtatattta atggcacatg tttcctgatt tttgaacggg aattcctcat cttcatttta 157500
cattgggccc tgtgaattat ttagccaacc atgttcacat tctcacatat acatacattt 157560
atttatttat tatttgtttg tttgtttgtt tgtttgtttg ttttttgaga cagagtctcg 157620
ctctgttggc cacgctggag tgcagtggca caatctcggc tcactgcaac ctctgtctcc 157680
cgggctcaag cagttctcct gcctcagcct cccaagtagc tgggattaca ggcgtgtgcc 157740
accatgcctg actaattttt gtatttttttg tagagacagg gtttcaccat gttggccagg 157800
ttcgtctcga actccttacc tcaggtaatc tgtccgcctc agcttcccaa agtgctggga 157860
ttacagacgt gagccaccgc ctatttattt tttttactga tcttgaaata aacctttctt 157920
gattctttat cctcagtatc cctatatcag cataactttt ggaaagagat cattcctgtc 157980
tttgcactct gtcttaaaca tactgcagtt catctctctt ctcttcccat agatggcttt 158040
tgttagattc accattgacc tcactgttgc taatccaaca ctcagttctc agctgcctct 158100
ccatgtctca tgagtagcat cagtagattg ggaggctcaa cccttcttgc tgcattttct 158160
tcatttagct tccaggacag catgctatct gctatcttcg agttcttcct tccttattcc 158220
ctaaaaagca gttttataca aatgtatagt tttatacaaa tatagtagca aagtatgtca 158280
aagctaaatc aatcattcaa tatttatata ttttcatatt aagattatga caggccaggc 158340
acagtggctc acagctgtga tcccagcact atgggaggct gaggcgggca gattgctgaa 158400
ggtcagaagt tcaagaccag tctggccaac atggtggaac cccgtctcta ctaaaaatac 158460
aaaaattagc caggcgtggt ggtggatacc tgtagtctca gctactcggg aggctgaggt 158520
ggagaattgc ttgaatccca gtggcagagg ttgcaatgag ccgagattgc accactgcac 158580
ttccagcctg ggagaccagg caggactccg tctcaaaaaa aaaaaaaaaa aaaaaaagat 158640
tatgcaaatt aaagcaattt taacatttat aattgataaa tgagctttgc tttagtatat 158700
ctgttttcta ggtttggaat ttcaagataa ctcctgccac cctggcaatt taaaagcttt 158760
tattatttag atttgaaact attctgtatt gagtactgag tgtttcttaa ggagctcagc 158820
atattccaat agtcagtctg atttaactga gacgtatctg aaccagagtg tcccttattc 158880
tatcagaaat acttacatta atatttcatt ttaaaagctg cattaataat agcctaaatt 158940
gtagtttggt tcattaataa tctgaacttt ttttttcctt tttttttttg agacagagtc 159000
tctctccatg gcccaggttg gagtgcagtg gcccgatctt ggctcactgc aacctttgcc 159060
tcctgggttt gaacttttgt ttgaaagtac aggtatctgg tgggagagaa gcgagtacat 159120
taacttttaa aaatttgtta tacaggatta tctgaacctt cttctattgc aaaacatgaa 159180
gatagtttgc ttaaggattt atttcaagac tacgaaagat gggttcgtcc tgtggaacac 159240
ctgaatgaca aaataaaaat aaaatttgga cttgcaatat ctcaattggt ggatgtggta 159300
ggtgtgcata tccttctata gtcaatttcc cacagattta gtgagagcct ggtgtgtgcc 159360
caggcactgt gctaggcacc aaggattaca aaggtgattg aagcagtcct ttgcctgaag 159420
gaactcacca gggaaaagta gtgattgtgt cacatacatg ataacacact gtgtttatat 159480
attttatagt ttagaaactg tttatctcaa tttggtaatt ataagtctat ctttaacaaa 159540
ttcaaagatc taaaacattg tgtattcctt aaatgtgtta aaaatagttt caaaaagtta 159600
gcttgaaagg agggaaaaga aaataaattt ttaagtttaa gagaaaaagt ccaaaaatag 159660
agtgatagat tcttaggaac taaaagtatc acaagagatc attatcttgg gctcacactt 159720
aaaacatttc agaaattttt ctatatgacg ttcattagta gaataagttc ccttgataaa 159780
ttgtacttat tgtcaagaga tcctatctat ttaaactaaa acattcatgc taatttttaa 159840
actagtttct tcttgttctg aacatgtaaa tcaataatta tttccctgtt gtgttcccaa 159900
aataaccaag tatatgtata tttatatata tgtatgtttt aaaataacat ttatagatgt 159960
gctttatgtt ctgattacag aagcaatgcg tgatttttgt agagaatttg gaaagtgcaa 160020
aaaatacaaa tgagaaaata aaaagtgact gtaattctac tacccggaga tgactaatgt 160080
taataattag ttgtgtttct tgccagtctg tctttgtgta tatgttacaa aattggaata 160140
atattttaga aataattttg attactgctt tttctctact atgacatgat gaacattttc 160200
ttatgtcatt acatactctc caaatataat ttttaatagt tacatatttc atctataatt 160260
taagcattct cccattttga acagaagctt gtttccaatt tttcttatta taattaacaa 160320
tgatgaatat atttgtacac aaatgcctga acgtctcctt tccttaagaa aggcagttag 160380
tgaaccaaag gatatacctt tttcaaagtc tattgctatg tcatctaatt gcttccagaa 160440
aggttaatga atatatgtgg actgtgtgtg ctcagccctt agctagtcaa tatggggaga 160500
ttttaaatga aaataggaaa gtggaaaagt aaggtggtag ccaggtgtgg tggttcatgc 160560
ctgttatccc agcactttgg gaggccaagg tgggtggatc acttgaggtc aggagttcca 160620
gaccagcctg gccaatatag caaaacctca tttctatcaa aaatacaaaa attagctggg 160680
cggtggtccg tgcctgtaat cccagctact caggaggctg agacaggaga atcgtttgaa 160740
ccctgggaag cagaggttgc agtgagttga gattgcacca ctgcactcca gcctgggcaa 160800
cagagcaaga ctctgtctca aaaaaaaaaa gaaaagaaaa gaaaaagtaa ggtgggtggg 160860
gcttgctctc aaagatcttt ctggttgagg tcattgacac acaaatggtg tagaaaactg 160920
tagcactaaa tcatgatgcc agaaagagct gggaatgcag atcttaatga atgaccttat 160980
caaagaaggt agggtagatg aggtggcacc cgagctggct ttgtaggaag tgtagggttt 161040
caacgtggca gagaggaaaa gtatttaagt acaaaggaac aatatagttg taggtatata 161100

-continued agtgataact gagccttcct gtacagctgt ttagatcaaa agatgaatgt tgggagccct 161160
ggcatacagg agtggtctga ctggacggtg gagaaggtga ggagaatccc tgcatgccac 161220
ttcgtcttta ctcctgccat gtttacttct tgggagaatt ttcctactgg cactagccat 161280
ttattattca aggccaaatt catctgtcag accctttgtg aaatctttcc agaatccata 161340
agacagcctc tcctgtgttc aaaatttttt tttttttgca ctttaatatg gtgcccatta 161400
cactcactgg tactcatgtg ctctggcatt tcatcttcaa agctgggtga actttattcc 161460
ttgtatctgt cccagaacct agcacggtat ctggtacata gtaaatgctg aatgagtgag 161520
agacctgata ggcaacagac acgatcaaag cagtactttc agaagatcag taaaacagta 161580
atgtacatgg ttttgaggag tgaaagagag actagaaaat gaaaggcaag ttagaagacc 161640
acatacaaga aggaacagga cttgaccact gaatatggag ggaggcatca cattttgaag 161700
cctaggtgat tagagtggaa gagtaacaca tttgaaaaat actgtcggcc gggcacagtg 161760
gctcacgcct gtaatcccag cactttggga ggccgaggca ggtagatcac aaggtcagga 161820
gattgagacc atcctggcta acacggtgaa accccgtctc tactaaaaaa tacaaaaaaa 161880
ttagctgggc atggtggcgg gcacctgtag tcccagctac tcgggaggcc gaggcaggag 161940
aatggtgtga acctgggagg cggagcttgc agtgagccga gattgcgcca ctgcactcca 162000
gcctgggcga cagagcgaga ctctgtctca aaaaaaaaaa aaaagaaaaa tactcttcat 162060
tgttacggga gtagggcaga gaagatgatg agtttgattg tggtttgagg tgttaattcc 162120
aaagaaaatg ttcactagct tttgggaagt caagactggc tctgagatga cagatgagaa 162180
caaggatgtc catctggaat tgctggcctg gaggagactg ttgaaaactt tgatgagttt 162240
tctttgtttt tgtttttgcc cttgcctctc acctcccact ttgatgagtt tttaaagtta 162300
gtgggaagag caggaacctg atccttgagg aacatttgta gaaagtggta gaaggaaggg 162360
gtaaccaagc agagaagttg gggaagggtt gcttcttgag agaagagccc aaaaaatgaa 162420
atgtcagtga ctacgaaagc agaagaggac tgcagtcagg ggagatgaag ggtgagggct 162480
ctggagatgg agaatggcaa attcactgaa ttgtgtctga gatgttttag gttcctttta 162540
tcgctaagct ccccggaatc atatttggtg gattcctgcc ttatttccca catattctgt 162600
cttttttttg tttttaaatc tcatttttgg cttgtttgtt ttgattttaa agataaaatc 162660
tttttataaa tacgattacc cctgaaactc ttctgctata tttacacatg tagttaacat 162720
ttttccattt gttagtttag gtttcctcct ggggatcatc gtacatttat ctgtcctcag 162780
ttcatttttg ttgcatcctc cattgtgctg agcacattat agatgcttgg gaggtatttg 162840
aggtcacatt aaattaggcg gtatccctta tggtaatggc taaccaccac atcttagggg 162900
ccatttgtga acttatggat tattctttta tctgtgttat tgttgaaagt gctaagtatt 162960
gactgggagc ccaatttatg tgtgtgtgca catttttcta gggaaaggcc cataagtttc 163020
attagattct caaagatgac ctattgctat atactatcat catgggtaat atgtttacca 163080
gaactttcct aattataaat gcctctgttt agaacttttg cctaacaggc atattcagat 163140
acagggatca gcagttattc tgggtggtgt gcgactaggg tggatagcag agttggtggc 163200
tttagattta ggaaatttga gttctaaaat cagtgctacc agtaatcggt gctgtgactt 163260
taagcaagtc acctctctgg gccagtttct gtcgcctagg ctggagtgca gtgacatgat 163320
cttggctcac tacaacctct gccttccaga ttcaagcggt tctcccacct cagcctcctg 163380
agtagctggg actacaggtg tgccaccatg cccggctact ttttgtattt ttagtagaga 163440
ccaggtttca tcatattggc cagtctggtc tcgaactcct gacctcgtga tccacccgtc 163500
ttggcctccc aagtgctggg attacaggtg tgagccaccg tgcccagcca gctctagtgt 163560
tttaatcaag gaaaattgct ctttggaact gcagtgtaag agagatggcc gtgctgcatt 163620
tcccagtact cattctcccc atgcagggac ctcatggagc tgcctgcatc ctcaggggta 163680
tgcttccttc tggtctcttc ctttgtcctg ggtcacttac ctgttgttgg gacgggataa 163740
ggaatgggtc acctccagtt acctgaggta ttaatattta tttacacccc tgtcctatct 163800
ccccagtttc ctcatacttc tgtgagtctc tgtgcatagc attgtgtcct acacataata 163860
tatttgcggc tggtgattat ggatcttttg ttgattctcc tggctccatg atatttcact 163920
aaaatttaat ggaagaagta ttactttaat tacaccttga atatttggta aaggactggc 163980
atagcaaaga catgatagca gagaggtgta agtgagaagt accaaggacc tccagttctc 164040
tacaaaagta ggcacgaaaa gctttatgaa attcgtattc aaggctgcca atattttttc 164100
tttttctttt tcttttcttt tctttctttt tttttttgag atggagtctc gctgtgttgc 164160
ccaggctgta gtgcagtggc atgatcttgg ctcactgcaa cctctgcctc ccgggttcaa 164220
gcaattcttg tgcctccgcc tcctgaatag ctgggattac atgcatgtgc caccatgcct 164280
ggctaatttt ttgtattttt ttttttaag tggagatggg gtttcactat gttggccagg 164340
ctggtctcaa actcctgccc tcaagtgatc tgcccacctt ggcctcccaa agtgttggta 164400
ttataggcat aagccactgc gcccagccct caatgttgtt tctgtctagc agacctacag 164460
ggaaattcag attcttccct cagcagaggc aaatgactgt aagagatgtc cctcagggat 164520
gtacagaaat accgtatctc actgattcta agaagcacac ttttccgcat tttaatactt 164580
ctgaaatcat gatgtgtctt ataattcatg gcagcttgta attcattgac agccctttt 164640
tctcctctta gtgctaagca cataaaataa cactatgctt atatcttaga ctgcatctta 164700
aatatgagga aatatagtag ttgagatgat taatgttaaa tgcaaaaatg ccaaaggtat 164760
cttttagtgt agtttatctg aaatagagag tatgttgaaa ggagtaatgt gaaattaggc 164820
tggaagaaag atcctagctt tctagagaac cagattgatg aatgaaatgt gggtactatg 164880
tgaagaagag tgtttatata acaatgtgaa atttattatt taaagaatta ttgtttctgt 164940
aattgaaatc aatcttattt aaatttttat tttttaaagg atgagaaaaa tcagttaatg 165000
acaacaaacg tctggttgaa acaggtatgt gtgtaaaatt caaacgggca cccaattagt 165060
gactgggaca cctattttta ttatatgtat tgtagcagaa atacaagagt atgtatattt 165120
gtgaatacaa atgaatacgt gactatatgg ccttggtgga ttggcaggac acagaaagat 165180
gagggtagat ggagttcttg tatttattca gctagtattt ttggagtgcc tattgtgtgc 165240
cagacactgt tatggggaaa cagcagtgaa caaaacagac aaaaaaccct gtagtattag 165300
tccgttctca cactgctata aggacatacc caaggctggg taatttataa agggaagagg 165360
tttaatggat tcacagttca gcatgactgg ggaggcttca caatgatggt ggaaagtgaa 165420
ggagaggcaa aggcatgtct tacatggcag caggcaagag agcatgttca ggggaactgc 165480
cctttataaa accatcaatt caagatgaga tttgggtggg gacacagcca aaccacatca 165540
cctgccctca tggaacttca ttctagtggg ggaaaaataa acaagttgta tagtacctta 165600
gaagctgata agcttgggga aaaacacact ggaaaagaag atagggagta ttggggtcgg 165660
gggtgtactt ataaaaatgg tggtcagaga aaacagcatt gagaagataa tgtctgaaca 165720
aagtcttggt ggagaggaag caagccatgt gtatatctgg ggaggagcgt tccaggcagc 165780
aggacctaca agtgcaaagg tttctgagct ggtgtgtgcc tagtgtgttt aagcagttgc 165840
aaggaggcca gtgtggctag cagtgagaga accattgggg agagggggtg taggagatgg 165900
catcagataa gcaagaagag gctggtggag tagcagctgc ttataggcca ctgcaaggat 165960
tctgactctc taaggtggaa atgggcaaga atgaaatgaa ttttttttta atagatagtc 166020
ccttttatat aaaggacttt tgttttttttc tgggccacca tacatatgtc ctaactgctg 166080
ttgagcgctt ccttttgttt ttatcatccc taatttttat acctactatt tgttttctaa 166140
ccccgaactc ctgaaaggca tatatgcttt tctcagggtg cagctcctaa cttgatcaca 166200
gaattgtaac tgcatggagg tagggtaagg tgttgaaata cgcagaatgt gcaataaatc 166260
caactccctt ttgcatggac cagaacagcc aaattgggtg acaatacatc tggaaaaaag 166320
aatgtttccc ttgaacctgg atattaagtg cctgtggctt caagtcctgg atatagtcag 166380
tcagttgatg ggagaagagt tgccgagcag agccatgaac acatctagct ctggttctca 166440
cctgtgtctc acagggacca tggtgagaac cactacacaa ggggacaggg ttatctggtg 166500
cccataataa gaaagacagg gaggtgttct ctattggggg tagagatgat ctcatgtcta 166560
aaatttctgg tgtgacaaaa aagtatggta ttcactgttt ttgactatta gttttattga 166620
aattgaggca gatttctttg ttttaaagga atggatagat gtaaaattaa gatggaaccc 166680
tgatgactat ggtggaataa aagttatacg tgttccttca gactctgtct ggacaccaga 166740
catcgttttg tttgataagt aagttatatt ctaaatatag ttttatattt tcaaaagaaa 166800
acatttgtat ttctattagg cactaataat ttttctccct tttgaaattg tttaggtata 166860
aaaatcaaat gacatgaccg catgtgcctg ggtatgatta catgttttat agatgaggaa 166920
acagaggctt agggtggttg ttcttttcca agatcacaga gctagcacat ggcagagtag 166980
gggggtcaca ccaaggggac tgatacctcc atttactctt tgttttacta gactacatat 167040
ttggcagact tctagatttt tttgtatgtt ttttacgtcg ttgaggtcat attttatgtt 167100
gaattgtgca tccttctagt tgtgtttaaa tactgtatcg tcattttccc acaatgagga 167160
atgctgggtt aattatcaat tcatctttag aggcatccta cctaggtgtg ttttgaggat 167220
tttttttttt ttaacttagg ggagaggaaa attctgggta ccagttttat ttttttctaa 167280
gaccactcct gggcaaatct gggaatttgt gcttatctta aagcactttg tctgattcga 167340
aagaaggcca tttggcatga ggacagagca actgctatgc aaaaatatct ttaatctttt 167400
gacacttttt acctccatgc ttcttaagaa gtgaacaaag cttgtaagga cacatgatgc 167460
agcttcctgg agcatcattt tattttcagt aattgaaaac atttttatat taaacatgga 167520
tatattacag aatagtgtgc aaaagccaca tgaatttgaa gacagcaaca ttttaaagaa 167580
atcttatgtt ggtggtgtgc tttcctagta tatggattct atactagact tttctcatat 167640
atgaattcac ttggtgggag agcttgagag gcatagctgc ttttcagggt catgcccagc 167700
ttggtgttca tggtctttcc ccatcaaagt aaaaaaacggc cagtatttgc gatgaaggaa 167760
gaagagcact gtggagggag tctaggagtg tggattcagg ttctggctgt atgcgtgccc 167820
attgtgtcaa tagcctgagt ctattctgtg tgtaaggtga ggtcttttca atcattagaa 167880
tctcaggctt ctgtgaaaat ttgtcagttc tggagtagat gcagaagaag gggttcagtt 167940
ctagtagagt tagatattta aggaagatat tcctggagca gggtccctat gtagcacgta 168000
tatcttatct gaagtatagt aatttaaaaa ttatttcatg caatcaatga taggcctgct 168060
tttatattag gcttatatta atacaattca tgtgcattgt ttaatttctg cattgttatt 168120
ttatatgtgt gtattttagt gcagatggac gttttgaagg gaccagtacg aaaacagtca 168180
tcaggtacaa tggcactgtc acctggactc caccggcaaa ctacaaaagt tcctgtacca 168240
tagatgtcac gtttttccca tttgaccttc agaactgttc catgaaattt ggttcttgga 168300
cttatgatgg atcacaggtt gatataattc tagaggacca agatgtagac aagagagatt 168360
tttttgataa tggagaatgg gagattgtga gtgcaacagg gagcaaagga aacagaaccg 168420
acagctgttg ctggtatccg tatgtcactt actcatttgt aatcaagcgc ctgcctctct 168480
tttatacctt gttccttata ataccctgta ttgggctctc atttttaact gtacttgtct 168540
tctatcttcc ttcaaatgaa ggtgaaaaga tttgtctctg cacttcagta cttgtgtctt 168600
tgactgtctt ccttctggtt attgaagaga tcataccatc atcttcaaaa gtcatacctc 168660
taattggaga gtatctggta tttaccatga tttttgtgac actgtcaatt atggtaaccg 168720
tcttcgctat caacattcat catcgttctt cctcaacaca taatgccatg gcgcctttgg 168780
tccgcaagat atttcttcac acgcttccca aactgctttg catgagaagt catgtagaca 168840
ggtacttcac tcagaaagag gaaactgaga gtggtagtgg accaaaatct tctagaaaca 168900
cattggaagc tgcgctcgat tctattcgct acattacaag acacatcatg aaggaaaatg 168960
atgtccgtga ggtctgtgat gtgtatttac aaatgcagat cttcttccat tttaagttca 169020
gaagttactt tcattaattt tggcagagta aacagcatga cccttaagta agactaagca 169080
tagattgagg gccagaattg ttgacatatt ttctataaaa gatctttact aaggcttgtt 169140
tcagttaaag cacctgcaaa atggggcatt tacacaaatc tcacttctcc acttccccca 169200
tcagcatctt ggataactct aaagaaaatt tagtgttata ttctaaggaa taatcctgcc 169260
atatttcttg gctctgacct gatgaattgt tttaatttct tggggtgagg gcagtgggtg 169320
aactgtttta attttgtctt cagtaacttt gtttctaaat tgtgataatc tgtaggcaga 169380
actccattat aacagttaat ggagttatca aaagttcttt taggctgggc gcagtggctt 169440
catgcctgta atcccaccac tttgggaggc cgaggtgggt ggatcatttg aggtcaggag 169500
tttgagatca gcctggtcaa catggtgaaa ctccatttct actaaaaata caaaaaattag 169560
ctgggcatgg tggcacatgc ctatagtcac agctactcgg gaggctgggg caggagaatc 169620
acttgaaccc aggaggcgga gattgcagtg agccgagatc acgccattgc actccagcct 169680
gggcgaccga gcaagactcc gtctcaaaaa aaaaaaaaaa aaaaaagttc ttttaaagaa 169740
tgagcctaat gtggaattta taagtataaa attcagtctt gtcactgtta tttcttctat 169800
tgtgtattat tttaaaccta tgactatagt aatattttca taattgaatg tacattaaaa 169860
ttatgtgaat tataatctgt aaagctattt taaatggaaa atttccatca ggtatgagga 169920
gacagaataa atctggcaaa atcacagcct ttatcccaaa agggacattt gatgtatata 169980
tttttaaaac tttttttcat atgttaatga tttaatttca ataagacttt ccttccttat 170040
tttattgtat ttcaataggt ttttggggaa catgtgtttg gtcacatgca taagttcttt 170100
catgctgatt tctgagactt tggtgcaccc atcataaaaa cttctaatgc ttgtgggttt 170160
gtgaagtatc tatttggtgg tagcataatg aaattagttt ataaggtttg gagctatcat 170220
tggagttttt aaaagtacat agatttgtta ggtaatggtt tagactgaga tggaatttaa 170280
taaatgtctg caaagtattg tgcaaaaggg tcatggctca tactactagg accaaggagg 170340
ttggttttat tttcagataa aaacagaggc agaggtggcc aggtgcggtg gctcacgcct 170400
gtaatcccag cactttggga ggctgaggca ggtggatcac gaggtcagga gtttgagacc 170460
agcctggcca atatggtgaa acactgtctc tcctaaaaat agaaaaatta gctgggcatg 170520
gtggtgtgtg cctgtagtcc cagccacctg ggaggctgag gcagaagaat cacttaaact 170580
tgggaggcag aggttgcagt gagccgaggt cacgccactg cactccagcc tgggggacgg 170640
agcaaggctc tgtctcaaaa taaaataagc agagaagtaa cagggtttac aatgccctaa 170700
attctaaatt atcctacact ttggaggcac agttcccata gaggacacca tccttcatag 170760
aggttcaggg ccagggaagc ccctggtcaa ggaaatggcc ttgtagaaag gggagcccct 170820
gctgcttagt ggctgggctc atccttcttt ttccttgtgg tggctccgag ctgctgagcc 170880
agctccctac taaagctggc tccagggaag actgttctgt gctcatgaaa ttagactgaa 170940
gtggtcccta ggaaatccaa aaataaataa agtgtgtatg tgaggaagat gaacagcttt 171000
ctaacatgta ttattctgaa ccaactttta atttggcatg aaattaatct caggctagag 171060
tctctcaaaa tattaaaata agtaaacact actgggcaag aataagtata tatagtaaga 171120
ataatttttt ttagtttatt gtaaaatatc caagtctatt ttaattttta atctatcaaa 171180
ataaaccact tgtaatataa gttgatgtgt aaatgaacat attttgtagt gtcttttaaa 171240
gcttatatct atagtagacc ttcaggctag tgtctgtccc tgagctgagt atagggtcac 171300
ttaccgttta gaggcagcaa tgggaggcag aaatcgattt ggcttctaac tcagtgtgtt 171360
tgttatatct taaaatatgt acacaattta caattattta atgcattttt atttttttcc 171420
taacaggttg ttgaagattg gaaattcata gcccaggttc ttgatcggat gtttctgtgg 171480
acttttcttt tcgtttcaat tgttggatct cttgggcttt ttgttcctgt tatttataaa 171540
tgggcaaata tattaatacc agttcatatt ggaaatgcaa ataagtgaag cctcccaagg 171600
gactgaagta tacatttagt taacacacat atatctgatg gcacctataa aattatgaaa 171660
atgtaagtta tgtgttaaat ttagtgcaag ctttaacaga ctaagttgct aacctcaatt 171720
tatgttaaca gatgatccat ttgaacagtt ggctgtatga ctgaagtaat aactgatgag 171780
atacatttga tcttgtaaaa atagcaaaat attatctgaa ctggactagt gaaaaatcta 171840
gtatttgtat cctggcaaat aatactaatt tataatccac agtaaagttc atcctttgac 171900
tgtgctggag aattccagtt gtatttgaag actgatttta aaacttttct gcatttggta 171960
aaggtatgta aactttcctg tactcactga gtaacagcta atctttaata taatattata 172020
ctgctatatt taaaaagctg actacttgat ataattactt aatgtgatgc ttgatataat 172080
aattacttaa tgtggccggg cacggtggct cacacctgta atcccagcac tttgggaggt 172140
cgaggtgggc gtatcacctg aggttgggag ttcgagacca gcctgaccaa cgtggagaaa 172200
ccccgtctct actaaaaata tgaaattagc cagggtggtg gtgcacacct gtaatcccag 172260
ctacctggga ggctgcggca ggagaatcgc ttgaacccag gtggcggagg ttgcggtgag 172320
ctgagatcac gccattgcac tccagcctgg gcaacaagag caaaactcag tctcaaataa 172380
taataataac aacaacttaa tgtgctgctg cttttccata accaacattt taaaaataaa 172440
tgaaaaacag gaattgggaa ctcctttaag gcttacttta ttctttagat gcttaattat 172500
tgtgttaact atttctgtag cttagcttcc actgtaaagt catacagtag acaactcctg 172560
tggacacgca gtagcatatc cttaacatta atttcagtcc tcttgtccac atttcccaca 172620
attaatagaa ccatcttcta tataaattgt ggtagtatct ctttatcctt gatcttagaa 172680
tagtcagtcc actacaatta catgaacccc atttaaaaaa catatttagg gccgggggca 172740
gtggctcaca tctgtaatcc aagcactttg ggaggctgag gcaggtggat caccagaggt 172800
taggagttcg agactagcct gaccaacatg gtgaagcccc gtctctacta agaatacaaa 172860
aaattagtcg ggcatggtag caggcgcctg tagtcccagc tactcaagag gctgaggcag 172920
gagaatcgct tgaacctggg aggtggaggc tgcagtgagc cgagactgcg ccattgcact 172980
ccagcctggc aacaagagca aaactctgtc tcaaacatat tttggtctaa atcattctgt 173040
gagaaaacaa tcttctaata tgaaacacag tattctaatt tggtatatgc acactgttat 173100
atacctgtaa tatttcagtt ttctctcctt cattctaaca attacaataa tagaatctta 173160
gagttgcaag ggcctttaga tgtaatcaat cttagcctat tactagtaca gcgtaaatga 173220
tttagtacag tataatgtat cacagttaaa acagttaaat tccatctcta aatgtcacca 173280
cttcaggtgt gaccaggtag caaacactga cagaaaccct cgttcaattt agaactctta 173340
gctgttgaga tcacaaacac ctcatttatt tataataagt aacctatcta agttcaagcc 173400
aatgctcttt ggaaggcgga ggagacccta tctaatttgc atttaatcgt aggcaggtgt 173460
ttaatgccat ttaatgagtg aaagcctggt gtgatgaatt tagattgcct gccagctacc 173520
taccttagtt cgtatacatc cctgatccct cttatactac cattactgtt acttatgatt 173580
tttatatata aatttttatc gacatctttc ttttgactta ttgaaacatg agtcacagcg 173640
ggctgcaatt ctgtccattt tatttttgca caggaaaaac tagtgagaca agattcaaac 173700
agtctctgtg aatcatctgt cagtggtgat gatcacgtta agtttcagaa gtgtagtaca 173760
tgatactctt aacaatttgt ctaaagcaat gtttctcaac caggggcaat tttgctccta 173820
agggaacatt taacaatgga gacattcttg gttatcataa ctggtgaaga agcaaggtat 173880
gtcattggca tctagtgagt tgaggctagg gtactgctaa agatcctaca atgcacagga 173940
tacccccatt ctgtaccaac acatatttat ccagcccaaa atgtccatag tgctaaggct 174000
gagaaaccct gttctaaagg ttcatgctgt ggtccaaatg tgtcctcccc caattcatat 174060
gttgaaacct attcccagcg tgattgtctt agatagaagg tggggccttg gaaaggtgat 174120
taggccatgg gggctctgct ctcatgaatg gggttagtgc ccttataaaa tagaccccac 174180
agagatagct agtcccttca gtcatgtgag gacacagcta gaaggcaccc tttgaggaag 174240
aggaccctca ccagacacca aatttgctgg tgccttgacc ttggacctcc caacctccaa 174300
aactgagaag tttctgttgt ttataatcca cccagtttat ggtgtactaa gacagttata 174360
ttaacaatga ataactaggc atgatttctc atggtataat ttagaagtat gcaagagaag 174420
tagttgaagc tctctgaaat ggaggcatag ccctttagac ccagtaaaga acgagaaatg 174480
catggtaaga aatgggtaac gatgggggat tgctgaatta gtataaacct tcaaagagat 174540
tatgggctaa ataagaaaaa ttactgggag atctgtagtg ataactgaat gacttttcat 174600
atttctgaac agcatttttc tatccagttt tgtttcaaca actaaaagga aacattttta 174660
catgtatatt ccatagcata gcatactaat cacatagaat cacattttga catctcttta 174720
ccataccaaa aaggctagtt aaatgttcat ttatcggtaa taaatactct tgacattttt 174780
ttttttgcat gattccaaga taagtggaaa ataagtaaac ctcgaaatgc caaaaacaaa 174840
gctggtagct tgataacaga aagtacgttc ttactaggaa gcagcctcct cctgccctga 174900
cacaaggaag tctcccaggc aggcacacag cttagtgctt atgcatcttc cctggccatc 174960
aggggttgca gaaacaatcc tgctgtccct agaatgcaca ccagggtgaa aacccacaga 175020
aaaatacgat caatcaccat ggcaacatac ttccaatcat cttgaatctg caaaacaaaa 175080
tgataaaaga aaaaaaacat ggagggaaag gcaaatgaat acattttcaa tactgaagat 175140
gtaatcaaca cgttgcagta gaagccattt tgtctctaat atgtaagaag ccctttttttt 175200
cctaattgat gtggtctgag gaaatccacc attctcaagt ttctgtttat gcaggagaga 175260
aacaggtata aaagatctgt catgttagat ctgtttcaaa tcagaagttt cctaaaaatg 175320

-continued

```
cataacctag tttttctaaa ctgaattcca attttataaa gttagtgaaa ccagttactt 175380
aggcttccat ggcaggattc tgggccttgg ttagaatggc taatatagtc caatataatc 175440
taccattgtt tcaaagtact ctatccagtt ttagatataa atttggcgca gtggctcacg 175500
cctgtaatcc cagcactttg ggaggctgag atcacctgag gtcaggagtt tgagaccagc 175560
ctggccaaca tggtgaaacc ctgttgaaac cctgtctcta ccaaaaatac aaaaattggc 175620
caggagtggt ggcacatgcc tgtaatcccc agctacttgg gaggctgagg catgagaatt 175680
tcttgaaccc gggaggcgga ggttgcagtg agcagagatc acgccactgc actccagcct 175740
gggcaacaga gcgagaccct gtctcaaaaa caacaaaata aatttccttt taacatctgt 175800
tccaaaaatg agataagcgt tatcagggca agtccatcct catcactctt tccctcccca 175860
ctgccctctc cacgatgccc agctgatcaa aagtcatttt tactcataag accaaagtat 175920
catgggatac tgtgcagttg gagagcaggt tgaacatcag aaataattgc tgacaataaa 175980
gtaaaagatg ggagaaaaag caagaccaat tgtatataat acagcttcaa tttgggcttg 176040
aaataggaag gaaaattgta attatactcc tagacaattc agaaagcaaa gaagccataa 176100
ttgaattgag agaacccatg agtcagctga ttttgaagca ataatgaaat taataaatta 176160
catgctgcct ctttattata agtatactga aatggcgctg ggagatgaag attttacatc 176220
accattgtga gcctgagtaa atgtgttctc ttggtgacac tactgtcata ggtaaaatta 176280
gaattatgat gccatatttg ccatgaggta cttcatttga attcctaaga ctggtttgtg 176340
tgtgcttcag atacaccttg agatgtgaga ttcctaccca ccccctacca gccacctcct 176400
aaggctctag gaggcagagg tgtggaaaag cagagacttg gagacaaact gattagaatc 176460
ccagctctgc tccttttgag ttgtgagaat ctgggtaaat tccatgaccg ctcttagcct 176520
caatttcctt atctgtaaaa tggggataag aacagtactt ccctcagaag cttgtttcag 176580
aacagagtcc ttaatgaata gagcctagtg atactaatgt tgatttataa aatgaccctt 176640
actcaagcct catgaagaaa gatgacactt gggttttata catgaataga aatagtggtg 176700
caaaaagagc tggctggaca gaaattttat atcttttttt ttttttgag acagggtctt 176760
gctttgttgc tcaagctgga gtgcaggggt gcaatcatgg cttgctgcag ccttgacctc 176820
ccgggctcaa gtaatcttcc ccactcagct tcctgagtag ctggaactac aggtgtgtgt 176880
cactacactt gggcaatttt ttgtttttttg agacgcccag gctggagtgc agtggcatga 176940
cctcgcctca ctgcaagctc cacctcccag gttcaagcaa ttctcctgcc tcagcctctt 177000
gagtagctgg gattacaggt gcctagcacc atgcccagct aatttttgta tttagtagag 177060
atggggtttt atgttggcca ggctggtctc aaactcctga cctcaggtga tccacctgcc 177120
ccagcctccc aaagtgctgg gattgcaggc gtcagccact gcacccggca ttttttttttt 177180
ttttttgaaa cggagtctca ctctgtcacc taggctggag tccagtggtg tgatcttggc 177240
tcactgcaac ctctgtctcc cgagttcaag caattcttgt gcctcagact cccgagtagc 177300
taagattaca ggctcatgcc accaccaccc cccggttaat ttattgtatt tttagtagag 177360
atggaggttc accattgttg gccaggctgg tcttgaactc ccaacctcag gtgatccacc 177420
tgcctcggcc tcccaaagtg ttgggattac aggcgtgagc cactgcacct ggcctgattt 177480
ttaaattttt tttgtagaga aagggtttcc ctacgtggcc caggatggtt ttgaactcct 177540
gggctcaagt gatcctcctg ccttggcctc ccaaagtgtt ggattacagg tgtaagccac 177600
tgtgcctggc ttatatctag ctcctaaagt ctttaaagca caatgatatt ggccattttc 177660
tgatgagtca cagatgttag gcaaagtggt gaactagccc aaattgagag ctggcccaga 177720
```

agcatgagaa gactacttta aagacccaga aactgggaag gtgtggccag agactggggc 177780
tggcaggggg aggggcttgg tggaggggag agctagggag atctttgttc ccctgccact 177840
ttgcctcttt agcctgccac tcccagccca gagatgcagg ttcaggggt ccctcacaag 177900
cccagcagag cctggctaaa gggaagtgca gagaactgag ctgcccattg actggtggag 177960
cctgaggctt tcctcctctc ctttgtagcc ccctggattt atttctcttc ttattggcat 178020
gccttctcaa gaatgtttat ggataaatgt tcttctgagg gctcaaaagg ccaggtgtgg 178080
tggatcacac ctttaatcct agcactttgg gaggccaagg cgggcagatc acctgaggtc 178140
gggagttcaa gaccagcctg acaaacatgg caaaatcccc tctctattaa aaatacaaaa 178200
aattaggcat ggtagcgggc gggtacctgt agtcccagac acttgggagg ctgaggcatg 178260
tgaatcactt gaacctggga agcagaggtt gcagtaggca gagattgtac tactgcactc 178320
cattctgggt gacagagcaa gactccatct caaaaaaaaa aaaaaatagg taaaactaat 178380
caattatcaa ataagtcagt ataatggttt tttaaaaaat taattaatta attaaagaaa 178440
ggacttcact ctgttaccca ggctggagtg cagtggcatg atcacagctc actagacttc 178500
ctgagctcca gtgatcctct cacctcagcc tcctgagtag ctggaactac aggcacgtgc 178560
caccacgcct ggctaatttt tgtatttctg ttagagacgg ggtttcgcta tgtttcccag 178620
gctggtctca aactcctgat ctcaagccat ccacctgcct cagcctccta aagtgctagg 178680
attacaggcg tgagccactg cgcctaagcc aggatggtgg gtaccaagca gggagggaga 178740
cactgactgg caagggcatt ggggaacttt ctaggggccc tgggagtgtt ctatatcttt 178800
acctgggtct tggttacatg gttgtataca tgatgtaaaa actcattgag atgtacactg 178860
aagaggtgtg cactttactc cacgtaaatt cttcctcagt gagaacacat atacaattag 178920
aaagtaaaaa taaaggccag gtgcggtggc tcatgcctgt agtcccagca ttttgggaga 178980
ctgaggtgag cagattgagt cgaggagtct gagaccaacc tgggcaacat ggcaaaaccc 179040
catcggtaca aaaaaattag ggtatggtgg cggggcatct gtagttcaag ctactcggga 179100
aactgaggtg ggagaatcgc ttgagctggg aggcggaagt tgcagtgagc caagattgcg 179160
ccactgcact ccagcctggg caacagagca ggaccctgtc tcaaaaaaat aaataaaaat 179220
aaaaatataa cctcaattaa ccaatactaa ctggagatca tctggcccca tgccctttc 179280
cagcctacat cctaatctag tctattggca tcaggtgttt tcatggtcca gcctgccagc 179340
ctgctggcag cctggtggct agcttcaggg taccacatac caagctttat catcccattt 179400
tacagaagag aaaacaggct cagagaggtg aggtaacata cccaaggaca tataactggt 179460
cttaacacag gccactgact ccagagggca atttcttaac cccctaccct atgccttgcc 179520
ccacgaggaa cccataaata tttgttgaat gaatgaatga ccaatgtaat aaaagccata 179580
tccttacctc tttggcttca ttttgtgctt tcatattttc agcaatatac ttgacacttt 179640
ggatggcttc tttgatttct ggtgacaaag cagagaggga cagcacagca tcaacagatt 179700
cagaactaga gcttctcgtg aggttagcac tgaaattgga gatttttatc ctgcggtggt 179760
ggcagtaacc acacatcccg tcctggcagg ggtagccctc cttgcagcct ttggactctg 179820
cgcggctgaa gcaattcaga tttgagagct cggcaccgta gaggggcctc ggcttctgag 179880
cgttgccctc gttgcttgtt ggcctggtca tgaacatgac cctggggagc aggttcaaga 179940
atacagtctt cacccatgag ggcattgtgt gtgtcgtcgg ggttctgtag tgcacgttga 180000
gcacgaagac ggtgatgacg atggacaagg ttacaaaaat catggtgaac aggaggtact 180060

-continued ctccaatcag ggggatgacc agcgaggtgg aagggatggt ctcagtgatc accaggagaa 180120
acaccgtcag ggagaggagg acagaaatgc acagggtcac cttctcaccg cagtcggagg 180180
gcaggtagaa gacgagcaca gtgaggaagg agatgagcag gcaggggatg atgaggttga 180240
tggtgtagaa caagggcagg cgccggatgt acagcgagta tgtgatgtcg ggtagatct 180300
cctcgcagca gttgtacttg atgtcgtgtt tgtagcctgg ggctttgatg atggcccact 180360
cgccgctctc ccaatagtcc ttgaggttca tggaagagcc gatcaggacc agatcgattt 180420
tcgccttatc gtaggaccag gaaccgaact tcatggtaca gttttggtaa tcaaacggga 180480
agtaggtcac gtcgatttta caggagctct taaagatggc cggaggtatc caagtcacct 180540
ccccagtgta cttgagtaag gctttggtct tgtcgtccac ctggaaatcc ccaacagcac 180600
tgcaaagaca aagagggggc acagtgacac acggtcatta acacttggtc atattgtggt 180660
catctcaacc agcttctcac agtaagtaat gatttggaag gcactggaag atgagagcta 180720
aagtgccata aaaggtcacc catttcctgg ccccatttac caacagggat actgaggccc 180780
aagctccctc cccaacaaca atctgagata tggatcactc cctgccccag ggcaggccac 180840
cagttcatcc cacaatacag gtcccaaact gatagactcc caaatgcccg aagaggattg 180900
gtccccottt aattaaagaa atgggaggaa ggtcatcctc ctggagccag gtgctgaagc 180960
agcctttggg attatttgcc acccagggtc cctgaggctt ggccctctcc tcattcagtc 181020
tgtaccgggc gcctaatgtg tgtgtgaaac cagactatgg atgtggaagg ggctgcacag 181080
accacccagg ggagtccacc cccattaaac ggaaccttgt cagatggatt tacttccaaa 181140
ccctatctct ggatcctgat ttgaccattc cctgtaccct ccccaccccc attcttccca 181200
gtactgtttt acaataatca tgttttgctt ccttgtcttt cgaattcagc ctaacaggtt 181260
tcttcacttt ctgtgtccct atccccattt tctccccatg tttcttctcc cttccttttc 181320
actatgtgca tcctgacatt tattttcaca cagaaataga cattttctt tttctttgag 181380
acagagtctc actctgttgc ccaggctaga atgcagtagc tcactacaat ctctgtctcc 181440
cggggttcaa gcaagtctcc tgctcagcct cctgagtagc tggaattata agcatgtacc 181500
acaaacgctc agctactttt tctattttta gtagggatgg agttttgcca tgttggctgg 181560
gctggtctcg aactcctgac ctcaagtgat ctgcccacct cggcctccca aagtgctgag 181620
attacaggct tgagccactg cctggcctta gacatgtacg tttttctagg aatagtcttg 181680
ttggtttgtt cgacagaaaa tcagctgatg atccctgttg agtcttgcat tgggcattcc 181740
atccgcgatg gccagatgag gccatctgag agcaaggcca gttgcttcca caacaatggc 181800
cctgcccagg aaggttctta aacattcctc ggatcagccc tgttaagttt cttagccttg 181860
tgaaggcatt tacatcctcc aaagggagca actgccatac tcctttgcct tgtaaacaat 181920
gacaaagcct aaacatttag ggatatcctt gtgctgctgt aattggatgg gaacctgtga 181980
aaacagaagg ggaatgttgt ggtgcatgtg cttcttcctt gctagtctct cctgggtctc 182040
ggttgagcag gatcattacc catgaaggct caatgccaaa gccactaact atctttcctc 182100
tggttggcta gtttgccccc aatggtgccc tgctgagttt atacattctt agccccaatt 182160
tcactcccac catgccctta attccctacg agtattcctg ctcctggctc caggaaaaag 182220
ggagaggtag gagggtgggg tggaggtgaa catccacaca gtccccaagt ggactcagcc 182280
catgtttagc actgaggggc cctggagagg gctgggctaa gcagaaggtc gaaaagaccc 182340
tcaggaaggc agaggcctcc tgaaccaatt ccatacagca tcctggatca acaaaatgtc 182400
agagcggcaa gggagcttca gagcccaggg tctggtccag gggttggcaa gctgtggtcc 182460
tctttctgta aataaaatct ggggggaata gtgccactgc cttttgttgt ccattatcta 182520
tagctacttt tgagctccag gggcagagat gaatagctgt gaccgtcact gtatgaccca 182580
caacgcctaa aatatttatt ctctggccct ttagagaaaa catttgctag cccctgctct 182640
agtccaacac cttcattttg ccaaagagaa aactgacggt caaaggacag gaatgacttg 182700
ctcgagactc cacagagttt atggcagaac cttggccatt cagaacttgg gtccccaagt 182760
gaggagacac agaaatgtgt gcatgtgccc aaagaacata tactagaggt tagctgagct 182820
tggctgatgg ctcatttctg gggatcctgg tcactgtggc tgctgcccac agcacccctg 182880
gggtgtgtcc acccagatca gaaggcctgt gtgctgcctg gggcagtgtc aacagtcata 182940
tctctactag cagaagacag aacatgcaga cccagctgga gactggggtc tggcacagca 183000
ccagcctcat aaagggcact cagtaaatat ttgttgacct aacgaatgac caaaaaataa 183060
atgaaagctg ggtgtggtgg ctcacacctg taatactaat actttgggag gctgaggcgg 183120
gcagatcacc tgaggtcagc agtttgagac cagcctggtc aacatgacaa aaccccatct 183180
ctactaaaaa tacaaaaatt agccaggtgt ggtggtgcac acctgtaatc ccagctactc 183240
gggaggctga ggcaggagaa ttgcttgaac ccaggaggtg gaagctgcag tgagctgaga 183300
tggcaccact gcactccagc ctgggtgaca gagtgagatt ctgtctcagt caatcaatat 183360
cacacccaga gatagctggc agcaagggac agcattggtg ggaagggtct gagcaatgta 183420
ctgccaaacc atgtgaggca attaaaaaaa gaaaaggtag tatgggtgca aatgatcagc 183480
tgaggtagca ctatcataca gggggcattt aagaacagaa gtggggtggg gtggtgaggg 183540
ctatgagaaa gatcatgatg gcatgggttt ttaaaatctc tctaaatttc ttcagaaaaa 183600
tagggcaact aggatgacag caaaataaca aatctgatca cattgtcaac aaagttaggt 183660
tacacagcac ctcaggatat gagagtgtgc ggtcagacca ccaccaccag caggacctgt 183720
gggacccaca tgcgattagc tgcggggtag aggcagccgg gggaaaagaa agaagggttc 183780
tcatgtccta agatcctaag agtgccagac acaggaatct ccaaaaagtg gctgcccctc 183840
aaaagacgag gaccccactc tgcactgaat cctcagcaag gggaacaatg gaacagagag 183900
ggctccacag gttccaattt gtgggcaaga accaaaaaaa tcccgtggga atccactcag 183960
tgtctgcaga ggtcagtcag tgctgacgtg ggctcttgag gatgtcagaa atgcctccca 184020
aaacctccct ttcagaagga cagagaccca ctcagagaaa aagctgctta tggtagaatc 184080
caaactcaac agggtaagaa gtggggatga gaagagaaag aaggttcaga aactgaagtc 184140
agcatccaga ggcagcagct cgtggagatg ccatgactgt gcggtcatgt catgactgag 184200
gtgtcatgac tgtggagact ggggaggtgg ccatgcattg agacaagtgg cacctcaagg 184260
taactaccgt cttctcctat tccccccaag aacttgccct aaaagtaaag caaggctatc 184320
tatttaaaca agagcaacga agctttatga aaacatattg taagaaaaac acaaactggg 184380
tacagcagct catgcctgta atcccagcac tttgggaggc tgagacaggt ggattacctg 184440
aagtcaggag ttcgagacca acctggccaa catggtgaaa ccccgtctct accaaaaata 184500
caaaaaaaaa tttagctagg cgtggtggca gtcacctgta gtcccagcta cttgggaggc 184560
tgaggcagaa gaattgcttg aatctgagag gcagaggttg cagtgagcca agatcatgcc 184620
attgcactcc agccttggta acaagagcaa aaaaacagaa gatgtctcaa aaaaaaaaaa 184680
aaaaatacaa acacaagtaa ctgaattaac acacacgcag ataacagcaa ctacaaaaat 184740
agagccacca agcagatgaa gctgacgata atctgatatt acaaattaaa tgaaaagaaa 184800

-continued ctaagaaatt tttcaaaatt gtgaaagaac agaaatcaga aaagataagg gataatttgg 184860
ttaaatgaaa gaatgtataa agaactagca gaatttagga aagaattagg aaaaagaaaa 184920
aaatcatttt agaaataaaa ccagaagagg ccaggggtgg tggctcaggc ctgtaatccc 184980
agcactttgg gaggccgagg tgagtggatg acgaggtcag gagatcgaga ccatcctggc 185040
taacacagtg aaaccccgtc tctactaaaa aaaatacaaa aaaattagcc ggatgtggtg 185100
gtgggcacct gtagtcccag ctacttggga agctgaggca ggggaatggt gtgaacctgg 185160
gaggcggagc ttgtagtgag ctgagatcat gccaccacga gagtctgtct caaaaaaaca 185220
aaacaaaaca aaacaaaaaa cacacaaaaa agaaaaccag aagaaacata agaacaagca 185280
gtctgggtgt gatggctcac acctgtaatc ccagcacttt ggaaggctga ggcgggcaga 185340
tcatttgaag tcaggagttt gagaccagcc tggccaacat tgtgaaaccc catctctact 185400
aaaaatacaa aaaattagct gggcatggtg gcacacacct gtaatcccgg ctactcagga 185460
ggctgaggca ggagaatagc tggaacccag gaggcagaga ttgcagtgag ccaaggcact 185520
ccagcctggc caacacagtg agactctgtc tccaaaaaaa aaaaaaaaaa gatttcatg 185580 gaagataaag aggagccaag aattttacac ccagccaagt tacctaaaag tattctctaa 185640
aaaggttaca atgaattatg aacttgccag aacacagagt atacagtgtc catgaatact 185700
ctgaggattc tgtcagcaaa tgaactttag aaaacaaaat atcacaggag aaaggctggg 185760
aatgatggct cacacctgta atcccagcac tttgggaggc cgaggagggt ggatcacaaa 185820
gtcaggagat tgagaccatc ctggctaagt caggagattg agaccatcct ggctaaaacg 185880
gtgaaacccc gtcgctacta aaaaaataca aaaaaattcg ggtggagcca aaatggccaa 185940
ataggaacag ctccggtcta cagctcccag catgagcaat gcagaagatg ggtgatttct 186000
gcatttccat ctgaggtacc aggttcatct cactagggag tgccagacag tgggtgcagg 186060
atagtgggtg cagcgcactg tgcatgagcc aaagcagggc gaggcattgc ctcacttggg 186120
aagcacaagg ggtcagggag ttccctttcc tagtcaaaga aaggggtgac agatggcacc 186180
tggaaaatcg ggtcactccc accctaatac tgcacttttc caacgggctt aaaaaacggc 186240
acaccaggag attacatcct gcaccttgct cggagggtcc tacacacacg gagtcttgct 186300
gatggctagc acagcagtct gagatcaaac tgcaaggcgg cagcgatgct gggggagggg 186360
cgcctgccat tgcccagcct tgattaggta aacaaagcag ccgggaagct cgaactggat 186420
ggagcccacc acagcccaag gaggcctgcc tgcctctata ggctccacct ctgggggcag 186480
ggcacagaca aacaaaaaga cagcagtaac ctctgcagac ttccctgtct gacagctttg 186540
aggagagtaa tggttctccc agcacgcagc tggaaatctg agaacgggca gactgcctcc 186600
tcaagtgggt ccctgacccc cgagcagcct aactgggaga cacccccaa gtaggggcag 186660 actgacacct cacacggccg ggtactcctc tgatacaaaa cttccagagg aacgatcagg 186720
cagcagcatc tgtgggtcac caagatccac tgttctacag ccaccgctgt tctgcagcca 186780
ccgctgctga tacccaggca aacagggtct ggagtggacc tctagcaaac tccaacagac 186840
ctgcagctga gggtcctgtc tgttagaagg aaaactaaca aacagaaagc atatccacac 186900
caaaaaccca tctgtacgtc accatcatca aagaccaaaa gtagataaaa ccacaaagat 186960
ggggaaaaaa cagagcagaa aaactggaaa ctctaaaaat cagagcacct ctcctcctcc 187020
aaaggaacat agctcctcac cagcaatgga acaaagctgg acggagaatg actttgacaa 187080
gttgagagaa gaaggctcca gacgaccaaa atactccaag ctacaggagg aaattcaaac 187140
caatggcaaa gaagttaaaa actgtgaaaa aaaaattaga caaatggata actagaataa 187200

-continued ccaatgcaga gaagtcctta aaggagctga tggagctgaa agccaaggct ggagaactac 187260
gtgaagaatg cagaagcctc aggagccgat gcaatcaact ggaagaaagg gtatcagtga 187320
tggaagatga aatgaatgaa atgaagtgag aagggaagtt tagagaaaaa agaatagaaa 187380
tgaccaaagc ctccaagaaa tatgggacta tgtgaaaaga ccaaatctac atctgattgg 187440
tgtacctgaa agtgacgggg agaatggaac caagttggaa aacactctgc aggatattat 187500
ccaggagaac ttccccaatc tagcaaggca ggccaacatt cagattcagg aaatacagag 187560
aatgccacaa agatactcct cgagaagagc aactccaaga cacataatag tcagattcac 187620
caaagttgaa atgaaggaaa aaatgttaag ggcagccaga aagaaaggtc gggttaccca 187680
caaagggaag cccatcagac taacagcaga tctctcggca gatactctac aagccagaag 187740
agagtggggg ccaatattca acattcttaa agaaaagaat tttcaaccca gaatttcata 187800
tccagccaaa ctaagcttca taagtaaagg agaaataaaa tactttacag acaagcaaat 187860
gctgagagat tttatcacca ccaggcctgc cctaaaagag ctcctgaagg aagcgctaaa 187920
catggaaagg aacaactggt accagccact gcaaaaacat gccaaaatgt aaagaccatc 187980
aaggctagga agaaactgca tcaactaacg agcaaaatca ccagctaaca taataatgac 188040
aggaccaaat tcacacataa caatattaac tttaaatgta aatgggctaa atgctccaat 188100
taaaagacac agactagcaa attggataaa gagtcaagac ccatcagtgt gctgtattca 188160
ggaaacccat ttcacacgca gagacacaca taggctcaaa ataaagggat ggaggaagat 188220
ctaccaagca aatggaaaac aaaaaaaggc aggggttgca atcctagtct ctgataaaac 188280
actttaaacc aacaaagatc aaaagagaca aagaaggcca ttacataatg gtaaagggat 188340
caattcaaca agaagagcta actatcctaa atatataggc acccaataca ggagcaccca 188400
gattcataaa gcaagtcctt agagacctac aaagagactt agactcccac acaataataa 188460
tgggagactt caacacccca ctgtcaacat tagacagatc aacaagacaa agttaacaac 188520
gatacccagg aattgaactc agctctgcac caagcggacc taatagacat ctacagaact 188580
ctccacccca aatcaacaga acatacattt ttttcagcac cacaccacac ctattccaaa 188640
attgaccaca tagttggaag taaagcactc ctcagcaaat gtaaaagaac acaaattgta 188700
acaaactgtc tctcagacca cagtgcaatc aaactagaac tcaggattaa gaaactcact 188760
caaaaccact caactacatg gaaactgaac aatctgctcc tgaatgacta ctgggtacat 188820
aacgaaaggt aggcagaaat aaagatgttc tttgaaacca atgagaacaa agacacaaca 188880
taccagaatc tctgggacgc attcaaagca gtgtgtagag agaaatttat agcactaaat 188940
gcccacaaga gaaagcagga aagatccaaa attgacaccc taacatcaca attaaaagaa 189000
ctagaaaagc aagagcaaac acattcaaaa gctagcagaa ggcaagaaat aactaaaatc 189060
agagcagaac tgaaggaaat agagacacaa aaaacccttc aaaaaattaa tgaatccagg 189120
agctggtttt ttgaaaagat caacaaaatt gatagactgc tagcaagact aataaagcag 189180
aaagaagaat caaatagatg caataaaaat tgataaaggg gatatcacca ccgatcccac 189240
agaaatacaa attaccatca gagaatacta caaacaactc tacgcaaata aactagaaaa 189300
tctagaagaa atggataaat tcctggacac atacactctc ccaagactaa accaggaaga 189360
agttgaatct ctgaatagac caataacagg agctgaaatt gtggcaataa tcaatagctt 189420
accaaccaaa aaaagtccag gaccagatgg attcacagct gaattctatc agaggtacaa 189480
ggaggagctg gtaccattcc ttctgaaact attccaatca atagaaaaag agggaatcct 189540
ccctaactca ttttatgagg ccagcatcct cctgatacca aagctggcag agacacaacc 189600
aaaaaagaga attttagacc aatatccttg atgaacattg atgcaaaaat cctcaataaa 189660
atactggcaa accgaatcca gcagcacatc aaaaagctta tccaccatga tcaagtgggc 189720
ttcatccctg ggatgcaagg ctggttcaac atatgcaaat caacaaatgt aatccagcat 189780
ataaacagaa ccaaagacaa aaaccacatg attatctcaa tagatgcaga aaaggccttt 189840
gacaaaattc aacaaccctt cacgctaaaa actctcaata aattaggtat tgatgggatg 189900
tatctcaaaa taataagagc tgtctatgag aaacccacag ccaatatcat actgaatgcg 189960
cacaaactgg aagcattcct tttgaaaacg ggcacaagac agggatgccc tctctcacca 190020
ctcctattca acatagtgtt ggaagttctg gccagggcaa ttaggcagga gaaggaaata 190080
aagggattca attaggaaaa gaggaagtca aattgtccct gtttgcagat gacatgattg 190140
tatatctaga aaaccccatt gtctcagccc aaaatctcct taagctgata agcaacttca 190200
gcaaagtctc aggatacaaa atcaatgtac aaaaatcaca agcattctta cacgccaata 190260
acagacaaac agccaaatca tgagtgaact accattcaca attgcttcaa agagaataaa 190320
atacctagga atccaactta agagggatgt gaaggacctc ttcaaggaga actacaaacc 190380
actgctcaat gaaataaaag aagatacaaa caaatggaag aacattccat gctcatgggt 190440
aggaagaatc aatatcgtga aaatggccat actgcccaag gtaatttata gattcaatgc 190500
catccccatc aagccaccaa tgactttctt cacagaattg gaaaaaacta ctttaaagtt 190560
catatggaac caaaacagag cccgcatcgc caagtcaatc ctaagccaaa agaacaaagc 190620
tggaggcatc acactacctg acttcaaact atagtacaag gctacagtaa ccaaaacagc 190680
atggtactgg taccaaaaca gagatataga tcaaaggaac agaacagagc cctcagaaat 190740
aacgccacat atctacaact atctgatctt tgacaaacct gacaaaaaca agcaatgggg 190800
gaaaggattc cctatttaat aaatggtgct gggaaaactg gctagccata tgtagaaagc 190860
tgaaactgga tcccttcctt acaccttata caaaaattaa ttcaagatgg attaaagact 190920
taacatgtta gacctaaaac cataaaaacc ctcgaagaaa acctaggcaa taccattcag 190980
gacataggca tgggcaagga cttcatgtct aaaacaccaa aagcaatggc aacaaaagcc 191040
aaaattgaca aatgggatct aattaaacta aagagcttct gcacagcaaa agaaactacc 191100
atcagagtga acaggcaacc tacaaaatgg gagaaaattt tcacaaccta ctcatctgac 191160
aaagggctaa tattcagaat ctacaatgaa ctcaaacaaa tttacaagaa aaaaacaaac 191220
aaccccatca aaaagtgggt gaaggatatg aacagacact tctcaaaaga agacatttat 191280
gcagccaaaa aacacatgaa aaaatgctca tcgtcactgg ccatcagaga aatgcaaatc 191340
aaaaccacaa tgagatacca tctcacacca gttagaatgg cgatcattaa aaggtcagga 191400
aacaacagat gctggcgagg atgtggagaa ataggaacac ttttacactg ttggtgggag 191460
tgtaaactag ttcaaccatt gtggaagtca gtgtgccgat tcctcaggga tctagaacta 191520
gaaataccat ttgacccagc catcccatta ctgggtatat acccaaagga ctataaatca 191580
tgctgttata aagacacatg cacacgtatg tttattgcgg cattattcac aatagcaaag 191640
acttgcaacc aacccaaatg tccaacaagg atagactgga ttaagaaaat gtggcacata 191700
tacaccatgg aatactatgc agccataaaa aatgatgagt tcatgtcctt tgtagggaca 191760
tggatgaaac tggaaaccat cattctcagc aaactatcgc aaggacaaaa aaccaaacac 191820
cgcatgttat cactcatagg tgggaattga acaatgagaa cacatggaca caggaagggg 191880
aacatcacac accagggact gttgtggggt ggggggaggg gggagagata gcattaggag 191940 atataccctaa tgctaaatga cgagttaatg ggtgcagcac accaacatgg cacatgtata 192000
catatgtaac aaacctgcac attgtgcaca tgtaccctaa aacttaaagt ataataataa 192060
taaaatttaa aaaaaaactg taaagcagtg gcaaacaaac aaaaaaaaaa ccaaaaaaaa 192120
ccacaaaaaa attagccagg cgtggtggcg ggcgcctgta gtcccagcta cttgggaggc 192180
tgaggtagga gaatggcgtg aaccagggag gcggagcttg cagtgagccc agatcatgcc 192240
actgcactcc agcctgggcg acagagtgag actccatctc ggggtggggg gaaaaaaaag 192300
aagagaaatc cttaacagag ggtgaatcct gagcaattga agttctaact aggagaagag 192360
agagaacatg agttggatga ttttctctaa atgttatttt cagcttcaga tttcaaagaa 192420
attccttatg atatttgctc ctctccacag ccaatttgca acattttgct acgcctctca 192480
ttattgctaa aatcataaat cctacagtac tccagctgtt cactcaagat tgccagcaag 192540
gaaatggcta taaaacgcaa aacatgaaga ttaaactttt tgctcatttt cttaattgta 192600
gcttagcaaa aattctctac accctgccca gttcccttaa gagcatttga accatgtgat 192660
tcctacgaca attcagtgca agaagaaaaa aatctgcaag cctgttgagt ttatattgtg 192720
tcccagttct ttgatgacca gtttacaaat acaaattaca tacaagaaac atttataagt 192780
gctgtgtttc cttgggaaaa cagtaaataa aacatggact gtctttagag tgagtaaaga 192840
cccacttttg tttttgccag agaccagaaa gtgggattca gtataaaaca tagcttctct 192900
agtcctgaca ctaactgtaa aatcaatact actaataaga aaacattatt ttgtactaat 192960
atggcataaa aacctagaag tattcttagc attaaaatca gaatagacta attctacatc 193020
aactgttttg ctgaaaatgt ttaaatgtaa atgtaaaagg tttaaatatt caaacatttt 193080
aactctaaaa tgcaggtaca aaaatgatat tcttcaatac ccagagaact aactagcata 193140
ttgcaaaata tcaactaaaa tttatgtcag tccaatgaaa gagcttaaat gtgggaagta 193200
tcagttttgt gtggacttag agaaaaggga ggggttttgg aggtgctatg atgagcagga 193260
cctgtctggc agaggaagaa cctttgcaag agagaaagag gagaggcctc ccaaaactgg 193320
cgggaagatg cacattccgg atccatagga gactggaagt ggcccactgt gaaggactgg 193380
ctcgagagca gcttctctcg atggcaggag ccagggaagt ctttttagtc ctggactcac 193440
ccttctcaac tacgacctgg atgcagccac ccagacgggc tgggagcacg gggcccagaa 193500
tgctcatcct actctgtaca tgggaacctt gcttcacata cttggggggc tatcaatcct 193560
ttctccaagg cccagacctt ttcccagtgg gaggaggcct gcagggtaca ccgtgtagca 193620
gggtaactgt ctgatggcag gtttgctgtt gggagagtag agaagaggtt tggggacaca 193680
ggcagagaca ggctggggtg cccagctcag ccccctgatc acagcatcgg cctcctgcat 193740
ccactgccca cagtggcccc aaagccacag tggatggctg agaccacccc agacctggct 193800
gtgccacaca tccactctgg gcctcagtcc tcatctgtga aatgtcaggg aagggccaga 193860
tcagggatcc ccaaagcaag ctggtcacac agccccccagg acagctttgt gaaaacaccc 193920
attcctaggc ctacccagac ccactgactc agtgtttctg tggggcagga cctggggaca 193980
ggtatagaga ttttttggat aacgtaatac atattaactt tagaaaagac agtgaggaac 194040
aaagaataaa atattttgaa ttcaggcacc tgtatttttt tttttttttt ttttttgaga 194100
cggagtctca ctgtcaccca ggctggagta cagtggtgtg atctaggtca ctgcagcctc 194160
tacctaccag gttcaagcga ttctcctgcc tcagcctctg gagtagctgg gattacaggc 194220
acacgccacc atgcctggct aattttttgt atttttagta gagatggggt tttggtatat 194280
tggccaggct ggtctcgaac tcctggcctc cagtgatcct cctgcctcgg cctcccaaag 194340
tgctgggatt acaggcatca gccaccatgc ctggccaaac acctgtattt ttaaaaagct 194400
cattggggct gggcatggtg gctcatgctg taatcccagc actttgggag gccaaggcag 194460
acagattgct tgaggtcagg agttcaaaac cagcctggcc aacatggcaa aaccccatct 194520
ctactgaaaa atacaaaatt agccaggtgt ggcagcacgt gcctgtaatc ccagctactt 194580
gggaggctga ggcaggagga tttcttgaac ccaggaggtg gaggttgctg tgagccgaga 194640
tcccaccact gcactccagc ctgggtgaca gtaagactca gtcttccccc ccccaccccc 194700
ccaaaaaaaa agctccttgg taaccatgcc agtcagcagg ctgggaaccc tgggactaca 194760
cagcttaggc ccacccagct atgatcttct ccaacaccct cattctcttt caaagacaag 194820
gtgaggaggg accgtttact ccattcctgt ctgtttgcac agagctgcta acagatgcta 194880
cattccaggt gccccgggca tctgagcctt cccccctccac acactggggt tggtccttgg 194940
cccatggatc tttccagcct tatgtcccac agtccagcca atgaggtcac cttggctgcc 195000
catgacatac tctcctgcct ccccgggccc tcctctgctc catctccctg tcctgagatc 195060
ctacacaatc ttcaggattc acttcaaatg ccaattcttc cttgaaactt tcccaatgcc 195120
atcttccacc cacccatgcc tgctttgaag ccactcagca cactgctgct ctctgtggct 195180
ctccaacatc tctggtacct ggtatgtagt agttgctgat tacataccta tggactgaac 195240
aaatgaatgc agccttcttg gaaaaggcca aggaaggcca ggttttaagc acagtgggcc 195300
aaaaacccag agcccaggct gacagccctg agagggcgtg ggccccccag caccttactt 195360
gttatacagc acaatgtctg gcttccagat cttctgtgca gggacacgca tgaactctgc 195420
cccaccatag tcagaggggt tccatttcag cttgtagtca ttccagatct cggggaagga 195480
agcagggagg gagaaggaga cggtaaaaga atcagcctgg ttttacttcc cgtggcacca 195540
cccatcttgg tgactcccca cccctgctgc atgtgaccga accacatcca tgccatgatc 195600
acatagtcca acttctcctg tgggtgtagt gcaggagaga gcacacggct ggctctgcgg 195660
gccacctcct ggcactaggg aagccactgc ccccataacc atgagcaagc ccagcccctc 195720
atcaaccaaa cagggcctac tcgtgctttc tctggtcact tctagtgcca ggtggagact 195780
cctggacttc atgcatcatg tccaggtcca tgtgcctgtt tacagcccct gaatggctct 195840
ccaggggtgt tttccaacat agacactctt tcaccccaag gttaagcaag actggactct 195900
gaaagattcc gggggaagaa tccatgaccc ctgcagggcc caggaagtgt ctgggtccag 195960
aggctgggag gtctgagtcc tgagcaccag aggagagagg ggtgaggctg cggccacaga 196020
gggaacgtgt gcatcaagta ctgggtgggg cactgtgccc atctggcttt ccaacctcct 196080
ggggatgaag gctgtgtgtg ctgagtgctc agctggccag gctggcagaa gggtcacccg 196140
caggccaatg ggccattatg tctcctggca agtctggaca aagcctccct ggggaggaca 196200
tgtggaaggc aatttcttgg cctcgatctg aacaggaaaa tctactccca cgctaccaac 196260
aacagcagca tcttattctg acttaagaat gagtataggg gctgtgcaca gtggcttctg 196320
cctgtaaccc cagcactttg ggaggctgag gtgtgtggtt tgcttgagat caggcgttcg 196380
agaccagcct gggcaacatg gcgaaaccct gtctctataa caaatccaaa aattagccag 196440
acgtggtggt gcacagctgt ggtcccagct acttgggagg ctgaggcagg agaactgctt 196500
gaaccctgct ggtggagatt gcagtgagcc gagatcacgc cacagcactc cggcctgggt 196560
gacagagcga gatcccgtct ggaaaaaaaa ctgagttttt agcaagaggg agagaaggag 196620
gtgtctcagg caccacccca gggtttgggg gcagggcttc aatctcaggt tcgtactctt 196680
ctgttgtgtg aacatggaga atgtctttct ccaggctgca acctgtccat ctgggacttg 196740
aggggttggg ccctacagtc cttccagggg gactgtaggg cagtgcatgt gacctcaagc 196800
cttagaagag atatatctgc cagtcagtgg accccaatct gggttccaca gaagtaaatg 196860
aagcctggtc tttaggcctt tcttggttca cctaaagcaa ataaaacagt caccaccagg 196920
gggcagcagt gcctagggtc tggtcactta cttgcttgag ccacaggttg gtctccatga 196980
tctggtttac ttcatcctag aaagaggaat taaagttgac aggagaatta caaaacaaga 197040
ctaattctgg gaaaggctcc tccagaagcc ccggtcccca tggccacggc tcgtggcttc 197100
cagcactcac caccttcacc agctgagaca tggacacctc gaaatggatg atgactgggt 197160
cagacacgtt ggctacaggc cggatgatct cattgtaatc ttcaaacagc cgctcaaata 197220
gacggtgctc agcctctgag gccctggcca ctgtgggaag cagccctgtc agtccctggg 197280
gaaatcgtta cttaacctcc cccacccagc ccagcagaaa catcacccat ctacagcatc 197340
ccctccacct gtggggggat tctgtggaac cctagacttt caggccagtc taacccagtg 197400
ggttacaaaa tgggaaactg aggcccaaga ggggcaggat tctacctggc cacacgcatt 197460
cagtgagaag cacagtggtt gcaagcctgg gctctggagt tggacagatc tggtgcaaat 197520
cctgacaaat cacttgtaag ctgtgtgagc ttaggcaagt ggcttaacct ctctgaacct 197580
gtgtctttac cagtcaaaat aaggattata aacgtatcca cctcaaaggg ttgttgtgaa 197640
ggaagtgcac agcttggtgc tgcggtaaga ggtcaagaac tattcgcaat cttttcctgg 197700
gttgtttctg ccgggtgggg gtgtggggca aatgctgtct gcctgggtac agccactcac 197760
tgcttccacg atggaaagat ggccagtccg ctcccagggg cagggccaac cacggtcgcc 197820
caggcccagg tcttctacct cccagcctcc gggagaacac agcccaggtc tgggcctctc 197880
ctgcattcca ccctgtaggg gtggccacca gccctcttag aagccaaggc actgtgtgac 197940
tcccgtgatc tcgtgtgacc cccagctctt gctgatgctg tcttcatatc ctgatgaaag 198000
actctgacct ctgcaaccct tgggcacccc tctttgttcc taagccacac cccagcacaa 198060
gtgaggcata ccgggtcagc tgtcttctga ttcccacgta cagatctggg ggcagcttgg 198120
ggaagcggga ggagaatcct ctaggaagtt gaatccaact tcctcaggtc ttgaaatagg 198180
atttttcctg ctccccactc tccttcccca ggatgaaaga agggtcccag gcaggaggtc 198240
ggttgagagc gtatggcgtt ctgagtagtg caggcctcgg caccgagggc ggaaagcgct 198300
ctgagctcac agccgcacga cagaccgccg gcctgggccc tccaggaatt ccctgcagcc 198360
ttgcccggtc cccgactctc gctacccacc agccctccca ggcacccaag agcctcccag 198420
cggcgggcca gggccggctt cccccagcag gctcctctgg agagcgggag gaagacagga 198480
ggcgctctcc cggtggaggg tccctcagcg acgcagccag gagcgctagg aggctacaac 198540
cggaggagag gctggcgctc cagctccagc cccagtcccg aagcgactcc cctcttcccg 198600
aggtggcctt ggccaagtct tcagccatct ccgtcaaatg aggaggtggg cgggatgcag 198660
acggtggagc gggaggcttg ggcgcgccag tttgggagcc agtgcgcggg gcagggcgac 198720
gggcagcgcg gggacgcgaa tccccaactc ctgcgcccaa gacgaaggac ccggtctcga 198780
cctccccatc acccggcgcg taccagcgcc cgctcagtga ctcccaggtt tggtggtggc 198840
taggggtggg aggtgagccg aaagggaaaa agccacccca cccaagtcgc cgccgggctg 198900
gagccagtct gcgcgggttc cgagtccccg gcgacggcgc cagccctctc cgctcgcccg 198960
cgcggtgttc tcgccggcag cccctccgga ccccgcgccc cttctcgggc gcccgtccct 199020
ccggagccct aacgcctgtg cgcgtacctg gcagcagaga cagcagcagc agcagcagca 199080
gccgcggcgg cgacagcgcc aggggcagcg agagcgggcc agagcccatg gctggtggcc 199140
gggctggccg cggacccgga cggtcgggag cgggcgcggc ggtcgcagag acggcctctc 199200
cccgcgcggc tccagcgcag accccagacc tggagccgtg cgggcggaga cgcgcggggc 199260
tcctctccgc ttcgccgccg ctgggtttcc agcgccctcg gacccgcggg aggacaggaa 199320
ccatccggag tgaagctgcg ccaggcgcgg gcgggcgggc gggcgtgcgc ggggcggggc 199380
gtacgtgcgg taggggaagg ggctccaggt cccagtcccc agcgccgggc gagctccttc 199440 tccgccggc tgggtgctcc ggccggcggc gtccgaccag atctgagcag gtgctgtcac 199500
caccaccagg aaggagaggg actcagtttc tgtcccaggt ttccggggcg tgtgcagctc 199560
ccgcaggggg ttgggaccac cgggctaggc gggcgccgta ggagagacgc taacacaccc 199620
tgggaaggac gccttgtgta tctcatgcta ttaaataatt gttaaatatt ttagccggga 199680
gcagtggctc acgcctgtaa tcccagccag cactttggga ggccaaggcg ggcggatcac 199740
gaggtcagag accatcctgg ctaacatggt gaaacctcgt ctctactaaa aatactctac 199800
aaattagccc ggcgtggtgg caggcacctg tagtcccagc tactcgggag gctgaggcag 199860
gagaatggcg tgaacccggg aggcagagcc tgcagtgagc cgagattgcg ccactgcact 199920
ccagcctggg tgacagagtg agacttcatc tcaaaacaaa acaaaacaaa acaaaaaaac 199980
ttagatatag tactggtatt tttttttaa gtccttatag cttaggggtg ggtggaagtt 200040
agttgaaaca atattggcta tgagttgata attgtcgagg caggatgatg gtacctggag 200100
gtttgttata ctgttctctt aactttggaa tacgtttgga ttgttcctta atgaaaaatt 200160
ttttggggtg atcagaccca accccaggcc atgggggtga caaagtcagg cggagtcaaa 200220
agaatgagaa aagacaagag agaaagcggg accaggcggc caacgtatgg aggctacgaa 200280
ggcccccagc tgtgggagcc cacgctattt attggtgatc aaagaaacag gtggtgagga 200340
tgtgggggtt gaaaggaagc ggtgtatcaa gcaaatgaac tacagctgtg acggtagttc 200400
acctcccatc ccaaagtgct gggattacag gcgtgagcca ctgtgtgcag cctcatctgc 200460
tcttctgatg gagcaatctg agagggcaat ggggttccca ccctagtccc ctgcagaacc 200520
tgtccccttc cccgccacca tctgcaaccc caagaatgtg cactgattgg ccaggcaggg 200580
tgccctggag cctcctgccc tctctgacca ccccaccaggg atggggggca ccttgatgtt 200640
ggcttctttg acatcctttt attgcaggag gaagttctgt cataaactct cctcctggca 200700
ttcagcaaat ggagagtcac ctttatcatt tccagaatgt gctgtttacc catattaaaa 200760
ccaaacaaaa ggagacagtt tgtggaatgg aaaatgtaag aattgggacc cacctctcag 200820
gcctccaatt acagcattct caactcttgg caaatgtccc ccattgggac aatactgtaa 200880
gttatatatc caacaaagga cttgtatcca gaatgtataa ggaactctca aaactcaaca 200940
ctaagtgtag atgcatatga ggggtcttac tggggtgatg cagatgttct aaaactggat 201000
tctggtggta agcttacgac aactctttga attgtacttc aaatgggtgg attttatggt 201060
atgtaaatta tacctcaata aagttgtttt ctaaagaaag tctcaatggt aagaaaacga 201120
acaatttttt aaatgagcaa aagagttaaa cagactcttc accaaagagg tatacagaag 201180
acaaaaaaaa aaaaaaaagc acgtggaaga tgttcaaatc actagccatc agggacacgc 201240
aaattaaaac cagggtggaa tccagttgct gaacaactgg atctctcata ctttggtggg 201300
attgcaaaat ggtatagcca ctccagaaaa cagtttgaca gtttctttct ctttcttttg 201360
ttcttttttt tttttgacag agtctcgctc tgtcacccag gctggagtgc agtggcacga 201420
tctcggctca ctgcaacctc tgcctcccag gttcaagcaa ttctcctgcc tcaacctccc 201480
gagtagctgg gattacaggt acacactacc acacctggct aatttttgta tttttagtag 201540
agacagggtt ttaccatatt ggccaagctg gtcttgaact cctgacctta ggtgatctgc 201600
cgccttggcc tcccaaagtg ttggggttac aggtgtgagc caccatgccc ggcctcaaca 201660
gtttcatata aagttaaata tacacttacc atataaccta gcaatcaccc tcctgagtgt 201720
ttaaataaat gaaaactttt attcatacac aatcctatat gtgaatcttt atattagctc 201780
tattcataat tgccaaaaac tggaaacagc ctaaatgtgc gtcaacatca taccactgaa 201840
cactcctcag caatacgaaa aaaacccaac ttgattgaat ctcgaaggca ctatgctgaa 201900
ttaaagaagc cagtctccaa aggtcactac tgtatgattc catttaaatg gcattcttga 201960
aaagacccga ctgtagtgaa ggagaaaaga tatgtggttg ccaggggcta ggagtgcagg 202020
gagtcaggac tctaaaggaa tagcaggacg gagttgtttt gcgtgacaga tctttcctgg 202080
gtcctgattg tgatggtggt tataccaatc tatacatgtg ttaaaattcc tagaactata 202140
tatttaaaag tcaattttat tgtataataa tttttaaaac agaatttttt agaacatcct 202200
cctccattcc acaaatattt tgagtgccta ctacatgcca ggcactgtgc aaaaggcagt 202260
atgtgcgagg agtgaatcag agcatccgtg tgggagacag acctgaaccc agccatgaga 202320
gagaagtgga aagtgaccag caccgcagtc atggaggagc aggtcatgcc tttcagatgg 202380
gggaactagg gatggctgct cagaggaggg gcatctggac ttgaaggagg ggtaggagcc 202440
attcattcat tcaacaaaca tttattgagc acctactgtg tgccaagctc tgtcctaggc 202500
cctggggata ctaccacgaa tgtgaaggag caggtccctg ttctcatgga gctcacactc 202560
tagtgggtga gctgtggatg acatacatgc caccagataa gagcgacagg tacacaggag 202620
tgctcgagga aggaggcagg gtaacgtgac tgtagggagg ctgctttaga atgattgggt 202680
ggttagggaa ggcctctcag aggaggtgac attggagcaa agaatggatt ggagccatgc 202740
cctgactgat gtggctgtgg aaagagcttg ggaagccctg gggggaagagg aagaaggttc 202800
aggtagaaga tagggaaggc caggcatagt ggctcacact tgtaatccta gcactttggg 202860
aggccgaggc aggtgggtca tttgaggtca ggagttcgaa atcagcctgg ccaacaaaaa 202920
tacaaaaatt agctgggcac ggtggcggct ttctgtaatc ccagctactt gggaggttga 202980
ggcaggagaa tcacttgagc ctgggcgata tagcaagact ccgtttaaaa gaaaaaaaaa 203040
aagatgatga tatggcaaat gccaagcctc tgagctggga agaatctaga agtgtgtgag 203100
gaactggaca aggggaagtg gagagagatg gtgatggaga ggcaggccgg caccatgcct 203160
gaagcatagt aggtgctgct acgaagtcat ctttatcccc attgcccggt gcagggaagg 203220
aagacaggcc agaattgaac tgtctgaagc tccctcctac tggggcttcc tgggatccct 203280
ccaaggcatt cagagaggac agcccaggcc cccatccttg cctgttccac ggctgtggct 203340
ggtttgatgg ggttgatggc caatgctcac atatttactt agggcctcat cagccacaac 203400
ccagaaagaa gcagcaaagt gcccacccgg ccactcacat cctctcaccc cacaacccag 203460
ggggccctca gtcacgctgg gcagcgtagg gcccctcaga agctgcatgg gtctggaaga 203520
ggggcggtag gaagagcccc acagtgccca ggacgcacac aaacatgaac acccacagga 203580
acagccggtc caccaccata gccacgtact tccagtcctc aacgacctgc aggcagacag 203640
aggagttggt cacaggtgcc aagtactggg gtccctcctt tccccgagtc aggcccttac 203700
tctctggcca gggactccac aggccacagg cgtggaactg catactaggg gggcaagttc 203760
tgagtcccag gctggcctcc cagctgggca gctctgagcc tctctggctg ttctccacct 203820
ccacccctgc ctgtccccca cagcgttgga ggggcactgg gaacttgggc tgtacagaaa 203880
agctaggaat gtgagggctt gttaatacta catattatga tttgaaaaca aaatctggtt 203940
atacatagga gatagggcct gaggatctca aagccccaac ttctcatttt taccccaaac 204000
tcactgcctg agctggttct agctaaagaa agaactaggt ggctcccacc tagttcagtg 204060
agagcagaga aaccggggct tacagaacac ctggaaatcc tgctgtttaa tttgttcaag 204120
tctgttcaca gcagtgtctg tttcctgtaa ttaagaccca gcctcctcct gctgcatcat 204180
tcaggtctct ctggtcttct tagatcctgc tgcggggtgt gaggttggca gagacctggc 204240
tggcctccag aggggccacc agagatgggc ctgtctcctt tgcactgggg gagaacctag 204300
agaaacgcct gtgtgcccag ggtcctggcc tccctcgccg atgcctgctt tcacacccct 204360
aggcctggct ggctcacact gcattcattc cctggcagag acgggctgga tcagaaggct 204420
tcggagatca gcagaggctc tggagttgga aatgtgggca gcaacgggca tgctgacgtc 204480
agtgacccag tttgtcaagg ccctgtcaat ggtgtaccta acgtgcaggc taatcctgtg 204540
tcaagccaac cccgacacct gcaaccaagc acgcctgcac ctgtccccaa gactcagcag 204600
gcacacacag ctctctccac agagcactcc ttggctttcc tgggtttctt tttaacagcc 204660
ctaatttcaa gcgggggtgt gtgtgtgtgt gtgtgtgtgt gtgtgtgtgt gtgtgtgtgt 204720
ttccccccttt taatattttt gtgctattta tagtgaccag ttaatcaggg tgggtaaaag 204780
tactgaagat gagaagcggc gtgggctggc ttaggggcag gcatgctcta gaagggaaga 204840
aagcctcttt tctccaacca tccataagaa agtcaatcaa ccaataagcc ggccatgtgc 204900
tcagtgcagg gcaagaaact aggaagggca agaaagttta aggatgacag gcagatctgg 204960
gtacagagcc tgggccagct gtttgacact ggccaagtca gtgaacctct ctgagcttcg 205020
ctttgaaagc ctccttattg taaatggggg ttctactaaa agccacttca caggattcca 205080
gggagggtta gcagtaatgt atgtcagctc ccagcagagc acctgatgtg tgattggagc 205140
ttaatgaaca ctggtgatta taataactgg tcctgcctgg ctccttccct taagaggctt 205200
gtaattaatt gagctagaaa gagcagaagg cacgtgagtg ccaagggggt ggtgaggtct 205260
tcagaagagt tcagggtggg tgccggctca gccagggatg caggagacca gtacttctca 205320
atctagaatg tgcacacgaa ccaccaggga ttggttaaaa atgcaggctc caatatgtct 205380
ccgccagaga tcctggctca gtcagaaagg gtggtcccac agtgttgccc acgtggttct 205440
cacttagcca gcagggcccc aggctgcaca ttaatgattg ggaaccaatg aattaggtga 205500
tgctgaccta cagaatgatt taacctaagt aatagcgtga tcgaattaac gttttagaaa 205560
gtgaaatctg agagtcctat agagctgtgc ttctcaaact gcaatgggtc tgggaatctc 205620
ctggggacct ggttaaaatg caggtttgga gctagcaggt ctggattggg gcctgagact 205680
ctgcatttcc gataagctcg caggcgatgc cggtgctgct ggtccaagaa ctacaccaga 205740
agaatatctc atgtcctata ttccatttgt ttgcatttct cttcttttct tggcacagtg 205800
tgattctggg gctgttcctg ctcttttctc tgtgggctaa ctaatggaat gccagcgctt 205860
ctccttgaga atgcagcgag tggaaagcaa tctcaaaacg gtaagaatga gacgtccact 205920
tttgtccatg cagctgcaca ggggcagaca ccatgttgca tagtaaaaac ctgtccaaag 205980
aatctgatct gaaggtgtta atatgagaac attcacaaga gcatgaaact tgctctccct 206040
cctggtatgg aaatgggtgt gaaaatttgt caccaccaca ttctgtgttg ttactatgac 206100
attgtcctta gaagtgttat ttattcaaag gagtcatgtg aaataccag actccagcac 206160 tcattgcttt atcctgtgaa agtaaattaa acctcttttt aaaaaatccg taattctagg 206220
tcaggttcgg tggctcaagc ctgtaatccc agcactgtgg gaggctgagg tgggcagatc 206280
acctgaagtc aggagctcaa gaccagcctg gccaacatgg tgaaaccccg tctctattaa 206340
aaatacaaaa attagccagg tgtggtggca ggcacctgta attccagcta cttgggaggc 206400
tgaggcagaa gagtcacttg aacctgggag atggaggttg cagtgagccg agattgtgcc 206460
accacactcc agcctgggcg acaagagcaa aactccatct caaataaata aataaaataa 206520
aaatctgtaa ttctagttag cacaatcgat taattcatta ccctggtaat catagtattt 206580
ttactgatgt tcctatagcc ctggaagcta taagtgcttg aatggcttct ttgcaagtct 206640
gaacagaata gggcagatgc gcttggtacc ccagcccgcc tgtgttccct aaagcctgca 206700
gagtcacttc ccagccttcc atttctggca cccgcatttc ctctctcctc tgcctcaggg 206760
ctttctccag caccaagggt gcttgttctg gcaggctggc attacctgga agcacaggag 206820
agttaaagtc ctggggctac cctcatcctt tagggaatgg gggctggtgg gtaaatacct 206880
cagcctcctt ccaggggggt gatcctgagg cttgttccca cgggtctgca agggtactga 206940
gtcccgggta cccacggcag tatcctgctc attcattctc ctttccctgt ctcactttcc 207000
ctccttcctc actgtgcttc ccaggatcac atctcaagta aaccacctgc acccaagtcc 207060
ccatcttggc gtttgcttct gggacaccta aaacaaacaa actaaatcac tggcacgtcc 207120
ttcctctccc cggatgcatg aagctataat atttaacaca aactcatttc aattttggat 207180
tccttattca gagtttgaga gtccttgtct cctatgaatt aactgcagga agtgggaagc 207240
tggtgctact atctgagccc tttctgttgg gcaggtgggc aggggctggt tagcaactta 207300
cactctggtc ttcatcgtca ttcttcatgt gctgggcgat gaagctgaca ccttctaatg 207360
cctcctgcac atcctgtcgg aacctcccag aggaccgcag ccagaaatcc ctggggatag 207420
ccaccggggt agagccggct ggagacttgg aagctgcaga ggcggggttc acaaagtaca 207480
tggagttccc atagaagttg gaggggctgg tggaggtggc ggtggcctcg ggcttggtca 207540
cgcatgactt gctgggcggg aaggctctgg ccgggctgct gtcggggcca gggcgcttca 207600
tgaagaggaa ggtaggcagc ttgtgcagga agcagcgctt gacccagggt gccatggtgt 207660
gggtgctggg cgagcggtgg tgcacattga gcacacagac gctggtgacg atggagaagg 207720
tgaccagcac catggtgaac atgaggtact tgccgatgag aggcacatcg agggaggtgg 207780
gtggcacgat cttggagatg agcagcagga agaatgtcag tgccagcagc actgagatgc 207840
acagtgtcat cttctcgccg cagtcggatg gcaggtagaa gacgaggatg gccagcaagg 207900
tggtgagcac gcaggggatg atgaggttga tggtgtagaa cagaggcttg cgcttgatga 207960
tgaagtcgta agtcacgtcc acgtagctgg ggtcttgtgg gttcactgtc cttctccctg 208020
ggagggccac tatgtcccac tcaccactgg gagtaaagtc atccatgctg gctgtgggcg 208080
tcatgaggac catgtctatc tccgtgtggt cataggtcca ggagcggaac ttgagggtgc 208140
agttctgctg gtcgaaggga aagtacttca cctcaatctt gcaggcgctc ttgtagatgg 208200
cagggggcag ccacaggacg ctgccgttgg accggactat caagttggtg tagacagaca 208260
cctcataggt cccgtcggcg ctgggcaggg tcagggcatg gagaacatcg tgaaacccat 208320
acacaaaacc tggcctgttc tcagaactca ctgaagagcc ctttgggatt atttcccact 208380
aatcaccctt ccaatccccc aggccctcac tgaaaggagg ggtctgcttt tgttagcaac 208440
tatgtggtgg agagagccct aacatcaaag cacccccctt tttttttttt ttgagacaga 208500

-continued ctcttgctct gttgcccagg ctgagtgcaa tggtgcaatc tcggctcact gcaacctctg 208560
cctcccaggt tcaagcagtt ctcctgtctc ggcctcccaa gtagctggga ttacaggcat 208620
gcgccaccac gcccggctaa ttttgtattt ttagtagaga cggggtttct ccatgttgat 208680
cgggctggtc tcgaactcct gatctcaggt gatccacccg cctcggcctc ccaaagtgct 208740
gggattacag gtgtgagcca ccacacccgg cccatcaagc actcttaagg cttcccatgg 208800
aatagctcat ttaagcctct cagtagtcca gtgaggcagg ttttattatt atccccattc 208860
tacagatggg aaagccaaag cccaaagagg ttaagtgact tcttcaaggt cagaaaactt 208920
gtaagcagga cagctgagat ttgaactcag gtctgtctgt ccccagacca cacactttga 208980
gccatttcaa gctactgctg gtgtaatcac gactcaggaa aagtctcttt ggcttcctcc 209040
acctgcctaa gatatttaca cacagtaagt cagtggtacc aacaccaaca ctggcaaagc 209100
aacagaggct caaaaggata gtatggaaca cagaaagggt gctgggttca aggtcaggac 209160
actgctgtgg tcccagctct gcttcagtga atcagacaag gtccctcccc tccctcagcc 209220
tccaactccc catctgtaac tgagggctct ggctctgctc acctctgttt ctcttctagc 209280
ttgatggcct ggaaggctgg gtaaagcaga gatggggctc agggttggac tcaggcctgg 209340
atgactctta gggctgggcc tgctgccctg gcctggctgt caccaggcct ccaccaaccc 209400
tgccactcac ttgttgtaaa gcacgatgtc aggcaaccag atgcgctttg cagggatcct 209460
caggatgttc acaccctcgt agcgggagct gttccaggtc aggcggtaat cagtccattc 209520
ctggacagac aggcaaggcc ctgtcacttg caggtccact gccaccaaag ggcagcccta 209580
aagaaaagat ctctggggct cagggccctt cagggcactt acctgtttca gccagacatt 209640
ggtggtcatg atctgctctc gctcattctg gggagggaaa cggggctatc agttcaccag 209700
gaaggaggag cctcacaaat ggattgcact ttattgtgca aaaggctgtg agctccaggc 209760
ccacgtgacc aactgccacc ccaacatctc ttggatggcc caaaggcatg tcacactcag 209820
catgtttgac acaaagctca tgatcttccc cagaacctgg tcctcctttg gcttcattgt 209880
ctcagtgaat ggcaccccta gccatccagt tccacaagcc agaagcgtgg acactgtctc 209940
tgacactttg ctctctgatc catcaataag tcttgtaagc tatatcttct aaagcaactc 210000
atatttgtct gcttctctcc accgccacca tcatctgtca cttagactac cgcaggagcc 210060
ccctaactgg tcttcctgct ctgtcctggc ctgcctttag tctattctct acatggtagc 210120
cagggtgatc cctttacaat ctcaatccct tctactaatt gttctgctgc cacatctcat 210180
ccaaagtaaa agccaaagtt ctgcttagag tccacaaggc cctagtgatc tgcctcccca 210240
ccacccctca tcccattagc tctatgacct cttatctcaa cactccgcca tttgctcatt 210300
ccacttcccc tgcactgcct ctttgctcct gcacacactg ttccctttc ctggaaaccc 210360 cctgggatgc ttccacactt tattctgtta tcagaaatgt catcctatct gagaaatctt 210420
ccctgaccta cataaaatag cacctcggtc cctgccctgc cttctctttt tctttctttc 210480
tttctgtctt tcttttcttt tctttctctt tctttctttc tttctttctt tctttctttc 210540
tttctttctc tttctctctc tctctctctc tctctctctc tctctctctc tttctttctt 210600
tctttctttc tttctccctt tctttctttt ctttcgtgtg tgtgtgtgtg tgtatttctt 210660
gagacagggt ctcactctgt cacccaggct ggagggcagt ggtgtgatct ttgctcactg 210720
caacctccac ctcccaggct caagcgatcc tcccacctca ggctcctgag tagctgggac 210780
tacaggcaca ggccaccata cctggctaaa ttttaaaaaa ttttttgtgg agatggggat 210840
tcatcatgat gcccaggctg gtctcaaatt cctgagctaa agtgatccat gcatctcagc 210900
ctcccaaagt gctggcatta caggtacaag ccacctcacc cagtctcctt attttttttt 210960
cgtagcattt ctcacccccta aacaccatct atctatctgt gtattgtctg ccacctccca 211020
ctagaatcta atggctatga gaaaataagg cagatagaag agtatgtaac atgttggata 211080
ctccataaat attttttgaa tatacaggaa tcctaccata ataatccagg ccaccataat 211140
ccatgtctca cctggaccat gtaagaccct cctaactggc ctatgttcat tctgtacacc 211200
accaccaccg ccaccataca cacacataca tctcttcttc gtacgcagcc caaataaacc 211260
ttccaaagtt cctgtcattt cctccctcaa ttttatccct gtttagatta attccttggc 211320
ttccttcacc tacagaataa aaatcttgct ccttcgcagg gtctacgggg ccttgccagg 211380
tttcccagcc tcacttcacc tccctatgtc cctctgttct gtcctccagc cccctggcct 211440
tctttagtac tttggataag tcttgtgttc tcagtctgta caattttggt gcctctcctt 211500
tatcaagata acttccagca tactgatctc actttgggag tcatttcctc aaggaaccta 211560
caactagata agattatcag taagataagg tttggctgcc agtaacagtg atccagagta 211620
acacaggctt aaataaagta gaaattcatg tccctctcat gttaacactt tagacatata 211680
tggcagttct gctctacaaa gttctgatag gtacccagat tctttccaac tttcttctcc 211740
accataccta gagtgtggcc ctcataagaa tggatcaaaa taactgttgg agctctaacc 211800
acaaattcca cattccaggc tgttggtggg aagggaggag ggagaagaag aatgcatggc 211860
aatttgtctc attttgatta gaatatttag gccatttaca tttaatgtag ttactgatat 211920
atttgggctc aaacttaccc cctgagcttc cacagcatca gatctgcccc cctgcatacc 211980
cccgatctct tgccaagtgg catttgggtc tttatgtcat tttcctcaca tgtctgggag 212040
taaagacgag gttcagggac ttgagcttgt gtactctggt gtcttccagg agaatgtgtc 212100
aagtacaggg gagatggctt ggaaagagga agactcagag gagagtcaag gacatcaaaa 212160
caggcaagcc caggagcagg aaaagagatg agagtcagca gaggaaacag tgctggggca 212220
ggggagcagg tggaagggtc agggaataag gggggctgga gaggtggggg tggggatgct 212280
ggcgagggag tgcctggctc accagactct ggagtcaatg acaaaaacagc tgctttgaca 212340 agcctgcttt ccttacccag ccctaaatcc ctacctgctc tctaaaaatt tccatcttta 212400
aactggttgt acctataacc ctccctcctc aaataaataa acaaaccctg gcaacccaca 212460
acctaatatt tactgtatac acaagctttc ggaaatataa cttgcatggg tgggggctgg 212520
tggccgcatc ccctcctcct tctggtagcc gctatcaccc tatagggccg gcagagcaga 212580
tctgaccagg tagcctgagt ctggaagtgc ggcagagcct cctgctcgtt caccctcact 212640
agggcagcag ctgcaccgca gcagctgggt tcaactcatt aagcaagaag ccctgggctg 212700
gacaataaca ctcagacacc agcctgagca agcctggctg aaagccctcc ttccttctgg 212760
tccgactacg gagggagagg ggcagagagt acacagctct ccagccctcc ccatcctggg 212820
gctgtgcgtc ctcccaggag atggagccag tcattaattt ggccaaagcc ttcctgaggg 212880
ctgtaggttt gacaggctgg gtgtgtgtgg gccaaccgtg ctagagagag agtctggcat 212940
ttcagaaggc agctacctgg ccagaggagg gtcagccccc ttggtggtct ctttcccctg 213000
gctggacaca gcgccctgca ctctcccctt gtgaatgttc ccccagagct tcttccaggg 213060
acggagttct aaccctgtgg atggggacat gggaaggttt acaataggcc atggttccct 213120
ctgacatctc caactcagag gcagcaaaga gaagagaaat tcccaggcac ctcctccctc 213180
agcaccccca cctctgcccc acatccacat atggacaacc tgacaatggt acctgtgaat 213240

-continued

```
gctgccatcc actcctcctt tccatgcctg cagcagccac gcccactgtc catccctcac 213300
cagcctggct caataggtgc tgcactgcct ctggtcctgc ccctacacct gggcctctct 213360
gtacctatca gttcccccag tctggttttt acttctccca acaagtaaga agcatgtaag 213420
gttatctgag cagtctaggg gagagaatag ggtggggctg taaagacaag gaggagaagc 213480
ttatggtcat gctggagacc cagctgagca gagtctacag caggcccatt ggctgcctac 213540
ccaatggtca tcctgctcct accctcattt cttctttgtt agaacaaaat catgacttca 213600
ttaaatattg gacacctatg aacttcatgg acccttctgc agcctccctg acacgtactg 213660
gtaagtctaa gtcaactata gtagtttcat tcctttgacc aatgatcgcc tggggcttgg 213720
gcatgagcgg cctctccacc tgagcctgag ccacagctgc cctctgcacc taccacgctg 213780
ataagctggg ccagggagag ctgcagcttg atggagatga gctgtgagga gctggtggct 213840
gggcggatca ggttattgta acgggttttg ttcagaaggt cgtccatcag cttttcctcc 213900
gcattggcca cgcggcagtt ccctgagaaa acacacagtc agacctgctg ggcccttgtg 213960
cacctgaccc ccactgcagc ctgtggcagc agggagagct gagagggagc acaggtgccc 214020
ttagggctgg ctgaagcagc gaaggtgctg gcaggcctgt ctctccttga ggacttcaaa 214080
ttaaatacac tcaacacaga gctcagctgt ctcctcccat gccatacttc ttcctcctcc 214140
tcttccctct agcagtgaat ggcatcccac tctacatatc tggtacaaaa gctgggtgtc 214200
tcttcttgac ctctcccttg gttcatccaa gtggccactt agtcctgtct ttttttgtat 214260
gagacagagt ctcactctgt tgcccaggct ggagtgcggt ggtgtgatct cggctcactg 214320
caacctctgc cacctgagtt caagcaattc tcctgtctca gcctccagag tagctgggat 214380
tacaggcctg cgccaccaca cccggctaat ttttgtattt tagtagagac agggtttcac 214440
catattggcc aggctgttct tgaactcctg gcctcaggtg atccacccac attggccact 214500
caaagtgctg ggattacagg tgtgagccac cattcccggt cctagtccta tcttttacct 214560
tccaagtccc tcagtctgtt ctccttatct ctactgctac agccatgtcc ccacctcccc 214620
acccctgccc tcctcctggt ctctccaccc gcagtctctc cctgctatcc atgtaccata 214680
cagtgccaga gtggtctttc tacagcaaac tggtctaggg cccttcccta cccacaactc 214740
tcagagctgt aggtggactt aaaaatcaaa tgttttggct tggcgttcaa ggccctttcc 214800
ccactgacac tggcttatct ttctcaatct gatttctcc cacctctcta cctctacccc 214860
agatactcag atactctctc ttctggccat agcctactgt ttgcctttcc ccctgtgacc 214920
ttcactgtct cacttcctgt tttttccttt ttttttttt agagacaggg tcttgctatg 214980
ttgcccaggc tggtttcaag tgattcctcc tggattcaaa ggatcctccc acctcagcct 215040
ccttagtagc tgggactaca ggtgtgcacc accacaccca gcttgtctca cttctttgaa 215100
cagactcttt cttctgccaa gattgccccc agcccaccag ttatgaatta tctgagggtc 215160
tatcttgtgc cagggacttt actacatttc gagggtaaca gcaagcaaaa accagaaacg 215220
gttcctgaca ccagagcact tacagtgcag gggagcagcc ccattactca catgtgagtt 215280
tgggtgcaga aatgggtacg aggtggtgct ttccctaaga agaaacagag ctgagatgga 215340
ggggattttc cgggttcaga cttagaccta cagagtgtaa ggtccctctg agacaccaaa 215400
tggaggggtc cagctggcag ctggctcctc atctggagct tcgaggagag gtcttagctc 215460
agagccatat tcaagaccca gcctaaatac cgcctcatgc agggagcccc cctgaccttc 215520
catagcctca aatctgcccc tctgcatacc cccgatccct tgccaagtgg catttgggtc 215580
tttatgtcat ctccctcacc tgtctgggag taaaggtgag gttcagggac ttgggcttgt 215640
```

gtactctagt gtcttcaggg agaatgtgta aagcatagag ggggcagctt ggaaaaaggg 215700
agactcagag gagactcaag gacatctgag gaggcaagcc tgggaggagg aaaagagatg 215760
agaatgagca gaagaaacag tgccggggca gggaagcagg tgggaggatc agggaataag 215820
aggggccgga gaggtggggg cgggcatgct ggtgaggggc tgcctggctc gccaggctca 215880
ggagtcgatt acatcttcct gcaagggcca gttcacctag ttgcaccaaa ccccttcctc 215940
tgtgggtagg gccagaaggc ccagagcaca gaccaaccca attaggcagg cctgaggtgg 216000
acttaggggt gggtgctggg ctggactcct ggttgtgggg agcagccgcc accctgccga 216060
cttcatccac tttccaactc gctgcctatc tggaacagat gcaatattta gtgccttgtg 216120
aaagatgctc ctagtgcacc tgctgcctgc tgcccctccc ccaggctgcc ctgggctctc 216180
cagagggggg tcctatggat gcttggccta gattctgagc cctgcttctt atatccagga 216240
cccctttccc agaggccagc tgcttgagta ccctggaagc cagtctgtag ccccaggcta 216300
gagctgggtc cctcccacag cccttcttta gcatgtttgt ttggactgac ttatttcata 216360
gagaggggtg tgtcttgccc aagcccatct ggcatgtctg aggcagctct ggggtcagaa 216420
tctgcagctc ccatccccca gccctgcaat actaggggag gctggatccc acatctctga 216480
agtcccacta ggctggtctg acagggctcc caagcgcagg gctgctctgc aggctgtggg 216540
gctcatgctc cagctccgag cccacctgat gtgcccgggt ggctcacctt tgggcctgtc 216600
ctgcctctca ggcattcagc tgacccggag ggactccccc atcttgacca ccagctgtgg 216660
gcttgagtta gaggttccca gaactttaga ccatttagcc caacccccta tttctcagct 216720
ggggaaactg agaccaaaga gggaagaaac tttctcaagt gcccccagca agtcagagga 216780
ggaaccaggt ataggagcct ctttccgaca gaggtcttcc ctgacccctg agccttcttc 216840
agtgcctcat tagcttccct gtaaggagac tgccccacag agcctggaaa tggtgctgtc 216900
ccgggcagtg tgtgcccatg actgcgcctg tgtttgtact tgtgagtgta tggccggggg 216960
gccgggggg tggtgcactg aagggtggga ataaacagca gggatactgg ggactggaat 217020
gcaccccact tgccccccaa aaaggggcga cggagcccag cccagcccag cacatgctta 217080
gactttccaa tctactgaat gtctgtgagg cctgctgggc tcaaaggaca aggaacaggc 217140
ctttcacccc caggtggcag gggtggccca ggatgggtgg aagcttctgc agcacggtca 217200
ggggtcacat cccagcccat gggctgacag ttaaacagag aagccgccac taggggtcag 217260
tcatgattca atgattctga tgaggagtgg gccccaccag cctctgccca gggttttgtc 217320
ttccaggcct tcttgggaag aattgttccc tgccagaaag ggctaataa tctgagagga 217380
agccatagct ggaattctaa actgtgtgag tgtgtgtcca gtttggaaag gtatatccaa 217440
tctaaaaatt tgtattgaaa aaatggaaag atatacctat tgttttggaa tacaaactac 217500
agaaagtaac agttaacaga atcttattgg aaagattaga ttctgcatct ggaaaggcag 217560
agtgattttt caactggggt gtatgtcctt aactgaggaa gggaacatga tatttatatt 217620
aaaaggcagc tatgattttc ttttttctga gacggagtct tgatctgtcg cccaggctgg 217680
agtgcagtgg catgatctca gctcactgct gcaacctcca cctcccgggt tcatgccatt 217740
ctcctacctc agcctcccga gtagctggga ctacaggcgc ctgctaccac gcccggttaa 217800
ttttttgtat ttttagtaga gacggggttt caccacatca gccaggatgg tctcgatctc 217860
ctgacctcgt gatccgcccg cctctgcctc ccaaagtgct gggattacaa gtgtgagcca 217920
ccgcgcctgg cctatgattt ttctttatgt agagaattta tcttttataa agagcttatt 217980

-continued acatactatt agtgcttctt caatcatgtg tattaatcac ctggattcct aggctttatt 218040
cccagagatt ctgatcctgt aagcctaggg tgggacccag aaatctgtac agggtgatac 218100
aggctgcccc aggaccacac ctaagaaaca ctgccactgg cccccacaca catccaagtc 218160
tccaaatatg taggcagggc acattctctc catagaacag atggggaacc tgaggtccag 218220
gatggtgaaa gaaatggcac agggtcaccc agctagtaga agagccacga tacacagact 218280
gcctgcagac accatctttg atgagagctc cacctcttta taggagtagt acaaactact 218340
ttctgtagtt tgtattccaa aatgatgggt atatctttcc attttttcaa tgtaaatttt 218400
tagattggat atgctttccc aaactggaca cacactcaca gtttagaatt ccagctatgg 218460
cttcctctca gattattagc tccttatata ttccctgact cctacctcct gcctccccta 218520
tggtgggtct ctatccaagg aagaggtagc cctggtcctc taggctgact ggggcttgga 218580
ggaaaagcct gggtgactgt aggagctaga agggcccttg gaattcaggt ggggaaactg 218640
aggccctgag aaggcagtcc tcacatttgc attctacctg gagaagggct gggtctcctt 218700
cctgagtggc aggcccaact tcaccagcct ggccctcagt caagctggct gtccaggccc 218760
ggcacacctc gggtgggtga ccagaggcag cggtgccata aaatgtgttt gctgggagat 218820 ccaccccaa agcacaaaac attccagggc tgctgatttg ggcaagcccc cttccttctc 218880
ggcccagtgt ccccatctct accaccgctg tgtgggaggg gacttctctc taaggctgag 218940
cagcagattc gctcccaagc gcctacaccg cccaggtggc cggctcctct gcacccacgc 219000
ttcaagaaag tcacctctta ggcaaggaag gagcctcggc cctgttggga gcgggagtcg 219060
gtatactccc agcctcccag actgctgggg atgacccgcg gtgcctgcaa agccggtgtc 219120
atccagccca ctgcccagcc cacagacact cgccctggag ggtggccctg gccctggcag 219180
cggctccgag aagaggcggc ccccactcca aacctggcag acccacccac gcaggcccgc 219240
ccccgctgcc tcagcgagtg ggctcagccc tgcccacgcc cccatctggc cgggacaatc 219300
tcgggccact cccccgggcg cagggcaccc tcccttccct cccacctgtg gccagtccag 219360
cccctttcag cccaacccag gcgcccctcc ctccttcccc gaaaagaact caccgcgccc 219420
gcaaagggcg accaggaaga aaaggaccag ggaaggcgcg cgcctcatgg ccggcggggc 219480
cgggtggcag ccgccgcgag ctccgctgtg gggtcacagg gcacccgtga gccgcgcggt 219540
cgagtgagcg ccggtcctgg cccccgaggt ttgctggcgg ggcggcgctc actaggaccc 219600
cgcggagagc cccgccgagc cccgcccact cagggatgta ctgggcccgc tgctccgccc 219660
cgacgccccc tgggtggtct ggaccccacc tgccgcctgg cttccctatc tcttcgggcc 219720
tcgcaacctt cccccaagga aggcaggcag gacagtgcgg gcacccttgg tacagctggg 219780
gagactgagc cctcgagggc ggcggacgct agcgcaggat ccctctactg ttggggaaag 219840
agcatgtgct tgagcgggga ggtccttggg ctttgccttc cctcacctcg aagacgcttt 219900
taggcaaatg agtcatctca ggttcattcg catggggttt gctgaaagaa aggacactgc 219960
tgggtgagcc gacgcgaggg agcgctgctc tctgcagact ttgcagggag gacacttagg 220020
aaaagtgagt ggaatctggg agggtgaata gctcagggcc cctcacccag cttgggggct 220080
ggggaaggag cagagttaaa agggaatggg gctggagtgg gctggcctcg tcctccccca 220140
tgggccttcc aatctgggct gaacagaggc cgctcaggtg attcaagcac atccctctac 220200
tagccagggt gtccttgacg cgtttttgga atcagtacca ttcccttgcg ggtgggggga 220260
cagcccccac ctcgggaact gcagcctcaa ttctggatct agaagggcct ctggcagctt 220320
ctccaactct ctcagtccgg tcctcatacc tgctcccttg tgtgggccct aacaggcaaa 220380
tctgacaact ggaggaacaa gacaggaagg gcggggtcta agggaaccgc ctgtaaaaag 220440
gcagctttgc caccttatct ccaggactct cagtcttgct ttcatattgc tccccccacg 220500
tcattttgct ataatctgac atgttgacat atggtcttta aaagcaacaa caacaacact 220560
gttgaagtga agcggacttc ccctttggga tgctttggag aagttaggat tgagggcatc 220620
ctctcttctc caaactgcag cagtaatagg taagatatgt aaagtaaata aagacatggc 220680
aaggctggaa aataggataa tcatctccat gaaccaaaac cagaaaagaa atgcaaagtg 220740
gttggaggct gaagagcctg gagcctgttg ggctttggaa accaaagaca gtggcaggtc 220800
ctttgggata agcggggacc aaaagactct tggctagaag ctgggagctt gggtgtatgc 220860
cagtacttga aaggatgctg ggagcgggag gcctgctgct gatccgtggt ctgtatccct 220920
ggctttatcg gatgtgtaca tccccaatat acccaggaca ggagcttgga aaggacataa 220980
aacctggagg ccactgcaga gctgtaaaag ttaggctagc aaaggggata cgatgaaata 221040
ggtttttata gagctttgac atgtattttc tttaaataaa aagaagagct aattatctat 221100
tgagaataat ataatcttgg tacaaaacta gaacaaggat gtacaaggaa aacacattat 221160
agaacaatct gaattatggg tctttgtcac agagagacag cacagagcag tggccagtgc 221220
attgcttctg gagccaggca tccggatttg tattctggtg ccactaatct tctctgtgac 221280
cttaggcaaa atgatttgcc ttcagtgtgc cttaacttcc tcatatataa agggggaaaa 221340
taaccttcac aataagcctt ttaggataaa atgaaataat tcatgtaaag taacttaaca 221400
atacccagaa cctagaaaac caaataaatg ttagctatta acttttatga acatggattc 221460
caaaatttta aataatacca agttgaatac agcaatgtac acacacacaa acaatgcatc 221520
atgatgaatt aggtttcatt acaataacgt aagggcagag tcaacatcag ataattcact 221580
attagcaagt taggtttttt ttttgagaca gggtttcact gttgcccagg cctgagtgga 221640
gtggtgggat cttggctcac tgcaaccttc acctcccagg cccaagcgat cttcccatct 221700
cagccttcca aagtgctggg attacaggca tgcaacacca tgcctggccc tatctttctt 221760
aatgtgtagc aattatcata attaatggta aaactttaga agcaatttcc atcaaagtta 221820
ggacgtaaac aagggtgctt tctatcactg tttcttttga acatggcact ggaggtccta 221880
ggcaatgtgt taggttaata catatgaaat tgccattttt ttaagattat gagatgccca 221940
acatcagaaa tgtatgtgat tcaacctata atagaaatga aggaaataaa attttaaaat 222000
tggaaagaaa aaactacctg tatttgcagg caggtatgat tgtctatgca gaaaatccaa 222060
aagaatatac agataaattg ttaagactag taagagttag caaggttgaa ttcaagatca 222120
tctttaaaaa agaaaaaacc tattagcatt cctatacatc agtaataaca aattagaaaa 222180
tgaaatagaa aaagagattc taggccgggc acggtggctc acgcctataa tcccaggcct 222240
ttgggaggct gaggcgggcg gatcacgatg tcaggagatc gagaccatcc tggctaacac 222300
ggtgaaacct cgtctctact aaaaatacaa aaaaaaaaaa aaaaaaaatt agctgggcat 222360
ggtggcgggt acctgtagtt ccagctactt gggaggctga ggcaggagaa tggtgtgaac 222420
ccaggaggca gagcttgcag tgagcggaga ttgcaccact gcactccagc ctgggtgaca 222480
gagcgagact ctgtctcaaa aaaaaaaaag attctattca caatagtaac aaaaacctta 222540
gaatatatct agcaaaatat acgtaaggcc tttcatgaag agtgttgcta tggtctgaat 222600
ctgtcttcca aaacacattt gttaaaattt aattgccaag ataatattaa gaggtagggc 222660
ctttaaggag tgattaagtc ataatggcaa gtcctcatag atgacattag tgtcttataa 222720

-continued aagggcttgt gtggggggtt tatctgttcc ttctgctgca tgagaacata gcatttgtcc 222780
cctccagagg agccagcatt caaggcacca tcttggaagc agataccagg ccctcactag 222840
acactgtacc tgctggtgcc ttgatcttgg acttcccaac ctccagaact gagaaaataa 222900
acttctgttg tttgtaaatt acccagtctc tggtattttg ttatagcact acaaaaggcc 222960
taagacaaat acaaaaatac tcaggaagag ctgactaaat tgaaatatag accatatata 223020
ttatgaatgg gaggactcaa tactataaac atattacttc tcaccaaatt aatctataaa 223080
ttcaagcaat tctcaaacaa atcccaatag attttttgt gaacttgaca ggctgattct 223140
aaaattcatg tagtaattga ggggccaaga acagtgtgca gacaccgctg gtgccctctc 223200
catacccctt ggcattgcca accacatata tgccagggag ctgatgcttt taagagcacc 223260
ctcagtgtat tcatcatgcc ttttcatttc ctgaatttcc tgatgttttg acagctgagg 223320
ccttgctgat cctggagaga ctgttcctcc cagggctagc caattccccg agacagtaag 223380
ggactcacct gcaaatgcac cttccatacg caaaccagcc aatccgaagc ccacaccccc 223440
agccacctcc ttcatcagac tgttatactg ggccattgtc cgtctaccct agtcatccca 223500
gggccatgaa ccagacaacc agggacagcc ctatgctctg gagccaagtg aaattattta 223560
aactattaat agctaatcct gtgcctgctt accctggctt gacttgcctt tctcttggat 223620
gccacaaata aagctcttgc ccacatttcc ccccagctcc ctttacttat tgaccaaccc 223680
tggtgcctcc ccatgtatcc ctgcctggca tgccatgtct cttgtttcta gggacctctg 223740
agtataaaaa actctacttc aggacagtca tttccatatc tgtgtgtctt gccatatcta 223800
atgaaaatct tgagtgcatt ttaaaacagc catgaagaaa gggagttggt ggataaatac 223860
cacagcttca ccacccctca gctggaataa ctgaagggcc cagtgagatt gagccccagt 223920
taccttttgt ggcaacctgc tcattaatgt accatctatt gactttcttc ccttccctat 223980
ctcacttctc accctcttac cttgcttcct ggaatcatct tctaaaaaaa tgcatgcacc 224040
caaatccttg actcaggctc tccttcaagc agaacccaaa tgaatatatt tttaaagaat 224100
aagaatgaca taggccgggc acggtggctt acccctgtaa tcccagcact ttgggaggct 224160
ggggcgggtg gataatgagg tcaagagatt gaaactatcc tggccaacat ggtgaaaccc 224220
tttctctact aaaaatataa aaaaattagc tgggtatggt ggcgcacacc tgtagtccca 224280
gctacttggg aggctgaggc aggagaatca cttgaacctg ggaggcagag attgcagtga 224340
gccaagattg tgccactgca ctccagcctg ggcgacagag tgagaccgtc tcaaaaaaaa 224400
aaaaaaaatg aatgacatag aggtcagtga gtaatggaag gtttaagatt tgtgtacata 224460
cgataatgtc ataggaatca ggacagttaa atgttgaggg ggatgtacaa attgaccact 224520
ggaagagaac gggagcccag caaaagatcc atgacacacg gaaacttgaa ataagacaga 224580
agttgccttg tagatcattg gggaaaggat ggatattcta aaaacgatgt tgggacaatt 224640
gattatccat atgggaagta aatacaacta gatccctagt tcacaccgta ccaaaaataa 224700
aatccaggtt cattaaagat ttagtttgaa aagcaaaact ttgaaagcat ttagaagcaa 224760
acataggagg atatcattat gactggggta gtgtcttagt gtgggctgct ctaacaaaat 224820
gccatagaat gggtggctta aacaacacac gttgatttct cccagttcta gaggctagat 224880
gtccaagatc agggtgccac catggtcggc tcttggtgag ggcccacctc ctggttcaca 224940
gagggccatc tttttgtatc ctcacatggc agagagcaag acagacagga ggcaactctc 225000
ctgcatctct tcttatgaag gtggtgatcc catcacgaga gctccaccct cctgacctaa 225060
ttactttcca aaggccccat ctcttaacac cattatattg gaggccagga tttcaacata 225120
taaatttaga ggggacacaa atattcaatc cataacaagt agaaagtaat ttcctaaaca 225180
aaatactgaa agtggctggg tgtggtggtt catacctgta ataccagcat tttgggaggc 225240
tgaagcagga ggattgcttg agcccaggag ttccagacca gcctgggtga cataacaaga 225300
ccccatctcc tctctctata taaaaaatta gctgggtgtg ctggtgtgtg tctgtagtcc 225360
tgtacttagg aggctgaggc gggaggatca ctggagccca ggagtttgag gctgcagtga 225420
gttgtgattg agccactgca ctcctgcctg ggcaacaaag tgggactgtc tcaggagaaa 225480
aaaatattaa aagcataagc tcaaaagaaa aatggtaata gatttgactt cactaaagta 225540
tttaaacttc tattcaacca aacataccac aaatgaagtt taaagagaaa ccgtagatta 225600
gaagatattt gcaattcata taatcaaagg atacatatct agaatattta aggaattata 225660
tatataaaca ttttatatat ataaacatta atattttaaa aagtcaacca accaaaagaa 225720
aagtgggcaa acaatatgaa catgtaattc atagaaaaga aaacttgaat gacctgcaaa 225780
cataggaaga ggtttaccat ggataggagt gaggggaatg gacacagaag tgataatgag 225840
atactagcat tcctatacat caataacaac aggttagaaa atgtattaga aagagattca 225900
gccgggtgca gtggctcacg cctgtaatcc cagcactttg ggaggccaag gcgggcagat 225960
cacaaggtca ggagatcgag accatcctgg ctaacatggt gaaaccccgt ctctactaaa 226020
aatccaaaaa aaaaaaaaaa aaaaattagc cgggcgtggt ggcaggcacc tgtagtccca 226080
gctacttggg aggctgaggc aggagaatgg catgaatcca ggaggcggag cttgcactga 226140
gccgacatca caccactgca ctccagcctg ggcaacagag cgagagactc catctcaaaa 226200
aaaaaaaaaa aaaaaaaaaa gagattctat tcacaatggc aacaaaaacc ttacgataaa 226260
tctagcaaaa tatacataag gcctttcatg aagagtattg ctatggtctg aatgtgtctc 226320
ccaaaattca aattaattgc caagatgata gtatgaagag gtagggcctt taagaaatga 226380
ttaagtcata agggcgagcc ctcgtggatg agattagtgc tttataaaag ggcgtggggg 226440
tggtagggcc gggcgaggtg gctcatgcct gtaatcccag cactttggaa ggcctaggcg 226500
ggtggatcac gaggtcagga gatcaagacc atcctggcta acgcagtgaa accctgtctc 226560
tactaaaaat acaaaaaatt agctgggtgt ggtggcaggc acctgtagtc ccagctactc 226620
aggaggctga ggcaggagaa tggcatgaac ctgagagacg gagcttgcag tgagccgaga 226680
tcacaccact gcactccagc ctgggcgaca gagcgagact tgcctcaaaa aaaaaaaaaa 226740
aaaggaaaaa gaaaaggcat gggggtgaat ctgttccttc tgctgcataa gaatatattc 226800
ttattgttgg ctgggcacag tggctcacac ctgtaatccc agcactttgg gaggccgagg 226860
cggatggatc acaaggtcaa gagttcgaga ccagcctggc caacatggtg aaaccctgta 226920
tctactaaaa atacaaaaat tagccaggtg tggtggcaga tgcctgtaat cccagctact 226980
caggaggctg aggcacagaa ttgcttgaac ccgggaggcg gaagttgcag tgagccaaga 227040
tcggcgccac tgcactccag cctgggcgac agagtgagac tctgtctcaa aaaaaaaaaa 227100
aaaaaaaaag tagatatctt attgttattt tgagacaggg tctcactctg ttgcccaggt 227160
tggaatacag tggcacaatc actgctcact gctgcatcaa cctcctaggc tcaagtgatc 227220
ctcccacctc agcctcccaa gtagctgaga ccacaaccat gccaccacac ctggctaatt 227280
tttgggattt tttgtagaga ccgggtccca ctatgttgcc caggctggtc tcaaactcgt 227340
gggctcaagc agtcctcctg ccttggcttc ccaaagtact gggattacaa gtgtgagcca 227400
ccgctcccgg cagttcatat tattttgaaa gccctataac agcaagtgct agtaaagatg 227460
tggaacagca ggagcactcg ccaactgctg ctggggatgt aaactggggc tgccagtttg 227520
gagagaaatt gataatgtat tgtaaagtca aagatgcttc cgtccaatgc ctagcccttc 227580
catttctcgg tgtgtacccc agagacactc atttatatga taatgctcat agtcaccctt 227640
gtgtagtgag aattggaaac cacttagatg tccatcaaca agaacacgga ggaatgaact 227700
gtgggatact cacataatac aatatgatct ggagctgggg ccagcaaact accgcccatc 227760
tgccaaatct ggagctaaga agaatggttt ttataacatt aaagcactat aaaaaacaaa 227820
acaaaataaa acaatgcaaa gcaaagactg caacagagac catatgttgc ctgcaaagcc 227880
taaaatatct gctatatggc tttttacaca aaaagtttgc tgacccttga tctaaagtca 227940
caattattaa caaaaatctt taaaaaatgt taagcaaaaa agttttgaat atgtacaaat 228000
cacatataac atacgtggac atatacatat tagctaacat ttaaaaacat gtttaaagat 228060
acccacgtaa gtagcagaag aataaaattg cacgagtgat aaactctaaa ttcagagaag 228120
tggttacctc tggggatggg aagaaaaata atcatggggg gaggttctgg gggttttgtt 228180
tcataaataa atttgcttta gttcataaaa tgaaaaaaga aggtctgaag caaatatgac 228240
tacatatgag tatgtttgaa caactccgga taatggttcc caggtgtttg ttatgtgggt 228300
tcctatagat ttatgtatgt ttgaaatatt ttatcaattt tgtttttttt aaaggagtgc 228360
cttttcatga gtgtgcccag gaggaggatg gctgtggaca tgggcaggcg ccctccctgc 228420
tgtgcacccg gtcccttgtc tggcctagcc aggccccagc tgcaggctga gcaattgtcc 228480
ataggccaga gagactgaca tcctggcctg gggttctgcc cgtgactgtc gtgtgccctt 228540
cttacagttg ctttggcagt gggtgagcct agttggctcc actagctgag gcccaggctg 228600
cagtggtgct ggccagagag gatggagtta gcagcctggg acctgccaca aatgacagca 228660
ggagtcagag cccaacttcc ccatctgtgg agtgagatga tagatctcat ggtgtccaag 228720
gattcatcca gctctgtttt cctgggccca gggtttgtcc taagacctgt agctgatgcc 228780
ttgggctcca gactctctaa ttaaggaagt aagagccaag cagaagttgg tcttcacatt 228840
cctggctttt cacccccaac ctgaactgcc tttctctggc ttccccatca gtgctggtgc 228900
cccttgagga gaagccttac agaggaagag ttggccaaaa ggggcattta tgtgtgattt 228960
ggaaggcaga aggaaagagg cagccattgc tgtctgaagg tggccgtggc cgcaagtggt 229020
gtcactggcc aggtctaggt ccattctgcc ggtgtacagc aagtcaatca ctgtgacaca 229080
ggtcctgatt tatgcacaag gccaccaaac gaggaggggg aagaacagct ctcaaatcca 229140
cctctgcaga gataaggctt agggttgctt atgggctagg gaagtgtgat ggtctaagat 229200
gtggggagag gtgattggca gcggggaaaa atgaagtcat aggtttgttt cgtgcaagtg 229260
tagtcgggct ttgtgagatt tcatagggcg taagtgcaga aaatgatggc attagcatga 229320
tctgaaggtg gagtatttgg ccctctgaca tcaaaatgga ccttttctcg ggcattggca 229380
caggtccagt tgaagggtca gtgatctcaa ccagtttgaa ctggacagga gctggcccaa 229440
gttcctgaaa aacagctgaa gcaaccatga ccatggcaac ctatgactct gatctataaa 229500
gcagccagtg atctataaag cagccagtga aggttgaggt tcagccttca gtggactaag 229560
gcctcagggt tcatggataa aacaaaaaca aaacaaaaag caagcggcca aaagcaagca 229620
gggtggcagg cagacctgat caaattcacc ccttggtttc agcagtgaca gatgtagtgg 229680
tgctggcaaa tgccagcttg tcctcactct gccctgagtc cagctcttct ccccgactgc 229740
tgaccatatg acctgcactg accctaagtc taccataggc attttgtgca gatccacaga 229800
tgtgggagct ctgcaaggca cagctgccca gagacctctc cagggccttg cccttggtgg 229860
tcccaccaga agctggacat gtttcagctt ctcagattga ccgagaagtg gaccccttct 229920
ctgactctcc agctccctcc ccacacctct acttcccagc cctccacaa tcatgtaagg 229980
tctaattgtg caataaatcc cttagcccat aactcacatg gttctgtttc ttccctgact 230040
gaatcctgac acttccatca aggagggtgt aagcggcaag tgctctctga gccctgggaa 230100
cacaagtgaa ccaggatgcc cccaccctgg gtagccttcc tttctttagc agctccagaa 230160
gaaggcctgc ttccttcagc cccttagcag aacttttctt gaaaagggtt gcatctgccc 230220
cacacgagcc caaaagggct gcagggacag ggcagggtct tggatcctca tctcttagga 230280
caggtggtga ggaagccaca atatacctgg tagctacttg gtgctagata cttcatcatt 230340
ttgtcctcac aagaagctac tgccccatct tccagtgaga aagctgacag ggaaggagtt 230400
tggtgaagct ggagtttgaa cctgtgatta ccaagcagca aaatccacag gtccttcact 230460
tgtaacttgc ccacagctgc agcaggaggt ggagcagtaa ttcctgcctg tatctggcct 230520
ctgctgggtc atggggccat agtctcccag gccctgctgc tctctgctct tccccttcc 230580
acctgtgtgc ctcagtgtgc ctcaaggctg aacctcaacc ttcgctggct gctttataga 230640
tcactggctg ctttatagat cagagtcata ggttgccatg tctgaggcac acagcagctg 230700
aggccacaga gccagtagca ttggtggctc tgccagtggg gcctgaggac atgggtcagg 230760
gctgactcag acatgaggcc ttgtggagtg cagccactca gcctgaaggg cttgagacaa 230820
ggaacagctg gttcccaccc ctctggccag caccatctga ggcctcatca tctgggctgg 230880
tggtatctca gtgcctgctg ctggcctgat accttgctca gtctcagaga atcctctctt 230940
catgcagcag attggagtga gtttcctcca cggcacttcc ggcctggtga ctccacgact 231000
ttccatctat agatggtaat gaaggtagtg agctcaacag acaagggtac ccattttggt 231060
tctgccattt tggagctcca taaccctgga ctagctactt tctccttttc ctcatctata 231120
acggctgtcc tgatgcttca acaaggtaat gtgggtagag catgtcgcag tgatttggca 231180
ctcaataaat gctcagaaat gatggcggca ctaggggtgg tggtggaatg ggagaaatta 231240
taaaaactta tggttggatt gacttggcct caaatctgtt tggccactta gcagctgtgg 231300
tgggcaagtt atctcacatt tttgaggctt gctttttcca tctataaaaa gagggtgata 231360
gttgtcaccc cgctcatagg gttggtctga ggcttaaatg ggataatgaa agcctcagca 231420
gatagcacac caccccttcc ttctcttttc tcctatctcc tttataacag atgggaattc 231480
agtaggtgct taatagtggc atgatccttt gacaatgtaa tcctgactgt tgcttcctca 231540
atcagtcata actaatgatg tgtacttcca tctgaaagtt ctgagggagg caggacatta 231600
agctgtttca aattctggct ttaagtctaa agggttcact ctaccttgtc ctgaatcatc 231660
tcctccctcc ttcctgctaa tcagaagcat ctgggctttc aggacttatc ttggaaaagc 231720
cggccctgat tcctctcaat ctttatggac ctcctcattg aaggacctcc ttactccata 231780
tttgattctc catagcttgc ctcacctggc tccccagctg tccactgaca gccaggcaaa 231840
ggctggcagt gctggcggaa aacctgctgg gtgtttttct tccctttgt gactgtgacc 231900
actgcagaga tattcaaacc tcctagctgc aagaatgcag ttagctgcct gcctccagtg 231960
gctagcatct tcaggcttta cctcagcttt tgaggtagag gccacacttt tcctggcaag 232020
cccccaaacc aactactgag cacagcgaga gtcctagggc ctgccatttt tgctcaactc 232080
aaactccaag tcctcctgtt gcgggggctg aaactttgtt agatctggca tggcaatctg 232140
aagtcttccc ctgcccaatc cagctacctc ctcctcttat catttacagt aattactggt 232200
ccccactgaa ccctctccca ttcttaacta catctcagca tctgctgtcc agagcactta 232260
ccatctccag caccatggaa gggatgggtt gcaatgggct ccaggatgaa aggctgtgca 232320
gaggaagctc aatggcttca aggactccag accctcaggg gctaaaaagg gacctgagaa 232380
cctgtctctt ccaattcccc ctttcacttg ttcacatagc ataaagaccc agatctgtgc 232440
caggccatgt gcttcaggga tggatgaagc caggatccct cctctggatg aacttaccag 232500
ggagagaaga agcctaatgc tctgtaccag ggttttggca cgttgctggg aaagcctaat 232560
actcaaagag aattgaggta acattgctgg gtgctccacg taagggcaga tgttgatttt 232620
taagtctgcc ctgatggggt ctgatttcct tctgtttcct ttgttggaag tattttcaat 232680
ggagacacct taaacaataa caatgaccgc aaagaacatg cattcagtgc tttcccatct 232740
gctgagcact atgctaagtg tatcaggtaa agcctggatt aggagagact gcagaggtga 232800
gtcacagcat catgtgtcct gggcttgcaa tctgcagctt cctagctgtg taaccctggg 232860
caaactcttt aacctctctg tgcctcatgt ttttcatctg ttaagtaggg agatcaagag 232920
tatcttccgt gtacgtgctg tgaaaaatag gcaatgtgaa atccagacag gcagattccg 232980
gagtccagat catccctata ctgtctgtaa ctacagcact catctaaggt ctggtgaaag 233040
agctttttta aaaaaacttt taattgagat atatgtatag aatagttcac aaataaatgt 233100
tcagctaaat gaattttcac aaactgaaca cacctgtgta accagcatcc agctcaagac 233160
acagacatta ccagcaccct aaaagacccc ctgtacttcc tccaggtccc caccctccca 233220
aatggagcca ctgttctaat ttctaaatgg tatagattta tttcacctgg ttttaagagt 233280
ttccccccac cccaacttta tggacggata actggagtac aatcaactgc acattttaaa 233340
aatgtacaac ttgattagtg ttgtttgtgt tcactcatga agccaaaatt cagacagcaa 233400
acatttccat aatcccccaa agtttctcta tgcccctttg tcatccaccg ctccctccaa 233460
tcctgtccca ggctgatctg ctttctgtct ctatagatta gtttgcactt tctagaattt 233520
tgtatgaaca caattataca gtacataatt tttttttttt gagagtgaga cttgctctgt 233580
cacctagact ggagtgcagt ggcgtgatca tggctcactg cagcctcaac ccccaggctc 233640
aagcgatcct cccccacctc ccagcctccc tatcctagca gctgggacta cagctgcaca 233700
ccaccacacc tggctaattt tgtgtatata tacgttacat atctatatat atctatatat 233760
ctatatctat atatatctat atctatatat atctatatat ctatatctat atatatctca 233820
catataatta catatgtata taaaatagaa aaaattagcc ggatgaggtg gtacttacct 233880
attggtccca gccacttggg aggctgaggt aggaggatcg cttgatccag gggaggtcaa 233940
ggctgcagtg agccacgatg gtgctaccac actccagctc gagcaacaga gcgagaccct 234000
gtttcaaaaa caaaacaaaa attgttttag ttactctagg tcctgtccat tttcatatgc 234060
attttaaaac caacttttca aattctgaaa aaaagaaaca caacaatgtc tgctgaaaat 234120
tttggttgga attacattga gtatatagac aaactgggaa agaattatca tattgggcaa 234180
ttttgtgtct cccaatacaa aacatggcat atctctccat ttatttagtt cctcttcaat 234240
ttcacagtgt tctatagtgt tcagtgtaga ggtttgatag atttattttt aggtatttta 234300
taaaattttt ggtgccactc taaatgagat tttcaaaatt tcactttcaa attgtttgct 234360
ccgacataca gttagaagga ataaattcaa gactgggtgt gataactcac acctgtaatc 234420
ccagcacttt gggaggccaa ggcagccgga tcacttgagg tcaggagttt gagaccagcc 234480
tggccaacat ggtgaaaccc catctctact aaaaatacaa aattatctgg gcatggtggc 234540
acgtacctgt agtcccagct acttgggagg ctgaggcagg agaattgctt gaacccggga 234600
ggtggaggtt gcagtgagct gagactgcac cactgcactc cagcctgggc aagagagtaa 234660
gtctctgtct caaaaaaaaa aaaaaaaaag gaataaattc aatgattgat agcatagtag 234720
ggtgactagg gttaaacaaa aatgttctac actcatgaga tggacagcct aaatactgac 234780
ttgatcacta tgcattatat acacgtaaca aaatttcaca catgccccat aaatttgtgc 234840
aagtaagtaa ataaaaatca cttgtagaat aaagtaacac aaagcaaaaa aaaaaatttg 234900
ctgctaaaaa cttttatgat gaactctcct tcgtttcaca acagggatgt tgggagcacc 234960
cagatataca gggaattcct gcagcactca ttggcaaacg ctgtagaaga taagatgtca 235020
aaaagctgaa agaagagcag aatgactaat aagactccag agacgggcat aaaaacctcc 235080
cttcttctga ttcccttaat tatacctctc actttccaac acggggtttg ggttgctctg 235140
gtggtgagag ttggggcaga tcctgcagtg ggaaaagatc gaaggccctg ggccctctta 235200
ttctacattc tctccctagc acacctgcat gcatagctta caatatcttc tgtacattgg 235260
agaccaggca tctgccctaa gttccaggca tgtatctctc ataagccctt aaactcagct 235320
tctctagaat gaaactcaca atcttccctc caattgtttt tcttttcttc tttttttttt 235380
ttggagacag tttctgtcac ccaggctgga gtgcagtggt acaaccctgg ctcactgtaa 235440
cctctgcctc ctaggttcaa gtgcttctcc tgcctcagcc tcctgagtag ctggggttac 235500
aggcacatgc ccccacgact ggctaatttt tgtattttta gtggagacca tgttggccag 235560
gctggtctca aagtcctgac ttcaagtgat ctgctcacct tggcctccca aagtgctggg 235620
attacaggca tgagccactg cggccagcct caaacctgtt tcttacccaa tgtttccttt 235680
actgtaaatg gcaacctcct ccaccagctg cacaacacct aataggaata gtagtgaata 235740
tccagtaaat atttgttgta tggatgagtg aatgaagatt ggtagcatag aaagtgaatt 235800
tactctatat aagttttgaa gaaagttaac tcctttgagc tggcttggga tgtctcatgc 235860
ctgttcccat aatgctagag gcatatttat ttatttattt atttatgaga cggagtctca 235920
ctctgtcacc caggctggag tgcagtggca cgatctcggc tcactgcaag ctcagcctcc 235980
cgggttcacg ccattctcct gcctcagcct cccaagtagc tgggactaca ggcactcccc 236040
accacgcccg gcaatttttt gtatttttag tagagacagg gtttcactgt gttagccagg 236100
atagtcttga tctcctgccc tcatgatctg cccgcctcgg cctcccaaag tgctggaatt 236160
acaggcctga gccaccgcgc ctggctgagg catcataatt taaataaagt tccatcagac 236220
tctgtatcag agcaggtcct ttctcctgtg ttgctctggg acctcactga gaccacagct 236280
acaagcaggg aagagggtgg ggcacttttg attctgggga cacatatatc attattcctc 236340
acaatgactg tctcttgttt ctcttttttt tttttttttt tttttgagaa ggagtctcac 236400
tgttgcccag gctggagtac agtggcatga tctcagctca ctgcaatctc tgcctcctgg 236460
gttcaagata ttttcctgtc tcagcctccc gagtagctga gattacaggt gcctgccacc 236520
atgcctggct aatttttgta tttttagtag agatggggtt tcaccatgtt ggccaggctg 236580
gtcttgaact cctgacctca ggtgatccac tcaccttggc cttcccaagt gctgggatta 236640
caggtgtgag ccaccacgcc tagcctcttg tttatttcta tatcacctgg gccttggctc 236700
agtcctagaa cgcagagata ataaatgttt gaatgaatga atgaatgaaa taactccatt 236760
gtctaagtac tatttgtccc tttttataga taagaaatct ggggctcaga gactgccctc 236820
cctaggaagc agcaacaacc gggggacaaa cccagtcctc ttggtcccca gatcagtgat 236880
tcctctactg catcaagaaa gttgtaatta cttgcccttg gtgtcttgga aaaaaagaaa 236940
aaagaaagtt gtaataacta agtacagatt tcatttcatc ttctttccaa ctaatagttc 237000
ttaagtgctt cctgcatacc aggatgaagc tatcaatgtc ctcttgaaag cacagctaca 237060
agattttgaa gagggggaaa aaaaagcctt tctgctaggc cctgacctga accaattctt 237120
ggttatctaa agcagtggcc tccaaataaa aattcccaag accctccccc agaaattcta 237180
attcatgcat ctgaaggaga ggagatgcct gaaaacctct gttataaaca ctgctctggg 237240
ctgatgtggt atataggcca gctgctgcac acagttcagc aggaaggcag cagaaaggag 237300
ggtgaagagt aagcatcttt attactttat tcacatacat taactgagca tgtactatgt 237360
cccagtcact gttctaagtc ctagggatac agtagtggac aaaacaaaat ccttattctc 237420
cctcattcta tgggtggtgg gggtgtaaga tggggagaca atgaccaagt aaagaaatag 237480
ggccaggtga gggtggctca tgcctggagt cccagcactt tgggagcctg aagcaggtgg 237540
gtcatttcag cccaggagtt tgagaccagc ctgggcaaca tggttaaacc ccatctcttc 237600
caaaacaaac aaacaaacgc tagctgggta tgatggttca tgcctgtagt cccagctact 237660
caggaggctg aggtgggagg atcacttgag actgggaggc agaggtgagc tgaggtcacg 237720
ccactgcact ccagcctggg caacagagaa agaccgtgtc tcaaaaagaa agaaagaaaa 237780
agaaacatac aggataactg ctgcttgtgg tggtgaaggc tctagagaaa acaaaacaga 237840
gtgatgtgct gcagggtgac agagaagggg taccctagct ctctgaggag gtgacatttg 237900
agacctgaat gaccagaagg aaccaaccct actctgggag aagaatatta taggcagaca 237960
gagtaggaga tggcaaagtc acagagggac agtcttggca tgtgaggctg atgttgtgtg 238020
aacaaggaga acagcctaaa atatggttag acagagatag tgaggcagga atcatcattt 238080
aaggtcttca aattaggaaa agggtttagt ttcttctgga gagttttaag cagggagtga 238140
tgtgacatga ttgctttaat tggcttgttt tagctgctgg atgaagacaa gagtctaggg 238200
gttcaatgtg ggagcaggga accagtgagg aggctcacag gagtccaagc tagagatgat 238260
gatgggtgcg gtggctcatg cctgtaatcc cagcagtttg ggagggtgag gcaggtggat 238320
cacttgaggc caggagttca agaccagcct ggccaacatg gtgaaacccc ttctctacta 238380
ataatacaaa aattagccag gcgtgttggt gtgcacctgt aatcccagct actcaggagg 238440
ctaaggcaga aaaattgctt gaacctggaa ggcagaagct gtagtgagtc gagatcacgc 238500
cactgcactc cagcctgagc aacagagcaa gactccgtct taaaaaaaaa aaaaaagtga 238560
atataaatat gactacaaaa ctgcctgtga gctgctactc tgggcacact gcctatgggg 238620
tagccctgtc ccacaaggag cagtccctct gctgttgcag tacactgcag cttcaataaa 238680
agttgctaac agcactggct cacccttaaa ttgtttcctg ggagaagcca aaaaccctcc 238740
tgggctaagc cccgattctg gggctcacct gccctgcatc aatattctcc tttctagtaa 238800
aaacctacta tgacgtggca ctcttctgga catttgataa acttacctct gctttcccat 238860
caggtctgtg aggtggtgta gttcttgcca tttgacaggt aagtcggcag aggctcatag 238920
agggccccac gtcacagtcc ctgtaagggt cagtgcgacg actggaaccc aagtgtgtgt 238980
cacactgacc tcatgcttgt ccatcactcc acacagcctt cgatgcagga aataggctgg 239040
tttctgatgc acctggtgtc tgagagaagc tttggttctt tcacttttca gctttgccct 239100
ggcctgggcc caggccctac tcccgaggtc aggcttgtcc caagagaggc ggggctaggg 239160
tgggtaatta tctcagcggt tgctgtgagc tccatccagc tcaggtgagt cttgggatcc 239220
tggcttctca aactttcacg tgcacacaat tgcctgggga tttgattgaa acgcagtttc 239280
tgactcagca ggacaagggt ggggtccaca tttctttctt tcctctcttt ctctcttctt 239340
ccaaaatctt tttaataaga gggtaggcgc cagggttagt ttttgtagtc tcggctggcc 239400
ctttgacctc tggcgcgctt gaacttccgg cccttggagc ggacgtaggc tttggtgtgg 239460
ctgtgcggcg ttcctggggc cttgccgaaa tgccggtaca cctcttggcc cttgagagaa 239520
ccaaagagcg gaatggtgct gctgcccttg ggggagtcca gggccagctg gtcaaaagtg 239580
aggatcttgc cccctgcccc gccctgagga tgcggcggca gcccggctgg tcacacacag 239640
tgcacacacc ttcaggttga gaacctcctg aacccgcaca tcatccatta tggtccccaa 239700
gaccacggcc attttgtttt cccggccagg aagcttcatc ttccggatca tctgagcaac 239760
agagtgaccg gttggtgcga ctcataaaca gcctcttcag tacaacctgg ttgaatatgg 239820
agttgatttg tctggccaga aagctgtaca gcttgaccaa cagcctcagg tagatatccc 239880
ggctcttggg ctccttgcgc ggaacgtttt ttggtccttg ttggggcgga tgtcaactcc 239940
catgatggcg cctcctgctc ggccagttcc ggaaagccag gtttctaatt tctaacaagc 240000
cccgggtgat gttgttacca aggtccacct gccacagttt atagagggcc gtggaggtgg 240060
gagtggggtg gggtaggcag aggagagaaa caggaggttg cagttgggac agctgtgctc 240120
atcctcactt gtaactgact ctcgtaaatt gtcatttaac ttctcaacac ccaccctcct 240180
ccctcatcaa tatgataaag aaagaacatc agaacatctg tgttcttggt ctcccaggaa 240240
agcccaccca gtcaggaccc caggatgtgg caggcaagtc cctccctccc cctgaagccc 240300
cagtgactcc agctctaggt gcttatgctg gggtgggggc aggacactgt gaatctgcag 240360
ctgctcccca cattgttgag gggagcgcat agtatgtggg gagaggtgag gagaggactt 240420
tcctcttcct agaacttctg gtctggtccc cagggcacag gtgttaatga agaaggagga 240480
atggcctctt cctaatgggc ctttcaaggc ctgccagagc cagcagggtg ggcaggggac 240540
agggaggaac ttgtgcttcc cggcagggac aggaacccgc tggatgcacc gctttgacct 240600
tggctcattg taaacatgct ctaatgtggg gcgttgaagc caagagatgg gacaattatc 240660
attgcaaggg aagttatctt aaagttaatt tataaattcc agtcaaggtc ctaaaggaat 240720
tgttagaagg gagggtggta gtgaacttgg taaattcact ttaaaatcac tggtaaatgg 240780
agagaaaaat caagtaaata ctgaaagaaa aaaagaatgt agggggctat aacagttata 240840
aaagatatac caatgtcatg tagtagaaag cccagaagtc ccacgtatac tttaaatatt 240900
tagcaaatga cacatttggc atttcaaaat ggagaggaaa taaatatggc tgaaaaaatt 240960
aaggatttga tctttcttca aaccgcatgc taacataaat tccaaatggg acaaatagtt 241020
aaatataaac aaggaaaata gaatgaaata gaagaaaaca tttatataat gtcaacgtga 241080
gggaggccat cctaagttta acatggaaat agaaaccata aaggaaagat tggaaacgtg 241140
actgcaaaaa gatttatgat ataaaaatgt cataaaatta ataagcaaat aaatcaggag 241200
aatttaatgt atgtcagaca gggagttaat atcggtacaa atcaatagga aaaagacata 241260
ttcccaatag gaatgggcac agggcatgaa tatgtagttt aaaaataagt agatatggct 241320
gggcgtggtg gctcatgcct gtaatcccag cactttgggg ggctgaggtg ggcagaccac 241380
ctgaggtcag gagttcaagg ccagcctggc caacatggtg aaaccccatc tctactaaaa 241440
atagaaaact tagccaggca tggtggcagg cacctgtagt cccagctact caggaggctg 241500
aggcaggaca atctcttgaa cctgggaggc ggaggttgca gtgagccgag atcacgccac 241560
tgcactccag cctgggtgac agagcaagac tctatctcaa aaaataaaaa agtagaaatg 241620
accagtaaat atatgaaaca actgtaacca tgagaacaat aaaagaaatg tggccaaacg 241680
cagtgactca cgcctgtaat cccagcactt tgggaggccg aggtatgagg attgcttgga 241740
gctagcagtc cagcaccagc ctgggcggca aagtgaaacc ccatacctac aaaaaaaaaa 241800
aaaaaaattt tttttttttt gagacagttt cactctgtca cccaggctag agtgcagtgc 241860
cgcgatcatg gctcactgaa acctctgcct cccaggctca agcgatcctt ctgcctcagc 241920
ctcccaggta gctgggacta caggtgcaca tcaccacaac cagctaattt ttgtattttg 241980
tgtattcacc atgtggttcg tgctggtctt aaagttctgg acttaagctg cctgcctcag 242040
cctttcaaag ggtttggatt acaggcatga gccactgcaa caacaacaac aaaaaactct 242100
caagtttttt ttattttttt taattagctg ggcatggtga tgcacacctg tagttccagc 242160
tactccagag actgaggcag aaagattgcc tgaatccagg cttcagtgag ctatgattga 242220
gacactgcat tcctgcctgg gtgaccaagc gagaccctgt cttaaaaagg gaggaggaag 242280
aggaggagag gactaaaacc acaagacacc tctttttcct gctgaattgg cagagataaa 242340
aaagatataa tgacagctgg acagggaaga gtttgagtaa acagacactt atccactgct 242400
ggggctgtaa actggaacaa ctgttctgta gggccaaagc cctaaaaatg ccccatctgt 242460
ttgtaccaga acttttattt ctagaaatag atcctgaaga aataatcaga tgtgcaaaat 242520
gaatgcatca atatgcatca cagtcgcact cacacatgga atattgaaac tgcctaaatg 242580
tgcacccatg aatccaaaca actttcttct tgctcaccca tcagtcaccc aagtccttca 242640
gtcaagtttt aaaaaccaaa gcacctgtga tttagcctaa ggagctttgc cccccttgtgc 242700
tgcacagggc agggccagat tgagctcttt gcagtggagc agaaagtccc atccagcact 242760
agagaagtga gtagctactg aggatttaac ttgtgctttg tttcttggtg tccagaagga 242820
atagaaagca ttttctgtct ccctagggac ctgtttttgt ctctaaaacc tggcttctta 242880
ccactcttgg gccctcaaag cctgacatgg ttggatccac ccctcacctc ctcccctgct 242940
caccacctag gaagcctctt cttagctcca gccacgcagg tcttctttca gctcttcaaa 243000
ctcatcatgc cctctctggc cacacagtct ttgcacatgc tgttcccttt gcccagaact 243060
tctcccattc tctcctgcct ggttacttct gaacttgaac gtccctgtct caggaggcta 243120
tccttggcct aagtttttat aggttccttt tgcgctctgc attctaccta caatttcaca 243180
ttaatttatg caagtgtttt gtttctgtct ctctctccca agattctcag caccatgtgg 243240
cagttgtatg tagctccagt atccacacgg tgcatgacac atggctgggc ttcaacacgg 243300
ctaacccatg gctctaggag attttctttt attatttctt tggtaacccc ttgccctttg 243360
ttttctctgt tctctttctg gagtgtcaac tggttggttg aacttgaatc agtccttgaa 243420
gtattttatt tctcctcttg tatttttttt tctttttttat gttttgtctg cattctagac 243480
attccatcaa ttttatttc caagccatct agcaagtttt attttggtaa ccatattttt 243540
aattgtaaaa agttacttct tttttgagat ggagtctcac tctgtcgcct aggttggagt 243600
gcagtggcgt gatctcagct cactgcaacc tctgcctccc aggtccaagc ggttcttgtg 243660
cctcagcctc ccgtgtagct gggattacag gcacaccact gcatctggct aatttttgca 243720
tttttggtag agacggggtt tcaccatgtt ggcctggctg gtctcaaact cctgacctca 243780
ggtgatctgc tcacctcggc ctcccaaagt gctgggagta caggcatgag ccactgtgcc 243840
tggccaaaaa gttacttctt ttatgtttgc acacacatgt tcacagcagc attattcaca 243900
atagccaaaa ggtggaaaca actcaagtgt ccatagacag atgaatggat aaacaaaatt 243960
tggtatatcc atacaatgga ctattattca gccttaaaaa ggaaggtaat tctgacacat 244020
gctacattag tgaaccttga agacattatg catgtgaagt aagccagtaa caaaggacaa 244080
ttattgtatg atttcactca tatgagatac ttagagtagt caaattcatg gagacagaaa 244140
gtagaatggt ggttgccagg atcggggcca gccagggatg gggaattttt gcttcatggg 244200
tacagagttt cagttttgca agataaaaaa gtgttctgga gatggttgtt gatgacggtt 244260
ttagaacaat gtgaatatcc ttaatgccac tgatgtggtt agactttgtg tccccactca 244320
atctcatctt gaattataat ccccaggtgt ttaggaaaag acctggtggg cagtgactgg 244380
agtatggggg cagttttccc tatgggggca gttttcccca tgctgttctc ttaatagtga 244440
atgacttctc acccgatctg atggttttat aactggtagt ttttcctgca ctgacgcata 244500
ctctctcctg ccctcacgtg aagaaggttc ttgcttcccc ttctcctgcc atgattgaag 244560
tttcctgagg cctccccagc catgtgtaac tgtgagtcaa tttaacctct ttcctttgta 244620
aattacctag tttcgggtag tatctttata gcagcgtgaa aacagactaa tacagccacg 244680
gaactgtaca tttaaaaaag gttaaaatgg tgaattttat attatgtatt tgccacaatc 244740
tttaaaaaga taattgtttc tctgttcctt tttttttaa tatcttgggt gtgttttttt 244800
taagttgtat ttccttgagc tttcctgaga atacacgttt tctttatttc tttttaatct 244860
tttattctct gaaggttctc taaggacttc tttggctctt tctccttcac tttggaagct 244920
tttctaaaat atatggggct acctggtgtc cttccatatc taaaggaact ttgtgcacag 244980
gccaaagggg gttatgtgca cgcgggcaga gcttagagtg ggaaccagtc attacactca 245040
tggaccccta aatgccgcca taagggggct tcctcaaggg tgccgaccac tacactagca 245100
gcacctatct caccaggcag tatacacagt tctctttaga gacagtctct gatttttttc 245160
cttggggtaa gtgcctggct gaacccatga cttgggggaa agggcattaa ctgtccctac 245220
ctggatcttc gtttattctg cctgttccag ccccatttc actttgccct ctgtgatacc 245280
tgcgctggag cctggaggct ccctcaggtt ctcataggca gatggctcag ccccgctgca 245340
ccccagcccc tctaatctac cccacaggtc tctaactcct tttcattttc cagatgaaat 245400
cacttgtctg ctaatgacta acgactttct tccatcctct ttgtttcttt ttttcttttt 245460
ttttttttt tttttttggt tgaggaagag tcttgctgtg tcgcccagac tggagtgcaa 245520
tggtgcaatc tctgctcact ataacctccg cctcccgggt tcaagcaatt cttctgcctc 245580
agcctccaga gtagatggga ttataggcac acaccaccat gcccagctaa tttttgtatt 245640
tttagtagag atggggtttc gccatgttgg ccaggccggt ctcaaactcc tgacctcagg 245700
tgatctgctc acctcggcct cccaaagtgc tgggattaca ggtgtgagcc accgcattca 245760
gcctgtcatg tttgttgttg tggcttagac tgtttaaaac actggtccat cagttgaatg 245820
gaaggagagg atataaatgt gccttctcag tccccatctt gaatcccatt cattcccaca 245880
gctgctgccc taactcagcc tcatttttct acctgagata ttgtggctct gccacctcca 245940
gccccttcgt ccccagcaca tgctgcgaca gccagggtga ccttccaaaa gcaggaatct 246000
gagtgtagat ccctgtttga actcctcagt tgacctttag aaccagcagg atcaaatctt 246060
ccatgacatt caaggccttt cgtgagctgg actctgcctg tatctctagc ctcatctctt 246120
tgtagtttct cagtgagctg tgctcttaga tgcctcctaa tgttagctca tgctggcccc 246180
tggcctggaa cactcttttc ccccttctat tcttagatgg cttgaatccg tctgctggag 246240
gaaggaatac ttatgcccct actcttgttt tttccttgca cgtggaggga aatcatcagg 246300
gtaactctcc tggactccca tttccgcacc acccacctcc ctgcaggagc tccagcattg 246360
cctcctccag acagccctgt gtgattgtcc agtctggggc aggttcctct tctgtccttt 246420
acagtctccg atatacttaa cacactaaat ggccagggcc tgaagagagg cagagcagaa 246480
caagtcatgt ttggtggctc ctatctgcac agcccacatc cacgtcttgg ggtacagcag 246540
gaatctaagc ccctctggct aagctgttcc catgccattc agcatggagg cagcagtgcc 246600
tgtcactagg caggagctaa gttctgcatc ctcctggctt actccctccc tcctctacta 246660
gttttggtta ccgggattcc ttcatagcag cctccctctc aggttagcct ttgtccccaa 246720
tccagatgcc tatagagtca catcaccatg ggagggtatg attatgattc cccaaaactg 246780
accctgccct agaagccaag tgaattgtgc agtatgagtc ctgaagctcc ttttgggttc 246840
actctccaac taactccatg tctttttag ggaatggttt ttgtgacctt gtctgtaagc 246900
gctggaggtg tacgcatgcc tgatagaaag gtgcacagaa cccatttgtg tagaagctta 246960
aggagaaaag aaccgggcca ggcacggtgg ctcacccctg taatcccggc actctggaag 247020
gccgagatgg gcagatcaca aggtcaggag ttcgagacca gcctggccaa catggcgaaa 247080
ccctgtgtct gctaaaaata caaaatttag ccaggcatga tggtgggtgc ctgtaatccc 247140
agctacttgg gaggctgagg caggagaatc acatgaaact gggaggtgga ggttgcagtg 247200
agctgagatt gtgccactgc actctagcct gggtgacaga gcaagactcc atctcaaaac 247260
aaacaaacaa acaaaaaaat atatatatat atataaagag gcgtattgaa cagcatgtcc 247320
ctgattttgg tgatccatgt ttgaaataag tctaccacag actgataaat ctaaaatgaa 247380
acaaaactca gtgtgccaag tgtggtacaa tgcggtccta cagttaaatt gggttgtccc 247440
cacttcccct cccccagaga tgtagatgag gtatgaaagg gagcagagct ggcctgggag 247500
ggagagggga ggaggaggag gaggagatgg ggatggtcgg ctctgttccc tgagggagtt 247560
gattcataaa ctgctacaga agtggctcag aaagcatgct ctgaggaaca ttaacttgta 247620
agcccctgct accagccctg aaaaagcatt ccaaaccaaa taggtttggg aacccagagc 247680
acccaatgcc tctcctgggg agtcccaatt tacattggca tattaaaggc tctgagaagt 247740
cccacagtaa ataaacttgt atatttttga ttaatccagt tcttcccaaa tgtctttaaa 247800
tttgttaaca ttctatgaaa atattttaag aaatgttgtg tactttagga tttttctact 247860
caaaatttgg ttcccagcca ggcatagcgg ctcatgccta taatcctggc actttgggag 247920
attgaggtgg gtggatcact tgagcccagg agttcaagac cagtctgagc aacatgatga 247980
aaccctctct ctacaaaaaa taaaaaaataa aaataaatgc aaaacaaaca aaaactttgg 248040
ttgcgggacc tgcagcatta gcatcacctg caagcttgtt agaaatgcat aatcatagat 248100
cccgtcccag aactacagat tcagaattct ggggctaggg cctaagaatc tgcatattaa 248160
tcagccttcc aggtgacttt tatgtatcct ggggttggat gatccctgct ttagggcagt 248220
ggttttcaaa gtgtggcccg tgaaattctg gaggtcccca aagccttttt agaggatcta 248280
caaggtcaaa gttattttca taatagacta tgatgttagc cttttgcatc gatcatggaa 248340
aagcaatggg gagtaaaact tcagtgccct aacccacatc aaggcggtgg caccaaactg 248400
ttctggtgat catagttttc ttcaccatca cacacttaca gcaagtggaa cttggcattt 248460
catttctgac tgcccttgat aaagcaaata tatatgtatt aattttgtga aatctcaacc 248520
tctgagttca catcttttta ataatctgtg aacaaatggg aggtagacat aaagcacttc 248580
tgtttcatag caaagtataa atatctagac gaaaaatatt tgtgcagtct ttgagttgca 248640
agttgaacta gttgcatttt tcatgaaaca ccatttttgc ttgaaaagat ggtggacagg 248700
acaggcacgg tggctcatgc ctgtaatccc agcacttcgg gaggccgagg cgagtggata 248760
acgaggtcag gagatcgaga ccatcctggc taacacggtg aaaccccgtc tctactaaaa 248820
atacaaaaaa ttagtgggcg tggtggtggg tgcctgtagt cccagctact tgggaggctg 248880
aggcaggaga atggcgtgaa cctgggaggc ggagcttgca gtgagccgag attgcgcccc 248940
tgcactctag catgggcgac agagtgagac tcttgtctca aaaaaaaaaa aaaaaaaaaa 249000
aaaaaaaaaa aaaaaaaaaa aaaaaaagga tggtggacaa actacttatt cagagatgga 249060
tattgtctaa aaaatgaaca aagtaagctt gccacttcaa gggaaactga cagtacttat 249120
aggcaatagc atttgagctt tcaagtgaag atgagaattt tggaaaactt gtatttgcta 249180
ccacaagctt aatatctttc caatacttac agacttttct ctttcttttt tttttttgac 249240
agagtttcat tcttgttgcc caggctagag tgcagtggca caatctctcg gctcactgca 249300
acctctgcct tcttggttca agcgattctc ctgcctcggc ctcccgagta gctgggatta 249360
caggcaccca ccaccacacc tgtctaattt ttgtatcttt agtagagacg gggtttcac 249420 catgttggcc aggctggtct cgaactcctg accttgtgat ccgcccgcct cggcctccca 249480
aagtgctgga attacaggcg tgagccactg cgcccggcca cttacagact tttctgatga 249540
gattgtggta agaataataa acatgatttt ttaaaaatac tatatgataa aatgcatcaa 249600
catctgaaag atctgcataa ctcagaacac caatattttc caattgacca atgcataatg 249660
ttacaaaatc atgcataggt aaaaaatcca tctgaagtgc aagatagatc aatggatttt 249720
agagtcacaa agtactgaaa tttcatcgat atggtttccg aatccacatt gcaattaacc 249780
tttaagaagt accacttgtt gagttttgat gtagtattta agaaaattat ccgcaattat 249840
ctgaaaagac tgttaaaata ttccgccctt ttcccacacg ggcattgact gtatctgagc 249900
ttgcttctct gggctccgta aaataggact aaatgctgag gaccagcagg tgcgggggga 249960
cagtctgctc tctggagtca gcagataaaa tgcaaggtgt ctggggcacc cagagctcta 250020
atacttaata ctcatcagct tccactgcag ctgacataaa gacgcactta gcaaggggtg 250080
tgtgctgctc cagggaggaa atgagggtaa ttgaaattaa cttggctcct gctgtttttt 250140
cctcctttcc taatcaccgg gaaatctgct gttagtggag caggagagcc tgagggccaa 250200
tgctccaggg agtcaggggc tcaattaagc ttcagtaaat tggatttctg gccgtgaggc 250260
catggggctg gggttggcat tgaggcatga gctgccagac ggtattaggc caaggactga 250320
ccagatgggc ccagtagcta attcaatctg gcttcccaga aacaggactt ggaaggccag 250380
agctatgggc ctggacagct gtgactccag ctgggagggc aagatcttat gtggcactgg 250440
gcccaccctg tggctcgtct cagggagtcc tgtgcccggc atctggcctc agccagctgt 250500
gcactaacaa tcctgataac cagtgataag tggcagttta gtgctaggga aaaagcccag 250560
cctggggatt gggggccagg gctgtgggct ccacacaggt atcagcttgc tctaggagtg 250620
aatttaggta agtctcattc tctaggacta acattcttgc ttctatgggc tgccatagtc 250680
ttaaaaaaaa aaaaagaaaa aaagagtcag aaaactcaga atgggagaga ggctgaaact 250740
aagagattgt aaggtacatg gatgtgcttt ggtctaggaa caggccaagg cggatattca 250800
ggcctgcatg actcagctag tttggtgcac aagtgcacac ctccacttgt tatataacct 250860
gtttgtgtaa gttcatactt ggctttaagt tactatggtc tgtaaaaggt ataactgtcc 250920
tgctgatgct gtgcatgggg cttggctctt gggtgtctcg gctcggctca acatggcttg 250980
gcatggcagg tgcgcgggtg cccagagaaa gagagagaga gtcaaagctc tccatcttgc 251040
agatggacag gagggagtca ggacccaact tggcttgctt gtgcccagag agagaaagag 251100
ttaagctgct gaccctgaag gcaaaggaga gctggctgca caactgtgcg tgggggcagc 251160

```
cagctcaagc agccgagaca gggtgaacag tgtgtgagta agttgttaat gagaaagcta 251220
atttaaataa gctgtgtaag agagctgctg ctgaataaac catagtcacc tgcctatggc 251280
cccccgagtg ttctttctgc ccatccacgc actccccttg gacttcagca tgggctggac 251340
ctggaccccg ggatctgaca gagatcatag tagataaaga tagaatgaga tagagacaga 251400
gagaggcaga gagtgagtca ggtacacaag agaggcagaa aaagatacaa acaacaggga 251460
gagggagaga cagctagaca gagcaagaca aagatacagt tggcttagag agcagagaaa 251520
aaaagacagg aagagagaga ctgaagccaa agtttcacta caaaatgaat gttctaagtg 251580
ggggcggcag ggcttttttt tcttttcctt aatagttcct aacctggtct taaaaaccca 251640
gttcccaaat ggtcagagaa ggccccattc tcattcttgg aaaagaggag aaggagagtt 251700
tttctctgtg cttctcccgg ttgctttctc caaccagggc acggaattcc aaatttggag 251760
cagccctagc agcccgagct gtctggtcag ttggcctcag ccgagtctgc accaaaaatc 251820
ttcccaaacc tcacacagag tcctcacacc agcccctttc tgggccttag accaccccag 251880
ctgtcagagc tgcaatggaa aggtcagggc caggccagca cagcatccct gtgtcctgat 251940
tggcatgaat cctccatcgt ttcctgccca gcccttcttc ccagaagtca caccgtggga 252000
gttcctgtgt cctgctgtgt cccactttct gacacccaaa actcaccgtg tgtcatccct 252060
tcaggccttt tctctcttgg actgggcctg ccagagactg aactcacatc aggggtctct 252120
ggcagactgg ccggccactc ccatgcctgc cagggacttg tttcccattt tctgtcccac 252180
cccaacccat gctgcagccc caggtgtccc tcatctgcac caagccaggc ccatctcttg 252240
gctatccagt aactactggg agtcagggac acagagtttc agatcctcag cttccctact 252300
ggggcatggt gagccaggga gagaatggac agacttgagc agcggttctt ggcttggacc 252360
acacattggc atcatctggg agctgtcaaa gccacccatg tgccaggatc ccacccctga 252420
gagactctgt tgtagttggc ctggggagtg gcctggacat tgggattttg aaaagctccc 252480
agggtatcct gatatgcatc cagggttaag aaccagtgtc atcaacccag gcctgcgcca 252540
gaaagagtcc accccagacc tcacctgcca gagactcaga gacagccagg ccccggccca 252600
gggtaacaca gctggaaggg gcagagtggt gctggccaga gttcctccat catcttcctc 252660
agctcctcac ccccttcaac tccagggaca agagctctgt ctcttacctt ggtctgtcca 252720
ctctgaactc tgggatccca ggagttgagt tctgtattca cctgttacca acaacatgtt 252780
cctctctgac cctcatctcc tcgactgtag tttggagaga atagtaacca cttcacaggg 252840
ttgcagtgac aattaaatga gtttaatatg ttaaaggctt atcatggtgc ctggcactta 252900
gtaagcacta aaatgttatc tattagtatt gcggttactg ttattgttcc cacaaagaaa 252960
gcatgaacaa acaacagagt ctggctggca atttggggga gtggggcaat ccaatggtgt 253020
atgttatgag ttgaacagtg gcctcccgaa aagacatgtc catttcctaa cccgcatacc 253080
ctgtgaatgt ggtgttattg gggaaaaggg tctttgtagg tataatcaag gatttcaaga 253140
tgagatcgtc tgagcggggc ctaaatccag tgtgtcctta taggagacag aaaaggaaag 253200
gcacaaaaaa gaccatggga agacagaggc agaggctgga gtgatgcagc catgagttaa 253260
agaatgtctg ggtcccccag gagctggaag aggcaaggag ggactctgcc atagcacatt 253320
ccgagggaac gtgggcctgc cagcaccttg atgtcagacc tctggcctct agaactgtga 253380
gcaaagttct gggattttaa gccaaccatt ttgctttaat ttgttacaac agctgcagga 253440
aagctacctt cagagctaaa tgttgctggc tagaaacatc cctggaccag gacagttggc 253500
ccattagtca taccttaggg aggtgggatt gggggtagcg gctcagcact gccctgtgtt 253560
```

ggtgctacag gggggctcag gcctgaggac cttctggggg ccaggcactg gagctgcccc 253620
cttcactgtg gaggcctcaa caagttcctt cccctctgta ggcctcaccc acccccctac 253680
ttggcgtttt gcatgtctct gtgagtcttg gggagaaaag acccccatgt gatcaactcc 253740
tctgaggtca ggcctggcaa ggccaggagc acctctggtg tgaagtagat gctcacccac 253800
ccctccctgc gctgcccagg acttcagggc ccagacctcc caagctaatg gctaatggct 253860
aatgcaacca gaaaatgagc cctctcattc tacggccggc tctccccaaa tggacttgag 253920
gagaatgaga tctaatgaag tcttttctat gggatagttc caaagcttcc ctgtggtcag 253980
ccgaggggca ccatgaggaa gcatgtgtct gggcaacagg cccctgtgtg ttgccaggca 254040
agcctaaggg ggtccatgga gggctttgtg tccaggggct ctcagtggtg acaccagcag 254100
ggccagcagt ttctgagggg ctacccaccc acacctcttc attcccactc taactatgag 254160
gtgtgtgtat gggtggggct gggggaggca ggagcagctg cttgagggac accaaggaca 254220
acttggtgaa cactgacact aaaaggaaag ccaagttcat tgagtccagt ggtctcatca 254280
tacagctggg aataccgagg cccggagagg ggagggacta aggttatacc gtgatcagca 254340
gctaagctga tatgggagcc cagactctct gtctgcccat gagaagtgtg tgtttacaaa 254400
gcacatgctt gggataaggc ttccctatgt gtgggttgaa gggttggggt gagcacgttc 254460
atgcaacagt ccgtggctga cagcgctagg tgcccatttg gattgcgccc tatggggaag 254520
atgtccaact tgatggcttc cttgagcact ccatgcaagg gggaaagtca aacacaagag 254580
gcggggccca gcacagtgcc caggtcctta tggaggaggt ggaggaagag aaacaggagg 254640
ggtgggcgag gagaagtttg cggctgagca gggtcagaaa aggaccctgg agcactgttc 254700
ctcagtggat gggcaagctc cgttctcttg tggggacttt tatttcttcc ccttgggaaa 254760
ccattctggg ctcctgatgt gccttagacc acagatctaa cacacacttg caaaagcact 254820
ccaaggaggg cgagcaccaa ctccctccca ccccaatggg cgctgccagc ccggcactgt 254880
ggggctccaa gctcagcacc aggtgaagaa ccagtgtctg ccggacgacg gactcactgt 254940
gtgcagaaca cggtgctagg ccctgcggga gttcagtgag aggattaagg aagaaataat 255000
ttaccatctc aatgcattga gattccaacc ctgtgggaaa ctgcctgatc tgaaaacctt 255060
tacagaaagc aggtaaatgt atgcagatct tcacggccta agtaattttc taataaggca 255120
tgaaaataca gcgagtggtt tgggtgagga aggaggaggc aggcttgaag cagggctttc 255180
agggagggga ggggcaatgc ctgacattaa agacagggag ggttgtggct gggaagtaca 255240
gtggtgagcg caagaggccc aggccctgga gcccccagcc tgcttcacag tctgtgatct 255300
cccttggagc tgtggaaggg ttttttggtc tccacagtga gccggctttt tagaaatggg 255360
cacattgtaa ttgtgtatat ttatgggtac aatttgatgt gtcaatacag atatgctcca 255420
taatgatcaa ctcagggaag taggacaacc atcccacatg catgtatcat ttcttatatg 255480
caatggagta ctattcagcc ataaaaagaa taaaatcctg tcatttggaa caacacgggt 255540
gaacctggag gataccatgt taagtgaagt aagccaggca cagacaggca aatagcactt 255600
gatctcactc acatgtggaa tctaaaaaaa aagtgaattc agggcctggc ccagtggcct 255660
gtaatcccag cactttggga ggccaaagtg ggcagatcac ctgaggtcag gagttcaaga 255720
ccagcctggt taacatgggt aaaccccatc tctatgaaaa atacaaaaat tagctggatt 255780
tggtggcagg cacctgtaat cccagctact ctggagacta aggcaggaga atcacttgaa 255840
ccaggaggta gagattgcag tgagccgaga ttgtgccatt gcactccagc ctgggccaca 255900
cactccatct caaaaaaaaa aaaaaaaaaa aaaaattttt gtttaaatgt gcactcagga 255960
accacctgag cgagcattca gtggtgccca gtggagtgca gcttgatctt tgctacttcc 256020
cctcattcct agatgttttt gcaggaacaa ctccttttat catttggttc tgtcttgttt 256080
ctcagtatgg tgtccttgag tggagtctca gtcactctct ccactgtgtg tagctcccct 256140
cttagactgg gaatgctctc agcagaggtc tgctgagaga gggacagaag agagaaggga 256200
agaagcaaaa caaactccca gtgttgagac ctttcctcaa tacaggtctt atgtatttca 256260
gtcaaagata tttctctttt aattgtgggg aaatacatga aacaaaactt accgcttcaa 256320
ccgttttcaa ctgtatgatt cggcggcatt aagtacactc acaatgctgt gtaactgtca 256380
tcactaatca ttgcagaacc ttttcatcac tccagaagga accccgtacc caggaagctg 256440
tcacttccaa tcctgcctct tcccctaggc actggttgcc actaatctgc tttctgtctc 256500
tggatttgcc tctgtgtcaa ggagatgttt tgttctttgt gttccactta aaatgcaaat 256560
aaccatagga gaacccataa tctacacttt cttttctttt cttttctttt tttttttttt 256620
tttttttttg agatggagtc tcgcttggtc gcccaggctg gagtgcagtg gtgcagtctc 256680
ggctcactgc aagctccatc tcccaagttc acaccatttt cctgcctcag cctcccgagt 256740
agctgggact acaggtgccc gccaccatgc ctggctcatt ttttttgtat ttttagtaga 256800
gacggggttt cactgtgtta gccagaatgg tctcgatctc ctgatcttgt ggtccacccc 256860
cctcaacctc ccaaagtgct gggattacag gcatgagcca ccgcacccgg cccataatct 256920
acactttcaa ttccattaat ttcaacaata cccaccctcc actcacctcc atagtttgga 256980
aattttcatt ttagagacag ggtcttgctc tgtcacccag gctggagtgc attggctcaa 257040
tcacagctca ctgcagcctt gaagtcctgg gctcaaacaa tcctcctgcc tcagcctccc 257100
aagtagctgg gactacagat gcacatcatc atgtctggct atttttttat tttttttatag 257160
agacagggtc tcaaattgct gcccaggctg gtctcaagct cctggtctca agcaatcctc 257220
ccacctcagc ctctgaaagt gtttggatta caggcatgag acaataagcc cagctaggaa 257280
tgatgtaatc cctacatgtt atggggaaaa cactagcctg gaggttcaga gaccggggtt 257340
ctagctcatt ctgtccaaag ttatgtgatc tcttatggat gaggatccct gattctcttt 257400
aggccttaac aatccccatc ctgaggcatg ggaggtggac ttggctaata aattccaggg 257460
ccttctgcac ctttgacctt ccagtgccat agtagaagtc cattgacccg gcagagcaca 257520
gggtgggtgg gacctgggtg actgggtgcc aggaggaagc caggcctggg gatatgggga 257580
gcactggtga gggctcagac ttggcctgcc tcacccactg ctgggctcgg ggccagccct 257640
gtccacatta gcttcctggc tggtccaaag ccctaggcag agtctgcagg tgggatgtgc 257700
cagtccctgt cataatgcct gctctggggt gagcctcctg gaggcctcaa gcagtggcct 257760
tcctgggcag gctgaggcag gacagggcag ggcaggcctg ggggaccggg aaggggcaga 257820
ggtcagggca gggtggctgc agaatgggat gcaatgtcct caacccagag gctcccttgg 257880
ccctacttgc cccagctcat gagagcctgg attctgagat ctgccaggac tggggctcag 257940
cactgcctat ggaaacaggt gtggcaggga aaaaaattat aaccaaatat ttgtagttac 258000
atcttctccc ttctggaaag ggagggtccc ttgtttgtgg gcccttggcc tcctggacat 258060
tattgtgtgg tgaagggaga aaggttgaga tgcagagtta gagaaactaa gagggtccac 258120
ttgaggaaag atgggggaac cccaggaggg gaggagggga caccctgggg aagtgggggg 258180
ctttccaggg aggccaagaa ggtggggcag gatgcagaaa gtcagagcac agttctgagt 258240
tttggagaca gcaagagaaa agagggaggg atttggataa ctaaaggact gggcttgtgg 258300
agagaaacgt ttagagattt gggagatagt gtatcatgtg atgtattatg aaaacccctt 258360
cttcatatcc ctagaaaacc accactgatg atttatggta caattcagtg cttttgcaga 258420
gagattggtg tctctctttt ttttttaata acgcattggc ttggctccat ttaaattaca 258480
ggcagacatc ttcagcagat tttattcatg ttccattagc taaatattgg gtttcctatt 258540
ttctgggttg cctgaaacca ctttgtaggc ccttccacag tgggaggcac ctcagaaatc 258600
acctctttgg cctgcagctc catcttccca agctctgggg tttcttgaat gagtggcctc 258660
gttcagaaga taatatagca tccctaatcc gaaaatccga aattggaaat ggttcaaaat 258720
ccaaaactgt ttgagtgccg acatgatgct cgaaggccag gttcaaagga aatgctcatt 258780
ggagcatttt ggatttcaga ttttcaaatt ccaaaatctg aaaaaaaaaa tctaaaatcc 258840
aaaatacttc tctaattgta tcctgggatt gcagttgggt cctgacctgc cagctaaggc 258900
agtgagcagt caatagcggc tctccatgca ccccttccgc gcctcaccct cccacgggct 258960
ccctgctggt tggactagtg catcagcccc cagcctcccc ttgcacctgc tggaaagcgg 259020
gcatgatgct cctgccctgc cttcctggat cctggaacac tgtgacaatt gcaggattcc 259080
agccagggaa aatgctacac ggtagaagta cttggtacac aaagttcctc caaagaggag 259140
gttccagcaa tggcacagca gccctgggag agtctgtgac tgtgtccacg cctccagctc 259200
tggcccctgc ctcttgggga gctgctcagc atcgccctca gagtgagagg aagtgggcct 259260
caagctcagg cctgcttctc cttccccatg gccttcctgt ggcctctgac ccatctgtga 259320
aatgagggca gtagtgtctt cttcagtgcg ctgctgggag gtcagagaga atggatgcaa 259380
agtgccgaac acaaaccccc agcactggga ggtgctccct ctacggcacc ttgaatccca 259440
gtccagaatg cagcgcacaa gacatttgat cttaaatttc ttgatcttaa atgcaacact 259500
tgagtttctg aagtcaaggt cccccttcctg ggcagtcagg tatgccttag cgctctggtc 259560
ctatgtgaag tctgggggct tggtatgcag ggagatacct gtcctctgtc atccttccac 259620
cttggttgcc actgagacat ccatttttct ctccatcgtt tctgttctgt ggcaggccca 259680
ggatcacccc agagacacca ttgttgccgg gggtgaaagg aaatgctatg caagagagtc 259740
aggggtcccc ctgcctcctg cctccatccc tccctctgct gtaccatatc ctcccccaca 259800
gcagtgaagt ttagagctgc cgctggctgg aatgaggggg aaggcaggaa ggagaaaacc 259860
tgttaatatt tcaaagcttg cttccatccc agtgacctat atgtctgaat ataaatgttt 259920
ctttgagcca tccttctgcc ccaccacagc agtgaggcca caggagagag ggaagacatt 259980
taggaagaga tgagttcata gaggggaggg agagatgagg gagctctcag aggccatctg 260040
gatagtgtac ttcccattcc cccatgggga cacgtgtatg gccccccttcc taattacttt 260100
gcgtgcttta aagccaatta gcggagagcg ctaatgggat ttcacagagg ggctccctgg 260160
ccatatggct cagggcctcc ctgggtgcac cggggatggc atttgggaag ctcagggagt 260220
gacagatggg tttggtgaca ttcaggaaat tatgcagacc tgctcagtcc tgggcctggg 260280
gccctgattc atggcaggcc ttgggaagtc aggggccagg gagggaggac aaatgtgaat 260340
taatgatcac aggagtgtgt tccaccagcc cccttttggaa ctcaagggcc ctttaaataa 260400
agcagagtgt agatgggttt cctgaggctt ctcccacccc agggctgcct tgtgcaggga 260460
ggtggaggag gaacttcccc ggactccata aagaatatgc agagtggaac ctgctctgtc 260520
gcttgcttgg gcaaatcact tctcctttct aagcctcagg ttcctgtctg tgaaacagga 260580
taaaccacct ctcctaacag tgtggattca ttgagatcat gggtggaaat tcacctggcc 260640
atgcttgata caatatgaat gctgaatata gctagcaggc cactgtcctc actgccctgg 260700
gccaaatgaa aagcatgctg aaatagagac cccagcgtgg gggcagtggc aggaaggata 260760
aaacagtcac ccacccctga acccacaccc ccagggaggt gcctgcagga ggaggcattg 260820
aaacaggaac ctggagaatg agaaagactt cagaaggaag agaaagggag aaggcagtcc 260880
ccgtgtccag aggggcataa gcaaaggctc tgagacagga aagcatcccc tggttctgag 260940
gacgaggctc cttatgcatt ggaaatgaga atagaatgac aagtggtggg tcttgggtgt 261000
tccatgaaaa cataggcttt attgtgtagg ccatggggag ccctgaaaat ttttgaggag 261060
gtaaatagca ggatatgacc tatgtgttgg aagcatagat tggagggggc aagactggag 261120
ccagaaaggc caattcaggc gagaggggat gggaagggct gggagtcaag agaggccatg 261180
ggtgttgtga tgatggactc aacaggtctc ggtaagtaat ggccatgcag gtgggggtgg 261240
ggggtctaag acgatgccca gcagcttgat aggaattctt aggggctgaa agggctgtac 261300
agagattgga gtcaggatta ggggagcagc aggcaagagc ggggtgatga gtttgtgttt 261360
ggatgtggtg aattggagga ggccgtccag gccattacca gcagctgcgt gggactaaat 261420
cccagggatc cgtaagagtt acttgcttgg ggttccctat cctccccaag atcgcggcac 261480
tgttgagtgg gcaacccaca cctgggtgtt ggccgtgggg gttctgggca gccccagctg 261540
aatgctgtgt gacctggctt cattgcgtcc ctcacctccc atgctgtgtg ctccagtggg 261600
cccaggacag gggttctctg aagtgtgggg ctcagctgtt ccacctcctc tgccacaccc 261660
cgggggtcag tgtccctctt tgtgggtgcc atggctctgc tccccctaga ctttgttttt 261720
ttttgagaca gagtctcact ctgtcgccca gactggagtt cagtggtggg atctcagctc 261780
tctgcaacct ccgccttcca ggttcaagga attcccgtgc ctctacctcc caagtggctg 261840
gaattgcagg cacgcgccac cacacccagc taagttgtat ttttagtaga gacagggttt 261900
cgccatgttg gtcagactga tctcaaactc ctggcctcaa gtgatctgcc tgcctcggcc 261960
tcccaaagtg ctaggattat aggcatgagt caccgcacct ggccaagtcc cccagatttt 262020
gtagcttcac cttgtcagga tctccatgtc agctgcagag aacgtccctc aggatggcta 262080
cctggggatt gcctccccac acactctaat taaaaaaata aataaaaata aaagccccgg 262140
cgtggtggct cacacctgta atcccagcac tttaggaggc caaggcagat agatcacctg 262200
aagtcagcag tttgaggcca gcctggtcaa catggtgaaa ccccatctct actaaaaata 262260
caaaaaatta gccaggcgtt gtggcaggcg cctgtaatcc agctactcga gaggctgagg 262320
caggagaaca gtttgaacct ggaaggcaga ggttgcagtg agctgagatt gagccattgc 262380
actccaacct gggtgacaag agtgaaactc catctcaaaa aaaaaaaaaa aaaaaaaaaa 262440
agataaattt aatctccctt attggactca atgattaaaa atggaattgg agtttttact 262500
ctcatgctcc ctggcttgag tgagctgtgc agaggcagca ggggcagcac cagcagcctt 262560
cagacagctc acaaggcctg gcaaggagat gtatttaggc tttcccaggt gttaccagga 262620
gaagcaagct gctgtccggg aaaaggcaaa ggtcaacatt tgcaacctgg gatttcattg 262680
aaaagaatat ctgggaaatt accactgact gaacaactga ttcagagaat gattagatgt 262740
tctaaccaca cacacactta ttctctcctt agactttata atcctcattc gacgagcatc 262800
attcatccaa taagctctta ctgagcgtct tcttctgtgt caaatgttgt gccaggcttt 262860
ggggacacag atgtgaagac aggattacac atggaggaac ctggactttg gggtacctca 262920
gggtacagag tgtaatccca cccctttatc acctatgcca agccaatcat ggaatggtat 262980
gcccccagcc tcaatgatgg cttccgaagt gggaacttga ccttaagtgt tctgagcaga 263040
gaaaaaccta ggacttttgt cccatggcaa aggaaaaaga gctttcttct ggatgctgca 263100
gaaggtagat gtgatacctg gcacagctgc agtcatttta tgactatgag gaaggctgga 263160
ggacagaaaa ggaaacagaa gagagaagag ccctgatcca attctgccta cacatggcgg 263220
gttgccagac tacagtttga acagcctaca cattcctttt aaataaaagg aagtgattta 263280
aataaatcaa tctgtagcca agagctctaa ctgaaatggg caagtattat gtgcctgcca 263340
tttacatgac aaatttaatt gagtcctcac aacagctttt taatgtagaa attgacaacc 263400
tcattttaca gatgaaaata tcaaacctgg tggtgaaatg actttctgag gtcgccccat 263460
tacataagta agggatttgg gttctagaag tttgactcca acaccttttt gctgcaatac 263520
aaagctgctt actgtgttgc atgggaaact tcatcaaatt cttctctctc tttgggatcc 263580
tcctgggatt gtttttcctg tttttgtttt tgaaactaga gaatggatca agtttcattg 263640
ctgggttgac aagggcatgc aggggcacag gccatgtgag gcatgatgcc agaccccagg 263700
cccttgcaga gagtttgggg aagccttcag gacgtgtgga attgcagagg caggaccaca 263760
attagctaga tctgaagagg caggggaccc agctgccatc tgggctctga gtagaaaaag 263820
agaaatcaga gccttataga aaagacatct gtaccttgtt ctgcagacag acttcctgct 263880
atgatgcacc tccttatttt ttgcatacgg agcaggcttg acatttatgt agattgattc 263940
caacttggca ttttgaccaa aggcgctatt aaccctttcc ctcccgtcct gggggaaaaa 264000
tggcttgtgg ggcctgaccc acaagtgacc ccatcaggct gttccggccc ttttctggcc 264060
tagtctctgg ctgggaatgg atggcttctt tatgaccctg aggaggtatg gccaacagga 264120
agcacagtcg ctctcttctg agctcatttt tcaccctggc tggttttgct ggagatgcaa 264180
ccaaagctaa atctcaattt tgggggcagg aggagccgtc ggtggagtca tctgcacctg 264240
ggctgttaga taaaacctcc atgcagcctc tagaagccaa actcaagatt taaaggggaa 264300
gagctttatt ttgttgacaa ttgctttaca attcacttag taacacgcca cgtcttcgta 264360
cagaggtatg cactttcaca ctgctgctcc atccgatcct agttacatcc ctaaaagggg 264420
acaggcatgt gtcaggatcc tcttttcact ctgaggatac tgaagcccag agaggtcaag 264480
ccagttgccc tactttgcac agctgttcaa tggtcaagtc agtggtttta gcctctgaca 264540
atccagcggc ctttctatta caccgcactg cctttcatgc agatttagag ggaaacagaa 264600
agaatctgtg ctccagtgca ccgtctcccc gtaggactgt gagctgctca aggcagggtg 264660
gtaatggagt cacatctggg cagcatgacg tggagcacca ctgatatttg ggagtccatt 264720
tgggactgga taatttttg ttttacagac atttaaacga gtctgccttt agcattcctg 264780
gaccctggtc actaaacccc aacagtgcct cctcattctt ataaaaccct cctccccaca 264840
aaaaaaaaag ccccagacat ttccaaatct cccagggtgg agggaacaga gtggagtaga 264900
agtgggcagt accacccttg gttgagaacc cagtctttgg aataagatgg ctgaggtttc 264960
aaaccttgtc tctgctctcc ctagcagggt gacctcggag gtctggcttc ctgattcaga 265020
acatttaccc cagagagtaa tcaggaagat gaaacgagct aatggaccca aagcacgaag 265080
ctccatgcca acatgagatg ttttgatcaa gtaactaata aaaataacaa atgaaatcct 265140
gtcgcattaa gagttggccc tagtatgttt acagtaggtg ttccataaat gtggctttct 265200
tcttctgcat tctcagcatc tacctcaaca accacatcaa caaaaacaaa catttattgg 265260
cttacttttt atacataaag catttagcaa agaatttgac acattgcccc atttattccc 265320
acaacagccc tatgaggtag ttatattatt gtccctatct tacaaatgtg ggaactgaga 265380
gcagagattg attaactgta gcctgtgggc caaatccagc cactgcccgt tgttactgga 265440
acatagcctt gttcattcat tcatgtgttg tctatggctg ctgccattta cattgagtag 265500
ttgcttgcag cagaaaccat atatggcctg catagcctaa aatattcagt gtctaaccct 265560
ttataggaag agtttactga cttctactct agaaggttaa tttataaggt gacaaaacta 265620
gttatggtgg aggcatgagt ccaactccgt tcagtttgat tccaaagctc aggctcttgg 265680
ttgtcacata ctcccactgg aggcggtgga ttttcattaa gtggtcgtta gacactgaaa 265740
tcgtaaaaca tttattttaa aatagattat gttatatatt tggtttttat tgtggtaaaa 265800
tgtctgtaat gtaaaacata ccatttaacc atttttaagt gtacagttca ctgccattaa 265860
gtgcattcac aatgctgtac aaccatcacc attatccatt tccagaactt tttcatcatt 265920
ccagacagaa acgctgtagc cattccacag taactcccca ttccctctcc cccagcccct 265980
aataatcact attctacttt tgtctctgtg aatttgccta ttttaggtac ctaatgtaag 266040
tggactcata aagatttgtc tttttgtctc ttattccatt tagcatgttt tccaggttca 266100
tctatgttgt aagatgtatc agaattttat tcctttttaa ggcagaataa tgtcccattg 266160
tgtgtagtgt cagatgttcc tccatttact gtggagttac ttcccaataa acccactgta 266220
aaagaaaaat attgtaagtc acaaatgcaa ttaatacacc caacttactg aacctcatag 266280
cttagcccag cccacattaa acatggtcag aacacttaca ttagcctaca gctgggcaat 266340
atcatctaac acgaagccta tattataatc agatgttgac tatctcatgt aatttattga 266400
atactgaaag tgaaaatcag aatggttata tgtgtacttg aagtacagtt cctgttgaat 266460
gtgtatcact tttgcaccat tgtaaagtca aaaaatatta attcaaacca ttgtggggca 266520
gggcatgttg gctcacgcct gtaatcccag cactttggga agccaaggca ggtgagtcac 266580
ctgaggtcag gagttcaaga ccagcctgac caatgtggtg aaaccccgtc tctactaaat 266640
acaaaaaatt agccatgggt ggtggtacat gcctataatc ccagctactt gggaggctga 266700
ggcaggagaa tcacttgaac ctgagaggca gagattgcat tgagccaaga ttgtgccatt 266760
tactccagcc tgagcaacaa gagcaaaact tcatctcaaa aaaaaaaaaa aaaaatacaa 266820
catcataagc tggggaccat ctgtgtttgt ttttgaatag atagtacatg catagagtac 266880
aaaattcaaa agatgcaaag gacctagagt gaagagtgaa tctctctcct atcccttccc 266940
cctccaggcc ccagctcccc tcccaagaga caaccagtgt tactgcattc ttgtgtatct 267000
tttctgagag ggtctaagca tgctcagcat ctaggtttca atagtatttt taaatatatt 267060
ttcacacaag tattactaca cctggcatat tgttcctgca tctttctgat aacctttttc 267120
tttcttgaga cagggttttg ctctgtcacc aaggctgcag tgtagtgaca caatcatagc 267180
tcactgcagc ctcgacctca cctactcaag caatcctccc acctcagcct cccaagtagc 267240
tgagaacaca agtgtgtgcc atcacacccg actaattttt ttgcttttgt agagatgtgg 267300
tctcactatg ttgcccaggc tggtctcaaa ctcctgagct caagccatcc ttctgcctga 267360
gcttcccaaa gtgctgggat tgcaggtgtg agccactgtg cctggtggct cacacattaa 267420
gtattcttaa taatatgtct tgcagattgt tttgtatcat tatatctaga gctatctcac 267480
tcaacaactg catataatcc cactgcatga atgtatcatg atttatttat ctggtcatta 267540
taagtagaca tttaggttgt ttttaatctt tttcagttat gaacagctct atagtgaatg 267600
ttcttttcat tttttgttgt ttttgagatg gagtttcact ctgtcgccca ggctggggtg 267660
cagtggcatg atctcagctt gctgcaactt ttgcctcctg ggttcaagcg attctcctgc 267720
ctcagcctcc tgagttgctg ggactacagg tgcgtgccac cactcccagc taattttta 267780 tttttagtag agacggggtt tcaccatgtt ggccaggctg gtctcgaact cctgacctca 267840
ggtcatctgc ccaccttagc ctcccaaagt gctgggatta caggtgtgag ccactgcgcc 267900
tggcctcttg tcatgttttt aagattagtt cttaaagcca gtgtagtaga agatgaagca 267960
tgtttctcac cctctccatg ttggactgca tttttcaggg aaattgtgct atctggagaa 268020
ccatatttgg ctcagaggat caggagtgct tggatcctac cctggtctaa ctcctccctt 268080
ccccacatct gggccaatga gagatggagg aaaaaaagca aggaacaact cattcttggg 268140
ctgaaagcct aaggatgtgg tcattggagg acaaaaagca aggaacaact cattcttaga 268200
ggggctgaaa gcctaaggcc atgctcattg gaggacaacc cttcctctaa cccagagttt 268260
ctctttgact tttttctttt cttttttttt ttttgagact taagtcttgc tttgtcaccc 268320
aggctggagt gcaagggtgc aatctcagct cactgcaatc tccggctctc gggttcaagt 268380
gattcttgta cctcagcctc ctaggtagct gggactatgg gcacctgcca ccacacttgg 268440
ctaatttttg tatttttggt agagatgggg ttttaccatg ttggccaggc tggtctcaaa 268500
ctcttgacct caggtgattt gcctgcctca gcctcccaaa gtgctgggat tacaggcatg 268560
agccaccgca cctggcctct ctgacatttt ggactagata gaccttttt ctatctagtt 268620
ctttacctca atgtagaggt cacaatgtca ggctaaggct ttctaataaa gcttctggtt 268680
gtcatgtagt gggagagagg agagctgaaa tcagtattgt gagatatggc tgaaatgtct 268740
gctgtagctc caggtgagag aggcccaaga cctagcatgg gaacaaaacc tcccaagatc 268800
tggcaagcca agcaagtttc tgctttcttg atgttcctct ctgatgcata aagatcacag 268860
cttttgccag ccaaggtggc tcatgcctgt aatcccagta ctttgggagg ctggggcagg 268920
aggattgctt gagcccagga gttttggacc aacctgggca acatggctag accccatctc 268980
tacagtaaaa aaatacaaaa attagccagg catgatggcg tgcacctata gtcccagcta 269040
ctcgggaggg tgaggtggga ggattgcttg atcctgggag gcagaagttg cggtgagctg 269100
agatcacacc actgcactcc agcctgggag acaaagtgag accctgtctc aacaaaacaa 269160
aagaaaacac ctttgaaaag agatggggta aaaaagatca cagaacaaag agttaaaaaa 269220
aaaaaacaga ttgttcttta attaagaaca actagggctg ggcagaattg aagctgtttc 269280
ccctgccaga tgattggaca ccttgccttt taggagcagg gtctggatgg gagtggggga 269340
aaagcttcct tcaaaaccaa ctttcagaga gttggatgct ttttggagag gactgaattt 269400
ggattaggca ttcatattta tttctgccct ttgcagtcat gtcatgcaag ctaaatcgtt 269460
tcttaaaacc agtatttcca ccccttccaa aaggaacttt atcatgtaaa ctgagcgcct 269520
gcaatccaac cctataatga cttgattcgt cctgggaaag ctcctgcctt taatcctttt 269580
ctccctcatc tcctggtgcc aggaagggcc cccacaggac cctcccaggt ctggaggtgt 269640
tcctcactgt cactctctcc tcctcacatc acctgctggc cccgaggcct tctcagtgat 269700
ggggagggtt tggctagagc cttagcggga ggaagccagg agatgcttcc ctaggtcaat 269760
ccctgggcag gccccacttc cttcatttcc tcattcgttc atccagttaa cacatgctta 269820
gtgcttctca tatgccaagc actgtgctct gcacttcact ctgtgagctc tgataatagg 269880
gactagtatt agttttcatt tatggatgag gaaatcaagg ctcagagggg ttaagtcact 269940
tgcctgagac cacatggtta atgagtggct ttgctgtact ggggacctag agtctgaatc 270000
cagccaagcg acttccaatg ccaagctcac accagatcca cactcggagc agaggaagcc 270060
acattgcagc ggaaaacaag ggcttcctgg aagtggtatg tggcctgagg ccaggaaaga 270120
ccaggctggg agagggctac tgactgctta ctgtaatcag cttcagattt tcggcatcaa 270180
caaggcagaa ccccagtgag acaggccagg gtgacaggag gctctttggt gaccctggat 270240
gggctctgct catggggatt tgatcccacc attagttttt gagctcttgc cacatgccag 270300
acacaggccc tgccccagga atcccacata ttatcatgtg ccatggcctg ggtctcggct 270360
atggcttcag tggctcatgt tcccctcttc ctggacaccc atcttggacg atcctacagc 270420
ctcaggccaa ggcatcccca gaatcccccc aagcttctgg gcccctgcct ggcaagactg 270480
atgctgatca gagtcctgcc ccatccccct gctcccagtc caggccaggg atggcttcta 270540
tttacctggg tcttccccga gctcagctga gctccagctc atagtgaatc acatgttggg 270600
aatcagctga gagctggccc tgaagatccc tgaataatgc atcaaagccc ttctcccctg 270660
cagagccatt agggtggggg tgagggggat aatgcagagg agtcagtgtg tttcccaccc 270720
caggaagaat actagggttc caaaggcctt tgccctggtg tgcatgggct tgagactcaa 270780
aggtccacag gactgggtga cccagtacat aggtaaacca aggcgggttt cggatgacta 270840
caaaaccagt acatcctcca aaagagggca aaggaggttc agcttccaaa tattcagact 270900
tttgccattg gaaactttaa gaaaacaaaa caacatttta tttttagcat ccatataaaa 270960
gttgtattgc atggtttatg gttttgtttt tattttgaat tttctcccct gtgcagaagc 271020
accaaagcat cttcagtgct aagacctgga aaagtcgaag tccctcctgg agatccagtc 271080
acaccacagg agagcagagc tgggggtgcc tgctgagttc actccatcca ccccacccca 271140
ctcccagaac cgtacaggct gagcagtcca ggccaattca ggtaccctct tctggctcta 271200
tgaagaaagt ctaggaaggg agtggagagc tgcagagaag aaagagggag gggatcagaa 271260
ggaggaggag gagcaagagg aggaagggga gggggagggg gaacagagtg ccagactgac 271320
agaaattttt gcacctcctg gcatcctgtt cccaccctgg gcctaactga gccttcccag 271380
gtgctatgca ctgaatgttt gtatcctgca tgatgaaatt aatgccctta taggaagaaa 271440
cacgagcaag taggccttct ctctctctct ttgccgtgtg aggatatagc aaggaggttc 271500
cataggagaa accaagaaaa gagtcctcac ccaacccaaa ccatgctggc agcctgatct 271560
ccaacttccc agcctctaga actatgaaaa ataaatgact gtctaagcca cctagtaatt 271620
tgttatagca gcctgagctg actaaggcac cagatcacta tgtgacttgg ctgcctactc 271680
tctctctttg ctgtccagac tctggggacc ctggttctct gccctttctc tagctctcct 271740
tctctgtgtg ccatccttct cgcagtctgc agcctctgct gatccttagt ccactgctct 271800
tgggcatctc ttccacctgt gaccactctc tcctcattcc ctctgggatg agctcactcc 271860
cctttggtac caattactat ctatggctgt gggtcttgac cttggataga ctctccaggg 271920
actctgagtg attggtctgg gtgcagcctg gccatagggc attctgaaag ctccccaggc 271980
cattctaata tagaccactg gacagtaaag ggttagtttg ctcagcagcc ttgggtcact 272040
ccaaccctgc acattccaaa aagaggattg gcccttgacc acatctgggg agataacttt 272100
agaatattct gccttttatt tatttattta tttttttttt tgaggtggat tctcactcca 272160
ttgcccaggc tggagtgcag cggcacgatc tgggctcact gcaaactctg cctcctgggt 272220
tcaagcgatt ctcctgtctc aggttcccga gtagctggga ttgcaggcac ccaccaccag 272280
gcctggctaa tttttttcta tttttagtag agacggggtt tcgccatgtt ggccaggcta 272340
gtctcgaact cctgacctca gttgatccac ctgcctcggc ctcccaaagt gttgggatta 272400
caggcgtgag ccaccatgcc cacacctggc tgaatattct gccttgtaag aatgtttttg 272460
tatgcctgag actttgggcc ttggtgtatc aatacgactt ctttaaggac tgaagcctga 272520
gtagctgggg tcagtcaccc aggagctgca tgcctgcatg actgaccccc caagaaaaac 272580
cttgaacact aaggcttgcc tgggtgggct tcccaggtag acaacactta gcatgtgctg 272640
tcacacatca ttgctgggag aattaaccac tgtctgtgca actccactgg gaaagcataa 272700
ctggaagctg gtgcctggtt tctcctagac tttgtccctt ttccctttgc ggattctaat 272760
ctgtatcttt tccctgtaat gaaccatgac caagggtata atggcttttc taagtccttt 272820
gcatccttat aacaaatcat tgagcccatg gctggtctta gggatcctct acacgaccac 272880
caagaccagg aacactgagc tgcagtatac acattgctga gccccactcc agagattctg 272940
attcagtgca cctggggtgg gcttagcagc ctgcctggtt agtaagttcc ccaacactct 273000
gctctgctcc cattcagtga atacaggctg catggctgcc tgtcccctct ccctaccctc 273060
taaaggccag tcacccagtc ctctcaacca tctccacagt ctcatctctt ccttcttacc 273120
ctcctctttg cttcatcccc cagtttcatt ccactcgcca cactgtagcc aaattaaaat 273180
ctgagtctgg cgtttccctt tgggaaggtg ctcagtagct acgtacatgt gttccaaact 273240
cttggtggca ttcagggtct ttcttggcct tttcagcctc ccctctaacc acaacacata 273300
ctgtcccttc cagccttggg gaattccttg cagcctcaga ataggaggcc tcctccatct 273360
gcagtgccct ttgcccccct ctctacatcc tctcctagtc tactcaccag cctggattgc 273420
aattgctcat ttgcttacct gacccccccct ctctatgcca gaacctggca gcttcataca 273480
agtcccttaa taactatatg ttcaatgaat gaatgaatga atgaatgaat gaatgaatga 273540
atgagagtct tgttcatctg agttcccaag gcccagcatg gtgcttggca catgataggt 273600
tcaaataaat gagagatgaa tgaacagctt ttgcacccca ccctcaagcc cacctccctt 273660
cctttgtctc ccctcctttc tgtcattctc ctttatcact gagggtcctt ttttggttat 273720
actctgattc tgctacccag gggcacttct gtggaaagcc tcagctgcct cctgattggt 273780
ccttttacct ccagccccag cagataagga actgagagct tgcagggggc agctgaggaa 273840
gactgcaaat cagtgtcaaa tatctatgta gagctgaact tgatttgaac ctcccataag 273900
cccagggagg gtggcaatat tctcatcaat ttacagatga ggaaactgag gttcagagag 273960
gttgagtgtt tgcacatagt agcttgatag cagagatggg atgagaacac agaccttcag 274020
ccatacatct ttgtgctctt ccttttagcc agacaccagg ggccttgaag gccacaaaaa 274080
aagtattttg gcctttggat agttcagggc tacattccct tcgccagtct tgtcttctta 274140
aattgctact tttgatgctg actgatctcc agccccaggt aaaatacaca cagttttgtc 274200
actatgtcaa gcagaaacaa gttcagtgct gggaaaggaa gtcaaactct ccttggaaaa 274260
agtcagatgg gacgtactac ttttaggccc agctggatgt gcaaggagag agcccccaga 274320
cccctgccac aggcgccagc tccctcacca gcagggtgca ccagtgtttc tccttcttcc 274380
cagagacctt gctctgcctg ataaagctcc agctcttggc aggcactcaa ggccttcact 274440
atctcactgt gactgtaggt cagacacatt ctagattgac agaatatcgc ccatggggct 274500
gaaacccaca aaataccttc agtgttggcc agagggacta tggggtttgg gttggcccat 274560
ctctttggga acagctgaac tgagaaatgc aaaccacctt cctgactgcc ccggggagga 274620
ggaatcagca gggtagcatg ggaaacacat ctcgcagcac taggcatgca atggataata 274680
attacatctg gtaaatgggg tatccatcac ctcaagcatt tatcctttgt atcacaaaca 274740
atccaattac attcttttag ttattttgga atgtataagt aaattattat tgactacagt 274800
caccctgttg tgctattaat actaggtcat attctttcta actaattttt tgtaccatta 274860

-continued acaaccccca cttccttacc atcaccccac taccccttcct agcctctggt taccatcctt 274920
ctactctatc tccatgagtt cagttatttt aacctttagc ttctgcaaat aagtgagaac 274980
atgtgaagtt tgtttttctg tgtctggctt agttcactta acataatgac ctccagttcc 275040
atccatgtgg ttgcaattga cacatagacc aatgaaatag aatagagaac ccagaaataa 275100
attcatacat ctacagggaa cttatttttg acaaaattgc caagaataca cattgtggaa 275160
aggacagtct cttcaataaa tgtttctggg aaaattggat atccatatgc agaagaatga 275220
aatcaagccc ctatctcttg ccatattaaa aaatccaatt ttctcagcat catttattga 275280
agagactgtt ctttccacaa tgtgtattct tggcatctgt ttttatgcca gtaccatgtc 275340
gttttgacta cttagctctc tagtataatt tgaagtcagg taatgtgatt actctagttt 275400
tgttcttttt gtttaggata gctttgtcta tgctgggtct tctgtaattt catataaatt 275460
ttaggatttt tttctatttc tgtgaagaat gtcattgatg ttttgataga cattgcattg 275520
aatttttaga ttgctttggg tactatggac attttaacaa tactgattct tccaatccat 275580
gaacatagaa tatcttttca tttcatttgt gtcctcttca atttcttgta tcagtatatt 275640
gttttcattg tagagaactt ttacttcttt ggttaattcc tatgtatttt attttatttg 275700
tagctattgt aaatggaatt aatttcttga attctctttc agattgttct ctgttgacat 275760
atagaaatgc cactgaattt tgtatgttga ttttgtatcc gacaacttta ctggattagt 275820
ttatcagttc taatagtttt tttgtgtgtg agtctttagg gttttccaaa tacaagatta 275880
tgtcatctgc aaataagaat aatttgactt cttcctttcc aatttggatg ccctttattt 275940
ctttctctta tctgtttgct ctagctagga tttccaaagc tatgttgatt aacagtgatg 276000
aaaggtgatg aaagtgggta tgcttgttat gttccagatc ttacagaaga ggctctcagt 276060
tttctcccat tcagtatgaa actagctgtg ggtctgttgc atatggcttt tattatgttg 276120
aggcatatgc cttctattct cagtttttca agggttttct aatcaggaat ggatgtgaaa 276180
ttttatcaaa tgcttttcca gcattcattg aaatgatcat gtagttttgt cattcattct 276240
gttgacatga tgtatcacat tgattgattt gtgtaggttg aactgtcctt ccgggatgaa 276300
tcccacttgg tcatgatgaa tgatcttttt aatgtgttgt ggaattcaat ttgctaatgt 276360
tttattgagg atttttgcat ctatattcat cagtgatatt ggtctgtatt ttttgttctt 276420
taatgtatct tcagttttgg tatcagggta atactagcat tgtagaatga gtttggaagt 276480
attccctcct ctatttttgg aatagtttgg gtaaggttgg tattagttct ttagatgttt 276540
ggtagaattc agcattgaag ccattggttc ccaggctttt ctttgctggg ataattttta 276600
ttgctgcttc gatttcatta tttgttattg gtctattcag gttttggatt tcatcatggt 276660
tcaatcttgg taggctggat gtatctagaa atttatccat ttttagtagg ttttcctatt 276720
tctttgcata tagttgctta tgatagccac tagtgatcct ttgaattttt gcggtatcag 276780
ttgtaatgtt tcctttttca tctttgattt tttttacttc ggtcttttct ctttttttct 276840
tagtcttagg ctaaaagttt gtcagtgttg tttatctttt aaaaaaaaca acttttcatt 276900
tcattgatgc tttgtatagt ttccttcatt tcaatttcat ttatttttgc tctgatcttt 276960
cttatttgtt ttcttctact aattttgggt ttgatttgct cttgcttttc tatttcttta 277020
aaatgtattg ttaggtggtt tatttgatgt ttttctactt tttaaaagta gatgtttata 277080
gctgtaaact ttcctcttac tactgctttt gttgtatccc ataagttttg gtgtgttttg 277140
tttccattat catttgttcc aagaaatctt tcaatttcct tcttaatttc ttcattgacc 277200
cacagcatat tatttaatct tcatatattt gtatagtttc caaattttct gctgttatta 277260
atttctagtt ttattccatt gtggccagag aagatgcttg atattatttt agttttttg 277320 agtgttttaa gacttgttgt gtgacctaag atatgatcta tccttgagaa tgatcaatgt 277380
gctgaggaaa agaatgtgta ttctgtagcc attggataaa atgttctgta aatatctatt 277440
aggtccattt atctacagtg aagatgaaat tcaatgtttc tatgttgatt ttctgtccag 277500
aagatctatc caatgctgaa agtagggtgt taaagtctcc agctattatt gtattgggtc 277560
tatctctctc tttagctctg atagactttg ctttatatat ctgggtgctc tagtgttggg 277620
tgcatatcta tttaaaattg ttatatccta ttgctgaatt gacctctctc tctcgttttt 277680 tttttgttt tgtttttttg tttttttgat ggagtctcac tctgtccccc aggctagagt 277740
gcagtgttgt gatctcagct cactgcaacc tccacctccc agattcaagt gattcgcctg 277800
cctcagcctc ccgagtaact gggactacag gcacgcgtca ccacacccag gtaatttttt 277860
tgtattttag tagagacggg gtttcacaat gttggccagg atggtctcga tctcctgacc 277920
tcgtgatctg cccaccttgg cctcccaaag tgctgggttt acaggcatga gccaccgtgc 277980
ccagccctga attgatccct ttatcattat ataatgacct tctttgtctc ttcttatagt 278040
ttttgtcttg aaatttattt agtctgttat aagtatagcc actcctgctc tttattagtt 278100
tcattggcat ggaatatctt tttccatccg tttattttca atctgtgtgt gtctttgtag 278160
gtgtagtgtg tttcttgtag gcaataactc attgggtctt tttttttaa tccattcagc 278220 tactctttca ttggagagtt tagtccatta acattcaata ttattattga tcaggcctac 278280
agggcgtaag gacttactct tgccctttc ttatttgctt tctagttgtt atggtcttct 278340
ctttcttctt tccttccttc cttcctttct tccttttggt gaaggtgatt ttctctggat 278400
gtaaaattta atttcttgtt tttgtgtgtg tgtattcatt gtatgttttt ttgatttcag 278460
attaccagga ggcttgcaaa tactatctta taacccatta ttttaaactg atgacacctt 278520
tatattgctt gcataaagaa gcaaacaaat aagcaaaaag aaaacacaaa aactttacac 278580
tttcactttg tccctcagcc ttttaacttt ttgttgtttc tatttacatc ttattgagct 278640
gtgtcttgaa aagttgttgt agttattatt tttgtttggt ttatctttta gtctttctac 278700
tggagtcatt tacacacaat aattacagtg ttatattctg tgtttttctg tgtacttact 278760
attaccactg agttttgtac cttcagatga tgtcttattg ctcgctaata tccttttgtt 278820
tctgattgag gaccttcctt tagcatttct tgtaggatag gtctggtgtt gatgaaatcc 278880
cacaactttt gtttgtctgg gaaagtcttt atttctcttt caggtttgaa ggatattttc 278940
gctggatata ttattctagg gtaaaatatt tttttcttca gcacttaaaa tatgtcatgc 279000
cagccaggca cagtggctca cacctgtaat cccagcactt tgagaggccg aggcgggtgg 279060
atcacaaggt caggagttca agaccagcct ggccaacatg gtgaaacccc gtctctacta 279120
aaattacaag cattagccgg gtgtggtggc agacacctgt aatcccagct actcaggagg 279180
ctgaggcagg agaattgctt gaacccaggg ggcagaggtt acagtgagcc gagatcacgc 279240
cactgtactc cagcctgggt gacagagcaa gactcggtct tgaaaaaaaa aaaaaaaaaa 279300
aaaaaaaaaa tatatatata tatatatata tatatatata tcacaccaca ctctcctggc 279360
ctgtaaggtt tccactgaaa gtctgctgcc agatgtatta gagctccatt gtatgttatg 279420
tgtttctttt ctcttgctgc tttaggatcc tttctttatc cttgaccttt gggagtttgc 279480
gtattaaatg ccttgaggta gttttcttta ggttaaatct gcttggtgtt ctataacctt 279540
cttgtacttg aatatttata tctttctcta ggtctggaaa gttctctgtt attatccttt 279600

-continued

```
tgaataaact ttctacctct gtctattttt ctacttcctc tttaaggcca ataactctta 279660
gctttgccct tttgaggcta ttttctagat cttgtaggca tgcttcattt tttattttt 279720
tgtctcctct gtgtattttc aaatagcttg tcttcaagct cactaacttt ttcttctgct 279780
tgatcaattt tactattaag agactctgat gcattcttca ttatgtcatt tgcatttttc 279840
aactacagaa tttctgcttg attcttttta attatttaat catgttaaat ttatctgata 279900
gaattttgaa tcctttctct gtgttatctt gaatttaagt ttcctcaaaa ccactatttt 279960
tttttttgt ttttttgag acggagtctc gctctgtcgc ccaggctaga gtgcagtggc 280020
gtgatctcgg ctcactgcca gctccgcctc ctgggttcac accattctcc tgcctcagcc 280080
tcctgaatag ctgggactac aggtgcccgc caccatgcct ggctaatttt ttgtattttt 280140
agtagagacg gggtttcacc atgttagcca ggatggtctc gatctcctga actcgtgatc 280200
cgcccacctt ggcctcccaa agtgctggga ttacactatt ttgaattctc tttctggaag 280260
gttacatatc tctgtttctc taggattggt ccctggtgcc ttagtttgtt tgatgaggtc 280320
atgttttcct ggatggtctt gatgcttgtg gatgttcatt agtgcctggg cattgaagag 280380
ttaggtattt actatagtat tctcagtctg ggcttgtttg tactcatcct tgggaaggct 280440
ttccaggtac ttgaaaggat gtgggtgtta tgatctaagc tgtatctgta ttaggggact 280500
ctccaagccc agttatgcta tggtgcttga agactcatag aggtattgcc ttggtggtct 280560
tggataagat ctggaagaat tctctggact accaggcaga gactcttatt ctttacctgt 280620
aatttctcct aaatagtttc agtctctctt tctctctctc tctcgctctc gctctctcgc 280680
tctctgctga gccacttgga gctgggagtg ggctgacaca acatccctat ggccaccacc 280740
actgagactg cactgggtca gacctaaagc cagcaaagca ctgggtctca ctcagggccc 280800
actgtcaaca ctacctggct atcgcctatg ttcactcgag gccctggggc tctacagtca 280860
gcaggtggca aagccagcca ggcttgtgtc cttcccttca gggcaacgag ttccctcagg 280920
ccctggtggg tccagagatg ctgtctggga gccagggact agagtcaaaa accttagaaa 280980
tttacctggt gctttattct atgatggctg agctggcact gaaaccatga gacaaagtcc 281040
ttgccattct tccttcccca ttccacagga ggaggagcct caccctgtgg ccacctccac 281100
aggcccacag ggagtgctgc caggctactg tcaatgttca cttagggccc aagggctctt 281160
cagtcagcct gtggtgaatg cttctaggcc tgggactcac ccttcagggc agtgggctcc 281220
cctctggccc agggcaggtc caatagcttg tctggtccag ggcttgtcta atagccaagg 281280
cctagaatca gtaaccacaa gagcccattt ggtgctctct gccccattgt gtccagggag 281340
gtacctaagc tgcaagacaa agtccctttt acctttccct ctgcttttct caagtagaag 281400
aagtctctca ccacagccac catagctggg aatatgctag gtctcacctg aagccagcat 281460
gtctcagagc cttactccag gcccaaagca taccacctgg gtatcactgt tggctctgca 281520
gggcccaagg gctcttgagt cagcaggtga tgaatcctgc caggactggg ttctttcctt 281580
caaggcagca gattcccttt tggcccaggg tgtgtctaga aatgtcactt caggagctag 281640
gttctggaat gggggcctct ctactctgac tggtgttcta tcctactgtg gctgagctgg 281700
tatccaagat gtaagacaaa gtcctcttta ctcttccccc tcctctcctc aagcaaaagg 281760
aagaagtcag tttagttgtt gcaagctgcg ctgcctgggg ttgcgggagg ggtggtgcaa 281820
gcactccctt ggctgccctg gctggtgtct ctctaggttg tgtgccacct gagtccactg 281880
gctctgagcc cagcatggca tcaggacttg actaggagtt gaagtcctta tggtctagac 281940
tgcctttcaa gtgtatttag ggccccaggg cataatagcc tgccatgcca aggcttgtca 282000
```

aaacccaagc ctcaagcctc ctaactactg ggatgggtga acccctctgg gtagggctgg 282060
tctaaatgct ccctccatgg gcaggtgtca catgagttcc acctggtttc actttctgct 282120
gtgacagggc agcactgagt tgaaggcaga gtcccacagt tgctgcattc tccctccccc 282180
aggtgcacag attctcagca ccacagcggc cgctgctggg agatgggaga ggaatggcct 282240
cggtgtttca agactgtctc tcctaccctc ttcagtgcct ctttcagtgt tatgaagtta 282300
aacccaggta ctgtgagtcc tcacctgata tttggttctt atgatgatgc tttttggtg 282360
tagacagttg ttaaatttga ttttcctgca aggagaatca ctgatggaga ctgctattca 282420
gccatcttgc tctgcccctc ctccctcact taactttacc tcctaagagc cctgtttcca 282480
aatacaatca catagggtt agggctccaa gtgtgaattt tggggagaca caattcagtc 282540
tatagcattt ggacttggga agagggagga agagaatatt cagaggaagg tcacagtgta 282600
agcaacagta tggaggtggg aaagttcagc tcatggatag gaaaaattga tccaagttgg 282660
cagggcccac agggagatgt ggtggggtgg tgagaggtgg ccacatcaaa agaaccttga 282720
atgccaggct gaggtgggag gcatttcctg tcatgtagaa ggtgccatga ggtggtgggg 282780
agggtaacag gatgaaagga tatttgggag gatggatctg gcatcagtga tgggtagggg 282840
taaggagtga acaaagctgg aggccaggaa actggacaca tggcccagag ttcagggtta 282900
ggctcttcaa aggcagtttc cacactgagt tcccatgtgg atccaagcat acagggggta 282960
gatgatttgg aaaagcaaaa ccattctctt cccattacca cacagtttcc cagctgagct 283020
catcaccaga gtcctacaaa tcagacagtc aacctgcccc aaactcttcc cctagaagct 283080
gtgacccaga aggagtcctc atcgagctgt agcccaggga caccgcagcc tgagcaggac 283140
tgcacctgtt cccccccagg agcctcatct ctgtctggcc tggctttggc ttcaaatgcc 283200
ctcagctttg gcttcaaaaa ctgttgagtc agattcatga gagctctggc cttcttcagt 283260
ttagggattt ttaaatagtt tttttcaagc aggcagtaga tgagctctgc ttgcttacct 283320
ctaagaattg gctagaactc acagaaagct gttatactca tagttatggc ttgattacat 283380
ggaaaggaga cagattaaaa tcagccaggg gaagaaaggc atagtgctgg gtccaggaga 283440
gcaccaggca tggagtgtcc attatccctt ccccatgcag tcagagtgca ttaccctccc 283500
ggctttgcta tgtgccaata cacatggagt attctcagcc agtgaggctc cctcaagcct 283560
cagtgttcag ggtttttatt ggaacttcat caaagaggca tgattgattg tccatgtggc 283620
tgctctcagt ttccagtctc cagtcctttt aggggtgacc taaagcctgg actctaaatc 283680
acatagtcac ttttcctggc ttggctagtt cccactatct ttttttttt ttcttttttt 283740
ttttttttga gacggagtct cactctgtca cccaggctgg agtgcagtgg tgcgatctcg 283800
gctcactgca agctctgcct cctgggttca cgccattctc ctgcctcagc ctcccaagta 283860
gctgggacca cgggtgccca ccatgacgcc cagctaattt tttgtatttt tagtagagac 283920
gaggtttcac catgttagcc aggatggtct cgatctcctg accttgtgat ccgcccgcct 283980
cagcctccca aagtgctggg attacaggtg tgagccaccg cgcccggccc ccaccatctt 284040
attattagac tatccatcat gacccaagat ccccaggcaa agatattcct atcaggcatt 284100
acgtgttgaa gattacctcc caggagtcta ggacaaaagc cagacctttt tttggtcaag 284160
cttaattttt taacatgtca tcattctgtt atccttccta tctgttttat cttcaaaata 284220
accctaattg atgggttatt ttggttatct ataataaaca taagaatgtt tattatagat 284280
gagatctcaa aggaaggac acttgagcaa agttgcacag ttgatccttg actcatggta 284340

-continued caagactctt tccactactc tgagagccct gagtcctgag aagaagatgg aaggaaggtg 284400
ggtatacgtg tgtgtgcacg tgtgtgtgtg tgtaaatgta tttctaatga gtatgtgtgg 284460
atatatgtgt gtctctgtgt gtgtgtatac atgtggaggt ctgtgtgtct atatgtatgt 284520
ttgtgtgtgt gtgtgtgtgt gtacacatgc tcagggggaa ggttaaagag aaaatcagca 284580
gggtgcagtg gtgcacacct gtaatgccag ctacacaaga ggtagacagg ggaggatcac 284640
ttgagcctgg gagtttgaga gagagaaaat ttcaataatc ttcttcttgc agttagaagg 284700
aaaaacctgg ggctgagcat aaagagacat aaagcacagc ataaagaggc agagaaatgt 284760
ctaagggaga acaagtgacc aagaattaat tagttcatct ataaagaaat agagcacttt 284820
agcagcagaa taaaactgga agataatttc ctctagagcc ctgataatct ttgtgagaaa 284880
actgttggtc acattaattg caaaaacttg caggactctc tgcaacagaa ctggctagta 284940
aaaccatctt tataaaactc actatgctac aagtggcatt caactctttc tcaaccaaga 285000
tttcacaaac ctatctccag cttccagatg gtgagggaaa gtgtgatgag actttatgat 285060
aaattgtgcc tgtctctgag cccatctcct cccgttgaag aggaggaaaa tgaggatagc 285120
acattataac cctgcctgac aaaagtcaca agataagcaa ataattatta ttaaaaccag 285180
agagtcctat aatttattca tgaatcccac acattctata ttagatcttc catttcaatt 285240
tcttgtattc tttgaagcaa atttataaga tttgaattat tcagaaaagc tcccaagcta 285300
atataagaaa acactttaac cacaggaagt atcatgctac acaatatggt gtggtggtga 285360
agggtgcagg ctctaaaacc agaaaaccca ggttcaagtc ctggccctac caccttggga 285420
gagttacatg gtctctctgt gcctccattt ccccatctaa aatgtgggga tgacaataat 285480
agtgtctatt tcacagagtt gttttgagga aaataatata tgtaaagcac tgtgaacagc 285540
agtcagtgct atgtaagtgt ttgctctagt tattttaaca ttttggatta taaatatcta 285600
ccctgttatt cagatgacaa gcatccctaa gctgataaca tgatgaagag ctcttgtgtt 285660
ccttgatttt ccctcagctt tgtgaggaaa agaataccac atgaagaaga acaactcaag 285720
caggggtgag aaggaaactt ggcttaagtt tggggggctt gagtttatta ggcttttgtc 285780
ttctaaaaat ctcctaagct tcattgataa gatgtttaat atcaatctag ctaaaaagga 285840
ccaatatacc ccacaaaaca ctgagttaga cataaaaaca gaagggtaat aaatgaaata 285900
tggaaaacta cacaaccaga aaaataaaca actaccagta cccaaaacat ggctaaatct 285960
cacaggatta tgttgagtga aagaagccag ccacaaacct gcacatactg aatgatccca 286020
tttatatgaa gttcaagaac aggtgaaact aatccatggt gacagaggtc aggatcctgg 286080
ttaactttgc agggacagca actaagaagg cgcaagaggg agccctctgt gctgatggga 286140
acattctgta tcttgagctg agtggcggtc acatgagtgt gcacatatgt aaatagtaag 286200
gagttgtagc ttaaggtata tgcacctcgc tgtatgtaag atactgtctt agtccatgtg 286260
tgctgctgta acaaaatatc tgagactggg taatgtgtaa agaacaaaaa tgtatttctc 286320
acagttctgg tgggtgggaa gtccaagatc aaagcgccag caggtttgta gtctagtgag 286380
ggctgctctc tgcttccaag atggcacctt gaatgctgag tcctccagag gtgagaaacg 286440
ctgtgtccca gcatggtgga aagaacagaa aagcaaaaga agaaaactga gctaggtcgc 286500
tccctcaagc cctttcataa ggtcgctaat cccattcatg agggggctcc tccctcacga 286560
tttagtcatc tcctaaagac accacccctt aatactatca catgggggtt taagttccaa 286620
catgaatttt ggaggagaca caaacattcc aaccatagca aatatacttt actaaaaaga 286680
aaaaaaaagg aaaatcttgt ctctaaacat gatattttaa gtgtttatat atttacagcc 286740
caattttctg cttgcttaca tagatatttg tgaccatgag tgtcattctt agctgagaaa 286800
atgttcagta aatttaaaaa agcctcacat tatctattaa tatcttactc agataagatc 286860
aaatttctaa cctagatttt aggttaagat agaaacccat ggtcatttgc tgcaatgtga 286920
gaatgacaca gagagatatt aattagcaga attccactat aaaactaaat ttaagggcac 286980
agttctctac taatgactcc tccagacaaa tcaattactt ggatatcaat gaatcaacta 287040
aaaatggaag tgagaacagt ttgagtcctt tttgcaatgg atggatgttt acgagactat 287100
taagtgaaga cggttcagaa acaaggagat aaatggcatg ctaatttggg gttgaatgga 287160
gtaatggggt gatcttggaa atataagaat cctgcttaat ggggcttgtc tgcttgtaat 287220
ttgataaact aatatatgta aattcaatga gataaaggac atgagcactc agaacaaaat 287280
tacaggaata aatttagcaa agaggcacca aagttgagat aagggtcact gttccacgtc 287340
tgacatcttt aattcttgag tcatggggat ggtaagccag agaacagagt cttctgactg 287400
gaagctaaaa ccagcctttg gggtgggttc agagacactg ttcagactca agatgcgaaa 287460
gcagatgttg ccctgttgaa aatatcccaa ttgcaagggc attttcaaag acagtggtgc 287520
ttgggggaaa gagaatgctg tgtgtttaaa aagaaaataa attaaaagaa agaatggaaa 287580
caaggaagaa aaagtgaccg gagggtaggg ttgcaatatg ttctggtttg caaggtacag 287640
ctaaggttat gtctgttgtg ccggtgcaat tataatagtg tccctttcac tctccgaaga 287700
atttggatga taaagcatat gatcacccta ccaaagagag gaaatgagcc agacgaccca 287760
tgtgtctatt tcaaacagtg tggactgatc cgcagccctg tgccactgcc cagatgagcg 287820
gtgtgcacaa cctctgcctt gccctacccc gccctgctcg ggtctccagg aaggctggag 287880
cggaaccctc ggctcccgcg ctgctctggt gccacctgca ggttatatgc gggaactgct 287940
tctctccacc ctactaccct ccacccagcc tcccgacccc gaccctggat agccttggac 288000
ttggccaaaa gacattcaga gcacacgaag ccctggctgg ggagtgggct ggaccctgca 288060
atgaagcccg cgttacagaa tcagacgagc ccagcttaaa ccaacaaggc caagctcctc 288120
ctcttcctac ccactcctgt cctgtctcat tttgtagacg ggaaactgaa gcctaattca 288180
gatttttcgt tggtaggatt gtgaagcata cagctggagc ctcccaggtg ccattcccca 288240
catctgtctt tccgctacca ctttaggata gtgaggaagc aagagagctt aagcttacta 288300
agctcctact gtgtactggg cacagagtgg acacttttct ctccagcctc gcaattgatg 288360
ggaaagaggt gattatacaa ctaggagaca ggatcagagt gggctagcga tgtgcttaca 288420
gtctctcagc tgaaactgga acccaggggt ctttgactgt aaagctagtg ctcgttttgg 288480
gtctccagct tgagcaatag ttgcaaaatg caaagagcac ctgaaaatct aatatcaatc 288540
catataagac tgtattgtaa acagaaacat ggagtgtctt tgtgggggtg atggcaaggt 288600
ggggagatta tctcaattct atgtaacctg ggaactcttg gaggaaaatg aagcatgact 288660
gagtgcaatt tgtctgataa acaaaatctg tcaggacgtg ggaccttatt ggtcctgggt 288720
agtgaaggta agaaatcatg gtgctggacc tttcttaaag tgcttataaa atcactcagg 288780
gcctcagtgc ctccaccttc tccatgaccc caggcagttt ccccatctgt cttcatccta 288840
ctgcctggca cactatccat caaactgctt ttggggttat gtctcaataa aacaaaaatc 288900
atggtgggag tcatttacac cctagtgaga gtcatctaag attccctttt cttctcagac 288960
cttttagctg aagttggtta tgagagagga tggggagggg gaaaagggtt ggggcgagca 289020
ctcttggagc ttgcactgtt tcttgccggt gcccaggcac aatgcgaata tgtcagtcta 289080
aatggagagc tccatgcatg ttcctctcta atccgtttgt caccaatacc agttcccaag 289140
gcagagcccc aggagggctg gactgaagga cctggaggta atagaaaaca acttggcttt 289200
gggtttcagg tcaagctgtg ccatgacttg ctgtgtaaca tcagacaagt cagttcacca 289260
ctctgcactt cagtgacctc atctgtaaaa ggctggtctg gactagatta atgattttct 289320
ttaggttttg caattgtttt gttgttgttg ttttgttttg ttttgttttg aaacggagtc 289380
tcactctgtt gctcaggctg aagtgcagtg gcacgatctc agctcactgc aacctctgcc 289440
tcctgggttc aagtgattct cctgcctcag cctcccaagt agctgggatt acaggtgtgt 289500
gccaccacac ctagctaatt tttgtatttt tagtagagat gtggtttcac tacattggcc 289560
aggctcatct ccaactccca acctcaggtg atccacctgc ctcggcctcc caaagtgttg 289620
ggattacagg cgtgagccac cgcacctggc ctgcaattgt tttttgtttt aacattatat 289680
tcaattcttc ctccatcttt attaaagtat aattgataaa taaaaattgt gtatgtttac 289740
agtgttcaat gtgatgtttt gatatgtgca tacattatga aatgattaaa tcaagttaac 289800 atttttcatca cctcacatac ttttattatt atttttgtgg taagaatatt taagatctat 289860
ttgcttagag tagtgtttac tagaggtgag gaagggtaag ggagaggggg tagccaaagg 289920
ttggctaaca ggttaagaga tacaagagta catggctggt ggctaacgcc tataatccta 289980 ccccttttagg aggctgaggt gggaggatca cttgaaacca ggaatttgag accagcctgg 290040
gcaacatagg gggatcccat cactataaaa aatttagaaa ttagccaggc atgttggtgc 290100
atgcctgcgg tcccagctac tctggaagct gaggtgggag gatcacttgg gcccaagagg 290160
tcaaggctgc agtgagctgt gattgcacca cttcactcca gcctaggggg cagagtgaga 290220
ccctgtctga aaaagcaaaa gacaaacaaa caaacaaaca aaaaacccca gctagatagg 290280
aggaatagtt ctagtgtttt tttgcactat agggtgatga taattgatga caatttatta 290340
tatattttcg aatagctaga agagtgcatt ttgaatactc ccagaacaaa gaaaggataa 290400
atgtttgagg tggtggagat gctaatcgcc ctgatttaat tattacatat tgtatacatg 290460
tataaaaata ttatactgta ccccacaaat acgtacaatt attgtgtcaa ttaataataa 290520
taaaagcaaa aaatcttctt ttagcaattt tcaagtatat attattatta actatagtca 290580
ttctgtacaa cagatctcca gaacttataa cattatattt aatttcaatc aaagcgctag 290640
atacacagag ttaagaacaa aatggggctg ggtgcggtgg ctcacccagt ggattacgcc 290700
tgtaatccca gcactttggg tggatcacga ggtcaggaga tcgaaaccat cctggctaac 290760
atggtgaaac cccacctcta ctaaaagtac aaaaaaaaaa ttagctaggc ctggtggtgt 290820
tcgcctgtag tcccagctac tccggaggct gaggcaggag aattgcttga acctgggagg 290880
cggaagttgc agtgagccaa gatcatgcca ctgcactcca gcctaagtgc cagaatgaga 290940
ctttgtctca aaataaataa ataagtaaat aaaaataaaa ttttaaaaag gaacaaaatg 291000
gtatctggag caagaaatcc tcagtacaaa aaaaaaagga agaagaaaaa agaacaaaat 291060
ggtaataata ggcttatatc aaaaagcatt tcctatgccc tttcttttct tgcctttgtg 291120
ttgggagaaa ggctgagtgc tgggagagaa gccgaggtgg gcttggaaca tgtccggggt 291180
ccggggtccg gggtctaaaa cctctcatgg cctttggaat gtgtctagac ttgctggctc 291240
cttgcttcta gcactcccat tatctcaagt agccatatgt ttcaaagaaa atgctacacc 291300
atcacagctg tagcttatat gcttgatatg tcacttcctt tcaaccccca catcctcacc 291360
acctgcttct ttttttgatc accaataaat agtgtgggct cccagagctc agggccttca 291420
cagcctctat actagtgttg gccccctggt cccactttct ctctcaactt gtctttcctc 291480

-continued attcctttga ctccaccgga ctttgtagcc cccacgtcct ggtgttgagt ctgatcaccc 291540
caacaccttt gtatcctaat tcccagaggc cgtcacttta aattcatttt gctacttcct 291600
ctggtatttg catcatattt ctaaagaatg tttacgttgc tatttcttga tttgttttct 291660
tcagtatctg tctacttcct ggaatagcac agtatagggc ttacctccct tatgaggtct 291720
taacagtttc cttgcctcca ttctaccaat ttcactggat caaaatcttg tgaaatcaaa 291780
agcatttaca ttcttgtaga tatctaaatt ttgtttccta agccaagtcc tgcactgaaa 291840
ttgtttcatt tcttcctttt tttccccctg gagttaataa ttgcttcaaa ttttttccct 291900
tcgtttgctt atatgttttt gtacctatta actacctttc tttcagttac tccaactgat 291960
ctatgaaatg cctggtaata attatctaaa actaagatac acgagctact ctatcagccc 292020
tgttattttc ctggaggctt ccctctctcc cttgccctcc atccttatgc tccaaactgg 292080
actcagctct cagcctgtgg catggctggc attctgacat gtctctgcac cattgtgtga 292140
atttcctgct gcctcttctg tgtgcatctc ctgttccctt gccccagatc ttctttttcc 292200
ctggttcact gtctcattat gttgcagtac atcttccagt ggcttcctga aaagcagtga 292260
atggaagcca agctttctta ccttcacata ttttagaatg tcattgttct accccaactc 292320
ctgattaaca gtttggctgg atataatgct ctaatttgaa agtaacttct cacattggga 292380
aatactgctc tattattttc tagttcccag tgttgttggt aagaagtcag tatcgtgcag 292440
aatcttggct ctttacatgt gacctgtctt ttctctctgg aagatattag gatttctat 292500 ctttggattt ctcaatgatg tgccttgttg taggtctttc ctcattcact ttgctagtca 292560
cttggtagac tcttttgaat tagaaaattt tgtgcttcta ttgcgggaag ccacgagcag 292620
gtttgagtga gctgggtaat cacattcttt tcttccaagg acagaggtat caaggccctg 292680
ggaaccttat aagtggatgg ggagaaaggg ggcctgaggt gaatccaaca aagctgcagc 292740
atcctctgag ctcatgtccc aaggctaggc tctgcctgag gacaggagac atgggtgaga 292800
cccacttcct gcccagtctc atagtggggc tcaggacaca catggtccag gaggttccca 292860
gccccagcta catttacatg cacctacctg catgcagcaa tcagtgagcc acaggacaac 292920
ttaggggaag gggcagctcc agagagcagg ataggaggga ggtaaatgat tatgggtggg 292980
gagtggcctt gtgaggaagg ggcaaagtca gggctctgtg tgtgtgtgtg tgtgtgtgtg 293040
tgtgtgtgtg tgttgtgttg tgtattgggg gaaatgggga gaatattttg tctgccccct 293100
tttctggcca ctgcacccct tttttcatga atagtttttc ttcccatcat ggactgagtg 293160
tctctgtctc ctccaaattc atatgttgaa gccctaaccc tctgcatggc tgtatttgca 293220
gatgaggcct ctcaggaagt cattaagttt gaatgaggtc ctaagggtgg ggccctgatt 293280
cagtaggatt agtgtcctta taagacaaga caccagaggg tgcactcact ctctctctgc 293340
acaaatacaa agaagaggtc acatgagtgc acaatatggc agccacctac aggccaagag 293400
aagaggcctc agaatgaaac ctaccttgct ggcactttgg tcttggattt cccagcctcc 293460
agaaccgtga caaataaatg tttgcagttt aagccaccca tctgtggtat tttggcatgg 293520
caccctgaac tgactaatac atctcccggc cctgcttcaa ccacatgaca ctagagggct 293580
tggcagtttt agcgtcccag ctacccagcc aacccagacc agaccaagca gaaactttct 293640
tctggaattt ttttgtttgt ttttttgaga cggagtctca cactgtcgcc caggctggag 293700
tgcaatggca caatctcagc tcactgcaac ctccgcctcc tgggttcaac tgattctcct 293760
gcctcagcct cccgagtacc tgggattaca ggcatctgcc accacgcccg gctatttttt 293820

```
gtatttttag taaagacaag gtttcaacat gttggatagg ctagtctgga actagtgacc 293880
tcaggtgatc cacccgcctt tgcttcccaa agtgctggga ttacagtcat gagtcaccac 293940
accgacctat ttaagctgat tctttaaggg tgagtagaaa ttttttccag gtgaataaaa 294000
ccttgagata ttccaagcag agaccagcag gtgcaaagac acagggatat acagatgttg 294060
aaatttacca accactgcta gattagaaaa aacaaaaagg aaacaatcaa aataaaaatt 294120
taaaattaaa aatcacctaa aaaaaaaact aggaatgggc ttggccagag gtcacattgc 294180
aattgagtta actatgacca tagacactca gtaatggatg gaagttttag ggaaaaacat 294240
aacattctca ggttgttgca gagtatctag aacaatttag aaatacaggc attgaattct 294300
gggaatagtt acactgtagt gaaatcatgt ccttctctgc atatgaagca tatatgtgtc 294360
acactgttca aagtgctgaa aatcagactc ttctcaagga gctcatgagc aatcaaggga 294420
gatggatggg ggagcaactg attatcatgt gacaagtgag gtaatagaga tatgactaag 294480
atgctatcaa aacaagaata aaggaattat tcataatata tggagtgctg gggaaagatt 294540
tctcaaatga agccagctgg gcgtgatgtc tcacacttgt aatacccaca ctttgagggg 294600
tggaagtggg aggatccagg aggatctagg agttcaagac cagcctggtc gacagagcaa 294660
ggccctgcct gactctatat ttgaaaaaaa aaaatttttt ttaaataaag tgatatttga 294720
gcactctgga gcaccataca aatataggac agacaaggaa tgtatccagc ttaatttggg 294780
ttaacatttt tttgaaattt tatattgcaa aaatagtaca tattcactgt tgtgaaatta 294840
ggaaaaattg ataggcaagg agggaggtct acaaagctct ccatagatcc actgtactga 294900
gacaatgctt aatgctttga tggatttatt gtatactttc tatgcatatg catgtaatgt 294960
atacatacat gtgcatggtt aaatagacat ggttctcctt ggtgttctgt ttatccatgt 295020
attgttatga agtaaatccc caaaaagtac atttgctttg cccaagggag tcttttgcta 295080
catactgctg tacataagga aaactaaaaa actggctaac ttttcagcct tgtgaccttg 295140
tggtgattca gatagaggct tcatcaaagg cagattcaga aatgaacttg gtgtgtgtgg 295200
gtggttatgc ttggcattat tgtttgtagt agtatgatag ggatgacttc agtgtccacc 295260
aacagggaac tggttaagtc aactgtggta catccaaacg atgaatactg tgcggttgta 295320
aagaagaatg acaaagacct ctgaactcat gtggaagaac ttggatatat tgtgtgtgtt 295380
ttttaaagga acaaggaatg ctatagtatg tatggtatgc tactttttgt gttgagagag 295440
aagagtagaa taagaacata catttgtatt tgcaaagata aattctgaaa tgatatataa 295500
gaaaccaatt aaaagtgttg gctgtggaag gagaataaga ctgtgaatgg gattttgcca 295560
catactttta tagatagtta tatttaaatt ttttctgaac tatgtatttg tacacatgac 295620
ccttttaaaa ataagcaaat gaacgaatga agtaggatta tgcgaaagaa ataagaaaaa 295680
aggatctaag gggctgccca actttttagt acccagtgaa tattaatata taacaatagc 295740
agcaaaaatt ggaagagtag ccccaggagg gtagggagtc agccattcct ttgtcttttc 295800
ctaaatttca tatattttta aaaagtactc tgagaacaat aaaataattt gaaacaaata 295860
tgtctccaga tctcttaaaa taaaaggagg atagggcagc tttatgtagt gcacttccca 295920
aaaattgact gatttacctc aagaggcagg gattctagca tacatgggat acatacagga 295980
gaaaaaaata agaaaaagaa aagagattta catataaata aatgaaaata acacttcttc 296040
ctgattataa aggaaatcgc attctttttg taataatttg gatgactgat attaagaaaa 296100
atctttaatt tgccactcaa aacattctgg tttgttgctt tttatacttt ttttatgcat 296160
ataaaccttt taaaaactag aatcgtaata tatagtcttc tgtcacttac tatattttgg 296220
```

gcatatttct gtggcagtaa atatatcctg gcatcatttt taatagctgg atgtatatta 296280
agttaatcat tgctattcca gaggtgaatt ttcttatata tacattttaa tggtctcaag 296340
caagcatttt tggactaaat tcatagaagt agaatttctg gaggaaaata atttttaggg 296400
tttttaatag aaattttcaa attattctcc aggaaaagtg actcaggtta tactcccacc 296460
aacaaggaca gagctctagg ttcccctttc catttgtcat ctttgctgcc tttatacaga 296520
aaatctcatt gttttcatca catttctttg gtttctagtg cttttgaatt tttttatacg 296580
cctattggtc atttttattc ttgtgagaag tgcctgtttc tccattgccc attttctgtt 296640
gaaaatcatt tgtttttttc tcagtaattt taaagatttc tttaaagact aaggatacaa 296700
accttttatc tgtcactgag gttacaaaaa ctttctccca gtaagtagtt tgtcatttca 296760
cttgatttcc tttctcgctt tctttttct tttcttttt tcctttcctt tcctttcctt 296820
tgctttcctt tcctttcctt ttgctagcca agctccaaag tcacatttca cttaattttc 296880
atcctgccaa atttgaaaac attttaactt agtgatttta gtgtaaacag gagcaggaga 296940
gagtgtattt aagtcttgtt ctgtcaccca ggctggagta tagtgccata atcatagcta 297000
ctgcaggctt aaactcctgg gctcaagcaa ttttcccacc tcagcatgcc aaatagctag 297060
gactacaagt gtgtaccacc atgcccagct aatttttaaa ttttttttgt ggagatgtga 297120
attcgctatg ctaaccagcc tggtcttgaa ctcctgactt caagtaatcc tcccaccttg 297180
gcttgccaaa gtgctgggat tacaggtgtg aactactgct cccggctgag agtttagttt 297240
tgtttgctag tggcgatctt ggtatctttt catatttgag gctttgttgc tagtgctgaa 297300
gtattacact caccatccaa ggtttaaagg acttttgttt taatattgaa cagatggaac 297360
tgtttagttc tgcatctttg catgtataca aaatgtgcct agcaggactc tgctttatat 297420
cctttgaaag caagaagtaa tacagtaaaa ctttgcctgg ctagaggctt tgaaagaatg 297480
gagtattctg atttaattct attaatttgg aagtatgaaa gtcaaaataa ttcaaaactt 297540
atatttcctg ttgaatgcaa tttgaaaata gagtcaatga ttccactttt cttctctagt 297600
aagtttggac gttctgatct acttggtgtt ttattacaga actgctagtg tgcctgagac 297660
ttacattgtg aagatacttt tttaaaactt gagaggtaag agggtgtaaa tggtattgta 297720
tgagatcagg ctggatgaga actgactctt gtaaatatac tttttagact gaatttctgg 297780
ttgccatctg ttttcttatt taactcataa aaataaaaca cattggatgg agggtgggag 297840
taggaaggag atttatgtct tttaattgca tgtcattgtt tcatatcaag acagaacata 297900
tggtatccct ggctttggac ctacagaagg aaacacattt ttctacctgc tgtatgccag 297960
aggttcttga acacctggag ggatgaccac agcacagatt gctgagccct actccagagt 298020
ttcttgattc accaggtcca gggtggggcc tgagaatttg cacttataaa aagttctcag 298080
gttctgctgg tgctgctagt ccagagacta catttttgag aaccactctt gtctactaac 298140
tgtgaattgt agaactctag aaaaaagctg aggagccaag atggccgaat aggaacagct 298200
ccagtctaca gctcccagcg tgagagacgc agaagacggg tgatttctgc atttccatct 298260
gaggtaccgg gttcatctca ctagggagtg ccagacagtg ggcgcaggtc agtgggtgca 298320
tgcactgtgc accagccgaa gcagggcaag gcattgcctc actcaggaag tgcaaggggt 298380
cagggagttc cctttcctag tcaaagaaag tggtgacaga cggcacctgg aaaatcgggt 298440
cactcccacc tgaatactgc ccttttccga ctggtttaaa aaacggcgca ccaggagatt 298500
atatccctca cctggctcgg agggtcctac gcccatggag tctcgctgat ggctaccaca 298560
gcagtctgag atcaaactgc aaggcggcag cgaggctggg ggaggtgcgc ctgccattgc 298620
ccaggcttga ttaagtaaac aaagcagccg ggaagctcga actgggtgga gcccaccaga 298680
gctcaaggag gcgtgcctgc ctctgtaggc tccacctctg ggggcagggc acagacaaac 298740
aaaaagacag cagcagcctc tgcagacttt aatgtccctc tctgacagct ttgaagagag 298800
cagtggttct cccagcacac agctggagat ctgagaacgg gcagactgcc tcctcaagtg 298860
ggtccctgac ccctgatccc cgagcagcct aactgggagg caccccccag caggggcaga 298920
ctgacacctc acacggctgg gtactccaac agacctgcag ctgagggtcc tgtctgttag 298980
aaggaaaact aacaaacaga aaggacatcc acaccaaaaa cccatctgta catcaccatc 299040
atcaaagacc aaaagtagat aaaaccacaa agatggggaa aaaacagagc agaaaaactg 299100
gaaactctaa aaagcagagc acctctcctc ctccaaagga atgcagttcc tcaccagcaa 299160
cggaacaaag ctggacggag aataactttg acgagctgag agaagaaggc ttcagatgat 299220
caaattactc cgagctatgg gaggaaattc aaaccaaagg caaagaagtt gaaaactttg 299280
aaaaaattta gaagaatgta taactagaat aaccaataca gagaagtgct taaaggagct 299340
gatagagctg aaaaccaagg ctcgagaact acgtgaagaa tgcagaagcc gcaggagccg 299400
atgcgatcaa ctggaagaaa gggtatcagc aatggaagat gaaatgaatg aaatgaagca 299460
agaagggaag tttagagaaa aaagaataaa aagaaatgag caaagcctcc aagaaatatg 299520
ggactatgtg aaaagaccaa atctatgtct gattggtgta cctgaaagtg acggggagaa 299580
tggaaccaag ttggaaaaca ctctgcagga tattatccag gagaacttcc ccaatctagc 299640
aaggcaggcc aacgttcaga ttcaggaaat acagagaacg ccatagagat actcctcgag 299700
aagagcaact ccaagacaca taattgtcag attcaccaaa gttgaaatga aggaaaaaat 299760
gttaagggca gccagagaga aaggtcaggt taccctcaaa gggaagccca tcagactaac 299820
agcggatctc tcggcagaaa ccctacaagc cagaagagag tgggggccaa tattcaacat 299880
tcttaaagaa aagaattttc aacccagaat ttcatatcca gccaaactaa gcttcataag 299940
tgaaggagaa ataaaatact ttacagacaa tcaaatgccg agagattttg tcaccaccag 300000
gcctgcccta aaagagctcc tgaaggaagc gctaaacatg gaaaggaaca actggtacca 300060
gccactgcaa aatcatgcca aaatgtaaag accatcgaga ctaggaagaa actgcatcaa 300120
ctaacgagca aaataaccag ctaacatcat aatgacagga tcaaattcac acataacaat 300180
attaacttta aatgtaaatg gactaaatgc tccagttaaa agacacagac tggcaaattg 300240
gatagagtca agacccatca gtgtgctgta ttcaggaaac ccatctcacg tgcagagaca 300300
catataggct caaaataaaa ggatggaaga agatctacca agcaaatgga aaacaaaaaa 300360
aggcaggggt tgcaatccta gtctctgata aaacagactt taaaccaaca aagatcaaaa 300420
gagacaaaga aggccattag ttaatggtaa agggatcaat tcaacaagaa gagctaacta 300480
tcctaaatat gtatgcaccc actacaggcg cacccagatt cttaaggcaa gtcctgagtg 300540
acctacaaag agacttagac tcccacacat taataatggg agagtttaac accccactgt 300600
caacattaga cagatcaacg agacagaaag tcaacaagga tacccaggaa ttgaactcag 300660
ctctgcacca agcagaccta atagacatct acagaactct ccaccccaaa tcaacagaat 300720
atacattttt ttcagcacca caccacacct tttccaaaat tgaccacata cttggaagta 300780
aagttctcct caacaaatgt aaaagaacag aaattataac aaactatctc tcagaccaca 300840
gtgcaatcaa actagaactc aggattaaga aactcactca aaactgctca actaaatgga 300900
aactgaacaa cctgctcctg aatgactact gggtacataa tgaaatgaag gcagaaataa 300960
agatgttctt tgaaaccaac aagaacaaag acaccacata tcagaatctc tgggacgcat 301020
tcaaagcagt gtgtagaggg aaatttatag cactaaatgc ccacaagaga aagcaggaaa 301080
gatccaaaat tgacacccta acatcacaat taaaagaact agaaaagcaa gagcaaacac 301140
attcaaaagc tagcagaagg caagaaataa ctaaaatcag agcagaactg aaggaaatag 301200
agacacaaaa aacccttcaa aaaagtaatg aatccaggag ctggtttttt gaaaggatca 301260
acaaaattga tagaccgcta gcaagactaa taaagaaaaa aagagagaag aatcaaatag 301320
atgcaataaa aaatgataaa ggggatatca ccaccgatcc tacagaaata caaactacca 301380
tcagagaata ctacaaacaa ctctatgcaa ataaactaga aaatctagaa aaaatggata 301440
aattcctgga cacatacact ctcccaagac taaaccagga agaagttgaa tctctgaata 301500
gaccaataac aggagctgaa attgtggcaa taatcaatag cttaccaacc aaaaaaagtc 301560
caggaccaga tggattcaca gctgaattct accagaggta caaggaggaa ccggtaccat 301620
tccttctgaa actattccat tcaatagaaa aagagggaat cctccctaac tcattttatg 301680
aggccagcat catcctgata ccaaagcctg gcagagacac aaccaaaaaa agagaatttt 301740
agaccaatat ccttgatgaa cattgatgca aaaatcctca ataaaatact ggcaaaccga 301800
atccagcagc acatcaaaaa gcttatccac catgatcaag tgggcttcat ccctgggatg 301860
caaggctggt tcaacatatg caaatcaata aatgtaatcc agcatataaa cagaaccaaa 301920
gacaaaaacc acatgattat ctcaatagat gcagaaaagg cctttgacaa aattcaacaa 301980
cccttcacgc taaaaactct caataaatta ggtattgatg ggatgtatct caaaataata 302040
agagctatct atgacaaacc cacagccaat atcatactga atgggcacaa actggaagca 302100
ttccctttga aaacgggcac aagacaggga tgccctctct caccactcct attcaacata 302160
gtgttggaag ttctggccag ggcaattagg caggagaagg aaataaaggg tattcaatta 302220
ggaaaagagg aagtcaaatt gtccctgttt gcagatgaca tgattgtata tctagaaaac 302280
cccattgtct cagcccaaaa tctccttaag ctgataagca acttcagcag tctcaggata 302340
caaaatcaat gtacagaaat cacaagcatt cttatacacc aacaacagac aaacagccaa 302400
atcatgagtg aactcccatt cacaattgct tcaaagagaa taaaatactt aggaatccaa 302460
cttaaaaggg atgtgaagga cctcttcaag gagaactaca aaccactgct caatgaaata 302520
aaagaagata caaacaaatg gaagaacatt ccatgctcat gggtaggaag aatcaatgtc 302580
gtgaaaatgg ccatacggcc caaggtaatt tacagattca atgccatccc catcaagcta 302640
ccaatgactt tcttcacaga attggaaaaa actactttaa agttcatatg gaaccaaaaa 302700
agagcctgca tcgccaagtc aatcctaagc caaaagaaca aagctggagg catcacacta 302760
cctgacttca aactatagta caaggctaca gtaaccaaaa cagcatggta ctggtaccaa 302820
aacagagata tagatcaaag gaacagaaca gagccctcag aaataatgct gcatatctac 302880
aactatctga tctttgacaa acctgacaaa aacaagcaat ggggaaagga ttccctattt 302940
aataaatggt gctgggaaaa ctggctagcc atatgtagaa agctgaaact ggatcccttc 303000
cttacacctt atacaaaaat taattcaaga tggattaaag acttaaacgt tagacctaaa 303060
accataaaaa ccctagaaga aaacctaggc attaccattc aggacatagg catgggcaag 303120
gacttcatgt ctaaaacacc aaaagcaatg gcaacaaaag ccaaaattga caaatgggat 303180
ctaattaaac taaagagctt ctgcacagca aaagaaacta ccatcagagt gaacaggcaa 303240
cctacaaaat gggagaaaat ttttgcaacc tactcatcca acaaagagct aatatccaga 303300

-continued atctacaatg aactcaaaca aatttacaag aaaaaaacaa acaaccccat caaaaagtgg 303360
gcaaaggaca tgaacagaca cttctcaaaa gaagacattt atgcagccaa aaaacacatg 303420
aaaaaatgct catcgtcact ggccatcaga gaaatgcaaa tcaaaaccac aatgagatac 303480
catctcacac cagttagaat ggcaatcatt aaaaagtcag gaaacaacag gtgtggagag 303540
gatgtgaaga aataggaaca cttttacact gttggtggga ctgtaaagta gttcaaccat 303600
tgtggaagtc agtgtggcga ttcctcaggg atctagaact agaaatacca tttgacccag 303660
ccatcccatt actggctata tacccaaagg actataaatc atgctgctat aaagacacat 303720
gcacatgtat gtttactgcg acatcattca caatagcaaa gacttgcaac caacccaaat 303780
gtccaacaag gatagactgg attaagaaaa tgtggcacat atacaccatg gaatactatg 303840
cagccataaa aaacgatgag ttcatgtcct ttgtagggac aaggatgaaa ttggaaatca 303900
tcattctcag taaactatcg ccagaacgaa aaaccaaaca ccgcatattc tcactcatag 303960
gtgggaattg aacaatgaga acacgtggac acaggaaggg gaacatcaca ctctggggac 304020
tgttgtgggg tggggggagg ggggaggaat agcattggga gatataccta atgctagatg 304080
acaagttagt gggtgcagcg caccagcatg gcacatgtat acatatgtaa ctaacctgca 304140
cattgtgcac atgtacccta aaacttaaag ataataataa taaaaaaaaa gaaaaaaatag 304200 aaaaaagctt agtttggtgt gggaaaagaa gctcacaggt tatggagcaa atcatgtaag 304260
attcaaccct tgatctcagc ctagtgtgga attcaagtaa caagcaatac acagtgacat 304320
aacacaattc ttggttttca tgattgcaag tcatagccaa gtatcaagtg agaaattcag 304380
tttcatttgc aaggcttaga gaggccaggt gattctagaa aaataggcct tgtatatgct 304440
ttaaaccagt aaagagcttt gagtgcttat taaattgaaa gctttgtgtt tttattaatt 304500
ttttactttt tttttttttt gagatggagt ctcagtctgt cacccaggct gcagtgcagt 304560
ggtgtgacct tggctcactg caacttcggc ttccaggttc aagtgattct cctgcgtcag 304620
tctcccgagt agctgggatt gcaggtaccc atgaccacac ctggctagtt tttgtatttt 304680
tagtagagac ggggtttcac catgttggcc aggctggtct tgaactcctg acctaaggtg 304740
atccacccgc ctaggcctcc caaagtgctg ggattacggg agtgagccac tgcacccggc 304800
acaaaagctt tgtgttttta aagatattag acatgtttct tattttttaa aaaaaaaaat 304860
cttaataatg caggaaatta agaaaaactt tttccaaaaa aaagaattca ttgtgattat 304920
cttattggaa tgttggataa tatagtccac ttcattaaac atcaagcatg ctatggattt 304980
tccattttta taggagttgt atctcaattg aagtaacact ggtaattctt gtacttcatt 305040
tgaagatgaa aaatgtaggc caaaatcata gaccttgcat agaagctgga taatgaagac 305100
agctctggtg gaacacgtag acatatgcac actgatacac atatataaaa agtataagca 305160
catatatttt ttaaagttta tttttaaagt tttaaagctt ttaaagcaaa agccggcccc 305220
tcccctctcc tggagtgggc ggcccctccc tgctcctgga gtaggcaggc cccgcccctc 305280
tccccaagtg ggcgggacag cagttgcatg ggcagctttc cttgtgatgc cacaggttcc 305340
tctggacaca ctgctgcctg gccacgcctc ctttcccttt catctttctc actgaccaat 305400
gggcttggag cattaaggcc ccgccccatt ctgcattaca gtgtggccct ggttacacct 305460
cctctggctc agtcacacag ctgcctggta ggtgactgga ggtgttcgct gatgtggccc 305520
taaccctgcc tccctcccca ccccacgatg ttagaagaaa ctcaacagag gaaactggcc 305580
acagccaaga aaaaagtaaa acgcatcaga tcatggcccc cccaacccag ccacagatcc 305640
cctttgatgg caagaccact gccagagtcc ataccagccc ttaggcacac cgggctgggt 305700 cccccccacac tggcacctct gtgctccctc caaccaaagt cttgtcagtc agtcccgccc 305760
cttcagcaag cagctcaggc cctgccctca ccaatcaccc cagggtgact ttgggcgagt 305820
gacttctggg gctcccggct ccatactcag ccttcacatc ctgccacccc aagcccgacc 305880
tccctgagtt ctttgggctc acctctccaa ggacctgggt cccccagccc caggccccac 305940
cctcaccagt catccctggg tgactttggg ctggtgactc ctcgggcttc ctgctgcaga 306000
ctctgctctc ccctcctgct gacccaagcc cgacctccct gggctctttg ggctggtgtc 306060
tccgtggacc tgggtcccag ccctacatcc ccctgctcca ttgtgaatcg gtgactcagc 306120
catcacactg atgttgttcc ctccctcccc taggaggagt ggaatgtagt gatgtcacag 306180
tccccccagg aactgtcatt actgcttcaa gaccggcctt tgatcttaca acccagtccc 306240
ctaagcattc tcaccccatt tctggttcct gtggtcacag cacaaatttc cagctggaag 306300
gggaatgggg actatgggac ctaggggcaa gaggtttcag gctgccttac tcccttcaca 306360
tagacattga cagcgtgaaa agcctacaat tcccccgtga gctcaaaaca ttgacagtat 306420
ctctgggtgg caatgggaga acaggtttgg tttggtttgg tttgattttc tcccaggctt 306480
ctactctcca gagagacttt aacattattt tctcagttct ccacctcata ttctaattct 306540
tcatggttct gggaccagac tgcccttcag tcaatggtcg ctggagtgag atttgctcat 306600
cttctgtgga atagatctgg ggaaattgaa cttgacagct tgaatcttcc tcttatcatc 306660
ccaatctggg gtactttgag tgccacagga taagtgtggg agatctttct gaagcatcaa 306720
tttcccttga ttcccttgag agagaaaaag cattaatgta cttagggaag acagtcacat 306780
aggtttctaa gagtatacca gacttctctc tgaaatgaga cttgggttgt cctctttctg 306840
ataaattctg agatttaaca aaaaagctgc cttctgccat gaggacacat tgatataaaa 306900
gtttaagagg tactggtgca cttcttcaca ctaacagaca tgtgaggatg tatgactgta 306960
acccacacag agtgcagttc ctgtctactt aatgtttact tttctacctc tgcctctggt 307020
tttggtccct ggcagctgct gattcatggc aaaaccccag agcttggagt cagaagactg 307080
agtttaagtt ccattattgc ccctgccctt ttttttagct ataatatcca tctctctctg 307140
tcactaagtg atcgtgacaa caccttgtag ttgttggtgg cattaaatca gatggtgtat 307200
aagagtattt tgcaaaaact gtaaaggaga atgtggctgt agaggctgga agttctcaca 307260
agtattactg ctcttctttc ccacagctaa aagaatatca gcagaggaac agccctggtg 307320
ttccagcagg agcaaagaca aaaaagaaaa aaactggcag tagccctgag acaaccactt 307380
ctggtggctg ccactcacct ggggatgtga gtcttggctg gcctggctcc tggagacggg 307440
gggcccaagg ggcagtggag ggtaattgtt gagattgctg ggtactggtt aagaattctg 307500
ggtttgaatc ctgcctctcc atcttctaga gatctgattt atggcaagtt gcttgagctc 307560
tttgggcctc tcttttcact tctgtaaaat agggggaata ttgtttgact tccatttgtg 307620
aagtttaaat gagattcctt atggttgttt ttatgttaac ccctagtatg tggcctgctg 307680
taaacaccca ggatacccag gaaatggtca ttgctgtttg attttcctga tgcccagtct 307740
caaggggaag ctgggccaat gagtacagcc acttgccatc aggctgtccc tataggagtc 307800
actgaagggg gcccagggtg tggtgaggag agccccagac accaggagta agagaagatc 307860
taacttgcca ccagcttgct ggatgaccac agaaaaatca cttcttcctt tggacctcag 307920
tttcctcctc tgtaagatga tactggataa gatcagtgtc tttcaaactt gttttttagc 307980
tggagtcccc ttagttcaag tgaaccctta ctcaggagtc tgtttttttt aatggaggtg 308040
gaggtctgga gctctacgag attcatcacc catgtcctgg gcctgaggag aggggaccag 308100
tgagcatatt aagagctgca ttggtcagct gactccactc tgtgactgca tcgctcaggg 308160
gacttttcca tctatttgtt cctgcccctg gcaaggcagc aggtggccat ttggaagaat 308220
ggcacaggcc atggttttaa tctcctctgc tcttcttcag cgttttgttt ttctgaaccc 308280
acatcttcct cctaccctga ctttcttgct tctctctaag ccacttctgt ctttcgcccc 308340
ctgcccttgt ttttcccttg tcacctcctg tagattcagg acattctgaa ggtgcgggtg 308400
tccaacctta accactccaa tggggtagtg ctcccccatt ggacaagtgg aaggtgaggc 308460
agtgccaaga cccctctctg gctgctgtct ccagctgtgc atggccctga ggcttctctg 308520
gtttggggga tacttggcct ctgccttgtt ttatgttgct gccattaacc ttcagcctgt 308580
ttctgtctgc ttcttcacct gcttgattga ttgggttttt tccttccccg catcttttat 308640
catcttggaa atgttgagac cttaaagttt aaaagtaatt tgggaataac agacagtgca 308700
ggcatgtggg atttggggct ttttttttt ttttttttt tttttgagac agagtctcac 308760
tctgtcaccc agactgaagt gcagtggtgt gatctcggct cactacaacc tctgcctccc 308820
aggttcaagt gattctcttg ccttagcctc ctgagtagct gggattacag gcacctgcca 308880
ccatgcccag ctaatctttg tatttttaga agagacgggg ttttaccacg tcggccagcc 308940
tggtgttgaa ctcctgacct caagtgatcc acccacctca gcctcctaaa gtgctgggat 309000
tacaagcatg agccaccatg cccggccctt gctgttttta tactttctct atatccataa 309060
ctgtttccta tgtaatcttt ttttgaattt ctcattttta taactcctgc atcatctgtt 309120
accctgaagg atctggaggt aagaggccct gggccaaggt gcagtgaccc tgcaggccag 309180
ccctccaacc tcctttcaca gcaggggctg ggtgcccctc tgccagctga aacagcccga 309240
cagcccacac acaccccagc cctaatgatt gttctctcca cctctcccca caatcctcct 309300
ccaactcctc ctctctgcat gcgcctcaga gtcggtacca agaactggaa gtagccctga 309360
actcaagctc cgcaataatc aatcaactaa atgaaaacat agaatcattg gtaagagtcc 309420
agtggggtcc cgtgattcca cgctgccaat cctggccttt agttcccctt ggggccctga 309480
agaaaggagc tgggggcccc tggtgccaag gacaaatggg gagctggagc acccaggcct 309540
cacctggagg gaccccagag caaggagcac acagcatggc tcttctgtca ctgccctctt 309600
tgccgactct cttctccaga caccccactc caatccttgc cacacatgcc ctggggttgt 309660
cacctctcag ggaagcacta gcctgactgg ttgtcagggg ccccgtattt ctgccctgac 309720
tcagtcccta atttgctttg agtctggaaa agccacctgt cctccttggg ctcatgtttc 309780
tggaggaggt agagcatctc tctgttagct ctgaaagtct gagatttaaa ggcccctaga 309840
atggaaacct gagggccaag ggctcctgtc tgtccttttc catcctatat ctgctgtgaa 309900
gaaccataac tgtcctgtat gtgctcagta actgtttgtg gaatgaaggc acctttctaa 309960
atcacaagca ggcagaaggg tgggcctttc tgagtctccg tctctagaag tttatgttac 310020
tgtccttttg agagaatcca gattcagact ttgagttctg tggctgtggg caaaaaccaa 310080
caaagaccca aatcctctgt ctttgggagc ttgaggagag ttgaccagtt cttgccattg 310140
gttctgagaa cattgccttt aaaatccatt cctgaccact gcttaccact tcctggtctg 310200
gggaatggag ttgagggggc caccctcagt cacctgaatt tgactctccc cacagaaaca 310260
gcagaagaaa caagtggaac atcagctgga agaagtaacg tgatttcttt gctcacaaca 310320
tgactgctgg gtttgggggg cactcagatg tagaggcgcc aatctcgtct cacccactcc 310380
cagcctgggg aagaaggctc acccctcaga ttccacccca tccccacagg gtccctgata 310440

-continued acctggtccc atgggtgggc ctgtcctggg gcattggtgg cattctgggg gcatgtctct 310500
tgctatgcca tgtctgcctc cctgtggtaa gagccctgtc ttcctcttcc tataggaaaa 310560
gaaagcaaat aaggaaatac acaaagcaca aacggagcag ttagaggtga gtggtgggtg 310620
gggagttttc tcctgtcctc cggagaatgt ttctttcctt ctctttcagc acttgcttgg 310680
cttttctccc aaacattcaa ttccagacaa tcaacatcct cacgttggaa aaggcagact 310740
tgaagaccac cctttaccat actaaacgtg ctgcccgaca cttcgaaggt gggaatctgg 310800
gcatcccgtc atccttcaac ctggcacttt gacaggtctt tagggggagt cttttggccc 310860
ccatctcaac ctctctcatt acagaagagt ccaaggatct ggctggctgc ctgcaatact 310920
ccttacagca tattcaagaa tcggagcggg ctctctgtgc tgtgtctaca cagcagcagg 310980
aagaggacag ggtgagtccg accagctgcc ccatcccctg gcagcctggc ttcccagatg 311040
gaggagtgag cctaaaggtt ccttctccag gatggagtgt cctgcccaga aggcagcatg 311100
gtcatttctc gctgcttttg tgtatggttg ttagaggcag cctggggctg agtcagctgc 311160
tgtggctaat ttgggggca ctgttgggag taagcactgg atgcagagct cagaggccaa 311220
gtttctgccc tgcccttacc tggttgtggc cttggccaag tcctaggtgg ggtatttggt 311280
acttgtactg tgaacagaag agtacctttt gtatgttacc atttctgtag agagaggaaa 311340
ggtgtgtgtg tgtactatta taagatacat aaaatatgtc tgcaagcatt cctaaaaaac 311400
tcaggagaga gtaacagggt gcctgggaga cacctccctt ctgtaccttc tgagttttgg 311460
actatatgaa tgtatcatcc tttcaaaaag tgaacaaaag attaattttc cccttcctat 311520
ctgtgctccc acccccagca agaaaaatgg gcttagagaa tcagatagac tcgggtgttc 311580
aaatctcagc tctgtctaag tgatcttagg caagcactta acttcaaata ctccatgttt 311640
ttcatctaca caatagaggt aatcctagta actgtgtcat atggtggttg tgaggattaa 311700
atgggattgc tagcatggaa cctggtgaag cactccataa cggttcaaac agtggtagta 311760
ataacagtaa taacaatagc aatattatct gatctctctg ggcctctgtt agccagctgt 311820
aaattcgatc tctttccctc tcccttccaa ctttactgag ttcttttaat aaccaggcca 311880
cgggcttgga aatgccttga cctttactaa ccgagttgta tattgagcct agccctagcc 311940
cttttaaggg gcactgcccg ggctccccag atcgaaactt ctcactcttc accctccagt 312000
cctcgagctg cagtgaagcg gtcctccagc ggcggttaca gcagaccata aaggagcagg 312060
cactgctgaa cgcacacgtg acacaggtga ggctttgcag agggagggat gtggaaggaa 312120
gatgacccca ggtggccagg agcaggtgag gaccagtgac agcccttcct aacttgtgtg 312180
cccatttctt gcaggtgaca gagtcactaa aacaagtcca gctagagcag gacgaatatg 312240
ctaaacacat aaaaggagag agggcccggc agcaggagag gatgtggaaa atgtcggtgg 312300
aggtgaggtc tgacccttca gcccccatct tagataggtc actggatctt tctgggcatc 312360
tgtagaatgg gaatagtaca gccagaggtg gtcatgggtc tgggctttgt ggagatgggg 312420
gcagagatgc agatggtagc ctgtccagcc accagcccct ctctccaggg ccctttcccc 312480
tgtgctttcg gcaggctcgc acattgaagg aagagaagaa gcgtgacata catcggatac 312540
aggagctgga gagaagcttc tctgaactgc aaaaccagat gggtaagatg gggctggtgt 312600
gacctgggag caggactggc atcagaggtc tgtgggggtg gcttagaatg ccccagggag 312660
gtgggtggat ggaagggctt tgaggcagag ggaaagaggt ctgtgccagc agatggcaag 312720
ttttgtcatc tccatagcct cagggtcccc ataagcaaag agggaggagt gctcgttgtc 312780
agccacccac agtgctctct atgtgaaagt ggcttggaaa ctggctacca tcgggtgcga 312840
ggaatcatta gcagtgaggc catggccatg ggaagcctga gaggagctgt gcatcaagag 312900
gagggttttt ttttgtgcgg ggggtgggta gcgggggaaa tccagaggct cttattgcct 312960
gcttcatttc tcagctgagc cccagtcccc ggcaccccca gcagggacct ctgagttgga 313020
gcagctacaa gatgaggcca aacagctgag gaaggaagtg gagggactgg agggaaagct 313080
ccaatcccag gtggaaaaca accaggcctt gagtctcctg agcaaggaac aaaatgagag 313140
gctctgagag caggaggagc ggagggtgca ggagcaggag agactgtgtg agcaaaatgg 313200
gaggattcag gagcagcaga agaggctggg ggaggagggt gagaggctgc aaaagcagga 313260
gcagaggcta tggaagcagg aggaaaggct gcaaaaggag gaggagcagc acgaaagcag 313320
gaggagaggc tgtgggacca ggagaagagg ctgtgggaga aggagaggct acgaaagcag 313380
gaggagaggc tcacactctc ccagaaccac aagctcgaca agcagctggc cgagccacag 313440
tgcagcttcg aggatctggt gggttgcccc acctggggag cctgccctca tccctatccc 313500
tccaggcctt tgtttcccca cctgtaaaac ggggcagtgc agccctcaca tgaaatggta 313560
cttctaaagg cacctgtgag ccagagctca tcaggccctc ctctgatggc tgtgggggag 313620
aggggatgat ttttctaacc tgcctccacc tttccagtga catgggaggc agacaccaag 313680
ttcaggggtc tcccgctgca gtggatggcc actgattgtt tctgtccaga acaacgagaa 313740
caagagcaca ctgcagttgg agaagcaagt aaaggagctg aaggagaagc caggcgaggt 313800
gaaggagatg gtaacctcca ccccatccaa gaagggctgg gaggcgggca ccagcctctg 313860
gggaagggag gtgccaggcc aaaggcagct ccagctgggg ggcaggtgac cccagcaccc 313920
tccagggcag ccctatgaat gtttcttgct tcctgccctc tgacttttag aggtgggtag 313980
ccctgggttc ctcccaggtc tggacatcat ccccccagct agaggcatgg attcccccaa 314040
tcgggggaag agacagtggt acaagaggct ccttatgcgg ggcacattgg cttgcacctg 314100
taatcccagc acgttgggag gctgaggcag gagaagcact tgaggtcaag agtttgagac 314160
cagcctggcc aacatggcaa aacctcatct ctacgaaaat taaaacaaca ataaaaaatt 314220
agccaggcat ggtggcgcat gcctgtaatc ccagctactc aggaggctga ggcatgagaa 314280
tcgcttgagc ccgggaggtg gaggttgcag tgagctgaga ttgcaccact gcactccagc 314340
ctgggccaca gagtgacact gtctcaaaac aaaacaaaac aaaacaaaaa agcctcctta 314400
gattcaaact ggattccgac ctcggttcca ctggtcacca ttcaactact gttcatctct 314460
tagtctctgt ttctgtaact tcaaaaggaa gttagcattt tccttgcaga ggtgctgagg 314520
attgaatgag agaatacctg gaaagcatta ggcatgtagc acacttagca gatggtggtt 314580
ggctccctct gcttttccac cagtctgtgg cctacagttt aaatggtggg aagaaggaca 314640
tgagatctga ggctggggaa ggaggtatgg ggttctaggc aagggaggaa gcctcttagg 314700
cctggagcaa gggagcaggg tcctgggcag gtgacagagc cccacagtgc cctagctacc 314760
ctattaatgg gcccagaacc tggaagccag ccaccatgtg ccctcatgcc caggtcttc 314820
ctgcaggtgg agatgaagag ccaagagtct cagagtctgc agcagcagtg agactagtac 314880
ctgggtcacc tgcagcagta cgtggccacc tatcagcagc tgacctctga gaaggaggcg 314940
ctgcacaggc agttactgct gcagacccag ctcgtggacc agctgcagca gcaggaagct 315000
tggggcaaag cggtggctga gattataaca ttttaaaata tgaatacagt agtttaaaac 315060
aaagaaactg gaggaaggaa aagtagagaa agagatgcca attcaagtcc aaacctttat 315120
ttgccaagtt ttcttagaat gacttttacc aattgatgaa ttcctgtaaa cagaatgtat 315180
aatggaaata cggaaactgc ctaaagtggg attattcact gctactgtga tgctactgta 315240
atgtaataaa ttattaaatt gttgcaaagt gctgtttttg ccttaaaatt ttatgtgtct 315300
tgaaaactat agtattaaga gtattgagac tgtgaaaatg ctggggacag ttggcatgag 315360
ataatcagtt tttattttta tgaaattgta atgtaactat gcaagtgtgt ttattaaagg 315420
aacaaactaa aaagaagtta cgggaatttt aaaaagttgt gggatgaaaa agttatggga 315480
taaaaaatgc tgtggaaaag ttgtggcaaa agaagttgtg aaaaaaagta gaaaaatgtt 315540
ttatgaaaag tattttaaaa agttatgaaa aggaagttac gggatttttt tttaagtcat 315600
gggataaaaa taaaagcagg tctctgtcgg cacaagcctg gagaagtggg actggagact 315660
tcgcccccgc catggaccaa ccaccccttc ccagtcaccc ctttaccatt agggtggcaa 315720
gacaagatcc ctgcctaatg gggggagata aacagaccct ttggcacctg accagggctg 315780
agtccttaaa tttctggatg atgatgattg ttatttaaga gccagaggct ggcggagttg 315840
gtttgtttgg aggaggcctg atggcctccc ctactctcac caaagcaact tttccctcag 315900
ggggctccca tcttattcag agaggcagct gaggcgggac agtggggcta actgtagagc 315960
aggtgagggc tcgggctgct ggggtggccc cccttcccca gtgtacacat agtatctgtg 316020
taacattttg tatattccgg ggggtagggc cacccccttgt atcataccta ccagaggctg 316080
gagctggcat atgaggagga ggttctaatc attatttacg gctgggaaac ttatttattg 316140
atagcatagg acagaggaag gaggaggggga tggggtcctg gctgccttgg tgatgtgact 316200
cctgtttatt ttgctttcca ttttggaata aatggattta gccatactgc tcagcctggt 316260
gggttcccat ttccctcact gggtcctgga gtttgcgcca ctgaatgaag agccccagag 316320
tgagcatgtc cagctgggct gttggggacc ttccaggcct gttacctgta tgctgcctgg 316380
tgacacctgg tagattgcat ggggattgct atggcgccta tggggcacag tccggccctg 316440
acagccaaca ggctcagaag cctgatctag cggtggccgg gaaggcagat acgagcaccc 316500
aaggccactg acttccattc accccagtcg tcttcggttc cgtccccttg cctccctctc 316560
ctgtctgcac agggtggcct gttctgtctg gccctctaga gtgtcagctg ccccgcaggc 316620
tcctccaggc tgagttcatg gtcctgcccc ctagtggcca gagccagctt cacaggataa 316680
gagccagcta agctccaggg gctttccagg aagtgtccct tggaaagggt gtggcctttt 316740
caccgctccc aacagcaccc tagaaatggc ttggcttttt ccctcccctc agctccacag 316800
agaacacagc cagcagagga cacattcccc atcatccaga aatgggtttg attctcagcc 316860
aagggacacc agggctggta gagactgtca ggccacacag ctgcctgcac agcaccccca 316920
tgcttggtgg ggggtgggag ggatggcggg gggtgggacg gtgggggggt gggacggatg 316980
gcgggggctg gctgtccaca ggctgggcat gacaggcagg ctcactggag gtggcacact 317040
ttggaggggc agtgtcaggg gagaccttcc ttttgttggg ccacaagact ccacaaggac 317100
agcacggtga ctgattccca gtgctagagg cgaggtggtc ggccatatgt aggtgtgtgt 317160
gtgtgtatat atatatatat atatgtatat ttatatatat atttatatat atgtatattt 317220
atatatatat ttatatttat atatatatga gtatttatag ctatttatag aacaaggcag 317280
gggcatacca cagaggggcc acaagttttc agcaatggtc acacctggat gtgtcagctc 317340
accactacaa cagactaagt cacagatgaa gggggctggc tttggggctg gggagccact 317400
gtcaagtcac aggacacccg cccaggcagg cttggaaagg gaggtctctg agaagaggag 317460
gatctgttta gaggttggag tggggctgga gctctcagga tgggatggac ttgcctaacc 317520
caatcagttg gcagttggag aaaagcagag agaaaatagg agagagaata gcaagcagag 317580
agctggtgat gcaagcgcag agcacgggca tgtcgcagca gctgtgggag ggccggggag 317640
gggagcgcgc aggtgcgggt gtagcaaagg ttcctggaaa agaggggctg gaagggaaag 317700
gggaggaaga tggagggaga agccagagct tcacaggtag tgcctggggg ctgcggcagc 317760
cctccccagc tcacacacac tggcctctcc catggcaccc aggcagtgca cccacacttc 317820
agaccaatgc tcagccgctt tgggcttctc tcttctctgg tcaccctgcc ttccaaccca 317880
ctggcccagg gccacctctt gcttggggag ccccacccaa cagccacctg gcctgataag 317940
gaacactgct tgaaccaaaa tggtgaagct ataagggatg gatggctgga gtgagtacca 318000
gaggcccctc tggtggtgag aaagtccagg gtcctctgaa gggaccctgg ggaaggcagg 318060
gagggcaggt agccggatgc cactggccat agacttataa gtctaagagg ggagcctcag 318120
ctggttgcgg ggtgaggggg gctgcaagtt tcatagctga ggctgggtcc ttcctgctgg 318180
gaaaagcaga agagggagag tccatggcag gagaggcagg tgggctcgct aggcggagct 318240
cagctgggcc agcaggcact gtggtcccct tggctgaata gcacaggcga cccctaggag 318300
caacaggcca aggtgcgtga gcctgctggt cggcgatagt gcttcagtgg gggccaggga 318360
ccctgccttc agtcacacgc tagcagctgc ggtggtacct ggcagggagg gaagggggct 318420
gtgtgtccct gcctggcctg tgaagtgtgt tgtgggatga ccgtgtgtat gggactctta 318480
aggttttatc ctagatcacc agggattgcc aacagataga ggaggtggga ccctgactat 318540
cacccctcct ctgcagtggg tttgactctt gacactccca ggctgggatc tggataccct 318600
gacctggcag catgactcag actgcacgac aggtacagcg tgcccaggat gacgttccta 318660
gacctctagc tgcctcagag tccagccgca cacacaaccc cgtccaagct cccagcccct 318720
acaccataaa tcatgagctc tctgccctct ctgatgacta cagagagcac ccatgtctgc 318780
cagcttgggc atggagactg ttccaacagc ccccaggctc agccatggag gccttgggca 318840
gtggcgctga gtcccatggc ttgcagggaa gggaggtgag agagccagca gcacgaggac 318900
agaaagagga aagagcaaat ctgcagctcc agaagggagg ggcagggagc ctggatctga 318960
ggtcccaggt gcgccccgt gtggagccgg tgcagcgggg caggaacacc gttcatggag 319020
caggcggtga ggcatgtacc taccatggct gatgctcctc agggaccact gatagtgatt 319080
ctgaaagcat cagatcaaca tgacaggtca cacgcatggg tggggcaggc ctggggttgg 319140
gggacacaca cacacgcaca tgccggggtg tgcacacaca tgctatgagg ccccacagca 319200
tgcacagccg gcatgcacac gctaacacac atgtccacaa cacgcatacg cctccttccc 319260
cgccacatcc tggtacccag caccctcact ggctggcacg tgcagcacag atctggggtg 319320
tgcagccact tggcacactg aagcacacat gtgagcagag tcacaacaca gaagctcacc 319380
caaacacaga ggtatttgca ccagctccct gcacactcat gcctggcatg ctcagaggac 319440
caccggtgct gctcatggag acagggcttg ctcgctaatg ttcagctgtc atttatttac 319500
ctcaggtcag agagtctgac ccacctgaga gccttccatg gctccctatg gcctgcagca 319560
ttgagcccca aaagtcaaac tcttcggact ttgaaggtct tccaccctat gccccaccct 319620
ccccacagat gattctgagg atggcgggag aggtcagctg tgactctttt gctcaactgt 319680
tggacaagag taggcttgaa gttgataatc tctattcctc tcccgggtag tgcttctcaa 319740
acttcaaaga gcataggaat cacctggaaa tcttgttaaa tgcaaatttg cttcagctgg 319800
gctgggtgag attgccagtc cgtatgtcta acaaactccc aggtgagcca atgctgctgg 319860
cccactgacc accccctggg taacaaagct ctatggtttt aatttgcatt tccccagtgg 319920
ttagtgttga ggatctattc atgtgcttta agttaactca tttttaaaac ctaaataaat 319980
gtacttaaaa aggaaacttt tgctatagga ggccaaggca ggtgaattgc ttgagcccag 320040
gcattcaaga ccagcctgaa caacatggtg aaactccgtc tctacaaaaa ataaaaaaaa 320100
tccagcatgg tggcatgttc ctatggtttc agctactcag gaagtgaggc aggaagattg 320160
cttgagcctg ggaggtcgag gctgcagtgg ctgtgattgc accattatac tccagcctag 320220
ctgacagagc aaaaccctgc cttaaataaa tgaataaaaa gaaacttgtg gttagtggtt 320280
ctcaaagtgt ggtccctgag ccagcagcat cagcatcccc atcagctgag aacttgttag 320340
aaatgcagat tctcaggcgc caccccagac ctcctgaatc agaacctctg aggcgtgggt 320400
tcagtgacct gtggtttaac acgccctccc ggtgagaatc ggtctcattc actacagata 320460
gaaggaaatg gttaaaatca attcatccgc atatcgccta aaatcctcct gtgggcccca 320520
ggttggcaca gcacactttt gggcaggagc cccactcaca gaggccgtga caagaatgct 320580
cctgcccctg gggttgtgca gtgacagctc acacagctcc acgtggcggt tctgagtttg 320640
ggaagcgctg atgtagtcct actgcagccc ttcctgccct tcaccggact gaggaaatcc 320700
aggctctgag gagggcgaga cttgccctag gtcacccagc aacatggtca gtctcctttc 320760
ccagggccct cacaatgcgt ggcctgttta aagcctgcct ctattcactg ctgagtgaaa 320820
aatccagctt caaaacagaa tatggggaag gatactatct tgtgcaactt aagtttatag 320880
ctgcagatac atgagaaaaa aagtctgaaa atactgttga agtagttact tggggagaga 320940
aggggtttgc tggtttttgt gtttttaact tttatatttc acaattttta tcacaatgtt 321000
tagttacata atcaaaattt attaaatgtt aaaaattgac atgaagcctg atccagccac 321060
agcctatcat tggcagagcc aggaagcctt ccagatacag cagccctgca cctgcccccg 321120
gtcacaccct gggcctgggc acatgctagg tcctctgtct ggacaccctc accccctggt 321180
ggcctccatg tcagtaccca ccagcacctc ctgtgggcga gggccgcccc tgcatccagc 321240
cctgggtacc ccctagccca gagggcacct catggtgtga gagtccgcct gcctgtctct 321300
aaagagagga aagctccttg ggacatgtgt tctgcttgac ccatcacctc tggcctggta 321360
cagaaaggtg gacagtgggt atttggtgaa taaatgaatg aatgattgga acgaaccccc 321420
taaatggtga tttcctgagg cccttctcca gctggcccag gtggaaccag ttccacgttt 321480
cacaggaaag ccaggtgtga ggagtggggc aggtgtgtgt gaggggccag gttcttgaag 321540
gctgcatgga aacggagctg gtggcaggtc tgggggtggc agtgctgctg taggagcctc 321600
agggagggct catccctgga atcccccagg gtatcctagt gcccccagct gctgcatggc 321660
atgagaattc ctggctggtg ggggacacac aaggacttgt ttggattggc cacctggtcc 321720
agcccaagga gctgcgcctc cagcaccttg gggaaaaaaa agcacttttg atgtgtgaca 321780
acagctgcag gcaaggggag ggagaggtgt gctgggcctc ggccttagaa gccagaagcc 321840
agttcatgcc cctacttggt ctacgtggga aagggatgtg gcctcggcta gctctagggt 321900
cctgggttat ggaaagggcc cttccttatg gacccagtga cttaggctga cccagcccct 321960
ccctgagcct catcagtgaa accagggctg ggccagggct ctcaacacct cccagctcca 322020
acctctggct ttgtcccagg agggcaggag atcagacaga ggtgacccgg gctccctatt 322080
tacctcaacc tccttgtgaa gcctccctct ttctgcctgt gaggtgggtg gggctggaaa 322140
gaggggcatt cacctgtggg tctctgactt ctctgcccag gtgtgcctgg ggagtctggt 322200
ctatacccgg tgctctgcta taccccacag cctggtcaca acctccctgc ctccagagca 322260
gccctggccc agggaagaag cgggtctctg catccaatga taggtagaaa atgaacgtgg 322320
ggatgatagc actggaaagg agtcaaggag gaggtgcctt cccaaggatg tggagggttt 322380
ttccagaatg gaacttgact ggggtgggca aacatcagga agtgggaagg gtggctccct 322440
ctgtgggagc tggggcaact tgcctgggcc aaatggtggt aggctgtggg tgtagggtgg 322500
gcagagctgg ggtgcccaga gcctggggtc cctgtccttg cagaggactg gaatgcaaaa 322560
caagtgcccc ctgccttctg gctgcgggac atcctctgct tccaagccca gacatacacc 322620
tgctgccaca agcccctgag gctcttcaga ggaccaatgg gcagccacac ccatgctggg 322680
ccagcctgct gggcccacct gcaccctggt cagagcccat gactgagggg actctctggg 322740
gacaatgggg gcagtctcat gctgccctct tacaggtgga tcagtccctg ggatctggtg 322800
ctgggctggg gtgggctgag gctgttctct gctggggtac ctggtggaca gcaggtggag 322860
caacttctcc ttggctttcc tggaccccag gacacagctg aacactgcac tctaccctgg 322920
atgccttcag atgggaccat gggaaggaag aggggctacc cctgcagggg gccaggaccg 322980
tggcccatgc ttgctccccg cagcaggcac ctcctctcca gattgacatc acctgattcc 323040
tgaaggcctg ggctactgac cagagtccca acatcctcac caaggtctgt ttttacatca 323100
gagcagctag tacatgagtt cggagctgaa gggggcagag agagaacaca gggctctgtt 323160
aagagttctt ggctccctgc tgtggtgggc cccgtagaag gccccccaaa aatttgcagc 323220
tgctataagt cactgggagg aagctgcagc agacacgtgt ttctcagcct ggtagatgca 323280
gaggggtgtc cggaccccca actgggaggc ccaaatgtgg cagtgcagga attctagcca 323340
gctctgggac cctgggcaag tcatgtaacc tctcagaacc ccattcctgg tcaccatggg 323400
gctcttgtgt ggatgtaaac aaccctcagg ccacttatgt cccatcagtg gaagcctagc 323460
atgggtggag acccccgaga ctgaactcag tggcgggatc cagccttccc agctcttcta 323520
catagagccc agagctagca gggtgggctg cctggagaag caggcactcc tgtgggctgg 323580
agaacatgag cagtggtccc tttgggaagg tggaagaggc tgtggtcagt ggaggccata 323640
atggggcaga ggttggacag aaggggcatg atcggggaat ctgagaccca acagagactg 323700
gactgaggac tctgtgccac tcaggcagtg gaaactgagc tatggctggg acccatggtc 323760
ctgagtgagg cctggccagt cttggaagct gtgccaaagg tggcttcatg taagggtgca 323820
tctgagcact tttttttttt ttttttgaga tggggtcttg ctctgtcatc caggctggaa 323880
tgcagtggca cgatcatagc ttactgctgc ctcaaactcc tgggctcaag tgattctccc 323940
acctcagcct cccaaagcgc tcaaattata ggcctgagct acagagctgg gttttaaatc 324000
ttaatatctc ctcctggtct gcttccctgg ctgacacaca tgctggcatc ctgcgcctag 324060
acaaacatgt ttctggactt ggttccattt gttctgacgg gcttctctct ctcaatgacc 324120
gcacgttaca ttatttggct attcttacac atttccgtat agaactgagg gttagtgtat 324180
taatgtcaaa gttctactgg tttttcgagg ctgggtggaa tgtttgggtt aatttagttg 324240
tgggcatctt gacaatatag gcttttcctc caggaatggt gattctggga cgcaggtttt 324300
gcacattctg gtttattgct tggctcgctg ccacagaggg atggcactgc tccacacacc 324360
atgccctaga gatgtcccac cttatctgtc taaatcaagc tggatgttct cagctgacag 324420
gatatcatat cagtgctgtg gggactcact cccctcaacc cgagacgaag tgaggtggag 324480
actatggagc agatccgtgc cgactgcatt tgcccttcct gacccgcact gctgctgggt 324540
ggggctgtgt ctgagctgat agagggcatt gatttgggca tggggagggg tcagtactgg 324600
agagatgccc ctcacctccc ttagctcctc ctgtccactc aacacttggt caccaaggtc 324660
cccgacttcc aggcctcagt caccactaac gaggtgctgc atgggaacaa agcgtaggcc 324720
cacaacctgg agttcaggtc actcctcctt ccagttgaag cctctatccc tcccaggtga 324780
ttccagcctc atttctccat gggccaaata tcctaaacaa aggcctggac agggggtctt 324840
tatccgagtg cccaaaaagc acatgcagaa aggctctgca tgccccctgt ggcctgccag 324900
aggtaagagc ctgcccgtca aaatgcacaa tcctggttct tgcagggagg tgaggagggg 324960
aggaagaaaa ggtccatctc attctttcat caggaaccta aacttgggaa agccagatat 325020
agtacatttc ttaatgatcc tgatactttt ataactggtt acagctgggt cacatgcaca 325080
actgttttct aacatctttc aactggccac ataacaccat gtaatttatt tttttatttt 325140
tattttttaa ggccaggggg agtggctcat gcctgtaatt tcaacatttt gagaggctga 325200
ggcaggaaga ctgcttgagg ccaggagttc gagaccagcc tgggcaacac agcaagaccc 325260
tgtatgcaat ggaaaacaac cctatttcaa aaaaaatatt ttttgagtac agtggcttga 325320
ttacagctca ccgtagcctc caactcctgg gctcgagtga tactcccacc tcagcagctg 325380
ggactctcag agcacacccc cacatctggc tgatttttta atttttggta gagatgtggt 325440
ctcactatgt tgcccaagct ggtcttgaac ttctggcctc aagagatcct gccaatgtga 325500
cctcacaatg cactggggtt gcaggcatga gccaccatgc agcccctgca aaatctaact 325560
gtccttcagg tgctcctttt ggacctccta gctagactgc cattggcaaa tgccagttta 325620
ttatccaccc acatgtatgt taatggattt cccatgtttt atttgtctag accaggcttt 325680
ctccacagca gcactgttga tgtttagggc tggacagttc tctgttctgg agctgtttgc 325740
gcctcgcagg atgtttagca gcatccccag cctccgcctg ccacatgcca gcagcactcc 325800
tcagtgtgac agccaaagtg atttcagata ctgtcaaata tccccagggc ggcaaaatca 325860
cctccagttg agaactgctg acctaaaacc ctctggaaca atgttagatc atggtaatga 325920
tagcgcatac tgctcctgac cttaatggga atacctctag catcaaagta tactagtacc 325980
tgtatactac tgtctgggct gttattagta cactgtatta gtccattctc actccgctat 326040
gaagaaatac ccaagactgg gtagtttata aagaaaagag gtttaaattg actcacagtt 326100
ctgcatggct ggggaggcct caggaaactt acaattatgg cagaagactc ctcttgccag 326160
ggcagcagga gagagaagga gagccgagca aaggggaaag cctataataa aaccaacaga 326220
tctcgtgaga actcactcac tatcacgaga acagcacggg agaaactgcc cccatgattc 326280
aattatctcc acctgggccc acacccttga cacgtgggga ttattgcaat tcaagatgag 326340
atctggatgg ggacacagag ccaaaccata tcatatcctt tatattagca tactgtatca 326400
aagtataatt ttctttttttc tttccttcaa gagagagcct cgctctggct ctggctggag 326460
tgcagtggca cgatgtcatc ccacggtaac ctctgcctcc tgggttcaag caattcttgt 326520
gcctccacct ctcaagtagc tggaactaca ggtgtgtgca accacaccca actaattttg 326580
atttttttttt tttttttgag tacacatggg gttcgacatg ttggccaggc tggtgtcaaa 326640
cgcctggcct caagtaatcc catcacttca gcctcccgaa gtgctgggct tacaggcatg 326700
ggccactgca cccagcctga agtataattt tcacaatgtg aaaagcttga ctttcataca 326760
gataatgaag gaatacgtat aagatatttt ctttaattta caagggagtc agcaacacgg 326820
tgaagctagt tcaaggagca ttttgagaga cagtgtctgt agtgctccag gaagggcatt 326880
ccgaaatgca ttctgagata gagacaaaac ttgttaatat cctataggga ggctgggcat 326940
ggtggctcac acctgtaatc ccagcacttt gggaggccaa ggtgggtgga tcacctgagg 327000
tcaggagttc aagaccagcc tggccaacat ggtgaaaccc cgtctctact aaaaatacaa 327060
aaattagcca ggcgcggtgc tgggtgcttg tagtcccagc tacttgggag gctgaggcag 327120
aagaatcact tgaacctggg aggtggaggc tgcagtgagc cgagatcatc ccactgcact 327180
ccagcctggg tgacagagca agattctgac ttaaaaagaa aatcatatcg ggaaataaaa 327240
acgtcacctt tgggagttat cttttctact ggacagaaat ctgtaagcta acatatatac 327300
atattctcca gtatattcat aacatattct gtagtatatt tccctgcact agtgcttttc 327360
aaagcatggt ctcaaattgg aagcatcagc gtcacctggg aacatagaca tgcaatgctt 327420
aggccccacc tcagtcctac tgagttagaa actctggtgt gaggcccagc agccggtttc 327480
acaagccctg cagggcatga tgatgcactc taatgtgtga ggaccacggc tctaaataat 327540
caatctttaa tagtaaaaca agtatctatg aaacaatgct ccagtatgac attaaaaggg 327600
cacaccatcc accttttaac tttatttctc aatttagata ttttgtctga tgttaaattt 327660
gctgttttgt ttctcaaata ctcttaagac agttttcatc tgttcctaat tttctctttt 327720
taaataaaaa atggttttcc aaatctgtcc attttactct tctttaacct attgatagga 327780
tgaagtaaaa gttgaaccat tcttaccttt tttttttttt tgagacggag tctcaccctg 327840
ttgctcaagc tgactgaaat gcagcggtgc aatctcggct gactgcagcc tccatctccc 327900
aggttcaagc gattctcatg cctcagcctc ctgagtagct gggattacag gcacccgcca 327960
ccacgcccaa ttcatttttt tttttttttt gtagagacag gttttgccat gttggccagg 328020
ctggtctcca actcctgacc tcaagtgatc tgcctgcctc agcctcccaa agtgctagga 328080
ttacaggcat gattacccac atctgccagc ttgggcacgg agcctgtttc aagagccccc 328140
aggctcagcc atggagcctg ggggactttg ggaccgtggg ggctggccct ggtacctgcg 328200
tccagctggg atgctctgca cctgcagcca ggagtcatcc acgggccccc gtgggcgtgc 328260
tgacagtggt cgtgttgatg ttcaccgatg ttgctgggtg cctccgtcag cacgtggcgc 328320
ttgcgcagca tctcgccgcc ccactgtgcc ttctctgcca actcctccat cagcgtgttc 328380
tggtccccat gcgagtacag gttggacagc agctctgaga agatgaattc cttggtctga 328440
gagtgggcaa agagggaagg aggttgggac ctgatacctg tgccaccctg gccaccccgc 328500
tgggccctgc taggactgtg tgctggactt ggagccccaa gtatggcttt tcagatgcgg 328560
cttctacact gcttcaactt gaagatctgc gtccccactg ccttttctca ctcagatggg 328620
gacactgaag tccagaggaa aagccacctg tccaaggtca cagatctgga aggggaccca 328680
ggacctgtca tgccaccagg acacctgtct actcagttta aaaaaatttt ttttggaggt 328740
aggatgtcgt tctgtcacca ggctggggta ccgtggatga gatcaccact cactgcagcc 328800
tcaacctcct gggctcaaag tgatgctcca acatcagcct gttgagtagc taggactaca 328860
ggcacgtgcc accaccaagc ccagctattt tttaaatttt tgtgtagaga ccaggtctca 328920
ctatgttgcc caggtttgtc tcaaactccc gggctcaagt gatccttgac ttggaagagc 328980
cctgtgtttc tggcctgggc agccaagtat tcaggaaccc tccctggcca cacggtcatt 329040
gcctgttctg ggccaccctc atccgtatat cccctggacc gcagctgttg gctgctctga 329100
ccctgagagc cgatttggac aatgggagct gaggtgctgg ctgaggccat gccaggcttc 329160
ctggaggtca tcgctatttt tagtctttta ctggggagtg tgtttgtaat agtttcaggc 329220
ttactaatag caccaacaag agtgccctga tttctgccaa atgaggaggg atatgggaat 329280
catatttgcg ggggaaattt gattctgagt cctggggtga gcctgggggg tttctgttca 329340
tctcgtgttg ggtcaggatt gccgagagtg acagggagtg agctcaccca tgccgacagc 329400

-continued tagggcagtg ttgggagcgc cgctgccctc agttctgtac tgggtcccag gcgctgccag 329460
gaggagccga ggcgagtggg cgtggctctg gcgagtgccc gccccttccc tggcaccgca 329520
ggccgacctg gcccctccca cactgctggg ccttgcatgg tcctgcagcg cctccttgtg 329580
agcggctcgc ggtacggtct cccctgcagc ttgctttaga aagcggggtc gccacaccaa 329640
caggtgcttt aaagagtgcc aaggcggtgg caggctcccc gctgttatca agactgcagg 329700
ggcccataac ccgcctctgg gctggagcct cagtgtttta atgagcttcc cagactagtg 329760
gttgcaagga ggccagtcct gcagcacagc gattggcctt cagaaacaca gggagggagt 329820
tgtgtggtca gctgcattca ggagacggga gttacacagg attgaaccac gttctgcagc 329880
aggacttcta ggagcctttt aaggcgctga gcatcgtctc ccaaatttag ctgaccatgg 329940
gacaccttct catctcccag aggaaccttc caggcctgag gcagaggtgg ggtctggctt 330000
cccgggtgcc agcctgggcc gaggggtctc tgtcagctcc tgactgagga gcaaatgaag 330060
aattatactt cgggctcgtg ttctgcagca caggagtgtt gggcgccgta ggtttggggt 330120
ttgtgggggc tgtgggctga cagctgttgg ggagaaagga ctggtggtgg ggaccctgtg 330180
ccccgttcac acggagcctc ctcccacctg ctggggctgg cagcccggtc tgcagagcca 330240
ggcaggaggc ggaacctgag aaatccacac gcggggaccc ctgtgcttgg gcgttctctg 330300
ttctctggtg ctcccatgtt ccagaacaca cactggtgaa ttcggaattt aaataaagct 330360
ggcctttctg accttaagcc tctggatgag agttaagcat gtccaggtag tagtgggtgt 330420
tttgaaacat aaaaggttgc accctcgtgt gtgcctgtgt taaaaggagc ccacgcagcc 330480
gacagcagca ggagcaaatg gcctgctctg atggggacag gcaggaagtc cttcggggca 330540
tttctgtttc atcacagctt ttcctggggc tggtgagtct gttgggcctt tggttgacag 330600
ggaagcgcat gagcccatgt tggtggatac aaagcatctg gggcctggca gaatccagag 330660
aggggaagat ggtggcccca gtgttggagg aactggccta ttttgtgatc cccagagacc 330720
agtgtgactg acccattagt gctacaaatc catagccagg cctcaggaca gcttttggtt 330780
ttgtttttat taagccactg accagtggtt aggagcaagt ggatcataac cttaacattt 330840
tattgaaaat tggagccctg acctggggat gtgaaaccca cgagctgcac atttctctgt 330900
agactgcatc tggacacttg tcacattgcc gactaggtct gacagtcatc accaggactg 330960
cctgggcctg tgttcattcc cagtcaatga atcctgggac acagacgtcc tggactcgtg 331020
cccggtgcca ggcctcgtgc ctgcccaagg atgcagacat acccaccatc accatgcaag 331080
tgccaggagc tcttctcagc gcttatgtgt gggaacacga gtaatcccac accctaggag 331140
gtggcactac tgttacccca gtgtgcagat gaggaatcag aggccacaaa aggcagtgac 331200
ttcagtcaca cagcaagcat gtggcagagc tggagtgcag gccatcattc tgaacctgcc 331260
tcttgctggg cctttgttcc ttgtcacctc tctgcagaag gtgggcctcg tcccctgcat 331320
caggccccca gcctggccag tgctcttccc accctgcccc aggccacctg ctgtgcctgt 331380
gagggctgtg tgtgagcact ctctggagcg ccgctgattc tcttgtctct cccctgcgtc 331440
ctgccaggaa gctgatcagt atctcctttg gggacctgaa ccctttcccc gtacgccaga 331500
tccggaaccg acgtgcctac cacttggaga aagtccggct ggagctgacc gagctggagg 331560
ccatccgtga ggacttcctg catgagcggg acaccagccc tgacaagggt gagctggtca 331620
gtgacgagga ggaggatacc tgagtgggct ccgggacgct gctcttcctg ccttcacaac 331680
caaagtgtgc ccaaagggtg aaagtgcact taaaagccag aatgtaacgt gtgtggcctc 331740
tggggatctg ctgggcagat gtcccaagcc aggctgccct tcctcatttc ccactgtgcg 331800
gggggcaggg gtgggaggtc taatctgttt acagccattt ccgtgccata cttttggtta 331860
tacatatctc agtcacgctt tctgcctgat tggtggatcc tcgggcttac cagtggctat 331920
ttgcaagagc ctgtttccag cctccgtcag cctgtcggtg ctctgaccct ctgaaacctt 331980
gctttgctgg gcatctcccc atattctctc tcctgtacat agtgggcagt ggtgtgtggt 332040
tttgaatggc agtgctatga aggatgccca ctatgcttca ggcacctgta ggccagaggg 332100
ttgctgcctc aggcataagg tcggtatgaa aaggggctgc cttagaaaag caggcacatc 332160
ctttgttcag aaatggccac tgtagaaagc ccgtgaacct cccactggtg gctttaagct 332220
gccagccatg ccccatttct agaatagcct gtgctcttcc acacacaact cttccaacag 332280
tggctcccag cctgcatggg gagggcctgg ctgcccagac acccaccctc acttctcatg 332340
gccagcctgt gtttgcagat cactgggctg ctctgtcccc agcttgcccc atgcctgaca 332400
tggctccatg agattctgtg gaatgccctt cttgactcgt ggaaatcatt caccaagtac 332460
gatgggatgg gattccaagt aaacagtgga ccgtcatatt gcaaagcagg cccacgcctg 332520
ggctggcctt ggttgagggg atggaggaat gttttcgggg gtgctttgca gggcagtggt 332580
gcagccgcag tgtgaacggt cttggacagc tgaaaaccat ggcctccttg ggatggcca 332640
gtgctcctgg tgtctcctcc acctgcctgg gttgtgcagg aggccagctg ccagtgcctg 332700
gggctgggaa acttttttgc ttggggcagg cttgggcgag ctctcccaga tgtgtgccca 332760
ccccaccact gcctggaagc atccttgttc tctgccagga tgcagggtca ctgttgcctc 332820
tgacacagca gtttctggga actcagagga ctgcctttct gaaggctggg gagaggcttt 332880
gagcaaggag cttgttttg cttaatccct ctagaccatc cctgatgcgt agatgtgaga 332940
ggatgttttc tggcacagtg ttatgaaaat acaggagaaa cagtctcagt ggaatgtttc 333000
atattacccg aaaaaaactg gaaaccatcc tctgttgata cgaacacact gagactaaga 333060
attgaagtaa tgcagtttta agaagtactt ttttcctatt attttttgct gtcaactttc 333120
tagcaatgcc acggcaaagt tggtgtttca gcacatgcta gagtgagctc cggcttcgtg 333180
tctttagcgg agttggttaa tgtttcactg ggtagacgga gctggcctct atatttagcc 333240
agaagccttt gcctcttttc aggcatcaaa aatgggtgtt gtcattgtct ttgagaacag 333300
caatttgagg tctgactcct tcagttgtcc tgtgagctgg gcgttgcagt ccgctcgaat 333360
caagtgttgg aaacccccca ccccacccct cagcccatcg tgaaacgaca gctgtcagcc 333420
tggggggtgg ctgctgagga ggtgcagcag gaatggggct gggcccgtgg gccagcacca 333480
gctgccctta ggttttactt tccaagccaa tggcccctgg aacatgccag cacacactgc 333540
catgtcctgg ggctaagagc tgcctttagg gacaggctcg tgttgtccag tttgccctga 333600
gagatgcacc tgaccagggg cccgtcgtgg ctgcaaccca cggtggtatg ttagtgtttc 333660
caggcagttg tcagcagctg ccgggtagtg tgtgtgtgcg acagcaggag agttcctgga 333720
ggaaagggac tggggacact ttctcagagg ttctcctgcc tggaatcaag tgatgcgtgt 333780
ccagaaggca agagagggcg gctccgcctg gttaaagttt gggaacggga cggagccaac 333840
tcctccttcc aggactgtgg gccccactct tttgcgctaa cacttcccct ccctcgggtc 333900
actgaggaaa gagctgctct gtcccctcca gtgccctgaa ggtccctggc ctccactggc 333960
tgccatggca gggggccctt ctgacagggg ctgccccaag ctgctgttcc tcctctgaac 334020
cttcacccca acacccagcc cgtggcccct gcaaggggga ccctgccagc tgggaaaccc 334080
aaaggcctgt ccaaatgcgc gcaccaggac cgaggggagc tccctcccca catctgctgc 334140

-continued gaattgccag cttttaaatg gatggggttt tttatgggtt gaacctctgt taatactttt 334200
gtacactctc actacagttt atatttttat aggctatttt ctcaaggtgt ttctagattc 334260
cacatatcta ttttatataa caagttctta tgttatgtgt gtgactccct tgtgtgtatc 334320
tgtgccagcc tcagcctccg agttgctttt ccctctggcc ctgactctca ctgactcacc 334380
gatgtgatgt gcaggcccac ttcttacccc agatagcctc gggtgctgcc tgtagtcatg 334440
ctgacagctg tacagtagcc gccaagactg ctgacggctg gagacggttc tggtttcaac 334500
aactacggta tattgatatc ggaagtattc tagacagatc ctcagttggg ttttctagct 334560
acatgtttgt attgcacaga tccccacctg ccatcctata gtgttgtctt cctgtgtgtt 334620
ccggggcttc tgggcagctg ggcctgcccg gggaagtcct tgcaggtggg aggccataca 334680
gagacccagt gtgtgccact gagcgtccca ccgctgctgg gcaactggag gactgcaggg 334740
ggcgccaggt gactctctcc ttttatatca cagcagctcc tgtgctgacc ttcaagttat 334800
gttttggaac tgtaatacta aaggaagaaa taaactacta atttgtataa tattctgcat 334860
tgaaattcag ttatagtcac tagtgatggg gctcacccca agggcttgga gggtggggca 334920
gggcttattg gtgttgcggg gggcgaggag gggctctcca accttccagc ctggcgtttc 334980
tgggtgtctc tgcccttggc tcaccctggg gcgggtgcat caggatgcct ttgccagcag 335040
gggcagcctt gggaggcccc aagaaccatg gccaagctgc aggtgtgggc tgggggcacc 335100
gaggtgggaa agccggaagc tggagactcc ctgtgtccgg ataacccccc gcccagccac 335160
aaagaacagg catgcctcct tccgccagct gtgccatgcc ctgcctgagt cacaggcttg 335220
tttgtctccc gtcttggctg acagctcagg cccagctgcc actggggaca cccccagtca 335280
tcagtggaaa acacccaaga atgatgaaga ccaaaggggt tcccataggg gtgtttcggg 335340
gtggctccat caaggattcc cagacagggc aggccaaggc ctggcaggct tttctcttct 335400
ggggacgtgg attcagcgag gctggggggtt cctggagtca cgcagcagag cggcggcggc 335460
agagctggga cagggactgg ttcggtgtgt gggtcaggag caagtcgaca ggccctgctc 335520
cccacccctt ggaagggagt gccaccaggg gccgttctga ctaaggcctg ggaagccgtg 335580
actcagagcg tgggtcccca gggtctcttt gggccagccg ggctgctgca gacagacagg 335640
aagcacgcct gacgctcctc caccctcggg cagcacagcg gggctgggac tcacgctagc 335700
ttgcccagca acttgctttc ctgcgtgaac tctggcaggc tgccctctct gtgcaaagcc 335760
accactggga cctgcttggg gccctctccc tcttccacct gctcagggta gcctggagct 335820
tggaggtggg cagtcggagc ctaggatggg cctgtgtcac cagggcatgt gcccttgggc 335880
caggtacttc ctctcagagc cttgagttcc tcctctgagg atcgggcttg ttggtgtgaa 335940
atgaggtgag catgttgaat tggggagcag caggacacgc acctgcaggc agctgccgtg 336000
gccatgctcc ctccctccct tccaagtcct gggacagacg ctcatcgccg aggggttcag 336060
cctctgatac tgtttcttgg tctcagcccc taaggagtaa ttttatttta ttttttttgt 336120
gtgagatgga gtctcgctct gtcgcccagg ctggtgtgta aaggtgcgaa ctcagttcac 336180
tgcaacctcc gcctcccagg ttcaagcgat tctccttcct cagcctccca agtagctggg 336240
attacaggtc cccatcaccg cacctggcta atttttgtat ttttagcaga aatggggttt 336300
tgccacattg gccaggctgg tttcaaactc ctgacctcag gtgatccgcc cgcctcagcc 336360
tcccaaagtg ctgggattac aggtgtgagc caccgcgccc agccaggagt gattttcagt 336420
ggtgtcccct ccatccccag catataccca gccctgagtg gctgcggctg ccacatgcag 336480

-continued gctccagggc tacattcacc tttcgtccag ggttgtcata cgctggagag tagaatgtga 336540
gaggtgaccc ctgtaggctg cagggcgagc tctctgaacc ttagtgtccc ccacctggag 336600
aaggggcgta acaccttcca gggggagggc tgaggaagaa attgtcaacg gctgagtcta 336660
aggctcacag ccagaggcca gggttggatc cagggctggg cctgggcctg gggggacagt 336720
gtccgcccct tccccagcct cccgcccctg gtcaggccag gaccctcttc aaagcacctt 336780
catgcccatc tgttccctgc tgtgggcact actgtctggc tccatgggac tagattttat 336840
gggaggggaa ggggctgtgg gtaggcaggt gccaggtgct ggaccataga tcagcgtggt 336900
aggaacctgt agctggggct ggtggtggga aaggggccaa cctgaggcag tgacaattag 336960
cccagcccta tctctgggca cagagatgaa gggacacgtg gggacacagt agggcacagc 337020
tggccagcct gctcttcccc tctctgcctg ctttttgcag aagagtcaac agatagaaca 337080
gacagggcca gggaggtccc catgggggcc ccagtcccca ccactccagg gggcagtccc 337140
tgcaagtgac atggtgggct caatccctgt ggaacaggtc tctgaggacc acagagtggg 337200
gccccaggga aggctgggag cctgagctga aggcaggcag caagtaaggg ccaagccgtg 337260
cccctgcccg gaagaccttc ctgcccccag aaccccaccc tctgcagaca gccctccctg 337320
gggagcagcc ccccagcttc tgaggccttc cgtgcctcac cagatgccat gctctcaggg 337380
actcattttc tacgctgccc cctgcagatc tgtcccagag gagcaggtga aaagccacgc 337440
ctgccgaggt gctgtggcgg tggagttttg ggcagagggg tggggggaag agtttctcac 337500
ttttaagatt ctccaaatcc aagacgaagt cacgctgtgc tttggaatgg tagatgctca 337560
tttatgtaaa atcataataa atgttacaca aactgttaga ataaaaaaat accttttttg 337620
agggggagga ggtccccagc ctgctgctgg gtagtgagag ggggttagca ccattagggc 337680
gcagggggcg ggagctccgc cacagcccgt ggtgggcact gaggtctgtc ggtcggtctg 337740
tgcatcctgg cgcagtcagc ggcgggcaac ccgctgatgg cctcgggagg gggcgccgtg 337800
gctgggcgga gagcacgagc ggcagcactg ggtgcggatg gtgggcagct ggcagcggcc 337860
cagtaggcgc agcgtctcgc agaacccgaa ggacaggcgg tcccgctcac agcctggagt 337920
gggggggcag agaggcatca gaaccagtag cttggggtac ccagaacctg gctccctacg 337980
ccaaccacct taaggaggct ccagcagctc cccaccaagc agagagcccc agtttctgga 338040
gcggctcccg aaccggagtt gcaggtctcc aactgttgct gtctctgtcc cacctactca 338100
tggccaaccc caggactcga gaacgggtgc tgctgggctg aggtttctgg aggaaaggtc 338160
ctgagacccc accctgaccc cctcacatgc ctgttaaaga gcctgcccag ggcgacgcct 338220
tgccacccca tctccatcct tgctcatccc tggtgttccc ggacagatcc tggcacagaa 338280
ctgcggtccc ggggcctcct gccagcctgc agcggcctct gcccccgact cccgccaccg 338340
ccccctgccc cagtgcatct gtcctgccag gcctccgtga ccacctccag ccacaggggc 338400
tgtactcagc ctcgggttct gagtcacagg gtcccatctc ccaggccagc ctcccacttc 338460
tcaggtgggc cacgaagcct agagtgagtg ggccttacag gccgtcagcg gaaaccagag 338520
actgagccca gcctgctggg gagggaggcc agctgcaggc tgtgcttgtc agggctgagg 338580
cttggctggg ccctcctgcc ccgtggttat cagagctatt ttgggaagtg gcttgtttcc 338640
agcctcctgg ccttgctcct gatgccactg ccactgctga cagcccccag ctgccacccg 338700
ggccctgctt actccagcag acctccctgg ggaggaggag caggaaggca gcagccagcc 338760
ctgggcctgg gacatccccc aggcccggca gagggcacga ggcagcaggc aggctcctcc 338820
accccagctc caggcagagc tccaaagtgc acatctgcag gcctgcatcc tggtcgcccg 338880
gggtgacctc agacaagctg cttcacctct tgggcctcgg ttccctcctc tgtcaacccc 338940
acctccacag caaatggatg tggccatgct gtgtcactgc agtgagcaca cacacacgag 339000
tttcccagct ttccacatgt cccgccaact gtcccacaga ccagcagaac atctgggaat 339060
tccaggtctc caagtccaag acaccttccc agcccccctc cactgttcac tgatggcaga 339120
aaactcctca cttaggacag cttctagttc agccacctaa ccagccccca tagcccactc 339180
cctgcagccc actcacaccc gcccctggga gaccttgcaa gcccagagcc tcctgggcca 339240
tccgtccttg gttctaggcc cccaggggcc tcagtttctg ttctctgccc catctggtcc 339300
tcccccactg ggatcataac cacccccgctc cctgtggcca gccctagcca taaaggtgag 339360
agacgtggtg ccagcaccca gctcaggtag cacataggag tgctctgaga tgctggctgg 339420
gtgcgtgctg agggcaggca ggacagggtg ggggcgctgc cactgggcct tgaggtttga 339480
ggcaggaaga ccacccatgc cagaggcagg gcagcgaggc atggcagggg ccactctgag 339540
cctgaatgag ggctgcccag gagctggcac aggtagagaa ggcagcgttg gacaagggga 339600
gaaggcagac cggggagatt gcaggggggcc ctgaatgcca gcttgagggc cctggctgag 339660
gactctgtcc taggggcagg gagcagacag ccaatagcac aggggacaca gctcttcacg 339720
ccacggcttc tggattcctt agactggcag ggtcagcccc aggccctctc cctgaccttg 339780
caattgggga tgacagtggc tgtgggggag gggaaaaagc caccttccct gagcaccacc 339840
tggatcccca cgcagtgctg cgtgcttcat gcccagacct catttatgca aggatggggc 339900
ttggcagccc ctttattcag cacatgaagg ccctgagagg gaaatggagc ccaaggccac 339960
acagctggtg aggggagcct aggtgacact ccagggccac cccatttcct gccctcagca 340020
cttccgggag cagctggggc tgcaggaagg aagtgtatga ctgtgtgtgt gtgtgttggc 340080
gtgtgtgtgt gtgtgcgcgc acgcacacat gctggaggcg gcggcagggg tgtccagaac 340140
cacctctacc tcaggccctt ccaccaggac ccagctggcc aggaaacccc ccaccactgg 340200
gattaacagg accctggaag ggaggccctt cctgcctcaa accccattac ctcattagca 340260
ggaccctgga aaggaggccc ttcctgtggt tccattgctc actctaggca gtcctctagc 340320
cagggaatgg acaggccagg gctggggaca gggactcacc caggcccagt tttcacacag 340380
cctcagggac atccctggtc tcactgtggg aagactgaga cctagaggag aaagagctta 340440
cccaggttca cacagcaaat caggggccag ggccactccc tctactcccc caaggtcaga 340500
cagctgccta tgggatgttg tgtggccggg actccccttg actgactccc agcacagccc 340560
agcctccagc atggcatcct gtggcatcag gattttcagt ggccatgtgg ctcctgagcc 340620
cagactacag atggaaccag ccagtgccgt gggcacaatg gtttgacgac cccatttccc 340680
catcaccctc cccaccccac ctcacttcag cagggagcct ggggtcaggg gactcacggg 340740
gaggctcgac gggctcacaa tcctcggtgc cacacggccg ggagctctca ggccaggcct 340800
cgtggccaca ctggtcactg tcttcctcgg gcagccctgt ctgggtgttg acacacttga 340860
ccaggcgccg ctggacacca ccaccacagg ggcctgagca ctgaggggag cgggggagga 340920
atgagtgtct ccagggccag ccctagcagt gggggcaggg acacctcctc tgggaagccg 340980
tccctgcgcc ctgtgcctga ctggcctggc cttgctccca gccgccccct cagtgcctcc 341040
tggagcacct ggtcccattc ctagagccca cttggtgctg gaaccccact ctcacttgtg 341100
ggatcggctc ctgcagaggg aaggggcgtg agaaccgtgg gacagccctc ggggcggcag 341160
ggcagtgagc ccctcacaca ggacatgcct gagaagcctg ggcaggggcg ccgggatgga 341220

-continued gccctgatgc agcagtgggc agagatgtgg gcgagacacc gctgtgcccg agggacaggg 341280
cagaggacct gccgcagccc atgggcagga gggcaggaga cagtttcaca gccggggccc 341340
agcccgccag gcttcgttgt tatcagccct aaacatgcac tgagtctgtg ccagtgtcat 341400
gctgtgcccg gccctgtgct tcgttgcgtt ccttcattta atcctcctga ccctcctctc 341460
ctaagctgtt ccagttttac agatgagaaa acagtgaccc agcaacgcaa agcaacctgc 341520
ccagagtcac tcagcagcca gtcggacaaa gacgcaaacg ctggcccagc tgactccagg 341580
acccagctca gggcccaaat ctgagatttc tgaacccctc agttccaaac aggcccagca 341640
gaaggtgtcc tgcccatctg aggcccctct tacgcccccct tctgccgctg gcctttgccg 341700
ggctccccgg ccccctcaag ctcgtcattc ctgcctcaga cttcacacct gatgtccctt 341760
cgatccctgt ccttggcatc actgactcct ccctcgggtc tcaaccccag acccctcctt 341820
ggaaggcctt ccctgacacc acagcacacg cgccctttcc ttgtctgttt ctccctggca 341880
ggtgtgagca ccagccgggc ggggcctcgt ccagtgacag ggccacaaag agcctggctc 341940
acagcacaca ctccacagct ccttcaccca acccaagact gaccaggcgc caccaagcac 342000
ttgctccctg ctcctccccg cagcccggct cacctggccc cagggcccca ccacccactg 342060
cgtgcagggg tgggtgttgc agggccgggt ggtgttgggt ctcagcgcct cctcgcagag 342120
gcctggctcc gggcaggtca ctagacgctg ctgctcacca ccgccacagg cctcggagca 342180
ctgggtgggc agggaaggag tcagggcaca gccagggtct gagggcgtcc cctccccccca 342240
actcaacggc caggcctcac ctccctccag gaagatgtgt accagctgag gcagggctgg 342300
gccccgcagg gccggtgcgc aggcggcttg gcaggcccgg gctgacaatg gaagggccgc 342360
agtggccgga ggtcccgtgt gtccacacac tgcacgtccc gcactgagga acctccgccg 342420
cagctgcggg agcactgggg accgagagac gtgtatggac acatccccat gtgcaggccc 342480
acaggcgtga ccccgtgagg tgtgtggcgg gaaaggcatc caggcccacg ccccagcccg 342540
ggggaatagc tgaagaaccc cagcgagagg ccaaggctgg caggccccag gcaaaaggtg 342600
gcatggccag ggctgccac gggctgggac agacagagaa agggaggaac aaaggcaagc 342660
tggtgaaaga caagtccaga tggggtcaaa gatacagagg aaaggagaca ggccaagcca 342720
gacaaagatg agaagactcc caagagattc agaatccggt gtgatcgggc acacagatgt 342780
gcagcctggg gccctcccct tccctgccgc tctcagaaca caggccgtgg ggaaccaggg 342840
ctccacccca tgccctggga atgcctgtcc tggctccatc ctcacgcacc ttactccagt 342900
tgcctgagtg ccaggtggca cagggccgca ggtggcagcg gcgggcaggc tggggccggc 342960
cagcgggggc gcagtcctca tcccggccgg agctacagcg caccggcctc cagaccgcac 343020
ccaggccaca ggtggtagag cactgcgggg cagagacccg tgaaagccag gcagatccca 343080
tccccgccag gcctccacag ccaggaaact acccacctag gctagcgaga cctcagcaag 343140
acaggggccc tcttctgggc ctcagtttcc ttatttgcaa aataggctcc ttcacccacc 343200
tcccaggaag accgtgagaa tgaaaagtca aatcccctca gcaaccagcc gtccctgctc 343260
acatgggaca aagggcctgt gttccagtgt cattggtgca gaggtggggg gaggggaccc 343320
tgtgggcacc ccgaccagct atcttgacca gcctcgtcgc ttcccagagg caccagggaa 343380
ggaaggctgg gtcctggtac cagcagccaa atcgctgggt atccctgcgc aaaacaagcc 343440
ctgtgggcct cagcctgccc cttcccgccc caaaattagg gatctgaaca gaagcttcct 343500
tctcctgcag tgaccatctg ggacccaggg gaggggcact agccagcttc tttctggcag 343560
ctcagacccc tgcaggtcac tgccaaagga gggtggagcc actgagggca gagccaggtg 343620
gcagtgggct gagcccagcc tggagaagcc aggtccagcc tcagggaagc tgctgcctgc 343680
tggggaggac tgggcctggc ggccatgcgg ggaccgtccc cactgcacag ctgtctgagc 343740
cagctccatt ctggggtgtg ctgtgctgcc agagtgtgcc tgcccctgcc ttccctgagg 343800
ccccctgtgc tgcccaggaa tggggcccgg ggtcccctca tccccctaat cctgggaacc 343860
cctgccccaa gagaggctag acagacggcg cctgtgtccc actctgctca ttttcagatg 343920
aggaaatagt caccaaggtc ctgcgcaaac tccctgcccg cccagcccac accacttgcc 343980
tcgctccagt ttcccgcttg ccagccggcg ttcctgacaa ccaacgggtc cgcgggggc 344040 cccgcttcag ccaggctggg agccagcggc tgggtctcag ggactctgtg gctgttggcg 344100
gggctgtccc aagctggtgt ggacagcagc ctagagctca ggggcacctc agggctgagg 344160
gactcaggct gacccttggg tcctgggttc agggcaggct caggcatgtg cccgaggcca 344220
gtcagggttg tggggaggaa ggtcccccac actgccacag tctgcaggtc ccatgagcct 344280
ggtcctgggg ttgggaagga gggagtcccc ggctccaggg aactgtccct gaccttcatc 344340
tctggcagag gggctatggg aggaggaagg agagaagcca ccccaacagt gggccacagt 344400
tcactgtcca caggccccag gccaccctcc agagctggct cccaggccac tgtgcctcct 344460
gtccacagct ccgccacgtc aggactagga gaggagtggg tgctgccaac aggggacaaa 344520
gggggcagcg tggagctggg tctcgggggc aggtggggtg ctcctcggcc cttgggttcc 344580
tcatcatcct tgaaaacctc attggtcctg tcccgccatg gagggggcag ctggctctgg 344640
ctgtccttgc caactgggaa atcattttgg ctctcagggg tggcaggtgt ctgcaggcca 344700
tcagtggaaa ccctgggcca ggacaggctg gggagcccaa gatctggggc ccctatgggg 344760
gtgtcttcct caggcaggaa attgatcaaa gggttcccag gggtctgctc tgagggtggg 344820
ggtggggagc ggccggcctg gctaggccaa gggctcgggg accaaggtcc cagtaccccc 344880
tcctccttgg ctgcaggagg ctctgtggca ggcacggggc tacccgtgga gggcgcagca 344940
ggatggctgt gtggtggggg tgtccggtcc cctgtccccg ccaggtctag atcgggctcc 345000
tcagagggcc cgtaggacag atcctcgtgg aaattgatga aattgtagtc gtagtagaag 345060
tcgtccacaa acacgggccc cggcaggtcc agctctggag cctcctcctc aatggcgttg 345120
cccatggtgc ctggcttggg tgatgaggcg ggtgaagggc gtggggccag gtggtgcggg 345180
atgaagtcag cctcgttgaa gagctcgtgg ctggaggagc cgctgcctga gccttcaggg 345240
cccagtgtgc ccaggggcca ccgacagagt ggcagagagc aggtgacttc gctggctggc 345300
tgctgggcct cgtcacaggg gacaccggtg tcattggtgc agaggacatt tcggcgctga 345360
gtgccctccc cacatgtcac tgagcactgc aggggaagcc agggtgaggg gcttaccctg 345420
ggaggcaggc tgccagggga cgctggggca aggctgggta acctgtccac tgcccgatgt 345480
cagagtggca gagaccccag ccagccctct ctggcccttc ccagctcaag gccatgactg 345540
tggccatgct tgccaggggc ttcctgatcc ctgaggcttt agagtcaggg gctggaccct 345600
ggaatgccca ggttccctcc cacccacaag gtctccagga aggctgtctg cctccctgta 345660
gctgaagacc aagggtggag ctggaggcgg gccccttccc atcccacact cacctgagac 345720
cagttcccca cagcccaggt ggccggacag ggtacatggc ggttgcaagg ggtttcagta 345780
gggggccggg gaaggtgttc acaggcgggt ggctccaggg cgctctgctc atccagcccc 345840
acgctgcgga tgcagagcac ggcccggcgg gagaggcccc caggcccgca ggagctggag 345900
cacagctgcc actcacctgc ccaccacctg gcgagggcac acaggtggca tcagtgtggc 345960

-continued atcagacagg tggcctgcag gctcaccagc aggggggccc aggctgggct tccaggccct 346020
cggcatttgg gtagagctgg gactgaggcc agtggttgat tctccagagc tccaagctca 346080
ggtaagtgtc ctgccctcaa agcctggtga catggcacag cccctccgct cctgccagcc 346140
tcccctcagg aaaactgagc atgacctaag gcctgtttcc acatccaggg acccaaagag 346200
gaggaccaca ggtgtccagg ctggcctagg ctggggtgag gggtaaccgg gggttggggc 346260
ttcagccttg ggaagagaat aaaagcccgg ctccctctgc tcctccccag ggcctccagg 346320
gacccagatg tagggacctg tggcagaccc aggatgcctg gggtgggga gttggcgggg 346380 gatggggtgg ggagttggcg ggggatgggg gtggggagtt ggcgggggat ggggtgggga 346440
gttggcgggg gatgggggcg ggctcacctg gcagggcagg gctgctcgct gcacttcctc 346500
tgttggtcat caggccggcc cagggggtca cagtgctcct cgtccacggg ccctgcctgc 346560
cgctccaagc agtacacatt ctgcctctgc acacctaggg gccacggggc tcagcctggg 346620
actggcaccc aggtgcccac cacccaagac ccaaagacac cctctctgcc agaaccctcc 346680
cagaacagcg ccttactgcc cgtgtcagga tgccttactg cccatgtcag gatgaaggca 346740
gacctccacc gtcgcctcct cactgtcctc ctggttctca cccgcccccct ctcctatgta 346800 gcctcccctc tgactggagg ggtggcagag tgtggatgtt tagtgggttg ggtgcccaga 346860
ccctctgcat cccagctgag atgcctgggc agctcatttg gcctctctga acctcagtgt 346920
cctcctctgt aaagtgggag caacaatcct gcctcctcca tgtcctggag ggaggactgc 346980
gtgtgttctt gcatgtgcag gctcagcccg tgcccggcac atcctaagag ctcgatccat 347040
gccagctgct gttagcatgc aaacccagcc atggctcctg ccaccctccc ctcagggaaa 347100
ctgagagtga cctgaggcct atttccacat ccaggaccc aaagaggagg accacaagtg 347160
tccaggctgg cccaggctgg ggtgaggggt gaccggggct ggggcttcag ccttgggaac 347220
agaatgaaag cccgattccc tctgctcctt cccggggctg gcttgggtga tgaggcgggt 347280
gaagggcatg aggccaggtg gcgcaggatg aagtcaacct cattgaagag ctcgtggctg 347340
gaggagccgc tgcctgagcc ttcagggccc agtgtgtccg gggcccaccg acacatcatc 347400
ccaccatcca cacccttccc aatggctcag agaacctccg gacaagaaat ggggcatcaa 347460
ggggcagccc ctgctctcca tccccacacc aggcttggca ctgctcctgt ccttcacacc 347520
ctctgtcact gccaaccctg gggcctttgc acagccacgc tcctcacctt ggacactcac 347580
ttccatactg cctgttgagg cccagctgca ggaccccctc tgctggtggc tctgccttct 347640
ctgctccacc ccctgccccg tggtcccgag agtaagttgt ccctcccctg agctgccagt 347700
cccacatccg tccccctctt tcctcaccaa cagattctga ttttgttcaa gacagcaatg 347760
ggacctgctg aaaacacacc ccactgccgc tcccttgcaa ctaggggggt ctgggacaca 347820
gtactggctc gggagaaaaa ggcacaagtc cctcgctggg agtcagccct tttccctctc 347880
cttcttcctg cccagaacac tgcaagagcc ctggaaggga ggacaccatc tgtggcaagc 347940
aggagtggag gggaggctgc tgtgacaagg acggtgtggc tgagggccag tcagctccag 348000
gtcccgccag cttagactgt gcatctggga cttcctgcct gagacaaaga acccctgtct 348060
gttccagcca ccacagggca cttgcctctg cagatgctcc caagtggtcc acctgcgaag 348120
cagccaattt gctgaaagac agttccccaa atgtctagtg ctgcaagtgt atttgttggt 348180
tttcaagttt gtccaattaa agacacctgt attaggccag gggcagtggc tcacacctgt 348240
aatcccagca ctatgggaag ccaaggcggg caaatcacct gaggtcagga gttcaagacc 348300
agcctggcca acatggtgaa accccatctc tactaataat aaaaaaatta gccgggcatg 348360
gtggcacgtg cctgtaaatc ccagctactc gggaggctga ggaaggagaa tcgctggagc 348420
ctgggaggcg gaggctgcag tgagccgaga ttgtgccatt gcactccagc ctgggcaaca 348480
gagtgagact ccatctctaa caaataaaat aaaataaaat aaataaaata aaataaaata 348540
gcaaaataaa ataaagacag ctgtattaga taaaatgggt ttcctagctt tggaaggtat 348600
ctgcccagtt ctccagtttc actttgtcat cataatagca tttgaaggaa tgctcaaatg 348660
tctgtatctc agattcccaa ttctgagacc ctgaggatac tgagtgtcaa caatgggaag 348720
actgagggga aaaggggaga actaagagac aaagggggaa actgaggtgt ggggagatca 348780
aggaatggca ggggagacca agcaggggga ggaagaccga ggggcgttgg tggggggggac 348840
tagggggctg gggggagacc aaggaatggt gggggagacc gagctgtgag aggaggactg 348900
aggggtgtgg cgggggtact ggagggctgg agggagaccg agggatatgg tggggagacc 348960
gaggggtatg gggggagacc gaggggtatg gggagactg agaggcatgc ggggagactg 349020
aggagtatgg gaggagacag agggccagag gggagactga ggagcagtgg ggaggagaca 349080
gagagagagg ggactgagga gcatggggag agagggaaat ttggggagga agagtcagag 349140
ttaatgaaat tgccctactt tttataaata gtttagggaa ataagtcagt gtggtgaggg 349200
gccactggac tggtctatcg agggggagct gtgtcccctg gagggagaac gccaagagct 349260
ggagcacact gaacatgcgc cgcgagccag cacccacctg cctcatccat gtaccctccc 349320
agcgggcctg ggacacaggg caatcgctag cctcatctca cagatggaga actgaggctc 349380
agagaagcaa acttccaaac ccgtggtggc ccagcagtga gctgggagct gaagccagtg 349440
tccctgtcca gacactaagc ccctgcaggt ggggctgtgc ctgcccact tctcacctct 349500
gccgcaggtg actgtgcact tggtccaggg cccataatgc caggagaaca cgggcggcgg 349560
gacctcgtcg tggccacctg cctccctgtg gatggtgtac tcgtagtgca ccccagggtt 349620
gctctcctgg aacagcagct gggtgggcag gcgggggccc atgagcacaa ggtgtcttct 349680
ccatccaccc agtcctaaag gagctgaccc cagccacctc tgtgaactgc agctacaaga 349740
ttgggccatt ttaaagatgg ggaaactgag gtagaggccg cagcaggagg gcctggctca 349800
gagccaggct ctgtgactga accagggctc actcctccag gacgagacct gccatggagg 349860
gtgctgggcc tggggactcc gcctctgctc cccccgcctg ggccacggga ggcaggcacc 349920
tggatccaga caggctcctt ggtgggaccc ggggacgtga ggttctccca gttgcccctg 349980
cgtgcgtatg tgaaggtggt ccctgccacc tggtagtccc cgttccactg gatggtccag 350040
ccaccattga ggaagtactt ctccgggtcc tcgctccgca gtgccaggaa gttggcagcc 350100
tcggcaacct cttggatgcg gatctcgcgt gcgcccgctg ggatcagccc cacatccaca 350160
taccctgtca gccaagggtt gtgcataggt tgtgcccagg gtgagagggt tgcttatccc 350220
cacccgctcc cctcatgtct ctccccactt gcctccgcct gctgatgcca aagctttaaa 350280
gtctgagctc cctaaattgc tcggatctgt catgggtcac caaaacctcg cagaggtgcc 350340
acaaatcctg accccgtggc catgccccat cactcctctc ttggggacct acactggtct 350400
catcataagg ctggatccat tccctactct aagggctggc tggcatcttc tttctaaaaa 350460
aaccaaagtg cccaggcctt tctcctggga caccctcctc atccccatgc ggcctgcttt 350520
tattcattca cttccatcac acccatcacg tgccaggcac tactctcagc acctcacatg 350580
tgtaagctca tgggtaatgg ccctatagca taggtactat tgttatcccc attttacaga 350640
tgagcaaagt gaggcagaca gggatagtaa cgtacatgaa catcctgctg cggtatgagc 350700
agcctccatg gccagtgctt tatccaccac actgcactgc atctctggga gaaaatctaa 350760
gcttctcagc ctggcactca aggccccata gctggccctg ccttcccttc ttgcctccag 350820
gctctggcac aagctcttct ttcctccatt tggaatgccc tttccatctc ttctgagttt 350880
tatgattcag ctcgacttcc gcctcctaca ggaaaccttc cctgacttcc ccaggccagg 350940
accttcttcc tcagtgctcc cacagccctc cgggcctccc tccactgcac tggtcacacc 351000
aaaaggttct gtcccccctcc aggactaagc gcttcacctg catgtcccca tcacctagca 351060
cacagtcagt acttgagcaa cgtgtgcaaa acagaccgga ggtgaggaca cggagctggg 351120
gtctcagaag cttcaggagg agactaccat tctttggaag gccaaggggc cacacacaag 351180
ccgggttggc cctatctggg gtgtctggga caggaggact ccccatgggg acaggtctct 351240
gcacatgggc caggggtccc ctgactcctg caagaatcca ccccagcaag gcttccctgc 351300
ttagccatct ccaggctggg tgggggccac gaggccaagg acaggggccc aggggagatg 351360
gggaaggggc catcaggtga agagcatacc cctccccaca gcggtcccac cccataccca 351420
ggccctcggc ctcctcgaag gtcccgctca cggtgtggca ggtggagccg ttgccgtggc 351480
acacaccaca gcggtcctcc atagcaccgg agtcaatctc gaagtcacag cccacgttct 351540
gcaacacaca aggaagggag ggccctggtg ctggcggcca gccctctgtg gccccagccc 351600
cggggccagc cagagtcagg agaagaaagc tgggagttgg ggtcgggagg cctctctctg 351660
gccctgcccc acctcagctg tgcctctgac ccaggtgaac ctctctactt ccctaagcct 351720
cagtttcctc agatgtgaga cggggagacc cacccctccc ttaaaggcat gtcatgagca 351780
tcacatgaga caagagaagg gaagagttct gcaaagcctg cgggcaggca ggggatctga 351840
cacgccacgg gctcctgagc agcgcgtgca gggaatttca acgtcaaagg cactgggggt 351900
tggcacctcc ctcctggtcc tcctcggagc ccaggccttg ataccccaga ggcttagagg 351960
gcaagaagca gggacaagta ggtcgctggg gacatgggca aagaggagag gccgtcattg 352020
ttattaaaaa taagaataga aattgttacc acacactgag ggctactctt tgcggctcag 352080
agccctctgt gtcacctatg ccacctcatt taaccccttc tatcagggag caaaccactg 352140
cctgtggtca gccagccagc aagaggtcaa gccactgcct gagctccggt ttcctggctg 352200
gggcggtgct ggtgcaggca tccagggaga cgcagggggg cgaggcctga ctggaagggt 352260
ccccagtgcc aggaggcgtg gtaggggctt tgccttagag gtcatagagg gtacgggctg 352320
ggaagcccga tggtagagca tggggagggt ggcccgagga ggaccaggag ggacccagga 352380
gagaacctgg ggcccgccat ggcccgagga ggatcaggag ggacccagga gagaacctgg 352440
ggcctgccag tggggctggg ggcaggcagt gctgggagag cctcttccta accaggcaca 352500
ccttacagat gccgttgatg cagaggtccc ggctggctcg gacctggtag caggggggtgc 352560
catcgaccac ggcgtcccgc agcttctcgg caaagtactc attcgcgggc cggcagtgca 352620
gctcgcaggg gttcactgag ggcccaagta gaagagtcat cagcaacagc tggggcggga 352680
gtatggaggc caccaggaag acccctccgt gacacacatc catggcaggc tggaggctcc 352740
caagcagcac caacatgctg gaggctccgg ctgggctgat agctatctgc aaggctgcag 352800
actggggagc taggggcgag cagcagcccc aggggacagt gggagtggcc caggcttggg 352860
gtgaagactg ggcctcctgc tcgcatcaca gggtaacctt ggacccacac acccccagcc 352920
ctctaagcct caatgtctcc atgggggggca gcactcaccg tcattgacca cgggcaccca 352980
tgtgtgcagc tggcccttgt agagcatagc gtcaaagtgg ctgcactgga cgtggcggaa 353040
ggaggggcgg ccagcagggc aggcctgcag gttgcagagg cggaagcgct tgcgctcacc 353100
cacacagtat ctgcctttgt atttgggcct gtggggagaa ccggggtggg ccccagtgac 353160
ggcccagtga gtgctactgc atggccacag cccagagcaa gcaacttcct cctgcatcca 353220
caccccgaga tccctgctgc ccagctttgt gcacgctgct cccctccctt gggctgccca 353280
ccctctggcc cagacacact ctccctgttt gtaaggacct gtggggaggt ggcagcagga 353340
agcctgagct ctgcccccaa cctacagtgt gaccgtgggc aagtcttcgg ccaccctctg 353400
ggcctcagtt tcctcatgta taaagtgggg ttggggctgc ttctgcagag ggctgttgag 353460
aagctgggac aagctgcagg catgactagc actggctgga gggactgctc cgagtctcca 353520
gcccatgaca ccagcatcct aacgagccct tgagtcctca gccttcctcc tggtggcagt 353580
acccccagcc cgggtctaaa ggaagtgcct agggccccag ccagctgaaa ggtctgacct 353640
agcacagctc ctgaaatcct ccgcatctag gccagggtcg ctggccccca cccagctcag 353700
acctggaggc caggaggcag ggaggggcac aggccactct tgggtaagcg cagggccctg 353760
ggtggggctg gctgtgaacc ccatgcctgc cccgggtggc ctcctgaagt gaagatcagc 353820
cgggtagtgc ctcggtctac agtaccactt gcctctgctt ctcaccagat cttcacaccc 353880
cctgcacccc caccccccg tttagatggg gaaacagagg cccagagagg tgaagtcgct 353940
cacgtcaggc caccccttca gtgctgtccc atcctcccag ctgctccgtc tcatctcaga 354000
cctttgttga gcctctgagg ccaccaagcc cctcccgctg agtgcccact acagatgagc 354060
tgcagggctg agggcctggc ctgcataaac tgcatttgcc cctgactaca actttactgg 354120
atgggcactg ctattataca gatggggaaa tggaggccca gagaaggggt gaagaggaga 354180
ttcgaaccct gagccatcta aggtccaggg cccatgctct tccccactgc cctctcctgc 354240
ctccttccag ccagcagctg ctttgccatg tggcctctga tgagtctctc tagtctctgg 354300
gcctcagtgt ccccctctct ggaaaggggt cagaagtggg gaccctgtca gcccccagaa 354360
cactccttga aagtgactta aggtggcctg gacactcgga ctgaccatta tcaggacact 354420
tctaagagcc aggggctggg acagagccaa gctcctgcaa tcggctgact gtttgggtcc 354480
ctctgtccca ctgcccaagg gcaccctggg ccccacactc acgtaggctg cgtgcactgc 354540
cgctcggcgc tctgtacgcc catgccacag ctccgtgagc agatggacca ggcgctccag 354600
ccagaccagc caccatccac ggcctcgggc cggaagccca cgggtacgca ctccccactg 354660
agacaccact actgagacag acggaggtag agccacccca cccccaagtc tatcagtcat 354720
cctcacccta gtgagaacaa ggtgggtggg aaggctgcga aaggcacaga ggggaaggat 354780
ggaaggtgag agaggcaccc tcacaatcat cacaatcatc tgtgacccag gccacatgga 354840
ggagctgagc ggggagtaaa acagcccaca tgctgactca gctgaagaca ccctggggaa 354900
tcatggaatc aagccctggc cccaatgcct ccactttgca gatgggggct tgggctgcag 354960
agagcgtggg gctctgctag gagcacaagc aagactgtga gccggggctg accccagggc 355020
ctggtcacag caggaagtct ggcctctcac acacccactg ccgggactgg ggacatcccc 355080
taccttattc tccccacacc gggtgccgtc cacagctgca tccagcttgg agtgacaggt 355140
ggtccccaca gagcaccaga gtgtgtggca gacattctgc gaggaggagg gcatgggcca 355200
taccctcaca ccctccccag tgccgccacc caccctgccc ccctccctgt ccccaagggt 355260
cccctgggca cccctccaca tggcaggggc ccacagaccc ccagaggttc cttcttgtgt 355320
gcctgctccc accttcctcc ccggaccatg tggtggtgtg gggcgcccgg ggctgcgctg 355380
ctcagagcgg tccccagctg tccacacctc tcccggccca gcccctcctc tggaaacact 355440

-continued

```
cctgttagaa gatcacttca ggcgatcttc gccaggataa acagaccctc tccacagggg 355500
ttccttttcc ctcttataag ccagctccag agaggcgaag ggacttgtcc gaagggtcac 355560
agttggtcca tggttgaccc agaattcaga gctgggtctg tggccgccca tccctggcct 355620
ctcccacagg ccacttgacg tctcacagtg tcactcaggg gcgcagccca ggccaggaga 355680
ggttgctccc aggctggcat ccacgggctg gtgagagctg ccccctgagc cctcctgccg 355740
ggtccccaca cccccacacc cacaccggcc ccactcacat ccatgtcctc gcagaaggca 355800
gagtaggccc cgtactggag gcggcactgg tggcttacat catagaggac gccaggtggc 355860
accgagggga agtcgataat gtccttggca ggagggtcgt ccaggcacag gccccaccca 355920
cggctaaaga tgggacggga ggatggaggg gggcgcagcc tgtgagaccc atcggagaag 355980
ccttggtggg gccgggacag gaggagaggt gggagggggc acagagccct acaactgtag 356040
gaaactccag cctccccgct cggctcagcc gatcctccac ctgcagccag cagcacaggc 356100
cctcccggcc tctctcatct cacctcctgg gcactccagc tggctaaaca atcccaaccc 356160
caatcccagg cctccgcaca cgctgccagg gcccttccct cagaaggcct cctggaccac 356220
caagccgtca tgtggccctg ctctccgacc ctgcagcctc cgtgtctgag cccagaccct 356280
ggagccaggc ccgacaagga tccggagaac atcacatcac agttgacaca acagagcctc 356340
cgacggcccc acccaggcag agaccttggg tcatctgtgg aaaggcgagg tctggaaagc 356400
agcccctccc ctgggagaga gcccagggca accatgcctg tcccgtttcc cccacacccc 356460
gacagggctg gcctccggcc tctgtcatac cctatctact cctgccttcc tccagctggc 356520
attccctggc agcggtagcg gggaaactgg cagacacaag caggcgccat ctgtgtccac 356580
cacacactcc tgctgctgtg gtgtggtgaa gacaaggctg ctcagacaca acaccatgag 356640
gcaggaagca tggaagcagg gaccctgggg agggcggccc agtcccttct ggcacccgct 356700
tctgcccctg cctcactctg tacaaccctc aggcatgcta ttgcttctgg gaccagtgac 356760
cagcctgctg cccctgctgg accttaggtg gccaccacta tggcttagca gcaggagtgc 356820
cctggcatgc tgaccaccct gcccatggct cattgctgtc ctggaggaac tggaggaagg 356880
tttgctgcct tctgggggca gcagtggctg gggagaattg agccacacag acttgcaggg 356940
ctggggacga cccaggcagc cacgacttgg gcagaaacaa tggagggagg caggacccgc 357000
gggacctggg gcctctagcc aggcagagga gatggggagg cacaaaccct ccagttctcc 357060
agtctgggtg gcctcagggc aggtggcgcc aggacagagg gtcaggatga gcatacagtc 357120
ctgattggga caggcagggg gttgcacagg gaagaagggc aaaggtgata gatcctggag 357180
tccagcaggg agagaaagag acactccgag atgtggagag gctgggagaa cacgaaaggg 357240
tcaggaaaca gggccaagac cactgaaggc aggtgtggag agaggctggg agggtggatc 357300
agaccatgga ctcccgaagc cctgatttca gaggaggggg cctggcagct tggagatcca 357360
gagtggagtg ggtgtttgcg tggtctccta aatcccccga ccagtgacag gcccccggcc 357420
ctgcccagag ctgcggagaa gaaagccaag gtgaccagac ttctactgag aaccctggaa 357480
tcctcctgga atcactcaga ctgcccatgc tggctggaaa cagatcctct aacatgggcg 357540
ttggcagatg agcagctgct ggatgcagtc ctagtgccca agatgatcac atgccaggct 357600
ggtccagggt gctgggggca taccctctca tttgctcctc acaacatcct gggcagactc 357660
taccatcatc tcccctcatg cactcagggc ccataggtca ctggccccgg gtcgcacaag 357720
agagatgtga tggccaggat ctggagccag gcccaggctg cctgcaccag gctgtgtcta 357780
ctcactgggc tacccccagt gcagggctcc tcccattcaa ctgcgagcct ggcctcaaat 357840
```

acttcacccc acatacaagt tcaaaaccat ggcagcgaga cctggtgggg agaaaggagt 357900
gtcccaagtg ctcctgcggc ttggggctcc ctgagcctcc ctgggcctgc acccggggca 357960
gagtatcagc ggcgggtggt ggggtcagct ggccctgggc tccctccttc ccgctagcat 358020
tctgtggctc gaggaggtag actgggggct cacccatccc agccaggggg tcctctgacc 358080
ctggggctga ggggtccaat gcacctcatc ccagcaccaa cagtccctgg gctgcagccc 358140
agcccttctg cttcctggct gccccagtgc tgactcgctg cacatgtggc tcctgcgggc 358200
ctgctgttgg gcagctgaag ccacaacaac ctctcagccc accctgggtg tgtgggagaa 358260
gtcgggagca tgaggcgacc ctcacagaat ccactgtgag aatcaggccg aggtgctgtc 358320
ttgggagtca gaaacccaag ttctactctt tgcctggcta tagatgctgt gtggccttgg 358380
gccttcacgt cctcatctac aagaggctga tcccaagcta caggggtata aatagcagtg 358440
tcttcttggg aaaaatcaca caggcggccg gcagccagcc cttccttcct ctggcaggct 358500
cactgccagg tcctctgcgc tgccgacaca cccggatccc caaacccgtc agcccttccc 358560
ctccacgccc ctccttaagc taattatagc ggggctgggc agtcccacaa gaggtcaaag 358620
gagacagtag gtgactccag tcagaagcct cactctcacc ttgagactgc aaagagctgc 358680
ctgccactga caggagagac ctgggggccc gctcccctgg ccacccctgg ccaccccagg 358740
gatctggtca tggagtcact gaatgggggg tccacggggt gaagtgaagg accccacatg 358800
tgacccagcc tgcctctctc cctgtagaaa tgctggcttt gaggaaagca gggaccaggg 358860
cctcccctcc tccccaccca ggtccaagtt gacactggtg aaatgctgtg acctctcccc 358920
agggtccctt aaagcacctg tcagtccgga aaggttctta gagttcttca ggtcaaccct 358980
cttggacaag ctccagaagc taccctccag tgccccccca ccacctcctg agggttcttc 359040
tgccccaccc tatactcgca tggccccggc ctctgcccag cctgccctcc acttacagca 359100
gcacccttct tcctcggcgt ggaagctggc ctttagaagg caggctcctt ctccgagtca 359160
ctgttcctga ccccaggagg gcttggtggc cctctcccca ttcctacaga cccacgagga 359220
ctgcatgcct cagtgccaat catccccaac tgtcatctgt ccatctcccc atggtgtgag 359280
ggcctggagg acaggcacct ggaggtctgt ctcctttacc acggtcccca cacacagggc 359340
ctgatggaca tggagtctgt ggacacagca agaacgagtt tggattcagc cctgtgggtc 359400
tacctggctg gataagcatc tatatgcagg aagccaaagg gcttcaggac cagccaggat 359460
gagagggtgg tctgtgagtg cctctgcgac gcccccaagt cctagaaaca ctgcctgact 359520
gtttggcact ttcggtgaat ctcactcatt ctgtccccca acctgcttgg gtggggccca 359580
tcctgtctct cctgtcccat ccccagcaag gagaccaaag gctgcaggct ggaagacagg 359640
ctgctgccac cctccccacc tccgcacacc ctcttccttc cacctcctgg gcctcgggag 359700
ggccctgctg cctgactccc aggatgcaaa ggtgaaagtg tgaaaggacc ttgggaggat 359760
ggggttcttc ttcctcccaa acacccctcc attggggagg cacgtattgc tctgcttctg 359820
tctggttctc cccggtgcca aggctctggg aggccccggc tggctctgac tctcaccctg 359880
tcctctcacc ctcaccccag gccccgagcc aagtccctca agcattccag cagctgaatg 359940
aggacagaga cttgtctgtc tgtctgtctg tcctagaacc aggctgttgg gcagcaccct 360000
gggtctgggc agctgggaac aagccctggg ggtgctgtgg gggcagctac tattctgatt 360060
ttctgaagcc attctctcat tctctgcctc tctctgggga aggagacaca ccctcctccc 360120
catcttcagg ccacttccct ggttcaagtc catcccatct atcacttggt aacagtggaa 360180

-continued ggaatagtaa tgagtgtgcg tgaaatgctt actgtgtggc aggcactgtg ctaagcactg 360240
cacgcgtttt ctcacttatt cctcatatca catgcacaag gcaggcccat catcatgtcc 360300
attttttgag gcttaagagc taatataact tgtctgccaa cacaggtaga agcctgggcc 360360
acagtctagg ttcttttttt tttcccaaga tggtcttgcc ctgtcgccca agctgaactg 360420
cagtggtgtg atcttggctc actgcaacct ccacctccca ggttcaagca attctcctgc 360480
ctagcctccc gagtagctgg gattataggc gtgcaccacc acgcccagct aatttttgta 360540
tttttagtag agacagggtt tcaccatgtt ggccaagctt gtctcgaact cctgacctca 360600
agggatccgc ctgcctcagt ctcccaaagt gctgggttta taggtgtgag ccaccgtgcc 360660
tggccagtct aggtccttaa ccaccaaaca aaactcttct ctgcttccaa tcccaccccc 360720
caccccagta ctccctcttc cactggaggc cagcatcctt gctcttacat ccctaatgga 360780
cctggtcaca tccctgctta agccccacag tgagtggact tctagaaaaa tatggcatgt 360840
tgagcagaca gatttatcgc tgctcccttc caaaactcca ctatgatgac agtagaggaa 360900
ataaacaagg cataaatcca taaggggtga tgatgggtaa tgaaggatgt caacaagatt 360960
ctggaagctg ggaagcagat ggccaggcag tagctgactt ggtagagtga taaaagctga 361020
gagccaactg cctgcaggga ggaaccaccc agaaggagaa gcccggaaag gctcaggaat 361080
ggagtttcca gggacccctc agggccttag tgccaggagg gctgaagaca gtagggctga 361140
aagtctgtaa gaaccgatca gaccctagag cccctcccca accctgagta gccaagtgat 361200
ggccacctgc cacccagcag agggccgggg atcactccct ggggagggtg aaccaggagg 361260
ctctggccca ggaatggtag acatacatga aggcccaagg cagaaggacc tacagagaaa 361320
aggggacgag caaaatctac acattgaagg gtaagaaaca cgccaagctg gaatgctgca 361380
gccagacata cactctccca ggaaaagcct agaggattcc tctcggaaaa ctgaatcact 361440
cagaaaaatg acctcagata ctgaaattag aggatctccc caaaatagcc cccatccaaa 361500
ccagtccttc agcagagact tggaagagtc ctgcccaagt ccacaaactg cacaatgagt 361560
atctctgcat ctccttgcta tatatgaaat acagccaatg cattttaaga aaactttttt 361620
ttgagacaga gtctctctct gttgcccagg ctggagtaca gtggcgcaat ctcagttcac 361680
tgcagcctct gcctcccggg ttcaagcgat tctcctgcct cagcctcctg agtagctgtg 361740
attacaggca ccagccacca ggcctggcta atttttgta tttttttttt ttagtagaga 361800
cagggtttca ccatgttggc caggctggtc tcaaactcct gacctcaaga gatccgcctg 361860
ccttagcctc ccaaagtgct gggattacag gcgtgagcca ccacgcctgg ccaaggaaac 361920
tgttaacatg aaacaaatat ttttttaaaa ataacccaaa ggaaagaaaa acatttcagg 361980
gaacagaaga aaaaagtcaa atccatgtaa gtaataacct cgcagagata agagaacata 362040
ctgtacccat gaaacaagaa taggatcaaa aggtgcacag gttgagcatc tccaatctca 362100
aaatccaaat gctccaaaat ccaaaacttt tgagcactaa catgatgctc agaggaaatg 362160
ctctttggag cacttcagat tttggacttt cagactgggg attctgaact gctaagtata 362220
atgcaaatac tcaaaaatta aaaaaaaaat ccaaaatcta aaacacttct ggtcctaagt 362280
atttcagatg agacactcaa tgtatattta gtgaatgaga aagtttaaga aattaaaagt 362340
agaatgaaaa aaatgaaaat tttaatagaa ggattgtaaa gtatagataa atcagatgcc 362400
ccctagaaaa tagaaacagg tggctgggca cgctggctca tgactgtaat cccagaactt 362460
tgggaagctg agggaggagt ccagaagttc aagcccagcc tgagcaacac ggcaaaaccc 362520
catctctaga aaaaattaaa aattaaaaaa ttagctgggt gtggtggcac acacttgttg 362580
tcccagctac tcgggatgct gaggcaggag gatcatttgt gcctgggagc ccaaggctgc 362640
agtgagccat gattgtggca ctgcactcca gcctgggcaa caaagcgaga ctcaaagaaa 362700
gaaagaaaga cagagagaga gagggagagg gagaggaaga ggggggaggg agggagggag 362760
ggagggagga tagaaaagaa aataaaatag aaagagatga aaaattgtaa aatgtttaaa 362820
aataagaaag tgagagaata gctgaatatt aagggttcca gaaagagaaa atgtaagaaa 362880
gttgtcaaat aaataataca acaacagttc aagaactgaa gggcacaagt ttctagatta 362940
aaacagtcca atgagtgctc cctcaaatta aaatagacca aggcatatac tgtaaaattt 363000
aaaatcacca aaaagagaga gagaaagaga gagagtccta aaagcttcca gattttttaa 363060
aaggtcacat tcaaatcaca atggtatggg acctctacag agcaatattg gaaactagaa 363120
gacaacagaa aaatgccttc gacattctga agaagagtca cttccaaccc gaagttgata 363180
tcaaatcaaa atatcaatca gatgtgaggg aaggataaag acactttgag acaggcaaac 363240
catttacctc catgcactct ttctcagaaa gctgcttgag gatgtgctcc accaaaacaa 363300
attaaaaaaa aaaaaaaggt acctccccat aaaaaaagta gcatgggatc caagaaacag 363360
gaagaccctc catgaatatt ttggggcagg tctagaaagc atccagtcta aactggagga 363420
cacagggaag ttgggaggag ggtccaagaa agaagggaac tgctggatta tctggtaggg 363480
attacctttg ggaaaactgg attaaaagac atcttataaa actattaaag gatctggaag 363540
gcctggagaa gcaatgaaaa ccaagcaaat aaaaaacttg ttcttaaaaa gaaatgccat 363600
ctagatgggg cgcagtggct ctcatctgta atcccagcac tttgggaggc caaggtggtg 363660
aatcacttga ggtcaggagt tcgagaccag cctggccaac atggaaaccc catctctact 363720
aaaaatacaa acattagctg ggcaggggtg gcaggtgcct gtaatcccag ctacttggga 363780
ggctgaggca tgagactcac ttgaacccag gaggcagagg ctgcagtgag ctgagattgc 363840
accactgtac tccagctgga gcagcagagt gagagtctct caaaaaaaaa aaaaaaaaga 363900
aaagaaagaa agaaatgcca tcttattaca acacttagtt cagacatcaa gatttacagc 363960
cataataatg aaaatgcgga atatggactt aatccaaata tgttaacact aaattgggat 364020
gaaaagtgag gggacaaatg tatgtacagg aagtgatgca agggtgctaa atcccaacct 364080
tccagataat atctaaactg gaaaatcaat aaatgagagt ctagcaatac tttttggaaa 364140
taggaaagta aatacaagaa aaagctaaca atgttaagtt tgaaggtggt tgcctagaaa 364200
aaagcaatgg agggtgggga gaagtggggc aggtgtacaa tgctctgctg ttgccatctt 364260
ctattatttt tttttttga gacggagttt ttttgctctt gttgcccagg ttggagtgca 364320
gtggcgcgat cttggctcac tgcaacctcc gcctcctggg ttcaagtgat tctcctgcct 364380
cagcttccca agtagctggg attacaggca cacgccacca cacctggcta atttttgtat 364440
tttcagtagg gaaggggttt caccatgttg gccaggcttg tctcgaactc ctgacctcaa 364500
gtgatccacc tgcctcagcc tcccaaagtg ctgggattac aggcataagc caccacaagc 364560
aaggtccgga cagtaagcaa ggtctgatgg gacaaaagag cctgtatctg agcagaggag 364620
acacaggcaa tgtctgtgtc caccattcct tgctgcccca tttgcatctc acatttactt 364680
tggtccatga gctcagaacc tataatgtgt aggagttcgg tgagactcaa agcaattaga 364740
tgttaaacat gttatgtcaa caactgagta agggacagga gagcactgac aggcccagag 364800
gctgcatttt ccatttgaac cagacttact tcaaatgcag aaagaagaca atgaccaagg 364860
tgccccatca tcctttctta cccatgttaa cacccctgta ttagccaatc gctatgcaga 364920

-continued aaatgaagac acgggaggaa agagaacccc acagttcctt ctcctttcag tctttccttc 364980
ctcattggta agaaaaggta gacagcctgg gtagaatgtg cacataccaa ggagtgagat 365040
gaaaccagtt gagataattt tattctgttt catcctctgg taaatatgag ctacaaaaga 365100
cgaattgtat aatttcagtg actctgcata caagttaata cagctcacct ttgaacaaca 365160
tggatttgaa ctgcacaggt ccacttacat gtggattttt tttcacctct gccacccctg 365220
agatcatccc ctgcctttct cctccctcct cagcctactc aacatgaaga ggatgaggat 365280
cctcttccac ttaatgaata tccacttcca cttaatgagc agtgaacata ttttctcttc 365340
cttatgattt caataacatt tgcttttctc tagcttactt tattgtaaga atacagtata 365400
tattatatac aacatacaaa atatgtgtta actgtttatg ttatcagtaa ggcttccagt 365460
caacagtagg ctattagcag ttttgggcga gtcgaaagtt atacatggat tttcaattgc 365520
acaggagtca gcacccctga cccccgagtt cttctggggt cagctatact catatttgca 365580
tttaaacctg gcactgcaca aaataaagat gaatggtaca atttatgcca ataatttaaa 365640
tttaaaactt tttcttactt agaacattaa atagcaaatt tgaaaaaaaa aaaacaaaaa 365700
aacaccagaa caggccgggc atggtgcacc gctcatgcct gtaattccag cactctggga 365760
ggcaaaggtg ggcggatcac ctgaggtcac gagttcaaga ccagtctggc caacatggca 365820
aaagctcgtc tctactaaaa atacaaaaag tagccagccg ttgtggcaca cgcctgtagt 365880
cccagctact caggaggctg aggcaggaga atcgcttgaa cccgggaggc ggaggttgca 365940
gtgagtcaag atcgtgccat tgcattccag cctgggcaac acagcgagac tctgtctcaa 366000
aaaacaaaca aacaacaaca acaaaaacac cagaacaaat gaagagaaca tgaaaaaaaa 366060
ggagaaagct tcgtatttca gttcccttaa tggccccttc ttcctgtctc tgaccggacc 366120
ttgtggctgt ccctcacctc ctccagcttc atttcctacg cagcctttgc tcccatagcc 366180
ttgctcaggg ttccgccgtt ccctgaaagc tctcccgctc ctttaccgct acaggccttt 366240
ctcaggcttc ctctaccaag aacaccattc ttctcccttc tgcacatgtg tgaattcttg 366300
ctcctcctcc aagttcaagc ctccttccag gaggacattt gggatgccgg caccacatct 366360
ttgccaggtg cccctctgtt tccctctacc ctggccctgc agtgtgactg tctgcatcac 366420
ccccattaga ccttgacctc atgtatcaag atcttgcccc tctgcttccc tctaccccgg 366480
ccctgcagta tgactgtctg catctctccc agtagacctt gacctcatgg atcaaggtat 366540
aggggcccag ggctgggga cttactcaag gaacctggtg atatactggc ggctgcagcg 366600
ggaccaggtg aggggagcgg cgtcgtacag gagctgtgga gacatgatga aaggtcgttt 366660
cccaacgggc tcacagtcat tgccgcttcc gtcatgctga atgccaaaac tgtgtgagag 366720
cacaggcccc aggggcgggt gagccggcgg gaggctgcca gcctgccctc ccctggacac 366780
ccacaaggtg cgcagtccta gttcccaggg ctggttctgc cacccaatgg ctgcacccaa 366840
tggctgcaga aagtcacatt cccctctctg agcctcagtt tcctgaatgt aaaatgaggg 366900
tatgacagct agtatcccaa gggctcctgt tccagcctga aatgagggcc agggacccag 366960
agcagccctg cccctgcctg ggggccagcc agcaatggca aatcaggtgg cacagatgtg 367020
ggcccgtgat ggcccctgca agctcactgg cctcaagaac agtctgacag cggttcccac 367080
tcacaggtcc ttgtcccaag gctgtgcact tgagttaagg gatctgagct gctgtatcac 367140
agaaaggtct ccagagacca tccttgggaa ggatacaaga aaaattattt cctgagcatc 367200
tactatgtgc caggggccat gctaagcact ttcagaaaca caatctcact cagttctcat 367260
tattaccctc aggaaggctc agagagtcta aggaactagc tagggtaaca cagccaggaa 367320

-continued attgcagtac tgtggcaggc tgttctttct gcagccataa gcagcttcaa ggtcctgcag 367380
gcacggccat cgcctacgaa acccggacgt ctgaatggat gaccccaaca gctttgaccc 367440
acagaacgtt ctgggagcct gcctttgatg gcttgctaga caatctaaga tgctgccata 367500
ttcgccagct caacagccag ggcacaggtg gctggaggcc tgtgaagaca ggagcctcag 367560
gcagcagtgt cagatagagg gagccttgga catcactgaa tccaaacccc tcaatctatg 367620
ggaagcacac agaggcccag agagggcagg cactggccca ggccacagag caaacaggaa 367680
cagggacagg gatcgagagt aaaaaataca gcactgaggg caatggggag ggacagccaa 367740
agacctacaa tgattttccg gcccatcaca actccccttt aaataagact ccctccaggc 367800
cagtcctaga gatgcccagg cagccctctc tcctgcttta cagggaagca gcctggttgt 367860
ggggagggga cagtgcaggg gcagcacatg gccagtcagg gctccttttc cagagagctt 367920
cctttcccct ggactttgtg acccacaggc tggatacccg gtgcccccag gctgcgaggg 367980
tgaagctcgg ctctcagtgt agcaatgggg gcaggcacag tacctgtgcc cgagctcgtg 368040
ggctacagtg aaggccagcg gcaggcccgt gtcctcgttg atgctgcagc tgcggtgcgg 368100
ctggcacatg cccgccacat gggacagtcc cagggtctca cagggccggt tcatggctgc 368160
acacaggtcc tttctgcaca ggcaaagaag cagccttcag gctaacctgg cccagtgcca 368220
ggcccacctg agctaaggcc agggaagggt ccccccgaat tgatcccaag cgaaaaggat 368280
gtctctccca ccgttctgtg acatgaggcc agcacggtgg ccgcttggga agcaggtgct 368340
ctcatttaca cacaaccggc tgggcatctc tttggccctt gagagcacag acccgcacag 368400
aacaattttg gttactatcc agcaggggtg ctgacagatg cctccagagt ccagcagagg 368460
gaaaataact gcctctggac agatcagcag ttgccggagg ttaggggagg aaggtggctg 368520
tgactataaa cgggtagcat gagacatcct tctgatggga cagatctgta tctagactgt 368580
gggggtgggt aggtgaaccc acaatgatga aactgcaaag aactgaatac acacacacac 368640
acaaagggaa gtacgtgtgg aactgatgag atctgagtaa gtctgtggat ggtatcagtg 368700
tcagtttcct gattgggata ctgtgctcta gtcatgcaag atgttaccac tgggggaaat 368760
ggaggaaggc tatacaggcc ctctctctat tatttctgat aacagcgaga aaatccacaa 368820
ttatttcaaa ataaaaagac ctccccaagt gcggacagaa tccagccttg ggccaaaggt 368880
gcgcaaactc tcctcaaaat tgggctccct gacagcacgg ccccctcctc caccagggct 368940
tcttctgcag ggccgggaag cacctcctga gatgcaggct cccaccctcc tgcggctgca 369000
gtacctggtg agcaggatgg cagtgtcatg gtgcagggga tgggcatccc ccttcatgtt 369060
gatgcttttc tgccacttgc agaagctctt cagggtgttg tctgcatggt gcgtgatctt 369120
taggtcctcc tgggggcaga gagagtgact gctcatgcct cccctgagtt ccaagaaggt 369180
caggcccaat tctcccccat acgaaggcag gagacagagg cccagcaggg aagtgggagg 369240
cccgcaggca ccagtcgagc ttccagcctg accatccctc ctgtaggaac ctcctgcaga 369300
ggacctggga cctgagagag ggtcagtcag gaaccagggg gtggcagggg acacggtcca 369360
ggccaaggcg gccttcactg tgcccttcca taaagagcag cacaggtcat gcggcaggag 369420
ggctctggca gccgaagcca ttgccgggca gcgtgggacc acatgaccac tcacctcctc 369480
atcttccagc aggaccaggc gcacaatggt gatgtggatg gggttcccaa tgctggggtc 369540
atgaaacagg ccagccacct gcccaagaga tgggggggtc aggttgtcac gaggatgaag 369600
gatacaagca gccaatgccc accccaaccc acccacccac gcagggcaac gcacacctgt 369660
gctcacacac agggactctc acactggtgc acacaggctg cacagtggac aggcgatgca 369720
tgtgcaccaa tgcatgagtg tccccacacc tcacacacac tgccccaatg tggcagcagc 369780
agaacctgga gaggacaaga ggcctccgag gccccttccc agagttgcag cctctcctga 369840
gcctcagttt gggatctgct tcccagtacc aactccatgc ccacccagca caggcgatgg 369900
cagctcagac ctccaaattc tggtttcttg gcctgtcgca gggccctagt cctacaactg 369960
ccagggctat gatagcagtg ccctcctgac ctggggatgc caggaccagc atcccaggag 370020
tgcaccctcc aatgaggcat agaactgggc agggctcaga gggtagagtg agggtaggca 370080
caggcctatg gagcctgccc actgctctgc tattccattt ccccggggct gacagccatg 370140
gggccaagga ggcaggtgtg cacatctatc agaggcccca tggctacatg gggctcccta 370200
ctgagaccca ggagacgggg ctatccccaa agatggaaga taagccaagg tgaggggaaa 370260
tggctgggga aagccatctg ctcttttaaa actccctcag aacaaaaaag aggccagccc 370320
atgactgggg acagctggca ggttcccaga gggcagggat ggcagaacag gccagttgtg 370380
agttggcttc tagcaatgca tcaagaaaaa gaatattcaa atagcaagga accaaacaaa 370440
cactgttaag agggcaccaa agtccctgat tatggggatg aatgacactc tcagaaccca 370500
aggtcagaaa tggggaagat aaacagcgat atcatgtgcc accgtcacct ccacacacag 370560
gctgggagcc cgggagcctt gaaccacctt tctccaatac aaccaaccaa tttttgcctc 370620
ccaagttttg cccgactctg tctcttctct ccatctccaa caccactgcc tcgtccaagt 370680
taccatcatc atttcgtctg ctcagttgtt gaggtctcct acgagtgtcc ccatattctg 370740
cggcccctcc agaccacctg cagcctagca gctccaccat cgatctttga aatgcaaacc 370800
tcatcatgac atgcctttgc ctaaggcagt aagtggttct tcactgtcca ggaaaaggac 370860
agaagtcccc agcctagcca acaggcttct tggatctggt ccctgccttc ctctctgacc 370920
tccccttgcc tctgaggtca ggagttcgag accagcctgg ccaaatggtg aaacccgtct 370980
ctactaaaaa tacaaaaatt agctcggcat agtggtgcat gcctgtaatc ccagcccccct 371040
gggaggctga ggcaggagaa tcactggaac ccgggaaggc agaggctgca gtgagctgag 371100
attgcaccac tgcactccga cctgggcgac agagcaagac tccatctcca aaagaaagaa 371160
agaaagaaag agagaaagag agagagagaa agaagaaaga aaatggggta aaaagggacc 371220
tgtcttgcta tccttgggac agacccaccc aagctctagg actcaggtct gagtctagca 371280
cggggagaat gctgataaat tggggtctgt aggtagcatt ggtaaagaaa gatgaggctg 371340
tcctgaaggt ggctgtgggt cagatactgc agcagccaaa aaaatagccg cagccaacct 371400
caatcgagct taacacgtac agtccctgtg ctgggggctt agcatgcatt atctcattta 371460
atcttcttac ttctaaggta ggcacaatta tcctcgtttt acaaatgagg taagtgaagc 371520
tcaaagagag ggtaaaactg ggctcagaac ccaggtttcg ctgcttcaaa gcccctgctt 371580
atatcctaag tttggggaat gctgcctgcc tattctgttg gggattctca atgcatattt 371640
actttgaagg gtctgagaag tcctgtagta acgaagtctg ttttaccttt tttttttttt 371700
tcttttgaga cagagtctca ctttgtcact caagatggag tgcagttgca tgatctcggc 371760
tcactgcagc cgctgcagcc tccacctcct gggctcaagc aatcctccca cctcagcccc 371820
tcaagtagct gggactacag gtgtgcacca ccatgcctgg cccgttttac tttttttaac 371880
cctgtgtggc caaacttatt caacagcagc atcttttttt cacagtgcac tactggcatt 371940
ctttggaaca cactccctga aatattcctt gggaaatgct acaatgagac agagtcccca 372000
agtgtaggat catgctcttc cacatccatc actttatccc aggtagagcg atggctctca 372060
acaagtcagt cttaaataaa catctgatcc cgagggaaca tctgttcccc atccttctgg 372120
cccaccccgg ccaccatggc ttcccagctg cccctctcca gggcaggtta aggggcacag 372180
gggacagaat ggggctttgg aggtagacag acctgagctc cagtcccagc tgtaccactt 372240
actagctgcg tgaccttgag cgagcccctt gacctctctg aatctttgtt tcctcaactt 372300
gaaaatgggg gtgagggccg ggagtggtgg ctcaagcctg taatcccagc actttgggag 372360
gacgaggcgg gcagaatagc ctggccaatg tggtgaagcc ccctctctac taaaaataca 372420
aaaactagca aggcatggtg gggcacgctt gtaatcccag ctactcagga gactgaggca 372480
ggagaatcac ttgaacccag gaagcggagg ttgcagtgag ccgagattgt gccattgcac 372540
tccagcctgg gtgacaagag tgaaattcca cctctaaaga agtaaataaa taataaaatg 372600
ggggtgaggc ttagatgagg tggtgggtgt tgaacactgc acaaaaggta gacagatatt 372660
cacaaggctc cagccctaac ccaccagggc cttaggccgt ggctccacag tccaggcttc 372720
ctcagaggct ggccatatgg gttcccatgt ccctgccatc cctgcagcct cctagggggt 372780
ccagcactgt caggctcata ggtgccccca tcctgtcctg aacaatgctg ggctcaccag 372840
ctcagaaaag cttgatattg tcagagcagg tgagtgtgag aaccagtccc accctctccc 372900
cgaggatggg gctcaccaag tgaatgggta ggtcctatga gccagggcaa ggcagccagg 372960
aaggggccag gccctggggc aaaaacacct gaatcctgtc acccaggtta agttatgggg 373020
tacctgttgg gttgggcagg tcttttttttg tttttgtttt tgtttttttt gagatggagt 373080
ctcgctctgt cacccaggca ggagtgcagt ggcacgatct cagctcactg caaccttcgc 373140
ctcccaggct caagcaatcc tcccacctca gactcccaag tggctaggac tacaggtgtg 373200
cacaaccaca cccaactatt ttttgtattt tggtagaaat agggtttcac catgttggcc 373260
aggctggtct ccaactcctg acctcaagtg atctgcccac cttggcctct caaagcgctg 373320
ggattataac catgaaccac aatacccagt cgggtgcgtc ttactctgcc cagaatctgg 373380
agcatagggg acactcagaa aagtgggggt gaaatgaacc cagttaacca ttggtggctc 373440
aagtcagcct ccagggtctt tcaggctgag cccccaaagt gctgagaatg agaaggaggg 373500
aacctcaggg cctgagaact tggccttgcc ccttgctcca cccctatagc ccaggggctg 373560
ggccctgctg tccagcaata gccctgctga accctggctg ttagtggctc ccctccctgg 373620
gcagatgaag cttgatctgg gccttcaagg cctcaaatgc caggcagaag gctgtgactt 373680
ttattccata tggaacaggg agccaatgag ggtgtcccag tgagggaaga actggcccag 373740
agctgcactc actgatgagg actcaagtag tggggacgtg gtggccagca ggtagagata 373800
acagccctgg atgcagcccc ttcctctctt tgagcctcag gtttcacagc gataaactag 373860
ggggccagac actgcatgat ctcagagggt acttccttta gggttgcagg aggtgagggg 373920
ctggcagggg gaagcagcag cataggatcc tggccccagg gctcctttag atattatcct 373980
gttcacagca cacgcactta ccttgccccc aacaacccag cccaggagag aaacagggtt 374040
atatggtggc ctgccaacca ggtggctgct aagaatgcca ggggcagaga tctttcctcc 374100
caggggctgc aggaagcagc ttggagcctg aggcctccac gggcacccac agggcaggag 374160
cagggagtgg cagctctgca gtagtcggct ccaggaatcc cagctgcaat cagccacagt 374220
gcccccggtg ggacttagga cacctgagct cccatctggc tctgccctgc ctggttgtgt 374280
gacctgggca agttactcgc cctctgaagg cctctgatat ctcatccatc atgtggggtc 374340
aagagcagtt tgcccacccc acaaggtact gtcgtcatgc ccagttcaca gatgagcagg 374400
ctgagactca gaaggggcaa gtgacttgcc caaggctacc agctagtgac catagaactg 374460
cacagattct tctaactgta atgtgtgctg atgtctcagg cagagtctca ggcagagtgt 374520
agtctgatca ggcatttctg tgtttccagc atctagcaca ggtcctgaca caaaggaagg 374580
aagtatctgt gcagggaaac atgaaggacc caactagtct acaagccccc caggcaagca 374640
cagggttgtg gctgcctcag tctcccactc ctgctccccc tcctagtggc atgacaccct 374700
atggtgtccc cacagcagcc ctctgcccag gctctctcat agtgactagc tgccaagacc 374760
cccacccctt cctggcctca ggagcttgga tacccttctt cctacttggg gcctagacct 374820
gggtctgggg tccagcctga cagccttcct gccctgcacc cactctttgc accccacccc 374880
ccaacaccat ccccgccacc cgctcctggc ccacacagac tcaccatgtt catgatggtc 374940
agcacatagc tctcaacctg cggctgtccg tggtactcca ccattttggc atcagctact 375000
accagggtct ccacccactt ctctttgctg accgaccgct ggtgtagacg cctcagccgt 375060
ggccgccgcc actgctgccg ctgctcccaa cgctcccgtc gagactccag ctctgggtac 375120
actggaggcc cagatggggt ggagttagct gccagtggac aggcccaggg cacacgtctc 375180
cagggcctct cctcagtgag ctctctctgg ggcactggga accacacagg gatcagaggc 375240
caggggcctg aattcgcctc ctggctctgt cccagatctg tgctgtgtgg ctctgcctgg 375300
tcactttcct tttctgatct tgagattccc tgactaaaaa taggaataaa ttgcctcaca 375360
gggggacctc aaagggcaaa tgaaatggtg gatataaaca tggtaaagta ctgtgtccat 375420
gggaggggaa ctcctgggcc tgacaaagct ggcaactggg cccctatctc cccgtgtcac 375480
ttcctcccac cctgggggct tagtgcatcc caacacaggc tgaccccacc ctctaaaccc 375540
cagcctgggg aggctggcca agacccagcc cagcttgccc tactgggcct gctcccctga 375600
cccaggctgc tccagatcag aagaggaagc acatctatga agctgaggaa actgaggcca 375660
agaagcatgc ctctgtggat atgtgctcca gcaaatgcag taccagagct gtgggcagcc 375720
tgagattggc ttgctagcca agcattcccc aaaccccagc aacccttagc aggcagctcc 375780
tcacctggac tggccggcac tactgctgct ctgcagagga ggcactgggt accacactcc 375840
aggtcccaat aatagaggtt agttattcta gggtgggagc agggtggtgg tgggagggaa 375900
gttcctggct agtggccctg ttggagctgg gcacagctca cccggcctgg gcactggagg 375960
aagaacggct ggcagagcca ggtaccatag gctgttggcg gggagggagc agagggaggc 376020
tgagccccaa cgtgggagaa gtaggtgaga tggagcgagg aaggtcagtc taggggattg 376080
actggggcag gcccgaaagg cagaggacac agtcttgtgg cacaattaag ggcacaggct 376140
atggtaaagt atccatctgt ctgtctgtgt catctggtct aaggggcact gggcatgggg 376200
atgttaaggg gggcttctag aaaggcccct tcatgtcccc aggcccagca cccacccgag 376260
aactgggagc agaagagcat accttgcact ccacaggtgc ttggagcact ggaatcaccc 376320
cgctgtgcca gcctctccgg ggcctgacgc ttgtacacca catggggctg ggcgtggcca 376380
ggccgggccg gggcactgtc caggggctca atgaagtagt cctcgttgga gagctggaac 376440
acacctttct ggggaagaag caccagggtc acacagggag ggctggccct cagctgctct 376500
tcttgcacgt cccagaggcc cgtcctgctc agctgagccc ccactgccca caccacctgt 376560
gactgcccgc ggacacactg tactttcctc ccgctgggcc tttgctcact ctgtagcctc 376620
catctggaaa gcccttctct gccatttcac acacagccaa accttcaaag cggagctcag 376680
aagcctccgc ccctggggat gctgccccac acacccaccc cattaggaga gggaaatgtg 376740
tctgcatcca aatctgacaa aacggtgtct tagtcccaga cagccatcct gagtggggca 376800
gcttgtgccc aggcctccag gctattctcc atctcctctg catgccagcc atttccagca 376860
ctgtgctccc tcccagctgg ccagggcttc tgaccttccc tctatctccc taaggcaatg 376920

-continued aatcactcca aaagcatcca cagccacacc cgagcggagg agatgcccac ggccaccagg 376980
acaccctgtt ctctgggccc agggctgccc agagaaggga agctggcagg agtgtcttgg 377040
acatgtccgc cagcattcag agtccaggga ggggaggggc cctgggaagc atctttgatg 377100
cccactacct cctgaggaag ctcagggctc caacaggaaa gaaggtttta tgtccctcgg 377160
acttcccctc ataggcacca attctgcccc ttgggtcaca caggaccagg gggcctggag 377220
ggagggctgg agagtgcatc agctcttggg tctggagacc tgggtatgaa tgcggagtcc 377280
ccccctcccg cccaccactc actgaatgac taggtgaccc tgggcaagtt cccctctgag 377340
cctgtttcct catctgtgaa atgggaatga tgccccatgt gcacagctgt ggcacaggct 377400
caacaagatc aattgtacat taagggacag gcacaggctc cataaatggg aatactgtgc 377460
agggcagatg ggccttcaaa ggtccagacg ttgtgcagct tgcgttgtgg gctgccctgt 377520
cattaggccc tgtgcggcca cagcccatgg tttttgcctg agcaatctaa gctgagggcc 377580
tcctgggaac agtggacgct gagagtgtgc acacatcccc tactcctccc aaacccccac 377640
cctccagagc tgggagagtg gggctggtca cctgaacacg aacagaaagg ggccctactc 377700
tgcctggagt ggaagctgct ctaatcagca cccaatcagg gagcaattag ggctgcagta 377760
gccagcacca cccttcagcc aggcgaagcc aggaagctga gacctgcttt tcctggagtt 377820
ctgattcgag cagaggggct gaaaggggtt cctcaccaca ccctgcataa tggctacagg 377880
gtgaggggta gctttcctgg agaaaagcag cctaaaggga cctgtgaagg aacagtcata 377940
actgatgccc caaggaagag aagtcaactg ctttttcagt tacttagtcc agtcaaacgg 378000
aggttctcaa aatgggatct ctggacctgc atcttcaata ttacctgaga tgttttcaga 378060
aatccaagtg tttgggcgct atcccagacc tatcctgcaa aaattctgtt taaacagggc 378120
ctgcaggtga tttgagctca tattaaactc tctttttctt tttctttctt tctttttttt 378180
tttttgagag tgcctggggt ctcgctgtgt cgccagctaa gcgcaatcac cacaccctac 378240
atccttgaat tcctgggctc aagtgatcct ttcgcctcag cctcccaaat agctgggact 378300
acaggtgcac caccacccgg ctttcacatt aaactttgag aactgttatc ctagagatca 378360
acgaggcctg cgttgtcact cccactttac aggcgtgaat accgaggctg gcagagaaaa 378420
agtgcactgg gcaaagccac cagacaagtg cgtggcaagg ctagagccaa tctgcacatc 378480
ccaccacccg agactgcccc aagtatacat gtcccagctc actcaccagg ccgtcgcagg 378540
cgctgatggc cgccaggcca ccctcgagct cagggtcctg cacctcgcca agcaggtggc 378600
aggccggggt gtgggcccgg atgtgcgcgc ggcccaggcc gccgcgccgc cgcgtctcgc 378660
tcacaaagcc gggcgccagc aggtgctgat tggcggtcag gttgaagcgc agctcgcgcc 378720
cgcggtattg tagctcgtag aaggcgggcg cgtctcggcg cacagataca tcccgcttgc 378780
gcagtgcgcg gggccacagc tcgtaggaca ggaaggagcc ccccgcgtcg actcgaaccg 378840
ggtgcacgat gtccagtgcc gcccggccct cggttgcacg tcctgcaggg agagaaccac 378900
aaacgcctag gcccagggca gacccgggtc cttgctggtg gccggggacc agaagggagc 378960
ggccaagagg gggctgctgg agtcagagta tctggattca aatcctcgcc gggctatcta 379020
ctaactctgc tatttcatct ttccgtgcct cagtttctcc atctggatcg ttgcagtaac 379080
ttcttttgtt gttattgttg tgttttgggt tttttgtttg tttgttttga gacagtctcg 379140
ctctgtcgcc caggctggag tgcgtggcgc gatctcggct cactgcaacc tccacctcag 379200
gagtagctgg gactacaggc acacgcgacc acgcccagct attttttgta tttttagcag 379260
acacaggatt tcaccatgtt ggccaggctg gtctcaaact cctgaactca ggtgatacgc 379320

-continued tcgcctcggc ctcccaaagt gctgcaatta caggcgtcag ccactgcgcc cggcctggat 379380
tgctgcggta acttcttaac aggtctctct gttttcacta ttgcctaccc caggtgcccc 379440
tcccctcgtg ttttcaccaa gggaaagcag ccagaaagat tcattcaaaa ccagcgcgat 379500
catcgtctta ctctgctcat cgtcttactc tactcatcgt ctctcctgca atggcgccca 379560
tctcactcag agcaaaagac aaagttctag cctgtatgag gccctaggca aggtgacctc 379620
tccaatctca tgtccagcta cacagcctta gttccctcca ctccacccac tggcctcctt 379680
gcagttcctc cacaggccag acgtgctcct gcttcaggat tttgcattgc tgttccctac 379740
acctggaaca ctcttctctc tgttttccac atggctaaac cattcacttt tgggttgttg 379800
ttcaaatgtc tccttctcaa tgaggcctcc tctaacgact ttattttaaa attgcaactc 379860
cctagctctc cctatccccc ttccttgctt tatttttccc cacagcactc ctgacatacc 379920
atatcactta gcattttcat tatttttctt atttatttgt tttctccctt ccctcccagt 379980
gtagtctagg aaggcaagaa tctatattct ttgcccctgc tttttttttt gaaatgggtt 380040
cttgctctgt cacccagaca ggagtgcagg tgggcaatca tagctcactg cagcctccaa 380100
ctcctgagct cgagccatcc tcccatctca gcctcccaag tagctgggac tacaggtggg 380160
tgccaccaca cttggctaat ttttttttat ttttaatttt tttaatacag atgggatctc 380220
actatgttac ccaggctggt ctcaaacaaa ctcctgggct caagtgatcc ttctacctca 380280
gcctcccata gttctgggat tacaggcgtg aggcaccaag gctggccctg gataattttt 380340
tatttttttt tgtagagatg ggagttttgc tgtgttgccc aggctggtct cgaactccag 380400
gtctcaagcg atcctcccac ctcagcctcc taaattgttg ggattacagg tgtgagccac 380460
cacacttggc cctttatatt ctttgttaaa gatttaagtg ttagaggaag tgtccagaac 380520
ttagtccttt tttggtattt attgaatgac tctgtagaat gcagataacc acagcactta 380580
caatctcgat gctgtcgtga ggattaaacc tggtggagct actcccttta gcagtgcctg 380640
agccactggt tgaatatgat ggcaattatg attgttatga ttattattag cctgacggat 380700
ttaaaaatgt gctctcagat gcgtgagcat tctgcaagtg tctccaggcc tcctggattg 380760
gggagacaga gaaagaccac cccactgggg ctccctggcc gctaaccacc acttcaacag 380820
ggtagctctg gtttctttct tttacatgca agaattcatt taaagaaagg ttccagggat 380880
ggaaaaaatt ggcagacctc tgctcaggcc cttgcagttt aaaaacccct ctctgttgct 380940
ctgtcctcct ggatttccta gtaaggcctg gattcttatc ctttttttgcc acaaacccct 381000 tctcctcaga acaatgtttt gaaatgcata aaataaaata cacaggagtg gttgggcacg 381060
gtggctcatg cctgtaatcc tagcactttg ggaggccgag gcaggcaaat cacttgagct 381120
caggagtttg ataccagcct ggccaacata gtgaaacccc atctctacta aacatgcaaa 381180
aattagccag gcttggtggt gcctgcctgt aatcccagct actcaggaga ctgaggctgg 381240
agaatcactt gaacctggga ggtggaggtt gtagtgagcc gagatcgcat cactgcactc 381300
cagcctgggc gacagagtga gaccctgcca caaaaaaata aataaataaa ataaaacata 381360
caggagtacc aaggaaattg attagattga aatacagtta tcaaaataat ttaaggccag 381420
gcatagtcgt tcatacctgt aatcccagaa ctttgggaga atgagatggg aggatcactt 381480
gagcctagga gttcaagacc aactgggcaa cataatggga acttgtcact acaaaaaaaa 381540
aaaaattagc caggcaaggt ggtgcacacc tatagtccca gctacttgga atgctgaggt 381600
gggaggctct cttgagccca ggaggtcgag gctgcagtga gtcatgatgg cgccactgca 381660
ctccagccta ggtgatagag tgagacatta tctcaaaaac aaaacacaac aaaacaaaaa 381720

-continued ataatttaaa aagtagggtg tggaattata ctttaaacaa gattttgtgg caaatttaac 381780
aactatggtc ttttttttt tttttgagac agagtctctc tctgtcaccc agggtgtagt 381840
gcagtagctc aatcttggct cactgcaacc tctgcctccc aggttcaagc aattcttgtc 381900
tcttagcctt tcaagtagct gggactacag ctgcatgcca ccactcccag cgagttcttg 381960
tatttttagt agagacgggg ttttgccatg ttggcaaggc tggtcttgaa ctcctggcct 382020
ctagtgatcc actcacctca gactccaaaa gtgctaggat tacaggcgtg agccactgtg 382080
cctggcaact atggatattt tgaagtagtg atgaacgtaa accttatttc aagatacgtg 382140
caacaactgt aatgagatag aaaaatattt ggtttgctgt attggtaaca aaaccacagg 382200
tgctgctggg atttgctaat aatattcata attgagggaa atgctaaatt tcgttgagag 382260
attacaaaaa gtaaatatgt aatattttcc cattcaagtt cacggatccc ctcagttcac 382320
ggtcccttag gctgtggacc ccaggttagg acacctgcag taaggtgtcc agactgcttc 382380
ctaggtgaga cagcaaaggg aggctcagag aggtggagag actggcctag agccacacag 382440
taacagtgag agtggcagtg ctgagactga gactcaagtc ccccaaatgg tttcagtctc 382500
ttcagtaaca ttgctctata ttctcaacag tccatccctt actgggcctc agtttcccca 382560
tcattaatgt gaaagagttg aattagatca cgtttctcaa atctctttgg acaccagttc 382620
tagtctcaag agaaatctca tgtgccgggg gttgggggag ctctggcatc catgctttcc 382680
cccctctttt ccctctctgc agttcccagg ctctaaagag cacagttagg gaacttggca 382740
atccggagtt tctcgattgg atttataccc agctcccagg atcctggctg ttcacgacaa 382800
tagactcttc aggctcgcat gaatgcctga gcgccctgct gacatcccac cagggttcct 382860
tctgctgctg cccagcccga agctccatcc cagcaggctg cggaaaccaa acttgccctc 382920
cagtctgtcc tctgccgaac tgcacgtaga gtgccctgca catgccagtg ctgtgcccct 382980
gctgagagca tctccctctg ctcacaaccg ccgcagcgat gccagcctca aagagctttc 383040
tctgagagtc aagagactgg gtaggctggg gcaacgtgct gtgtggctct gagctaatct 383100
tccccatcat tgagcttcag cgggccacta gtgcaaggat tttccagacc tcacagatga 383160
atttcttaaa aaaaaattcc caggccccat cccagactca ctaaatcagc atttccagga 383220
aactaggact agggactagg aagctatgtt tttaccaaga gcctccggga actgtgatcc 383280
tcaggaaagt taggaaatcc cccactggga gtgaacctgg ctggtcatca gcagtacctg 383340
gagagctctg aaaaactgca gatgcccagg acccagccca gagattctgg ttgcacagat 383400
ccagggctct gggggcccta gaatgtgtat tttctgtgtt tttctagacc ttcccaggga 383460
ttctgatcta gccagttcag aggctggcat tcagaagcca ccggactgga tgatttaagg 383520
cgacttcttg ctctgacatc ctaataaggg catatgggac tacaactcct caaccacagc 383580
gtgcagattt gcttgtgttg atcagttatt gattttttgg tttgttttgg ctgacacaaa 383640
tattgaaaaa cgttttagtc aattgccaat gtttaagaat cacatgatct tgtacaaaaa 383700
tctcaatttt cagcttttct tgaaaagtct tatcatccat ccatgtcagg cttaaattgc 383760
tccctggcag aagtggctgg ggtggagcag tgagttccct ttaggaaggg cctatgctcc 383820
ccggtcctca gtccccacca ctccatattc attcccagta ctgtggctgc aagtaggctc 383880
cctttcccat catgcttgtg tttcctttca ctcagtaaag aatggaaaag tgggaaaaca 383940
agagataggc caagaggccc catgtttcag gaaaaatctg tctccctacc caccttgttt 384000
gctcatttac gttacctgcc tagtccacgg catttggtat gtgacccttg gctactaact 384060
gtgagggggc actaggtgct ccaaagtcca ggaaagtggg taagacacca tccttgcctt 384120
caaatggaga aatggccaga cgcagtgcct cacacctgta atcgcagcat tttggaagac 384180
cgaggagggc agattgcttg agttcaggag ttcgagacca gcctgggcaa catggtgaaa 384240
tcccatctct acaaaaatac aaaaattagc caggcatggt ggtgtatgcc tatagtctca 384300
gctactccgg aggctgaggt gggaggatta cttgagcctg ggaggcggag gttgcagtga 384360
gcagaaattg taccactgta ctccagcctg gatgacagag cgagactctg actccccccc 384420
ccaaaaacac acacacacac acacacacac acacacacac acaaaaaaaa aaaaaaaaaa 384480
aaaaaaaaaa cagaaaaatg ggtgcagtag acccaagacc cccactctgg cacagtgctg 384540
acaaggtcca agcaagggga aaggatgaca ccttatggat gcattggaat gaagaaaagt 384600
ttcatcaagg aggatgcatt tgagatgtcc cttaacatat gttaattcaa cagtgaagac 384660
aagaagggcc tcatggtggt aggggcactg tgtggtaaac cctcagagaa gtggggaaaa 384720
gccagaagta agaaagggca acaagaagtt taatcttggt ccaggcatgt gttttgtaaa 384780
atgggaggca atggagggac aaaataatgc actatagagc atgggctttg aaagtaacaa 384840
gacccagggc aggcccaagt gggccactta atagttgtat aatctgagtc actgcatatc 384900
tctgggtttg tttcctcatc tgcttggaga atccaggcca gaaaacgtaa ggaagggagc 384960
ccaggtcaag gagacgaaaa tgacagagat agggaagaac tacttcccag gttcactcgc 385020
agtgggagat ttcctaactt tcccaaggat cacagttcgt ggaggctaca actccaaggc 385080
ttgtttttgt tttgttttgt ttatgttttt gttttttttga gagagagttt cgttcttgtc 385140
ccccaggctg gagtacaatt gcatgatctt ggctcactgc aacctccggc tgctgggttc 385200
aagcaattct cctgcctcag cctcccaagt agctgtaatt acaggtgcaa gccaccatgc 385260
ccaactaatt tttgtatttt tagtagaggt agagtttcgc catgttggcc aggctggtct 385320
cgaactcctg acctcaggtg atccacccgc ctcagcctcc caaagtactg ggattacagg 385380
catgggccac catgcccacc ctccaacact tgttttaagt gagtattaac gttggttccc 385440
agggcaagga caatcccagc caaggcagct aaagatgagc tgaaggtcag gggggcactg 385500
atgccaacca gctctaaaat tctcaactgg gggagctaca tgacactctt ttaggcaagt 385560
tttgtcctca aatgcatgtg gttggggaat ggaagcaggt atgtaactga ggaatcaacc 385620
actggggaga aaaggcccca aaagcttaaa aaaaataaag tatctctggg gaagaaccca 385680
tgccccagcg gatgtacagt cctgttgaga atacctgctg tagatcctgg gcaaatattg 385740
caagacagaa attccagatg acttacaaag aagcatccta ttaagttcaa aaatgtggac 385800
agggctaagt agagctatgc cgcaggtgaa aagcattcgg attagtgagc tctagagcca 385860
gagaggctgt gtttgaatcc cagctctgct acccatatct gtgagaccat gggtaaatta 385920
ctcaaccact cagaatctca gtttctccat ctgtaaaatg gggatgataa taattacagc 385980
tgctctcttt ggttgtgtaa gaattaaatg agttagtatg taagtgctta taacaacagc 386040
tggcacatag caaatgtgag ctaagttatg actgaaaatt agcaagagaa cttctaaagt 386100
atatttagct ttttctttta aaaacttgtt gttttatctg tttgcctaat ggcttaaaaa 386160
caaacaaaac aaaacaaaac aaaaaacatg tttttattta tttatttctt ttttttttt 386220 ctgagatctc ccaggctgga gtgcagtgat gcgatcgtgg tttactgcag ccttgacctc 386280
ctgggctcat gcaatcctcc cacctcagcc tcccaaatag ctgggactac aggcgtggac 386340
taccaggcct ggataatttt taaatttttt tgtagagatg gggtctcatt atgctgccca 386400
ggctggtctt gaatttctgg gctcaaacga tctgcctacc ttggcctccc aaagtgctgg 386460
aattacaggt gtgaatcact gtgtctggtc taaaacatgt ttttcaatca acaataaaag 386520

-continued aatagactta caggatgttg ccacttttat tgcaataatt tttttcttgt tttgttcaga 386580
ttttttcttt tgagacagtc tccctgtgtc acccaggcta gaatgcagtg gtgcgatctc 386640
ggctcaccgc aacctctgcc tcctgggttc aagcaattct catgcctcag ccttccgagg 386700
agctgggatt acaggcatgc accaccatgt ccagctaatt tttgtatttt aatagagatg 386760
gagtttcacc atgttggcca ggctggtttc gaactcctgg cctcaagtga tccgccagcc 386820
tcagcttccc aaagtgctgg gattacaagc atgagccact gcagcccgcc agcattacct 386880
ttttttatag tgaacttgta ttgttttgcc attaaaatat ttttaaaaag tgcaggggta 386940
agtttaaaaa taagtaactt tcactgtagc ctagttgacc tcactcagta gagatgttgg 387000
tggctgaaac tagcaccacc cagtgccagc aaggagtaat tgcaggttcc agtctcgacc 387060
ggttatgtgc ttgcaacaaa gctgagcctg cagagttcaa gtgacagtgg gatggcaaca 387120
ggcaccattc aagaggactg ccagagattc atggccaaat ctattctgcc aagtcaggag 387180
gtctgttctg attggaccaa gctcctgcca cattgggtgt taaatacttt taatatctcc 387240
cctgggtgac agaactgtca ctttggagct tctaccaaag aaatgccaag atggtgttta 387300
ccctcacctc cctatcaaga acctgagtta caatccagcc cttcaaatga cccacagctc 387360
atgccaagga ggaaaaataa ctggcagggt ggggggtagt atgtgaatgc cctcctctgt 387420
gagttctagt atgcacagaa acacatgcac acagagttca catgtgccat acggcatgag 387480
gaggacacat gactgggctc cagcctcaga aaccctagca ggtccctggg tcagtcacaa 387540
gtggggaaaa gggatatatt ttcctaaaag tgagcccagg atgagccctt tggtcttaaa 387600
gaaggtaaca ttcagtggta ggaggagccc caggcttagg tcctgggctt caaagaaaat 387660
gacaaacagg ccagcagcct cagagtcacc aatcctgagg gagtgcagaa caggaaggac 387720
cccatgctct atatctatgg gaacactaga gacagacttc acccttggag tgtttgtgcc 387780
cagattaggt tggagagagt gcctggcctg cctccaccct caaacagcag gtccaggtca 387840
tctggggagt cctgggtcgg cctggcagat taataaaaat aatgaccact acattgtagt 387900
cactgtgtcc tgcctgagca actgacatat tcaatatctc atttaatcct cataagaatc 387960
ccacgaggtt gaccgcaccc aactcttccc acagctgcca gggggccagg acccaagtcc 388020
tgagggaagc attttcctgc tctcccattc ccatcgcccg gttcatcctc ctcagccccc 388080
agctctggac agtggaaaac acaagcctca ttcaggaagc tcaggagtcc aaccccacag 388140
gtcgctctac tctgagcctg tttgctggtc cataaaagga ctttccatca cttgctttgc 388200
acggttgttg tggagatgat gagaaataag aacccgtgag gctggcacac agtaggtgct 388260
cattaaatgt tcgctccctc tgcgctctgc gcatggctgc tagaccaaat ctttccaaaa 388320
cactgctttc atcagctgct cccctcaacg gcttcccaaa cctctaagat caagagtcaa 388380
tgtccccatc cttcccgccc agactacttt ctcgtcacaa tccctccagt ggggaggcag 388440
gtcgacccca tcccagcaag caaccctaat ccagtccccc gactgatgct ccccagggga 388500
gggccccact ccctccacgc ccttctagct catccagaat ccatccatcc ttccagtctc 388560
tccaacctca tgcccctcct ctcctacaaa gcctgccggt cggctctatt gcaggactct 388620
ccccactatc caccggctcc cctgactggg agctccctga gcaccgggcc tggggtctcc 388680
tacatcctcg gttactgaat tcccaggccg gctgcgtcgg acgcgccagc agcgcggccg 388740
cccggcaggt cgccgccaaa caagagtctg gacgcaggcc agaggctcgt cggaggccgg 388800
cccggcgggg cggggagagt taacccatgg ccgggaaaag aagctcctgc tccccgctcc 388860
actcccggcg tcttcacact tggggaaggg agaggcagga agtgcaagga ccgcgcaaga 388920

-continued cccggccccc cgagccgcca ggggccgcgc cagcagccca gatgcggtgg gcgggagctg 388980
ggggggcggc ggggtcccgc gaagacctgc gacctggcgc cctcgccggc tgtgtcccgg 389040
ccagcccgct ttccaggcga gcctcgctaa ggagtgtgag aaaccaaatc ctcagtgggt 389100
aaaccgcgct ccgtccagcc cactcggacg agagctctcc cgggagccag gcgcgttgct 389160
gcacccgagg tggggaaacc ggagcccgaa gagcggaagg ggcttattcc aggcgacagg 389220
cagtgtcagt aactgaatca ggggccgagg aagtttcccc agaagcgcgg cttcgctccc 389280
ggcccggccc gaccccgact actgtcccct aatacccagg gagcggaaga cgcgaccaac 389340
tccaggcaca gcggagccgg cgcggggtcc acaaaggtga ggagggacaa aaccgagact 389400
gggggagcgg gaaggggtgg caggcccggc tggccgggga ggggcggaca cccacctggt 389460
gcgggtccgg gggcgccggg agccagagcg cagaggagca ggaggagggg gcgcagcaaa 389520
ggcgcggggc tgcggggact ggggccgccg ggcatggcag gaaccgggcg gccgccgggt 389580
gaccccgcgc gcacgctctc gtccgtcccg tccggtcgct gcctggtccc aggtccggct 389640
caggacatgc ccggccggcg tgcagctccc ggcgacccgg ccccgactcc gttcggctgc 389700
gctcggtccg cgggcaacaa aggctgcagg gcccgccccc ttggccgctg cagaggcaaa 389760
gaaaagacaa gagagctaga aggagagaaa gaaagaaaga aagaaaggga gggagagtga 389820
gggagggcgg ctgccggccc ccgccccgcc cctcggactc cttcccccgc ccctggcccc 389880
gccccgcccc ggccggcccc ggcctcatcg gccccgcagg ccgtgctcgc ctcaagggct 389940
ggccggcccg gcgcaggcag cgccccgcaa cggatgtccg ccccccctcgc cccccctgtcc 390000
cgagcgcccc ctgccggcgg agccctgcca ggcctttccg accccggccg gttgaggacc 390060
cccggaaaga atctggaatt tccagaatta atgtgttgtc cctaaattgg gctccacgag 390120
gtgcccttcg ctgtgttccc caggccaagc agggcagccc ctcaaaaggg gacgcgggag 390180
gcctccagag ggccacaccg gggggccctgc ttcaaagcta tctgcggaga caggcctggg 390240
ccctccctgg acagacagcg gttgcccgcg cgaggtgggg ccccgcagtt cctcgtctcc 390300
tgactcctct cctagtgcgt ttgcttgaag cagagcgcag agttgagccc acaggcgggg 390360
gaccgcggct tcgcccaggc cagcgcccac agactttcag caggggctcc cggggagcct 390420
ggaggccggc caaccccagc ctcacatccc aggccagcct ccgcctccaa caccggccgt 390480
ctgtccttcg tggccccagc cctggctctg gcttccggct cccccttcccc ctgtgctccc 390540
aggagcttcc tttctccctt ctgccgtcac taaacatggc cctgtaccga ggacgcccgt 390600
cttgtcctcg gggcggttgc ggtcagcttc ctccccttgg ttagtctttg tgtgcccccct 390660
gccctctgag gcccgcacac ctcctcattg tccaatctcc tgggcccttt cattcaattc 390720
ctggaagctc acttctggct tcctctccac cctcaacctg tctgtcctct agggaatttg 390780
tgtagtacag ggtcacctac ttcctccatc tcatctccag tgaccttcca ctccacctca 390840
gccatcaggt ctcagggcca aagcctgggc tgtgtcatcc ctcagaactg ctccatcttg 390900
gaaatccgaa gctcaggtgc ccccctgtca gacccgactc tgcagtcctt tccaccttca 390960
cagtcccact atgtattgct cttcctccag tcccttgata ccttcctctt cgcccaacct 391020
accagcccct cctggcttca cctacttccc tcccagctac atctactgct tgactcctgg 391080
cccctaccca accaccttgc atttcttccc cactgcttac accagctggt cttgctgctc 391140
agtgacatgg acaattcaga ccaccacatc ctaccatgca cactgcatac aatgagcctt 391200
tgtagctggc acccactcac ttctccctcc atctggacac agtgaaacag gtgccctcca 391260
gcagtcagag acaatgcttc caccagggct ctgtggctcc ctcccctcct gtctcctcaa 391320

-continued

```
aggtcctgct ccaggtgtcc cccgctttcc ttggtctcct tgggttggtg accgtcagtc 391380

taaaaacatt cttgtcttcc tcctattaaa gatactgata atagctgggt atagtggcac 391440

aggcctgtag tcccagtgat actcaggagg ctgaggaggg aggattactt gaacccagaa 391500

gttccaggcc agtctgggag acatactgag acactgtctc tagggaaaaa caaacaaaca 391560

aacaaaaagc aggcaaggtg cctcacacct ataatctcaa cactttggga ggctgaggtg 391620

ggagggtcac ttgagccccg agtttgggac cagcctgggc aacatagtga aacaccgtct 391680

ctacaaaaaa attaaaaatt agcccagcat ggtggcatat gcctgtgatc ccagctattt 391740

ggggggctga ggtgggagga tcacttgagt ccaggagatt gaggctgggc caggcctggc 391800

cccaccaatg agcagtagcc aagatcacgc cactgcattc cggcctgtgc aacaaagtga 391860

ggccctgtct caaaaaaaac aaaaaaagta ctgataatac ccctccatgg actgggtgtc 391920

ccctctaatt cccaccccac atatctgctc cctgtcttag tcaaacttct ccctcaaggt 391980

tgtctagatt ccccctttc ccatttgtac ctcaggctaa gcctcttgtc cccccatctt 392040

ggtgtcaaag ccaaattcct tctccacctt gacctgcaca gtgcattcta gagataccct 392100

ccctgttcac atacctccac tctgccctca tcacctggca catctcttct tcactccata 392160

agatcaagta tgcactgcag acccagggca ctggggacac agctgtgaac agg        392213


<210> SEQ ID NO 2
<211> LENGTH: 599
<212> TYPE: DNA
<213> ORGANISM: Homo sapiens

<400> SEQUENCE: 2

tgtgtcactg tgccccctct ttgtctttgc agtgctgttg gggatttcca ggtggacgac     60

aagaccaaag ccttactcaa gtacactggg gaggtgactt ggatacctcc ggccatcttt    120

aagagctcct gtaaaatcga cgtgacctac ttcccgtttg attaccaaaa ctgtaccatg    180

aagttcggtt cctggtccta cgataaggcg aaaatcgatc tggtcctgat cggctcttcc    240

atgaacctca aggactattg ggagagcggc gagtgggcca tcatcaaagc cccaggctay    300

aaacacgaca tcaagtacaa ctgctgcgag gagatctacc ccgacatcac atactcgctg    360

tacatccggc gcctgccctt gttctacacc atcaacctca tcatcccctg cctgctcatc    420

tccttcctca ctgtgctcgt cttctacctg ccctccgact gcggtgagaa ggtgaccctg    480

tgcatttctg tcctcctctc cctgacggtg tttctcctgg tgatcactga gaccatccct    540

tccacctcgc tggtcatccc cctgattgga gagtacctcc tgttcaccat gatttttgt     599


<210> SEQ ID NO 3
<211> LENGTH: 599
<212> TYPE: DNA
<213> ORGANISM: Homo sapiens

<400> SEQUENCE: 3

ttattgaaga gatcatacca tcatcttcaa aagtcatacc tctaattgga gagtatctgg     60

tatttaccat gatttttgtg acactgtcaa ttatggtaac cgtcttcgct atcaacattc    120

atcatcgttc ttcctcaaca cataatgcca tggcgccttt ggtccgcaag atatttcttc    180

acacgcttcc caaactgctt tgcatgagaa gtcatgtaga caggtacttc actcagaaag    240

aggaaactga gagtggtagt ggaccaaaat cttctagaaa cacattggaa gctgcgctcr    300

attctattcg ctacattaca agacacatca tgaaggaaaa tgatgtccgt gaggtctgtg    360

atgtgtattt acaaatgcag atcttcttcc attttaagtt cagaagttac tttcattaat    420
```

-continued

```
tttggcagag taaacagcat gacccttaag taagactaag catagattga gggccagaat    480

tgttgacata ttttctataa aagatcttta ctaaggcttg tttcagttaa agcacctgca    540

aaatggggca tttacacaaa tctcacttct ccacttcccc catcagcatc ttggataac    599

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4

ctatttccct ctggccccgc cc                                              22

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5

atcgattttc gccttatcgt                                                 20
```

SUSCEPTIBILITY VARIANTS FOR LUNG CANCER

CROSS-REFERENCE TO RELATED APPLICATIONS

This application is a U.S. National Phase of International Application No. PCT/IS2009/000001 filed Feb. 16, 2009, incorporated herein by reference, which claims priority to Iceland Patent Application No. 8716 filed Feb. 14, 2008.

BACKGROUND OF THE INVENTION

Lung cancer causes more deaths from cancer worldwide than any other form of cancer (Goodman, G. E., *Thorax* 57:994-999 (2002)). In the United States, lung cancer is the primary cause of cancer death among both men and women. In 2007, the death rate from lung cancer was an estimated 160,390 deaths, exceeding the combined total for breast, prostate and colon cancer (America Cancer Society, www.cancer.org). Lung cancer is also the leading cause of cancer death in all European countries and is rapidly increasing in developing countries. While environmental factors, such as lifestyle factors (e.g., smoking) and dietary factors, play an important role in lung cancer, genetic factors also contribute to the disease. For example, a family of enzymes responsible for carcinogen activation, degradation and subsequent DNA repair have been implicated in susceptibility to lung cancer. In addition, an increased risk to familial members outside of the nuclear family has been shown by deCODE geneticists by analysing all lung cancer cases diagnosed in Iceland over 48 years. This increased risk could not be entirely accounted for by smoking indicating that genetic variants may predispose certain individuals to lung cancer (Jonsson et. al., *JAMA* 292(24):2977-83 (2004); Amundadottir et. al., *PLoS Med.* 1(3):e65 (2004)).

The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread. Early detection is difficult as clinical symptoms are often not observed until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for this and other cancers, lung cancer remains difficult to diagnose and treat effectively. Accordingly, there is a great need in the art for improved methods for detecting and treating such cancers.

Environmental Risk Factors for Lung Cancer:

Smoking of tobacco products, and in particular cigarettes, is the largest known risk factor lung cancer with a global attributable proportion estimated to be approximately 90% in men and 80% in women. Although the risk of lung cancer associated with tobacco smoking is strongly related to duration of smoking, and declines with increasing time from cessation, the estimated lifetime risk of lung cancer among former smokers remains high, ranging from approximately 6% in smokers who give up at the age of 50, to 10% for smokers who give up at age 60, compared to 15% for lifelong smokers and less than 1% in never-smokers (Peto et al. 2000 BMJ, 321, 323-32, Brennan, et al. 2006 Am J Epidemiol 164, 1233-1241). In populations where the large majority of smokers have quit smoking, such as men in the US and UK, the majority of lung cancer cases now occurs among ex-smokers (Doll et al. 1994 BMJ 309, 901-911, Zhu et al. 2001 Cancer Res, 61, 7825-7829). This emphasizes the importance of developing alternative prevention measures for lung cancer including the identification of high risk subgroups.

Genetic Risk Factors for Lung Cancer:

Notably, only about 15% of lifelong smokers will develop lung cancer by the age of 75, and approximately 5 to 10% of lifetime smokers will develop another tobacco-related cancer (Kjaerheim et al. 1998 Cancer Causes Control 9, 99-108). A possible explanation for this large differences in risk for individuals with similar level of tobacco exposures could be that genetic factors play a determining role in lung cancer susceptibility (Spitz et al. 2005 J Clin Oncol 23, 267-275). Identifying genes, which influence the risk of lung cancer could be important for several aspects of management of the disease.

Segregation analyses predict that the majority of genetic risk for lung cancer is most likely to be polygenic in nature, with multiple risk alleles that confer low to moderate risk and which may interact with each other and with environmental risk factors. Many studies have investigated lung cancer susceptibility based on the presence of low-penetrance, high-frequency single nucleotide polymorphisms in candidate genes belonging to specific metabolic pathways. Genetic polymorphisms of xenobiotic metabolism, DNA repair, cell-cycle control, immunity, addiction and nutritional status have been described as promising candidates but have in many cases proven difficult to confirm (Hung et al. 2005 J Natl Cancer Inst 97, 567-576, Hung et al. 2006 Cancer Res 66, 8280-8286, Landi et al. 2006 Carcinogenesis, in press, Brennan et al. 2005 Lancet 366, 1558-60, Hung et al. 2007 Carcinogenesis 28, 1334-40, Campa et al. 2007 Cancer Causes Control 18, 449-455, Gemignani et al. 2007 Carcinogenesis 28(6), 1287-93, Hall et al. 2007 Carcinogenesis 28, 665-671, Campa et al. 2005 Cancer Epidemiol Biomarkers Prev 14, 2457-2458, Campa et al. 2005 Cancer Epidemiol Biomarkers Prev 14, 538-539, Hashibe et al. 2006 Cancer Epidemiol Biomarkers Prev 15, 696-703).

For cancers that show a familial risk of around two-fold such as lung cancer (Jonsson et al. 2004 JAMA 292, 2977-2983, Li and Hemminki 2005 Lung Cancer 47, 301-307, Goldgar et al. 1994 J Natl Cancer Inst 86, 1600-1608), the majority of cases will arise from approximately 10%-15% of the population at greatest risk (Pharoah et al. 2002 NatGenet 31, 33-36). The identification of common genetic variants that affect the risk of lung cancer may enable the identification of individuals who are at a very high risk because of their increased genetic susceptibility or, in the case of genes related to nicotine metabolism, because of their inability to quit smoking. Such findings could potentially lead to chemoprevention programs for high risk individuals, and are especially of importance given the high residual risk that remains among ex-smokers, among whom the majority of lung cancers in the US and Europe now occur.

SUMMARY OF THE INVENTION

The present invention relates to methods for risk assessment of lung cancer. Thus, the invention relates to methods of determining a susceptibility to lung cancer in human individuals, including methods of determining an increased susceptibility to, or increased risk of developing, lung cancer, as well as methods of determining a decreased susceptibility or decreased risk of lung cancer or determining a protection against lung cancer, by evaluating certain markers and haplotypes that have been found to be associated with susceptibility of lung cancer. The method also pertains to methods of assessing response to therapeutic methods and/or therapeutic agents using the markers of the invention, as well as to methods for monitoring response to therapeutic agents and/or methods, using the markers of the invention, and to kits and apparati for use in the methods described herein.

In one aspect, the present invention pertains to a method for determining a susceptibility to lung cancer in a human individual, comprising determining the presence or absence of at least one allele of at least one polymorphic marker in a nucleic acid sample obtained from the individual, or in a genotype dataset from the individual, wherein the at least one polymorphic marker is a marker within the C15 LD block (SEQ ID NO:1) that is associated with risk of lung cancer in humans, or a marker in linkage disequilibrium therewith, and wherein determination of the presence of the at least one allele is indicative of a susceptibility to lung cancer.

In another aspect, the invention relates to a method of determining a susceptibility to lung cancer in a human individual, the method comprising determining the presence or absence of at least one allele of at least one polymorphic marker is a marker within the C15 LD block that is associated with risk of lung cancer in humans, or a marker in linkage disequilibrium therewith, and wherein determination of the presence of the at least one allele of the at least one polymorphic marker is indicative of a susceptibility to lung cancer in the individual.

In another aspect, the invention relates to a method of determining a susceptibility to lung cancer in a human individual, comprising determining whether at least one at-risk allele in at least one polymorphic marker is a marker within the C15 LD block that is associated with risk of lung cancer in humans, or a marker in linkage disequilibrium therewith, and wherein determination of the presence of the at least one at-risk allele in at least one polymorphic marker is indicative of increased susceptibility to lung cancer in the individual.

In certain embodiments, the at least one polymorphic marker is selected from the group consisting of the markers set forth in Table 4 and Table 6. In some embodiments, the at least one polymorphic marker is selected from the group consisting of rs1051730, and markers in linkage disequilibrium therewith. In some embodiments, the at least one polymorphic marker is selected from the group consisting of rs55853698, rs55781567, rs8192482, ss107794645 and the markers set forth in Table 4. In some embodiments, the at least one polymorphic marker is selected from the group consisting the markers set forth in Table 4. In one preferred embodiment, the at least one polymorphic marker is rs1051730 (SEQ ID NO:1). In another preferred embodiment, the at least one polymorphic marker is rs16969968 (SEQ ID NO:3).

In another aspect, the invention relates to a method for determining a susceptibility to lung cancer in a human individual, comprising determining the presence or absence of at least one allele of at least one polymorphic marker in a nucleic acid sample obtained from the individual, or in a genotype dataset from the individual, wherein the at least one polymorphic marker is associated with a gene selected from CHRNA5, CHRNA3 and CHRNB4, and wherein determination of the presence of the at least one allele is indicative of a susceptibility to lung cancer.

Being "associated with", in this context, means that the at least one marker is in linkage disequilibrium with at least one of the CHRNA5, CHRNA3 and CHRNB4 genes or their regulatory regions. Such markers can be located within the gene, or its regulatory regions, or they can be in linkage disequilibrium with at least one marker within the gene or its regulatory region that has a direct impact on the function of the gene. The functional consequence of the susceptibility variants can be on the expression level of the gene, the stability of its transcript or through amino acid alterations at the protein level, as described in more detail herein.

In one embodiment, the at least one polymorphic marker is selected from the group consisting of rs1051730, rs680244, rs1948 and rs569207, and markers in linkage disequilibrium therewith. In one preferred embodiment, the at least one polymorphic marker is selected from the group consisting of marker rs1051730 (SEQ ID NO:2), and markers in linkage disequilibrium therewith. In one embodiment, the at least one polymorphic marker is selected from the markers set forth in Table 4. In another embodiment, the presence of allele T in the polymorphic marker rs1051730 (SEQ ID NO:2) is indicative of increased susceptibility of lung cancer for the individual. Certain embodiments include a further step comprising assessing the frequency of at least one haplotype comprising at least two polymorphic markers.

The susceptibility of lung cancer to which the polymorphic markers as described herein relate to may be in the form of an increased or a decreased susceptibility of lung cancer. In some embodiments, the susceptibility is increased susceptibility of lung cancer characterized by an odds ratio (OR) of at least 1.20. In another embodiment, the susceptibility is increased susceptibility characterized by an odds ratio (OR) or relative risk (RR) of at least 1.25. In yet another embodiment, the susceptibility is increased susceptibility characterized by an odds ratio (OR) of at least 1.30. In another embodiment, the susceptibility is increased susceptibility characterized by an odds ratio (OR) of at least 1.35. In other embodiments, the characteristic odds ratio is any other non-integer value between 1.0 and 5.0.

In certain embodiments, the at least one allele or haplotype predictive of increased susceptibility of lung cancer is selected from the group consisting of rs1051730 allele T, rs680244 allele G, rs1948 allele C, rs8034191 allele C, rs2036534 allele T, rs11638372 allele T, rs4887077 allele T, rs6495314 allele C, and rs1996371 allele G.

In some embodiments, the susceptibility is decreased susceptibility of lung cancer characterized by an odds ratio (OR) of less than 1.0. In certain embodiments, the susceptibility is increased susceptibility characterized by an odds ratio (OR) or relative risk (RR) of less than 0.9. In certain other embodiments, the susceptibility is decreased susceptibility characterized by an odds ratio (OR) of less than 0.8. In another embodiment, the susceptibility is decreased susceptibility characterized by an odds ratio (OR) of less than 0.75. In other embodiments, the characteristic odds ratio is any other non-integer value between 0.1 and 1.0.

In certain embodiments, the at least one allele or haplotype predictive of decreased susceptibility of lung cancer is selected from the group consisting of rs1051730 allele C and rs55787222 allele −8.

Another aspect of the invention relates to a method of assessing susceptibility to lung cancer in a human individual, comprising screening a nucleic acid from the individual for at least one polymorphic marker allele or haplotype within SEQ ID NO:1 (C15 LD Block) that correlates with increased occurrence of lung cancer in a human population; wherein determination of the presence of an at-risk allele in the at least one polymorphism or an at-risk haplotype in the nucleic acid identifies the individual as having elevated susceptibility to lung cancer, and wherein the absence of the at least one at-risk allele or at-risk haplotype in the nucleic acid identifies the individual as not having the elevated susceptibility.

In one embodiment, the at least one polymorphic marker is selected from the markers set forth in Table 4, and markers in linkage disequilibrium therewith. In another embodiment, the at least one polymorphic marker is rs1051730 (SEQ ID NO:2). In one such embodiment, the presence of allele T in marker rs1051730 (SEQ ID NO:2) is indicative of increased susceptibility of lung cancer in the individual.

Another aspect of the invention relates to a method of determining a susceptibility to lung cancer, the method comprising: (i) obtaining sequence data about a human individual identifying at least one allele of at least one polymorphic marker, wherein different alleles of the at least one polymorphic marker are associated with different susceptibilities to lung cancer in humans; and (ii) determining a susceptibility to lung cancer from the nucleic acid sequence data, wherein the at least one polymorphic marker is a marker associated with the C15 LD block, or a marker in linkage disequilibrium therewith. In one embodiment, the method comprises obtaining sequence data about at least two polymorphic markers.

In a general sense, genetic markers lead to alternate sequences at the nucleic acid level. If the nucleic acid marker changes the codon of a polypeptide encoded by the nucleic acid, then the marker will also result in alternate sequence at the amino acid level of the encoded polypeptide (polypeptide markers). Determination of the identity of particular alleles at polymorphic markers in a nucleic acid or particular alleles at polypeptide markers comprises whether particular alleles are present at a certain position in the sequence. Sequence data identifying a particular allele at a marker comprises sufficient sequence to detect the particular allele. For single nucleotide polymorphisms (SNPs) or amino acid polymorphisms described herein, sequence data can comprise sequence at a single position, i.e. the identity of a nucleotide or amino acid at a single position within a sequence. Alternatively, the allele can be the allele of the complementary strand of DNA, such that the nucleic acid data includes the identification of at least one allele which is complementary to the allele at the opposite strand.

In certain embodiments, it may be useful to determine the nucleic acid sequence for at least two polymorphic markers. In other embodiments, the nucleic acid sequence for at least three, at least four or at least five or more polymorphic markers is determined. Haplotype information can be derived from an analysis of two or more polymorphic markers. Thus, in certain embodiments, a further step is performed, whereby haplotype information is derived based on sequence data for at least two polymorphic markers.

In certain embodiments, sequence data about both alleles of polymorphic markers associated with the C15 LD block are obtained, and the identity of at least one haplotype based on the sequence data is determined, and a susceptibility to the condition is determined from the haplotype data.

In certain embodiments, determination of a susceptibility comprises comparing the nucleic acid sequence data to a database containing correlation data between the at least one polymorphic marker and susceptibility to lung cancer. In some embodiments, the database comprises at least one risk measure of susceptibility to lung cancer for the at least one marker. The sequence database can for example be provided as a look-up table that contains data that indicates the susceptibility of lung cancer for any one, or a plurality of, particular polymorphisms. The database may also contain data that indicates the susceptibility for a particular haplotype that comprises at least two polymorphic markers.

Obtaining nucleic acid sequence data can in certain embodiments comprise obtaining a biological sample from the human individual and analyzing sequence of the at least one polymorphic marker in nucleic acid in the sample. Analyzing sequence can comprise determining the presence or absence of at least one allele of the at least one polymorphic marker. Determination of the presence of a particular susceptibility allele (e.g., an at-risk allele) is indicative of susceptibility to lung cancer in the human individual. Determination of the absence of a particular susceptibility allele is indicative that the particular susceptibility due to the at least one polymorphic marker is not present in the individual.

In some embodiments, obtaining nucleic acid sequence data comprises obtaining nucleic acid sequence information from a preexisting record. The preexisting record can for example be a computer file or database containing sequence data, such as genotype data, for the human individual, for the at least one polymorphic marker.

Susceptibility determined by the diagnostic methods of the invention can be reported to a particular entity. In some embodiments, the at least one entity is selected from the group consisting of the individual, a guardian of the individual, a genetic service provider, a physician, a medical organization, and a medical insurer.

In certain embodiments of the invention, determination of a susceptibility comprises comparing the nucleic acid sequence data to a database containing correlation data between the at least one polymorphic marker and susceptibility to lung cancer. In one such embodiment, the database comprises at least one risk measure of susceptibility to lung cancer for the at least one polymorphic marker. In another embodiment, the database comprises a look-up table containing at least one risk measure of lung cancer for the at least one polymorphic marker.

In certain embodiments, obtaining nucleic acid sequence data comprises obtaining a biological sample from the human individual and analyzing sequence of the at least one polymorphic marker in nucleic acid in the sample. Analyzing sequence of the at least one polymorphic marker can comprise determining the presence or absence of at least one allele of the at least one polymorphic marker. Obtaining nucleic acid sequence data can also comprise obtaining nucleic acid sequence information from a preexisting record.

Certain embodiments of the invention relate to obtaining nucleic acid sequence data about at least two polymorphic markers associated with the C15 LD block. Other embodiments may relate to obtaining sequence data about more than two polymorphic markers, including three, four, five, six, seven, eight, nine or ten or more polymorphic markers.

The markers associated with the C15 LD block are in certain embodiments markers within the genomic segment with sequence as set forth in SEQ ID NO:1 herein. In some embodiments, the markers are markers associated with one or more of the CHRNA3, CHRNA5 and CHRNB4 genes. In some embodiments, the markers are selected from the group consisting of rs1051730, and markers in linkage disequilibrium therewith. In one embodiment, the markers are selected from the group consisting of the markers set forth in Table 4 and Table 6. In one embodiment, the marker is rs1051730. In another embodiment, the marker is rs16969968.

Obtaining sequence data may in certain embodiments relate to determining the presence or absence of at least one allele of at least one polymorphic marker in a nucleic acid sample obtained from the individual, or in a genotype dataset from the individual. Obtaining information about the absence or presence of particular marker alleles represents sequence information for the marker, identifying particular marker alleles.

In certain embodiments of the invention, a further step of assessing the frequency of at least one haplotype in the individual is performed. In such embodiments, two or more markers, including three, four, five, six, seven, eight, nine or ten or more markers can be included in the haplotype. In certain embodiments, the at least one haplotype comprises markers that are all in LD with rs1051730 and/or rs16969968.

Yet another aspect of the invention relates to a method of identification of a marker for use in assessing susceptibility to lung cancer in human individuals, the method comprising (a) identifying at least one polymorphic marker within the C15 LD block, or at least one polymorphic marker in linkage disequilibrium therewith; (b) determining the genotype status of a sample of individuals diagnosed with lung cancer; and (c) determining the genotype status of a sample of control individuals; wherein a significant difference in frequency of at least one allele in at least one polymorphism in individuals diagnosed with lung cancer as compared with the frequency of the at least one allele in the control sample is indicative of the at least one polymorphism being useful for assessing susceptibility to lung cancer. In one embodiment, an increase in frequency of the at least one allele in the at least one polymorphism in individuals diagnosed with lung cancer, as compared with the frequency of the at least one allele in the control sample, is indicative of the at least one polymorphism being useful for assessing increased susceptibility to lung cancer. In another embodiment, a decrease in frequency of the at least one allele in the at least one polymorphism in individuals diagnosed with lung cancer, as compared with the frequency of the at least one allele in the control sample, is indicative of the at least one polymorphism being useful for assessing decreased susceptibility to, or protection against, lung cancer. In another embodiment, the significant difference in frequency is characterized by a statistical measure. Obviously, a decrease in frequency of a polymorphism in individuals diagnosed with lung cancer is indicative of the polymorphism being useful for assessing decreased susceptibility, or a protection against, lung cancer. Likewise, an increase in frequency of a polymorphism in individuals diagnosed with lung cancer is indicative of the polymorphism being useful for assessing increased susceptibility of lung cancer. In one embodiment, the at least one polymorphic marker is in linkage disequilibrium with at least one marker selected from the group consisting of rs1051730, rs680244, rs1948, rs8192475 and rs569207.

The invention also relates to a method of genotyping a nucleic acid sample obtained from a human individual, comprising determining the presence or absence of at least one allele of at least one polymorphic marker predictive of increased risk of lung cancer in the sample, wherein the at least one marker is selected from the markers set forth in Table 4, and markers in linkage disequilibrium therewith, and wherein determination of the presence or absence of the at least one allele of the at least one polymorphic marker is predictive of increased risk of lung cancer in the individual. In one embodiment, genotyping comprises amplifying a segment of a nucleic acid that comprises the at least one polymorphic marker, by Polymerase Chain Reaction (PCR), using a nucleotide primer pair flanking the at least one polymorphic marker. In another embodiment, genotyping is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis. In one embodiment, the process comprises allele-specific probe hybridization. In another embodiment, the process comprises allele-specific primer extension. In one preferred embodiment, the process comprises the steps of (1) contacting copies of the nucleic acid with a detection oligonucleotide probe and an enhancer oligonucleotide probe under conditions for specific hybridization of the oligonucleotide probe with the nucleic acid; wherein (a) the detection oligonucleotide probe is from 5-100 nucleotides in length and is capable of specifically hybridizing to a first segment of the nucleic acid whose nucleotide sequence is given by SEQ ID NO:1 that comprises at least one polymorphic site; (b) the detection oligonucleotide probe comprises a detectable label at its 3' terminus and a quenching moiety at its 5' terminus; (c) the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and (d) a single base gap exists between the first segment and the second segment, such that when the oligonucleotide probe and the enhancer oligonucleotide probe are both hybridized to the nucleic acid, a single base gap exists between the oligonucleotides; (2) treating the nucleic acid with an endonuclease that will cleave the detectable label from the 3' terminus of the detection probe to release free detectable label when the detection probe is hybridized to the nucleic acid; and (3) measuring free detectable label, wherein the presence of the free detectable label indicates that the detection probe specifically hybridizes to the first segment of the nucleic acid, and indicates the sequence of the polymorphic site as the complement of the detection probe. In one embodiment, the copies of the nucleic acid are provided by amplification by Polymerase Chain Reaction (PCR)

Yet another aspect of the invention relates to a method of determining a susceptibility to lung cancer in a human individual, the method comprising determining the identity of at least one allele of at least one polymorphic marker in a nucleic acid sample obtained from the individual, wherein the at least one marker is selected from markers associated with the CHRNA3 gene, the CHRNA5 gene, and/or the CHRNB4 gene, wherein the presence of the at least one allele is indicative of a susceptibility to lung cancer in the individual.

In certain embodiments, the polymorphic markers associated with susceptibility of lung cancer are indicative of a different response rate of the subject to a particular treatment modality for lung cancer. In one embodiment, the treatment modality is selected from the group consisting of surgical treatment, radiation treatment, targeted drug therapy and chemotherapy.

The invention furthermore relates, in another aspect, to a method of assessing an individual for probability of response to a therapeutic agent or method for preventing or ameliorating symptoms associated with lung cancer, comprising: determining the presence or absence of at least one allele of at least one polymorphic marker in a nucleic acid sample obtained from the individual, wherein the at least one polymorphic marker is a marker within the C15 LD block that is associated with risk of lung cancer in humans, and wherein determination of the presence of the at least one allele of the at least one marker is indicative of a probability of a positive response to the therapeutic agent or method.

Another aspect relates to a method of predicting prognosis of an individual diagnosed with, lung cancer, the method comprising determining the presence or absence of at least one allele of at least one polymorphic is a marker within the C15 LD block that is associated with risk of lung cancer in humans, or a marker in linkage disequilibrium therewith, and wherein determination of the presence of the at least one allele is indicative of a worse prognosis of lung cancer in the individual.

A further aspect relates to a method of monitoring progress of a treatment of an individual undergoing treatment for lung cancer, the method comprising determining the presence or absence of at least one allele of at least one polymorphic marker in a nucleic acid sample obtained from the individual, wherein the at least one polymorphic marker is a marker within the C15 LD block that is associated with risk of lung cancer in humans, or a marker in linkage disequilibrium therewith, and wherein determination of the presence of the at least one allele is indicative of the treatment outcome of the individual.

The treatment for lung cancer can in certain embodiments be selected from surgical treatment (surgical removal of tumor), radiation therapy and chemotherapy. In certain embodiments, the radiation therapy is brachytherapy. The therapeutic agent useful for chemotherapy may be any chemical agent commonly used, or in development, as a chemotherapy agent. In one embodiment, the agent targets an epidermal growth factor receptor. In certain such embodiments, the agent is gefitinib (Iressa) or erlotinib (Tarceva). In certain other embodiments, the agent is an angiogenesis inhibitor. Such inhibitors can for example be antibodies that inhibit the vascular endotheliar growth factor, such as Bevacizumab.

The methods of the invention can, in certain embodiments, further include steps of assessing at least one biomarker in the individual. Such biomarkers are biochemical molecules that are descriptive of the health status of the individual, and whose measurements are useful for aiding in, or use in, determination of a susceptibility to lung cancer. Certain other embodiments may further comprise analyzing non-genetic information to make risk assessment, diagnosis, or prognosis of the individual. The non-genetic information is in one embodiment selected from age, age at onset of the disease, gender, ethnicity, socioeconomic status, previous disease diagnosis, medical history of subject, family history of lung cancer, biochemical- and clinical measurements. Analysis of combined genetic and biomarker and/or non-genetic information can be performed using analysis methods known to the skilled person. In one embodiment, overall risk is calculated by logistic regression.

The invention also relates to a kit for assessing susceptibility to lung cancer in a human individual, the kit comprising (i) reagents for selectively detecting at least one allele of at least one polymorphic marker in the genome of the individual, wherein the polymorphic marker is a marker within the C15 LD block that is associated with risk of lung cancer in humans, or a marker in linkage disequilibrium therewith, and (ii) a collection of data comprising correlation data between the polymorphic markers assessed by the kit and susceptibility to lung cancer. In one embodiment, the at least one polymorphic marker is selected from the group consisting of rs1051730, and markers in linkage disequilibrium therewith. In one embodiment, the at least one polymorphic marker is selected from the markers set forth in Table 4. In another embodiment, the at least one polymorphic marker is marker rs1051730 (SEQ ID NO:2).

In one embodiment, the reagents comprise at least one contiguous oligonucleotide that is capable of hybridizing to a fragment of the genome of the individual comprising the at least one polymorphic marker, a buffer and a detectable label. In one embodiment, the fragment of the genome to which the oligonucleotide is capable of hybridizing has a sequence as set forth in SEQ ID NO:1. In one preferred embodiment, the reagents comprise at least one pair of oligonucleotides that hybridize to opposite strands of a genomic nucleic acid segment obtained from the subject, wherein each oligonucleotide primer pair is designed to selectively amplify a fragment of the genome of the individual that includes one polymorphic marker, and wherein the fragment is at least 30 base pairs in size. Ideally, the at least one oligonucleotide is completely complementary to the genome of the individual. Mismatches can however be tolerated, as is well known to the skilled person and further described herein. Thus, the at least one oligonucleotide is in certain embodiments not completely complementary to the genome sequence of the individual. In such embodiments, the oligonucleotide can be about 99%, about 98%, about 95%, about 90%, about 85% or about 80% identically to the genomic sequence of the individual. In other embodiments, the oligonucleotide comprises one mismatch, two mismatches, three mismatches or four or more mismatches, compared with the genomic sequence of the individual. In certain embodiments, the oligonucleotide is about 18 to about 50 nucleotides in length. In other embodiments, the oligonucleotide is 20-30 nucleotides in length.

In one preferred embodiment, the kit comprises (a) a detection oligonucleotide probe that is from 5-100 nucleotides in length; (b) an enhancer oligonucleotide probe that is from 5-100 nucleotides in length; and (c) an endonuclease enzyme; wherein the detection oligonucleotide probe is capable of specifically hybridizing to a first segment of the nucleic acid whose nucleotide sequence is given by SEQ ID NO: 1 that comprises at least one polymorphic site; and wherein the detection oligonucleotide probe comprises a detectable label at its 3' terminus and a quenching moiety at its 5' terminus; wherein the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; wherein a single base gap exists between the first segment and the second segment, such that when the oligonucleotide probe and the enhancer oligonucleotide probe are both hybridized to the nucleic acid, a single base gap exists between the oligonucleotides; and wherein treating the nucleic acid with the endonuclease will cleave the detectable label from the 3' terminus of the detection probe to release free detectable label when the detection probe is hybridized to the nucleic acid.

Another aspect of the invention relates to the use of an oligonucleotide probe in the manufacture of a diagnostic reagent for diagnosing and/or assessing susceptibility to lung cancer in a human individual, wherein the probe is capable of hybridizing to a segment of a nucleic acid whose nucleotide sequence is given by SEQ ID NO:1 that comprises at least one polymorphic site, wherein the fragment is 15-500 nucleotides in length. In one embodiment, the polymorphic site is selected from the polymorphic markers set forth in Table 4, and polymorphisms in linkage disequilibrium therewith. In a preferred embodiment, the at least one polymorphic site is rs1051730 (SEQ ID NO:2).

Computer-implemented aspects are also provided. In one such aspect, the invention provides a computer-readable medium having computer executable instructions for determining susceptibility to lung cancer, the computer readable medium comprising: data indicative of at least one polymorphic marker; a routine stored on the computer readable medium and adapted to be executed by a processor to determine risk of developing the at least one condition for the at least one polymorphic marker; wherein the at least one polymorphic marker is a marker within the C15 LD block that is associated with risk of lung cancer in humans, or a marker in linkage disequilibrium therewith. In certain embodiments, the computer readable medium contains data indicative of at least two polymorphic markers. The data may be indicative of at least one polymorphic marker comprises parameters indicative of susceptibility to lung cancer for the at least one polymorphic marker, and wherein risk of developing lung cancer in an individual is based on the allelic status for the at least one polymorphic marker in the individual. In certain embodiments, the data indicative of at least one polymorphic marker comprises data indicative of the allelic status of said at least one polymorphic marker in the individual. The data may further be indicative of at least one haplotype comprising two or more polymorphic markers. The routine may also be adapted to receive input data indicative of the allelic status of said at least one polymorphic marker in said individual.

Another computer-implemented aspect provides an apparatus for determining a genetic indicator in a human individual for lung cancer, comprising: a processor; a computer readable memory having computer executable instructions adapted to be executed on the processor to analyze marker and/or haplotype information for at least one human individual with respect to at least one polymorphic marker within the C15 LD block that is associated with risk of lung cancer in humans, or a marker in linkage disequilibrium therewith, and generate an output based on the marker or haplotype information, wherein the output comprises a risk measure of the at least one marker or haplotype as a genetic indicator of lung cancer for the human individual.

In one embodiment, the computer readable memory further comprises data indicative of the frequency of at least one allele of at least one polymorphic marker or at least one haplotype in a plurality of individuals diagnosed with lung cancer, and data indicative of the frequency of at the least one allele of at least one polymorphic marker or at least one haplotype in a plurality of reference individuals, and wherein a risk measure is based on a comparison of the at least one marker and/or haplotype status for the human individual to the data indicative of the frequency of the at least one marker and/or haplotype information for the plurality of individuals diagnosed with lung cancer. In another embodiment, the computer readable memory further comprises data indicative of the risk of developing lung cancer associated with at least one allele of at least one polymorphic marker or at least one haplotype, and wherein a risk measure for the human individual is based on a comparison of the at least one marker and/or haplotype status for the human individual to the risk of lung cancer associated with the at least one allele of the at least one polymorphic marker or the at least one haplotype. In yet another embodiment, the computer readable memory further comprises data indicative of the frequency of at least one allele of at least one polymorphic marker or at least one haplotype in a plurality of individuals diagnosed with lung cancer, and data indicative of the frequency of at the least one allele of at least one polymorphic marker or at least one haplotype in a plurality of reference individuals, and wherein risk of developing lung cancer is based on a comparison of the frequency of the at least one allele or haplotype in individuals diagnosed with lung cancer and reference individuals. In certain embodiments, the risk measure is characterized by an odds ratio (OR), a risk ratio (RR) or an absolute risk (AR).

In certain embodiments of the invention, linkage disequilibrium is determined using the linkage disequilibrium measures $r^2$ and/or $|D'|$, which give a quantitative measure of the extent of linkage disequilibrium (LD) between two genetic element (e.g., polymorphic markers). Certain numerical values of these measures for particular markers are indicative of the markers being in linkage disequilibrium, as described further herein. In one embodiment of the invention, linkage disequilibrium between markers (i.e., LD values indicative of the markers being in linkage disequilibrium) is defined as $r^2>0.1$. In another embodiment, linkage disequilibrium is defined as $r^2>0.2$. Other embodiments can include other definitions of linkage disequilibrium, such as $r^2>0.25$, $r^2>0.3$, $r^2>0.35$, $r^2>0.4$, $r^2>0.45$, $r^2>0.5$, $r^2>0.55$, $r^2>0.6$, $r^2>0.65$, $r^2>0.7$, $r^2>0.75$, $r^2>0.8$, $r^2>0.85$, $r^2>0.9$, $r^2>0.95$, $r^2>0.96$, $r^2>0.97$, $r^2>0.98$, or $r^2>0.99$. Linkage disequilibrium can in certain embodiments also be defined as $|D'|>0.2$, or as $|D'|>0.3$, $|D'|>0.4$, $|D'|>0.5$, $|D'|>0.6$, $|D'|>0.7$, $|D'|>0.8$, $|D'|>0.9$, $|D'|>0.95$, $|D'|>0.98$ or $|D'|>0.99$. In certain embodiments, linkage disequilibrium is defined as fulfilling two criteria of $r^2$ and $|D'|$, such as $r^2>0.2$ and $|D'|>0.8$. Other combinations of values for $r^2$ and $|D'|$ are also possible and within scope of the present invention, including but not limited to the values for these parameters set forth in the above.

In other particular other embodiments of the methods, uses, apparatus or kits of the invention, the presence of at least one at-risk variant, i.e. an at-risk allele in at least one polymorphic marker or an at-risk haplotype, is indicative of lung cancer at an early age, i.e. lung cancer with an early occurrence or onset. Early onset is in some embodiments categorized as onset before age 75. In other embodiments, early onset is categorized as onset before age 70, before age 65, before age 60, before age 55, before age 50, before age 45, or before age 40. Other values for categorization of age at onset are also contemplated, including, but not limited to, all integer values of age, and such age categories are also within scope of the invention.

It should be understood that all combinations of features described herein are contemplated, even if the combination of feature is not specifically found in the same sentence or paragraph herein. This includes in particular the use of all markers disclosed herein, alone or in combination, for analysis individually or in haplotypes, in all aspects of the invention as described herein.

DETAILED DESCRIPTION OF THE INVENTION

Figure 1:
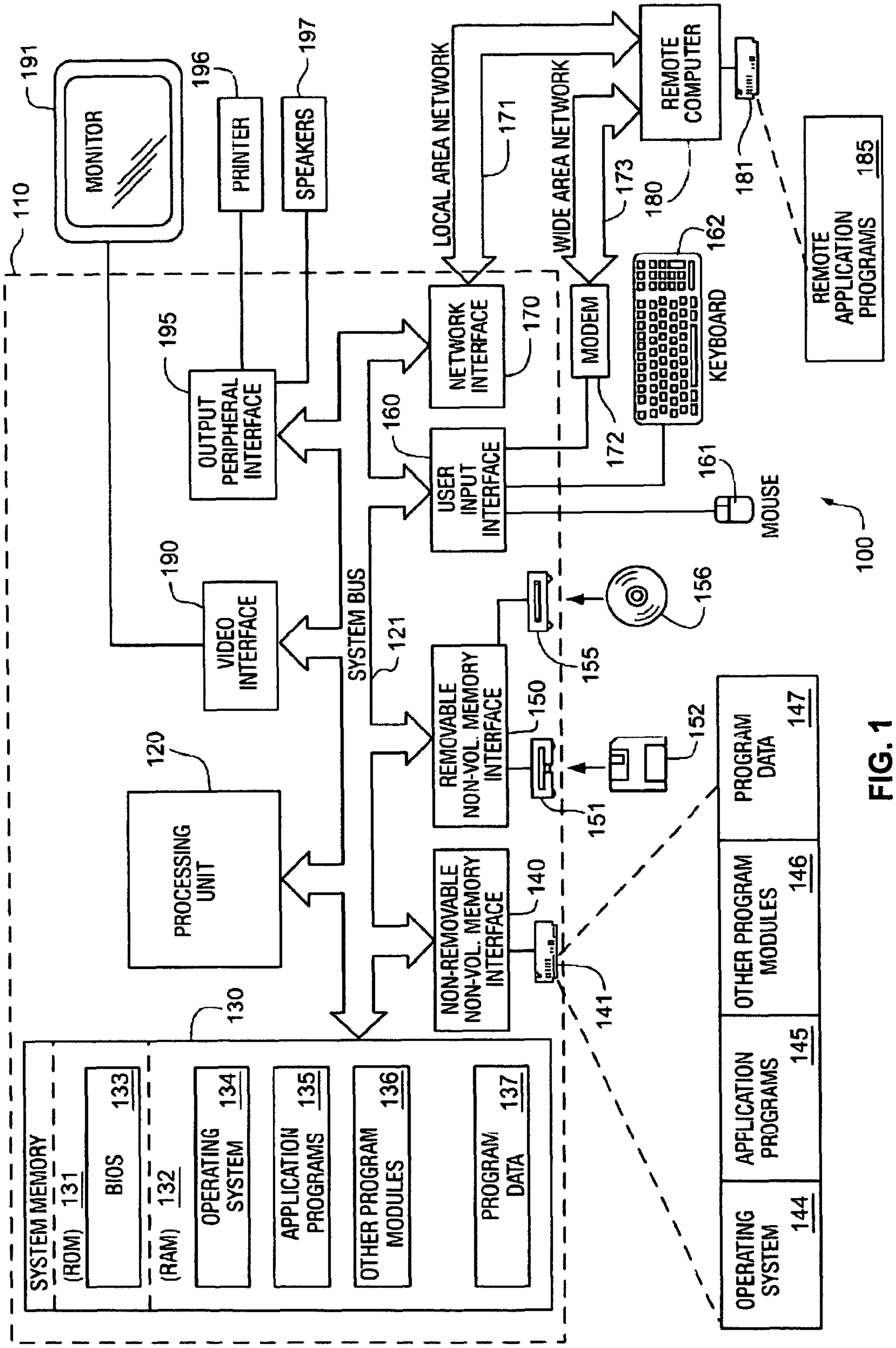
FIG. 1 provides a diagram illustrating a computer-implemented system utilizing risk variants as described herein.

A description of preferred embodiments of the invention follows.

Definitions

Unless otherwise indicated, nucleic acid sequences are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by the ordinary person skilled in the art to which the invention pertains.

The following terms shall, in the present context, have the meaning as indicated:

A "polymorphic marker", sometimes referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including SNPs, mini- or microsatellites, translocations and copy number variations (insertions, deletions, duplications). Polymorphic markers can be of any measurable frequency in the population. For mapping of disease genes, polymorphic markers with population frequency higher than 5-10% are in general most useful. However, polymorphic markers may also have lower population frequencies, such as 1-5% frequency, or even lower frequency, in particular copy number variations (CNVs). The term shall, in the present context, be taken to include polymorphic markers with any population frequency.

An "allele" refers to the nucleotide sequence of a given locus (position) on a chromosome. A polymorphic marker allele thus refers to the composition (i.e., sequence) of the marker on a chromosome. Genomic DNA from an individual contains two alleles for any given polymorphic marker, representative of each copy of the marker on each chromosome. Sequence codes for nucleotides used herein are: A=1, C=2, G=3, T=4. For microsatellite alleles, the CEPH sample (Centre d'Etudes du Polymorphisme Humain, genomics repository, CEPH sample 1347-02) is used as a reference, the shorter allele of each microsatellite in this sample is set as 0 and all other alleles in other samples are numbered in relation to this reference. Thus, e.g., allele 1 is 1 bp longer than the shorter allele in the CEPH sample, allele 2 is 2 bp longer than the shorter allele in the CEPH sample, allele 3 is 3 bp longer than the lower allele in the CEPH sample, etc., and allele −1 is 1 bp shorter than the shorter allele in the CEPH sample, allele −2 is 2 bp shorter than the shorter allele in the CEPH sample, etc.

Sequence conucleotide ambiguity as described herein including the accompanying sequence listing is as proposed by IUPAC-IUB. These codes are compatible with the codes used by the EMBL, GenBank, and PIR databases.

| IUB code | Meaning |
|---|---|
| A | Adenosine |
| C | Cytidine |
| G | Guanine |
| T | Thymidine |
| R | G or A |
| Y | T or C |
| K | G or T |
| M | A or C |
| S | G or C |
| W | A or T |
| B | C G or T |
| D | A G or T |
| H | A C or T |
| V | A C or G |
| N | A C G or T (Any base) |

A nucleotide position at which more than one sequence is possible in a population (either a natural population or a synthetic population, e.g., a library of synthetic molecules) is referred to herein as a "polymorphic site".

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population. An "indel" is a common form of polymorphism comprising a small insertion or deletion that is typically only a few nucleotides long.

A "haplotype," as described herein, refers to a segment of genomic DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles. Haplotypes are described herein in the context of the marker name and the allele of the marker in that haplotype, e.g., "4 rs1051730" refers to the 4 allele of marker rs1051730 being in the haplotype, and is equivalent to "rs1051730 allele 4". Furthermore, allelic codes in haplotypes are as for individual markers, i.e. 1=A, 2=C, 3=G and 4=T.

The term "susceptibility", as described herein, refers to the proneness of an individual towards the development of a certain state (e.g., a certain trait, phenotype or disease), or towards being less able to resist a particular state than the average individual. The term encompasses both increased susceptibility and decreased susceptibility. Thus, particular alleles at polymorphic markers and/or haplotypes of the invention as described herein may be characteristic of increased susceptibility (i.e., increased risk) of lung cancer, as characterized by a relative risk (RR) or odds ratio (OR) of greater than one for the particular allele or haplotype. Alternatively, the markers and/or haplotypes of the invention are characteristic of decreased susceptibility (i.e., decreased risk) of lung cancer, as characterized by a relative risk of less than one.

The term "and/or" shall in the present context be understood to indicate that either or both of the items connected by it are involved. In other words, the term herein shall be taken to mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or the can contain information about multiple markers, and they may also comprise other factors, such as particulars about diseases diagnoses, racial information, biomarkers, biochemical measurements, therapeutic methods or drugs, etc.

A "computer-readable medium", as described herein, refers to an information storage medium that can be accessed by a computer using a commercially available or custom-made interface. Exemplary compute-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample" as described herein, refers to a sample obtained from an individual that contains nucleic acid (DNA or RNA). In certain embodiments, i.e. the detection of specific polymorphic markers and/or haplotypes, the nucleic acid sample comprises genomic DNA. Such a nucleic acid sample can be obtained from any source that contains genomic DNA, including a blood sample, sample of amniotic fluid, sample of cerebrospinal fluid, or tissue sample from skin, muscle, buccal or conjunctival mucosa, placenta, gastrointestinal tract or other organs. The term "lung cancer therapeutic agent" refers to an agent that can be used to ameliorate or prevent symptoms associated with lung cancer.

The term "lung cancer-associated nucleic acid", as described herein, refers to a nucleic acid that has been found to be associated with lung cancer. This includes, but is not limited to, the markers and haplotypes described herein and markers and haplotypes in strong linkage disequilibrium (LD) therewith. In one embodiment, a lung cancer-associated nucleic acid refers to an LD-block found to be associated with lung cancer through at least one polymorphic marker located within the LD block.

The term "antisense agent" or "antisense oligonucleotide" refers, as described herein, to molecules, or compositions comprising molecules, which include a sequence of purine an pyrimidine heterocyclic bases, supported by a backbone, which are effective to hydrogen bond to a corresponding contiguous bases in a target nucleic acid sequence. The backbone is composed of subunit backbone moieties supporting the purine an pyrimidine heterocyclic bases at positions which allow such hydrogen bonding. These backbone moieties are cyclic moieties of 5 to 7 atoms in size, linked together by phosphorous-containing linkage units of one to three atoms in length. In certain preferred embodiments, the antisense agent comprises an oligonucleotide molecule.

"Lung cancer", in the present context, refers to clinically diagnosed lung cancer. The term encompasses all subclassification of lung cancer, including non-small cell lung carcinoma (CSCLC), squamous cell carcinoma, adenocarcinoma, bronchioalveolar carcinoma, large cell carcinoma, small cell lung carcinoma (SCLC), and combined patterns or subphenotypes of lung cancer.

The "C15 LD block", as defined herein, refers to the genomic region flanked by the SNP markers rs4436747 and rs1383636. This genomic region corresponds to a region of the genome with extensive linkage disequilibrium (LD), as described herein, and within which variants in linkage disequilibrium with rs1051730, also called surrogate variants, can be found (e.g., as set forth in Table 4). The region is located between position 76,501,063 and 76,893,275 in NCBI Build 36, and has the sequence as set forth in SEQ ID NO:1.

Association of Genetic Variants to Lung Cancer

A genome-wide association study of SNP markers on a chip containing approximately 317,000 such SNPs has resulted in identification of significant association to markers on Chromosome 15, within the nicotinic acetylcholine receptor gene cluster. As shown in Table 2, marker rs1051730 has been found to associate with increased risk of developing lung. The marker, and markers in linkage disequilibrium therewith, are thus useful for detecting an increased risk, or increased susceptibility, of lung cancer. Any one of these markers, alone or in combination, are useful in the methods, kits, apparatus, uses and media described herein. Exemplary markers in LD with rs1051730 are shown in Table 3 herein, and additional markers useful for practicing the invention as described herein are listed in the tables presented herein, including Tables 4 and 6.

Further variants have been identified through sequencing of the CHRNA5, CHRNA3 and CHRNB4 genes, as described further herein. These additional variants, including rs16969968, can also be useful for diagnostic applications for lung cancer, as described herein.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome. For example, the human genome exhibits sequence variations which occur on average every 500 nucleotides. The most common sequence variant consists of base variations at a single base position in the genome, and such sequence variants, or polymorphisms, are commonly called Single Nucleotide Polymorphisms ("SNPs"). These SNPs are believed to have occurred in a single mutational event, and therefore there are usually two possible alleles possible at each SNP site; the original allele and the mutated allele. Due to natural genetic drift and possibly also selective pressure, the original mutation has resulted in a polymorphism characterized by a particular frequency of its alleles in any given population. Many other types of sequence variants are found in the human genome, including microsatellites, insertions, deletions, inversions and copy number variations. A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles.

All such polymorphisms can be utilized in the methods and kits of the present invention, and are thus within the scope of the invention.

Due to their abundance, SNPs account for a majority of sequence variation in the human genome. Over 6 million SNPs have been validated to date (http://www.ncbi.nlm.nih.gov/projects/SNP/snp_summary.cgi). However, CNVs are receiving increased attention. These large-scale polymorphisms (typically 1 kb or larger) account for polymorphic variation affecting a substantial proportion of the assembled human genome; known CNVs cover over 15% of the human genome sequence (Estivill, X Armengol; L., *PloS Genetics* 3:1787-99 (2007). A http://projects.tcag.ca/variation/). Most of these polymorphisms are however very rare, and on average affect only a fraction of the genomic sequence of each individual. CNVs are known to affect gene expression, phenotypic variation and adaptation by disrupting gene dosage, and are also known to cause disease (microdeletion and microduplication disorders) and confer risk of common complex diseases, including HIV-1 infection and glomerulonephritis (Redon, R., et al. *Nature* 23:444-454 (2006)). It is thus possible that either previously described or unknown CNVs represent causative variants in linkage disequilibrium with the markers described herein to be associated with lung cancer. Methods for detecting CNVs include comparative genomic hybridization (CGH) and genotyping, including use of genotyping arrays, as described by Carter (*Nature Genetics* 39:S16-S21 (2007)). The Database of Genomic Variants (http://projects.tcag.ca/variation/) contains updated information about the location, type and size of described CNVs. The database currently contains data for over 15,000 CNVs. In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realise that by assaying or reading the opposite DNA strand, the complementary allele can in each case be measured. Thus, for a polymorphic site (polymorphic marker) characterized by an A/G polymorphism, the assay employed may be designed to specifically detect the presence of one or both of the two bases possible, i.e. A and G. Alternatively, by designing an assay that is designed to detect the opposite strand on the DNA template, the presence of the complementary bases T and C can be measured. Quantitatively (for example, in terms of relative risk), identical results would be obtained from measurement of either DNA strand (+ strand or − strand).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Additional variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (Chen, X. et al., *Genome Res.* 9(5): 492-98 (1999)), utilizing PCR, LCR, Nested PCR and other techniques for nucleic acid amplification.

Specific methodologies available for SNP genotyping include, but are not limited to, TaqMan genotyping assays and SNPlex platforms (Applied Biosystems), mass spectrometry (e.g., MassARRAY system from Sequenom), minisequencing methods, real-time PCR, Bio-Plex system (BioRad), CEQ and SNPstream systems (Beckman), Molecular Inversion Probe array technology (e.g., Affymetrix GeneChip), and BeadArray Technologies (e.g., Illumina GoldenGate and Infinium assays). By these or other methods available to the person skilled in the art, one or more alleles at polymorphic markers, including microsatellites, SNPs or other types of polymorphic markers, can be identified.

In certain embodiments, polymorphic markers are detected by sequencing technologies. Obtaining sequence information about an individual identifies particular nucleotides in the context of a sequence. For SNPs, sequence information about a single unique sequence site is sufficient to identify alleles at that particular SNP. For markers comprising more than one nucleotide, sequence information about the genomic region of the individual that contains the polymorphic site identifies the alleles of the individual for the particular site. The sequence information can be obtained from a sample from the individual. In certain embodiments, the sample is a nucleic acid sample. In certain other embodiments, the sample is a protein sample.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have been developed, and such methods are also contemplated to be useful for obtaining sequence information. These include pyrosequencing technology (Ronaghi, M. et al. *Anal Biochem* 267:65-71 (1999); Ronaghi, et al. *Biotechniques* 25:876-878 (1998)), e.g. 454 pyrosequencing (Nyren, P., et al. *Anal Biochem* 208:171-175 (1993)), Illumina/Solexa sequencing technology (http://www.illumina.com; see also Strausberg, R L, et al *Drug Disc Today* 13:569-577 (2008)), and Supported Oligonucleotide Ligation and Detection Platform (SOLiD) technology (Applied Biosystems, http://www.appliedbiosystems.com); Strausberg, R L, et al *Drug Disc Today* 13:569-577 (2008).

It is possible to impute or predict genotypes for un-genotyped relatives of genotyped individuals. For every un-genotyped case, it is possible to calculate the probability of the genotypes of its relatives given its four possible phased genotypes. In practice it may be preferable to include only the genotypes of the case's parents, children, siblings, half-siblings (and the half-sibling's parents), grand-parents, grand-children (and the grand-children's parents) and spouses. It will be assumed that the individuals in the small sub-pedigrees created around each case are not related through any path not included in the pedigree. It is also assumed that alleles that are not transmitted to the case have the same frequency—the population allele frequency. The probability of the genotypes of the case's relatives can then be computed by:

$$Pr(\text{genotypes of relatives}; \theta) = \sum_{h \in \{AA, AG, GA, GG\}} Pr(h; \theta) Pr(\text{genotypes of relatives} \mid h),$$

where θ denotes the A allele's frequency in the cases. Assuming the genotypes of each set of relatives are independent, this allows us to write down a likelihood function for θ:

$$L(\theta) = \prod_i Pr(\text{genotypes of relatives of case } i; \theta). \quad (*)$$

This assumption of independence is usually not correct. Accounting for the dependence between individuals is a difficult and potentially prohibitively expensive computational task. The likelihood function in (*) may be thought of as a pseudolikelihood approximation of the full likelihood function for θ which properly accounts for all dependencies. In general, the genotyped cases and controls in a case-control association study are not independent and applying the case-control method to related cases and controls is an analogous approximation. The method of genomic control (Devlin, B. et al., *Nat Genet* 36, 1129-30; author reply 1131 (2004)) has proven to be successful at adjusting case-control test statistics for relatedness. We therefore apply the method of genomic control to account for the dependence between the terms in our pseudolikelihood and produce a valid test statistic.

Fisher's information can be used to estimate the effective sample size of the part of the pseudolikelihood due to un-genotyped cases. Breaking the total Fisher information, I, into the part due to genotyped cases, $I_g$, and the part due to ungenotyped cases, $I_u$, $I=I_g+I_u$, and denoting the number of genotyped cases with N, the effective sample size due to the un-genotyped cases is estimated by $$\frac{I_u}{I_g}N.$$

In the present context, an individual who is at an increased susceptibility (i.e., increased risk) for lung cancer, is an individual in whom at least one specific allele at one or more polymorphic marker or haplotype conferring increased susceptibility for lung cancer is identified (i.e., at-risk marker alleles or haplotypes). In one aspect, the at-risk marker or haplotype is one that confers a significant increased risk (or susceptibility) of lung cancer. In one embodiment, significance associated with a marker or haplotype is measured by a relative risk (RR). In another embodiment, significance associated with a marker or haplotype is measured by an odds ratio (OR). In a further embodiment, the significance is measured by a percentage. In one embodiment, a significant increased risk is measured as a risk (relative risk and/or odds ratio) of at least 1.2, including but not limited to: at least 1.2, at least 1.3, at least 1.4, at least 1.5, at least 1.6, at least 1.7, at least 1.8, at least 1.9, and at least 2.0. In a particular embodiment, a risk (relative risk and/or odds ratio) of at least 1.2 is significant. In another particular embodiment, a risk of at least 1.3 is significant. In yet another embodiment, a risk of at least 1.4 is significant. In a further embodiment, a relative risk of at least about 1.5 is significant. In another further embodiment, a significant increase in risk is at least about 1.7 is significant. However, other numerical values bridging the above for defining risk measures are also contemplated, e.g. at least 1.15, 1.25, 1.35, and so on, and such cutoffs are also within scope of the present invention. In other embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 20%. In other embodiments, a significant increase in risk is at least 30%, at least 40%, at least 50%, at least 60%, at least 70%, at least 80%, at least 90% and at least 100%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype of the present invention is one where at least one allele of at least one marker or haplotype is more frequently present in an individual at risk for lung cancer (affected), compared to the frequency of its presence in a comparison group (control), and wherein the presence of the marker or haplotype is indicative of susceptibility to lung cancer. The control group may in one embodiment be a population sample, i.e. a random sample from the general population. In another embodiment, the control group is represented by a group of individuals who are disease-free. Such disease-free control may in one embodiment be characterized by the absence of one or more specific disease-associated symptoms. In another embodiment, the disease-free control group is characterized by the absence of one or more risk factors for lung cancer (e.g., non-smokers). Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to smoking history, food and drink habits, geographical location of main habitat, and occupational risk factors. In another embodiment, the risk factors are at least one genetic risk factor.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes.

In other embodiments of the invention, an individual who is at a decreased susceptibility (i.e., at a decreased risk) for lung cancer is an individual in whom at least one specific allele at one or more polymorphic marker or haplotype conferring decreased susceptibility for lung cancer is identified. The marker alleles and/or haplotypes conferring decreased risk are also said to be protective. In one aspect, the protective marker or haplotype is one that confers a significant decreased risk (or susceptibility) of the disease or trait. In one embodiment, significant decreased risk is measured as a relative risk of less than 0.95, including but not limited to less than 0.9, less than 0.8, less than 0.7, less than 0.6, less than 0.5, less than 0.4, less than 0.3, less than 0.2 and less than 0.1. In one particular embodiment, significant decreased risk is less than 0.8. In another embodiment, significant decreased risk is less than 0.7. In yet another embodiment, significant decreased risk is less than 0.6. In another embodiment, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. In one particular embodiment, a significant decrease in risk is at least about 20%. In another embodiment, a significant decrease in risk is at least about 30%. In another embodiment, the decrease in risk is at least about 40%. Other cutoffs or ranges as deemed suitable by the person skilled in the art to characterize the invention are however also contemplated, and those are also within scope of the present invention.

The person skilled in the art will appreciate that for markers with two alleles present in the population being studied (such as SNPs), and wherein one allele is found in increased frequency in a group of individuals with lung cancer, compared with controls, the other allele of the marker will be found in decreased frequency in the group of individuals with lung cancer, compared with controls. In such a case, one allele of the marker (the one found in increased frequency in individuals with lung cancer) will be the at-risk allele, while the other allele will be a protective allele.

A genetic variant associated with a disease or a trait (e.g. lung cancer) can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes k=3"×2"; where n is the number autosomal loci and p the number of gonosomal (sex chromosomal) loci. Overall risk assessment calculations usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk is the product of the locus specific risk values—and which also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider a total of eight variants that have been described to associate with prostate cancer (Gudmundsson, J., et al., *Nat Genet* 39:631-7 (2007), Gudmundsson, J., et al., *Nat Genet* 39:977-83 (2007); Yeager, M., et al, *Nat Genet* 39:645-49 (2007), Amundadottir, L., et al., *Nat Genet* 38:652-8 (2006); Haiman, C. A., et al., *Nat Genet* 39:638-44 (2007)). Seven of these loci are on autosomes, and the remaining locus is on chromosome X. The total number of theoretical genotypic combinations is then $3^7 \times 2^1 = 4374$. Some of those genotypic classes are very rare, but are still possible, and should be considered for overall risk assessment. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Using the same quantitative approach, the combined or overall risk associated with a plurality of variants associated with lung cancer may be assessed. Such variants may be all genetic, or they may represent a combination of genetic and non-genetic risk variants.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet* 29:217-222 (2001); May, C. A., et al., *Nature Genet* 31:272-275 (2002)).

Linkage Disequilibrium (LD) refers to a non-random assortment of two genetic elements. For example, if a particular genetic element (e.g., an allele of a polymorphic marker, or a haplotype) occurs in a population at a frequency of 0.50 (50%) and another element occurs at a frequency of 0.50 (50%), then the predicted occurrence of a person's having both elements is 0.25 (25%), assuming a random distribution of the elements. However, if it is discovered that the two elements occur together at a frequency higher than 0.25, then the elements are said to be in linkage disequilibrium, since they tend to be inherited together at a higher rate than what their independent frequencies of occurrence (e.g., allele or haplotype frequencies) would predict. Roughly speaking, LD is generally correlated with the frequency of recombination events between the two elements. Allele or haplotype frequencies can be determined in a population by genotyping individuals in a population and determining the frequency of the occurrence of each allele or haplotype in the population. For populations of diploids, e.g., human populations, individuals will typically have two alleles for each genetic element (e.g., a marker, haplotype or gene).

Many different measures have been proposed for assessing the strength of linkage disequilibrium (LD). Most capture the strength of association between pairs of biallelic sites. Two important pairwise measures of LD are $r^2$ (sometimes denoted $\Delta^2$) and |D'|. Both measures range from 0 (no disequilibrium) to 1 ('complete' disequilibrium), but their interpretation is slightly different. |D'| is defined in such a way that it is equal to 1 if just two or three of the possible haplotypes are present, and it is <1 if all four possible haplotypes are present. Therefore, a value of |D'| that is <1 indicates that historical recombination may have occurred between two sites (recurrent mutation can also cause |D'| to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value indicative of markers being in linkage disequilibrium can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, 0.99 or 1.0. In one preferred embodiment, the significant $r^2$ value is at least 0.2. Alternatively, linkage disequilibrium as described herein, refers to linkage disequilibrium characterized by values of |D'| of at least 0.2, such as 0.3, 0.4, 0.5, 0.6, 0.7, 0.8, 0.85, 0.9, 0.95, 0.96, 0.97, 0.98, 0.99. Thus, linkage disequilibrium represents a correlation between alleles of distinct markers. It is measured by correlation $r^2$ coefficient or |D'| ($r^2$ up to 1.0 and |D'| up to 1.0). In certain embodiments, linkage disequilibrium is defined in terms of values for both the $r^2$ and |D'| measures. In one such embodiment, a significant linkage disequilibrium is defined as $r^2$>0.1 and |D'|>0.8. In another embodiment, a significant linkage disequilibrium is defined as $r^2$>0.2 and |D'|>0.9. Other combinations and permutations of values of $r^2$ and |D'| for determining linkage disequilibrium are also possible, and within the scope of the invention. Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http://www.hapmap.org). In one such embodiment, LD is determined in the CEU population of the HapMap samples. In another embodiment, LD is determined in the YRI population. In yet another embodiment, LD is determined in samples from the Icelandic population.

If all polymorphisms in the genome were identical at the population level, then every single one of them would need to be investigated in association studies. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, N., et al., *Proc Natl Acad Sci USA* 99:2228-2233 (2002); Reich, D E et al, *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294: 1719-1723 (2001); Dawson, E. et al., *Nature* 418:544-548 (2002); Phillips, M. S. et al., *Nature Genet.* 33:382-387 (2003)).

There are two main methods for defining these haplotype blocks: blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, S., et al., *Science* 310: 321-32324 (2005); Myers, S. et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks (LD blocks) can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait, and as such are useful for use in the methods and kits of the present invention. One or more causative (functional) variants or mutations may reside within the region found to be associating to the disease or trait. Such variants may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. One example of such an embodiment would be a rare, or relatively rare (<10% allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc.* 8, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a linkage region, for example, association of all possible combinations of genotyped markers is studied, provided those markers span a practical region. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of a significant marker and/or haplotype association.

Haplotype Analysis

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics,* 60(2):368-75 (2004)) as a natural extension of information measures defined for linkage analysis, and is implemented in NEMO.

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families for the linkage analysis, first and second-degree relatives can be eliminated from the patient list. Furthermore, the test can be repeated for association correcting for any remaining relatedness among the patients, by extending a variance adjustment procedure described in Risch, N. & Teng, 3. (*Genome Res.,* 8:1273-1288 (1998)), DNA pooling (ibid) for sibships so that it can be applied to general familial relationships, and present both adjusted and unadjusted p-values for comparison. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

An association signal detected in one association study may be replicated in a second cohort, ideally from a different population (e.g., different region of same country, or a different country) of the same or different ethnicity. The advantage of replication studies is that the number of tests performed in the replication study is usually quite small, and hence the less stringent the statistical measure that needs to be applied. For example, for a genome-wide search for susceptibility variants for a particular disease or trait using 300,000 SNPs, a correction for the 300,000 tests performed (one for each SNP) can be performed. Since many SNPs on the arrays typically used are correlated (i.e., in LD), they are not independent. Thus, the correction is conservative. Nevertheless, applying this correction factor requires an observed P-value of less than $0.05/300,000=1.7\times10^{-7}$ for the signal to be considered significant applying this conservative test on results from a single study cohort. Obviously, signals found in a genome-wide association study with P-values less than this conservative threshold are a measure of a true genetic effect, and replication in additional cohorts is not necessarily from a statistical point of view. Importantly, however, signals with P-values that are greater than this threshold may also be due to a true genetic effect. Thus, since the correction factor depends on the number of statistical tests performed, if one signal (one SNP) from an initial study is replicated in a second case-control cohort, the appropriate statistical test for significance is that for a single statistical test, i.e., P-value less than 0.05. Replication studies in one or even several additional case-control cohorts have the added advantage of providing assessment of the association signal in additional populations, thus simultaneously confirming the initial finding and providing an assessment of the overall significance of the genetic variant(s) being tested in human populations in general.

The results from several case-control cohorts can also be combined to provide an overall assessment of the underlying effect. The methodology commonly used to combine results from multiple genetic association studies is the Mantel-Haenszel model (Mantel and Haenszel, *J Natl Cancer Inst* 22:719-48 (1959)). The model is designed to deal with the situation where association results from different populations, with each possibly having a different population frequency of the genetic variant, are combined. The model combines the results assuming that the effect of the variant on the risk of the disease, a measured by the OR or RR, is the same in all populations, while the frequency of the variant may differ between the populations. Combining the results from several populations has the added advantage that the overall power to detect a real underlying association signal is increased, due to the increased statistical power provided by the combined cohorts. Furthermore, any deficiencies in individual studies, for example due to unequal matching of cases and controls or population stratification will tend to balance out when results from multiple cohorts are combined, again providing a better estimate of the true underlying genetic effect.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different genotype. For a disease, a relative risk of 2 means that one group has twice the chance of developing a disease as the other group. The Risk presented is usually the relative risk for a person, or a specific genotype of a person, compared to the population with matched gender and ethnicity. Risks of two individuals of the same gender and ethnicity could be compared in a simple manner. For example, if, compared to the population, the first individual has relative risk 1.5 and the second has relative risk 0.5, then the risk of the first individual compared to the second individual is 1.5/0.5=3.

Risk Calculations

The creation of a model to calculate the overall genetic risk involves two steps: i) conversion of odds-ratios for a single genetic variant into relative risk and ii) combination of risk from multiple variants in different genetic loci into a single relative risk value.

Deriving Risk from Odds-Ratios

Most gene discovery studies for complex diseases that have been published to date in authoritative journals have employed a case-control design because of their retrospective setup. These studies sample and genotype a selected set of cases (people who have the specified disease condition) and control individuals. The interest is in genetic variants (alleles) which frequency in cases and controls differ significantly.

The results are typically reported in odds-ratios, that is the ratio between the fraction (probability) with the risk variant (carriers) versus the non-risk variant (non-carriers) in the groups of affected versus the controls, i.e. expressed in terms of probabilities conditional on the affection status:

$$OR=(Pr(c|A)/Pr(nc|A))/(Pr(c|C)/Pr(nc|C))$$

Sometimes it is however the absolute risk for the disease that we are interested in, i.e. the fraction of those individuals carrying the risk variant who get the disease or in other words the probability of getting the disease. This number cannot be directly measured in case-control studies, in part, because the ratio of cases versus controls is typically not the same as that in the general population. However, under certain assumption, we can estimate the risk from the odds-ratio.

It is well known that under the rare disease assumption, the relative risk of a disease can be approximated by the odds-ratio. This assumption may however not hold for many common diseases. Still, it turns out that the risk of one genotype variant relative to another can be estimated from the odds-ratio expressed above. The calculation is particularly simple under the assumption of random population controls where the controls are random samples from the same population as the cases, including affected people rather than being strictly unaffected individuals. To increase sample size and power, many of the large genome-wide association and replication studies used controls that were neither age-matched with the cases, nor were they carefully scrutinized to ensure that they did not have the disease at the time of the study. Hence, while not exactly, they often approximate a random sample from the general population. It is noted that this assumption is rarely expected to be satisfied exactly, but the risk estimates are usually robust to moderate deviations from this assumption.

Calculations show that for the dominant and the recessive models, where we have a risk variant carrier, "c", and a non-carrier, "nc", the odds-ratio of individuals is the same as the risk-ratio between these variants:

$$OR=Pr(A|c)/Pr(A|nc)=r$$

And likewise for the multiplicative model, where the risk is the product of the risk associated with the two allele copies, the allelic odds-ratio equals the risk factor:

$$OR=Pr(A|aa)/Pr(A|ab)=Pr(A|ab)/Pr(A|bb)=r$$

Here "a" denotes the risk allele and "b" the non-risk allele. The factor "r" is therefore the relative risk between the allele types.

For many of the studies published in the last few years, reporting common variants associated with complex diseases, the multiplicative model has been found to summarize the effect adequately and most often provide a fit to the data superior to alternative models such as the dominant and recessive models.

The Risk Relative to the Average Population Risk

It is most convenient to represent the risk of a genetic variant relative to the average population since it makes it easier to communicate the lifetime risk for developing the disease compared with the baseline population risk. For example, in the multiplicative model we can calculate the relative population risk for variant "aa" as:

$$RR(aa)=Pr(A|aa)/Pr(A)=(Pr(A|aa)/Pr(A|bb))/(Pr(A)/Pr(A|bb))=r^2/(Pr(aa)r^2+Pr(ab)r+Pr(bb))=r^2/(p^2r^2+2pqr+q^2)=r^2/R$$

Here "p" and "q" are the allele frequencies of "a" and "b" respectively. Likewise, we get that RR(ab)=r/R and RR(bb)=1/R. The allele frequency estimates may be obtained from the publications that report the odds-ratios and from the HapMap database. Note that in the case where we do not know the genotypes of an individual, the relative genetic risk for that test or marker is simply equal to one.

As an example, in type-2 diabetes risk, allele T of the disease associated marker rs7903146 in the TCF7L2 gene on chromosome 10 has an allelic OR of 1.37 and a frequency (p) around 0.28 in non-Hispanic white populations. The genotype relative risk compared to genotype CC are estimated based on the multiplicative model.

For TT it is 1.37×1.37=1.88; for CT it is simply the OR 1.37, and for CC it is 1.0 by definition.

The frequency of allele C is q=1−p=1−0.28=0.72. Population frequency of each of the three possible genotypes at this marker is:

$$Pr(TT)=p^2=0.08,\ Pr(CT)=2pq=0.40,\text{ and } Pr(CC)=q^2=0.52$$

The average population risk relative to genotype CC (which is defined to have a risk of one) is:

$$R=0.08\times1.88+0.40\times1.37+0.52\times1=1.22$$

Therefore, the risk relative to the general population (RR) for individuals who have one of the following genotypes at this marker is:

$$RR(TT)=1.88/1.22=1.54,\ RR(CT)=1.37/1.22=1.12,\ RR(CC)=1/1.22=0.82.$$

Combining the Risk from Multiple Markers

When genotypes of many SNP variants are used to estimate the risk for an individual, unless otherwise stated, a multiplicative model for risk can be assumed. This means that the combined genetic risk relative to the population is calculated as the product of the corresponding estimates for individual markers, e.g. for two markers g1 and g2:

$$RR(g1,g2)=RR(g1)RR(g2)$$

The underlying assumption is that the risk factors occur and behave independently, i.e. that the joint conditional probabilities can be represented as products:

$$Pr(A|g1,g2)=Pr(A|g1)Pr(A|g2)/Pr(A)\text{ and }Pr(g1,g2)=Pr(g1)Pr(g2)$$

Obvious violations to this assumption are markers that are closely spaced on the genome, i.e. in linkage disequilibrium such that the concurrence of two or more risk alleles is correlated. In such cases, we can use so called haplotype modeling where the odds-ratios are defined for all allele combinations of the correlated SNPs.

As is in most situations where a statistical model is utilized, the model applied is not expected to be exactly true since it is not based on an underlying bio-physical model. However, the multiplicative model has so far been found to fit the data adequately, i.e. no significant deviations are detected for many common diseases for which many risk variants have been discovered.

As an example, an individual who has the following genotypes at 4 markers associated with risk of type-2 diabetes along with the risk relative to the population at each marker:

Chromo 3 PPARG CC Calculated risk: RR(CC)=1.03
Chromo 6 CDKAL1 GG Calculated risk: RR(GG)=1.30
Chromo 9 CDKN2A AG Calculated risk: RR(AG)=0.88
Chromo 11 TCF7L2 TT Calculated risk: RR(TT)=1.54

Combined, the overall risk relative to the population for this individual is:

$$1.03\times1.30\times0.88\times1.54=1.81$$

Adjusted Life-Time Risk

The lifetime risk of an individual is derived by multiplying the overall genetic risk relative to the population with the average life-time risk of the disease in the general population of the same ethnicity and gender and in the region of the individual's geographical origin. As there are usually several epidemiologic studies to choose from when defining the general population risk, we will pick studies that are well-powered for the disease definition that has been used for the genetic variants.

For example, for a phenotype, if the overall genetic risk relative to the population is 1.8 for a white male, and if the average life-time risk of the phenotype for individuals of his demographic is 20%, then the adjusted lifetime risk for him is 20%×1.8=36%.

Note that since the average RR for a population is one, this multiplication model provides the same average adjusted life-time risk of the disease. Furthermore, since the actual life-time risk cannot exceed 100%, there must be an upper limit to the genetic RR.

Risk Assessment for Lung Cancer

As described herein, certain polymorphic markers and haplotypes comprising such markers are found to be useful for risk assessment of lung cancer. Risk assessment can involve the use of the markers for diagnosing a susceptibility to lung cancer. Particular alleles of polymorphic markers are found more frequently in individuals with lung cancer, than in individuals without diagnosis of lung cancer. Therefore, these marker alleles have predictive value for detecting lung cancer, or a susceptibility to lung cancer, in an individual. Tagging markers in linkage disequilibrium with at-risk variants (or protective variants) described herein can be used as surrogates for these markers (and/or haplotypes). Such surrogate markers can be located within a particular haplotype block or LD block. Such surrogate markers can also sometimes be located outside the physical boundaries of such a haplotype block or LD block, either in close vicinity of the LD block/haplotype block, but possibly also located in a more distant genomic location.

Long-distance LD can for example arise if particular genomic regions (e.g., genes) are in a functional relationship. For example, if two genes encode proteins that play a role in a shared metabolic pathway, then particular variants in one gene may have a direct impact on observed variants for the other gene. Without intending to be bound by theory, let us consider the case where a variant in one gene leads to increased expression of the gene product. To counteract this effect and preserve overall flux of the particular pathway, this variant may have led to selection of one (or more) variants at a second gene that confers decreased expression levels of that gene. These two genes may be located in different genomic locations, possibly even on different chromosomes, but variants within the genes are in apparent LD, not because of their shared physical location within a region of high LD, but rather due to evolutionary forces. Such LD is also contemplated and within scope of the present invention. The skilled person will appreciate that many other scenarios of functional gene-gene interaction are possible, and the particular example discussed here represents only one such possible scenario.

Markers with values of $r^2$ equal to 1 are perfect surrogates for the at-risk variants, i.e. genotypes for one marker perfectly predicts genotypes for the other. Markers with smaller values of $r^2$ than 1 can also be surrogates for the at-risk variant, or alternatively represent variants with relative risk values as high as or possibly even higher than the originally identified at-risk variant. The at-risk variant identified may not be the functional variant itself, but is in this instance in linkage disequilibrium with the true functional variant. The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation genotype surrogate markers in linkage disequilibrium with the markers and/or haplotypes as described herein. The tagging or surrogate markers in LD with the detected at-risk variants, also have predictive value for detecting association to lung cancer, or a susceptibility to lung cancer in an individual. These tagging or surrogate markers that are in LD with the markers of the present invention can also include other markers that distinguish among haplotypes, as these similarly have predictive value for detecting susceptibility to lung cancer.

The presence of certain alleles at certain polymorphic markers (e.g., allele T in marker rs1051730) is indicative of increased risk of developing lung cancer. In general, homozygous carriers of an at-risk allele (e.g., individuals who carry two copies of the T allele of marker rs1051730) are of particularly high risk or susceptibility of developing lung cancer. Thus, in certain embodiments of the invention, the presence of two copies of an at-risk allele is indicative of increased susceptibility or risk of lung cancer. In other embodiments, heterozygous individuals carrying one copy of the at-risk allele are at increased risk or susceptibility of lung cancer.

The present invention can in certain embodiments be practiced by assessing a sample comprising genomic DNA from an individual for the presence of variants described herein to be associated with lung cancer. Such assessment includes steps of detecting the presence or absence of at least one allele of at least one polymorphic marker, using methods well known to the skilled person and further described herein, and based on the outcome of such assessment, determine whether the individual from whom the sample is derived is at increased or decreased risk (increased or decreased susceptibility) of lung cancer. Detecting particular alleles of polymorphic markers can in certain embodiments be done by obtaining nucleic acid sequence data about a particular human individual, that identifies at least one allele of at least one polymorphic marker. Different alleles of the at least one marker are associated with different susceptibility to the disease in humans. Obtaining nucleic acid sequence data can comprise nucleic acid sequence at a single nucleotide position, which is sufficient to identify alleles at SNPs. The nucleic acid sequence data can also comprise sequence at any other number of nucleotide positions, in particular for genetic markers that comprise multiple nucleotide positions, and can be anywhere from two to hundreds of thousands, possibly even millions, of nucleotides (in particular, in the case of copy number variations (CNVs)).

In certain embodiments, the invention can be practiced utilizing a dataset comprising information about the genotype status of at least one polymorphic marker associated with lung cancer (or markers in linkage disequilibrium with at least one marker associated with lung cancer). In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with the disease. A positive result for a variant (e.g., marker allele) associated with lung cancer, is indicative of the individual from which the dataset is derived is at increased susceptibility (increased risk) of lung cancer.

In certain embodiments of the invention, a polymorphic marker is correlated to lung cancer by referencing genotype data for the polymorphic marker to a look-up table that comprises correlations between at least one allele of the polymorphism and lung cancer. In some embodiments, the table comprises a correlation for one polymorphism. In other embodiments, the table comprises a correlation for a plurality of polymorphisms. In both scenarios, by referencing to a look-up table that gives an indication of a correlation between a marker and disease (e.g., lung cancer), a risk for the disease, or a susceptibility to the disease, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

The markers disclosed to be predictive of susceptibility to lung cancer, as disclosed herein, e.g., the markers presented in Table 4, may be useful for risk assessment and diagnostic purposes for, either alone or in combination. Even in cases where the increase in risk by individual risk factors is relatively modest, e.g. on the order of 10-30%, the association may have significant implications. Thus, relatively common genetic variants may have significant contribution to the overall risk (Population Attributable Risk is high), or combination of markers can be used to define groups of individual who, based on the combined risk of the markers, is at significant combined risk of developing lung cancer.

Thus, in one embodiment of the invention, a plurality of variants (genetic markers, biomarkers and/or haplotypes) is used for overall risk assessment of lung cancer. These variants are in one embodiment selected from the variants as disclosed herein. Other embodiments include the use of the variants of the present invention in combination with other variants known to be useful for diagnosing a susceptibility to lung cancer. In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as multivariate analyses or joint risk analyses, may subsequently be used to determine the overall risk conferred based on the genotype status at the multiple loci. Assessment of risk based on such analysis may subsequently be used in the methods and kits of the invention, as described herein.

A variety of biomarkers have been associated with lung cancer, and can all be useful in combination with the genetic variants disclosed herein. These include, but are not limited to, protein markers, non-protein small molecule markers, mRNA markers and DNA markers. Protein markers include, but are not limited to, epidermal growth factor receptors (EGFR), cytokeratins, MUC1, LUNX, KS1/4, telomerase, cell cycle proteins, such as cyclins (e.g., cyclin D1, cyclin A, cyclin B1) and cyclin-dependent kinases, G1-S transition proteins, such as Rb (retinoblastoma susceptibility protein), apoptosis proteins, death receptors, caspases, death-associated protein, Bcl-2 family, p-53, angiogenesis growth factors (e.g., VEGF, VEGFR-1, VEGFR-2, PDGF, bFGF, IL-8, collagen XVIII), inhibitors of angiogenesis, and markers of angiogenetic activity. These biomarkers may be used alone or in combination for risk assessment of lung cancer, in combination with at least one genetic variant as described herein. The skilled person will appreciate that expression of these protein factors can be made at the protein level, such as by monoclonal or multiclonal antibodies, or by other methods known to the skilled person. Alternatively, determination of mRNA levels of the corresponding mRNA precursor can be used as a measure of expression levels.

As described in the above, the haplotype block structure of the human genome has the effect that a large number of variants (markers and/or haplotypes) in linkage disequilibrium with the variant originally associated with a disease or trait (e.g., lung cancer) may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined. Such markers and/or haplotypes may in those cases be also used as surrogate markers and/or haplotypes for the markers and/or haplotypes physically residing within the haplotype block as defined. As a consequence, markers and haplotypes in LD (typically characterized by $r^2$ greater than 0.1, such as $r^2$ greater than 0.2, including $r^2$ greater than 0.3, also including $r^2$ greater than 0.4) with the markers and haplotypes of the present invention are also within the scope of the invention, even if they are physically located beyond the boundaries of the haplotype block as defined. This includes markers that are described herein (e.g., Table 4), but may also include other markers that are in strong LD (e.g., characterized by $r^2$ greater than 0.1 or 0.2 and/or $|D'|>0.8$) with one or more of the markers listed in Table 4.

For the SNP markers described herein, the opposite allele to the allele found to be in excess in patients (at-risk allele) is found in decreased frequency in patients with lung cancer. These markers and haplotypes in LD and/or comprising such markers, are thus protective for lung cancer, i.e. they confer a decreased risk or susceptibility of individuals carrying these markers and/or haplotypes for developing lung cancer.

Certain variants of the present invention, including certain haplotypes comprise, in some cases, a combination of various genetic markers, e.g., SNPs and microsatellites. Detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker allele or haplotype found to be associated with lung cancer, is one in which the marker allele or haplotype is more frequently present in an individual who is at risk for lung cancer (affected), compared to the frequency of its presence in a healthy individual (control), wherein the presence of the marker allele or haplotype is indicative of lung cancer or a susceptibility to lung cancer. In other embodiments, at-risk markers in linkage disequilibrium with one or more markers found to be associated with lung cancer (e.g., markers as listed in Tables 4 and 6) are tagging markers that are more frequently present in an individual at risk for lung cancer (affected), compared to the frequency of their presence in a non-affected or healthy individual (control), wherein the presence of the tagging markers is indicative of increased susceptibility to lung cancer. In a further embodiment, at-risk markers alleles (i.e. conferring increased susceptibility) in linkage disequilibrium with one or more markers shown herein to be associated with lung cancer, are markers comprising one or more allele that is more frequently present in an individual at risk for lung cancer, compared to the frequency of their presence in a non-affected or healthy individual (control), wherein the presence of the markers is indicative of increased susceptibility to lung cancer.

Study Population

In a general sense, the methods, uses and kits of the invention as described herein can be utilized from samples containing genomic DNA from any source. In preferred embodiments, the individual from whom the sample is derived is a human individual. The individual can be an adult, child, or fetus. The present invention also provides for assessing markers and/or haplotypes in human individuals who are members of a target population. Such a target population is in one embodiment a population or group of individuals at particular risk of developing the disease, based on other genetic factors, biomarkers, biophysical parameters (e.g., weight, BMD, blood pressure), or general health and/or lifestyle parameters (e.g., history of lung cancer or related diseases, smoking history, family history of disease).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset of lung cancer in any age range described in the above. It is also contemplated that a range of ages may be relevant in certain embodiments, such as age at onset at more than age 45 but less than age 60. Other age ranges are however also contemplated, including all age ranges bracketed by the age values listed in the above. The invention furthermore relates to individuals of either gender, males or females.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Styrkarsdottir, U., et al. *N Engl J Med* Apr. 29, 2008 (Epub ahead of print); Thorgeirsson, T., et al. *Nature* 452:638-42 (2008); Gudmundsson, J., et al. *Nat Genet.* 40:281-3 (2008); Stacey, S. N., et al., Nat Genet. 39:865-69 (2007); Helgadottir, A., et al., *Science* 316:1491-93 (2007); Steinthorsdottir, V., et al., *Nat Genet.* 39:770-75 (2007); Gudmundsson, J., et al., *Nat Genet.* 39:631-37 (2007); Frayling, T M, *Nature Reviews Genet* 8:657-662 (2007); Amundadottir, L. T., et al., *Nat Genet.* 38:652-58 (2006); Grant, S. F., et al., *Nat Genet.* 38:320-23 (2006)). Thus, genetic findings in the Icelandic population have in general been replicated in other populations, including populations from Africa and Asia.

It is thus believed that the markers of the present invention described herein to be associated with lung cancer are believed to show similar association in other human populations. Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Chech, Greek and Turkish populations. The invention furthermore in other embodiments can be practiced in specific human populations that include Bantu, Mandenk, Yoruba, San, Mbuti Pygmy, Orcadian, Adygel, Russian, Sardinian, Tuscan, Mozabite, Bedouin, Druze, Palestinian, Balochi, Brahui, Makrani, Sindhi, Pathan, Burusho, Hazara, Uygur, Kalash, Han, Dai, Daur, Hezhen, Lahu, Miao, Orogen, She, Tujia, Tu, Xibo, Yi, Mongolan, Naxi, Cambodian, Japanese, Yakut, Melanesian, Papuan, Karitianan, Surui, Colombian, Maya and Pima.

In certain embodiments, the invention relates to populations that include black African ancestry such as populations comprising persons of African descent or lineage. Black African ancestry may be determined by self reporting as African-Americans, Afro-Americans, Black Americans, being a member of the black race or being a member of the negro race. For example, African Americans or Black Americans are those persons living in North America and having origins in any of the black racial groups of Africa. In another example, self-reported persons of black African ancestry may have at least one parent of black African ancestry or at least one grandparent of black African ancestry. In another embodiment, the invention relates to individuals of Caucasian origin.

Ancestry is in certain embodiment based on self-reported ancestry. The ancestry or racial contribution in individual subjects may also be determined by genetic analysis. Genetic analysis of ancestry may for example be carried out using unlinked microsatellite markers such as those set out in Smith et al. (*Am J Hum Genet* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, have different population frequencies in different populations, or are polymorphic in one population but not in another. The person skilled in the art will however apply the methods available and as thought herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Utility of Genetic Testing

The person skilled in the art will appreciate and understand that the variants described herein in general do not, by themselves, provide an absolute identification of individuals who will develop lung cancer. The variants described herein do however indicate increased and/or decreased likelihood that individuals carrying the at-risk variants disclosed herein will develop lung cancer. This information is however extremely valuable in itself, as outlined in more detail in the following, as it can be used, for example, to initiate preventive measures at an early stage, perform regular physical exams to monitor the development, progress and/or appearance of symptoms of lung cancer, or to schedule exams at a regular interval to identify lung cancer in its early stages, so as to be able to apply treatment at an early stage which is often critical for successful lung cancer therapy.

The knowledge about a genetic variant that confers a risk of developing lung cancer offers the opportunity to apply a genetic test to distinguish between individuals with increased risk of developing lung cancer (i.e. carriers of the at-risk variants disclosed herein) and those with decreased risk of developing lung cancer (i.e. carriers of protective variants, and/or non-carriers of at-risk variants). The core value of genetic testing is the possibility of being able to diagnose disease, or a predisposition to disease, at an early stage and provide information to the clinician about prognosis/aggressiveness of the disease in order to be able to apply the most appropriate treatment.

Individuals with a family history of lung cancer and carriers of at-risk variants may benefit from genetic testing since the knowledge of the presence of a genetic risk factor, or evidence for increased risk of being a carrier of one or more risk factors, may provide incentive for implementing a healthier lifestyle, by avoiding or minimizing known environmental risk factors for lung cancer. For example, an individual who is a current smoker and is identified as a carrier of one or more of the variants shown herein to be associated with increased risk of lung cancer, may, due to his/her increased risk of developing the disease, choose to quit smoking.

Integration of Genetic Risk Models into Clinical Management of Lung Cancer:

Management of lung cancer currently relies on a combination of primary prevention (most importantly abstinence from smoking), early diagnosis and appropriate treatments. There are clear clinical imperatives for integrating genetic testing into several aspects of these management areas. Identification of cancer susceptibility genes may also reveal key molecular pathways that may be manipulated (e.g., using small or large molecular weight drugs) and may lead to more effective treatments.

Primary Prevention

Primary prevention options currently focus on avoiding exposure to tobacco smoke or other environmental toxins that have been associated with the development of lung cancer.

Early Diagnosis

Patients who are identified as being at high risk for lung cancer may be referred to have chest X-rays or sputum cytology examination. In addition, a spiral CT scan is a newly-developed procedure for lung cancer screening. Numerous lung cancer screening trials are currently taking place but presently, the U.S. Preventive Services Task Force (USPSTF) concludes that evidence is insufficient to recommend for or against screening asymptomatic persons for lung cancer with either low dose computerized tomography (LDCT), chest x-ray, sputum cytology, or a combination of these tests.

Many of the screening protocols being evaluated involve some form of radiation or and invasive procedure such as bronchoscopy. These protocols carry certain risks and may prove hard to implement due to the considerable costs involved. In light of the fact that only about 15% of lifetime smokers develop lung cancer, it is clear that the great majority of individuals at risk would be needlessly subjected to repeated screening tests with the associated costs and negative side-effects. The identification of genetic biomarkers that affect the risk of developing lung cancer could be used to help identify individuals should be offered extreme help in risk reduction programs such as smoking termination. In the case of failure to stop smoking, or in the case of ex-smokers, such genetic biomarkers could help in defining the subpopulation of individuals that would benefit the most from screening.

Less than 10% of lung cancer cases arise in individuals that have never smoked. Genetic biomarkers that predict the risk of lung cancer would be particularly useful in this group. The genetic component of this form of the disease is likely to be even stronger than in tobacco-related lung cancer. If genetic variants that affect the risk of non-smoking lung cancer were known, it might be possible to identify individuals at high risk for this disease and subject them to regular screening tests.

Variants over the CHRNA3/CHRNA5/CHRNB4 gene cluster have previously been reported as potentially associated with risk of nicotine dependence (Saccone, et al., *Hum Mol Genet* 16:36-49 (2007)). However, the evidence for association reported was weak, and a large number of other genomic locations were also reported as potentially associated with nicotine dependence. The present inventors have confirmed the suggested association of variants in the region to smoking phenotypes. The present inventors have also surprisingly found that the rs1051730 marker, and markers in linkage disequilibrium therewith, show strong association to lung cancer. While smoking is a known risk factor for this disease, the effect of the rs1051730 variant on lung cancer cannot be explained by the commonly used phenotypes for nicotine dependence (ND), such as smoking quantity (SQ) (which is correlated with the Fagerström score and nicotine dependence according to the DSM-IV criteria). This will be further described in the following.

The rs1051730 marker is associated with SQ as shown in Table 1. Of the 13,945 smokers studied by the inventors, 501 are known to have developed lung cancer. The SQ levels 1, 2 and 3 have a calculated relative risk of 2.1, 2.4 and 2.9 for lung cancer, respectively, compared with SQ level 0 (1-10 cigarettes/day). If it is assumed that only smokers developed lung cancer, the frequency of the rs1051730 allele T variant can be calculated as a weighted average, using these relative risk estimates. Then, the predicted frequency of the variant in lung cancer is [(0.305×0.260)+(0.350×0.459×2.1)+(0.380×0.214×2.4)+(0.391×0.067×2.9)] divided by [0.260+(0.459×2.1)+(0.214×2.4)+(0.067×2.9)], or 35.6% (see Table 2). It should be noted that this is an overestimate, since non-smokers are given a weight of zero in this calculation. Still, compared to the population frequency of 34.4% for the variant, the odds ratio for lung cancer based on this calculation is only 1.05, which is much smaller than the observed value of 1.31 (Table 2). It should be noted that even if the relative risks for SQ levels 2 and 3 were doubled, the calculated frequency and the corresponding OR value for lung cancer would only increase to 36.3% and 1.09, respectively. In other words, the SQ measure only explains a small proportion of the increased risk for lung cancer that is observed for rs1051730 allele T. The same conclusion will be reached using nicotine dependence phenotypes such as Fagerström score and DSM-IV criteria, since the frequency of the variant for these phenotypes is comparable to SQ.

These surprising observations show that the risk conferred by rs1051730 for lung cancer cannot be explained by their effect on the smoking quantity phenotype. Thus, there is an unexpected and surprising additional risk for lung cancer conferred by rs1051730 and correlated variants.

Methods

Methods for risk assessment of lung cancer are described herein and are encompassed by the invention. The invention also encompasses methods of assessing an individual for probability of response to a therapeutic agent for lung cancer, as well as methods for predicting the effectiveness of a therapeutic agent for lung cancer. Kits for assaying a sample from a subject to detect susceptibility to lung cancer are also encompassed by the invention.

Diagnostic and Screening Methods

In certain embodiments, the present invention pertains to methods of determining a susceptibility to lung cancer, by detecting particular alleles at genetic markers that appear more frequently in lung cancer subjects or subjects who are susceptible to lung cancer. In a particular embodiment, the invention is a method of diagnosing a susceptibility to lung cancer by detecting at least one allele of at least one polymorphic marker (e.g., the markers described herein). The present invention describes methods whereby detection of particular alleles of particular markers or haplotypes is indicative of a susceptibility to lung cancer. Such prognostic or predictive assays can also be used to determine prophylactic treatment of a subject prior to the onset of symptoms or prior to diagnosis of lung cancer.

The present invention pertains in some embodiments to methods of clinical applications of diagnosis, e.g., diagnosis performed by a medical professional. In other embodiments, the invention pertains to methods of diagnosis performed by a layman. The layman can be the customer of a genotyping service. The layman may also be a genotype service provider, who performs genotype analysis on a DNA sample from an individual, in order to provide service related to genetic risk factors for particular traits or diseases, based on the genotype status of the individual (i.e., the customer). Recent technological advances in genotyping technologies, including high-throughput genotyping of SNP markers, such as Molecular Inversion Probe array technology (e.g., Affymetrix GeneChip), and BeadArray Technologies (e.g., Illumina GoldenGate and Infinium assays) have made it possible for individuals to have their own genome simultaneously assessed for up to one million SNPs. The resulting genotype information, made available to the customer can be compared to information from the public literature about disease or trait risk associated with various SNPs. Methods for generating complete sequence information about the genomic sequence of individuals, which can be used for establishing genotype information (sequence identity at polymorphic sites), are also being developed. The diagnostic application of disease-associated alleles as described herein, can thus be performed either by the individual, through analysis of his/her genotype data, or by a health professional based on results of a clinical test. In other words, the diagnosis or assessment of a susceptibility based on genetic risk can be made by health professionals, genetic counselors or by the layman, based on information about his/her genotype and publications on various risk factors. In the present context, the term "diagnosing", "diagnose susceptibility", and "determine susceptibility", is meant to refer to any available method for such determination, including those mentioned above.

In certain embodiments, a sample containing genomic DNA from an individual is collected. Such sample can for example be a buccal swab, a saliva sample, a blood sample, or other suitable samples containing genomic DNA, as described further herein. The genomic DNA is then analyzed using any common technique available to the skilled person, such as high-throughput array technologies. Genotype and/or sequence results are stored in a convenient data storage unit, such as a data carrier, including computer databases, data storage disks, or by other convenient data storage means. In certain embodiments, the computer database is an object database, a relational database or a post-relational database. The genotype data is subsequently analyzed for the presence of certain variants known to be susceptibility variants for a particular human conditions, such as the genetic variants described herein. Genotype data can be retrieved from the data storage unit using any convenient data query method. Calculating risk conferred by a particular genotype for the individual can be based on comparing the genotype of the individual to previously determined risk (expressed as a relative risk (RR) or and odds ratio (OR), for example) for the genotype, for example for an heterozygous carrier of an at-risk variant for lung cancer. The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. Using the population average may in certain embodiments be more convenient, since it provides a measure which is easy to interpret for the user, i.e. a measure that gives the risk for the individual, based on his/her genotype, compared with the average in the population. The calculated, risk estimated can be made available to the customer via a website, preferably a secure website.

In certain embodiments, a service provider will include in the provided service all of the steps of isolating genomic DNA from a sample provided by the customer, performing genotyping of the isolated DNA, calculating genetic risk based on the genotype data, and report the risk to the customer. In some other embodiments, the service provider will include in the service the interpretation of genotype data for the individual, i.e., risk estimates for particular genetic variants based on the genotype data for the individual. In some other embodiments, the service provider may include service that includes genotyping service and interpretation of the genotype data, starting from a sample of isolated DNA from the individual (the customer).

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

In addition, in certain other embodiments, the present invention pertains to methods of determining a decreased susceptibility to lung cancer, by detecting particular genetic marker alleles or haplotypes that appear less frequently in individuals diagnosed with lung cancer than in individual not diagnosed with lung cancer or in the general population. Such variants confer a decreased risk of, or protection against, lung cancer. Exemplary variants include the alternate allele of the SNP markers shown herein to be associated with increased risk of lung cancer. In one embodiment, the protective variant for lung cancer is selected from the group consisting of rs1051730 allele C, or marker alleles in linkage disequilibrium therewith. In another embodiment, the protective variant for lung cancer is rs55787222 allele −8 (containing 2 copies of the microsatellite repeat).

As described and exemplified herein, particular marker alleles or haplotypes are associated with risk of lung cancer. In one embodiment, the marker allele or haplotype is one that confers a significant risk or susceptibility to lung cancer. In another embodiment, the invention relates to a method of determining a susceptibility to lung cancer in a human individual, the method comprising determining the presence or absence of at least one allele of at least one polymorphic marker in a nucleic acid sample obtained from the individual, wherein the at least one polymorphic marker is selected from the group consisting of the polymorphic markers listed in Table 4 and Table 6, and markers in linkage disequilibrium (e.g., defined by numerical values for $r^2>0.2$) therewith. In another embodiment, the invention pertains to methods of determining a susceptibility to lung cancer in human individual, by screening for at least one marker allele or haplotype as listed in Table 4, or markers in linkage disequilibrium therewith. In another embodiment, the invention pertains to methods of determining a susceptibility to lung cancer by identifying particular alleles at polymorphic markers associated with at least one of the CHRNA3, CHRNA5 and CHRNB4 genes. In one embodiment, the marker allele is more frequently present in a subject having, or who is susceptible to, lung cancer (affected), as compared to the frequency of its presence in a healthy subject (control, such as population controls). In certain embodiments, the significance of association of the at least one marker allele or haplotype is characterized by a p value <0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to lung cancer. These diagnostic methods involve detecting the presence or absence of at least one marker allele or haplotype that is associated with lung cancer. Haplotypes include combinations of alleles at various genetic markers (e.g., SNPs, microsatellites). The detection of the particular genetic marker alleles that make up the particular haplotypes can be performed by a variety of methods described herein and/or known in the art. For example, genetic markers can be detected at the nucleic acid level (e.g., by direct nucleotide sequencing or by other means known to the skilled in the art) or at the amino acid level if the genetic marker affects the coding sequence of a protein encoded by a nucleic acid associated with lung cancer (e.g., by protein sequencing or by immunoassays using antibodies that recognize such a protein). The marker alleles or haplotypes of the present invention correspond to fragments of a genomic DNA sequence associated with lung 5, cancer. Such fragments encompass the DNA sequence of the polymorphic marker or haplotype in question, but may also include DNA segments in strong LD (linkage disequilibrium) with the marker or haplotype. In one embodiment, such segments comprises segments in LD with the marker or haplotype as determined by a numerical value of $r^2$ greater than 0.2 and/or $|D'|>0.8$).

In one embodiment, determination of a susceptibility to lung cancer can be accomplished using hybridization methods, such as Southern analysis, Northern analysis, and/or in situ hybridizations (see Current Protocols in Molecular Biology, Ausubel, F. et al., eds., John Wiley & Sons, including all supplements). The presence of a specific marker allele can be indicated by sequence-specific hybridization of a nucleic acid probe specific for the particular allele. The presence of more than specific marker allele or a specific haplotype can be indicated by using several sequence-specific nucleic acid probes, each being specific for a particular allele. In one embodiment, a haplotype can be indicated by a single nucleic acid probe that is specific for the specific haplotype (i.e., hybridizes specifically to a DNA strand comprising the specific marker alleles characteristic of the haplotype). A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample.

To determine a susceptibility to lung cancer, a hybridization sample is formed by contacting the test sample containing a nucleic acid associated with lung cancer, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. For example, the nucleic acid probe can comprise all or a portion of the nucleotide sequence of the C15 LD Block (SEQ ID NO:1), as described herein, optionally comprising at least one allele of at least one marker described herein, or the probe can be the complementary sequence of such a sequence. In a particular embodiment, the nucleic acid probe is a portion of the nucleotide sequence of C15 LD Block (SEQ ID NO:1), as described herein, optionally comprising at least one allele of a marker described herein, or at least one allele of one polymorphic marker or haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the present invention, or markers that make up a haplotype of the present invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular allelic combination (i.e., a haplotype) and therefore is susceptible to lung cancer.

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al., (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes, or is capable of hybridizing, to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In another hybridization method, Northern analysis (see Current Protocols in Molecular Biology, Ausubel, F. et al., eds., John Wiley & Sons, supra) is used to identify the presence of a polymorphism associated with lung cancer. For Northern analysis, a test sample of RNA is obtained from the subject by appropriate means. As described herein, specific hybridization of a nucleic acid probe to RNA from the subject is indicative of a particular allele complementary to the probe. For representative examples of use of nucleic acid probes, see, for example, U.S. Pat. Nos. 5,288,611 and 4,851,330.

Alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are associated with lung cancer. Hybridization of the PNA probe is thus diagnostic for lung cancer or a susceptibility to lung cancer.

In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype associated with lung cancer, can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s) that is encoded by a nucleic acid associated with lung cancer. Further, the expression of the variant(s) can be quantified as physically or functionally different.

In another embodiment of the methods of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles or haplotypes associated with lung cancer. Therefore, in one embodiment, determination of the presence or absence of a particular marker alleles or haplotypes comprises sequence analysis of a test sample of DNA or RNA obtained from a subject or individual. PCR or other appropriate methods can be used to amplify a portion of a nucleic acid associated with lung cancer, and the presence of a specific allele can then be detected directly by sequencing the polymorphic site (or multiple polymorphic sites in a haplotype) of the genomic DNA in the sample.

Allele-specific oligonucleotides can also be used to detect the presence of a particular allele. An "allele-specific oligonucleotide" (also referred to herein as an "allele-specific oligonucleotide probe") is an oligonucleotide of approximately 10-50 base pairs or approximately 15-30 base pairs, that specifically hybridizes to a nucleic acid associated with lung cancer, and which contains a specific allele at a polymorphic site (e.g., a marker or haplotype as described herein). An allele-specific oligonucleotide probe that is specific for one or more particular a nucleic acid can be prepared using standard methods (see, e.g., Current Protocols in Molecular Biology, supra). PCR can be used to amplify the desired region. Standard techniques can be used to detect hybridization of the allele-specific oligonucleotide to the nucleic acid sample. Specific hybridization of an allele-specific oligonucleotide probe to DNA from the subject is indicative of a specific allele at a polymorphic site (see, e.g., Gibbs, R. et al., *Nucleic Acids Res.,* 17:2437-2448 (1989) and WO 93/22456).

In another embodiment, arrays of oligonucleotide probes that are complementary to target nucleic acid sequence segments from a subject, can be used to identify particular alleles at polymorphic sites. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light directed synthesis methods that incorporate a combination of photolithographic methods and solid phase oligonucleotide synthesis methods, or by other methods known to the person skilled in the art (see, e.g., Bier, F. F., et al. *Adv Biochem Eng Biotechnol* 109:433-53 (2008); Hoheisel, J. D., *Nat Rev Genet* 7:200-10 (2006); Fan, J. B., et al. *Methods Enzymol* 410:57-73 (2006); Raqoussis, J. & Elvidge, G., *Expert Rev Mol Diagn* 6:145-52 (2006); Mockler, T. C., et al *Genomics* 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. Nos. 6,858,394, 6,429,027, 5,445,934 , 5,700,637, 5,744,305, 5,945,334, 6,054,270, 6,300,063, 6,733,977, 7,364,858, EP 619 321, and EP 373 203, the entire teachings of which are incorporated by reference herein.

Other methods of nucleic acid analysis that are available to those skilled in the art can be used to detect a particular allele at a polymorphic site associated with lung cancer. Representative methods include, for example, direct manual sequencing (Church and Gilbert, *Proc. Natl. Acad. Sci. USA,* 81: 1991-1995 (1988); Sanger, F., et al., *Proc. Natl. Acad. Sci.*

*USA,* 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA,* 86:232-236 (1989)), mobility shift analysis (Orita, M., et al., *Proc. Natl. Acad. Sci. USA,* 86:2766-2770 (1989)), restriction enzyme analysis (Flavell, R., et al., *Cell,* 15:25-41 (1978); Geever, R., et al., *Proc. Natl. Acad. Sci. USA,* 78:5081-5085 (1981)); heteroduplex analysis; chemical mismatch cleavage (CMC) (Cotton, R., et al., *Proc. Natl. Acad. Sci. USA,* 85:4397-4401 (1985)); RNase protection assays (Myers, R., et al., *Science,* 230:1242-1246 (1985); use of polypeptides that recognize, nucleotide mismatches, such as *E. coli* mutS protein; and allele-specific PCR.

In another embodiment of the invention, diagnosis of lung cancer or determination of a susceptibility to lung cancer, can be made by examining expression and/or composition of a polypeptide encoded by a nucleic acid associated with lung cancer, in those instances where the genetic marker(s) or haplotype(s) of the present invention result in a change in the composition or expression of the polypeptide. Thus, diagnosis of a susceptibility to lung cancer can be made by examining expression and/or composition of one of these polypeptides, or another polypeptide encoded by a nucleic acid associated with lung cancer, in those instances where the genetic marker or haplotype of the present invention results in a change in the composition or expression of the polypeptide. The haplotypes and markers of the present invention that show association to lung cancer may play a role through their effect on one or more of these nearby genes. In one embodiment, the gene is selected from the group consisting of CHRNA3, CHRNA5 and CHRNB4. Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) of the invention showing association to lung cancer affect the expression of a nearby gene, such as one or more of the CHRNA3, CHRNA5 and CHRNB4 genes. It is well known that regulatory element affecting gene expression may be located far away, even as far as tenths or hundreds of kilobases away, from the promoter region of a gene. By assaying for the presence or absence of at least one allele of at least one polymorphic marker of the present invention, it is thus possible to assess the expression level of such nearby genes. It is thus contemplated that the detection of the markers or haplotypes of the present invention can be used for assessing expression for one or more of these genes.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a nucleic acid associated with lung cancer. An alteration in expression of a polypeptide encoded by a nucleic acid associated with lung cancer can be, for example, an alteration in the quantitative polypeptide expression (i.e., the amount of polypeptide produced). An alteration in the composition of a polypeptide encoded by a nucleic acid associated with lung cancer is an alteration in the qualitative polypeptide expression (e.g., expression of a mutant polypeptide or of a different splicing variant). In one embodiment, diagnosis of a susceptibility to lung cancer is made by detecting a particular splicing variant encoded by a nucleic acid associated with lung cancer, or a particular pattern of splicing variants.

Quantitative or qualitative alterations can be present in the polypeptide. An "alteration" in the polypeptide expression or composition, as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, lung cancer. In one embodiment, the control sample is from a subject that does not possess a variant shown herein to be associated with lung cancer. Similarly, the presence of one or more different splicing variants in the test sample, or the presence of significantly different amounts of different splicing variants in the test sample, as compared with the control sample, can be indicative of a susceptibility to lung cancer. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with lung cancer can be used. Antibodies can be polyclonal or monoclonal. An intact antibody, or a fragment thereof (e.g., Fv, Fab, Fab', $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of polypeptide encoded by a nucleic acid associated with lung cancer in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, the diagnosis of a susceptibility to lung cancer is made by detecting at least one marker or haplotypes of the present invention (e.g., associated alleles of the markers listed in Table 4, and markers in linkage disequilibrium therewith), in combination with an additional protein-based, RNA-based or DNA-based assay. The methods of the invention can also be used in combination with an analysis of a subject's family history and risk factors (e.g., environmental risk factors, lifestyle risk factors).

Kits

Kits useful in the methods of the invention comprise components useful in any of the methods described herein, including for example, primers for nucleic acid amplification, hybridization probes, restriction enzymes (e.g., for RFLP analysis), allele-specific oligonucleotides, antibodies that bind to an altered polypeptide encoded by a nucleic acid of the invention as described herein (e.g., a genomic segment comprising at least one polymorphic marker and/or haplotype of the present invention) or to a non-altered (native) polypeptide encoded by a nucleic acid of the invention as described herein, means for amplification of a nucleic acid associated with lung cancer, means for analyzing the nucleic acid sequence of a nucleic acid associated with lung cancer, means for analyzing the amino acid sequence of a polypeptide encoded by a nucleic acid associated with lung cancer, etc. The kits can for example include necessary buffers, nucleic acid primers for amplifying nucleic acids of the invention (e.g., a nucleic acid segment comprising one or more of the polymorphic markers as described herein), and reagents for allele-specific detection of the fragments amplified using such primers and necessary enzymes (e.g., DNA polymerase). Additionally, kits can provide reagents for assays to be used in combination with the methods of the present invention, e.g., reagents for use with other diagnostic assays for lung cancer.

In one embodiment, the invention is a kit for assaying a sample from a subject to detect the presence of a susceptibility to lung cancer in a subject, wherein the kit comprises reagents necessary for selectively detecting at least one allele of at least one polymorphism of the present invention in the genome of the individual (e.g., the markers set forth in Table 4, and markers in linkage disequilibrium therewith). In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism, wherein the polymorphism is selected from the group consisting of the polymorphisms as listed in Table 4, and polymorphic markers in linkage disequilibrium therewith. In yet another embodiment the fragment is at least 20 base pairs in size. Such oligonucleotides or nucleic acids (e.g., oligonucleotide primers) can be designed using portions of the nucleic acid sequence flanking polymorphisms (e.g., SNPs or microsatellites) that are indicative of lung cancer. In another embodiment, the kit comprises one or more labeled nucleic acids capable of allele-specific detection of one or more specific polymorphic markers or haplotypes associated with lung cancer, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers set forth in Table 4 and Table 6. In some embodiments, the marker or haplotype to be detected comprises at least one marker from the group of markers in strong linkage disequilibrium, as defined by values of $r^2$ greater than 0.2, to at least one of the group of markers listed in Table 4 and Table 6. In another embodiment, the marker or haplotype to be detected comprises at least one marker from markers in linkage disequilibrium to at least one of the markers listed in Table 4. In another embodiment, the marker to be detected is rs1051730.

In one preferred embodiment, the kit for detecting the markers of the invention comprises a detection oligonucleotide probe, that hybridizes to a segment of template DNA containing a SNP polymorphisms to be detected, an enhancer oligonucleotide probe and an endonuclease. As explained in the above, the detection oligonucleotide probe comprises a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In one of such embodiments, the presence of the marker (e.g., a particular marker allele) or haplotype is indicative of a susceptibility (increased susceptibility or decreased susceptibility) to lung cancer. In another embodiment, the presence of the marker or haplotype is indicative of response to a therapeutic agent for lung cancer. In another embodiment, the presence of the marker or haplotype is indicative of prognosis of lung cancer. In yet another embodiment, the presence of the marker or haplotype is indicative of progress of treatment of lung cancer. Such treatment may include intervention by surgery, medication or by other means (e.g., lifestyle changes).

In certain embodiments, the kit further comprises a set of instructions for using the reagents comprising the kit. In certain embodiments, the kit further comprises a collection of data comprising correlation data between the polymorphic markers assessed by the kit and susceptibility to lung cancer.

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or rnai molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

Treatment

Treatment for lung cancer can involve surgical removal of tumor, chemotherapy, or radiation therapy, as well as combinations of these methods. The decision about which treatments will be appropriate for a given individual take into account the histological type (small cell lung carcinoma (SCLC) or non-small cell lung carcinoma (NSCLC), localization and extent of the tumor as well as the overall health status of the patient.

Surgical removal of the tumor is generally performed for early-stage (stage I or sometimes stage II) NSCLC and is the treatment of choice for cancer that has not spread beyond the lung. About 10%-35% of lung cancers can be removed surgically, but removal does not always result in a cure since the tumors may already have spread and can recur at a later time. Among people who have an isolated, slow-growing lung cancer removed, 25%-40% are alive five years after diagnosis. Surgery is less often performed with SCLC because these tumors are more likely to have spread at the time of diagnosis.

Radiation therapy may be employed as a treatment for both NSCLC and SCLC. Radiation therapy may be given as curative therapy, palliative therapy (using lower doses of radiation than with curative regimens) or as adjuvant therapy to surgery or chemotherapy. Brachytherapy is a term used to describe the use of a small pellet of radioactive material placed directly into the cancer or into the airway next to the cancer. Radiation therapy generally only shrinks a tumor or limits its growth when given as a sole therapy, yet in 10%-15% of people it leads to long-term remission and palliation of the cancer. Combining radiation therapy with chemotherapy can further increase the chances of survival.

Both NSCLC and SCLC may be treated with chemotherapy. Chemotherapy may be given alone, as an adjuvant to surgical therapy, or in combination with radiotherapy. While a number of chemotherapeutic drugs have been developed, the platinum-based drugs have been the most effective in treatment of lung cancers.

Chemotherapy is the treatment of choice for most SCLC, since these tumors are generally widespread in the body when they are diagnosed. Only half of people who have SCLC survive for four months without chemotherapy. With chemotherapy, their survival time is increased up to four- to fivefold. Chemotherapy alone is not particularly effective in treating NSCLC, but when NSCLC have metastasized, it can prolong survival in many cases.

In recent years, new drugs have been developed that target specifically defined genetic changes in the tumor, also called targeted therapy. The most notable of these drugs are compounds that target the epidermal growth factor receptor (gefitinib (Iressa), erlotinib (Tarceva)) which is amplified in a subset of lung cancer tumors. Inhibitors of angiogenesis such as antibodies that inhibit the vascular endotheliar growth factor (notably Bevacizumab) have also been shown to prolong survival in advanced lung cancer when added to the standard chemotherapy regimen. Bevacizumab may be administered in combination with paclitaxel and/or carboplatin.

A number of agents are in early stages of clinical research, including cyclo-oxygenase 2 inhibitors, proteasome inhibitors, bexaroteine and the apopotosis promoter exisulind. Current developmental strategies include proto-oncogene inhibition, phosphoinositide 3-kinase inhibition, histone deacylase inhibition, and tumor suppressor gene replacement. The methods of the invention are also applicable in the context of treatment by any of such therapeutic agents.

However, despite these recent advances in lung cancer treatment, the prognosis of the great majority of cases remains poor and there is a great need for development of more effective drugs.

Direct Effect of Nicotine on Lung Tissue Through the nAChRs

Although traditionally not considered to be carcinogenic in itself, accumulating evidence suggests that nicotine contributes directly to lung carcinogenesis through stimulation of nAChRs in non-neuronal cells. nACh receptors are expressed in normal lung epithelial cells and respond to stimulation by nicotine by increased cellular proliferation and attenuation of apoptosis (Conti-Fine et al. 2000 Eur J Pharmacol 393(1-3):279-94, West et al. 2003 J Clin Invest 111(1):81-90). Furthermore, stimulation with nicotine or the nicotine-derived nitrosamine NNK induces a partially transformed phenotype in these cells, suggesting that nicotine may have a role as a tumor promoter in the lung (Ho et al. 2005 Toxicol and Appl Pharmaco 205(2):133-48). nAChRs are present on lung cancer cells of various histological types and stimulation with nicotine can promote tumor cell proliferation, tumor cell migration, invasion and reduce apoptosis of cells under hypoxia (Tsurutani et al. 2005 Carcinogenesis 26(7):1182-95, Xu and Deng 2006 J Biol Chem 281(7):4457-66, West et al. 2003 J Clin Invest 111(1):81-90, Heeschen et al. 2007 Nat Med 7(7):833-9, Maneckjee and Minna 1990 Proc Natl Acad Sci USA 87(9):3294-8, Maneckjee and Minna 2004 Cell Growth Differ 5(10):1033-40). Furthermore, nicotine stimulation has been shown to induce tumor angiogenesis both through a cholinergic pathway, independently from the angiogenic pathways mediated by growth factor receptors, and by promoting VEGF expression through nAChRs (Heeschen et al. 2001 Nat Med 7(7):833-9, Cooke 2007 Life Sci 80(24-25):2347-51, Zhang et al. 2007 Clin Cancer Res 13(16):4686-94). In particular, nAChRs containing the α-3, α-5 and α-4 subunits are expressed on SCLC cells where they serve as receptors for autocrine growth (Song et al. 2003 Cancer Res 63(1):214-21).

In light of the evidence above, it is conceivable that sequence polymorphisms in the CHRNA3/CHRNA5/CHRNB4 gene cluster might directly modulate the vulnerability to lung cancer through direct effect of nicotine on the lung tissue. If this is true, it is also possible that agents that modulate the activity of the nAChR in the lung may have a chemopreventive or even therapeutic potential.

Variants of the present invention (e.g., the markers and/or haplotypes of the invention, e.g., the markers listed in Table 4, e.g., the markers listed in Table 6, e.g., marker rs1051730 and/or marker rs16969968) can be used to identify novel therapeutic targets for lung cancer. For example, genes containing, or in linkage disequilibrium with, variants (markers and/or haplotypes) associated with lung cancer (e.g., the CHRNA3/CHRNA5/CHRNB4 genes), or their products, as well as genes or their products that are directly or indirectly regulated by or interact with these variant genes or their products, can be targeted for the development of therapeutic agents to treat lung cancer, or prevent or delay onset of symptoms associated with lung cancer. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants of the invention, or nucleic acids comprising their complementary sequence, may be used as antisense constructs to control gene expression in cells, tissues or organs. The methodology associated with antisense techniques is well known to the skilled artisan, and is described and reviewed in *AntisenseDrug Technology: Principles, Strategies, and Applications*, Crooke, ed., Marcel Dekker Inc., New York (2001). In general, antisense nucleic acid molecules are designed to be complementary to a region of mRNA expressed by a gene, so that the antisense molecule hybridizes to the mRNA, thus blocking translation of the mRNA into protein. By binding the appropriate target sequence, an RNA-RNA, DNA-DNA or RNA-DNA duplex is formed. The antisense oligonucleotides are complementary to the sense or coding strand of a gene. It is also possible to form a triple helix, where the antisense oligonucleotide binds to duplex DNA.

Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today,* 7:912-917 (2002)). Antisense oligonucleotides are useful directly as therapeutic agents, and are also useful for determining and validating gene function, for example by gene knock-out or gene knock-down experiments. Antisense technology is further described in Layery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002).

In certain embodiments, the antisense agent is an oligonucleotide that is capable of binding to a nucleotide segment of a gene selected from the group consisting of CHRNA3, CHRNA5 and CHRNB4. Antisense nucleotides can be from 5-500 nucleotides in length, including 5-200 nucleotides, 5-100 nucleotides, 10-50 nucleotides, and 10-30 nucleotides. In certain preferred embodiments, the antisense nucleotides is from 14-50 nucleotides in length, including 14-40 nucleotides and 14-30 nucleotides. In certain embodiments, the antisense nucleotide is capable of binding to a nucleotide segment of a gene within the genomic segment with sequence as set forth in SEQ ID NO:1.

The variants described herein can be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus protein expression, the molecules can be used to treat a disease or disorder, such as lung cancer. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today,* 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (*FEBS Lett.* 579:5974-81 (2005)). Chemically synthetic siRNAs and shRNAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., Science 296: 550-553 (2002)).

Since RNAi molecules, including siRNA, miRNA and shRNA, act in a sequence-dependent manner, the variants of the present invention (e.g., the markers set forth in Table 4) can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100:6343-6346 (2003), Vickers et al., *J. Biol. Chem.* 278:7108-7118 (2003), Agami, *Curr. Opin. Chem. Biol.* 6:829-834 (2002), Layery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of a disease, including lung cancer, or a defect causing the disease, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethyleneimine, encapsulated in anionic liposomes, a viral vector such as an adenovirus vector, or other pharmaceutical compositions suitable for promoting intracellular uptake of the administered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat lung cancer. Thus, the variants of the invention are useful as targets for the identification and/or development of therapeutic agents. Such methods may include assaying the ability of an agent or compound to modulate the activity and/or expression of a nucleic acid that includes at least one of the variants (markers and/or haplotypes) of the present invention, or the encoded product of the nucleic acid. This in turn can be used to identify agents or compounds that inhibit or alter the undesired activity or expression of the encoded nucleic acid product, e.g. a product of one or more of the CHRNA3, CHRNA5 and CHRNB4 genes. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating lung cancer can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents, Methods of Monitoring Progress of Treatment and Methods of Treatment As is known in the art, individuals can have differential responses to a particular therapy (e.g., a therapeutic agent or therapeutic method). Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent.

Accordingly, in one embodiment, the presence of a particular allele at a polymorphic site or haplotype is indicative of a different, e.g. a different response rate, to a particular treatment modality. This means that a patient diagnosed with lung cancer, and carrying a certain allele at a polymorphic or haplotype of the present invention (e.g., the at-risk and protective alleles and/or haplotypes of the invention) would respond better to, or worse to, a specific therapeutic, drug and/or other therapy used to treat lung cancer. Therefore, the presence or absence of the marker allele or haplotype could aid in deciding what treatment should be used for the patient. For example, for a newly diagnosed patient, the presence of a marker or haplotype of the present invention may be assessed (e.g., through testing DNA derived from a blood sample, as described herein). If the patient is positive for a marker allele or haplotype at (that is, at least one specific allele of the marker, or haplotype, is present), then the physician recommends one particular therapy, while if the patient is negative for the at least one allele of a marker, or a haplotype, then a different course of therapy may be recommended. Thus, the patient's carrier status could be used to help determine whether a particular treatment modality should be administered. The value lies within the possibilities of being able to diagnose lung cancer, or a susceptibility to lung cancer, at an early stage, to select the most appropriate treatment and/or preventive measure, and provide information to the clinician about prognosis/aggressiveness of the disease in order to be able to apply the most appropriate treatment.

The treatment for lung cancer can in certain embodiments be selected from surgical treatment (surgical removal of tumor), radiation therapy and chemotherapy. It is contemplated that the markers described herein to be associated with lung cancer can be used to predict the efficacy of any of these particular treatment modules. In certain embodiments, the markers of the inventions, as described herein may be used to determine an appropriate combination of therapy, which can include any one, two or three of these treatment modules. In certain embodiments, the radiation therapy is brachytherapy. The agent useful for chemotherapy may be any chemical agent commonly used, or in development, as a chemotherapy agent, including, but not limited to, cisplatin, carboplatin, gemcitabine (4-amino-1-[3,3-difluoro-4-hydroxy-5-(hydroxymethyl) a tetrahydrofuran-2-yl]-1H-pyrimidin-2-one), paclitaxel ((2a,4a,5β,7β,10β,13a)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate), docetaxel ((2R,3S)—N-carboxy-3-phenylisoserine, N-tert-butyl ester, 13-ester with 5,20-epoxy-1,2,4,7,10,13-hexahydroxytax-11-en-9-one 4-acetate 2-benzoate), etoposide (4'-demethyl-epipodophyllotoxin 9-[4,6-O—(R)-ethylidene-beta-D-glucopyranoside], 4'-(dihydrogen phosphate)), vinorelbine (4-(acetyloxy)-6,7-didehydro-15-((2R,6R,8S)-4-ethyl-1,3,6,7,8,9-hexahydro-8-(methoxycarbonyl)-2,6-methano-2H-azecino(4,3-b)indol-8-yl)-3-hydroxy-16-methoxy-1methyl,methylester, (2beta,3beta,4beta, 5alpha,12R,19alpha)-aspidospermidine-3-carboxylic acid), and etoposide (4'-demethyl-epipodophyllotoxin 9-[4,6-O—(R)-ethylidene-beta-D-glucopyranoside] 4'-(dihydrogen phosphate)). Chemotherapy agents may be used alone or in combination. In one embodiment, the agent targets an epidermal growth factor receptor. In certain such embodiments, the agent is gefitinib (Iressa; N-(3-chloro-4-fluoro-phenyl)-7-methoxy-6-(3-morpholin-4-ylpropoxy)quinazolin-4-amine) or erlotinib (Tarceva; N-(3-ethynylphenyl)-6,7-bis(2-methoxyethoxy)quinazolin-4-amine). In certain other embodiments, the agent is angiogenesis inhibitor. Such inhibitors can for example be antibodies that inhibit the vascular endotheliar growth factor, such as Bevacizumab (Avastin).

The present invention also relates to methods of monitoring progress or effectiveness of a treatment for a lung cancer, as described in the above. This can be done based on the genotype and/or haplotype status of the markers and haplotypes of the present invention, i.e., by assessing the absence or presence of at least one allele of at least one polymorphic marker as disclosed herein, or by monitoring expression of genes that are associated with the variants (markers and haplotypes) of the present invention. The risk gene mRNA or the encoded polypeptide can be measured in a tissue sample (e.g., a peripheral blood sample, or a biopsy sample). Expression levels and/or mRNA levels can thus be determined before and during treatment to monitor its effectiveness. Alternatively, or concomitantly, the genotype and/or haplotype status of at least one risk variant for lung cancer as presented herein is determined before and during treatment to monitor its effectiveness.

Alternatively, biological networks or metabolic pathways related to the markers and haplotypes of the present invention can be monitored by determining mRNA and/or polypeptide levels. This can be done for example, by monitoring expression levels or polypeptides for several genes belonging to the network and/or pathway (e.g., the nicotinic acetylcholine receptor family), in samples taken before and during treatment. Alternatively, metabolites belonging to the biological network or metabolic pathway (e.g., nicotine metabolites) can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of at least one at-risk variant of the present invention, i.e. individuals who are carriers of at least one allele of at least one polymorphic marker conferring increased risk of developing lung cancer may be more likely to respond to a particular treatment modality. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product. This application can improve the safety of clinical trials, but can also enhance the chance that a clinical trial will demonstrate statistically significant efficacy, which may be limited to a certain sub-group of the population. Thus, one possible outcome of such a trial is that carriers of certain genetic variants, e.g., the markers and haplotypes of the present invention, are statistically significantly likely to show positive response to the therapeutic agent, i.e. experience alleviation of symptoms associated with lung cancer when taking the therapeutic agent or drug as prescribed.

In a further aspect, the markers and haplotypes of the present invention can be used for targeting the selection of pharmaceutical agents for specific individuals. Personalized selection of treatment modalities, lifestyle changes or combination of the two, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

FIG. 1 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method or apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method and system may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to FIG. 1, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Although the forgoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

While the risk evaluation system and method, and other elements, have been described as preferably being implemented in software, they may be implemented in hardware, firmware, etc., and may be implemented by any other processor. Thus, the elements described herein may be implemented in a standard multi-purpose CPU or on specifically designed hardware or firmware such as an application-specific integrated circuit (ASIC) or other hard-wired device as desired, including, but not limited to, the computer 110 of FIG. 1. When implemented in software, the software routine may be stored in any computer readable memory such as on a magnetic disk, a laser disk, or other storage medium, in a RAM or ROM of a computer or processor, in any database, etc. Likewise, this software may be delivered to a user or a diagnostic system via any known or desired delivery method including, for example, on a computer readable disk or other transportable computer storage mechanism or over a communication channel such as a telephone line, the internet, wireless communication, etc. (which are viewed as being the same as or interchangeable with providing such software via a transportable storage medium).

Thus, many modifications and variations may be made in the techniques and structures described and illustrated herein without departing from the spirit and scope of the present invention. Thus, it should be understood that the methods and apparatus described herein are illustrative only and are not limiting upon the scope of the invention.

Accordingly, the invention relates to computer-implemented applications using the polymorphic markers and haplotypes described herein, and genotype and/or disease-association data derived therefrom. Such applications can be useful for storing, manipulating or otherwise analyzing genotype data that is useful in the methods of the invention. One example pertains to storing genotype and/or sequence information derived from an individual on readable media, so as to be able to provide the genotype information to a third party (e.g., the individual, a guardian of the individual, a health care provider or genetic analysis service provider), or for deriving information from the genotype data, e.g., by comparing the genotype data to information about genetic risk factors contributing to increased susceptibility to lung cancer, and reporting results based on such comparison.

Nucleic Acids and Polypeptides

The nucleic acids and polypeptides described herein can be used in methods and kits of the present invention. An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a marker or haplotype described herein). Such nucleic acid molecules can be detected and/or isolated by allele- or sequence-specific hybridization (e.g., under high stringency conditions). Stringency conditions and methods for nucleic acid hybridizations are well known to the skilled person (see, e.g., *Current Protocols in Molecular Biology*, Ausubel, F. et al, John Wiley & Sons, (1998), and Kraus, M. and Aaronson, S., *Methods Enzymol.,* 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA,* 85:2444-48 (1988). In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, the nucleotide sequence of C15 LD Block (SEQ ID NO:1), or a nucleotide sequence comprising, or consisting of, the complement of the nucleotide sequence of C15 LD Block (SEQ ID NO:1), wherein the nucleotide sequence comprises at least one polymorphic allele contained in the markers and haplotypes described herein. The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule. In one embodiment, the probe or primer comprises at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labelled (e.g., radiolabelled) and used as a probe for screening a cDNA library derived from human cells. The cDNA can be derived from mRNA and contained in a suitable vector. Corresponding clones can be isolated, DNA can obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

In general, the isolated nucleic acid sequences of the invention can be used as molecular weight markers on Southern gels, and as chromosome markers that are labeled to map related gene positions. The nucleic acid sequences can also be used to compare with endogenous DNA sequences in patients to identify a susceptibility to lung cancer, and as probes, such as to hybridize and discover related DNA sequences or to subtract out known sequences from a sample (e.g., subtractive hybridization). The nucleic acid sequences can further be used to derive primers for genetic fingerprinting, to raise anti-polypeptide antibodies using immunization techniques, and/or as an antigen to raise anti-DNA antibodies or elicit immune responses.

Antibodies

Polyclonal antibodies and/or monoclonal antibodies that specifically bind one form of the gene product but not to the other form of the gene product are also provided. Antibodies are also provided which bind a portion of either the variant or the reference gene product that contains the polymorphic site or sites. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, Yale *J. Biol. Med.* 54:387-402

(1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies may also be useful in pharmacogenomic analysis. In such embodiments, antibodies against variant proteins encoded by nucleic acids according to the invention, such as variant proteins that are encoded by nucleic acids that contain at least one polymorphic marker of the invention, can be used to identify individuals that require modified treatment modalities.

Antibodies can furthermore be useful for assessing expression of variant proteins in disease states, such as in active stages of a disease, or in an individual with a predisposition to a disease related to the function of the protein, in particular lung cancer. Antibodies specific for a variant protein of the present invention that is encoded by a nucleic acid that comprises at least one polymorphic marker or haplotype as described herein can be used to screen for the presence of the variant protein, for example to screen for a predisposition to lung cancer as indicated by the presence of the variant protein.

Antibodies can be used in other methods. Thus, antibodies are useful as diagnostic tools for evaluating proteins, such as variant proteins of the invention (e.g., CHRNA3, CHRNA5 and/or CHRNB4 proteins), in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting examples.

EXEMPLIFICATION

Example 1

The following contains description of the identification of susceptibility factors found to be associated with lung cancer (LC) through single-point analysis of SNP markers.

Methods

Subjects

For all studies involving Icelandic subjects, the study protocols were approved by the National Bioethics Committee (NBC) and the Data Protection Authority (DPA) of Iceland. The DPA encrypted all personal identifiers associated with information or blood samples using the third-party encryption system (Gulcher, J. R., et al., *Eur J Hum Genet* 8:739-42 (2000)). Overall the Icelandic study involves 10,995 subjects with information on SQ available in the GWA, an additional 2,950 subjects with information on SQ, and 4,203 never-smokers. In the LC study, 665 patients and 28,752 population controls were used (see Table 2 for details).

Smoking. All Icelandic subjects in the study of smoking-related phenotypes, including Icelandic population controls, were originally recruited for different genetic studies conducted over eleven years (1996-2007) at deCODE genetics and information on the number of cigarettes smoked per day (cpd) was available from various questionnaires. The cpd information was categorised into SQ level and used as a quantitative variable. Detailed information on SQ was also available for the foreign LC populations.

Nicotine Dependence. For a subset of the Icelandic smokers, information on the criteria used to diagnose ND was available from ongoing studies of ND and Anxiety/Depression (Thorgeirsson, T. E., et al., *Am J Hum Genet* 72:1221-30 (2003)). We excluded individuals with diagnoses of other substance dependence or abuse giving a total of 2,394 ND subjects. A score of 4 or higher on the FTND (Heatherton, T. F. et al., *Br J Addict* 86:1119-27 (1991)), or endorsement of at least three of the DSM criteria were used to assign affected status for ND.

Additional information on the Icelandic smoking and ND study group is available in the Supplementary Information.

Lung Cancer. Case control groups from three European populations were used in the studies on LC (Iceland, Spain and the Netherlands). Iceland: Recruitment was initiated in the year 1998 using a nationwide list from the Icelandic Cancer Registry (ICR). Approximately 1,265 LC patients were alive during the period of recruitment and of those 665 participated in the project. Information in the ICR includes year and age at diagnosis, year of death, SNOMED code and ICD-10 classification. Histological and cytological verification was available for 647 cases; the remaining 18 cases were diagnosed clinically. The Netherlands: The patients and controls were identified retrospectively through three different ongoing studies on genetic risk factors of disease. All three study protocols were approved by the Institutional Review Board of the Radboud University Nijmegen Medical Centre (RUNMC). A total of 90 patients and 2,018 controls are included in this study. Spain: The patients were recruited from the Oncology Department of Zaragoza Hospital in Zaragoza, from June 2006 to June 2007. During the 12 month interval of recruitment, 330 patients were invited to participate, and 292 enrolled (88% participation rate). Clinical information including age at onset and histology were collected from medical records. The 1,474 control individuals were approached at the University Hospital in Zaragoza. Study protocols were approved by the Institutional Review Board of Zaragoza University Hospital. All subjects gave written informed consent.

Genotyping

All 10,995 samples in the GWA study of SQ were genotyped using genotyping systems and specialised software from Illumina (Human Hap300 and Human Hap300-duo+ Bead Arrays, Illumina) (Barrett, J. C. & Cardon, L. R., *Nat Genet* 38:659-62 (2006). Marker rs1051730 was genotyped using a Centaurus assay (Nanogen) for 8,566 Icelandic samples and all samples in the foreign study groups.

Statistical Analysis

Adjustment for Relatedness in the Icelandic Studies

Evaluation of statistical significance took the relatedness of the Icelandic individuals into account by dividing the test-statistic with a correction factor. For the GWA this was done by the method of genomic control (Devlin, B., et al, *Nat Genet* 36:1129-30 (2004) using all 306,207 SNPs passing quality control. In all other comparisons genotype information for the total number of tested individuals was only available for SNP rs1051730, and the correction factor for the $\chi 2$ test-statistic was determined applying a simulation procedure using the known genealogy which we had previously employed (Grant, S. F., et al., *Nat Genet* 38:320-23 (2006)). We simulated 100,000 sets of genotypes for the SNP through the Icelandic genealogy of 739,000 individuals. The simulated genotypes were used in the applied tests resulting in 100,000 tests under the null hypothesis and the mean of the respective $\chi 2$ test-statistics gives the correction factor.

Regression Analysis

The year of birth had been rounded to the nearest 5. When year of birth adjustment was applied to study the effect of the variant, year of birth was treated as a categorical variable with four levels: ≤1930, 1935 to 1945, 1950 to 1960, and ≥1965. This divided the 13,945 smokers studied in groups of 3774, 3416, 4027 and 2728, which was the closest we could get to having four groups of equal size. The same categories were applied when analysing the data from Spain and the Netherlands.

Genotypic Odds Ratios

In general, the odds ratios for rs1051730 were calculated assuming a multiplicative model, i.e. the risks of the two alleles a person carries are expected to multiply. For example, if OR is the risk of T relative to C, then the risk of a homozygote TT individual will be OR times that of a heterozygote CT, and $OR^2$ times that of a homozygote CC. Additionally, genotypic ORs were calculated under the assumption of Hardy-Weinberg equilibrium in the controls (no control population showed a deviation from Hardy-Weinberg equilibrium).

Results

We performed a genome-wide association (GWA) study of smoking quantity (SQ), utilizing questionnaire data limited to basic questions on smoking behaviour that were available for a large number of lifetime smokers. The GWA scan comprises 10,995 Icelandic smokers who had been assayed with Infinium HumanHap300 SNP chips (Illumina). A set of 306,207 single nucleotide polymorphisms (SNPs), fulfilling our quality criteria, was tested. We focussed on cigarette smoking, with SQ reported as cigarettes per day (cpd). All SQ data were clustered into categories and we refer to them as "SQ levels", the SQ levels are: 0 (1-10 cpd), 1 (11-20 cpd), 2 (21-30 cpd), and 3 (31+ cpd). Each increment represents an increase in SQ of 10 cpd. Allele T of rs1051730 was most strongly associated with SQ, and the association was highly significant ($P=5\times10^{-16}$). The SNP is within the CHRNA3 gene in a linkage disequilibrium block (C15 LD block, SEQ ID NO:1) also containing two other nicotinic acetylcholine receptor (nAChR) genes, CHRNA5 and CHRNB4. Six other SNPs on chromosome 15q24 passed the threshold of genome-wide significance ($P<2\times10^{-7}$), but they are all correlated with rs1051730 ($r^2$=0.14-0.93). An additional 2,950 smokers from Iceland were genotyped for rs1051730 giving a total of 13,945 smokers (Table 1) with mean variant frequency of 34.7%, which is not significantly different from the frequency of 34.4% observed in 4,203 individuals who were genotyped and reported never having smoked (OR=1.01, 95% CI: 0.96-1.07, P=0.60). Indeed, the frequency of the variant in the 3,627 low quantity smokers (≤10 cpd), is significantly less than the frequency in those who do not smoke (OR=0.83, 95% CI: 0.78-0.90, $P=4.5\times10^{-7}$). The increase in frequency between levels varies, and the largest increase (4.5%) is observed between the lowest levels (0 and 1), whereas the increase between the highest levels (2 and 3) is just 1.1%.

Association of the same variant with ND was previously reported in a candidate gene study involving 3,713 SNPs (Saccone, S. F., et al., *Hum Mol Genet* 16:36-49 (2007)). We assessed the association with ND, defined as a score of 4 or higher on the FTND or endorsement of at least 3 of the 7 DSM-IV criteria. The variant is associated with ND in Iceland in a subset of 2,394 smokers from the SQ study tested both against 28,455 population controls (OR=1.17, 95% CI: 1.10-1.25, $P=3.3\times10^{-6}$), and 3,506 low-quantity smokers (OR=1.40, 95% CI: 1.29-1.52, $P=7\times10^{-15}$). Both the FIND and the DSM-IV scales include many items that are not based on SQ and their total scores are measures of ND severity. In our ND group, positive scores on most items in both scales show a trend toward higher frequency of the variant, as does the total score on both the FIND and DSM-IV scales. Thus the frequency of the variant increases with addiction severity, and is 46.8% and 43.8% for the highest decile of FIND, and DSM-IV, respectively.

We studied the effect of the variant on lung cancer risk. The study was based on 1,024 cases and 32,244 controls from Iceland, Spain and the Netherlands. The results (Table 2) represent the overall effect on LC including indirect effects through SQ and ND. Significant association was observed with LC for both the Icelandic data (OR=1.27, $P=4.1\times10^{-5}$) and for Spain and the Netherlands combined (OR=1.39, $P=6.6\times10^{-5}$). These two estimates are not significantly different from each other (P=0.34), and combining results from all three groups gave an OR of 1.31 (95% CI: 1.19-1.44, $P=1.5\times10^{-8}$). There was no significant difference in frequency of the variant between histological types of LC, which is not surprising given the small number of cases per group.

Genotypic ORs for LC and ND did not deviate significantly from those obtained for the multiplicative model, and no significant differences in the ORs between sexes were observed.

According to our estimates for Icelandic LC patients, the correlation between SQ and LC is consistent with numbers reported in other studies (Haimian, C. A., et al., *N Engl J Med* 354:333-42 (2006); Stellman, S. D, et al., *Ann Epidemiol* 13:294-302 (2003)). Combining these estimates with our estimate of the association of the variant with SQ, the expected OR between the variant and lung cancer is only about 1.05 in Iceland, which is well below the direct OR estimate for LC of 1.27 (95% CI: 1.13-1.43). These results were obtained as follows:

In the 13,945 Icelandic smokers studied, 501 are known lung cancer cases. Using logistic regression adjusted for sex and year of birth, compared to SQ level 0, levels 1 to 3 are estimated to have relative risks of 2.1, 2.4 and 2.9 for lung cancer, respectively. Notably, the biggest jump in relative risks occurred between level 0 and level 1. Assuming these relative risk estimates and applying them to the distribution of smokers in various SQ levels as displayed in Table 1, frequency of the variant in lung cancer patients can be calculated as a weighted average. Specifically, the predicted frequency is $$[(0.305\times0.260)+(0.350\times0.459\times2.1)+(0.380\times0.214\times2.4)+(0.391\times0.067\times2.9)]$$

divided by $$[0.260+(0.459\times21)+(0.214\times2.4)+(0.067\times2.9)],$$

or 35.6%. Note that this calculation assumes only smokers would have lung cancer (non-smokers are given weight zero) and hence could over-estimate the frequency of the variant. Still, compared to the frequency of the variant in population controls (34.4%), the OR is only around 1.05. Note that since the frequency of the variant in SQ level 1 is only 35%, to increase the predicted frequency requires increasing the weights of SQ levels 2 and 3. However, even if we doubled the relative risks for SQ levels 2 and 3, from 2.4 and 2.9 to 4.8 and 5.8 respectively, the frequency and OR predicted for lung cancer patients would only increase respectively to 36.3% and 1.09

These results mean that the effect of the rs1051730 variant on LC is not explained by its effect on the traditional ND phenotypes (SQ, FIND score or DSM criteria). It is possible that an effect on other aspects of smoking behaviour, smoking duration in particular, may account for the observed difference between the indirect and direct estimates of the LC risks. An alternative possibility is that the variant directly confers risk of LC e.g. by increasing the vulnerability to tobacco smoke or through other unknown mechanisms.

Calculating the population attributable risk (PAR) for the variant results in 18% for lung cancer. While this is at best a ballpark figure given the complex interplay between the variant, smoking, and smoking-related diseases, it is likely that the variant accounts for a substantial fraction of LC cases and the associated morbidity and mortality.

TABLE 1

Genotype Status and Smoking Quantity (SQ) Level of 13,945 Icelandic Smokers.

| Cigarettes per day | Genotype of rs1051730 | | | Total | Frequency |
|---|---|---|---|---|---|
| (SQ level) | GG | GT | TT | n (Freq.) | of T allele |
| 1 to 10 (0) | 1,743 | 1,558 | 326 | 3,627 (0.260) | 0.305 |
| 11 to 20 (1) | 2,727 | 2,865 | 810 | 6,402 (0.459) | 0.350 |
| 21 to 30 (2) | 1,145 | 1,416 | 427 | 2,988 (0.214) | 0.380 |
| 31 and more (3) | 341 | 448 | 139 | 928 (0.067) | 0.391 |
| All levels (Frequency) | 5,956 (0.427) | 6,287 (0.451) | 1,702 (0.122) | 13,945 (1.000) | 0.347 |
| Mean SQ level (SD) | 1.01 (0.85) | 1.12 (0.86) | 1.22 (0.85) | 1.09 (0.86) | |

TABLE 2

| Association of rs1051730 allele T with Lung Cancer | | | | | | | |
|---|---|---|---|---|---|---|---|
| | Controls | | Cases | | | | |
| Study Group | n | freq | n | freq | OR | (95% CI) | P |
| Lung Cancer | | | | | | | |
| Iceland | 28,752 | 0.342 | 665 | 0.398 | 1.27 | (1.13-1.43) | $4.1 \times 10^{-5}$ |
| Spain | 1,474 | 0.390 | 269 | 0.483 | 1.46 | (1.22-1.76) | $5.4 \times 10^{-5}$ |
| The Netherlands | 2,018 | 0.314 | 90 | 0.350 | 1.18 | (0.86-1.61) | 0.31 |
| Foreign combined | 3,492 | — | 359 | — | 1.38 | (1.18-1.62) | $6.6 \times 10^{-5}$ |
| All combined | 32,244 | — | 1,024 | — | 1.31 | (1.19-1.44) | $1.5 \times 10^{-8}$ |

TABLE 3

Association of markers in LD with rs1051730 to Lung Cancer (LC). Shown is the marker name, associating allele, numerical value of the LD measure $R^2$ to rs1051730 based on HapMap CEU data (http://www.hapmap.org), relative risk of the association (RR), the number of affecteds and controls and the allelic frequencies in those groups.

Lung Cancer

| marker | allele | $R^2$ to rs1051730 | p-value | RR | Naff | Aff Freq | Ncon | Con Freq |
|---|---|---|---|---|---|---|---|---|
| rs1051730 | T | — | 1.75E−05 | 1.30 | 610 | 0.404098 | 26229 | 0.342522 |
| rs8034191 | C | 0.93 | 3.49E−05 | 1.29 | 610 | 0.596721 | 26228 | 0.656093 |
| rs2036534 | T | 0.14 | 0.026071 | 1.18 | 609 | 0.79803 | 26218 | 0.77052 |
| rs11638372 | T | 0.44 | 0.04754 | 1.13 | 608 | 0.418586 | 26222 | 0.389597 |
| rs4887077 | T | 0.43 | 0.048422 | 1.13 | 610 | 0.415574 | 26219 | 0.386781 |
| rs6495314 | C | 0.44 | 0.068595 | 1.12 | 610 | 0.418852 | 26209 | 0.392232 |
| rs1996371 | G | 0.45 | 0.085206 | 1.11 | 610 | 0.418852 | 26223 | 0.393681 |

TABLE 4

Surrogate markers for rs1051730. Shown are marker names, position of the polymorphic site in NCBI Build 36, the position of the polymorphic site in SEQ ID NO: 1, and values for the LD measures |D'|, $R^2$, and p-value. Linkage disequilibrium was determined using genotypes from the HapMap Caucasian CEU dataset (http://www.hapmap.org).

A.

| marker | position (Build 36) | Position SEQ ID NO: 1 | \|D'\| | $R^2$ | p-value |
|---|---|---|---|---|---|
| rs4436747 | 76501063 | 1 | 0.784105 | 0.263895 | 3.65E−09 |
| rs2568498 | 76508987 | 7925 | 0.788769 | 0.276514 | 1.54E−09 |
| rs1394371 | 76511524 | 10462 | 0.804627 | 0.542323 | 5.30E−16 |
| rs12899131 | 76513940 | 12878 | 0.784105 | 0.263895 | 3.65E−09 |
| rs2568500 | 76513983 | 12921 | 0.777839 | 0.256775 | 8.52E−09 |
| rs17483548 | 76517368 | 16306 | 0.858671 | 0.712237 | 5.42E−22 |
| rs17405217 | 76518204 | 17142 | 0.858671 | 0.712237 | 5.42E−22 |
| rs17483721 | 76520786 | 19724 | 0.858671 | 0.712237 | 5.42E−22 |
| rs1847529 | 76522125 | 21063 | 0.788769 | 0.276514 | 1.54E−09 |
| rs8041628 | 76522410 | 21348 | 0.784596 | 0.274417 | 2.37E−09 |
| rs2656052 | 76527987 | 26925 | 0.858671 | 0.712237 | 5.42E−22 |
| rs2568494 | 76528019 | 26957 | 0.856736 | 0.726896 | 7.55E−21 |
| rs7181486 | 76528673 | 27611 | 0.858429 | 0.711836 | 1.09E−21 |
| rs17483929 | 76529431 | 28369 | 0.858671 | 0.712237 | 5.42E−22 |
| rs10519198 | 76529809 | 28747 | 0.788769 | 0.276514 | 1.54E−09 |
| rs12909921 | 76530315 | 29253 | 0.812377 | 0.282282 | 1.41E−08 |
| rs12910090 | 76530355 | 29293 | 0.788769 | 0.276514 | 1.54E−09 |
| rs2656065 | 76537604 | 36542 | 0.852863 | 0.70688 | 2.79E−21 |
| rs11639224 | 76540426 | 39364 | 0.821543 | 0.308926 | 2.70E−09 |
| rs1964678 | 76541055 | 39993 | 0.813921 | 0.237809 | 1.03E−07 |
| rs2009746 | 76541157 | 40095 | 0.858848 | 0.736891 | 1.59E−22 |
| rs17484235 | 76548469 | 47407 | 0.858671 | 0.712237 | 5.42E−22 |
| rs4299116 | 76553249 | 52187 | 0.806306 | 0.233961 | 2.88E−07 |
| rs1504550 | 76553305 | 52243 | 0.858278 | 0.731261 | 2.15E−21 |
| rs12910910 | 76554905 | 53843 | 0.8077 | 0.230774 | 2.33E−07 |

TABLE 4-continued

Surrogate markers for rs1051730. Shown are marker names, position of the polymorphic site in NCBI Build 36, the position of the polymorphic site in SEQ ID NO: 1, and values for the LD measures |D'|, $R^2$, and p-value. Linkage disequilibrium was determined using genotypes from the HapMap Caucasian CEU dataset (http://www.hapmap.org).

A.

| marker | position (Build 36) | Position SEQ ID NO: 1 | \|D'\| | $R^2$ | p-value |
|---|---|---|---|---|---|
| rs8043227 | 76555926 | 54864 | 0.813921 | 0.237809 | 1.03E−07 |
| rs17484524 | 76559731 | 58669 | 0.852974 | 0.705337 | 2.19E−21 |
| rs8042238 | 76561326 | 60264 | 0.809173 | 0.240375 | 2.02E−07 |
| rs8042260 | 76561429 | 60367 | 0.790462 | 0.222858 | 1.35E−06 |
| rs12903295 | 76566027 | 64965 | 0.85721 | 0.236711 | 3.84E−07 |
| rs12904234 | 76566439 | 65377 | 0.810067 | 0.236137 | 1.49E−07 |
| rs965604 | 76576278 | 75216 | 0.813921 | 0.237809 | 1.03E−07 |
| rs13180 | 76576543 | 75481 | 0.813921 | 0.237809 | 1.03E−07 |
| rs1062980 | 76579582 | 78520 | 0.810734 | 0.236646 | 2.16E−07 |
| rs4362358 | 76583159 | 82097 | 0.813921 | 0.237809 | 1.03E−07 |
| rs9788721 | 76589924 | 88862 | 1 | 0.871795 | 7.70E−31 |
| rs8034191 | 76593078 | 92016 | 1 | 0.871795 | 7.70E−31 |
| rs12591557 | 76598787 | 97725 | 1 | 0.366812 | 3.19E−14 |
| rs10519203 | 76601101 | 100039 | 1 | 0.871795 | 7.70E−31 |
| rs12914694 | 76601499 | 100437 | 1 | 0.38914 | 4.69E−14 |
| rs8031948 | 76603112 | 102050 | 1 | 0.871795 | 1.79E−30 |
| rs1504545 | 76605526 | 104464 | 1 | 0.372294 | 1.21E−14 |
| rs952215 | 76606208 | 105146 | 1 | 0.372294 | 1.21E−14 |
| rs952216 | 76606257 | 105195 | 1 | 0.361233 | 3.45E−14 |
| rs12902493 | 76606330 | 105268 | 1 | 0.372294 | 1.21E−14 |
| rs11636131 | 76608661 | 107599 | 1 | 0.372294 | 1.21E−14 |
| rs11632604 | 76608969 | 107907 | 1 | 0.372294 | 1.21E−14 |
| rs12910289 | 76609120 | 108058 | 1 | 0.366812 | 2.04E−14 |
| rs1504546 | 76611290 | 110228 | 1 | 0.372294 | 1.21E−14 |
| rs12906951 | 76612617 | 111555 | 1 | 0.366812 | 2.04E−14 |

TABLE 4-continued

Surrogate markers for rs1051730. Shown are marker names, position of the polymorphic site in NCBI Build 36, the position of the polymorphic site in SEQ ID NO: 1, and values for the LD measures |D'|, $R^2$, and p-value. Linkage disequilibrium was determined using genotypes from the HapMap Caucasian CEU dataset (http://www.hapmap.org).

A.

| marker | position (Build 36) | Position SEQ ID NO: 1 | \|D'\| | $R^2$ | p-value |
|---|---|---|---|---|---|
| rs3885951 | 76612972 | 111910 | 1 | 0.247573 | 2.53E−09 |
| rs931794 | 76613235 | 112173 | 1 | 0.871795 | 7.70E−31 |
| rs12916999 | 76613967 | 112905 | 1 | 0.380531 | 7.49E−15 |
| rs12915366 | 76618808 | 117746 | 1 | 0.345992 | 8.47E−14 |
| rs12916483 | 76619452 | 118390 | 1 | 0.363636 | 5.69E−14 |
| rs3813572 | 76619643 | 118581 | 1 | 0.372294 | 1.21E−14 |
| rs3813571 | 76619847 | 118785 | 1 | 0.372294 | 1.21E−14 |
| rs4886571 | 76620813 | 119751 | 1 | 0.366812 | 3.19E−14 |
| rs4243083 | 76620885 | 119823 | 1 | 0.369369 | 3.36E−14 |
| rs2292117 | 76621744 | 120682 | 1 | 0.372294 | 1.21E−14 |
| rs11858230 | 76622607 | 121545 | 1 | 0.363707 | 1.34E−13 |
| rs8025429 | 76623417 | 122355 | 1 | 0.369369 | 3.36E−14 |
| rs4887062 | 76624856 | 123794 | 0.943182 | 0.343351 | 9.61E−13 |
| rs4887063 | 76626770 | 125708 | 1 | 0.372294 | 1.91E−14 |
| rs8053 | 76628275 | 127213 | 1 | 0.372294 | 1.21E−14 |
| rs1979907 | 76629294 | 128232 | 1 | 0.386792 | 7.82E−15 |
| rs1979906 | 76629344 | 128282 | 1 | 0.394619 | 2.68E−15 |
| rs1979905 | 76629429 | 128367 | 1 | 0.385965 | 4.45E−15 |
| rs4887064 | 76629902 | 128840 | 1 | 0.385965 | 4.45E−15 |
| rs12907966 | 76630106 | 129044 | 1 | 0.385965 | 4.45E−15 |
| rs880395 | 76631411 | 130349 | 1 | 0.385965 | 4.45E−15 |
| rs905740 | 76631441 | 130379 | 1 | 0.385965 | 4.45E−15 |
| rs7164030 | 76631716 | 130654 | 1 | 0.385965 | 4.45E−15 |
| rs4275821 | 76636596 | 135534 | 1 | 0.333333 | 2.17E−13 |
| rs7173512 | 76636969 | 135907 | 1 | 0.333333 | 2.17E−13 |
| rs2036527 | 76638670 | 137608 | 0.963677 | 0.837627 | 2.25E−27 |
| rs588765 | 76652480 | 151418 | 1 | 0.37788 | 1.31E−14 |
| rs6495306 | 76652948 | 151886 | 1 | 0.4 | 1.60E−15 |
| rs17486278 | 76654537 | 153475 | 0.962446 | 0.895088 | 2.47E−28 |
| rs601079 | 76656634 | 155572 | 1 | 0.4 | 1.60E−15 |
| rs495956 | 76656985 | 155923 | 1 | 0.333333 | 2.17E−13 |
| rs680244 | 76658343 | 157281 | 1 | 0.4 | 1.60E−15 |
| rs621849 | 76659916 | 158854 | 1 | 0.4 | 1.60E−15 |
| rs7180002 | 76661048 | 159986 | 0.964252 | 0.867797 | 1.54E−28 |
| rs692780 | 76663560 | 162498 | 1 | 0.333333 | 2.17E−13 |
| rs11637635 | 76664205 | 163143 | 1 | 0.333333 | 2.17E−13 |
| rs481134 | 76664618 | 163556 | 1 | 0.394619 | 2.68E−15 |
| rs951266 | 76665596 | 164534 | 0.964252 | 0.867797 | 1.54E−28 |
| rs555018 | 76666297 | 165235 | 1 | 0.394619 | 2.68E−15 |
| rs647041 | 76667536 | 166474 | 1 | 0.392185 | 3.91E−15 |
| rs17408276 | 76668673 | 167611 | 1 | 0.320988 | 5.47E−13 |
| rs16969968 | 76669980 | 168918 | 1 | 0.901961 | 1.21E−31 |
| rs518425 | 76670868 | 169806 | 1 | 0.226415 | 1.13E−09 |
| rs514743 | 76671282 | 170220 | 1 | 0.320988 | 5.47E−13 |
| rs615470 | 76673043 | 171981 | 1 | 0.320988 | 5.47E−13 |
| rs660652 | 76674887 | 173825 | 1 | 0.320988 | 5.47E−13 |
| rs472054 | 76675049 | 173987 | 1 | 0.315353 | 1.37E−12 |
| rs578776 | 76675455 | 174393 | 1 | 0.212454 | 2.37E−09 |
| rs6495307 | 76677376 | 176314 | 1 | 0.385965 | 4.45E−15 |
| rs1051730 | 76681394 | 180332 | 1 | 1 | — |
| rs3743077 | 76681951 | 180889 | 1 | 0.392185 | 1.00E−14 |
| rs1317286 | 76683184 | 182122 | 1 | 0.901961 | 2.87E−31 |
| rs12914385 | 76685778 | 184716 | 1 | 0.787879 | 8.22E−27 |
| rs2869546 | 76694400 | 193338 | 1 | 0.333333 | 2.17E−13 |
| rs3743075 | 76696507 | 195445 | 1 | 0.308943 | 1.35E−12 |
| rs3743074 | 76696535 | 195473 | 1 | 0.325598 | 5.08E−13 |
| rs3743073 | 76696594 | 195532 | 1 | 0.315353 | 1.37E−12 |
| rs8040868 | 76698236 | 197174 | 1 | 0.759036 | 2.11E−26 |
| rs1878399 | 76699058 | 197996 | 1 | 0.4 | 1.60E−15 |
| rs1948 | 76704454 | 203392 | 1 | 0.242424 | 2.23E−10 |
| rs7178270 | 76708132 | 207070 | 1 | 0.347826 | 9.23E−14 |
| rs17487223 | 76711042 | 209980 | 0.926323 | 0.748065 | 5.19E−24 |
| rs950776 | 76713073 | 212011 | 1 | 0.285714 | 7.88E−12 |
| rs11636753 | 76716001 | 214939 | 1 | 0.342105 | 2.39E−13 |
| rs11637890 | 76722474 | 221412 | 1 | 0.353448 | 5.46E−14 |
| rs11633223 | 76722531 | 221469 | 1 | 0.369369 | 5.26E−14 |
| rs11634351 | 76731773 | 230711 | 0.747959 | 0.510482 | 3.07E−13 |
| rs1021070 | 76733918 | 232856 | 1 | 0.345992 | 8.47E−14 |
| rs7181405 | 76735207 | 234145 | 1 | 0.340426 | 1.43E−13 |

TABLE 4-continued

Surrogate markers for rs1051730. Shown are marker names, position of the polymorphic site in NCBI Build 36, the position of the polymorphic site in SEQ ID NO: 1, and values for the LD measures |D'|, $R^2$, and p-value. Linkage disequilibrium was determined using genotypes from the HapMap Caucasian CEU dataset (http://www.hapmap.org).

A.

| marker | position (Build 36) | Position SEQ ID NO: 1 | \|D'\| | $R^2$ | p-value |
|---|---|---|---|---|---|
| rs11638830 | 76735374 | 234312 | 0.768682 | 0.50015 | 1.70E−14 |
| rs17487514 | 76740840 | 239778 | 0.577029 | 0.240648 | 1.33E−06 |
| rs12899135 | 76741434 | 240372 | 0.729687 | 0.464109 | 7.89E−13 |
| rs12910237 | 76743393 | 242331 | 1 | 0.329004 | 4.10E−13 |
| rs1996371 | 76743861 | 242799 | 0.739121 | 0.476262 | 7.13E−14 |
| rs6495314 | 76747584 | 246522 | 0.739121 | 0.476262 | 7.13E−14 |
| rs922691 | 76751049 | 249987 | 0.936182 | 0.310116 | 9.53E−11 |
| rs12905641 | 76751417 | 250355 | 1 | 0.315353 | 9.23E−13 |
| rs11639372 | 76753710 | 252648 | 0.74855 | 0.483781 | 6.43E−13 |
| rs12902602 | 76754456 | 253394 | 0.751972 | 0.483132 | 9.37E−13 |
| rs1021071 | 76755234 | 254172 | 0.739121 | 0.476262 | 7.13E−14 |
| rs11072785 | 76755284 | 254222 | 0.736113 | 0.49926 | 1.22E−13 |
| rs11857532 | 76755323 | 254261 | 0.724283 | 0.41331 | 4.03E−12 |
| rs4886580 | 76756440 | 255378 | 0.721631 | 0.451338 | 1.29E−12 |
| rs8038920 | 76761600 | 260538 | 1 | 0.320988 | 5.47E−13 |
| rs4887077 | 76765419 | 264357 | 0.694601 | 0.406611 | 1.52E−11 |
| rs11638372 | 76770614 | 269552 | 0.694601 | 0.406611 | 1.52E−11 |
| rs922692 | 76771269 | 270207 | 0.694601 | 0.406611 | 1.52E−11 |
| rs12910627 | 76781988 | 280926 | 0.694601 | 0.406611 | 1.52E−11 |
| rs11072791 | 76784131 | 283069 | 0.694601 | 0.406611 | 1.52E−11 |
| rs11638490 | 76795005 | 293943 | 0.677562 | 0.38728 | 1.73E−10 |
| rs11629637 | 76806079 | 305017 | 0.698873 | 0.423336 | 6.02E−12 |
| rs3813565 | 76806665 | 305603 | 0.704707 | 0.447924 | 1.02E−12 |
| rs4887082 | 76812122 | 311060 | 0.694601 | 0.406611 | 1.52E−11 |
| rs12286 | 76838814 | 337752 | 0.661245 | 0.381187 | 9.19E−11 |
| rs1809420 | 76843824 | 342762 | 0.655389 | 0.361998 | 3.12E−10 |
| rs7174367 | 76851722 | 350660 | 0.647747 | 0.356148 | 1.33E−09 |
| rs7171916 | 76855006 | 353944 | 0.608975 | 0.302175 | 1.50E−08 |
| rs1994017 | 76867361 | 366299 | 0.917337 | 0.204002 | 9.97E−08 |
| rs12905740 | 76869419 | 368357 | 0.90045 | 0.204099 | 2.63E−06 |
| rs2277545 | 76870646 | 369584 | 0.510929 | 0.214706 | 4.42E−06 |
| rs1564499 | 76871863 | 370801 | 0.917337 | 0.204002 | 9.97E−08 |
| rs12903203 | 76871988 | 370926 | 0.539624 | 0.225571 | 1.78E−06 |
| rs3743057 | 76876062 | 375000 | 0.917337 | 0.204002 | 9.97E−08 |
| rs8038189 | 76886081 | 385019 | 0.920091 | 0.214074 | 4.66E−08 |
| rs922693 | 76886593 | 385531 | 0.919558 | 0.218072 | 4.83E−08 |
| rs1383636 | 76893275 | 392213 | 0.922667 | 0.224377 | 2.15E−08 |

Example 2

All exons, promoters, and 5' and 3'UTRs were sequenced for each of the CHRNA5, CHRNA3 and CHRNB4 genes in the nicotinic acetylcholine receptor subunit cluster in a sample of lung cancer patients (n=184), nicotine dependent smokers (n=176) and low quantity smokers (n=175). The regions that were sequenced are indicated in Table 5. In total, 111 variants were found, 47 of which were not present in dbSNP129. A full description of all variants is found in Table 6, including position, alleles, frequency and possible functional significance. Statistical analysis focused on 50 variants with minor allele frequencies greater than 1%. Results of this analysis are found in Table 7. Given the strong established effect seen with rs1051730, we expect to find significant results for this SNP and correlated SNPs. P-values which include an adjustment for the effect of rs1051730 are thus also included in the table.

We examined linkage disequilibrium (LD) among these polymorphisms in order to define equivalence groups in which all polymorphisms have $r^2>0.8$ to one SNP identified as head of the group (Table 8). Six equivalence groups are formed accounting for all but three of the polymorphisms with frequency greater than 5% (See Table 8). These three polymorphisms had strongest LD to the head of class A (rs1051730; $r^2$ between 0.64 and 0.79) and are thus reported together, with that group.

Genotypes from Illumina Human Hap300 chips are available for all subjects sequenced, as well as for additional subjects in each group. Information on linkage disequilibrium within the sequencing sample was used to identify appropriate tagging variants from the Illumina chip to effectively increase sample size for variants of interest.

rs16969968

The non-synonymous CHRNA5 variant rs16969968 has previously been highlighted in the literature (Saccone, S F, et al. *Hum Mol Genet* 16:36-49 (2007)). In European Americans, LD is strong between this variant and rs1051730 according to the Hapmap project data (D'=1, $r^2$=0.9; Table 4). We found these two variants to be equivalent in our sequencing sample.

rs1051730 Equivalence Group

In addition to rs16969968, several other SNPs were found to be in very strong LD with rs1051730 in Iceland. These include rs55853698, rs55781567 and rs8192482, all with $r^2$>0.93 to rs1051730/rs16969968. Because LD is so strong in Iceland, we cannot differentiate between these 5 SNPs. Another SNP, ss107794645, exhibited weaker LD with rs1051730/rs16969968 (D'=0.91, $r^2$=0.69). Within the sequencing sample this SNP gave a stronger risk than rs1051730 for nicotine dependence (OR=1.65 vs. 1.49) but not lung cancer (OR=1.53 vs 1.58). A single SNP assay was designed to further test this variant in Iceland. After additional subjects were genotyped, the OR of this variant is 1.26 (p=0.006, p=0.8 after adjustment for rs1051730) for lung cancer (n=645), and is 1.18 (p=0.02, p=0.8 after adjustment for rs1051730) for nicotine dependence (n=2068), both tested against low quantity smokers (n=535). These results indicate that risk associated with ss107794645 is due to its LD with rs1051730.

rs12907519/rs8192475

The results from our sequencing analysis alone indicate a significant protective effect of the C allele of rs12907519, a SNP located in intron 1 of CHRNA3. With low quantity smokers as controls, the variant has an OR of 0.34 for nicotine dependence (p=0.007 after adjustment) and 0.21 for lung cancer (p=0.0003 after adjustment). This SNP is within equivalence group D, in strong LD with rs8192475 ($r^2$=0.93) which is included on the Illumina chip. With all genotypes available for rs8192475, association of this variant is not significant for lung cancer (OR=0.78, p=0.5 after adjustment for rs1051730) or nicotine dependence (OR=0.87, p=0.9 after adjustment) when compared to low quantity smokers (see Table 3). Given the strong LD between these variants, we can rule out association of rs12907519 with either lung cancer or nicotine dependence.

Equivalence Classes in Illumina Samples

Four equivalence classes are headed by a SNP on the Illumina chip. A fifth can be tagged with $r^2$=0.98 by a haplotype of two SNPs from the chip. Results within the larger chip sample are displayed for all tagged classes in Table 9, with and without adjustment for the effect of rs1051730. One class (A) is headed by rs1051730. Within the chip genotyped sample analyzed here, the T allele is strongly associated with both nicotine dependence (OR=1.4, p=$7.4\times10^{-15}$) and lung cancer (OR=1.52, p=$1.5\times10^{-11}$). Of the SNPs which head the remaining 4 classes tagged by Illumina chips, with and without correction for rs1051730, only rs8192475 displayed significant association in any of the three tests within the sequencing sample In the larger chip-genotyped sample, several SNPs have significant p-values due to correlation with rs1051730. After adjustment for the effect of rs1051730 the SNP rs1948 has a p-value of 0.006. This presents the possibility that a protective effect for lung cancer might exist for a variant in this equivalence class which occurs primarily on the same background as the risk effect of rs1051730. Any such effect would be small, and is masked by the comparably strong risk associated with rs1051730.

rs578776

Figure 2:
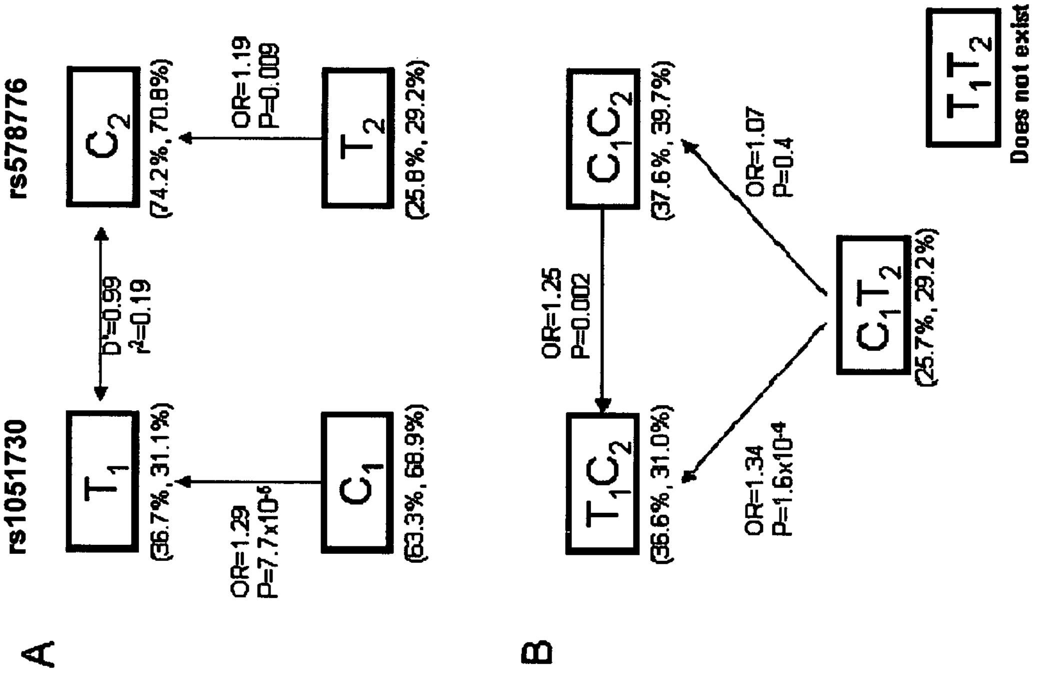
FIG. 2 illustrates the risk for nicotine dependence observed for rs1051730 (1) and rs578776 (2) based on the comparison of 2161 nicotine dependent individuals and 865 low quantity smokers. The frequencies for cases and controls are given in parentheses below the alleles/haplotypes, and the arrows point towards the allele/haplotype for which increased risk is observed. (A) displays the odds ratios observed for the two SNPs and the linkage disequilibrium between them, (B) shows the odds ratios between the three observed haplotypes. There is no significant odds ratio for the haplotype with the protective $C_1$ allele at rs1051730 and the risk $C_2$ allele at rs578776 compared with the haplotype with both protective alleles. The comparison of the haplotype with the protective allele at rs1051730 and the risk allele at rs578776 against the haplotype with both high risk alleles shows a significant odds ratio due to rs1051730 allele T.

The SNP rs578776 has recently been reported to be an independent, second risk variant for nicotine dependence within this LD block (Bierut, L J, et al. *Am J Psych* 165:1163-71 (2008)). We genotyped additional nicotine dependent cases and low quantity smokers so that our data set would be large enough to address the relationship of rs578776 to rs1051730/rs16969968. According to Hapmap project data, in European Americans LD between the variants is D'=1, $r^2$=0.2 (www.hapmap.org). In Iceland we see similar results (D'=0.99, $r^2$=0.19, n=3026). The risk allele of rs1051730/rs16969968 is fixated on the background of the major allele of rs578776. Therefore there are only 3 haplotypes possible. We find that all the risk associated with rs578776 is confined to the haplotype which includes the risk variant of rs1051730/rs16969968 (OR=1.34, p=$1.56\times10^{-4}$; FIG. 2). The frequency of the haplotype containing the protective allele of rs1051730 and the risk allele of rs578776 occurs at a lower frequency in nicotine dependence (37.6%) compared to low quantity smokers (39.7%). There is no evidence to support an independent risk for nicotine dependence associated with the rs578776 variant.

Rare Variants

Of the variants identified with sequencing, 59 occur at frequencies of less than 1%. Table 10 includes the number of carriers in each phenotype group for each of these variants. Among them are 7 missense mutations and one 20 bp exonic deletion. The exonic deletion occurs in CHRNA3 in one subject from the nicotine dependence group. This individual received a score of 4 on the FTND scale and did not meet DSM criteria for nicotine dependence. None of the rare variants alone can fully account for the signal observed. We cannot however rule out the possibility that among these variants are rare high penetrance variants which might influence risk of one or both conditions.

Three Length Polymorphisms: rs3841324, rs55787222, and rs60706203

Three length polymorphisms were genotyped directly in additional subjects. These include a 22 bp insertion/deletion, rs3841324, in the promoter of CHRNA5, identified in a scan for promoter polymorphisms affecting gene expression (Buckland, P R, et al. *Hum Mutat, rs*60706203, a 3 bp insertion/deletion in the leader sequence of CHRNA3, and rs55787222, a 4 bp microsatellite in the promoter region of CHRNA3. Additional rare alleles of each of the last 2 variants were identified with additional genotyping (see Table 6).

Results for association analysis of these markers are presented in Table 11. P-values were adjusted to take into account the effect of rs1051730. There is no significant association with lung cancer or nicotine dependence for either rs3841324 or rs60706203. In the case of rs55787222, a 4 bp microsatellite in the promoter region of CHRNA3, the allele containing 2 copies of the 4 bp sequence is not associated with either condition before correction for rs1051730. After correction, however, the p-value is 0.004 for association with nicotine dependence. Within this sample, the p-value for rs1051730 is 0.001 for nicotine dependence. It appears that the allele of rs55787222 which contains 2 copies (−8 allele with respect to CEPH 1347-02 reference) may be mildly protective against nicotine dependence. The risk allele of rs1051730 is fixated on this background, and the risk contributed by this variant is stronger than the protective effect which may be supplied by this allele of rs55787222. However, the risk for rs1051730 is observed for the comparison of both nicotine dependence and lung cancer against low quantity smokers. The possible protective effect of rs55787222 is only observed for nicotine dependence.

Expression

We measured expression of CHRNA5 in two tissues to address whether genetic variants in the cluster are associated with expression regulation. In particular, rs3841324 has been reported as a promoter regulatory element in cell culture (Buckland P R, et al. *Hum Mutat* 26:214-23 (2005)). We sought to test the effect of this variant on expression in vivo. Expression of CHRNA5 was strongly associated with rs3841324 genotype, with relative expression levels higher for the short allele in blood ($r=0.72$, $p=4\times10^{-71}$) and subcutaneous adipose tissue ($r=0.73$, $p=2\times10^{-63}$). Association with expression of CHRNA5 was also examined for the other SNPs within the LD block, with one marker from each equivalence class tested (see Table 12). All markers were significantly associated with expression. Adjusting for rs3841324 reduces the significance of the association for the other SNPs drastically, in subcutaneous adipose tissue only rs1051730 remains nominally significant (p=0.018) and three SNPs show nominally significant association in blood (minimum p=0.006 for rs1051730). Overall, expression in blood and subcutaneous adipose tissue is strongly associated with rs3841324.

However, we cannot rule out an additional comparably weak effect of another SNP, which was best captured by rs1051730. Expression of CHRNA5 was not associated with lifetime regular smoking, or with smoking within the past 24 hours (data not shown).

We have established that there is no risk for nicotine dependence or lung cancer associated with this variant independent of the risk associated with rs1051730 (Table 11). However, there is strong LD between the two variants. The T allele of rs1051730 only appears on the haplotype background including the long, or low expression, allele of rs3841324.

A careful characterization of the CHRNA5/CHRNA3/CHRNB4 cluster does not identify any variants with stronger association to nicotine dependence or lung cancer than rs1051730/rs16969968. Therefore the SNP non-synonymous SNP rs16969968 remains the variant most likely to have functional effects leading to the observed association signals within this region.

Materials and Methods

Subjects for Sequencing

Three groups of subjects were selected for sequencing analysis: (1) lung cancer patients (n=184), (2) nicotine dependent smokers without other addictions (n=176) and (3) low-quantity smokers (n=175) (See Table 13 for demographic information). Low-quantity smokers reported regular smoking for at least one year and reported only social smoking or less than 5 cigarettes per day. Subjects with lung cancer show the highest frequency of the identified risk variant, and generally constitute a population with high lifetime smoking exposure. Our sample of nicotine dependent individuals received the diagnosis based on questionnaire data addressing two systems of classification of nicotine dependence, the Fagerstrom Test for Nicotine Dependence (FTND) (Heatherton, T F, et al. *Br J Addict* 86:1119-27)) and the criteria of the Diagnostic and Statistical Manual, Version IV (DSM). Subjects met criteria under either or both systems (FTND 4+ or DSM 3+). Individuals with other substance dependence or abuse diagnoses were excluded. Our previous analysis indicated that the effect of the risk variant was to increase smoking quantity among smokers, rather than affecting initiation. Therefore, we used smokers with low consumption as a control group for study.

Subjects for Additional Genotyping

Certain variants of interest were specifically genotyped in additional individuals. For the length variants rs55787222, rs3841324 and rs60706203, the subjects included 567 lung cancer patients, 1623 nicotine dependent smokers and 608 low quantity smokers (See Table 14).

All subjects sequenced have also been genotyped with Human Hap300 or Human Hap300-duo1 Bead Arrays (Illumina; San Diego, Calif., USA). Additional subjects from each group have also been genotyped using these chips. LD information obtained in the sequencing cohort was used to identify tagging SNPs for testing in the larger sample, which included 669 lung cancer cases, 1950 nicotine dependent smokers and 4680 low quantity smokers (See Table 14)

The study protocols were approved by the National Bioethics Committee (NBC) and the Data Protection Authority (DPA) of Iceland. The DPA has encrypted all personal identifiers linked to phenotype information or blood samples using a third-party encryption system(15)(15). All subjects are of Icelandic ancestry.

Sequencing

The exons, 5' and 3' UTRs, and flanking sequences 1 kb upstream of CHRNA5, CHRNA3, and CHRNB4 were sequenced. Sequence for the region was obtained from NCBI build 36. A total of 57 primer pairs were designed. The position of regions sequenced (build 36) can be found in Table 5. PCR amplification and sequencing reactions were set up on Zymark ALH300 workstations, with amplification performed on MJR Tetrads. PCR products were purified using AMPure (Agencourt Bioscience). Dye terminator removal was performed using CleanSEQ (Agencourt) to repurify. Electrophoresis was performed on Applied Biosystems 3730 DNA Analyzers. Sequence editing and analysis were performed using deCODE Genetics Sequence Miner software. SNP calling was done by both manual inspection and automated calling. All SNPs identified through automated calling were then confirmed by manual inspection of the sequence traces. Insertion/deletions and microsatellites were identified by manual inspection. Simple, rare insertion/deletions were called manually.

Genotyping

Additional genotyping of SNPs was done using the Centaurus platform (Nanogen). Three variants, rs55787222, rs3841324, and rs60706203, observed in the sequencing, were genotyped in a larger population. For these markers primers were designed using Primer3. PCR reactions were set up on Zymark ALH300 workstations and amplification performed on MJR Tetrads. PCR products were pooled, an internal size standard added, and then resolved on Applied Biosystems 3730 DNA Analyzers. Primers and PCR conditions are available on request. Genotypes were called and edited using deCODE Allele Caller and deCODE-GT.

Expression Analysis

The variant rs3841324 was identified as a promoter element with significant effect on transcription of CHRNA5 in a genome scan for regulatory elements (Buckland, P R, et al. *Hum Mutat* 26:214-23 (2005)). We therefore examined its role in regulating expression of the gene in blood and subcutaneous adipose tissue using an expression cohort previously described (Emilsson, V., et al. *Nature* 452:423-8 (2008)). From this cohort, genotype and expression data were used from 446 individuals with blood samples and 376 individuals with subcutaneous adipose tissue samples.

RNA samples were purified using RNeasy Mini Kit (Quiagen), and integrity analyzed using Agilent 2100 Bioanalyzer. Total RNA was converted to cDNA using the High Capacity cDNA Archive Kit (Applied Biosystems). Two Taqman assays were designed for CHRNA5, so that positive results cannot be attributable to the specific assay used. The probes are located at different exon boundaries, one crossing exon 2 and 3, and the other crossing exons 3 and 4. Real-time PCR was carried out according to manufacturer's recommendations on an ABI Prism 7900HT Sequence Detection System. Quantification was performed using the ΔΔCt method (User Bulletin no. 2, Applied Biosystems 2001). A housekeeping gene, in this case GUSB, was run in parallel for normalization.

Statistical Analysis

A likelihood ratio test was used for analysis using $\chi^2$ statistics. In all cases p-values are reported both with and without correction for the effect of rs1051730. P-values are reported without correction for multiple testing. In the analysis of the larger samples generated from Illumina genotypes and individual genotyping of length polymorphisms, p-values are corrected for relatedness among affecteds as described previously using a simulation procedure with the known genealogy (Grant, S F., et al. *Nat Genet* 38:320-3 (2006)).

The expression data were log-transformed, adjusted for sex and age with a linear regression model, and the standardized residuals were used as the variable. There were 307 individuals present in both data sets and their residuals for the two tissues tested were highly correlated ($r=0.65$, $p=7\times10^{-39}$).

In analysis of equivalence classes in larger cohorts, genotypes for rs569207 are inferred. Allele T is tagged by a haplotype of allele C at rs1051730 and allele G at rs680244 ($r^2=0.98$ in the sequencing data) in the analysis of Illumina data. In the expression analysis genotypes were inferred using a two SNP haplotype based on allele G at rs680244 and allele T at rs578776 ($r^2=0.99$ in the sequencing data).

TABLE 5

Build 36 positions for regions sequenced

| Gene | Region | Build 36 position |
|---|---|---|
| CHRNA5 | 5' Flanking & Exon 1 | 76643986-76645528 |
| | Exon 2 | 76659873-76660680 |
| | Exon 3 | 76665714-76666400 |
| | Exon 4 | 76667349-76668117 |
| | Exon 5 | 76668894-76670363 |
| | Exon 6 & 3' Flanking | 76672141-76673771 |
| CHRNB4 | 5' Flanking & Exon 1 | 76720345-76721584 |
| | Exon 2 | 76714503-76715286 |
| | Exon 3 | 76710160-76711022 |
| | Exon 4 | 76708007-76709537 |
| | Exon 5 & 3' Flanking | 76703378-76704963 |
| CHRNA3 | 5' Flanking & Exon 1 | 76699749-76701312 |
| | Exon 2 &3 | 76697716-76698675 |
| | Exon 4 | 76696032-76696844 |
| | Exon 5 | 76680349-76682010 |
| | Exon 6 & 3' Flanking | 76674343-76676459 |

TABLE 6

Descriptive information on all variants from sequencing

| Marker | Ref SNP ID | Position (B 36) | Pos in Seq ID No: 1 | Major Allele | Minor Allele | Minor Allele Freq | Function | aa change |
|---|---|---|---|---|---|---|---|---|
| | | | | A: CHRNA5 | | | | |
| SG15S363 | ss107794609 | 76644594 | 143532 | G | T | 0.2% | near CHRNA5 | |
| DG15S1561 | rs3841324 | 76644868 | 143806 | 22bp[1] | — | 42.2% | near CHRNA5 | |
| SG15S468 | rs56182392 | 76644934 | 143872 | G | A | 1.3% | near CHRNA5 | |
| SG15S364 | rs503464 | 76644951 | 143889 | T | A | 21.4% | near CHRNA5 | |
| SG15S365 | rs55853698 | 76644994 | 143932 | T | G | 36.5% | utr | |
| SG15S366 | rs55781567 | 76645041 | 143979 | C | G | 36.8% | utr | |
| SG15S411 | ss107794620 | 76645331 | 144269 | G | A | 0.2% | intron | |
| SG15S412 | rs684513 | 76645455 | 144393 | C | G | 19.4% | intron | |
| SG15S312 | rs6495306 | 76652948 | 151886 | A | G | 43.3% | intron | |
| SG15S151 | rs680244 | 76658343 | 157281 | G | A | 43.4% | intron | |
| SG15S311 | rs621849 | 76659916 | 158854 | A | G | 43.3% | intron | |
| SG15S352 | ss107794606 | 76660070 | 159008 | A | C | 0.6% | intron | |
| SG15S469 | ss107794638 | 76660154 | 159092 | G | A | 0.2% | intron | |
| SG15S353 | rs569207 | 76660174 | 159112 | C | T | 21.0% | intron | |
| SG15S470 | ss107794639 | 76660617 | 159555 | A | G | 0.6% | intron | |
| SG15S344 | rs55982512 | 76666113 | 165051 | C | T | 0.4% | intron | |

TABLE 6-continued

Descriptive information on all variants from sequencing

| Marker | Ref SNP ID | Position (B 36) | Pos in Seq ID No: 1 | Major Allele | Minor Allele | Minor Allele Freq | Function | aa change |
|---|---|---|---|---|---|---|---|---|
| SG15S345 | rs555018 | 76666297 | 165235 | A | G | 42.5% | intron | |
| SG15S346 | rs647041 | 76667536 | 166474 | C | T | 43.1% | intron | |
| CHRNA5_0 | ss107794648 | 76667615 | 166553 | TC | — | 0.1% | intron | |
| SG15S347 | rs12898919 | 76667632 | 166570 | G | C | 4.8% | intron | |
| SG15S348 | rs2229961 | 76667807 | 166745 | G | A | 1.1% | non-synon | V- > I |
| SG15S471 | rs56201623 | 76669059 | 167997 | C | T | 0.1% | intron | |
| SG15S349 | ss107794603 | 76669155 | 168093 | T | C | 0.4% | intron | |
| SG15S350 | ss107794604 | 76669481 | 168419 | C | T | 0.3% | synon | |
| SG15S148 | rs16969968 | 76669980 | 168918 | G | A | 36.0% | non-synon | D- > N |
| SG15S351 | ss107794605 | 76670141 | 169079 | C | T | 0.4% | intron | |
| SG15S355 | ss107794607 | 76672424 | 171362 | G | C | 1.0% | intron | |
| CHRNA5_1 | ss107794649 | 76672962 | 171900 | ACT | — | 0.1% | utr | |
| SG15S356 | rs615470 | 76673043 | 171981 | C | T | 38.2% | utr | |
| SG15S357 | rs8192483 | 76673204 | 172142 | G | A | 0.1% | utr | |
| SG15S358 | rs55783657 | 76673213 | 172151 | G | A | 1.3% | utr | |
| SG15S359 | rs8192482 | 76673253 | 172191 | C | T | 35.7% | utr | |
| SG15S360 | rs564585 | 76673282 | 172220 | A | G | 24.8% | utr | |
| SG15S361 | ss107794608 | 76673351 | 172289 | G | A | 0.1% | utr | |
| B: CHRNA3 | | | | | | | | |
| SG15S389 | rs12899226 | 76674493 | 173431 | A | C | 4.9% | near CHRNA3 | |
| SG15S390 | rs55736590 | 76674550 | 173488 | C | T | 0.7% | near CHRNA3 | |
| CHRNA3_1 | rs34238957 | 76674771 | 173709 | — | CTCT | 38.3% | utr | |
| SG15S391 | rs660652 | 76674887 | 173825 | C | T | 38.2% | utr | |
| SG15S445 | ss107794646 | 76675048 | 173986 | T | C | 0.2% | utr | |
| SG15S392 | rs472054 | 76675049 | 173987 | C | T | 38.2% | utr | |
| CHRNA3_2 | rs35186448 | 76675294 | 174232 | — | CCCC | 20.9% | utr | |
| SG15S393 | rs56113144 | 76675406 | 174344 | C | T | 0.3% | utr | |
| SG15S162 | rs578776 | 76675455 | 174393 | G | A | 24.4% | utr | |
| SG15S394 | ss107794615 | 76676128 | 175066 | T | A | 0.2% | non-synon | I- > N |
| SG15S382 | rs56403513 | 76680842 | 179780 | C | T | 0.1% | synon | |
| SG15S383 | ss107794613 | 76681061 | 179999 | C | T | 0.1% | synon | |
| SG15S446 | ss107794633 | 76681390 | 180328 | C | T | 0.1% | non-synon | H- > Y |
| SG15S149 | rs1051730 | 76681394 | 180332 | G | A | 35.9% | synon | |
| SG15S384 | rs55958820 | 76681412 | 180350 | C | A | 1.5% | synon | |

TABLE 6-continued

Descriptive information on all variants from sequencing

| Marker | Ref SNP ID | Position (B 36) | Pos in Seq ID No: 1 | Major Allele | Minor Allele | Minor Allele Freq | Function | aa change |
|---|---|---|---|---|---|---|---|---|
| SG15S385 | rs8192480 | 76681475 | 180413 | T | C | 0.1% | synon | |
| CHRNA3_4 | ss107794647 | 76681496 | 180434 | 20bp[2] | — | 0.1% | frame-shift | |
| SG15S386 | ss107794614 | 76681539 | 180477 | C | T | 0.1% | non-synon | P- > L |
| SG15S387 | rs3743078 | 76681814 | 180752 | C | G | 20.9% | intron | |
| SG15S388 | rs3743077 | 76681951 | 180889 | G | A | 42.8% | intron | |
| SG15S447 | ss107794634 | 76696119 | 195057 | G | A | 0.9% | intron | |
| SG15S448 | rs4887069 | 76696125 | 195063 | C | C | 21.3% | intron | |
| SG15S376 | rs8192479 | 76696453 | 195391 | G | A | 3.1% | synon | |
| SG15S377 | rs3743075 | 76696507 | 195445 | G | A | 37.9% | synon | |
| SG15S378 | rs3743074 | 76696535 | 195473 | T | C | 38.0% | intron | |
| SG15S379 | rs3743073 | 76696594 | 195532 | A | C | 38.1% | intron | |
| SG15S380 | rs41280050 | 76696612 | 195550 | C | T | 1.7% | intron | |
| SG15S381 | ss107794612 | 76696708 | 195646 | G | A | 0.8% | intron | |
| SG15S449 | ss107794635 | 76696793 | 195731 | G | C | 0.4% | intron | |
| CHRNA3_0 | ss107794650 | 76698094 | 197032 | — | A | 4.1% | intron | |
| CHRNA3_0 | ss107794650 | 76698094 | 197032 | A | — | 0.2% | intron | |
| SG15S367 | rs8040868 | 76698236 | 197174 | A | G | 41.4% | synon | |
| SG15S368 | rs8192475 | 76698285 | 197223 | C | T | 5.0% | non-synon | R- > H |
| SG15S374 | ss107794610 | 76698484 | 197422 | C | T | 0.1% | intron | |
| SG15S375 | ss107794611 | 76698488 | 197426 | G | C | 0.2% | intron | |
| SG15S396 | rs7170068 | 76699998 | 198936 | C | T | 24.3% | intron | |
| SG15S397 | ss107794616 | 76700025 | 198963 | G | A | 0.1% | intron | |
| SG15S398 | ss107794617 | 76700033 | 198971 | A | G | 0.1% | intron | |
| SG15S399 | rs12907519 | 76700099 | 199037 | A | G | 5.0% | intron | |
| DG15S1563 | rs60706203 | 76700142 | 199080 | AGC[3] | — | 39.6% | non-synon | L/— |
| SG15S450 | ss107794636 | 76700424 | 199362 | C | A | 0.2% | near CHRNA3 | |
| DG15S1568 | rs55787222 | 76700428 | 199366 | (CGCC)2-7[4] | | | near CHRNA3 | |
| SG15S413 | ss107794621 | 76700491 | 199429 | C | G | 0.1% | near CHRNA3 | |
| SG15S414 | ss107794622 | 76700600 | 199538 | C | T | 0.8% | near CHRNA3 | |
| SG15S415 | ss107794623 | 76700884 | 199822 | T | C | 0.1% | near CHRNA3 | |
| SG15S466 | ss107794637 | 76700888 | 199826 | T | C | 0.1% | near CHRNA3 | |
| SG15S416 | ss107794624 | 76700993 | 199931 | A | G | 0.2% | near CHRNA3 | |

TABLE 6-continued

Descriptive information on all variants from sequencing

| Marker | Ref SNP ID | Position (B 36) | Pos in Seq ID No: 1 | Major Allele | Minor Allele | Minor Allele Freq | Function | aa change |
|---|---|---|---|---|---|---|---|---|
| SG15S417 | rs12911814 | 76701039 | 199977 | T | G | 5.1% | near CHRNA3 | |
| SG15S467 | rs13329271 | 76701285 | 200223 | T | G | 10.0% | near CHRNA3 | |
| C: CHRNB4 | | | | | | | | |
| SG15S402 | rs2904130 | 76703677 | 202615 | C | G | 36.0% | near CHRNB4 | |
| SG15S401 | ss107794618 | 76704151 | 203089 | C | G | 0.8% | utr | |
| SG15S400 | rs55952530 | 76704371 | 203309 | G | A | 1.5% | utr | |
| SG15S313 | rs1948 | 76704454 | 203392 | C | T | 34.6% | utr | |
| SG15S476 | ss107794644 | 76704907 | 203845 | C | T | 0.1% | intron | |
| SG15S410 | rs7178270 | 76708132 | 207070 | G | C | 40.5% | intron | |
| SG15S409 | rs56317523 | 76708398 | 207336 | C | T | 0.4% | non-synon | A- > V |
| SG15S408 | rs56235003 | 76708657 | 207595 | C | T | 0.8% | non-synon | R- > C |
| SG15S407 | rs3743072 | 76708817 | 207755 | C | T | 0.1% | synon | |
| SG15S406 | rs55919125 | 76709249 | 208187 | C | T | 4.3% | synon | |
| SG15S404 | rs56218866 | 76709284 | 208222 | A | G | 0.1% | non-synon | S- > G |
| SG15S405 | rs56095004 | 76709295 | 208233 | G | A | 0.7% | non-synon | R- > Q |
| SG15S403 | ss107794619 | 76709464 | 208402 | C | T | 0.1% | intron | |
| SG15S472 | ss107794640 | 76710242 | 209180 | A | G | 0.3% | intron | |
| SG15S473 | ss107794641 | 76710250 | 209188 | A | G | 0.2% | intron | |
| SG15S420 | rs12914008 | 76710560 | 209498 | C | T | 3.5% | non-synon | T- > I |
| SG15S419 | ss107794625 | 76710751 | 209689 | A | G | 0.1% | intron | |
| SG15S418 | rs28534575 | 76710900 | 209838 | A | C | 21.1% | intron | |
| SG15S474 | ss107794642 | 76710925 | 209863 | G | A | 0.1% | intron | |
| SG15S426 | rs12440298 | 76714644 | 213582 | A | C | 0.2% | intron | |
| SG15S425 | ss107794630 | 76714649 | 213587 | T | G | 0.2% | intron | |
| SG15S424 | ss107794629 | 76714670 | 213608 | A | G | 0.1% | intron | |
| SG15S423 | ss107794628 | 76714717 | 213655 | C | T | 0.1% | intron | |
| SG15S422 | ss107794627 | 76714925 | 213863 | C | T | 0.3% | non-synon | R- > S |
| SG15S421 | ss107794626 | 76715163 | 214101 | C | T | 0.1% | intron | |
| SG15S475 | ss107794643 | 76720731 | 219669 | G | C | 0.1% | near CHRNB4 | |
| SG15S430 | ss107794632 | 76720780 | 219718 | C | T | 0.2% | near CHRNB4 | |

TABLE 6-continued

| Descriptive information on all variants from sequencing | | | | | | | | |
|---|---|---|---|---|---|---|---|---|
| Marker | Ref SNP ID | Position (B 36) | Pos in Seq ID No: 1 | Major Allele | Minor Allele | Minor Allele Freq | Function | aa change |
| SG15S429 | ss107794631 | 76721203 | 220141 | A | T | 0.2% | near CHRNB4 | |
| SG15S428 | ss107794645 | 76721373 | 220311 | G | C | 40.7% | near CHRNB4 | |

[1]CTATTTCCCTCTGGCCCCGCCC (SEQ ID NO: 4)

[2]ATCGATTTTCGCCTTATCGT (SEQ ID NO: 5)

[3]The major allele contains 7 copies of AGC, the minor 6. With genotyping of 2798 individuals, one individual was identified with 8 copies.

[4]The marker contains 2-7 repeats of (CGCC); frequencies for alleles of rs55787222 are based on specific genotyping of this variant in 2935 individuals.
Frequencies are as follows - 2: 41.6%, 3: 0.07%, 4: 50.4%, 5: 7.4%, 6: 0.02%, 7: 0.6%

TABLE 7

Comparison of frequencies for markers with minor allele frequency greater than 1% in Nicotine Dependence (ND), Low Quantity Smokers (LQS) and Lung Cancer (LC). Padj - p-value after adjustment for the effect of rs1051730. Allele number for rs55787222 refers to number of copies of 4 bp repeat.

| | | | ND | | LQS | | LC | | ND against LQS | | | LC against LQS | | | LC against ND | | |
|---|---|---|---|---|---|---|---|---|---|---|---|---|---|---|---|---|---|
| Marker | Ref SNP ID | Allele | N | Freq | N | Freq | N | Freq | OR | P | Padj | OR | P | Padj | OR | P | Padj |
| SG15S149 | rs1051730 | T | 176 | 0.384 | 175 | 0.294 | 184 | 0.397 | 1.49 | 0.01 | — | 1.58 | 0.004 | — | 1.06 | 0.7 | — |
| SG15S347 | rs12898919 | C | 175 | 0.040 | 172 | 0.076 | 178 | 0.028 | 0.51 | 0.04 | 0.1 | 0.35 | 0.004 | 0.01 | 0.69 | 0.4 | 0.4 |
| SG15S389 | rs12899226 | G | 174 | 0.040 | 173 | 0.081 | 182 | 0.027 | 0.48 | 0.02 | 0.06 | 0.32 | 0.001 | 0.005 | 0.67 | 0.3 | 0.4 |
| SG15S399 | rs12907519 | C | 160 | 0.034 | 158 | 0.095 | 162 | 0.022 | 0.34 | 0.002 | 0.007 | 0.21 | 0.00004 | 0.0003 | 0.62 | 0.3 | 0.3 |
| SG15S417 | rs12911814 | C | 174 | 0.040 | 172 | 0.084 | 172 | 0.029 | 0.46 | 0.02 | 0.04 | 0.33 | 0.001 | 0.006 | 0.71 | 0.4 | 0.4 |
| SG15S420 | rs12914008 | T | 175 | 0.031 | 171 | 0.056 | 182 | 0.019 | 0.55 | 0.1 | 0.2 | 0.33 | 0.009 | 0.02 | 0.60 | 0.3 | 0.3 |
| SG15S148 | rs16969968 | A | 171 | 0.389 | 174 | 0.293 | 184 | 0.397 | 1.53 | 0.008 | 1.0 | 1.59 | 0.004 | 1.0 | 1.03 | 0.8 | 1.0 |
| SG15S313 | rs1948 | T | 176 | 0.335 | 174 | 0.351 | 184 | 0.351 | 0.93 | 0.7 | 0.3 | 1.00 | 1.0 | 0.09 | 1.07 | 0.7 | 0.4 |
| SG15S348 | rs2229961 | A | 176 | 0.017 | 174 | 0.003 | 183 | 0.014 | 6.02 | 0.05 | 0.1 | 4.81 | 0.1 | 0.2 | 0.80 | 0.7 | 0.7 |
| SG15S418 | rs28534575 | C | 172 | 0.183 | 170 | 0.244 | 182 | 0.206 | 0.69 | 0.05 | 0.3 | 0.80 | 0.2 | 0.9 | 1.16 | 0.4 | 0.3 |
| SG15S402 | rs2904130 | G | 176 | 0.349 | 174 | 0.379 | 184 | 0.351 | 0.88 | 0.4 | 0.6 | 0.88 | 0.4 | 0.4 | 1.00 | 1.0 | 0.8 |
| CHRNA3_1 | rs34238957 | 0 | 169 | 0.385 | 172 | 0.390 | 180 | 0.375 | 0.98 | 0.9 | 0.1 | 0.94 | 0.7 | 0.1 | 0.96 | 0.8 | 0.8 |
| CHRNA3_0 | rs34844435 | 0 | 175 | 0.963 | 174 | 0.934 | 184 | 0.973 | 1.83 | 0.08 | 0.2 | 2.53 | 0.01 | 0.04 | 1.38 | 0.4 | 0.5 |
| CHRNA3_0 | rs34844435 | 1 | 175 | 0.037 | 174 | 0.066 | 184 | 0.022 | 0.55 | 0.08 | 0.2 | 0.31 | 0.003 | 0.01 | 0.58 | 0.2 | 0.2 |
| CHRNA3_2 | rs35186448 | 2 | 175 | 0.191 | 174 | 0.239 | 181 | 0.199 | 0.76 | 0.1 | 0.5 | 0.79 | 0.2 | 0.9 | 1.05 | 0.8 | 0.6 |
| SG15S379 | rs3743073 | G | 175 | 0.386 | 175 | 0.383 | 177 | 0.376 | 1.01 | 0.9 | 0.08 | 0.97 | 0.8 | 0.08 | 0.96 | 0.8 | 1.0 |
| SG15S378 | rs3743074 | G | 175 | 0.386 | 175 | 0.383 | 184 | 0.372 | 1.01 | 0.9 | 0.08 | 0.96 | 0.8 | 0.1 | 0.94 | 0.7 | 0.9 |
| SG15S377 | rs3743075 | T | 176 | 0.384 | 175 | 0.383 | 184 | 0.372 | 1.00 | 1.0 | 0.08 | 0.96 | 0.8 | 0.1 | 0.95 | 0.8 | 0.9 |
| SG15S388 | rs3743077 | T | 176 | 0.426 | 170 | 0.465 | 176 | 0.395 | 0.86 | 0.3 | 0.5 | 0.75 | 0.06 | 0.9 | 0.88 | 0.4 | 0.6 |
| SG15S387 | rs3743078 | C | 176 | 0.190 | 173 | 0.237 | 179 | 0.201 | 0.76 | 0.1 | 0.5 | 0.81 | 0.2 | 1.0 | 1.07 | 0.7 | 0.6 |
| DG15S1561 | rs3841324 | del | 152 | 0.424 | 163 | 0.457 | 177 | 0.387 | 0.88 | 0.4 | 0.5 | 0.75 | 0.06 | 1.0 | 0.86 | 0.3 | 0.5 |
| SG15S380 | rs41280050 | A | 175 | 0.020 | 175 | 0.011 | 180 | 0.019 | 1.77 | 0.4 | 0.3 | 1.72 | 0.4 | 0.4 | 0.97 | 1.0 | 1.0 |
| SG15S392 | rs472054 | A | 174 | 0.388 | 175 | 0.386 | 184 | 0.372 | 1.01 | 1.0 | 0.09 | 0.94 | 0.7 | 0.1 | 0.94 | 0.7 | 0.9 |
| SG15S448 | rs4887069 | G | 175 | 0.194 | 174 | 0.241 | 181 | 0.204 | 0.76 | 0.1 | 0.5 | 0.81 | 0.2 | 0.9 | 1.07 | 0.7 | 0.6 |
| SG15S364 | rs503464 | A | 164 | 0.195 | 171 | 0.240 | 176 | 0.207 | 0.77 | 0.2 | 0.5 | 0.83 | 0.3 | 1.0 | 1.08 | 0.7 | 0.6 |
| SG15S345 | rs555018 | G | 174 | 0.422 | 170 | 0.462 | 175 | 0.391 | 0.85 | 0.3 | 0.5 | 0.75 | 0.06 | 1.0 | 0.88 | 0.4 | 0.5 |
| SG15S366 | rs55781567 | G | 165 | 0.394 | 171 | 0.307 | 181 | 0.403 | 1.47 | 0.02 | 0.5 | 1.53 | 0.008 | 0.6 | 1.04 | 0.8 | 1.0 |
| SG15S358 | rs55783657 | A | 176 | 0.009 | 173 | 0.006 | 183 | 0.025 | 1.48 | 0.7 | 0.9 | 4.34 | 0.03 | 0.1 | 2.93 | 0.09 | 0.09 |
| DG15S1568 | rs557872221 | 4 | 162 | 0.506 | 166 | 0.551 | 164 | 0.503 | 0.83 | 0.2 | 0.2 | 0.82 | 0.2 | 0.09 | 0.99 | 0.9 | 0.8 |
| DG15S1568 | rs55787222 | 5 | 162 | 0.071 | 166 | 0.087 | 164 | 0.052 | 0.80 | 0.4 | 0.8 | 0.57 | 0.07 | 0.2 | 0.72 | 0.3 | 0.3 |
| DG15S1568 | rs55787222 | 2 | 162 | 0.423 | 166 | 0.361 | 164 | 0.436 | 1.29 | 0.1 | 0.09 | 1.37 | 0.05 | 0.1 | 1.06 | 0.7 | 0.8 |
| SG15S365 | rs55853698 | G | 168 | 0.390 | 171 | 0.304 | 180 | 0.400 | 1.46 | 0.02 | 0.9 | 1.53 | 0.008 | 0.6 | 1.04 | 0.8 | 0.6 |
| SG15S406 | rs55919125 | T | 176 | 0.043 | 174 | 0.032 | 183 | 0.055 | 1.36 | 0.4 | 0.3 | 1.77 | 0.1 | 0.05 | 1.30 | 0.5 | 0.4 |
| SG15S400 | rs55952530 | A | 170 | 0.009 | 171 | 0.020 | 178 | 0.017 | 0.43 | 0.2 | 0.3 | 0.82 | 0.7 | 1.0 | 1.93 | 0.3 | 0.3 |
| SG15S384 | rs55958820 | T | 176 | 0.017 | 172 | 0.012 | 180 | 0.017 | 1.47 | 0.5 | 0.8 | 1.44 | 0.6 | 0.9 | 0.98 | 1.0 | 0.9 |
| SG15S468 | rs56182392 | A | 158 | 0.013 | 168 | 0.012 | 173 | 0.014 | 1.06 | 0.9 | 0.8 | 1.22 | 0.8 | 0.6 | 1.14 | 0.8 | 0.8 |
| SG15S360 | rs564585 | G | 175 | 0.223 | 173 | 0.301 | 183 | 0.221 | 0.67 | 0.02 | 0.2 | 0.66 | 0.02 | 0.2 | 0.99 | 1.0 | 0.8 |
| SG15S353 | rs569207 | T | 176 | 0.190 | 175 | 0.237 | 182 | 0.203 | 0.76 | 0.1 | 0.5 | 0.82 | 0.3 | 1.0 | 1.09 | 0.7 | 0.5 |
| SG15S162 | rs578776 | T | 175 | 0.223 | 175 | 0.300 | 179 | 0.209 | 0.67 | 0.02 | 0.2 | 0.62 | 0.006 | 0.09 | 0.92 | 0.7 | 0.8 |
| DG15S1563 | rs60706203 | del | 165 | 0.409 | 154 | 0.399 | 161 | 0.379 | 1.04 | 0.8 | 0.09 | 0.92 | 0.6 | 0.3 | 0.88 | 0.4 | 0.5 |
| SG15S356 | rs615470 | T | 176 | 0.386 | 174 | 0.388 | 184 | 0.372 | 0.99 | 1.0 | 0.09 | 0.94 | 0.7 | 0.1 | 0.94 | 0.7 | 0.8 |
| SG15S311 | rs621849 | G | 176 | 0.426 | 175 | 0.466 | 168 | 0.405 | 0.85 | 0.3 | 0.5 | 0.78 | 0.1 | 0.7 | 0.92 | 0.6 | 0.8 |
| SG15S346 | rs647041 | T | 172 | 0.427 | 172 | 0.471 | 177 | 0.395 | 0.84 | 0.3 | 0.6 | 0.74 | 0.04 | 0.7 | 0.88 | 0.4 | 0.4 |
| SG15S312 | rs6495306 | G | 176 | 0.426 | 175 | 0.466 | 168 | 0.405 | 0.85 | 0.3 | 0.5 | 0.78 | 0.1 | 0.7 | 0.92 | 0.6 | 0.8 |
| SG15S391 | rs660652 | A | 169 | 0.385 | 171 | 0.389 | 179 | 0.374 | 0.98 | 0.9 | 0.1 | 0.94 | 0.7 | 0.1 | 0.96 | 0.8 | 0.9 |
| SG15S151 | rs680244 | A | 176 | 0.426 | 156 | 0.474 | 168 | 0.405 | 0.82 | 0.2 | 0.7 | 0.75 | 0.07 | 0.9 | 0.92 | 0.6 | 0.8 |
| SG15S412 | rs684513 | G | 172 | 0.180 | 156 | 0.215 | 168 | 0.188 | 0.80 | 0.3 | 0.7 | 0.84 | 0.4 | 0.8 | 1.05 | 0.8 | 0.6 |
| SG15S410 | rs7178270 | C | 174 | 0.402 | 172 | 0.445 | 177 | 0.370 | 0.84 | 0.3 | 0.8 | 0.73 | 0.04 | 0.6 | 0.87 | 0.4 | 0.4 |
| SG15S367 | rs8040868 | C | 175 | 0.429 | 174 | 0.382 | 182 | 0.431 | 1.21 | 0.2 | 0.04 | 1.23 | 0.2 | 0.02 | 1.01 | 0.9 | 0.8 |

TABLE 7-continued

Comparison of frequencies for markers with minor allele frequency greater than 1% in Nicotine Dependence (ND), Low Quantity Smokers (LQS) and Lung Cancer (LC). Padj - p-value after adjustment for the effect of rs1051730. Allele number for rs55787222 refers to number of copies of 4 bp repeat.

| | | | ND | | LQS | | LC | | ND against LQS | | | LC against LQS | | | LC against ND | | |
|---|---|---|---|---|---|---|---|---|---|---|---|---|---|---|---|---|---|
| Marker | Ref SNP ID | Allele | N | Freq | N | Freq | N | Freq | OR | P | Padj | OR | P | Padj | OR | P | Padj |
| SG15S368 | rs8192475 | T | 176 | 0.040 | 175 | 0.083 | 184 | 0.027 | 0.46 | 0.02 | 0.05 | 0.31 | 0.001 | 0.004 | 0.67 | 0.3 | 0.4 |
| SG15S376 | rs8192479 | T | 176 | 0.028 | 175 | 0.026 | 182 | 0.038 | 1.11 | 0.8 | 0.7 | 1.52 | 0.3 | 0.8 | 1.37 | 0.5 | 0.5 |
| SG15S359 | rs8192482 | T | 175 | 0.380 | 173 | 0.292 | 183 | 0.396 | 1.49 | 0.01 | 1.0 | 1.59 | 0.003 | 1.0 | 1.07 | 0.7 | 1.0 |
| SG15S428 | ss107794645 | C | 172 | 0.451 | 161 | 0.332 | 183 | 0.432 | 1.65 | 0.002 | 0.1 | 1.53 | 0.007 | 0.5 | 0.93 | 0.6 | 0.4 |

TABLE 8

Equivalence classes for SNPs with minor allele frequency greater than 5%. All variants with frequency greater than 5% were grouped into equivalence classes based on $r^2 > 0.8$. A lead SNP for each class was chosen, and r2 for each variant to that SNP is listed. Three variants do not fit into these classes. They are listed separately under class A, to which each has the strongest LD.

| | Class | | | | | | | | | | | |
|---|---|---|---|---|---|---|---|---|---|---|---|---|
| | A | | B | | C | | D | | E | | F | |
| | rs1051730 | $r^2$ | rs680244 | $r^2$ | rs1948 | $r^2$ | rs8192475 | $r^2$ | rs578776 | $r^2$ | rs569207 | $r^2$ |
| Head | rs16969968 | 1.00 | rs34238957 | 0.82 | rs2904130 | 0.92 | rs34844435 | 0.88 | rs564585 | 0.99 | rs35186448 | 0.99 |
| | rs8192482 | 1.00 | rs3841324 | 0.91 | | | rs12898919 | 1.00 | | | rs503464 | 0.86 |
| | rs55853698 | 0.93 | rs60706203 | 0.87 | | | rs12899226 | 1.00 | | | rs3743078 | 0.99 |
| | rs55781567 | 0.93 | rs621849 | 1.00 | | | rs12907519 | 0.93 | | | rs7170068 | 0.87 |
| | | | rs6495306 | 1.00 | | | rs12911814 | 1.00 | | | rs684513 | 0.83 |
| | | | rs555018 | 1.00 | | | | | | | rs28534575 | 0.83 |
| | rs55787222 | 0.64 | rs647041 | 0.99 | | | | | | | rs4887069 | 0.96 |
| | rs8040868 | 0.79 | rs615470 | 0.82 | | | | | | | rs13329271 | 0.90 |
| | ss107794645 | 0.69 | rs3743075 | 0.81 | | | | | | | | |
| | | | rs3743074 | 0.81 | | | | | | | | |
| | | | rs3743073 | 0.81 | | | | | | | | |
| | | | rs3743077 | 1.00 | | | | | | | | |
| | | | rs660652 | 0.82 | | | | | | | | |
| | | | rs472054 | 0.82 | | | | | | | | |
| | | | rs7178270 | 0.80 | | | | | | | | |

TABLE 9

Association Results for Equivalences Classes in Larger Samples. P-values include correction for relatedness among groups; Padj1 adjusts the P-value for the effect of rs1051730 (LQS = Low Qantity Smokers; ND = Nicotine Dependence; LC = Lung Cancer)

| | | | LQS | | ND | | LC | | ND against LQS | | | LC against LQS | | | LC against ND | | |
|---|---|---|---|---|---|---|---|---|---|---|---|---|---|---|---|---|---|
| Marker | Class | Allele | N | freq | N | freq | N | freq | OR | Padj | Padj 1 | OR | Padj | Padj 1 | OR | Padj | Padj 1 |
| rs1051730 | A | T | 4676 | 0.309 | 1950 | 0.384 | 669 | 0.404 | 1.40 | 7.1 × 10−15 | — | 1.52 | 1.5 × 10−11 | — | 1.09 | 0.2 | — |
| rs680244 | B | G | 4680 | 0.556 | 1950 | 0.595 | 669 | 0.593 | 1.18 | 9.2 × 10−5 | 0.3 | 1.16 | 0.01 | 0.03 | 0.99 | 0.9 | 0.2 |
| rs1948 | C | C | 4674 | 0.650 | 1950 | 0.682 | 669 | 0.667 | 1.15 | 0.001 | 0.4 | 1.08 | 0.2 | 0.006 | 0.93 | 0.3 | 0.04 |
| rs8192475 | D | C | 4674 | 0.947 | 1948 | 0.954 | 668 | 0.958 | 1.15 | 0.2 | 0.9 | 1.28 | 0.09 | 0.5 | 1.11 | 0.5 | 0.6 |
| rs569207 | F | C | 4675 | 0.751 | 1950 | 0.787 | 669 | 0.809 | 1.22 | 3.0 × 10−5 | 0.2 | 1.41 | 3.1 × 10−6 | 0.03 | 1.15 | 0.09 | 0.2 |

TABLE 10

All variants with frequency less than 1%.

| Markers | Ref SNP ID | Allele | Number of Carriers of Minor Allele LQS | ND | LC |
|---|---|---|---|---|---|
| CHRNA3_0 | rs55665143 | (-A) | 0 | 0 | 2 |
| CHRNA3_4 | ss107794647 | (-20 bp)[1] | 0 | 1 | 0 |
| CHRNA5_0 | ss107794648 | (-TC) | 1 | 0 | 0 |
| CHRNA5_1 | ss107794649 | (-ACT) | 0 | 0 | 1 |
| SG15S344 | rs55982512 | T | 1 | 1 | 2 |
| SG15S349 | ss107794603 | C | 1 | 2 | 1 |
| SG15S350 | ss107794604 | T | 0 | 0 | 3 |
| SG15S351 | ss107794605 | T | 4 | 0 | 0 |
| SG15S352 | ss107794606 | C | 1 | 2 | 3 |
| SG15S355 | ss107794607 | C | 4 | 1 | 5 |
| SG15S357 | rs8192483 | A | 0 | 1 | 0 |
| SG15S361 | ss107794608 | A | 1 | 0 | 0 |
| SG15S363 | ss107794609 | T | 1 | 1 | 0 |
| SG15S374 | ss107794610 | A | 1 | 0 | 0 |
| SG15S375 | ss107794611 | G | 1 | 0 | 1 |
| SG15S381 | ss107794612 | T | 2 | 4 | 3 |
| SG15S382 | rs56403513 | A | 0 | 0 | 1 |
| SG15S383 | ss107794613 | A | 1 | 0 | 0 |
| SG15S385 | rs8192480 | G | 0 | 0 | 1 |
| SG15S390 | rs55736590 | A | 3 | 1 | 3 |
| SG15S393 | rs56113144 | A | 0 | 2 | 1 |
| SG15S394 | ss107794615 | T | 1 | 0 | 1 |
| SG15S397 | ss107794616 | T | 0 | 1 | 0 |
| SG15S398 | ss107794617 | C | 1 | 0 | 0 |
| SG15S401 | ss107794618 | G | 2 | 2 | 4 |
| SG15S403 | ss107794619 | T | 0 | 0 | 1 |
| SG15S404 | rs56218866 | G | 0 | 0 | 1 |
| SG15S405 | rs56095004 | A | 0 | 2 | 5 |
| SG15S407 | rs3743072 | T | 0 | 0 | 1 |
| SG15S408 | rs56235003 | T | 4 | 1 | 3 |
| SG15S409 | rs56317523 | T | 0 | 1 | 3 |
| SG15S411 | ss107794620 | A | 1 | 0 | 1 |
| SG15S413 | ss107794621 | C | 1 | 0 | 0 |
| SG15S414 | ss107794622 | A | 3 | 1 | 2 |
| SG15S415 | ss107794623 | G | 0 | 0 | 1 |
| SG15S416 | ss107794624 | C | 1 | 0 | 0 |

TABLE 10-continued

All variants with frequency less than 1%.

| Markers | Ref SNP ID | Allele | Number of Carriers of Minor Allele LQS | ND | LC |
|---|---|---|---|---|---|
| SG15S419 | ss107794625 | G | 0 | 0 | 1 |
| SG15S421 | ss107794626 | T | 1 | 0 | 0 |
| SG15S422 | ss107794627 | T | 0 | 2 | 1 |
| SG15S423 | ss107794628 | T | 0 | 1 | 0 |
| SG15S424 | ss107794629 | G | 0 | 1 | 0 |
| SG15S425 | ss107794630 | G | 0 | 0 | 2 |
| SG15S426 | rs12440298 | C | 0 | 1 | 1 |
| SG15S429 | ss107794631 | T | 0 | 2 | 0 |
| SG15S430 | ss107794632 | T | 1 | 0 | 1 |
| SG15S445 | ss107794646 | C | 2 | 0 | 0 |
| SG15S446 | ss107794633 | A | 0 | 0 | 1 |
| SG15S447 | ss107794634 | A | 6 | 1 | 2 |
| SG15S449 | ss107794635 | G | 2 | 1 | 1 |
| SG15S450 | ss107794636 | T | 1 | 0 | 0 |
| SG15S466 | ss107794637 | G | 0 | 1 | 0 |
| SG15S469 | ss107794638 | A | 2 | 0 | 0 |
| SG15S470 | ss107794639 | G | 3 | 2 | 1 |
| SG15S471 | rs56201623 | T | 0 | 0 | 1 |
| SG15S472 | ss107794640 | G | 1 | 1 | 0 |
| SG15S473 | ss107794641 | C | 0 | 2 | 0 |
| SG15S474 | ss107794642 | A | 0 | 1 | 0 |
| SG15S475 | ss107794643 | C | 1 | 0 | 0 |
| SG15S476 | ss107794644 | T | 0 | 1 | 0 |

[1]ATCGATTTTCGCCTTATCGT. Other alleles in paranthesis are indel polymorphisms of the respective alleles

TABLE 11

Association Results for Insertion/Deletions and Microsatellites. The results for the T allele of rs1051730 within the sample genotyped for length variants is included here in the table for comparison. P - includes correction for relatedness among groups. Padj corresponds to P-value after adjustment for the effect of rs1051730.

| | | LQS | | ND | | LC | | ND against LQS | | | LC against LQS | | | LC against ND | | |
|---|---|---|---|---|---|---|---|---|---|---|---|---|---|---|---|---|
| Marker | Allele | N | freq | N | freq | N | freq | OR | P | Padj | OR | P | Padj | OR | P | Padj |
| rs1051730 | T | 608 | 0.306 | 1623 | 0.359 | 567 | 0.384 | 1.27 | 0.001 | 0.001 | 1.42 | 8.5 × 10−5 | 8.5 × 10−5 | 0.98 | 0.8 | 0.4 |
| rs3841324 | del | 608 | 0.433 | 1623 | 0.403 | 567 | 0.399 | 0.88 | 0.08 | 0.8 | 0.87 | 0.1 | 0.4 | 0.95 | 0.5 | 0.8 |
| rs60706203 | ins | 608 | 0.398 | 1623 | 0.385 | 567 | 0.374 | 0.95 | 0.4 | 0.2 | 0.90 | 0.2 | 0.2 | 1.15 | 0.05 | 0.2 |
| rs55787222 | 2 | 608 | 0.382 | 1623 | 0.404 | 567 | 0.438 | 1.10 | 0.2 | 0.004 | 1.26 | 0.006 | 0.2 | 0.89 | 0.1 | 0.4 |
| rs55787222 | 4 | 608 | 0.536 | 1623 | 0.514 | 567 | 0.484 | 0.91 | 0.2 | 0.1 | 0.81 | 0.01 | 0.6 | 0.94 | 0.7 | 0.9 |
| rs55787222 | 5 | 608 | 0.076 | 1623 | 0.075 | 567 | 0.071 | 1.00 | 1.0 | 0.5 | 0.94 | 0.7 | 0.7 | 1.05 | 0.9 | 0.8 |
| rs55787222 | 7 | 608 | 0.004 | 1623 | 0.006 | 567 | 0.006 | 1.43 | 0.5 | 0.4 | 1.50 | 0.5 | 0.4 | 1.11 | 0.1 | 0.1 |

TABLE 12

Association analysis of the effect of rs3841324 genotype on expression of CHRNA5. Other variants within the block were tested as well by including the head of each equivalence class.

| | | | Whole Blood | | | | | | Subcutaneous Adipose | | | | | |
|---|---|---|---|---|---|---|---|---|---|---|---|---|---|---|
| Marker | Allele | Class | r | LCL | UCL | P | adjP1 | adjP2 | r | LCL | UCL | P | adjP1 | adjP2 |
| rs3841324 | 0 | B | 0.72 | 0.67 | 0.76 | 3.7 × 10−71 | — | — | 0.73 | 0.68 | 0.77 | 1.9 × 10−63 | — | — |
| rs1051730 | 4 | A | −0.54 | −0.60 | −0.47 | 2.0 × 10−34 | 0.006 | — | −0.53 | −0.60 | −0.45 | 3.9 × 10−28 | 0.02 | — |
| rs680244 | 1 | B | 0.71 | 0.66 | 0.75 | 4.3 × 10−69 | 0.03 | 0.1 | 0.71 | 0.65 | 0.75 | 3.6 × 10−58 | 0.07 | 0.3 |
| rs1948 | 4 | C | 0.58 | 0.51 | 0.63 | 1.3 × 10−40 | 0.8 | 0.5 | 0.56 | 0.49 | 0.63 | 2.0 × 10−32 | 0.8 | 0.6 |
| rs8192475 | 4 | D | 0.26 | 0.17 | 0.34 | 3.0 × 10−8 | 0.03 | 0.04 | 0.23 | 0.13 | 0.33 | 5.3 × 10−6 | 0.5 | 0.6 |
| rs578776 | 4 | E | −0.14 | −0.23 | −0.05 | 0.002 | 0.06 | 0.5 | −0.10 | −0.20 | 0.00 | 0.004 | 0.08 | 0.7 |
| rs569207[1] | 4 | F | −0.23 | −0.31 | −0.14 | 1.3 × 10−6 | 0.06 | 0.3 | −0.19 | −0.29 | −0.09 | 1.6 × 10−4 | 0.09 | 0.5 |

[1]rs569207 allele T (= allele 4) is tagged by a haplotype using allele G at rs680244 and allele T at rs578776 (r2 = 0.99)
adjP1 - adjusted for the effect of rs3841324;
adjP2 - adjusted for effects of both rs3841324 and rs1051730

TABLE 13

Demographics: Sequencing Cohort

| Cohort | N | Sex (M/F) | Age (yrs) |
|---|---|---|---|
| Low Quantity Smokers | 175 | 57/118 | 55.8 ± 18.4 |
| Nicotine Dependence | 176 | 79/97 | 50.6 ± 10.4 |
| Lung Cancer | 184 | 98/86 | 72.6 ± 10.8 |

TABLE 14

Demographics for cohorts used in analyses including additional genotyping

| | N | Male/Female | Age (years) |
|---|---|---|---|
| A - Length Polymorphisms | | | |
| Nicotine Dependence | 1623 | 602/1021 | 50.4 ± 11.2 |
| Lung Cancer | 567 | 291/276 | 70.6 ± 11.0 |
| Low Quantity Smokers | 608 | 192/416 | 58.4 ± 18.2 |

TABLE 14-continued

Demographics for cohorts used in analyses including additional genotyping

| | N | Male/Female | Age (years) |
|---|---|---|---|
| B - rs578776 | | | |
| Nicotine Dependence | 2161 | 758/1403 | 50.1 ± 11.3 |
| Low Quantity Smokers | 865 | 283/582 | 57.7 ± 18.8 |
| C - Illumina | | | |
| Nicotine Dependence | 1950 | 689/1261 | 51.0 ± 11.0 |
| Lung Cancer | 669 | 340/329 | 70.6 ± 11.0 |
| Low Quantity Smokers | 4681 | 1203/3478 | 63.9 ± 19.1 |

Age is in years ± S.D.

The invention claimed is:

1. A method for determining a susceptibility to lung cancer in a human individual, comprising:
   assaying a nucleic acid sample from the individual for an allele of a polymorphic marker, said allele being rs1051730 allele T, rs16969968 allele A, rs8034191 allele C, or ss107794645 allele C;
   detecting the allele in the nucleic acid sample;
   determining that the individual has an increased genetic susceptibility to lung cancer from the detection of the allele in the nucleic acid sample; and
   screening the human individual determined to have the increased genetic susceptibility to lung cancer for lung cancer using at least one procedure selected from a chest x-ray, sputum cytology examination, and low dose computed tomography scan.

2. The method of claim 1, wherein the allele is rs1051730 allele T or rs16969968 allele A.

3. The method of claim 1, wherein the allele is ss107794645 allele C.

4. The method of claim 3, wherein the allele is rs16969968 allele A.

5. The method of claim 1, wherein the allele is rs1051730, allele T.

6. The method of claim 1, wherein the allele is rs8034191 allele C.

7. The method of claim 1, wherein the determining of the increased genetic susceptibility to lung cancer includes calculating a risk measure that includes a relative risk or odds ratio of at least 1.2 attributed to the allele being detected in the nucleic acid sample from the individual, using an apparatus that comprises:
   a processor, and
   a computer readable memory having computer executable instructions adapted to be executed on the processor to analyze marker information for at least one human individual with respect to the polymorphic marker; and to generate an output based on the marker information, wherein the output comprises a risk measure of the polymorphic marker as a genetic indicator of susceptibility to lung cancer for the human individual.

8. The method of claim 7, comprising determining that the individual is homozygous for the allele of the polymorphic marker from the nucleic acid sequence data, and determining an increased genetic susceptibility to lung cancer for the individual by calculating a risk measure that includes a relative risk or odds ratio of at least $1.2^2$ attributable to the allele being present and homozygous in the genome of the individual.

9. The method of claim 7, wherein determination of an increased genetic susceptibility uses a database containing correlation data between the alleles of the polymorphic marker and genetic susceptibility to lung cancer.

10. The method of claim 9, wherein the database comprises at least one risk measure of susceptibility to lung cancer for the allele of the polymorphic marker.

11. The method of claim 10, wherein the database comprises a look-up table containing at least one risk measure of lung cancer for the allele of the polymorphic marker.

12. The method of claim 7, further comprising reporting the susceptibility to at least one entity selected from the group consisting of the individual, a guardian of the individual, a genetic service provider, a physician, a medical organization, and a medical insurer.

13. The method of claim 7, wherein the allele is ss107794645 allele C.

14. The method of claim 7, wherein the allele is rs1051730 allele T.

15. The method of claim 7, wherein the allele is rs16969968 allele A.

16. The method of claim 7, wherein the individual is a tobacco smoker, and wherein the method includes determining that the individual has an increased genetic susceptibility to lung cancer as compared to smokers who lack the allele.

17. The method of claim 7, wherein the computer readable memory further comprises data indicative of the risk of developing lung cancer associated with the allele, and wherein the risk measure for the human individual is based on a comparison of the marker status for the human individual to the risk of lung cancer associated with the allele.

18. The method of claim 7, wherein the computer readable memory further comprises data indicative of the frequency of the allele in a plurality of individuals diagnosed with lung cancer, and data indicative of the frequency of the allele in a plurality of reference individuals, and wherein the risk measure for the human individual is based on a comparison of the frequency of the allele in individuals diagnosed with lung cancer and reference individuals.

19. The method of claim 1, further comprising analyzing non-genetic information from the individual to make risk assessment, diagnosis, or prognosis of the individual.

20. The method of claim 19, wherein the non-genetic information is selected from age, gender, socioeconomic status, smoking history, medical history, family history of lung cancer, biochemical measurements, and clinical measurements.

21. The method of claim 1, wherein the determining of the genetic susceptibility is performed using a computer-readable medium having computer executable instructions for determining susceptibility to lung cancer in a human individual, the computer readable medium comprising:

data indicative of the polymorphic marker; and a routine stored on the computer readable medium and adapted to be executed by a processor to determine risk of developing lung cancer in an individual for the allele of the polymorphic marker.

22. The method of claim 21, wherein the routine is adopted to receive input data indicative of the allelic status of the polymorphic marker in said individual.

23. The method of claim 1, wherein the determining of the genetic susceptibility is performed using an apparatus for determining a genetic indicator for susceptibility to lung cancer in a human individual, the apparatus comprising:

a processor, and a computer readable memory having computer executable instructions adapted to be executed on the processor to analyze marker information for at least one human individual with respect to the polymorphic marker, and to generate an output based on the marker information, based on the presence or absence of the at least one allele in the nucleic acid sample, wherein the output comprises a risk measure of the at least one marker as a genetic indicator of susceptibility to lung cancer for the human individual.

24. The method of claim 23, wherein the computer readable memory further comprises data indicative of the risk of developing lung cancer associated with the allele of the polymorphic marker, and wherein the risk measure for the human individual is based on a comparison of the marker status for the human individual to the risk of lung cancer associated with the allele of the polymorphic marker.

25. The method of claim 23, wherein the computer readable memory further comprises data indicative of the frequency of the allele in a plurality of individuals diagnosed with lung cancer, and data indicative of the frequency of the allele in a plurality of reference individuals, and wherein the risk measure for the individual is based on a comparison of the frequency of the allele in individuals diagnosed with lung cancer and reference individuals.

26. The method of claim 1, wherein the individual is a tobacco smoker, and wherein the method includes determining that the individual has an increased genetic susceptibility to lung cancer as compared to smokers who lack the allele.

27. The method of claim 1, wherein the assaying comprises at least one technique selected from the group consisting of: polymerase chain reaction, allele-specific hybridization, allele-specific primer extension, allele-specific amplification, nucleic acid sequencing, 5'-exonuclease digestion, molecular beacon assay, oligonucleotide ligation assay, size analysis, and single-stranded conformation analysis.

28. The method of claim 1, wherein the assaying of the nucleic acid sample comprises at least one technique selected from the group consisting of: allele-specific probe hybridization and DNA sequencing.

29. The method of claim 1 wherein the determining that the individual has the increased susceptibility comprises calculating a risk score for lung cancer for the individual.

30. The method of claim 29, further comprising making a communication that includes the risk score available to the individual or to a third party.

31. The method of claim 30, wherein the communication is made available to the individual or third party by a secured internet interface.

32. The method of claim 31, wherein the communication is made available to a third party selected from a genetic counselor, a physician, or another health care worker.

33. The method of claim 1, further comprising making a communication that includes the genetic susceptibility to lung cancer available to the individual or to a third party, selected from the group consisting of a guardian of the individual, a genetic service provider, a physician, a medical organization, and a medical insurer.

34. The method of claim 33, wherein the communication is made available to the individual or third party by a secured internet interface.

35. The method of claim 1, wherein the human individual has never smoked, and the method comprises determining the increased genetic susceptibility to lung cancer as compared to human subjects who have never smoked.

36. The method of claim 1, wherein the human individual is an ex-smoker, and the method comprises determining the increased genetic susceptibility to lung cancer as compared to human subjects who are ex-smokers.

37. The method of claim 1, wherein the human individual is a smoker, and the method comprises determining the increased genetic susceptibility to lung cancer as compared to human subjects who smoke a similar quantity as the individual.

38. The method according to claim 1, wherein the step of determining an increased genetic susceptibility to lung cancer includes calculating a risk measure that includes a relative risk or odds ratio of at least 1.2 attributed to the allele being detected in the nucleic acid sample.

* * * * *